US012221609B2

(12) United States Patent
Chamberlain et al.

(10) Patent No.: US 12,221,609 B2
(45) Date of Patent: Feb. 11, 2025

(54) COMPOSITIONS AND METHODS TO RESTORE PATERNAL UBE3A GENE EXPRESSION IN HUMAN ANGELMAN SYNDROME

(71) Applicant: University of Connecticut, Farmington, CT (US)

(72) Inventors: Stormy Chamberlain, Oxford, CT (US); Noelle Germain, Watertown, CT (US)

(73) Assignee: University of Connecticut, Farmington, CT (US)

( * ) Notice: Subject to any disclaimer, the term of this patent is extended or adjusted under 35 U.S.C. 154(b) by 1005 days.

(21) Appl. No.: 17/271,982

(22) PCT Filed: Sep. 20, 2019

(86) PCT No.: PCT/US2019/052272

§ 371 (c)(1),
(2) Date: Feb. 26, 2021

(87) PCT Pub. No.: WO2020/061528

PCT Pub. Date: Mar. 26, 2020

(65) Prior Publication Data

US 2021/0332368 A1 Oct. 28, 2021

Related U.S. Application Data

(60) Provisional application No. 62/734,435, filed on Sep. 21, 2018.

(51) Int. Cl.
*C12N 15/113* (2010.01)
*C12N 15/86* (2006.01)

(52) U.S. Cl.
CPC .......... *C12N 15/1137* (2013.01); *C12N 15/86* (2013.01); *C12N 2310/121* (2013.01); *C12N 2310/122* (2013.01); *C12N 2310/128* (2013.01); *C12N 2310/141* (2013.01); *C12N 2310/531* (2013.01); *C12N 2740/15042* (2013.01); *C12N 2740/15043* (2013.01); *C12N 2750/14142* (2013.01); *C12N 2750/14143* (2013.01)

(58) Field of Classification Search
None
See application file for complete search history.

(56) References Cited

U.S. PATENT DOCUMENTS 5,478,745 A 12/1995 Samulski et al.
5,898,031 A 4/1999 Crooke
6,107,094 A 8/2000 Crooke
7,947,288 B2 5/2011 Paul
9,163,236 B2 10/2015 Jessup et al.
9,617,539 B2 4/2017 Rigo et al.
9,770,491 B2 9/2017 Beltran et al.
9,821,114 B2 * 11/2017 Cabrera Aquino ... A61M 5/178
10,597,721 B2 3/2020 Hatchwell et al.
10,739,332 B2 8/2020 Costa et al.
2005/0020521 A1 1/2005 Rana
2006/0024715 A1 2/2006 Liu et al.
2007/0135372 A1 6/2007 MacLachlan et al.
2007/0191294 A1 8/2007 Elmen et al.
2008/0213891 A1 9/2008 Manoharan et al.
2008/0249039 A1 10/2008 Elmen et al.
2012/0004283 A1 1/2012 Wu et al.
2015/0191723 A1 7/2015 Rigo et al.
2016/0313324 A1 10/2016 Quintana et al.
2019/0224339 A1 7/2019 Paul et al.

FOREIGN PATENT DOCUMENTS

EP 0890362 A1 1/1999
EP 0998945 A1 5/2000
EP 1016700 A1 7/2000
WO 9428152 A1 12/1994
WO 9511664 A1 5/1995
WO 9627677 A2 9/1996
WO 9704119 A1 2/1997
WO 9800524 A1 1/1998
WO 9822588 A2 5/1998
WO 9826048 A1 6/1998
WO 9853853 A1 12/1998
WO 9956784 A2 11/1999
WO 0040702 A1 7/2000
WO 0050573 A1 8/2000
WO 0147563 A1 7/2001
WO 2007124452 A2 11/2007
WO 2011111072 A2 9/2011
WO 2013151981 A1 10/2013
WO 2016086104 A1 6/2016

(Continued)

OTHER PUBLICATIONS

Bofill-De Ros, Xavier, and Shuo Gu. "Guidelines for the optimal design of miRNA-based shRNAs." Methods 103 (2016): 157-166. (Year: 2016).*

Xu, Jing, et al. "Construction of conveniently screening pLKO. 1-TRC vector tagged with TurboGFP." Applied biochemistry and biotechnology 181 (2017): 699-709. (Year: 2017).*

Lee, Dung-Fang, et al. "Combining competition assays with genetic complementation strategies to dissect mouse embryonic stem cell self-renewal and pluripotency." nature protocols 7.4 (2012): 729-748. (Year: 2012).*

English Translation of Chinese Office Action for application No. 201980076741.9, issued May 8, 2024, 7 pages.

English Translation of Korean Office Action for application No. 10-2021-7011023, issued May 21, 2024, 12 pages.

(Continued)

*Primary Examiner* — Robert J Yamasaki

(74) *Attorney, Agent, or Firm* — Carter, DeLuca & Farrell LLP

(57) ABSTRACT

The present invention relates to compositions and methods for activating expression from the paternally-inherited allele of UBE3A in human Angelman's Syndrome neurons using viral vector delivery of short hairpin RNAs, ribozymes, and/or microRNAs.

28 Claims, 7 Drawing Sheets

Specification includes a Sequence Listing.

(56) References Cited

FOREIGN PATENT DOCUMENTS

| WO | 2017081223 A1 | 5/2017 |
|---|---|---|
| WO | 2020051417 A2 | 3/2020 |
| WO | 2020061528 A1 | 3/2020 |

OTHER PUBLICATIONS

Konermann et al., "Transcriptome Engineering with RNA-targeting Type Vi-D CRISPR Effectors," Cell, Apr. 19, 2015, vol. 173, No. 3; pp. 665-676.

Meng et al., "Towards a therapy for Angelman syndrome by targeting a long non-coding RNA," Nature, Feb. 19, 2015, vol. 518, No. 7539; pp. 409-412.

Cydeciyan et al., "Mutation-independent rhodopsin gene therapy by knockdown and replacement with a single AAV vector," Proc Natl Acad Sci U S A, Sep. 4, 2018, vol. 115, No. 36; pp. E8547-E8556.

Williams, et al., Conference Report, "Angelman Syndrome 2005: Updated Consensus for Diagnostic Criteria," American Journal of Medical Genetics, 2006, vol. 140A; pp. 413-418.

"Viral Vector," Wikipedia, https://en.wikipedia.org/wiki/Viral_vector, dated Sep. 13, 2019; 8 pages.

"Transfection," Wikipedia, https://en.wikipedia.org/wiki/Transfection, dated Sep. 13, 2019; 9 pages.

Tiscornia et al., "Design and Cloning of an ShRNA into a Lentiviral Silencing Vector: Version A," CSH Protocols, Aug. 2008, vol. 3, Issue 8; pp. 1-5.

Stewart et al., "Lentivirus-delivered stable gene silencing by RNAi in primary cells," RNA, 2003, vol. 9; pp. 493-501.

Silva et al., "Selective gene silencing by viral delivery o short hairpin RNA," Virology Journal, 2010, vol. 7, No. 248; pp. 1-11.

O'Keefe, siRNAs and shRNAs: Tools for Protein Knockdown by Gene Silencing, Sep. 2, 2019, Princeton University, United States; 13 pages.

ShRNA Process and shRNA Diagram, Millipore Signa, Sep. 12, 2019, https://www.sigmaaldrich.com/life-science/functional-genomics-and-rnai/shrna/library-information/shmna-process-diagram.html; 2 pages.

International Preliminary Report on Patentability, dated Mar. 23, 2021 and Written Opinion of the International Searching Authority dated Feb. 20, 2020, 6 total pages.

Meng et al., "Ube3a-ATS is an atypical RNA polymerase II transcript that represses the paternal expression of Ube3a," Human Molecular Genetics, 2012, vol. 21, No. 13; pp. 3001-3012.

Moore et al., "Short Hairpin RNA (shRNA): Design, Delivery, and Assessment of Gene Knockdown," Methods Mol. Biol,, 2010, vol. 629; pp. 141-158.

Mcintyre et al., "A comparison of multiple shRNA expression methods for combinatorial RNAi," Genetic Vaccines and Therapy, 2011, vol. 9, No. 9; pp. 1-11.

Ma et al., Pol III Promoters to Express Small RNAs: Delineation of Transciption Initiation, Molecular Therapy—Nucleic Acids, 2014, vol. 3, E161; pp. 1-11.

Hammond et al., "Cellular selectivity of AAV serotypes for gene delivery in neurons and astrocytes by neonatal intracerebroventricular injection," PLOS One, Dec. 15, 2017, vol. 12, No. 12, e018830; pp. 1-22.

Grimm et al., [23] "Adeno-Associated Virus Vectors for Short Hairpin RNA Expression," Methods in Enzymology, 2005, vol. 392; pp. 381-405.

"Protocol: Cloning of oligos for sgRNA (CRISPR) or shRNA constructs," Genetic Perturbation Platform, Broad Institute, Aug. 2015; 8 pages.

Aschauer et al., Analysis of Transduction Efficiency, Tropism and Axonal Transport of AAV Serotypes 1, 2, 5, 6, 8 and 9 in the Mouse Brain, PLOS One, Sep. 2013, vol. 8, Issue 9, e76310; pp. 1-16.

"Viral Plasmids and Resources," https://www.addgene.org/viral-vectors, Sep. 13, 2019; 4 pages.

"PLKO.1—TRC Cloning Vector," https://www.addgene.org/tools/protocols/plko, Sep. 13, 2019, 11 pages.

International Search Report dated Feb. 20, 2020, corresponding to counterpart International Application No. PCT/US19/52272; 8 pages.

Fisher et al., "Transduction with Recombinant Adeno-Assocaited Virus for Gene Therapy is Limited by Leading-Strand Synthesis," Journal of Virology, Jan. 1996, vol. 70, No. 1; pp. 520-532.

Friden et al., "Blood-brain barrier penetration and in vitro activity of an NGF conjugate," Science, Jan. 15, 1993, vol. 259, Issue 5093; pp. 373-377.

Midoux et al., "Specific gene transfer mediated by lactosylated poly-L-lysine into hepatoma cells," Nucleic Acids Research, Feb. 25, 1993, vol. 21, Issue 4; pp. 871-878.

Altschul et al. "Basic Local Alignment Search Tool," J. Mol. Biol., 1990, vol. 215; pp. 403-410.

Zhang et al., "PowerBLAST: A New Network BLAST Application for Interactive or Automated sequence Analysis and Annotation," Genome Research, 1997, vol. 7; pp. 649-656.

Smith et al., "Comparison of Biosequences," Advances in Applied Mathematics, vol. 2, 1981; pp. 482-489.

Davis et al., "Direct Gene Tranfer into Skeletal Muscle in Vivo: Factors Affecting Efficiency of Transfer and Stability of Expression," Human Gene Therapy, 1993, vol. 4; pp. 151-159.

Capechi et al., "High Efficienc Transformation by Direct Microinjection of DNA into Cultured Mammalian Cells," Cell, Nov. 1980, vol. 22; pp. 479-488.

Chen et al., "High-Efficiency Transformation of Mammalian Cells by Plasmid DNA," Molecular and Cellular biology, Aug. 1987, vol. 7, No. 8; pp. 2745-2752.

Chen et al, "Short Technical Report, Expression of ssDNA in Mammalian Cells," BioTechniques, Jan. 2003, vol. 34; pp. 167-171.

Chu et al., "Electroporation for the efficient transfection of mammalian cells with DNA," Nucleic Acids Research, (1987), vol. 15, No. 3; pp. 1311-1326.

Feigner et al., Lipofection: A highly efficient, lipid-mediatedd DNA-transfection procedure, Proc. Natl. Acad. Sci. USA, Nov. 1987, vol. 84; pp. 7413-7417.

Yang et al., "In vivo and in vitro gene transfer to mammalian somatic cells by particle bombardment," Proc. Natl. Acad. Sci. USA, Dec. 1990, vol. 87; pp. 9568-9572.

Graham et al., "Characteristics of a Human Cell Line Transformed by DNA from Human Adenovirus Type 5," J. Gen. Virol., 1977, vol. 36; pp. 59-74.

Fallaux et al., New Helper cells and matched early region 1-deleted adenovirus vectors prevent generation of replication-competent adenoviruses, Hum Gene Ther. Sep. 1, 1998, vol. 13; pp. 1909-1917 (Abstract only).

Yeh et al., "Efficient Dual Transcomplementation of Adenovirus E1 and E4 Regions from a 293-Derived Cell Line Expressing a Minimal E4 Functional Unit," Journal of Virology, Jan. 1996, vol. 70, No. 1; paes 559-565.

Krougliak et al., "Development of Cell Lines Capable of Complementing E1, E4, and Protein IX Defective Adenovirus Type 5 Mutants," Human Gene Ther., 1995, vol. 6; pp. 1575-1586 (Abstract only).

Wang et al., "A packaging cell line for propagation of recombinant adenovirus vectors containing two lethal gene-region deletions," Gene Therapy, 1995, vol. 2; pp. 775-783 (Abstract only).

Lusky et al., "In Vitro and In Vivo Biology of Recombinant Adenovirus Vectors with E1, E1/E2A, or E1/E4 Deleted," J. Virol., 1998, vol. 72, No. 3; pp. 2022-2033.

Tresco et al., "Polymer encapsulated neurotransmitter secreting cells. Potential treatment for Parkinson's disease," ASAJO Journal, 1992; pp. 17-23.

Aebischer et al., "Gene therapy for amyotrophic lateral sclerosis (ALS) using a polymer encapsulated xenogenic cell line engineered to secrete hCNTF," Human Gene Ther. 1996, vol. 7; pp. 851-860 (Abstract only).

Davis et al., "Enzyme-Polyethylene Glycol Adducts: Modified Enzymes with Unique Properties," Enzyme Engineering, 1978, vol. 4; pp. 169-173 (pp. 169-170).

Burnham et al., "Polymers for delivering peptides and proteins," Am. J. Hosp. Pharm., 1994, vol. 51; pp. 210-218 (Abstract only).

Trapnell, "Adenoviral Vectors for Gene Transfer," Advanced Drug Delivery Reviews, vol. 12, 1993; pp. 185-199.

(56) References Cited

OTHER PUBLICATIONS

English Translation of Japanese Office Action from application No. 2021-515639, Mar. 5, 2024, 16 pages.
European Search Report dated Nov. 24, 2021, corresponding to counterpart European Application No. 19861996.7; 8 pages.
Germain et al. "Antisense oligonucleotides targeting UBE3A-ATS restore expression of UBE3A by relieving transcriptional interference," bnioRxiv, Jul. 10, 2021; pp. 1-33.

* cited by examiner

COMPOSITIONS AND METHODS TO RESTORE PATERNAL UBE3A GENE EXPRESSION IN HUMAN ANGELMAN SYNDROME

CROSS-REFERENCE TO RELATED APPLICATIONS

This application is a National Stage Application of International Application No. PCT/US19/52272, filed Sep. 20, 2019, which claims priority to U.S. Provisional Patent Application No. 62/734,435, filed on Sep. 21, 2018, the entire contents of which are fully incorporated herein by reference.

REFERENCE TO SEQUENCE LISTING SUBMITTED VIA EFS-WEB

This application includes an electronically submitted sequence listing in .txt format. The .txt file contains a sequence listing entitled "209670-9033-WO01 sequence listing-26874596.1.txt" and is 361,588 bytes in size. The sequence listing contained in this .txt file is part of the specification and is hereby incorporated by reference herein in its entirety.

TECHNICAL FIELD

The present disclosure relates to compositions and methods for activating expression from the paternally-inherited allele of UBE3A in human Angleman Syndrome neurons using short hairpin RNAs, ribozymes, and/or microRNAs.

BACKGROUND OF THE INVENTION

Angelman syndrome (AS) is a neurodevelopmental disorder affecting ~1/15,000 individuals. Individuals with AS have developmental delay, severe cognitive impairment, ataxic gait, frequent seizures, short attention span, absent speech, and characteristic happy demeanor. Neurons derived from induced pluripotent stem cells (iPSC) from AS patients exhibit a depolarized resting membrane potential, delayed action potential development, and reduced spontaneous synaptic activity. AS affects a relatively large patient population; a contact registry with >3,000 patients has been established and ~250 new diagnoses of AS are made each year. Individuals with AS require life-long care.

AS is caused by loss of function from the maternal copy of UBE3A, a gene encoding an E3 ubiquitin ligase. This loss of function mutation can be caused by any type of gene mutation in the maternal allele. UBE3A is expressed exclusively from the maternal allele in neurons. All individuals with AS have a normal paternal UBE3A allele that is epigenetically silenced by a long, non-coding RNA, called UBE3A antisense transcript (UBE3A-ATS). Reactivation of the paternal allele has been shown to restore UBE3A protein expression and alleviate behavioral deficits in an AS mouse model. The restoration of UBE3A expression in humans is expected to ameliorate the disease, especially if it is restored in infants.

There is no cure for Angelman syndrome, however, there are two approaches being pursued by pharmaceutical companies and academic labs to cure this disorder. The first is the use of antisense oligonucleotides (ASOs) to cut UBE3A ATS and activate paternal UBE3A. The second approach is AAV-mediated gene therapy to introduce the UBE3A gene back to the patient. The ASOs mentioned above do not cross the blood-brain barrier and require repeated injections into the spinal cord for life. The gene therapy to introduce the UBE3A gene back into neurons lacks the ability to regulate UBE3A mRNA and protein levels and requires the choice of a single protein isoform from three total, where the function of the individual isoforms remains uncertain. This may lead to overexpression of UBE3A, which may also contribute to another related disorder, Dup15q syndrome, and the absence of an important protein isoform.

BRIEF SUMMARY OF THE INVENTION

The present invention provides a novel treatment approach for AS through gene therapy by inhibiting the silencing of paternal UBE3A and enabling the expression of paternal UBE3A from its native regulatory elements. Increased expression of UBE3A in neurons and may ameliorate the effects of UBE3A-ATS on neurons listed above. All three protein isoforms may express using the endogenous regulatory elements that normally control their levels. Thus, overexpression is prevented due to the use of native regulatory elements. This approach may improve AS symptoms through a single treatment and thereby avoid the repeated spinal cord injections required for ASOs.

In one aspect, the invention provides a polynucleotide comprising a first nucleotide sequence encoding a short hairpin RNA (shRNA), ribozyme, or microRNA, wherein the shRNA, ribozyme, or microRNA is capable of inhibiting the silencing of paternal UBE3A.

In another aspect, the invention provides an expression vector comprising the polynucleotide having the first nucleotide sequence encoding the shRNA, ribozyme, or microRNA, wherein the shRNA, ribozyme, or microRNA is capable of inhibiting the silencing of paternal UBE3A; and a promoter.

In another aspect, the invention provides a viral particle comprising the polynucleotide having the first nucleotide sequence encoding the shRNA, ribozyme, or microRNA, wherein the shRNA, ribozyme, or microRNA is capable of inhibiting the silencing of paternal UBE3A.

In another aspect, the invention provides a pharmaceutical composition comprising the polynucleotide having the first nucleotide sequence encoding the shRNA, ribozyme, or microRNA, wherein the shRNA, ribozyme, or microRNA is capable of inhibiting the silencing of paternal UBE3A, or the viral particle comprising the polynucleotide, and a pharmaceutically acceptable carrier.

In another aspect, the invention provides a method of treating Angelman's syndrome comprising administering to a patient in need thereof, a therapeutically effective amount of the viral particle comprising the polynucleotide having the first nucleotide sequence encoding the shRNA, ribozyme, or microRNA, wherein the shRNA, ribozyme, or microRNA is capable of inhibiting the silencing of paternal UBE3A, or a pharmaceutical composition thereof.

In another aspect, the invention provides a method of activating or increasing expression of paternal UBE3A gene expression comprising administering to a patient in need thereof, a therapeutically effective amount of the viral particle comprising the polynucleotide having the first nucleotide sequence encoding the shRNA, ribozyme, or microRNA, wherein the shRNA, ribozyme, or microRNA is capable of inhibiting the silencing of paternal UBE3A, or a pharmaceutical composition thereof.

In another aspect, the invention provides a method of inhibiting the silencing of paternal UBE3A gene by the RNA antisense transcript encoded by SEQ ID NO: 1, comprising administering to a patient in need thereof, a therapeutically effective amount of the viral particle comprising the polynucleotide having the first nucleotide sequence encoding the short hairpin RNA (shRNA), ribozyme, or microRNA, wherein the shRNA, ribozyme, or microRNA is capable of inhibiting the silencing of paternal UBE3A, or a pharmaceutical composition thereof.

In another aspect, the invention provides a shRNA, ribozyme, or microRNA encoded by the polynucleotide described herein and capable of inhibiting the silencing of paternal UBE3A.

DETAILED DESCRIPTION OF THE INVENTION

UBE3A

Figure 1:
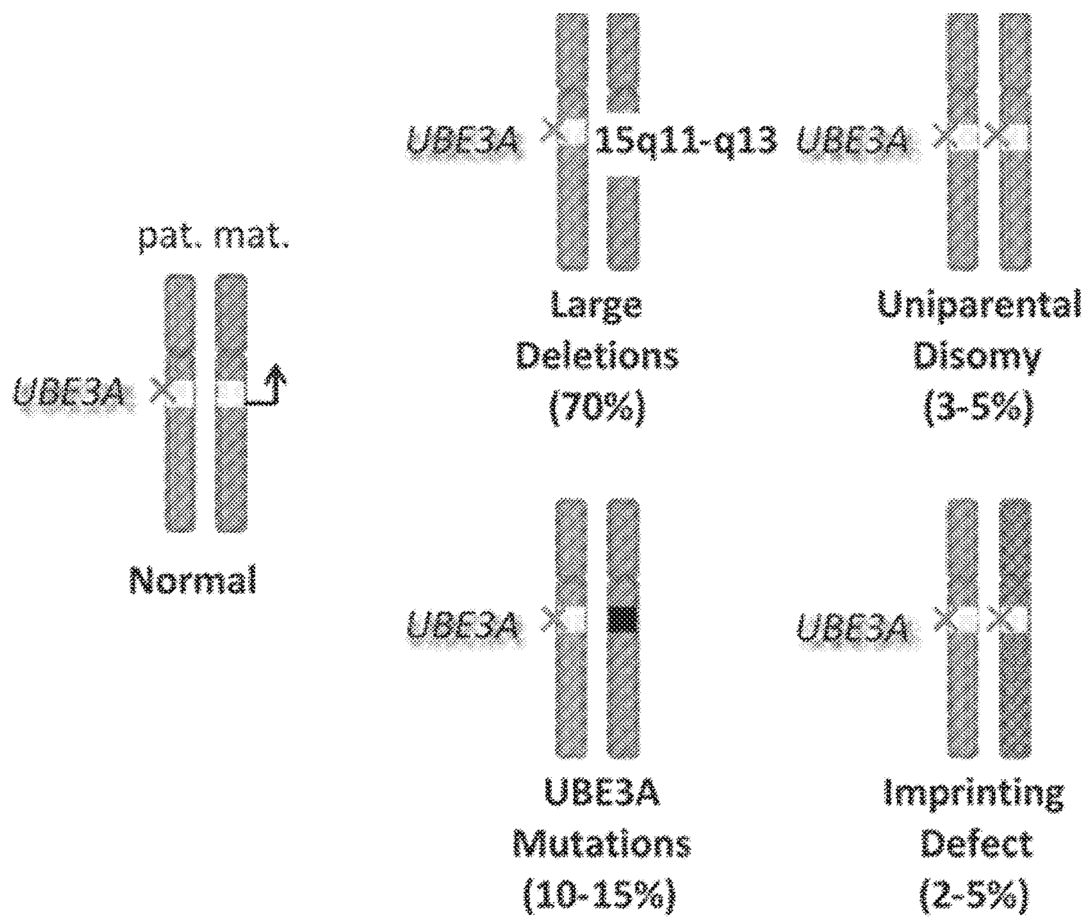
FIG. 1 shows chromosomal mutations in Angelman Syndrome.
Figure 2:
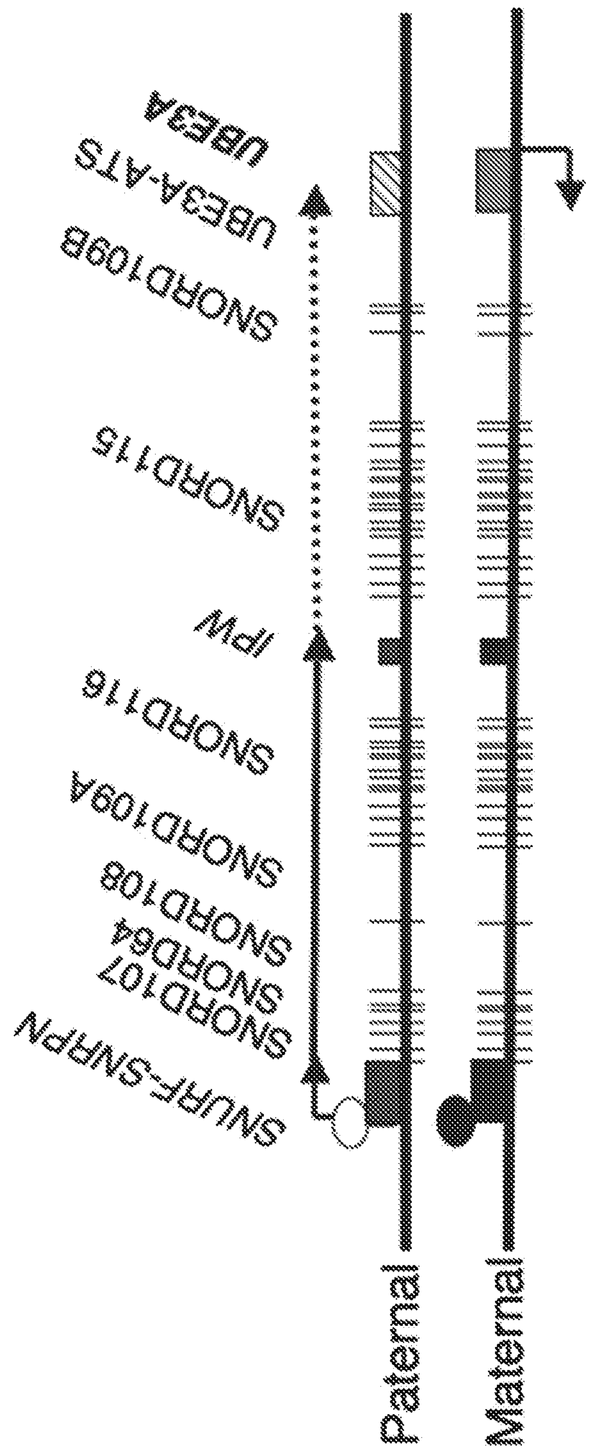
FIG. 2 shows a diagram of paternal UBE3A gene.

UBE3A is a gene which encodes the E3 ubiquitin ligase. The genomic coordinates for UBE3A are hg19 chr15:25,582,381-25,684,175 on the minus strand. There are three normal isoforms of UBE3A: Isoform 1 (accession number X98032); Isoform 2 (accession number X98031); and isoform 3 (Accession number X98033). In neurons, UBE3A is expressed exclusively from the maternal allele. The paternal UBE3A allele is epigenetically silenced by a long, non-coding RNA, called UBE3A antisense transcript (UBE3A-ATS) encoded by SEQ ID NO: 1. The genomic coordinates for UBE3A-ATS are hg19 chr15:25,223,730-25,664,609 on the plus strand. The following genomic coordinates are of particular interest: hg19 chr15:25,522,751-25,591,391 on the plus strand.

The compositions and methods of the invention are drawn to targeting the UBE3A antisense transcript (UBE3A-ATS) to unsilence the paternal UBE3A allele. Effective inhibition of UBE3A-ATS by short hairpin RNAs (shRNA), ribozymes, or microRNAs may result in a reduction in UBE3A-ATS expression levels and a concomitant increase in the expression levels of the paternal UBE3A allele.

In several aspects of the invention, the compositions and methods herein relate to the treatment or prevention of AS. In certain aspects of any of the foregoing embodiments drawn to a method of treating a patient or human in need, the patient or human in need has AS or is at risk for developing AS. As used herein, the term "patient in need" includes any mammal in need of these methods of treatment or prophylaxis, including particularly humans. The subject may be male or female. In certain aspects, the patient in need, having AS, treated according to the methods provided herein may show an improvement in anxiety, learning, balance, motor function, and/or seizures, or the method may return the neuronal resting membrane potential to about −70 mV, ameliorate the action potential development delay, increase spontaneous synaptic activity, and may ameliorate additional alterations in the neuronal phenotype relating to rheobase, action potential characteristics (e.g. shape), membrane current, synaptic potentials, ion channel conductance, etc.

shRNA, Ribozyme, MicroRNA, and Coding Sequences

According to an aspect of the invention, a polynucleotide comprises a first nucleotide sequence encoding a short hairpin RNA (shRNA), a ribozyme, or a microRNA that results in decreased expression of the UBE3A-ATS sequence SEQ ID NO: 1. For example, a portion of the shRNA, ribozyme, or microRNA may be complementary to the RNA sequence encoded by SEQ ID NO: 1 or a sequence contained therein.

The shRNA, ribozyme, and microRNA are RNA polynucleotides encoded by a first nucleotide sequence. The polynucleotide comprising the first nucleotide sequence may be a DNA polynucleotide suitable for cloning into an appropriate vector (e.g., a plasmid) for culturing and subsequent production of viral particles. In turn, viral particles may contain the DNA polynucleotide with the nucleotide coding sequence in a form suitable for infection. Thus, the first nucleotide sequence may be a DNA sequence cloned into a plasmid for viral particle production or encapsulated in a viral particle. As retroviruses carry nucleotide coding sequences in the form of RNA polynucleotides, retroviral particles (e.g., lentivirus) contain an RNA polynucleotide that comprises the first nucleotide sequence as a corresponding RNA sequence.

The first nucleotide sequence may encode the shRNA. For example, the first nucleotide sequence may be SEQ ID NO: 2. The first nucleotide sequence may also be a modified SEQ ID NO: 2 having the bold nucleotides in SEQ ID NO: 2 replaced by any of SEQ ID NOs: 9-508 and the italicized nucleotides in SEQ ID NO: 2 replaced by nucleotides complementary to those in SEQ ID NOs: 9-508.

The first nucleotide sequence may encode the ribozyme. For example, the first nucleotide sequence may be SEQ ID NO: 3. The first nucleotide sequence may be SEQ ID NO: 4.

The first nucleotide sequence may encode the microRNA. For example, the first nucleotide sequence may be SEQ ID NO: 8. The first nucleotide sequence may also be a modified SEQ ID NO: 8 having the bold nucleotides in SEQ ID NO: 8 replaced by any of SEQ ID NOs: 9-508 and the italicized nucleotides in SEQ ID NO: 8 replaced by nucleotides complementary to those in SEQ ID NOs: 9-508. The italicized nucleotides and the nucleotides complementary to those in SEQ ID NOs: 9-508 may be less than 100% complementary.

As used herein, "targets" means an operative RNA polynucleotide capable of undergoing hybridization to a nucleotide sequence through hydrogen bonding, such as to a nucleotide sequence transcribed from a nucleotide sequence within the larger genomic sequence of UBE3A-ATS. The hybridization of an operative RNA polynucleotide to a nucleotide sequence transcribed from a nucleotide sequence with the larger genomic sequence of UBE3A-ATS may result in the reduced expression of UBE3A-ATS levels in the presence of the operative RNA polynucleotide compared to the expression levels of UBE3A-ATS in the absence of the operative RNA polynucleotide. Preferably, the operative RNA polynucleotide comprises the nucleotide sequence of the shRNA, ribozyme, or microRNA that is complementary to the RNA sequence encoded within the larger genomic sequence of UBE3A-ATS. For example, the shRNA or microRNA contain nucleotide sequences complementary to the RNA sequences encoded by SEQ ID NO: 5 and SEQ ID NOs: 9-508 and the ribozymes contain nucleotide sequences complementary to the RNA sequences encoded by SEQ ID NO: 6 or SEQ ID NO: 7. The operative RNA polynucleotide thus refers to an operative portion of the shRNA ribozyme, or microRNA following assimilation of the shRNA, ribozyme, or microRNA into a target organism and processing into a functional state.

"Reduce expression" refers to a reduction or blockade of the expression or activity of UBE3A-ATS and does not necessarily indicate a total elimination of expression or activity. Mechanisms for reduced expression of the target include hybridization of an operative RNA polynucleotide with a target sequence or sequences transcribed from a sequence or sequences within the larger genomic UBE3A-ATS sequence (SEQ ID NO: 1), wherein the outcome or effect of the hybridization is either target degradation or target occupancy with concomitant stalling of the cellular machinery involving, for example, transcription or splicing.

Without wishing to be bound to a particular theory, the shRNA, ribozyme, and microRNA of the invention may inhibit the silencing of paternal UBE3A by: (1) cutting the RNA transcript encoded by SEQ ID NO: 1; (2) reducing steady-state levels (i.e., baseline levels at homeostasis) of the RNA transcript encoded by SEQ ID NO: 1; and (3) terminating transcription of SEQ ID NO: 1. For example, cutting and reduction of steady-state levels of the RNA transcript encoded by SEQ ID NO: 1 may occur via a mechanism involving a RNA-induced silencing complex (RISC). Both shRNA and microRNA may utilize RISC. Once the vector carrying the genomic material for the shRNA or microRNA is integrated into the host genome, the shRNA or microRNA genomic material is transcribed in the host into pri-microRNA. The pri-microRNA is processed by a ribonuclease, such as Drosha, into pre-shRNA or pre-microRNA, respectively, and exported from the nucleus. The pre-shRNA or pre-microRNA is processed by an endoribonuclease such as Dicer to form small interfering RNA (siRNA) or microRNA, respectively. For siRNA, the siRNA is loaded into the RISC where the sense strand is degraded and the antisense strand acts as a guide that directs RISC to the complementary sequence in the mRNA. For microRNA, a single strand from the microRNA is loaded into the RISC which acts as a guide that directs RISC to the complementary sequence in the mRNA. RISC cleaves the mRNA when the sequence has perfect complementary and represses translation of the mRNA when the sequence has imperfect complementary. In another example, cutting and reduction of steady-state levels of the RNA transcript encoded by SEQ ID NO: 1 may occur via a mechanism involving a ribozyme. Once the vector carrying the genomic material for the ribozyme is integrated into the host genome it is transcribed in the host into RNA. The RNA forms a secondary structure that has a catalytic domain and a region that is complementary to the target mRNA. When the ribozyme binds to the target mRNA the catalytic domain cleaves the target mRNA. Transcription of SEQ ID NO: 1 may be terminated by the torpedo mechanism wherein 5'-3' and 3'-5'exonucleases (e.g. XRN2) attach to the cleaved, uncapped end of the target RNA that is being transcribed. The 5'-3' exonuclease catches the polymerase and disengages the polymerase from the DNA. Thus, the shRNA, ribozyme, and microRNA encoded by the first nucleic acid sequence may increase expression of paternal UBE3A by decreasing the steady-state levels of UBE3A ATS RNA.

As used herein, the term "nucleic acid" refers to molecules composed of monomeric nucleotides. Examples of nucleic acids include ribonucleic acids (RNA), deoxyribonucleic acids (DNA), single-stranded nucleic acids, double-stranded nucleic acids, small interfering ribonucleic acids (siRNA), short hairpin RNAs (shRNAs), and microRNAs (miRNA). "Nucleotide" means a nucleoside having a phosphate group covalently linked to the sugar portion of the nucleoside. "Oligonucleotide" or "polynucleotide" means a polymer of linked nucleotides each of which can be modified or unmodified, independent one from another.

As used herein, a "short hairpin RNA (shRNA) "includes a conventional stem-loop shRNA, which forms a precursor microRNA (pre-miRNA). "shRNA" also includes microRNA embedded shRNAs (miRNA-based shRNAs), wherein the guide strand and the passenger strand of the miRNA duplex are incorporated into an existing (or natural) miRNA or into a modified or synthetic (designed) miRNA. When transcribed, a conventional shRNA (i.e., not a miR-451 shRNA mimic) forms a primary miRNA (pri-miRNA) or a structure very similar to a natural pri-miRNA. The pri-miRNA is subsequently processed by Drosha and its cofactors into pre-shRNA. Therefore, the term "shRNA" includes pri-miRNA (shRNA-mir) molecules and pre-shRNA molecules.

A "stem-loop structure" refers to a nucleic acid having a secondary structure that includes a region of nucleotides which are known or predicted to form a double strand or duplex (stem portion) that is linked on one side by a region of predominantly single-stranded nucleotides (loop portion). It is known in the art that the loop portion is at least 4 nucleotides long, preferably 6 nucleotides long (e.g. the underlined sequence in SEQ ID NO: 2). The terms "hairpin" and "fold-back" structures are also used herein to refer to stem-loop structures. Such structures are well known in the art and the term is used consistently with its known meaning in the art. As is known in the art, the secondary structure does not require exact base-pairing. Thus, the stem can include one or more base mismatches or bulges. Alternatively, the base-pairing can be exact, i.e. not include any mismatches.

In some embodiments, shRNAs useful in this invention include, without limitation, modified shRNAs, including shRNAs with enhanced stability in vivo. Modified shRNAs include molecules containing nucleotide analogues, including those molecules having additions, deletions, and/or substitutions in the nucleobase, sugar, or backbone; and molecules that are cross-linked or otherwise chemically modified. The modified nucleotide(s) may be within portions of the shRNA molecule, or throughout it. For instance, the shRNA molecule may be modified, or contain modified nucleic acids in regions at its 5' end, its 3' end, or both, and/or within the guide strand, passenger strand, or both, and/or within nucleotides that overhang the 5' end, the 3' end, or both. (See Crooke, U.S. Pat. Nos. 6,107,094 and 5,898,031; Elmen et al., U.S. Publication Nos. 2008/0249039 and 2007/0191294; Manoharan et al., U.S. Publication No. 2008/0213891; MacLachlan et al., U.S. Publication No. 2007/0135372; and Rana, U.S. Publication No. 2005/0020521; all of which are hereby incorporated by reference.)

In the present invention, shRNAs comprise a nucleotide sequence complementary to a RNA nucleotide sequence transcribed from within the full genomic UBE3A ATS sequence (SEQ ID NO: 1) and inhibit the silencing of paternal UBE3A by UBE3A-ATS. In further embodiments, shRNAs comprise a nucleotide sequence complementary to RNA sequences encoded by SEQ ID NOs: 9-508. In a more particular embodiment, a shRNA comprises a nucleotide sequence complementary to a RNA sequence encoded by SEQ ID NO: 5. In a particular embodiment the shRNA is encoded by the nucleotide sequence of SEQ ID NO: 2. In embodiments of the present invention, the nucleotide sequence comprised in the shRNA and complementary to the RNA nucleotide sequence transcribed from the UBE3A-ATS gene is 17-21 nucleotides in length. The complementary nucleotides may be contiguous or may be interspersed with non-complementary nucleotides. In some embodiments, the complementary nucleotide sequence is 21 nucleotides in length as indicated by the bold sequence in SEQ ID NO: 2. The shRNA may comprise a nucleotide sequence wherein 17, 18, 19, 20, or 21 nucleotides are complementary to the nucleotides in SEQ ID NOs: 5 or 9-508. The 17, 18, 19, 20, or 21 complementary nucleotides may be contiguous or may be interspersed with non-complementary nucleotides. The overall length of the shRNA, including the loop may be 40-50 nucleotides in length, preferably 44-48 nucleotides, more preferably 48 nucleotides.

As used herein, the term "ribozyme" refers to an RNA molecule that acts like an enzyme or a molecule composed of a protein comprising the RNA molecule and is also called a RNA enzyme or catalytic RNA. It has been found that ribozymes catalyze chemical reactions with RNA molecules with a definite tertiary structure and have catalytic or autocatalytic properties. Some ribozymes cleave themselves or other RNA molecules to inhibit activity, and other ribozymes catalyze the aminotransferase activity of ribosomes. Such ribozymes may include hammerhead ribozymes, VS ribozymes, hairpin ribozymes, etc. In the present invention the ribozymes comprise a nucleotide sequence complementary to a RNA nucleotide sequence transcribed from within the full genomic UBE3A ATS sequence (SEQ ID NO: 1) and inhibit the silencing of paternal UBE3A by UBE3A-ATS. In further embodiments, ribozymes comprise a nucleotide sequence complementary to RNA sequences encoded by SEQ ID NO: 6 and/or SEQ ID NO: 7. In further embodiments the ribozyme is encoded by the nucleotide sequence of SEQ ID NO: 3 or 4. In SEQ ID NOs: 3 and 4, the bold sequences are complementary to SEQ ID NOs: 6 or 7 and the underlined sequences signify the catalytic region of the ribozyme.

As used herein the terms "microRNA", "miRNA" and "miR" are used synonymously to refer to an about 17-21 nucleotide (nt) long, non-coding RNAs derived from endogenous genes. MicroRNAs are processed from longer (ca 75 nt) hairpin-like precursors termed pre-miRNAs. MicroRNAs assemble in ribonucleoprotein complexes termed miRNPs and recognize their targets by antisense complementarity. If the microRNAs match 100% their target, i.e. the complementarity is complete, the target mRNA is cleaved, and the miRNA acts like a siRNA. If the match is incomplete, i.e. the complementarity is partial, then the translation of the target mRNA is blocked. In embodiments of the present invention, the nucleotide sequence comprised in the microRNA and complementary to the RNA nucleotide sequence transcribed from the UBE3A-ATS gene is 17-21 nucleotides in length. The complementary nucleotides may be contiguous or may be interspersed with non-complementary nucleotides. In some embodiments, the complementary nucleotide sequence is 21 nucleotides in length as indicated by the bold sequence in SEQ ID NO: 8. The microRNA may comprise a nucleotide sequence wherein 17, 18, 19, 20, or 21 nucleotides are complementary to the nucleotides in SEQ ID NOs: 5 or 9-508. The 17, 18, 19, 20, or 21 complementary nucleotides may be contiguous or may be interspersed with non-complementary nucleotides. The overall length of the precursor microRNA, including the loop may be 50-1000 nucleotides in length, preferably 59-67 nucleotides, more preferably 67 nucleotides.

In the present invention the microRNAs are designed to target one or more nucleotide sequences transcribed from one or more nucleotide sequences within the full genomic UBE3A-ATS sequence (SEQ ID NO: 1) and inhibit the silencing of paternal UBE3A by UBE3A-ATS. In further embodiments, microRNAs are designed to target one or more sequences transcribed from one or more sequences selected from SEQ ID NOs: 9-508. In a more particular embodiment microRNAs target a sequence transcribed from SEQ ID NO: 5. In further embodiments the microRNA is encoded by the nucleotide sequence of SEQ ID NO: 8 where the bold sequence is complementary to SEQ ID NOs: 5 or 9-508.

Methods of determining whether a sequence is specifically hybridizable to a target nucleic acid are well known in the art. In certain embodiments, the shRNA, ribozyme, or microRNA polynucleotides provided herein comprise a nucleic acid sequence specifically hybridizable with a RNA sequence transcribed from the UBE3A-ATSSEQ ID NO: 1.

The shRNA or microRNA may comprise an RNA polynucleotide containing a region of 17-21 linked nucleotides complementary to the RNA target sequence, wherein the RNA polynucleotide region is at least 85% complementary over its entire length to an equal length region of a UBE3A-ATS RNA nucleic acid sequence. In certain aspects, the RNA polynucleotide region is at least 90%, at least 95%, or 100% complementary over its entire length to an equal length region of a UBE3A-ATS RNA nucleic acid sequence.

The shRNA or microRNA may comprise a nucleotide sequence at least 85% complementary to, and of equal length as, a RNA sequence encoded by SEQ ID NO: 5 or any of SEQ ID NOs: 9-508. The shRNA or microRNA may comprise a nucleotide sequence at least 90% complementary to, and of equal length as, a RNA sequence encoded by SEQ ID NO: 5 or any of SEQ ID NOs: 9-508. The shRNA or microRNA may comprise a nucleotide at least 95% complementary to, and of equal length as, a RNA sequence encoded by SEQ ID NO: 5 or any of SEQ ID NOs: 9-508. The shRNA or microRNA may comprise a nucleotide sequence 100% complementary to, and of equal length as, a RNA sequence encoded by SEQ ID NO: 5 or any of SEQ ID NOs: 9-508.

The ribozyme may comprise an RNA polynucleotide containing two regions of linked nucleotides complementary to the RNA target sequence, separated by a catalytic region, wherein the overall non-catalytic region of the RNA polynucleotide is at least 85% complementary over its entire length to an equal length region of a UBE3A-ATS RNA nucleotide sequence. In certain aspects, the overall non-catalytic region of the RNA polynucleotide is at least 90%, at least 95%, or 100% complementary over its entire length to an equal length region of a UBE3A-ATS RNA nucleotide sequence. In embodiments of the present invention, the nucleotide sequence comprised in the ribozyme and complementary to the RNA nucleotide sequence transcribed from the UBE3A-ATS gene is 17-21 nucleotides in length. The complementary nucleotides may be may be interspersed with non-complementary nucleotides. In some embodiments, the complementary nucleotide sequence is 21 nucleotides in length as indicated by the bold sequence in SEQ ID NOs: 3-4. The ribozyme may comprise a nucleotide sequence wherein 17, 18, 19, 20, or 21 nucleotides are complementary to the nucleotides in SEQ ID NOs: 6-7. The 17, 18, 19, 20, or 21 complementary nucleotides may be interspersed with non-complementary nucleotides. The overall length of the shRNA, including the catalytic loop may be 50-150 nucleotides in length, preferably 57-65 nucleotides, more preferably 59 nucleotides.

The ribozyme may comprise a nucleotide sequence at least 85% complementary to, and of equal length as, a RNA sequence encoded by SEQ ID NO: 6 or 7. The ribozyme may comprise a nucleotide sequence at least 90% complementary to, and of equal length as, a RNA sequence encoded by SEQ ID NO: 6 or 7. The ribozyme may comprise a nucleotide sequence at least 95% complementary to, and of equal length as, a RNA sequence encoded by SEQ ID NO: 6 or 7. The ribozyme may comprise a nucleotide sequence 100% complementary to, and of equal length as, a RNA sequence encoded by SEQ ID NO: 6 or 7.

In certain aspects, the shRNA, ribozyme, or microRNA, is a single-stranded RNA polynucleotide. In several aspects, the RNA polynucleotide is a modified RNA polynucleotide. A percent complementarity is used herein in the conventional sense to refer to base pairing between adenine and thymine, adenine and uracil (RNA), and guanine and cytosine.

Non-complementary nucleobases between a shRNA, ribozyme, or microRNA and an UBE3A-ATS nucleotide sequence may be tolerated provided that the shRNA, ribozyme, or microRNA remains able to specifically hybridize to a UBE3A-ATS nucleotide sequence. Moreover, an shRNA, ribozyme, or microRNA may hybridize over one or more segments of a UBE3A-ATS nucleotide sequence such that intervening or adjacent segments are not involved in the hybridization event (e.g., a loop structure, mismatch or hairpin structure).

In certain embodiments, the shRNA, ribozyme, or microRNA provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a UBE3A-ATS RNA nucleotide sequence, a UBE3A-ATS region, UBE3A-ATS segment, or specified portion thereof. Percent complementarity of a shRNA, ribozyme, or microRNA with an UBE3A-ATS nucleotide sequence can be determined using routine methods.

For example, a shRNA, ribozyme or microRNA in which 18 of 20 nucleobases of the shRNA, ribozyme or microRNA are complementary to a UBE3A-ATS region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a shRNA, ribozyme, or microRNA which is 18 nucleobases in length having four non-complementary nucleobases which are flanked by two regions of complete complementarity with the target nucleotide sequence would have 77.8% overall complementarity with the target nucleotide sequence and would thus fall within the scope of the present invention. Percent complementarity of a shRNA, ribozyme, or microRNA with a region of a UBE3A ATS nucleotide sequence can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the shRNA, ribozyme, or microRNA provided herein, or specified portions thereof, are fully complementary (i.e. 100% complementary) to a UBE3A ATS nucleotide sequence, or specified portion of the transcription product of SEQ ID NO: 1 thereof. For example, a shRNA, ribozyme, or microRNA may be fully complementary to a UBE3A-ATS nucleotide sequence, or a region, or a segment or sequence thereof. As used herein, "fully complementary" means each nucleobase of a shRNA, ribozyme, or microRNA is capable of precise base pairing with the corresponding RNA nucleobases transcribed from a UBE3A ATS nucleotide sequence.

An effective concentration or dose of the shRNA, ribozyme, or microRNA may inhibit the silencing of paternal UBE3A by UBE3A ATS by at least 20%, at least 30%, at least 40%, at least 50%, at least 60%, at least 70%, at least 80%, at least 90%, or at least 100%.

An effective concentration or dose of the shRNA, ribozyme, or microRNA may terminate transcription of UBE3A ATS by at least 20%, at least 30%, at least 40%, at least 50%, at least 60%, at least 70%, at least 80%, at least 90%, or at least 100%.

An effective concentration or dose of the shRNA, ribozyme, or microRNA may reduce steady-state levels of UBE3A ATS by at least 20%, at least 30%, at least 40%, at least 50%, at least 60%, at least 70%, at least 80%, at least 90%, or at least 100%.

An effective concentration or dose of the shRNA, ribozyme, or microRNA may cut UBE3A ATS and reduce it by at least 20%, at least 30%, at least 40%, at least 50%, at least 60%, at least 70%, at least 80%, at least 90%, or at least 100%.

An effective concentration or dose of the shRNA, ribozyme, or microRNA may reduce expression of UBE3A-ATS by at least 20%, at least 30%, at least 40%, at least 50%, at least 60%, at least 70%, at least 80%, at least 90%, or at least 100% and induce expression of paternal UBE3A by at least 20%, at least 30%, at least 40%, at least 50%, at least 60%, at least 70%, at least 80%, at least 90%, or at least 100%.

As used herein, the terms "UBE3A-ATS" and "Ube3A-ATS" can be used interchangeably without capitalization of their spelling referring to any particular species or ortholog. "UBE3A" and "Ube3A" can be used interchangeably without capitalization of their spelling referring to any particular species or ortholog. Additionally, "UBE3A", "UBE3A", "Ube3A", and "Ube3A" can be used interchangeably without italicization referring to nucleic acid or protein unless specifically indicated to the contrary.

Viral Vector

A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, plasmids that contain a viral genome, viruses, or artificial chromosomes. The term "vector" includes cloning and expression vectors, as well as viral vectors and integrating vectors.

As will be evident to one of skill in the art, the term "viral vector" is widely used to refer to a nucleic acid molecule (e.g., a transfer plasmid) that includes viral nucleic acid elements that typically facilitate transfer of the nucleic acid molecule to a cell or to a viral particle that mediates nucleic acid sequence transfer and/or integration of the nucleic acid sequence into the genome of a cell.

Viral vectors contain structural and/or functional genetic elements that are primarily derived from a virus. The viral vector is desirably non-toxic, non-immunogenic, easy to produce, and efficient in protecting and delivering DNA or RNA into the target cells. According to the compositions and methods of the inventions a viral vector may contain the DNA that encodes the shRNA, ribozyme, and/or microRNA of the invention. In particular embodiments, the viral vector is a lentiviral vector or an adeno-associated viral (AAV) vector.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). Lentivirus will transduce dividing cells and postmitotic cells.

The term "lentiviral vector" refers to a viral vector (e.g., viral plasmid) containing structural and functional genetic elements, or portions thereof, including long terminal repeats (LTRs) that are primarily derived from a lentivirus. A lentiviral vector is a hybrid vector (e.g., in the form of a transfer plasmid) comprising retroviral e.g., lentiviral, sequences for reverse transcription, replication, integration and/or packaging of nucleic acid sequences (e.g., coding sequences). The term "retroviral vector" refers to a viral vector (e.g., transfer plasmid) containing structural and functional genetic elements, or portions thereof, that are primarily derived from a retrovirus.

Adenoviral vectors are designed to be administered directly to a living subject. Unlike retroviral vectors, most of the adenoviral vector genomes do not integrate into the chromosome of the host cell. Instead, genes introduced into cells using adenoviral vectors are maintained in the nucleus as an extrachromosomal element (episome) that persists for an extended period of time. Adenoviral vectors will transduce dividing and non-dividing cells in many different tissues in vivo including airway epithelial cells, endothelial cells, hepatocytes, and various tumors (Trapnell, 1993; Chuah et al., 2003).

The term adeno-associated virus (AAV) refers to a small ssDNA virus which infects humans and some other primate species, not known to cause disease, and causes only a very mild immune response. AAV can infect both dividing and non-dividing cells and may incorporate its genome into that of the host cell. These features make AAV a very attractive candidate for creating viral vectors for gene therapy, although the cloning capacity of the vector is relatively limited. In a preferred embodiment of the invention, the vector used is derived from adeno-associated virus (i.e. AAV vector). More than 30 naturally occurring serotypes of AAV are available. Many natural variants in the AAV capsid exist, allowing identification and use of an AAV with properties specifically suited for specific types of target cells. AAV viruses may be engineered by conventional molecular biology techniques, making it possible to optimize these particles for cell specific delivery of shRNA, ribozyme, or microRNA DNA sequences, for minimizing immunogenicity, for tuning stability and particle lifetime, for efficient degradation, for accurate delivery to the nucleus, etc.

An "expression vector" is a vector that includes a regulatory region. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.). An expression vector may be a viral expression vector derived from a particular virus.

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). An expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or FIag™ tag (Kodak, New Haven, Conn.) sequences typically are expressed as a fusion with the encoded polypeptide. Such tags can be inserted anywhere within the polypeptide, including at either the carboxyl or amino terminus.

Additional expression vectors also can include, for example, segments of chromosomal, non-chromosomal and synthetic DNA sequences. Suitable vectors include derivatives of pLK0.1 puro, SV40 and, plasmids such as RP4; phage DNAs, e.g., the numerous derivatives of phage 1, e.g., NM989, and other phage DNA, e.g., M13 and filamentous single stranded phage DNA, vectors useful in eukaryotic cells, such as vectors useful in insect or mammalian cells, vectors derived from combinations of plasmids and phage DNAs, such as plasmids that have been modified to employ phage DNA or other expression control sequences.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; *BioTechniques,* 34: 167-171 (2003). A large variety of such vectors are known in the art and are generally available.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation).

In some embodiments, the viral vector used in the invention will be used at a concentration of at least $10^5$ viral genomes per cell.

The selection of appropriate promoters can readily be accomplished. An example of a suitable promoter is an RNA polymerase II or III promoter, such as the U6 promoter. Other suitable promoters which may be used for gene expression include, but are not limited to, the 763-base-pair cytomegalovirus (CMV) promoter, the Rous sarcoma virus (RSV) (Davis, et al., *Hum Gene Ther* 4:151 (1993)), the SV40 early promoter region, the herpes thymidine kinase promoter, the regulatory sequences of the metallothionein (MMT) gene, PGK (phosphoglycerol kinase) promoter, alkaline phosphatase promoter; and the animal transcriptional control regions, which exhibit tissue specificity and have been utilized in transgenic animals: myelin basic protein gene control region which is active in oligodendrocyte cells in the brain, and gonadotropic releasing hormone gene control region which is active in the hypothalamus. Certain proteins can be expressed using their native promoter. Other elements that can enhance expression can also be included such as an enhancer or a system that results in high levels of expression such as a tat gene and tar element. This cassette can then be inserted into a vector, e.g., a plasmid vector such as, pLK0.1, pUC19, pUC118, pBR322, or other known plasmid vectors. See, Sambrook, et al., Molecular Cloning: A Laboratory Manual, Cold Spring Harbor Laboratory press, (1989). The plasmid vector may also include a selectable marker such as the β-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618.

Coding sequences for shRNA, ribozymes, and microRNA can be cloned into viral vectors using any suitable genetic engineering technique well known in the art, including, without limitation, the standard techniques of PCR, polynucleotide synthesis, restriction endonuclease digestion, ligation, transformation, plasmid purification, and DNA sequencing, as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)). In a preferred embodiment, the shRNA, ribozyme, and microRNA DNA sequences contain flanking sequences on the 5' and 3' ends that are complementary with sequences on the plasmid and/or vector that is cut by a restriction endonuclease. As is well known in the art, the flanking sequences depend on the restriction endonucleases used during the restriction digest of the plasmid and/or vector. Thus, one of skill in the art can select the flanking sequences on the 5' and 3' ends of the shRNA, ribozyme, and microRNA DNA sequences accordingly. In another preferred embodiment, the target sites can be cloned into vectors by nucleic acid fusion and exchange technologies currently known in the art, including, Gateway, PCR in fusion, Cre-lox P, and Creator.

In some embodiments, an expression vector comprises a promoter and a polynucleotide comprising a first nucleotide sequence encoding a short hairpin RNA (shRNA), ribozyme, or microRNA of the invention. Preferably, the promoter and the polynucleotide comprising the first nucleotide sequence are operably linked. Preferably, the promoter is a U6 promoter. The first nucleotide sequence included in the expression vector may be SEQ ID NO: 2. The first nucleotide sequence included in the expression vector may be SEQ ID NO: 3. The first nucleotide sequence included in the expression vector may be SEQ ID NO: 4. The first nucleotide sequence included in the expression vector may be SEQ ID NO: 8. The polynucleotide comprising the first nucleotide sequence in the expression vector is preferably a DNA polynucleotide. The first nucleotide sequence of the expression vector is preferably a DNA nucleotide sequence. The shRNA, ribozyme, or microRNA encoded by the first nucleotide sequence of the expression vector may be as described in any of the variations disclosed herein.

As discussed below, recombinant viral vectors are transfected into packaging cells or cell lines, along with elements required for the packaging of recombinant viral particles. Recombinant viral particles collected from transfected cell supernatant are used to infect target cells or organisms for the expression of shRNAs, ribozymes, or microRNA. The transduced cells or organisms are used for transient expression or selected for stable expression.

Viral Particle

Viral particles are used to deliver coding nucleotide sequences for the shRNAs, ribozymes, and microRNAs which target UBE3A-ATS RNA. Viral particles will typically include various viral components and sometimes also host cell components in addition to nucleic acid(s). Nucleic acid sequences may be packaged into a viral particle that is capable of delivering the shRNA, ribozyme, and/or microRNA nucleic acid sequences into the target cells in the patient in need or human.

The viral particles may be produced by (a) introducing a viral expression vector into a suitable cell line; (b) culturing the cell line under suitable conditions so as to allow the production of the viral particle; (c) recovering the produced viral particle; and (d) optionally purifying the recovered infectious viral particle.

An expression vector containing the nucleotide sequence encoding the shRNA, ribozyme, or microRNA of the invention may be introduced into an appropriate cell line for propagation or expression using well-known techniques readily available to the person of ordinary skill in the art. These include, but are not limited to, microinjection of minute amounts of DNA into the nucleus of a cell (Capechi et al., 1980, Cell 22, 479-488), $CaPO_4$-mediated transfection (Chen and Okayama, 1987, Mol. Cell Biol. 7, 2745-2752), DEAE-dextran-mediated transfection, electroporation (Chu et al., 1987, Nucleic Acid Res. 15, 1311-1326), lipofection/liposome fusion (Feigner et al., 1987, Proc, Natl. Acad. Sci. USA 84, 7413-7417), particle bombardment (Yang et al., 1990, Proc. Natl. Acad. Sci. USA 87, 9568-9572), gene guns, transduction, infection (e.g. with an infective viral particle), and other techniques such as those found in Sambrook, et al. (Molecular Cloning: A Laboratory Manual, Cold Spring Harbor Laboratory, Cold Spring Harbor Laboratory Press, Cold Spring Harbor, N.Y., 2001).

When the vector of the invention is defective, the infectious particles are usually produced in a complementation cell line or via the use of a helper virus, which supplies in trans the non-functional viral genes. For example, suitable cell lines for complementing adenoviral vectors include the 293 cells (Graham et al., 1997, J. Gen. Virol. 36, 59-72) as well as the PER-C6 cells (Fallaux et al., 1998, Human Gene Ther. 9, 1909-1917) commonly used to complement the E1 function. Other cell lines have been engineered to complement doubly defective adenoviral vectors (Yeh et al., 1996, J. Virol. 70, 559-565; Krougliak and Graham, 1995, Human Gene Ther, 6, 1575-1586; Wang et al., 1995, Gene Ther, 2, 775-783; Lusky et al., 1998, J. Virol. 72, 2022-2033; WO94/28152 and WO97/04119). The infectious viral particles may be recovered from the culture supernatant but also from the cells after lysis and optionally are further purified according to standard techniques (chromatography, ultracentrifugation in a cesium chloride gradient as described for example in WO 96/27677, WO 98/00524, WO 98/22588, WO 98/26048, WO 00/40702, EP 1016700 and WO 00/50573), The invention also relates to host cells which comprise the nucleic acid molecules, vectors, or infectious viral particles of the invention described herein. For the purpose of the invention, the term "host cell" should be understood broadly without any limitation concerning particular organization in tissue, organ, or isolated cells. Such cells may be of a unique type of cells or a group of different types of cells and encompass cultured cell lines, primary cells, and proliferative cells.

Host cells therefore include prokaryotic cells, lower eukaryotic cells such as yeast, and other eukaryotic cells such as insect cells, plant and higher eukaryotic cells, such as vertebrate cells and, with a special preference, mammalian (e.g. human or non-human) cells. Suitable mammalian cells include but are not limited to hematopoietic cells (totipotent, stem cells, leukocytes, lymphocytes, monocytes, macrophages, APC, dendritic cells, non-human cells and the like), pulmonary cells, tracheal cells, hepatic cells, epithelial cells, endothelial cells, muscle cells (e.g. skeletal muscle, cardiac muscle or smooth muscle) or fibroblasts, Preferred host cells include *Escherichia coli, Bacillus, Listeria, Saccharomyces*, BHK (baby hamster kidney) cells, MOCK cells (Madin-Darby canine kidney cell line), CRFK cells (Crandall feline kidney cell line), CV-1 cells (African monkey kidney cell line), COS (e.g., COS-7) cells, chinese hamster ovary (CHO) cells, mouse NIH/3T3 cells, HeLa cells and Vero cells. Host cells also encompass complementing cells capable of complementing at least one defective function of a replication-defective vector of the invention (e.g. adenoviral vector) such as those cited above.

The host cell of the invention may be further encapsulated. Cell encapsulation technology has been previously described (Tresco et al., 1992, ASAJO J. 38, 17-23; Aebischer et al., 1996, Human Gene Ther, 7, 851-860). According to said specific embodiment, transfected or infected eukaryotic host cells are encapsulated with compounds which form a microporous membrane and said encapsulated cells may further be implanted in vivo. Capsules containing the cells of interest may be prepared employing hollow microporous membranes (e.g. Akzo Nobel Faser A G, Wuppertal, Germany; Deglon et al. 1996, Human Gene Ther. 7, 2135-2146) having a molecular weight cutoff appropriate to permit the free passage of proteins and nutrients between the capsule interior and exterior, while preventing the contact of transplanted cells with host cells Viral particles suitable for use in the invention include AAV particles and lentiviral particles. AAV particles carry the coding sequences for shRNA, ribozymes, and microRNAs in the form of genomic DNA. Lentiviral particles, on the other hand, belong to the class of retroviruses and carry the coding sequences for shRNA, ribozymes, and microRNAs in the form of RNA.

Recombinantly engineered viral particles such as AAV particles, artificial AAV particles, self-complementary AAV particles, and lentiviral particles that contain the DNA (or RNA in the case of lentiviral particles) encoding the shRNAs, ribozymes, and/or microRNAs targeting UBE3A ATS RNA may be delivered to target cells to inhibit the silencing of UBE3A by UBE3A-ATS. The use of AAVs is a common mode of delivery of DNA as it is relatively non-toxic, provides efficient gene transfer, and can be easily optimized for specific purposes. In one embodiment of the invention, the selected AAV serotype has native neurotropisms. In further embodiments of the invention, the AAV serotype is AAV9 or AAV10.

A suitable recombinant AAV is generated by culturing a host cell which contains a nucleotide sequence encoding an AAV serotype capsid protein, or fragment thereof, as defined herein; a functional rep gene; a minigene composed of, at a minimum, AAV inverted terminal repeats (ITRs) and a coding nucleotide sequence; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

Unless otherwise specified, the AAV ITRs, and other selected AAV components described herein, may be readily selected from among any AAV serotype, including, without limitation, AAV1, AAV2, AAV3, AAV5, AAV6, AAV7, AAV8, AAV9, AAV10 or other known and unknown AAV serotypes. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

The minigene, rep sequences, cap sequences, and helper functions required for producing the rAAV of the invention may be delivered to the packaging host cell in the form of any genetic element which transfers the sequences carried thereon. The selected genetic element may be delivered by any suitable method. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, 1993 J. Viral., 70:520-532 and U.S. Pat. No. 5,478,745, among others. These publications are incorporated by reference herein.

Selection of these and other common vector and regulatory elements are conventional and many such sequences are available. See, e.g., Sambrook et al, and references cited therein at, for example, pages 3.18-3.26 and 16.17-16.27 and Ausubel et al., Current Protocols in Molecular Biology, John Wiley & Sons, New York, 1989). Of course, not all vectors and expression control sequences will function equally well to express all of the transgenes of this invention. However, one of skill in the art may make a selection among these, and other, expression control sequences without departing from the scope of this invention.

Pharmaceutical Compositions and Therapeutic Treatment

The viral particles comprising the desired coding sequences for the shRNA, ribozyme, and/or microRNA can be formulated for administration to a patient or human in need by any means suitable for administration. Such formulation involves the use of a pharmaceutically and/or physiologically acceptable vehicle or carrier, particularly one suitable for administration to the brain, e.g., by subcranial or spinal injection. Further, more than one shRNA, ribozyme, and/or microRNA, or any combination thereof, may be administered in a combination treatment. In a combination treatment, the different shRNA, ribozyme, and/or microRNA may be administered simultaneously, separately, sequentially, and in any order.

Suitably, the pharmaceutical composition of the invention comprises a carrier and/or diluent appropriate for its delivering by injection to a human or animal organism. Such carrier and/or diluent is non-toxic at the dosage and concentration employed. It is selected from those usually employed to formulate compositions for parental administration in either unit dosage or multi-dose form or for direct infusion by continuous or periodic infusion. It is preferably isotonic, hypotonic or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solutions, Hank's solution, and other aqueous physiologically balanced salt solutions (see for example the most current edition of Remington: The Science and Practice of Pharmacy, A. Gennaro, Lippincott, Williams & Wilkins). The pH of the composition of the invention is suitably adjusted and buffered in order to be appropriate for use in humans or animals, preferably at a physiological or slightly basic pH (between about pH 8 to about pH 9, with a special preference for pH 8.5). Suitable buffers include phosphate buffer (e.g. PBS), bicarbonate buffer and/or Tris buffer. A particularly preferred composition is formulated in 1M saccharose, 150 mM NaCl, 1 mM $MgCl_2$, 54 mg/1 Tween 80, 10 mM Tris pH 8.5. Another preferred composition is formulated in 10 mg/ml mannitol, 1 mg/ml HSA, 20 mM Tris, pH 7.2, and 150 mM NaCl. These compositions are stable at −70° C. for at least six months.

The composition of the invention may be in various forms, e.g. in solid (e.g. powder, lyophilized form), or liquid (e.g. aqueous). In the case of solid compositions, the preferred methods of preparation are vacuum drying and freeze-drying which yields a powder of the active agent plus any additional desired ingredient from a previously sterile-filtered solution thereof. Such solutions can, if desired, be stored in a sterile ampoule ready for reconstitution by the addition of sterile water for ready injection.

Nebulized or aerosolized formulations also form part of this invention. Methods of intranasal administration are well known in the art, including the administration of a droplet, spray, or dry powdered form of the composition into the nasopharynx of the individual to be treated from a pressured container or dispenser which contains a suitable propellant, e.g., a gas such as carbon dioxide, or a nebulizer (see for example WO 95/11664). Enteric formulations such as gastroresistant capsules and granules for oral administration, suppositories for rectal or vaginal administration also form part of this invention. For non-parental administration, the compositions can also include absorption enhancers which increase the pore size of the mucosal membrane. Such absorption enhancers include sodium deoxycholate, sodium glycocholate, dimethyl-beta-cyclodextrin, lauroyl-1-lysophosphatidylcholine and other substances having structural similarities to the phospholipid domains of the mucosal membrane.

The composition can also contain other pharmaceutically acceptable excipients for providing desirable pharmaceutical or pharmacodynamic properties, including for example modifying or maintaining the pH, osmolarity, viscosity, clarity, color, sterility, stability, rate of dissolution of the formulation, modifying or maintaining release or absorption into an the human or animal organism. For example, polymers such as polyethylene glycol may be used to obtain desirable properties of solubility, stability, half-life and other pharmaceutically advantageous properties (Davis et al., 1978, Enzyme Eng. 4, 169-173; Burnham et al., 1994, Am.

J. Hosp. Pharm. 51, 210-218). Representative examples of stabilizing components include polysorbate 80, L-arginine, polyvinylpyrrolidone, trehalose, and combinations thereof. Other stabilizing components especially suitable in plasmid-based compositions include hyaluronidase (which is thought to destabilize the extra cellular matrix of the host cells as described in WO 98/53853), chloroquine, protic compounds such as propylene glycol, polyethylene glycol, glycerol, ethanol, 1-methyl L-2-pyrrolidone or derivatives thereof, aprotic compounds such as dimethylsulfoxide (DMSO), diethylsulfoxide, di-n-propylsulfoxide, dimethylsulfone, sulfolane, dimethyl-formamide, dimethylacetamide, tetramethylurea, acetonitrile (see EP 890 362), nuclease inhibitors such as actin G (WO 99/56784) and cationic salts such as magnesium ($Mg^{2+}$) (EP 998 945) and lithium ($Li^{+}$) (WO 01/47563) and any of their derivatives. The amount of cationic salt in the composition of the invention preferably ranges from about 0.1 mM to about 100 mM, and still more preferably from about 0.1 mM to about 10 mM. Viscosity enhancing agents include sodium carboxymethylcellulose, sorbitol, and dextran. The composition can also contain substances known in the art to promote penetration or transport across the blood barrier or membrane of a particular organ (e.g. antibody to transferrin receptor; Friden et al., 1993, Science 259, 373-377). A gel complex of poly-lysine and lactose (Midoux et al., 1993, Nucleic Acid Res. 21, 871-878) or poloxamer 407 (Pastore, 1994, Circulation 90, 1-517) may be used to facilitate administration in arterial cells.

The viral particles and pharmaceutical compositions may be administered to patients in therapeutically effective amounts. As used herein, the term "therapeutically effective amount" refers to an amount sufficient to realize a desired biological effect. For example, a therapeutically effective amount for treating Angelman's syndrome is an amount sufficient to ameliorate one or more symptoms of Angelman's syndrome, as described herein (e.g. developmental delay, severe cognitive impairment, ataxic gait, frequent seizures, short attention span, absent speech, and characteristic happy demeanor). Further, AS iPSC-derived neurons exhibit a depolarized resting membrane potential, delayed action potential development, and reduced spontaneous synaptic activity. Thus, a therapeutically effective amount for treating AS may return the neuronal resting membrane potential to about −70 mV, ameliorate the action potential development delay, increase spontaneous synaptic activity, or ameliorate additional alterations in the neuronal phenotype relating to rheobase, action potential characteristics (e.g. shape), membrane current, synaptic potentials, ion channel conductance, etc.

The appropriate dosage may vary depending upon known factors such as the pharmacodynamic characteristics of the particular active agent, age, health, and weight of the host organism; the condition(s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. For general guidance, a composition based on viral particles may be formulated in the form of doses of at least $10^5$ viral genomes per cell. The titer may be determined by conventional techniques. A composition based on vector plasmids may be formulated in the form of doses of between 1 μg to 100 mg, advantageously between 10 μg and 10 mg and preferably between 100 μg and 1 mg. The administration may take place in a single dose or a dose repeated one or several times after a certain time interval.

The composition of the invention can be enclosed in ampoules, disposable syringes or multiple dose vials made of glass or plastic. In all cases, the composition must be sterile and should be fluid to the extent that easy syringability exists. It must be stable under the conditions of manufacture and storage and must be preserved against the contaminating action of microorganisms such as bacteria and fungi. Sterile injectable solutions can be prepared by incorporating the active agent (e.g., infectious particles) in the required amount with one or a combination of ingredients enumerated above, followed by filtered sterilization.

The viral particles and pharmaceutical compositions of the present invention are preferably administered by a parenteral route including intravenous, intraarterial, subcutaneous, intraperitoneal or intramuscular injection or infusion, intrathecal or intracranial, e.g., intracerebral or intraventricular, administration. In one embodiment, the viral particles or pharmaceutical compositions are administered intracerebral or intracerebroventricular. In another embodiment the viral particles or pharmaceutical compositions are administered intrathecal.

In certain embodiments of the methods of this invention, the viral particles and pharmaceutical composition described above are administered to the subject by subcranial injection into the brain or into the spinal cord of the patient or human in need. In a particular embodiment of the invention the use of subcranial administration into the brain results in the administration of the encoding nucleotide sequences of the invention directly to brain cells, including glia and neurons. As used herein, the term "neuron" refers to any cell in, or associated with the function of the brain. The term may refer to any one the types of neurons, including unipolar, bipolar, multipolar and pseudo-unipolar.

EXAMPLES

General Methods

Human Embryonic Stem Cell (hESC) Culture and Neural Differentiation hESCs were cultured on irradiated mouse embryonic fibroblasts and fed daily with hESC media (DMEM/F12 containing knockout serum replacement, L-glutamine+β-mercaptoethanol, non-essential amino acids, and basic fibroblast growth factor). hESCs were cultured in at 37° C. in a humid incubator at 5% $CO_2$. Cells were manually passaged every 5-7 days.

hESCs were differentiated into neurons using a modified version of the monolayer protocol. Neural induction was begun 2 days after passaging by culturing cells in N2B27 medium (Neurobasal medium, 1% N2, 2% B27, 2 mM L-glutamine, 0.5% penicillin/streptomycin, 1% insulin-transferrin-selenium). N2B27 medium was supplemented with fresh Noggin (500 ng/mL) for the first 10 days of differentiation. Neural rosettes were manually passaged onto poly-D-lysine and laminin coated plates using the Stem Pro EZ passage tool approximately 14 days after beginning neural induction. Neural progenitors were replated at a high density around 3 weeks of differentiation, switched to neural differentiation medium (NDM) around 4 weeks of differentiation, then plated sparsely for terminal differentiation at around 5 weeks. NDM consisted of neurobasal medium, 1% B27, 2 mM L-glutamine, 0.5% pen-strep, non-essential amino acids, 1 μM ascorbic acid, 200 μM cyclic AMP, 10 ng/mL brain-derived neurotrophic factor, and 10 ng/mL glial-derived neurotrophic factor. Neurons were maintained in culture until 10 to 17 weeks of differentiation. The protocols for hESC maintenance and neuronal differentiation have been described previously.

Generation of shRNA and Ribozyme Vectors shRNAs and ribozymes were generated by annealing two complementary polynucleotides with the desired sequences. Specifically, the polynucleotides to generate shRNAs were comprised of the specific 21-nucleotide sequence to be targeted and its reverse complement, separated by a loop sequence of CTCGAG, and with a 5' flank sequence of CCGG and a 3' flank sequence of TTTTTG added for cloning into the plasmid vector. The polynucleotides to generate ribozymes were comprised of the specific 41 nucleotide sequence along with the same 5' and 3' flanking sequences for plasmid cloning. The annealed polynucleotides were ligated into the pLK0.1 puro vector (Stewart et al RNA 2003 April; 9(4):493-501). The shRNA and ribozyme sequences are under the control of the U6 promoter. The resulting plasmid was subjected to Sanger sequencing to confirm correct insertion of shRNA sequences.

Lentiviral Production and Transduction of Neurons

Lentiviral particles were made by transfecting 293FT cells with $2^{nd}$ generation packaging systems using Lipofectamine 3000. Virus was concentrated using the Lenti-X Concentrator Kit (Clontech) and viral titer calculated using the qPCR Lentivirus Titration Kit (abm). 10-week old neurons were plated on laminin-coated plastic dishes at a density of 1.3 cells per $cm^2$ and transduced with 10 viral particles per cell. Neurons were harvested for RNA seven days after lentiviral transduction.

Quantitative RT-PCR cDNA was synthesized using the High-Capacity cDNA Reverse Transcription Kit (Thermo Fisher Scientific) according to manufacturer's instructions. Quantitative RT-PCR was performed using Taqman Gene Expression Assays for each intended target and Mastermix (Thermo Fisher Scientific) on the Step One Plus (Thermo Fisher Scientific). Reactions were performed in technical duplicates, with GAPDH Endogenous Control Taqman Assay used as the housekeeping gene for normalization. Gene expression was quantified using the $\Delta\Delta C_t$ method.

AAV Production and Transduction of Neurons 551 shRNA 2 as well as a scrambled shRNA control were cloned into the pAV-U6-GFP vector and packaged into viral particles by a commercial vendor (Vigene). Neurons were transduced with the 551 shRNA 2 AAV9 particles using at least $1\times10^5$ viral genomes per cell. After 48 hours, neurons were imaged to visualize transduced neurons.

Example 1

To test the cutting abilities of ribozymes in vitro, ribozyme and target RNA sequences were in vitro transcribed and tested under controlled conditions. Specifically, primers including a T7 sequence were used to amplify the genomic sequence of the intended target. The PCR product was cleaned and concentrated before being used in an in vitro transcription assay with T7 polymerase. The DNAs were used in an in vitro transcription reaction with T7 polymerase. RNA was column purified using MEGAclear kit (Ambion). Ribozyme RNAs were prepared by annealing two complementary ribozyme polynucleotides. They were then end-filled with T4 polymerase and cleaned up and concentrated. The ribozymes were diluted to an appropriate concentration (5 pmol/μL) in ddH20 as a working stock. The ribozymes and target RNAs were combined in an in vitro cutting assay for 30 minutes at 37 degrees C. and visualized with ethidium bromide on a 2% agarose gel.

Figure 3:
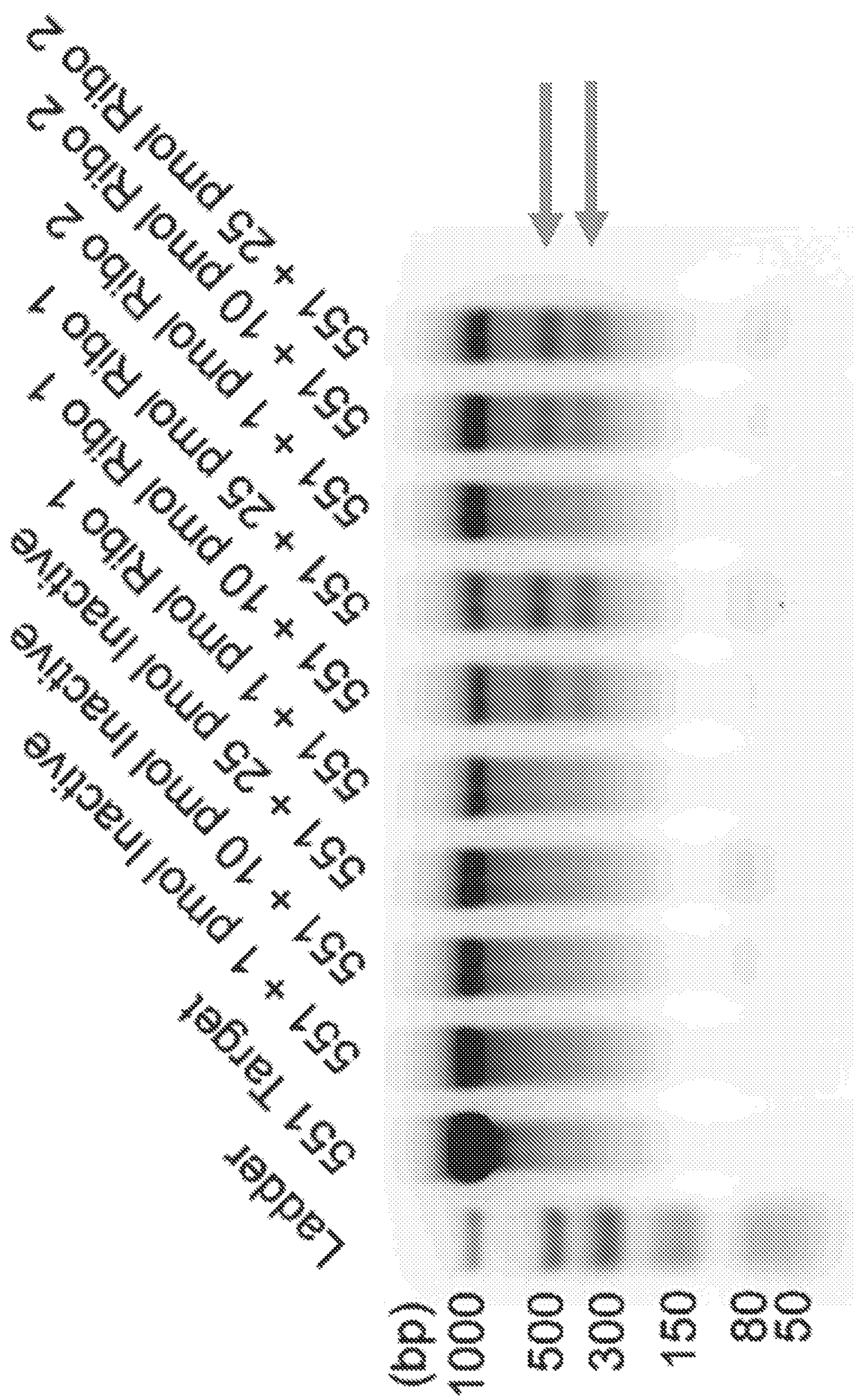
FIG. 3A shows Hammerhead ribozymes cut UBE3A-ATS in vitro. Hammerhead ribozyme and UBE3A ATS DNA were transcribed in vitro using PCR. The resulting Ribozyme and UBE3A ATS RNA were incubated in vitro (no cells and no vectors) and the cutting was visualized on agarose gel.
FIG. 3B shows Hammerhead ribozymes cut UBE3A-ATS in human AS iPSC-derived neurons.
Figure 3B:
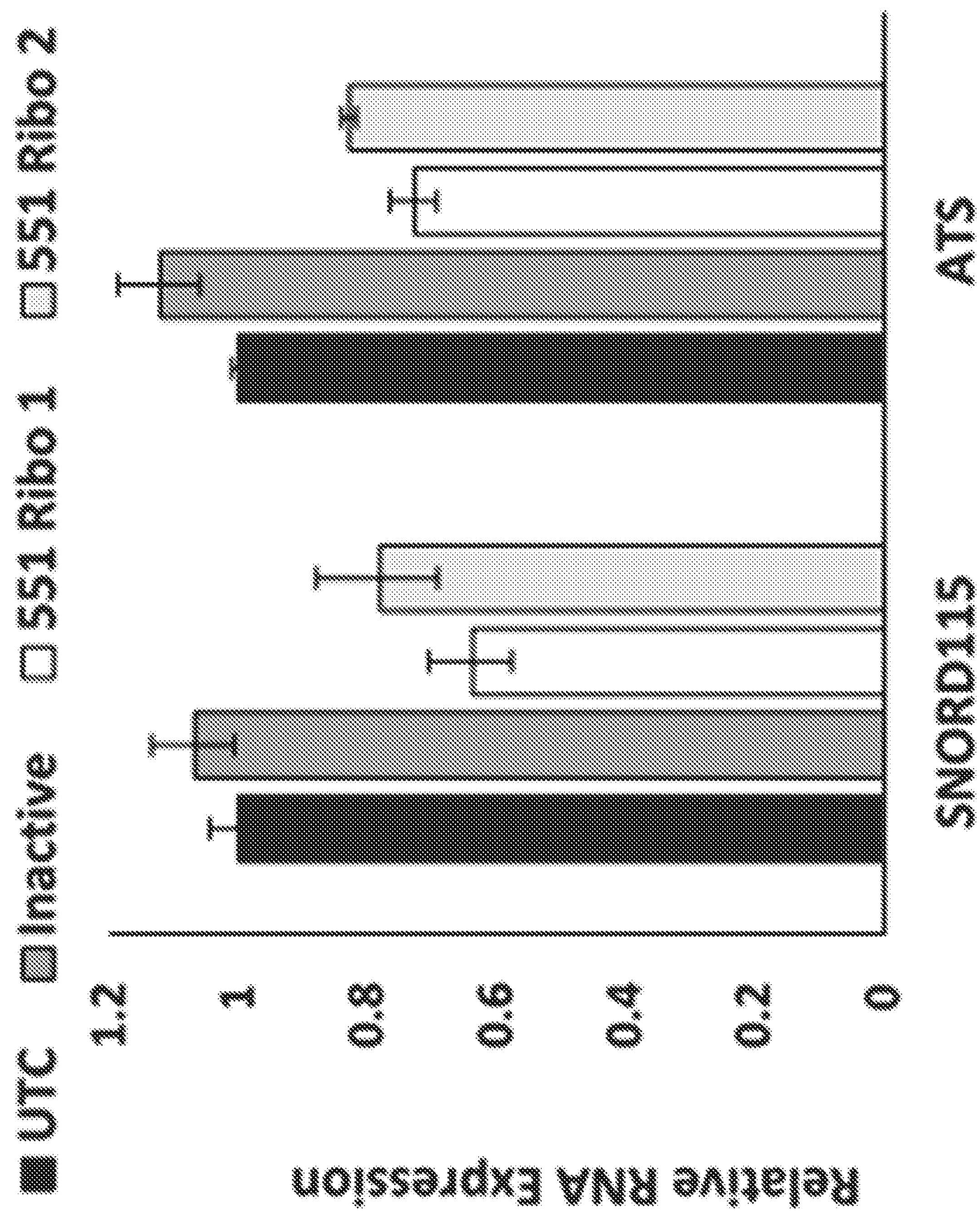

Hammerhead ribozymes, which are catalytic RNA molecules that cause hydrolysis of phosphodiester bonds in RNAs were tested first. These ribozymes cleave quickly and independently of other cellular machinery, and have been tested in clinical trials for HIV and certain tumors. Four hammerhead ribozymes were designed to cut near sequences targeted by functional ASOs. In vitro cutting assays revealed that the ribozymes, were active and can cut the UBE3A ATS sequence (FIG. 3A). The most active two ribozymes, 551 Ribo 1 (SEQ ID NO: 3) and 551 Ribo 2 (SEQ ID NO: 4), were encoded by lentiviral vectors which were packaged into lentiviral particles and used to transduce mature AS iPSC-derived neurons. UBE3A-ATS levels were reduced by ~40% (FIG. 3B).

Figure 4:
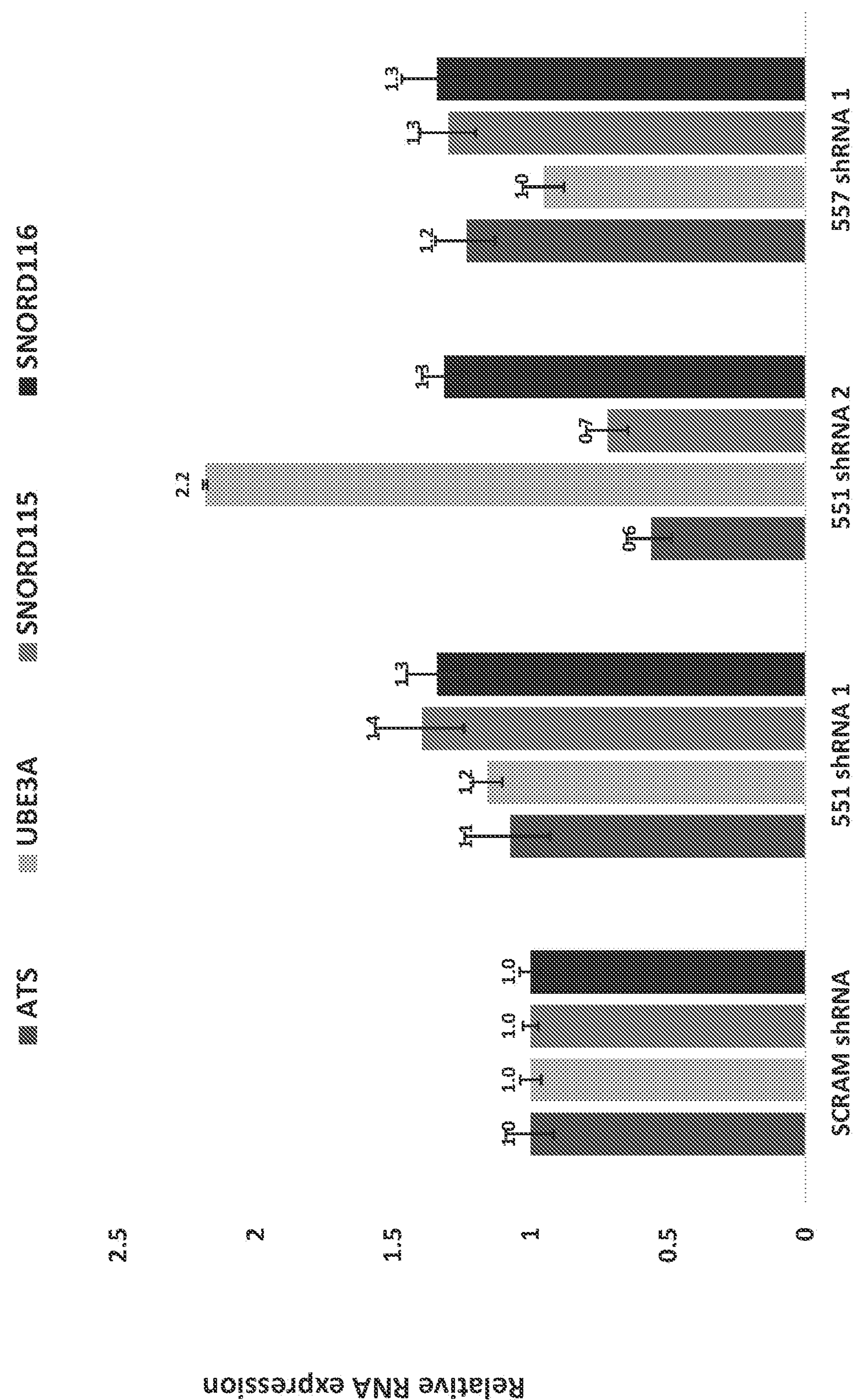
FIG. 4 shows shRNAs knockdown UBE3A-ATS and activate paternal UBE3A. RT-qPCR was performed in AS iPSC-derived neurons transduced with lentivirus to express shRNAs targeting UBE3A-ATS. One of three shRNAs knocked down both UBE3A-ATS and activated paternal UBE3A.
Figure 5:
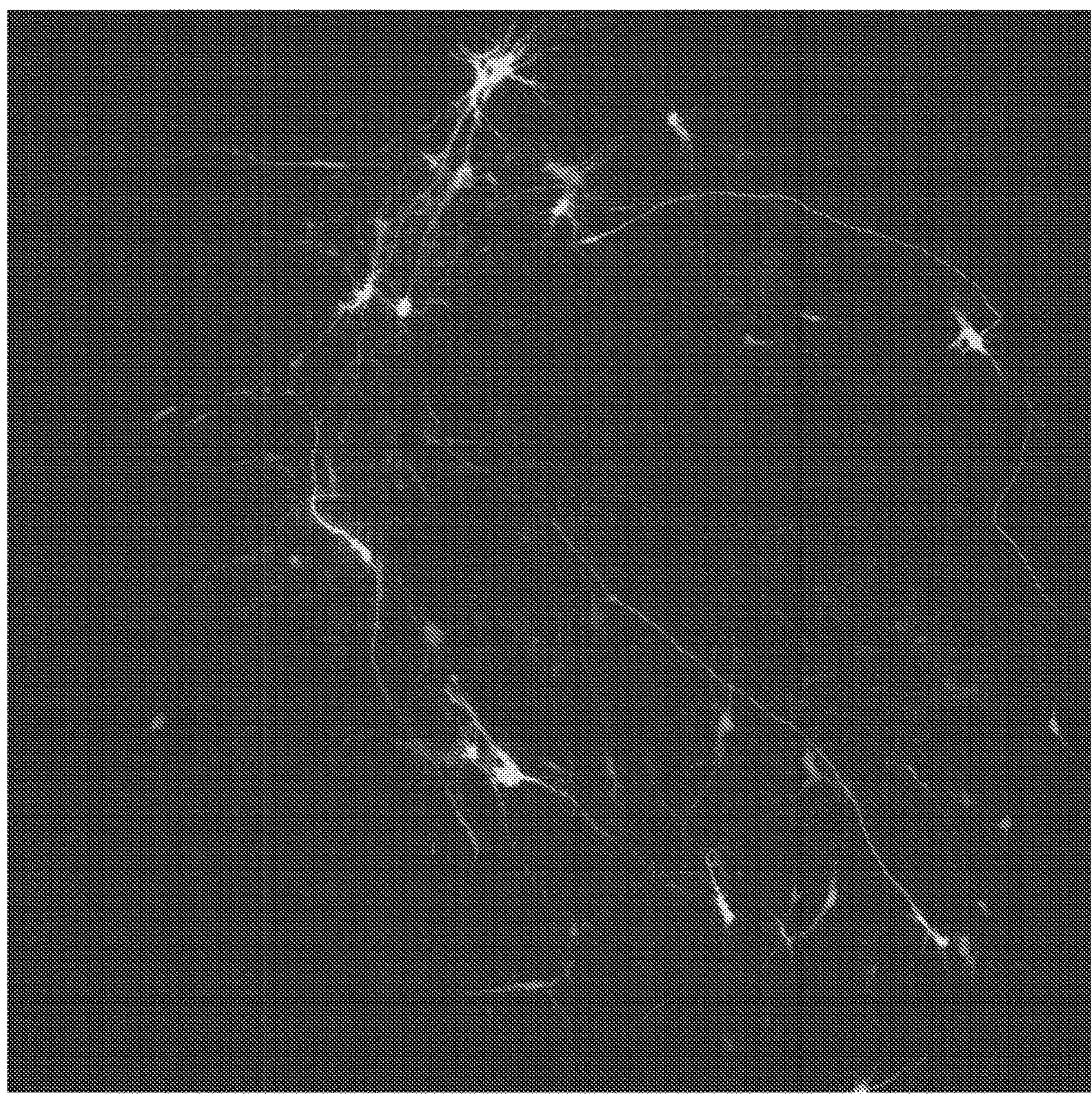
FIG. 5 shows AS neurons transduced with AAV9 particles carrying 551 shRNA 2. The AAV vector also carries EGFP, allowing for green fluorescence upon transduction of a neuron. These neurons were transduced with $1\times10^5$ viral genomes per cell.
Figure 6:
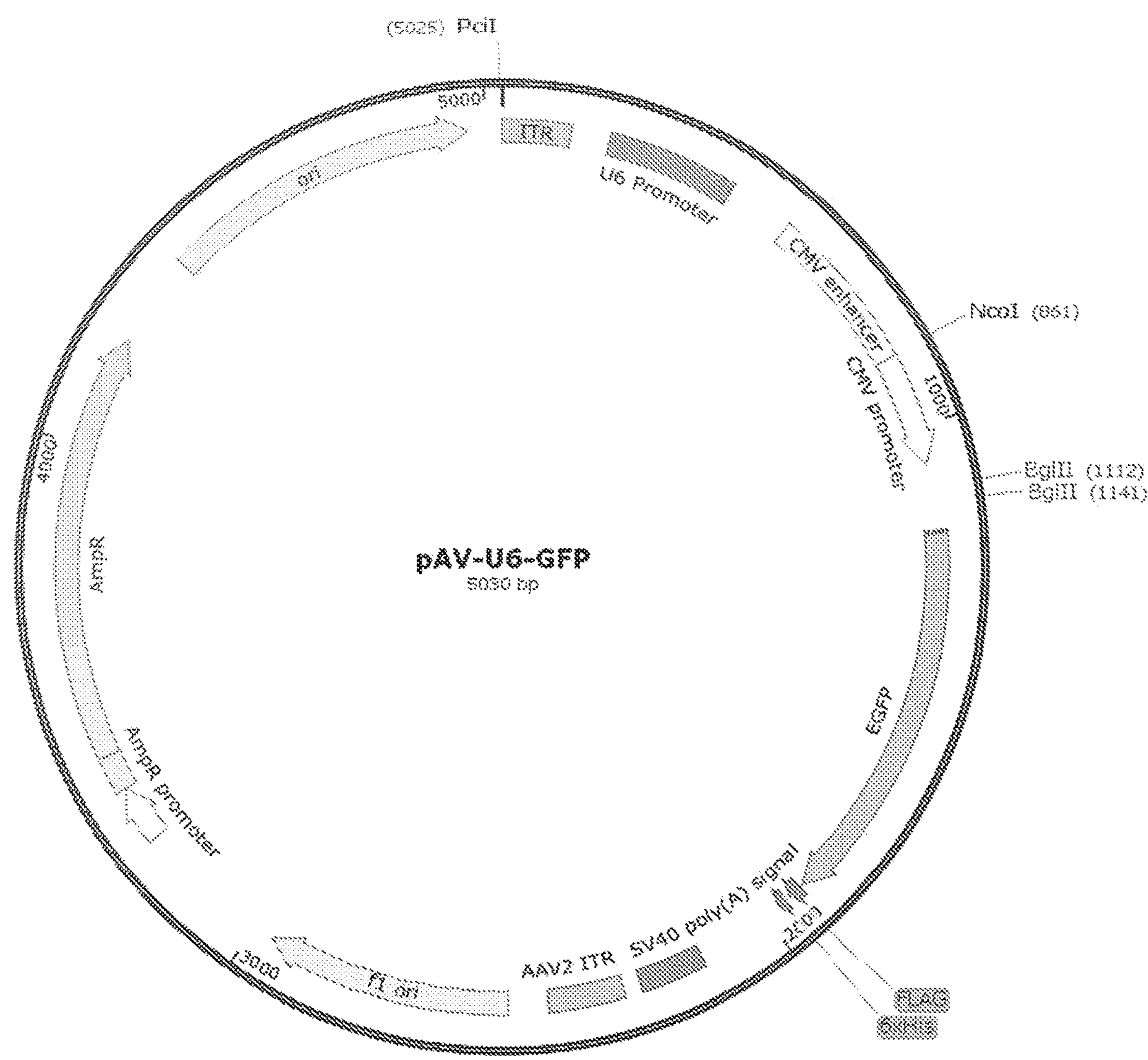
FIG. 6 shows the plasmid map for pAV-U6-GFP, the AAV vector 551 used to clone shRNA2.

Example 2 shRNAs were developed which targeted similar sequences in the UBE3A-ATS gene. shRNAs enlist the RNA interference pathway to knockdown RNAs. Four shRNAs were designed by cloning them into lentiviral vectors which were packaged into lentiviral particles and used to transduce mature AS iPSC-derived neurons. 551 shRNA2 (SEQ ID NO: 2) achieved 40% knockdown of UBE3A-ATS, and a 2.2-fold activation of paternal UBE3A (FIG. 4). These studies have been repeated by cloning the same shRNAs into adeno associated viral (AAV) vectors and packaging them into AAV9 particles (FIGS. 5 and 6).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

```
Sequences
Human UBE3A-ATS genomic sequence.
                                                            SEQ ID NO: 1
TGAGATGACCTAAACAACTGTGGAGAATCATTGATATATTTCCTTTTTTCACTGTTCATGTTGG

GTGAAAATAATCTTGTAGTGAAATTCACATGTTCTAAATATTGTTTTTTTACATCTTTATCTGG
```

-continued

CACATTCATAACATAGATGTTTCTATACATATTAGTACTGTAATCATACCATATATTATTCTGT

TACCCCACTTACTCCTTAAACTTTTAGTTAATTAAAGAGTTTTTATAAAGTCCCCCAATAGATT

TTTTTTTTTTGAGACATAGTCTCACTCTGTTGCCCAGGCTGGAGTGCAGTGGCGTGATTTTGGC

TCACTGCAACCTCCCCATCCTGGGTTCAAGCAATTCTCCTGCCTCAGCCTGCCAAGTAGCTGGG

ATTACAGGTGCCTGCCACCACGCCCGACTAATTTTTGTATTTTCAGTAGTGACAGGGTTTCACC

ATCTTGGCCAGGCTGGTCTTGAACTCCTGACCTCGTGATCCACCCGCCTTGGCCTCTCAGAGTG

CTAGGATTACAGGCTTGAGCCACTGCACCCGGCCAGATTTTAATCTAATTTTATTAGAACAATT

CAGTCATATGTTTTTCATGCTATGTATATGAGAGTTCCATTATTCAGATACTAAACAAATGTC

TACTGTACATTTACTGTTCTCACTGATGATGCATTAGATAACCATGCACAAAATAAGCCTGGCT

GTGGAAACGCTTATTTGTTGGGAGGGTGCTTGTTTGGATCGATGATGAGAATAATTGTCTGAGG

ATGCTGAGGGACTCATTCCAGATGTCAATCTGAGGTCCAGATGTGCGGCCCTCCAATAGGACAA

ATAAGACTCTCAGAGCCTGGCTCTATTTGGGGATCCCTCAGTGACAACATAGTACCCCTGTGAG

CGTGCCTTTTCTATCTCTTCGAAGAGGGCAGTGGCATCCTGTCTTATGAGTCAGTGTGCACTTT

AGTGTGCCTAGTGACCCAAGACTTGCTTTAATTGTAGATAGATACTTACATATAGGAAATATTT

CTTAAGTAACAAATGAAAAACTTTAGAAGATTGAATTAAGGGTCAAGCAACTGTGATATGTCTG

AAAATCTCATTAGTGTTGTGCTGAAAGAAGGAAATATGGCATGCCTCTATTAAATAATGACAGT

GGAACCAAGTTTATTGCTTTGTTATTTTTACTGTGGAGTATTTTCTAAGATTATTTTTGCTTTT

TTTTTCTTTCATGTTTTGCTGAGATAGAAGGCCTGGAATCTGATCCTCCACTTCAGAGAACAGG

GGTGAGTAGCTAAGCCATTATCTTTTGAAATTCATATGTCATGTGCTCTTTGCTAGGTCTTTAG

GTCGTTTTGTACATCTTTTCAGAAGCTTATTGGAGGACATTTTCATGATATGTCCTTTTCCTCA

TTGAGACCCTCACCATGTCACCTACACTATTGAATCCTTATCATTTCTCTTTTAATTTTAACTC

TCTTTTGCTTTTATGGAAAAATGTAGAATTTAAGAGAATTTTTGGCAATTTCATATTGGATCAA

AATGTATTGTAGTGAAATCCAGGTGTGCCAAAATATTAACAGATTTTCCCCATCTGTTTAATTA

TTGGGGTTTCAGAATAGAGACTCCATGGTTCATAATATCTTTGTGGTCATACTACATTATATTT

CTGCTTCTAATTTAATTATTAAATATTGACTTGAATTAGTCTTTTCCTCATTGTTGCAACAAGG

TAAGTTATATAGGAAATTTTCTTCTCTTGATGGCATGTCTGAGATAATCATAGATATAAGACAC

CTGGCTGGTTTCTAGAATGCATGTAATTTTTATTTCTTGATCTGTGTGTTGAGTACTTGCTGTG

ATTGCATCATGCAAATACATTGAGCTTTACAATTTTAGTGTATGCACTTTTCTACATGTATATT

ATTCTTCGATAGAAAGTAAAAAAAACTTATCGAACTAGTCAAAATATTGGTTAATACATAAAAA

AAGTCTCAAGTAGATTGTGTATTACATGGTGCTTGTTGATTGATGCCCTCATAATAGATCAAGT

GGGTTCTCTCTTTAGCACAGGGCTTTTTAGCAAATCATGTCATGAGTAGTTACTCAAGTATTTT

TATTTTAACACATTTATATTTTTTCTATGTATATTCTTAAATTCTCTTATACTTTTTTCTCTGT

TATAAAAACATGCTGAACAATCTCAAGTCTTAAGGATTGCAGTATTGTCCCCACATATTCATGT

ATTTTGGTACTCAATTCTTTATACTTTCTTTGACAGATCACTTGAACTGGCACATGTCTCTTGT

TTTGCAGAGAGGGAATTAATGTGATACCTTCATGCTTTTCTATTCTATGTGCTACATAATTGAA

TATACAAGCAAATATAGTTGTTAAGATTTAGTGTGATTATTTCTACACCACATGCAAAGAAGTT

TCTCATAGATCTTAATAGAGGCCCACATGCATTGTACAGTTTAGAATTTGGGGAAATATTGATG

AAGTTGGGTAAAGTATAAAGCCAAAAGTCAGAACAGTGAACTCCTTGCTTAAGGATTTCCTTGG

AGATTACTTAGTCAATACACAACTGATAAATTTAAGTGCTTTTCACCTTTTGAGTTCTCGACAT

ACTAAAGCTAAAATGTGTTTCAACTTTTAATCCTGCTTCCCTGATTTTCCCTTTTTTAGTCTGA

-continued

GATCAAAGAGTTTCAGCCATAAATTACTGCCAAGAGTAATCACTTCATTTTAAGAAAGCTTAAC

AATATAGAAGAATATAAAATTATTTATGACAGATGTATTTTTAACCTTTTCCCCATGCTTTCCA

GAGGAAATATGTTTAATCATCTGCCCTATATTAGGGAAAAACTTTCTATGCTAATACAAGTATC

TATCAATCCATTTATCTTTCTATATAAGATGTATTGATCATAACCAATTAACTTTACTGTAAAT

GAGCTTTAGATTTGACATTTTGGTAGTAATATATGTTGTACAATCTCCTGAGGTCCTATAGGTC

TTGAGGTCTCTATGTCAAAAACTATAGATGTGCCAGTGTCCTCAGTGAATGTGAAGGACACCAC

ATTTTCCTTAGCCATTTCTTGTTTTCAGAATAATGGTTATCAACATTTTGCTACTGCAAGATAC

CATACATTTATAATCGGAATATGCCAGTTTTTATGCACTCATGCCTCTGTTTCTGTAGAGCATT

CCCAGAATGAGTAATGCTTGAAAATTAGGTCCATGTGATTTCTTTAATGAGTTATAGTCAAATC

ATGAAATATTCAGGTTACCATTATTTCAGTAATGTATTAGAATGTCAAGGTAAAGTTATCTACA

TTGTATATATACACACAACATAGATATAATTTATACAACATCTATATTTATACAACAGATATAT

ATTTATGTATATATTTATACAACATAAAATATATTTTATTATTTAAACATAAAATATATTTTAT

TATTTAATATAGATTCTTAAGTGATAAATATGTTTAATATTATTAAAATAGGTTAAAATAGGTT

ATAGTTAGTACAGTGAAAATTGGCAGCCCTTTTACAAAACATATGCCATAACTATAGCATTTAT

CACTGACAGTCATACCAGGATAGTCTTTTATTTCCAATCACTTAAATATTCCTAATTGCAAAAG

AAATTTGAAGACTAAAATTCAGAAGTTTTGAAAGAGCCATTGCCTGGGTAAACTATACAGGTTT

CAGTTTTATTTATAATAATTATGAGGCCAGGCGCAGTGGCTCACACCTGTAATCCCAACACTTT

GGGAGGCCGAGGCGGGTGGATCACGAGGTCAGGAGATCGAGACCATCCTGGCTAACACGGTGAA

ACCCCATCTCTACTAAAAATACAAAAAATTAGCCGGGCGTGGTGGCGGGCGCCTGTAGTCCCAG

CTACTCGGGAGGCTGAGGCAGGAGAATGGCGTGAACCTGGTAGGCGGAGCTTGCAGTGAGCCGA

GATCGCGCCACTGCCCTCCAGCCTGGGAGACAGTGCGAGACTCCGTCTCAAAAAAAAAAATTAT

GTATATATTTATAAATTAATACTTAATAAATTAATAACTTGTGATAGGCAATGCAAAGATGACA

GTAAAAGGACAAAATTGATTAGATTGATAAAGTCCTGTTAACATGAAGAAATTGACCAGGATAC

CATCCACACTATAAAGTTAGAGAAATTTATCAGGACAATTCCCTAAAATACTCTTCTCAATTTT

AACATTGTAACAGGAATTTTTAAAATTTTGGTATTATGTGTGTTTCCTTCCAGATAATTTGAAC

AGATTCATATTTGGTATTTTTAAAAGCCATATCTTTGTCCTTAGTGCTGGCAATGTATTCTTGA

GAATGAACAAATAAGAGATACGTAAAAGCATAAGAGAAGGTATCAGGTTGAAGTAGTCAATCAG

TTATACAGAACACAAAGAATTTTATCTTGTATAATGTTTATATAGCTTTATAGAAGTGTGCTGA

AAGGGCTATAAAACATGGACATTATTATCTCATTGAAAGGTCCAATACGTACTGAAATACATGC

TTTTATTTTGAACCAACCACCCTATAAACGTTGTATGGCTTATTTAGATGAGAGCCCAGGTTGT

GTGTGTCTGTGTGTGTGTGTGTGTGTGTGTGTGTGTGTGTGTGTGTGTGTACCTGACAGGGA

AGCAAGAACATCGAGTTGCCAATGCACTCTGTCTATGGTTAGAATCATGCTGAAAACATGGCTC

CCCCAGTTCTGGAATGAGCCCACAGATCAAGCATTCCCCAAAGACATAGCAGGCTCAAATCCCT

GTGTACACAATATTTTATGATTATCTTATGTCAGTACTTTCAAAGTATACAGTTTGTGTGAAGA

CAAATCCAATGTCATTTTTCTTGGCTAGCCTATATGTGTGGTAAATCCATTATTTACTTACTTG

CTTCCTGAAAATTACAATTAGATTAACAAACTGCAGCAAAGTGGGCATGATGAGATAGAGATTG

AAGTGTAAGCTTATGTTAATGATGCCCTTGGTTTGGATAAACACATCTAAGAGAAAAATGGAAA

AACACACATGGCAGGGAAGCCTTGATAGAGCCAAAATATAGGATTGTATGTAGTAATGCAATCC

ATAGATGAGCATTTGGCAGTAATATTATTTTTCAGATATGGATAAAAATTGCTTAGGAGAGTAA

AGAGAGACAAAGTTGAAAGCAGGTTTATAGTAGGTGTTGTTTTAGTGTTGATCCCTTTTTGCTC

CAATAATCAAAGTGATAAATATTGAAAATTGATTCATGCAGCATTACTTACTCCATTCTAATTT

-continued

TTATATATGTCAAAAGTGCCATCTCCCAAACTGTGCTATCCCCTTCAGGAGAAGAGACTCTGCT

GAAGTTTATAAGGTTGACATATTGCCAGCTTCAATAATGTAAAGATGAAGTGTATACTGAATTC

TTAATGCAAATAACAACTCTATTGGAAAGTAACCCAGTTATAGAAGTGCTAATTTGTCAGGAGC

TGCCTTACCAAGATCATGATGAGTACAGTTATCTCAGGATTCTGAAAGATTGTTTTCCGATTTC

AACTAGTCTAGCTGAATGTTCCTTGATAGAAAGAGAGGACTTTTAGAATTGGTTCAATATGATG

ACCTCCTGAATTATCTCACATAGCCCGTTTGTACATGCCTTTCTTTTCTCTCAGAAAATGGCAC

TATCATAATAGCTTTCTTACACAGACTTCACCTTAGGGTTTTACATTAAGGGAGGGGTCTGGTG

TTTCATTTATTTTGAAGTATTTGTTGTTGATTGTGTACAGTGCTTGAGTAAAAAATTGAATATA

GAAACATCTAGAATATTTTTTTAAAGGATCAGTGTTTATAAAGTGAATTATTAGTGTCAATAAT

GTTGGGAAAGTTTTAAGAGAATATAGGAAACTTGAACATTACACAACTACAATGGGACCAAATT

GTGGGGTCTCATTATAGTTAATATTTATGTATTTTTTTCCAATTGATTTGTGTGCTTTTTTTCT

GCATGTTTTTGGCAGATAGAATGGCTATAACAAGTAACAGCATGTCAGGTAATAAAAATAAGCA

GAGCCCTATTCCTTTAAAAATCTTCACTGATGGGAGGGCCATAAAATAAGTCTTAATACATTTA

AAGAATTAAATTCATGTAAACCATGTTAATTTAATTCCACAATGATATTGAATTAGAAATAAGA

GGAATATCTCTTGAACATCTCCTAAATGTTTGGAAATTTAAATTAGCATTTCTGACCTATTTAT

TGGTTAAAAAAGATACAAAGAAAGGAAAATTGAAAAGTCTTTTGAACTGAATAAAAATAAAAAT

ATAGAATCTAAAACTTTATGGGATACTGACAAAACAGGATATAGGGAATAATTTATAGCACTGA

AATGCCTATATTAGAAAAGAAAAAAGGTTTTAAATCAGTAAATTTGTATTTTACCTTAAGAAAC

TTAGAAAAGAACAAATTAACCCAGACTTAAGTAAAATAAAGGCACTAATAAAGATAAGAGCAGA

AATCAATGAAATATAAAACAACAAAACACAGAGAAAAATTGAGAAAATTTAAAAATAGCCTAGT

GAGAAGATATTGATAAACTTGTAACCAGACCAATTTAAGAAAAAAAGTCAAAACACAAATACCA

ATATTTGAAAATGTAGGAGGGCAAATCATTACAGATTCTATGAATACTAAAATGATAATAAGGA

AAAATTATTTAAAAGGGGCATGTCAGCCAGGCATGGTGGCTTACCCCTGTAATCCCAGCACTTT

GGCAGGCCGAGGTGGGAGGATTGCTAGAGCTCAGGCATTCGAGACCAGCCTGGGCAACATGTTG

AAACCTTGTCTACACAAAAAGTACAAAAATTAGCTGGGTGTGGTGTTGCACACTTGTAGTCCCA

GTCACTTGGGAGGCTGAGGCGAGAGGATCACTTGAGCCCAGGAGGTTGAGGCTGCAGTGAGCCA

TGTTTGTACCACTGCCCTCCAGCCTGGGTGACAAAGTAAGACCCTATGTAAAAAAAAAAAAATG

TATGCCAACATTTTTCAATAACTTAAATGAAATGGAAAAATTCCTTGAAAGACACGAACTACAA

AAACTCAGTGAACAAGTAAATAACCTGAATAGCCCTGTATCAAGTAAATTGAATTTGTAGTTAA

AAGCCTTCCAACAGAGAAAACTTCAGGTACCTATAGCTTCATATGAAATGAAAAAAAAAATACC

AATCCTCTACAAGATTCCAGAACATTTAAAAGAAGGGAATATTTCCCAACTTATTCCATTTGGA

CAGCAATACCCAGGTAAGAAAAAGAGACACAGAAATTTAAAAAGAAGAATATACATTATTCCTT

AGGAACATAAATGCAAAGAAATCTAATCAAAATTTTGGCAAATGAAATGTAGAAATACTTTATG

ACCAAGTGAGAGTTACCCAAAGAATTTAAGGTTGGTTTTATATGTAAAGATCAACCAATATAGG

AAAATCACTTCTGGAAAGTCAGAGTAAGAAACTCCAAAAATCTACTCCTCCATAAAACCAATAA

CAGCCTTGATAGAAATAGTTGAAATTAATTTTCCAAAACTTTGGAAATTAACCAAAGGCTTACA

AAATTCCAGAGAACATTAATTCAAGAAAAATGGCTGAATCAGTAAGAACAGCCAGCTTTGTGGC

ATTTTAATATGACCCCTTCCCATGCTTTTCTCCCTAGTGCTGAGATAGTCTTAAAAATTAGCAG

GATAGCAACCACTGGAGAAGAAAGGTTTGGAAATTTCCCAAAAAGTTCCATCCCCATAGAATTA

TCACTATTTGACCTCTAAAGCCCAATCTATAGGATTTATATTCATTTGGACTGACTCAGAGCTC

-continued

```
ACTCAGTAAGGAAATCTCAATTTCAAGGTATTGGTCAAAAAGAATCCATGGCAATTGTTGACTA

TCACAACTGCCTGAAGTCTTGGTAACAGTTGGGATAAACAAGAAGCTGATCAAAAACTGAAAAC

TAAAATCTTGGGAATGAGATATCTACAGGATGCTTCAAAAAGCTTTGATACATTCCTGTTTATC

TAGAAAGCTACATGCAGGCTGGGTGCAGTGGCTCACACCTGTAATCCCAGCACTTTGGGAGGCC

GAGGCGTGCGGATCATGAGGTCAGGAGTTTGAGGCCAGCCTGACCAACATGGTCTCTACTAAAA

ACACAAAAATTAGCCAGGCGTGGTGGCGTGCATCTGTAATCCTAGCTACTCAGGAGGCTGAGAC

AGGAGAATCGCTTGAACCCGGGAGGCGGAGGTTGCAGTGAGCCAAGATTGTGCCACTGCACTCC

AGCCTGGGCGACAGAGCAAGGCTCTGTCTCAAAAAAAAAAAAAAAAAAAAAGCCACATGCATGTAA

TTGTTTACCTCTGGCTTTCCTTTTATGCTCTGGGCAAGCTAAGGAAGAGTTGTGAACTACCTAA

GTGCTGAATGGGAACCATAACACACACACACACACACACACACACACACACAGCACCTTAGTAA

AGGGTGAGAGGCATGTTAGTTAGAAGCATTAAAGGAAATCTCTTTCTAGTCATTATCTGTGCAC

TAACCTAACTGAGCAGAGACTTCAGTATCCACATACTACAGGGCATATAAACTTTACAGAATTA

GTCCAGGAAAATCATATCTAAAAAAAAAAAAAAAGCAGTAACAAAAATAAACTCTGGGAAAGGGG

AGAATATGATTTAAAGAGTTGCCACATTATACATAATATGTCTAGTGTTCAACAAAAAATTACG

AGACATGCAAAGAAATAGAAAAATATGGCACAAAGAGGATAAGATGAAGTCAGTGAAACTATCC

TCGAGGAAGACCAGATGTTGGTCTTACTAGACACAGACATTGAACCAGCTATTAAAAATACGTA

CACAGAACTAAGAAAAACATGTCAAAAGGGTTAAAGAAAGGTATAAAAATAGTGTCTTACCAAA

TATAGACTACCAATAAAGAGATAGAAATTATAAGAAAAGACAACATGAAAAAATATAAAGCAAA

AAAATTAGACAATTGAAACAAGAGGGCCTCTATTCGCAGATTTGAGCAGGCAGAAGAAAGAATC

AGTGAACTTGAAGATATGTCAACTGAGATTATCCAGTCTGAGCAACAAAGGTGGGAAAAAATGA

AGAAAACTGAGCAACAAAGAACTGTAGAACAGCATCTCTCATACCAATGGATACATAAACTGGA

GCCCTAGAAGGATGAAAAAAGGAGAAGGAAAGAAAACTTCCCAAATTTTAAGAAAAACATTAAT

TTATATACCCGAGATGACCAATAAAATCCAATTAAGATAATCTCAAAGAGACCAACACCTATAC

ACATCATAGTCAGCGTGTCAAAAGACAAACATAAGGAGAGAATTCTTGAAGATAGTAAGAAAAA

AATTATTCATAACATACACACCATCCTCAATAAGTCTGACAATTGACTTCTCACTGTAAACCAT

GCAGGCTAAAAAGGCAATGTACATAACCAAAGTGATGAAATAAAAACCTTCAACCAATCATTCT

AGATCCAACAAAACTATTGTTCAAAAAGAAGAAATGAAGACATTCCTAAACAAAATCTCAGAGA

AATGTTCTCTATAAGACTTGTCCTAATAGAAATGCTAAAGGAACTCCTTCGGTCTGAAATAGAA

AGGCACTGGAGAGTAAATCAAATCCACGAGAAGAAATAAAGAGAACCAGTATAAGTAACTACAT

GTGTAAGTTTAAAACAAAGTATAAATTTATTTTGTTTGTAACATTTGTCTTTTCCTATTTGATT

TAAAATATAATCTCAATTATAAACTTGTGTTGATGGTATTATATAAAGATGTAATTTTGGGTTA

TAGCACCAAAATGGCAGAATAGGAATTTTCTGTAGGTGTTTCCCACATAAGTATCAATTTTGAC

AACCATCCATGGGCAAGAGTACCTTGTGGGAGTTCAGGAGTTGACAGTAAAACTTCAGCACACC

AGAGGAGTAAAGAAATCTAAGAATAGATTCATTGGAAAGGGTATAAACAGTTTCACTTTACCTG

CATCACCAACCCCCAAAAGTGGCACAGCTCAGTAACAAGAGCCCATTATTTCTTCCACAGAGGA

AAAGGAGAGTATAATAAGTAAGTGTCCAGTTTCTCAAGACATACAGGCCCCTGCCCAAGAGATC

CACTTTATTTTCATCTCACCCAGAATATTGAGGTGATCAGCAAGGTGGAGTGGTTGGGAGAGGG

TAAAAGCAGGAAAGAGAGATGGGGACTCAAACAGCAGCCCATACTTGGAACTGCCATAGATCCT

ACCAGTTACTTCATGGACTCCATCAGGAACCCACCTATAAGCCACAGGGGATGCATCCCTCCCA

TCTTGCCAACAAAACCCCGAATGCTCCAAATGCCTCACCCACTCTTTGGCTGGCTCCCAAGTGC

GCTCCTGTGAAAAGCGAGTGAGTATCTCTGCAGATGGCTTGCAAGCACATGTTGACAGCTGGCT
```

-continued

CCACTCTGTAGAACTGGAAAAAAGCTCACATACATGAGAATTTCAGGACACTACCCTAAAAAAA
AAAATGAGACTTCAGCACCTGGCCTGGCTTTATGCAACCTAGAGAAGGTGATATGATTTGGCTC
TGTGTCCCCACGTAAATCTCATGTCAAATTGTAATCCCCACGTGTTGGACAAGGGACTTGGTGG
GAGGTGATTGAATCATGCGGGTGGACTTCCCTCTTGCTGTTCTTGTGATAGAGTTGTTATGAGA
TCCAGTTATTTGAAAGTATGTAGCATGTCCCCCTTCACTCTCTTGCACTCCTGCTCCACCTTGG
TAAGACTTGCTTGCTACCCCTTTGCCTTCTGCCATGATTGTAAGTTTCCTGAGGCCTCCCAGCT
ATGCTTCCTGTATGGCCTGCAGAACTGAACTGTGAGCCAATTAAACCTCTTTTCTTCATAAATT
ATCCAGTCTTAGGTAGTTCTTTATAGCAGTGTGAGAATGGACTAATGCAGAAGGCATACAACCT
TTAGAATTTGCCCCCTTGAGGGAACAAGATGTGTGAAGCAGGTTCATCCATAGAAAATGTCTGA
GAGAACCTCAAAATCCCTAACCTGACTAACTGATGAAAGTGTTTCTCTCCTAAGGCCAGTCAGT
AAAGACCAGAGGGGGTGACTGTTTCTTTAAATGCAAAGGCAGCAGCACAATAATTCAAGAAACA
TGAAAAATCAAGAAAACATGACACCACCAGAAGAACACAATCATTTTCCAATAACCAACTCCCC
AAAAATGGAGATTTACAAATTGGTTTATAATGAATTCAGAACAATTATGTTAAGGAAGCTCAGC
AAACTAAAAGGAACACCAATAGACTACTCTGTGAAGTCAGGCAAACAATTCATGAACAAAACTA
GAAATTCAAAAAAGAGAAAAATTATCTTAAAAGAAAACCCAGAAGTTATGGAGCTAAAGAATAC
AATGCATGAAATGAAGGAGCGTATCAACAGCAAAGTTGATCAAGCATAAGAAAAAAAAAATCTG
TGAAACTGAAGACTGGCTATTTGAAATTATTCATCAGAGGATTAAAAAAAAAAGAATGAAAAGA
AATAAAGAAAGCCTACAGGATGTATAAAACACCATCAAGAGAACTAATATAAGGATTATTGGAG
TCATAAAGGAGAAGAGAGAAAAGGGTAGAAAACTTATTTAAGAAATAATGGCTGAAAACTCTCC
AAATCTAGGAAAAGATATGAGCATCCAGGTATATGAAGCTCAAAGATCCCCGTACAGGATACAT
TCCAAAAAGACTTCACCAAAACACATGATAATCAAACTGTCAAAAGCAAAATCAAGACGATGAA
TAAACCACCAATCACTAAGAGGGAGACAGGATTCTTATGTTGTCATTATTATTTACATATAATT
TCAGTAAATGTTATTGGAAAATTTATAATGTTTTAAAAAAAGAAATTTGAAAGCACCGAAAGAA
AAGAGACTCATCACATACAGGGAACCCTTTTAAGGCATTCAAGAGATTTCTCAGTAGAAACCTT
ACAAAATAGGAGAGAGTGGGATGAACTATACAAGTGCTGCAAGGAAAAAAATGCCAACCAACGC
TTTACCTGGCAAATCTGTTCCTCAGAAATGAAGGAGAGAGAAGAACTTTCCTAGACAAACAAAA
GCTGAGGCAGTTCATCACCACTAGACCTGCCTTACAAGACATACTAAGGGGAGTTCTTCAAGCT
GAAATGATATGGCAATAGTTAGTAATATGAAATGATAAACCTCACTGGTAAAGGAAAGTACATA
GTCAAATTTAGAACACTTTGATACTATAATGATGGTGTATAAATAATTTTACTGTGCTATGAAG
GTTAAAAGACAAAAGTATTAAAAAAAACCCATAGCTGCAATAGCTTGTCAATGCATACTACAGT
ATAAAAAGATGTAAATTAGAACATTAAAAACATAGCATGCAAGGGTAGGGAAGTAAAAGTGTAG
TTTTCATATGTAATCAAATTTAATTTGTTATCAGCTTAAAATAAATTGTTATACCTATGTTTTA
TGTAAGTGTCATGGTAACTATAAAGGAAAAACCTCTAGTAGATACACAAAAGAAAAAGAGAAAG
GAATCAAAACATAACACTACAGAAAATTATCAAATTACAAAGGAAGACAGCAAGGGAGGAACAA
AGTAAAAAGAGCAAGAAAAAAATTTAACATAATGAAAACAGTAAGTCCTTACGTGTCAATAATTA
CTTTAAATGTAAATGGATTAAATTATCCAAACAAAAAAACAGACTGGACAAATGGATTTTAGAA
ACAACAACAACAACAAACACCGCACACACACACACACACACACAAACCACCCAGCCCCAACTAT
GTGCTGCCTACAAGAGATTTACTTCCACTTTAAGGACACATACAGGCTGAAATTAAAAGAACAG
AAAAAGATATTGCATGCAGATAGAAACCAGAAGAGAGGAGAGGCATCTATACTTACAGCATACA
GAAAAGATTTTAAGTTAAAAACTATATCAAAAGGCTAAGAAGGTCAAAATGGTGAAGCAGTTAA

-continued

TTGTTCAAGAAGACATAAAAATTGTAAATATTTATACACCCAATATTGAAGCACCTAAATATAT

AAGGCAAATATTAATACATATAAAGGAGAAATATACAGCAATACAGTAATAGTAGTGAACTTC

AGTGCCTCCCTTTCAAAAATGGATAATCCAGACATAAAATCAATAAGGAAACATTTAACTTAAA

CTTCACTTTAGACCAAATGGATCTAACAGACATTATACTGAACATTTCATCCAACAGTGGTAGA

ATTCACATTCTTCTCAAGCACACATGGAACATTCTCCAGGATAGATTATATGTTAGCTCACAAA

ATAATATTACAAAATTTAATAAAGCTGAAATATCAATTATTTTGCACCACAATAGTATAACACT

AGAAATCAATAACAAGATGGAAACTGGAAATTTACAAATATATAGCATTAACATATTCCTGAAC

AACCAATGGGTCAAAGAAAAAAATCAAAATAATTTTGTGACAGCAAAGTAGAAACACAACATAC

CAAAACATACAGGACACAGCAAAAGCAGTTCTATGAGGTAAGCTTATATTGATAAACACATTTA

AAAAAAGATTTTAAATAAACAACATTACACCTCAAGGAACTACAAGGAAGAAAAAAAAACAAGC

CCCATGTTATCAAAGGGAAGGAACTAACAAAGATCAGACAGAAATAAATGAAACATAGACTAGA

AAAACAATAGAGACTATTAATAAAACTTAGAGTTAGTTTTTAAAAAATAAAATCAACAAACCT

TTAGCTAGACTAAAAAAAGAGAAGACTCAAATAAAATAAAAAATGAAAGAGGAGACATTACAAC

TGATACCACAGACATACAAATTAAGAGAAAACTATATGCCAACATATTAGTTAACTTGCAATGG

GTAAATCCCTAGAAACATACAACCTACAAAAACTGAATCATGAAGAAATGGAAGATCTGAACAG

ATCAATAATGAATAAGGGAATTGAATCAATATTCAAAAATCTCACAAAAAGAAAAGCTCAGGAT

CAGATGGCTTCACTGGTGAAGACTGCCAACCATTTAAAAAAATTAATACCACTCTTTATTAAGC

TCTTCCAAAAAAATTGAAGAGGAGAAAACACTTTCAAATTCATTATAAGAGGCCAGTTTTACCT

TGATATCAAAGATTTAAAAAGAACACTTTGAGAAAGGAAAATTACAGGCCAAAACCCTTGATAA

ATATAGATGCAAAAATGCTCAGCAAAATACTAGCAAACCTAATTCAGCAACACATTATAATGGC

ATACATCATGACCAAGTGAGATTCATGCCTCGGATGCAGGATAGTTCAATATAATCAAATCAAC

AAATGTTACACTACTTTAACAGAATGAAGGATAAAAATCATATGATCATCTCGATGGTTGAACT

AGTTTACAGTCCCACCAACAGTGTAAAAATGTTCCTATTTCTCCACATCCTCTGCAGCACCTGT

TGTTTCCTAACTTTTTACAGATCACCATTCTAACTGGTGTGAGATGGTATCTTATTGTGGTTTT

GATTTGCATTTCTCTGATGGCCAGTGATGGTGAGCATTTTTCAAGTGTCTGTTGGCTGCATAAA

TGTCTTCTTTTGAGACGTGTCTGTTCATATCCTTCACCTACTTTTTGATGGGGTTGTTTGTTTT

TTTCTTGTAAATTTGTTTGAGTTCTTTGTAGATTCTGGATATTAGCCCTTTGTCAGATGAGTAG

ATTGCAAAAATTTTCTCCCATTCTGTAGGTTGTCTGTTCACTCTGATGGTAGTTTCTTTTGCTG

TGCAGAAGCTCTTTAGTTTAATTAGACCCCATTTGTCAATTTTGTCTTTTGTTGCCATTGCTTT

TGGTGTTTTAGACATGAAGACAGTGTGGTGATTCCTCAAGGATCTAGAACTAGAAATACCATTT

GACCCAGCCATCCTGTTACTGGGTATATACCCAGAGGATTATAAATCACGCTGCTATAAGCCAT

AAAAAATGATGAGTTCATGTCCTTTGTAGGGACATGGATGAAGCTGGAAACCATCATTCTCAGC

AAACTATCACAAGGACAAAAAACCAAACACCGCATGTTCTCACTCATAGGTGGGAATTGAACAA

TGAGAACACATGGACCCAGGAAGGGGAACATCACACACTGGGGATGGTTGTGGGGTGGGGGGAG

GGGAGAGGGATAGCATTAGGAGATATACCTAATGCTAAATGACGAGTTAATGGGTGCAGCACAC

CAACACGGCACATGTGCACATATGTAACAAACCTGCACGTTGTGCACATGTACCCTAAAACTTA

AAGTATAATTAAAAAAAATAATGCTGCTATAAAGACACGTGCACACGTATGTTCATTGCGGCAC

TATTCACAATAGCAAAGACTTGGAACCAACCCAAATGTCCATCAATGATAGACTGGATTAAGAA

AATGTGGCACATATACACCATGGAATACTATGCAGCCATAAAAAAGATGAGTTCATGTCCTTTG

TAGGGACATGGATGAAGCTGGAAACCATCATTCTCAGCAAACTATCACAAGGACAAAAAACCAA

ACACTGCATGTTCTCACTCATAGGTGGGAATTGAACAATGAGAACACTTGGACACAGGAAGGGG

-continued

AACATCACACACTGGGGCCTGTCGTGGGGTCAGGGTAGGGGGAGGGATAGCATTAGGAGATATA

CCTAATGTAAATGACGAGTTAATGGGTGCAGCACACCAACACAGCACATGTGTGCACATGTACC

CTAGAACTTAAAGTATAATAAAAAATAAATCATATCATCATCTCAGTAGATTTAGAAAAGCATT

TAACAATATTCAACATCCTTTCAGAACTAAAAACTCTCAATAAATCAGGTATAGAAAGAATGTG

CCTCAACACTATAAAAGCCACATATGACAAACCTGGAGGTAATATACTCAATGGTGAAAAGTAA

AAAGCTTTGACTCTAAGATCAGAACCAAAACAAGGATGTCCATTCTCACCACTTATATTTAACA

TAGTAGTTGAAATTCTAGCTAGAGCAATTAGGCAAGAAAAAAGGCACCCAAGTTGGAAAGAATG

AAGTTAAATTGTCTCTGTAGATGACATGATCTTATATATAGAAAACACTAAAGACTCCACCAAA

ATGCTGTTTTAATTAGAGCTTAAAAAAATAATTCACTAAAGTTGCAGGATACAAAATCAGTATA

CAAAAATCAGTTGCATTTCTAAACACCAAAAACAAGTTATCCAAAAAATTAAGAAAACAATCCT

ATTTGTGATATCATCAAAAAATAAAATACTAAAGAATACCAAAGAAACTGAAAATAAATGGAAA

TAAATGGAAAGATAGCCCATGTTCATGGATTAGATGAATTAATACTGTTAAAATGTTCATACTA

CCCAAAGCAACCTACAGATTAAGTGCAATTCCTACTAAAATTCCAATGACATTTTTCACAGAAA

TAGAAAACACACTCCTAAAGTTTGCATGGAACCGCAAAAGACTCAAATAGATGAAGCAATTTTG

AGCAAGAACAGTAAAGCTGGAGACATCACACTACCTAACTTCAAAATTTTATTAATCAAAACAG

CATGACATAAAAACAGACAGAAAAGACCAATGGAACAGAATAGAGAGCCCAGAAATAAACTCAC

GTTTATAGAGTCAACTAATATTCAACGAAGGTGCCAAGAGTACACAATGGGGAAAGTATAGTCT

CTACAATAAACAGCACTGGGAAGACAATATCCAAATGCAAAAGAATGAAATTACACCCTTATCT

TATACCATACACACAAATCAAATCAAAATTGATAAAGACTTAAATATAAGACCTGAAACCATAC

AATCTTTAGGCAAAAACTCATTGACATTGGTCTTGGCAATGATTTTTTTGATATGACACCAGAA

GCACAGGCAACAAAAGCAAACCTAAACAAGTGGGACCCTAACAAACTAAAAAGTTTCTGCACAG

CAAAGGAAACAATCAATCATCAGAATTAAAAGGCAATTTATGAAATGGGAGAAAATGTTTGCAA

ACCACATATCTGATAAAGGGTTAATATCCAAAAATATATAAGGAATGCATAAAATTCAATAGAA

ATAAACAAACAAATAATCCAATTTTAAAATGGGTGAAGAACCTGAATAGACATTTTTTCAAAGA

AGACTTACAGATAGGCAACAGGCATATGAAAAAATGCTTGACATCACTAATAATCAGGGAAATG

CAAATCAAAGCTCCAGTGAAATACCACCTCCAACTATTAGGATGGCTATTATCAAAAACTCAAA

AGAAAACAAGCTGGGGGAATGTAGAGAAAAGGGAAAAGAAGATCCTTATACACTGTTGGTGTGA

ATTTAAACTGGAATAGCCCTTATGGAAAACAGCATGGAGGTTCCTCAAAAAATTAAAAATAGAA

CTACTATATGATCCAGCAATTTCACTATTGAGTATATATCCAAATGAATTAAAATCACTGTCTT

GAAGAGGTATTTGCACACTCATATTTATTTCAGCATTATTCACAATAGCCAAGACATGGAATCA

ACCTAAGTGTTCATCAGTAGATGATTAGATAAAGAGAACGTGGTATATAGACACAGTGGAATCT

ATTTAGTGTTCAAAAAGAAGGAAATCCAACTTTTAAAATCCTTTAAAAAGTTAAACTCATAAAA

ACAGAGAGGAGAATGGCGGTTTCCAGGAACTGGAGGGTGGGAGAATGGGGAGATGTTGGTCAAA

AGGTACAAACTTTCAGTTATAAAATGAATAAGTTCTAGAGATCTAGTGTACAACAGCATTACTA

TAGTTAATAATAATATTTTTTATACTTGAAATTTGCTAAGAGTAAATATCAATATTCTCAATAC

ACACAAAACAGAACTATCTGAAGGCACTGATATGTTAATTATCTTCATTATAGTAATCATTTCA

CAATGTATAATGAATATCAAAACAATAGTGTACATCTTAAATATATACAGTTTTGATTTGTTAA

TCATACATCAATGAAGCTAGAAAAAATGTTGTAATTTTTAAAACAATAGTAATATAAATTAGGG

GTGAAGGAATTGACCTATGTTGGAGAAAAGTTTTTGTAAACTATTTAAATTAATTGGTATCCAT

TCAAGCTAGATTATTTTTAATTGTTAATTTAATTGTAATACTAAGGCAACCACTAAAAAAGCCT

-continued

```
TTAAAAAAATATAGCACTTGAGGCTGGGCATGGTGGCCCTCAATTATATATATAATATATATAA

AATATATATTATATATATAGTAGATGAACAACAATGGGATTTAAATGGTACACTAGAAAATATC

TGTTTAACAAAAAGAAAGCAATAGTGGAGAAATATAAGAACAAAACCATGTAAGATTTATAGAA

AATGAATAGCAAATTGGTTGACCTAAACCCTATCTTATAATTATATTAAAGATAAATGAAATAA

ATACTACATCAAAAGGCAGAGATTATCAGAATAGAGAAGAAAAATCCAAACCATAATTCAACCT

TATGTTATCTGTATTTAGAATATTTAGAGTCAAGACACAAATAGATAGAGTTCCATTTGGGCGT

GAAAATATTTACCATGCAAAATGTAATTAAAATAGAGCTAGAGCAGCAATACTAATATCTGACA

AAATATACTTTAACAAAAATTGTTGCTAAAGACAAAAAAGAACATTTTATAATAAGACACAACA

ATTATAAACATATACACCAAACAATAGAGCCCAAAATATACAAAGCAAAAACTGCTAGAATTGA

AGAAAGATAGAAAAATCAATGATTACAGTTGGAGGTGTCAATACCAAACTTTCAGTAATACACA

GAACAACAAGTCAAAAGCAAAAAGGAAATAAAAAACTACACATTATCATACAACACCTTAATAC

GATATCCAACAATAGCAGAATACACATTATTCTGAAGTGCACATGGAATATTCTTCAGGATGAC

ACATATTAGGCTGTAAAACATATCTTAATAATTTAAAAGAATTGAAATAATACAGCACATATTC

TCTGACTGCAAAATATTAAACCAATTACAGAAGAAAATGTGGGAAATTCACAATGATATGGAGA

TTTAAAAATACTTCAAAGTAACCAATGAATCAAAGAACAAATCACAAGAGAAATTAGAAAATAT

TTTAGATGAATAAAACTGAAGAAACAACATACCAAAATTTTGTGGTTGTAGCTAAAGCAGTGCT

TCAAGGGAAATGTATAACAGTATATCCCTAAATTTTAAAAAAATCTCAATCCAATAACCTAATT

TTTCACCTTAAGAAATGAGAGTGAAAGAGCAGACTTAACCCAAAGTAAACAGAAGGAAGAAATA

ATAAAGATTAGCATGGAGATAAGTAGTGAAAATAAAAACAATAGAGAAAATTAATAAACTTGAA

AGTTGGTTCTTCTGATATATCAGTAAAATTGACGTATTATTAGTTTGACCGAGAAAGAACAAAA

GAGAGAAGATTCAAGTTACTAGACATAAATGAAAGTATAGATATCACCTTACAGAAATTAAAAG

AATTCTAACAGAATATTGTGAAAAAGTGAATGTCAAAAAATTAAATTATATGAGATACACAAAT

CCCTCTAAAGGCACAAACTACCACAGCTGGTGTAAAAACATGAATACACCATTTACAGTTAAAA

AGACTGAATAGATAAAAATTTTAAGAAGAAATTGAGTAAGTAATTTAATTTTCAAACTATAATC

CCAAGACCAGATGTTTTCATTGGTGAATTCTACCAAACTTTAAAAGGATTAATATCTATTTTTC

ATACACTCTTTCCAGAAAATAGAAAAGGAGGGAACACTCTATAACTCACTGTATGAGGTCCGTA

TTACCCTTATATCAAGACCAAACATCATAAGAAAAGAAGACTAAAGACTTATGGTTTCTGCTCT

GATATGTTTGGAAGTCATCACTACTATTGTCACAAGGAAAAATCTGAACAAACTAAAGTCAACG

ATTTCTTAAACTAACCATAGAATTGAGGTAACGGGCGAAAACTGGAGATGTAGGCAAATACAAA

AAAAATCACAGTTTATCAGGAGCAGAAACTGCTGAAACCAGCAACTCGTATGAACATGTTAAGT

GGTAATTGACAAATTTCTGGAGATTGAATGTGGACTGGATTGAGAGTTAGGAACTCCTAAGTGC

CCAGTTTTTGATGACCCCACACACTTTTGTAAACTAGACTTCCAAGAGCCCCAGCAAGTTTCTT

ACAGTGAAGACTGCAGAAAAATCCCCTGATGCTTCAGATAGGAGGAAGGGAAAAGCAACTATTT

TGAAATAAGCCCAGGGGACAAGTAGTTATTTCTAAACACTCTCAGAGCATTTTCTTTCACACGG

CAGGGGGCTCCCTGCAAGGGAAGCTACTTTGCCTGAGCCTTGTCTGATGTAGGAGAAAAGGAAT

TGGATGGCTCAAGCTCCATCTAGCCTTTCTGATTTATATAAGGGAAGCAAAAAATAGGTTAAGA

AACTCTTCTGAAAGTCACAACTCAGATTTATTTTATATTTATTTATTTATTTATATTTTTTGAG

ACGGAGTCTCGCTCTGTTGCCCAGGCTGGAGTGCAGTGGCGCGATCTCGGCTCACTGCAAGCTC

CACCTCCCGGGTTCACGCCATTCTTCTGCCTCAGCCTCCTGAGTAGCTGGGACTACAGGCGCCC

AGCTAATTTTTTGTATTTTTAGTAGAGACGGGGTTTCACCACGTTAGCCAGGATGGTCTCGATC

TCCTGACCTCGTGATCCACCTGCCTCTGCCTCCCAAAGTGCTGGGATTACAGGCGTGAGCCACC
```

-continued

GCACCTGGCCTCACAACTCAGATTTAACCATAAGATTATAGAACACTTCTCCTCCCAAAACAGA

GATATAGATCAATGGAACAGAACAGAGCCCTCAGAAATAACGCCGCATATCTACAACTATCTGA

TCTTTGACAAACCCGAGAAAAACAAGCAATGGGGAAAGGATTCCCTATTTAATAAATGGTGCTG

GGAAAACTGGCTAGCCATATGTAAAAAGCTGAAACTGGATCCCTTCCTTACACCTTACACAAAA

ATTAATTCAAGATGGATTAAAGACTTAAACGTTAGGCCTAAAACCATAAAAACCCTAGAAGAAA

ACCTAGGCATTACCATTCAGGACATAGGCATGGGCAAGGACTTCATGTCTAAAACACCAAAAGC

AATGGCAACAAAAGACAAAATTGACAAACGGGATCTCATTAAACTAAAGAGCTTCTGCACAGCA

AAAGAAACTACCATCAGAGTGAACAGGCAACCTACAAAATTTTCACAACCTACTCATCTGACAA

AGGGCTAATATCCAGAATCTACAATGAACTCAGACAAATTTACAAGAAAAAAACAAACAACCTC

ATCAAAAAGTGGGCAAAGGATATAAGCAGACACTTCTCAAAAGAAGACATTTATGCAGCCAACA

GACACATGAAAAAATGCTCATCATCACTGGCCGTCAGAGAAATGCAAATCAAAACCACAATGAG

ATACCATCTCACACCAGTTAGAATGGCGATCATTAAAAAGTCAGGAAACAACAGGTGCTGGAGA

GGATGTGGAGAAATAGGAACACTTTTACACTGTTGGTGGGACTGTAAACTAGTTCAACCATTGT

GGAAGTCAGTGTGGCGATTCCTCAGGGATCTAGAACTAGAAATACCATTTGACCCAGCCATCCC

ATTGCTATATATATATATATATACCCAAAGGACTATAAATCATGCTGCTATAAAGACATATGCA

CAGGTATGTTTATTGCAGCACTATTCACAATAGCAAAGACTTGGAACCAACCCAAATGTCCAAC

AATGATAGACTGGATTAAGAAAATGTGGCACATATACACCATGGAATACTATGCAGCCATAAAA

AAGATGAGTTCATGTCTTTTGTAGGGACATGGATGAAATTGGAAATCATCATTCTCAGTAAACT

ATCGCAAGGACAAAAAACCAAACACTGCATGTTCTCACTCATAGATGGGAATTGAACAATGAGA

ACACATGGACACAGGAAGGGGAACATCACACTCTGGGGACTGTTGTGGGGTCGGGGGAGGGGGG

AGGGATAGCATTAGGAGATATACCTAATGGTAAATGACGAGTTAATGGGTGTAGCACACCAGCA

TGGCACATGTATACATATGTAACAAACCTGCACATTGTGCACATGTACCCTAAAACTTAAAGTA

TAATAATAATAAAAAAAGGCTACCTAAAAAAAAAAAAAAGAACACTTCTCCTCCCAACACCATA

TCACCACATCAACCAGGACTCCAGTGTAATAGCAGTGAATTCTAACTGAAAGAGGTGAAAGACA

CTGATTGTATTTAAGAAAGATCTTCTAAGGAAATCCAAAAATAGTAGGGGAGATCAAAACAAAG

ATACTAGAGGAAATTGAATATGTGACACCTATAGCTACAAAAAAATTAAACATAACATAGCCCT

AACCATATAAACATAAAACCTCACACAAAGACCTATTATCTGAGATTCTGTTGCCTGATACATT

GCGTTTTATTTCAATAAAAAAATTAGAGGGTATGTTAAAAAGCAGGAAAAGTTAGTCTAAAGAG

ACAAATTGAGCCTCAGAAGTAGGCTCAGATATGGCAGAGATTTGGCAATTATACCTAGAGTTTA

ATATAAATGATTAATATAATAAGTGTTCTAACAGAAAAAGGCAACATGCAAGAACGGATGGGTA

ATGTGATCAGCAAGAAGGAAACTCTAAGAAAGAAGTCAAAAGGAAATGCCCTTAGGAATAAAAA

ACAAGAAATAAAGAATGCCTGTGATGGGTTCCTCAGTAGACTGGACAAGGTCAAAGAATCAGTG

GATTTGAAAATATGTCAACAAAAACTGCCCCACTGAAATACAAAAGAAAAATAGAATTTTAAAA

ACGTAACACAATCTCCAAAACAGTGGGACAATTACAAAAGATGTAATGTGCCTAATGCAAATGA

CAGTAGGAGTATAAAGGGAGAAAGGAATAGAAAATCTGAAGTAATAATGGCAGAGAGTTTTCCA

AAATTAATGCTAAACCACAGATACAGCAAGCCCAGAGAACAACAAGGAGGAAATTTAGTAAAGC

GTCTGCAACCAAGTATGTCATATTCAGACTGACAAAACCAAAGGTGAAGAGAAAATATTGAAAG

AAGACAAAGAGGAAAATAAATATCAAGAAAATACATACGAAATACATCATACATACATAAGAAA

TACATCAGACCATACAAGCAAGAAGAGAATGGAGTGAAATGTTTAAAATGTTGAAAAAAAAACT

ATCAATTTGCAATTCTGTATCCAGTGAGATTATCTTTCAAAAGTGAAGAGGGAAATGGCAGAGA

-continued

AGTCATCTCCAAGACCTATGGTTTCCCTTCACAGAAACACTGAAAAATATGAACAAAAGTGGTC

AGAATTAACTTTCTAAGAATTCTATAAAATGGTAAAATGTTTACACCAGTAAAGCAAATGCTGA

ATTGAGAAGGCAACTTAAAAAGGTGAAGAAAACTTCGTATTATTTTTATGTGTCCTTGCCCCAC

GTCCTTCCCTACCTTAGTCTTGAAGATGGCAGCCCACATTTCTACTGTGGGGCTCTGGTTTCTG

TTTCCTGGTTCAAGAGGGAGAATAACAGACCTTACTTTTAGTCATTATTATTTCCTTCTTTCTG

ATTTCCTTGGGTTTATTTTGCTCTTCTTTCTACTTTATTGAAATGAGAACTAAGATTATGATTT

GAGACATTTTTCTAATGTAAGCATTTAGTGCTATAAATTTCCATCTCAACACTGCTTTAGTCAC

ATCCCACAAATTTTTATATGTTGTAATTTCACTTTCATTTAGTTCTATTTTTAAATTTTTTCTT

TTTATACTTCCTCTGACTCACAGATTACTTAGAATTGTGTTGTTCAGTTTTCAAGGATATTGTA

GATTTTCCTGTTTCTCTGTTGTCTAATAGTTCTGTTCCATTTTGTACAGATAGCTCACGCTGTA

TGATTTCAATTTTTTAAAAAATTGTGCTTTGTTTTATGGCCCAGATATGGTCTGTGCTGTGAAT

ATTCCATGTTATTATAAAGTATGCCTGTTATATTATTATATATATATAATATATATATAATTATAA

AGCATGCCCGTTTTGTATTGTTAGCAGAGTATTCTAGAAATGTCAATGAGATCTTGTTGGTTGA

TGGTGCTTTTCAGTTCTATATCTTTGCTAATTTTTTTTTTTTTTGCTTAGTAGCTATATGAGAT

TCTGAGAGAGGAAATTGAAGTCTCCAACCATAATTGTGGATTTGTCTATTTCTCCTATCAGTTC

TATCAGTTTGTGCATCACATATTTGAGGCTCTGTTGTTTGGTGCATACACAAGTGGAATCATTG

TGCCCTCTTGGTGGCTTATTTTATGATTATATAGTGCCTATCTTTGTGGTATTTTTATTTGCTC

TTAAATCTACTTTGTGTTATATTCATATACCCATTCTTTTTTAAAAAAAATTGTTTGCGTGATA

CATCTTTTCCATTCTTTTAATCTCAGCCTATCTGTGCCATTGAATTTGAAGTGAGTTTTCATAT

AGAGAACATATTATTGAATCATCATTTTAAAAATTCCTTTTGCCAATCTTTTTTATACTGAGGT

AAAATTGACATAAAATTTATCATTTTAAAGTGTACAATACAGTGGCATTTGGTAATACACATGT

TATGCAACGTTAACTCTACCTGGCTCCTAAATGTTTTCATCATCCCCAAAAGGAAACTTCATAC

TCATTAAGCAGTTAATTCCCATTCCTTCTCTCGGCCACTGGCATCCGCAAACCTACTTTTCTGT

CTCTATGAATTTACCTATTATGGATATTTTGTATAAATTGAATTATACAATAAGTGACCTTTAT

GTTTGGCTTCGTTCGCTTCGCATACTATTTTTCGATATTCAACCATGTTGTAGTATGTATCAGT

TTTATTTGAATAACTCAATTCTTTTTGTTGTATAGCTAAAAGTTGATTCCTAGGTCATAATGAT

AATTCTATGTTTAGTTTATTGAATAGCTGCCAAAGTTTTTCCACAGTGGCTCTGTCATTTTAAA

ATCCCACTAGCAATGGATGAGAGTTCCAATATCTCCACATCCTTACCAATATTGTTATTTTATA

TTTTTATAATTATAATTTTCCTAGTGAATACGCAATGGTATCTCATTGTGTTTTTGGTTTGCCT

TTCCCTAATGACTAATGATGTTGAGCATCTTACAATGTACTTGTTAACTATTTGTGTTCTTTAG

AGAAATGTCTATTCAAGTGCCTTGTCCATTTTAAAAATCGAGTTGTCTTGTTGACTTATGAGTT

CTTTAATACAGTAAACGCTTATCAGATATGATTTATAAGTATTTTAACCCATTCTGAAGGTCAC

CTTTTCACTTTTGTGGTAGACCATTATGCACAAAGGTTTTAATTTTGATAAATCCAATTTATCC

GCTTTTGTTGTTGTTTTTGTTGTTCGTGCTTTTGCAAAACCTAGTGTCATGAGGTTTTCTCATT

ATCTTTGGAGAATTTTATAGTTTGGGTCTATACATGTAGATTATTGATCTAATTTCCATTAATT

TGTGTGTATGCTACGAGGTAGGGGTCCAAATTCAATTTTTGCATTGAATTGAAAATTCATATTT

TCAGTTTCAAATTTCAACTGCATATTCAGTTGTTGCAGCACAATTTGTTGAAGAGATCATTCTT

TACCACAGGGAATGATCTGGGACCCTTGTCAAAAATCAATTGATCATAGATGTATGGGATTATT

TCAGACTTTAGATCTTGTTCCATGAATATGCCTATTTTTATGCCAGCACTGCAGTATTTTCATT

ACTGTAGCTTTATCATAAATTTTGAAATCAGGAAGTATGTATCCTCCAAGTGTGATTTTCATTT

GCTAGAGTGTTTTGACTATTTGGGGTCTTTGCAATTCCATATGAATTTCAGAATTGGCTTTTCA

-continued

TTTAAAAAAATGGTAGTTGAGATTTTCATAGGAATTATATTGAATCTACAGATCACTTTGGGTA

GTATTGCCATCTTAACAATATTGTATTCCAATCCATAAACACGGATGTATTGCCATTCATATCT

TTTTTTCTTTTCTTTCGGCAACATTTAGTATATGACACTTGTAACTCCTTGGTTAAATTTATAC

CTAAGCATTTTATCCTTTCTGATGCTGTTTAAATGGAATTATTTTATTAATTTCTCTTTTAGAT

GGCTTGTTGCAGGTGTATAGAAATAGAACTGATTATTGTGCTTTTATTGAATTATCTGAAACTT

TGCTGCATTTATTAACTCTAGTAGGTTTTTTTTTCTTTAAAGTTGTCTATATATCTTGCTCTG

TGAATAGATAATTTTACTTCTTGATCTCCAATATGGATGCCTTTCTTTCTTTTTCTTACCTAAT

TGCTGTAGCTAGAATTTTCAGTATAATGTATGATAGAAGTTGTTCACAACTATCCTTGTCTTCT

TTCTGATCCTAGGGGTATAGCTTTCAGTCTTTCACCATTAAGCACAATGTTAGCTGTGGGGTTT

TCTTAGATGCCATTTAATATATTAAGGAAGTGCTCTGCTATTTCTAATTGGTTGAGTATTTTTA

TTATAAAATGGTGTTAGATTTTATGACTTTATGTACTGCATAATTGAGATTATCATGTGGTCTT

TTCATTCGATTAATGTGGTATATTTTATGATTTTCATATGTTGATCCACCTTTATATTCTTGGG

GCAAATCCCACTGTGTACACGGGTTTTTTAGGGTCTCCTAATTTTCTTCATTCTTTTTCTTTTC

TCTCCCTGAGACTGAATAACGTTAACTGACCTATCTTCAAGTTTACTATTTTTTCTTCTGCTGT

TCAAATCTGCTTGAACCTATAGAGTGAATTTTTCATTTTACTTATTGAACTTTTCAGCTCCAAA

ATTTCTCTTTGGCTACTTTGTATAATATCTATCTCTCTATAGATATTCTCTATTTGGAAAGACA

TTTTTCTCCTGGTTTTCTTTACTTATTTGTATTTTTTAAAGTCTTTAAGCATATTTGAGACAGT

TGATTTAAGTATTTGTGTACTAAGTCCATTGCCTAAGCTTTTGCATAGAGATTTTATATTAATT

TCTTTTTTTTCTGTGAACAGGTCTTTTTTTTTTTTTTTTTTTTTTTTTTTTTTTTTAGAAAACTG

GACATTTTGAGTAGTATAAACGTGGCTATTTTAGAAATAATTTTCCTCCCTCCTTAGGTTTTGT

TTCCACTTGTTGCATGTTGCTGTTGTTTGCTCATTAGTGACTTTTCTAAAGTATTTTGAAAAGT

CTGTGTTCTTGATCATGTGGGTCCATTGAATTCTGTATTCTGTTAATTTCATAGTCAGCTAGTG

TTCTGAAAGTTCCCTTAAGTGCATAGAGCCAATAAAAGAAAAAGAAAAGAAACACAGAAAAAGA

AAAGAGGAAAAAAGGAGGGAAAGAGATTTAAAAAAATAATGTCGGTTGGGCATGGTGGCTCATG

CCTGTAATCCCAGCACTTTTGGGAGGCCGAGGCAGGCAAATCACTTAAGGTTGACCATCCTGGC

CAACACGGAGAAACCTTGTCTCTACTGAAAATATAAAATTAGCCGGGCATGGTGGCACATGCCT

GTAATCCCAGCTACTCGGGAGGCTGAGAGGTAGGAGAATCACTTGAACTCGGGAGGTGGAGGTT

GCAGTGAACTGAGATCACACCACTGCACTCCAGCCTGGGCAACAAGAATGAAACTCCATCTCAA

AAAAAAATAATAATAATAATGCCTTTGCCGATTTGCTCTGTGTTTGGGCCCTCATTCAATGCCT

AGTCAGGCCATTTACAACTCTCTCTTAACTTTCACTACCTGCTTGTGTACTGACTGAAGGCCAC

CTATAGGTGAAAGCTTAACATCATCTCAGATCTTTTTGGACCATGAATCCTACCCTGGGTATGC

ACATGATCTTCTTAATTTCCCAGTAGATGCAAGAGTTTTAGTGTTTTAAAAGTCCTTATTCCCT

CATCTATCTTCTTTTCTGACCTTTTTCAGTCTGCTTATTGTTCATCTGAACTGACATCCTTTGC

CCCAAGCGGCTGTGGCAAAAACTTTTACCTTTAAATGCTTTCACCACAAGCCACTTGGGAAGCT

GCCCCAGACCTGGGACTGCTCTGACCCTGATGAAACAAAGACAAGACCTTGTACAGCCAGGCAG

CCATAAGACAAGTCCATACCCAAACCACAGTTCTTTCAGAATAAGGTCTATATTGGATTCTCTG

GCCCTAGTAACCAGCATGAGTCTGGGCTTGCCATCTTCATGGCCACTTGTCTTAGTTTGCTAGG

GCTGCCATAACAAAATATGAGAGACTGAGTGGCTTAAACAAGAGAAATTTATTTTTTCACAATT

CTGAAGACCAGAAGTCCATTACTCTGAAATCTCTCTCCTTGGCTTGCAGATACTGCCTTCTTGC

CGTGTCCTCACACAGCCTTTTCTCTGTGTACACATCCCTGGTGTTTTTTAAGCCTGTCCAAATT

-continued

TTCTGTTCTTCTGAGGACACCAATCAGATTGGATTAGCGACCACCCATATGATCATTTTACCTT

AAGTACCTCTTCAAAGGTATCAGAGTAGTATATTTGCTACAGTTGATGAACCTGCATACAACAT

CATCACTTGAGGTCTGCAGTTTACATTAGAGTTCATCGTTAGTGTTATATATTCTAGGGTTTGT

TTTGTTTTGAGACAGAACAGAGTCTTGCTGTGTTACCCAGGCTGGAGCGCAGTGGTACAATCTC

ATTGCTACCTCTGCTTCCCAGATTCAAGCAATTCTCATACCTCAGCCTCCTAAGTAGCTGGAAC

TACAGGCGCACACCACCATGCCCAGCTAATTTTCGTATTTTTAGTGGAGATGGGGTTTCACCAT

GTTGGCCAGGCAGGTCTTGAACTCCTTGCCTCAAGTGATCTGCCCGCCTCAGCCTCCCCCAGTG

TTGGGATAACAGGCATGAGTCACCATGCCTGGCCTTATTCTATGGGTTTTGAAATGTATAATGA

CATGTATCCATCGTTGTAGTATTAGATAGAATAGCTTCATTACCCTAAAAGTCTTCTTTGCACT

GGGTTGAGTTTTAAAAGCTCTTTGATTATTTTATGACAGTTCCTTATTAGATATATCTTTTGCA

AGTATTTTTATCAGTCTGTGGTTATCTTGTCTTTTACAGAGCAGTAATTTTTAATTTTAATAAA

ATCCAATTTGTCAATTACTTATCTCATATGACTCTGGTGTTACATCTAAAATGTTACCACCATA

CTCAAGGTCACCTAGGTTTTCTCTAGGAATTTTATGGTTTTGCATTTTACATTTGGTGTATGAC

CCATTTGAAGTTAATTTTTGTGAGGTTGTAAGGTCTGTGCCTAGATTCATTTTTTTTTTTTTTG

GCATGTTACTTCAGTATTCATAAGAAACATTGTTCTGTAATCTTCTTTCTTATAGTATCTTAGT

CTTGCTTTAGTTTTTGGGCAATGCTGGCCTCACTGAATAAATTCAAAGTGTTCCCTCCTCTTCA

ATTATTTGGAAAAGTTTGAGAAAGACTATTGTTAACTGTTTTCTAAATTTTTGGTGGAATTTAC

CAGTGAACCAACTGGTCCTAGGCTTTTCTCCAGTAGGTGGTTTTGATTATGCTTTCAATCTCTT

TACAAGTTACACATCTATACAGACTTTTATAATTCAGTCTTGGTAGGTTGTGCGTATTTAGGAA

TCTGACCACTTCATCTAAGTTATCCAATTAGTTGGCATGCAATTATTCGTAGTTCTCTGAATAA

TCATTTTTATTTCCACAAAATTGGTAATATCCCAGTTTCCATTTTTTATTTCATTGAATCTTCT

TTTTTCTTAGCTAATCTAGCTAAATGTTTGCCAATTTTGTTGATCTTTTGGAAGAACCAACTTT

TGATTTATTAATTTTCTCTACTCTTTTTCTGTTCTTTATATTATTTATTTCCACACTAATCTTT

ACTATTTTCTTCCTTCTGTTGGCCTTTAATTTTTTTTTTTTAATTTTTAAGGTGTAAATTTAGG

TTGAGAAATTTTTTAAATGAAAGCATTTAGAGCTATAAATTTTCCTTCTGGTGTTCCTTTCACT

ACCTGCCATAAATTTTGATATGTTGAGTTTTTGTTTGTCTTGGAGTATTTTCTAATTTGTCTTC

TAATTTCTTCCTTGACCTATTGGTTATTTAAATGTATTTAATTTTTGCATATTGTGGATTTCCC

AGTTTTCCTTCTGTTATTGATTTCTAGTTTTATTCCATTGTGATCACAGAAGATATTTTGTATA

ATCGCAGTCTATTAACATTTATTAAGTCTTGTGGCCTAACAGAGGATCTATGTTGGAGAATGTT

CCAAGTGCAATTGAGAATACTATTCTGGTGCTATTAGGTGAAGTATTCTCTATATGTCTGTTAA

GTCCAATTCATCTATAGTGTTGACGTTTCCTGTTCCTTACTGATTTTCTGACTTATTATTCTAT

CCATTATTAAAAGTGGAGTGGTAAAGTCTCTATTATTGTAGAACTCTCTGTTTTTCAAGTCTAT

CAATATCTGTTTCATATATTTTGGAGCTCTGTTTGCTGCATATGTGTTTACAATTGTTATATCT

TCTTGGCAAATTGACCAGTTTCATCAACATAAAATATAATTCTTATTGTCTTCTAACAGTTTAT

TTTTCTTTTTACATAAAGCCTATTTTATCTGATCTTAGATTCCCTCACACTCCACCCCAGCACG

CTTTTGGTTACATTTACATAATATATCTTTTCCATCCTTTCATTTTCAACCTGTTTGTGTCTTT

AGATCTAAAGTGAATGTCTTACAGACAGCATAAGCTATGTCATTAAAAAAAATCCATTCTGCTTA

TCTCTGCCTTTTGACTGGGGAGTTTAATCCATTTGCATTTAAAGTAATCACTGATCATTAAATA

CTTTCAGTATTTTGTTGTTTTATGTATGTCTTATAACTCTTTTGCTCTTCATTTCCTTCAATAT

TGCCTTTGTGTTTAGCTTATCTTTTTGTGTCACACTTTGATCCCCTTCTCATTTCTTTTTTATA

TTTTCTTTGTGGTTACCAGGAGGACAATGTATCAACTTTTAAAGTTATTACAATTTTATTTTTT

-continued

```
TAAATCTCTCCCATTCGGGGATTTTAGGAAGGTTAAATAATAATGTAAATGAGATACCTAGAAC

AATATAAGCATTCAGGAATTATTAACTCAATTCCAATCCTTCCTCCACCTCCACCTCTTTCTCT

GTGAGATTATAGAAAAGATGACAAAAAGGATGTTTTCTGAGCCCTTTAATTGTTGAGAATGATC

TTTGAGAAAAAGAAAAAAAATGAAAGCACTAGGAATGTACAACAGCCTGGAAGTATAATTAAGT

GTAAATTAAATAGATAAAAGTTATAAGCAGAGGAAAGTATAGTAGAACTCAGTATTTAAAAGAG

AATCAATGTGAAAATTATATAAATTTATGTAAAATAAAACTACCAGACAAATCTGATATCCTTA

GGATTTTTCTTTCTTTCATGTGATTTCTAATTGCTACATATGACACTAAACCATTGATCTGAGC

TGTAAGAGAAACTGGAAATTGTTCTGTTATCTTTTGTAAGATTTCTAGAACATTTTGCCCTCAG

ACTTAAATGCCAACGTATTTCTCACTTATTGTTTACTGCTTTTGGATTTACATATGATTTGATT

CTTTCTTATCTCTTATCCTTACAATGTAATTCAAACTGATGCCAATTTAAGTTCAATTGCGTAC

AAAAACTCTACTCCTATGCAGCTCCGCCCCATCTAATTTACATTATTGATGTCGCAAATTCCAT

CTTTGTACATAGTTTACATATTAACATGGATTTATACATTTTTATGTATTTGGTTTTTAAATCC

TGTAGAAAATAAAAAGTCAACACACCAATATTAAAATAATACTGGTTTTTATATTTGTCCATGT

GCTTACCTTTATCAGTGTTCTTTACATCTTTATACGGGTTTGAGTTACTGTCTTGTGTCCTTTA

GTTCCAACCTAAAGAACTCCCTTTAGCATTTTTATAGGGCAGGTCTAGTGGTAATGAACTCTCT

GAGTTTTTATTTAGGGATGTCTTAATTTCTAGCTCCTGTTTGAAGTAAATTTTTCTGGATATAC

AATTCTCTGTTGATTGATTTTTGTTCATTTTCCCTTCAGCTCTTTTAAATACATTATCCCACTT

TCTTCTGCCTTCCAAGGTTTCTATTAACAAAATTCAGCTTATAATCTTATTAAAGATCTCATGT

ACATGAGTGGCTTCTCTCTTGCTGTTTTCAAGATTCTGTGACTTTGGTTTCTGATAGTTTAAAT

ATAATGTGTCTTATTGTGGGTCTCTTTGGATTTATCCTAGAGTTTCTTGGTCTTCTTACGTTGG

TATATCCATGTATTTCAAGACATTTGAGTAGTTTTCAGCCATTATTTCTTCAAACAATCTCTCC

TCTTTGGGGACTTCCATTTTACCTATATTGGTTCTTTTGATGGTGTGGCACCAGTCCCCTAGAC

TTTGTTCACTTTTTTCCAGTCTTTTATTTCTGCTTCTCAGACTCAACAGCTTCAAGTGTTCTGT

ATTCAAGTCTGCTGACTCTTTCTTCTTCCAGCTCAAATCTGCTGTTGGATCCCCCCTTGTAAAA

TTTTTAATTCCATTTTAGTGTTTTTCAAGTTAAGTATTTTTATTAGGTTCCTTTTTATAATTTC

TTTTTGTTGATATTCTCATTTTATTACACATAATTTGTCTGATTTCCATTAGTTTTTTTCTTTG

TTTTCCTTTAGCTCTTTGAAAATATTTAAGACATTTTAAAAGTCTTTATCCAAGTTCAATTTCT

ATGGTTCTGTAGAGATATTTTCTGCCAGTTTATGTTCTTCTTTTCCATGGGCCATGTTTTCCTG

TTTCTTTGTATACTTTCTAATTTTTGGTTGAAAACTGAGCATTTGAAAATAGAGCCAACTTTCC

CAGTTTCTGCAGAGAGTCTTTATGCCACAGTATTCGTTCACTGATTAACTGGGTATATCTAAGC

TTAGGGAGCAGCTGAGTCAAAAGTTTAAGGTCTTCTCAGGTCTTTTCTGAGTATACATGTTTCC

TATGCCTGTGTGAAATGTTCTCAATTTCCCTATATAAACAGCTACTTCTTCTTTTTTTTTTTTT

TTTGAGATGGAGTCTCGCTCTGTCACCCAGGCTGGAGTGCAGTCATCTCAGCTCACTGCATCCT

CCACCTCCCAGGTTCAAACAATTCTCCTATACAGGTGTGTGCCACCACGTCTGGCCAATTTTTG

TATTTTTAGTAGAGACAGGGTTTCGCCGTGTTGGCCAGGCTGGTCTCAATCTCCTGACCTCAGG

AGGATTACAGGCTTGAGCCACAGTGTCCAGCCTAAACAGCTACTTTTGAATGCTTTAATTTCCT

GAATAGTCTCAACCCAGTTTTTCCTTGAGGTCTTAGGTGGTCCATTGTATGTCTCCACCCATAG

TTGCTTGCCCCAGGCATCTGTGGGTCTGTGGTACCACTGCAGCTTTCACCACCTGTAGCTGCCA

CCTTTCCCTATCTGAGATCCAGGTTAGGTGAGAGAGATCATTCCTTCACGCAGTCCCATGACAG

GTTGGAACATTTCAAATAAGGTCTGTTCTGCTCCTCTGGTTGAAGGGAGAAAATTGGGAACCGG
```

-continued

TTTCCCACCTTCTACAAACCAAGATCTCATGTTGCCACGGGAGTGGCAGGGCAAGTGCAAGTGA

AAATGCCATACAATTTTCTACCATTTTGAACGCGGGTTTTTCTTCAATGGTCATTTGCTTGGTT

GCTGTAGGCCTTTCACTGTTTTCCAGAGCTCCCATAAGATTACTTTAGCCAGTTTTTTGTTCTT

TCCTGATGCTTCCCTGGCAGAGTAAGGGTTGGAACTTCCACCATTTTGCTGATTCATAACTCTG

TAGTCAGTTTTAAATATATTGATACTTGAGTTTGTTTTATGGCCCAGAATATGGTCTTGGTAAA

TGTTTCACATATACTCAGAAAGAATGTGTATTCTGATGTTGTTACATGGGCTGTTCTATAAATG

TTACTTAAGGTGGTTAATAATGTTGCTCAAGTCTTCTATATTCTTGCTGATTTTCTTTTATTTA

TTTATTTTATTTTTTTTATTATACTTTTAAGTTCTAGGGTACATGTGCACAACATGCAGGTTTG

TTATATATGTATACATGTGCCATGTTGGTGTGCTGCATCCATTAACTCATCATTTACATTAGGT

ATATCTCCTAATGCTGTCCCTCCCTGCTCCCCCCACCCCATGACAGGCCCCAGTGTGTGATGTT

CCCCTTTCCTGTGTCCAAGCGTTCTCATTGTTCAATTCCCACCTATGAGTGAGAACTTGCGGTG

TTTGTTTTTTTGTCCTTGTGATAGTTTGCTGAGAATGATGGTTTCCAGCTTCATCCATGTCCCT

ACAAAGGACGTGAACTCATCCTTTTTTATGACTGCATAGTATTCCATGGTGTATATGTGCTACA

TTTTCTTAATCCAGTCTATCATTGATGGACATTTGGGTTGGTTCCAAGTCTTTGCTATTGTGAA

CAGTGCTGCAATGAACATACGTGTGCATGTGTCTTTATAGCAGCATGATTTATAATCCTTTGAG

TATATACTCAGTAATGGGATGGGTGGGTCAAATGGTATTTCTAGTTCTAGATCTTGAGGAATCA

CCACACTGTCTTCCACAATGGTTGAACTAGTTTACAGTCCCACCAACAGTGTAAAAGTGTTCCT

ATTTCTTCACATCCTCTCCAGCACCTGTTGTTTCCTGACTTTTTAATGATCGCCATTCTAACTG

GTGTGAGATGGGATCTCATTGTGGTTTTGATCTGCATTTTTCTGATGGCCAGTGATGATGAGCA

TTTTTTCATGTGTCTTTGGCTGCATAAATGTCTTCTTTTGAGAAGTGTCTGTTCATATCCTTTG

CCCACTTTTTGATGGGGTTGTTTTGTTCTTGTATATTTGTTTGAGTTCTTTGTAGATTCTGGAT

ATTAGCCCTTTGTCAGATGAGGAGATTGCAAAAATTTTCTCCCATTCTGTAGGTTGGCTGTTCA

CTCTGATGGTAGTTTCTTTTGCTGTGCAGAAGCTCTTTAGTTTAATGAGACCCCATTTGTCAAT

TTTGGCTTTTGTTGCCATTGCTTTTGGTGTTTTAGACATGAAGTCCTCGCCCATGCCTATGTCC

TGAATGGTATTGCCTAGGTTTTCTTCTAGGGTTTTTATGGTTTTAGGTCTAACATTTAAGTCT

TTAATCCATCTTGAATTAATTTTTGTATAAGGTGTAAGGAAGGGATCCAGTTTCAGCTTTTTAC

ATATGGCTAGCCAGTTTTCCCAGCACCATTTATTAAATAGGGAATCCTTTCCCCATTTCTTGTT

TTTGTCAGGTTTGTCAAAGATCAGATGGTTGTAGATGTGTGGTATTATTTCTGAGGGCTCTGTT

CTGTTCCATTGGTTTATATCTGTTTTGGTACCAGTACCATGCTGTTTTGGTTACTGTAGCCTCG

TAGTATAGTTTGAAGTCAGGTAGTATGATGCCTCCAGATTTGTCCTTTTGGCTTAGGATTGTCT

TGGCAATACAGGCTCTTTTTTGGTTCCATATGAATTTTAAAGTAGTTTTTTCCAATTCTGTGAA

GGAAGTCATTGGTAACTTAATGGGGATGGCATTGAATCTATAAATTACCTTGGGCAGTATGGCC

ATTTTCACGATACTGATTCTTCCTATCCATGAGCACGGAATGTTCTTCCATTTGTTTGTGTCCT

CTTCTATTTCGTTGAGCAGTGGTTTGTATTTCTGCTTGAAGAGGTCCTTCACGTCCCTTGTAAG

TTGGATTCCTAGGTATTTTGTTCTCTTTGACGCAACTGTGAATGGGAGTTCACTCATGATTTGG

CTCTCTGTTAGTCTGTTACTGGTGTATAAGAATGCTTGTGATTTTTGCACATTGATTTTGTATC

CTGAGACTTTGCTGAAGTTGCTTATCAGCTTAAGGAGATTTTGGGCTGAGACGATGGGGTTTTC

TAAATATACAATCATGTCATCTGCAAACAGGGACAATTTGACTTCCTCTTTTCCTAATTGAATA

CCCTTTATTTCTTTCTCCTGCCTGATTGCCCTGGCCAGAACTTCCAACACTATGTTGAATAGGA

GCGGTGAGAGAGGGCATTCCTGTCTTGTGCCAGTTTTCAAAGGGAATGCTTCCAGTTTTTGCCC

ATTCAGTATGACATTGGCTGTGGGTTTGTCATAAATAGCTCTTATTATTTTGAGATATGTCCCA

-continued

TCAATACCTAATTTATTGAGAGTTTTTAGCATGAAGGGCTGCTGAATTTTGTCGAAGGCCTTTT

CTGCATCTATTGAGATAAACATATGGTTTTTGTCTTTGGTTCTGTTTATATGATGGATTATGTT

TATTGATTTGTGTATGTTGAACCAGCCTTGCAACCCAGGGATGAAGCCCACTTGATCATGGTGG

ATAAGCTTTTTGATGTGCTGCTGGATTCAGTTTGCCAGTATTTTACTGAGGATTTTTGCATCAA

TGTTCATCAGGGAAATTGGTCTAAAATTCTCTTTTTTTGTTGTGTCTCTGCCAGGCTTTGGTAT

CAGGATGATGCTGGCCTCATAAAATGAGTTAGGGAGGATTCTCTCTTTTTCCTATTTACTGTAC

ATTTATTCCACCAGTGACTAAAACAGGTGTATCAATAAAATCTGTTCCCTCAGGTTTTGCTTCA

GGTATTTTGAGGGTCTGTTATCAGGTGCATAAACAAGATTGTTATGTCCTATTCTTAAATTAAT

CTCCTTATAATTATGAAGTTAATTTTTTTTTTCTTGAGATGCAGTTTTGCTCTGTCGCCCAGGC

TGGAGTGCAGTGGCACAATCTCGGCTCAGTGCAACCTCTGCCTCCTGGGTTCAAGCATTTCTTT

GCCTCAGCCTCCCGAGTAGCTGGGGTTACAGGTACCTGCCACCACGCCCGGCTAATTTTTTTGT

ATTTTTAGTAGAGATGGGGTTTCACCATCTTGGCCAAGCTGGTCTTGAACTCCTGAACTCTTGA

TCCACCCACCTTGGCCTCCCAAGGTGCTGGGATTACAGGTGTGAGCCACTGCGCCTGGACCTGG

CCCGAAGTAAACTTCTTTACCCTTGCTAATGATCTTTGCTCTGAAGCATGCTTTGCTGGTATTA

ATATAGTCATTCCTTCTTTCTTTGATTCATGTTTGCAGGGTATATCTGTTTCCATTCTTTTACT

TTTAACCTATTGTCTTTATATTTAAAGTGCATTTCTTGTAAGTATAATTGGTTTCTTAAAATCC

AATTATCTGCCTTTTAAATGTCATTTTTATATGATTTGCATAAATATGATTATTATTACAGCTA

AATTGAAATCTGTCATCTTGCTATTTGGTTTCTATTTATCCCATTTTTTTCCCCTCTTTTTTTG

CTTTCCTTGAGATTGAACATTGTATTAGTTTTCTAGGGTTGCTGTAAGAAAGTGACATAAAGTG

GATGGCTTAAAACAACAGAAATTTATTGTTTCAGTTTGGAGGCTAGTCATCTGAAACCAAGGTG

TCATCAGGGCCGTATTCTCTCTGAAACCTGTAGGGAAGAATTCTTTCCTGCCTGTTCTAGCTTC

TAGCATTTTCCAGCAATTCTTGGCATTCCTTTGCTTGTAGATGTATCCCTCCAATCTCTGCCTC

TATCATAACATAGCCATCTTCTCCCTTTATCTGTCTATTCTTCTCATCTTATAAGAACATTAAT

TACTGAATTGGGGCCCAGCATAGATTAGGCCTAATCTCATCTTGAATAGGTTACATCTGCCAAA

GATTCTTCTTCCAAATAAGATCACTTTTACAGCTTTTACAGGTACTGAGAGTTAGAACCTCAAT

ATATCCTTTGGTGGGGACCGACCTCTTACCCATAAAAAGTATTTTATATGATTCCATTTTATCT

CCTTTTTAGGTTATTAACTACAATTTTTTTTTCTTTTTTTTGAGATGGAGTTTTGCTCTTGTAG

CCCAGGCTGGAGCGCGATTTTGGCTCACTGAAACCTCTGCCTCCCGGGTTCAAGTGATTGTCCT

GCCTCAGCCTCCTGAGTAGCTGGGATTACAGGCATGTGCCACCGTGCCTGGCCAATTTTTGTAT

TTTTAGTAGAAACAGGGTTTCACCATGTTGGCTAGGGTGGGTCTCAAATTCCTGACCTTAGGTG

ATCCACCCACCTCGGCCTCCCAAAGTGCTGGGATTACAGGCGAGAGCCACCACGCCTGGCTTTA

TAATTTTTTTTTAATTCAGTGGATGTTTTAGGGTTTATAGTATACATCTTTATCACAGTCTAGC

TCCAAGTGATATATCCCTTTATGTATAGTACATGACCCTTACAGTAGTGCATTTCCATTTTTCC

TCTCTGGCATTTAGGCTATTGCACACACATACACTCAATTCATCCCTTTGTGTAGATCCGTATT

TCCAGCTGCTATCTTTTGCTTCTGTCTGAAATATATGTATGATTTCTTTTATGACTATTTTGAG

AAATTTGGTTATGTGCATTTGTCTATTTTTCTTATGTACTTTTAGCTCATCAATCTTAAGTCTG

TGAGTTTATAGTTTTTAAAAACAAATTTGAAATTATTTGGCTATTATTTCCTCAAATATTTTTT

TCTGCCGCCCCTGCTTTCCCTTTCCTTAGGGATCTCTGATTTCCACCTATATTACTCTGATTGA

AGTTGTTCCACGTCTCTTTTGAAAATCTCTGAAAAATCTTTTATCATTTGGATAATCTGTATTT

GTACATCTTCAAGTACATTAATATTTTCTTTTGCAATGTTTAATCTGCTGTTAATCCCATGTAG

-continued

TGGATTCTTCATCTCAGGTATTGCTGTTTTAATCTCTAGAAATTCCATTGAAGTCTTACTTGAT

GAAAAAGGCAGATAAAAACAAATGTTGGCAAAGATATGGAGAAATCAGAATCTGCACACACTGA

TGATGGGAATGTAAAATGGTCAAGGCAATTTGGAAAGCAGTCTGGCAGTTTCTCAAAAGGCTAA

ACGTAGTTCCCATATGACAGCAATCATTCATCTAGGTATATACTCCAGAGAAATAAAAACATAT

CCACACCAGAACTTGAACATTAATTTTCATAGCAACATTATTCCTAGGGGTTTAAAATTTTTTA

CATTATTTTTATTTAAAATAGAGACAGGGTCTCACTACGTTGCATAGGCTGGTCTGGAACTCCT

GGAATTAAGCATTCCTCCTGCCTTTGTCCTGTTTTCTCCACTGGAAAAGAATAAAACTTTGTAC

ACTTGGACTAACAACTCCCGATTCCCTCCTTTACCAACATGCCCCACAGCCTCTAGTAACTTAC

TCTCTACTTTCATGAATTCAACTTTTTTAAGATTCCACATATAAGTGAGATCATACAATATTTG

TCTTTCTGTGCCTGGCTTATTTCTCTTAGCATAATGTCCTCCAGATTCATACATGTTGTCTTAA

ATGACAGGATTTACCTTCCTTTAAAGGCTGACTAGTACTTCATTGTGTATATGTATCACATTTT

CTTTATCCACTTATCTGTTGATGGGCACTTAAATTGTTTCAATGTCTTGGCTACTGTAAGTAAT

GCTTCAATAAACATGGGAATGAAGATATCCCTTCAACATATTGATTTCTGTTCTTTTGGATAAT

ACTCAGAAGTGAGATTACTGGATCATATGGTTGTTCTATTTTTTTCAGAAACCTCCATACTGTT

TTTCATAGCGGCTGTACTAATTTACATTCCCACTAACAATGCATGAGTTCACTTTTCTGGACAT

CCTCCCCAACACTTGTTATCTTTCATCTTTTTCATAAAAGCCATTATATAATAGGTGTGAAGTG

ACATCTCACTGTGGTTTTGATTTGCATTACTCTAATAATTAGTGTGAGCATTTTTTTTTTTTCA

TGTACCGAATGTCTTTTGAGAAAGGTCTCTTCATTCCTTTGCCCATTTTAAAATCAGGTGGTTT

TCTTGCTCTTGAGTTGTTTGAGTTCCTTATGTATTTTAGATATTTACCCATTTCCAGATATATC

ATTTATATTTTTTCCTATTCTTTGAGTTCCCTCTTCACTGTGTTGTTTCCATTGCTGTGCAGGT

CTTTTATTTTGATGCCACCCCATTTGTCTATTTTTGCCATGCTTTTGCAGTCATATCCAAAAAA

ATCATTCCCAAGACCAATGCTGTGGAGATTTCCCCCTATGTTTTCTTCAGTAGGTGTACAGTTT

TAGGTCTTATATGTTAAGTTTTAAATCTATTTTTTTATATGGTGTAAATAAGGGTCTAATTTAA

TTCTTTTGCATGTGGATATCCAGTTTTCCCAACACCATTTATTGAAGACCCTGTCCTTTTATAC

TTTTCAGTATGCAGATCTTTTACCTCCTTAAATTTACACCTCAGTATTTAATATTTGTTGCTAT

TATGAGATTTTCATAATTTCCTTTTCAGATAGCTCATTAATAGTAGATGGAAACACTACTGATT

TCTGTAAGATGATTTTGTATTACGGAACTTTACTGAGTTTGTGTATCAGTTCTACCAGGTTTTA

GTTTTGTTCTGGTGGAGACATTACAGTTTTTTGTATATGGTTATGTCATCAGTAATTACAGATG

ATTTAACCTATTCCTTTCCTATTAGGATGCCTTTTTTTTCTTTCTCTTGTCCAACTGCTCTGGT

TAGGACTTCTAGTACTATGTCAAAAAGTGATGAGGGTCGTACATGGCCTCCATACCTAATCTGT

TGAGAGTTTTTACCATGAAACCAGGTTGAATTTTGTCAAATGCTTTTTCTGCATCCATTGAGAT

GATCATATGATTTGATTTACACCCTCCATTTTGTTATGTGGTATATCACACTTTTTGATGTGCA

TATGTTGAACCACCCTTGCATCCTAAGGATAAATCCCACTTCATCATGGTGAATCATTCTTTGT

ATTCGTGAATCCAGTTTGCTAATATATTGTTGAGGATTTTTGCATCCATGTTCATCAGGGATAT

TACTTTGTAAGTTTCTGTCCTTAAAGTGTCTTTCTCTGGCTTTAATAACAGTGTAACACTACCC

TTGTAAAATGAATTTAGAAGTATTCCCTCTGCTTCATTGTTTTGGAAAAGTTTGAGAATTTTTA

TTAGTTCTTTAAATGTCTGGTAAAATTCAGTAGTGAAGCTGCCTAATCCTGGGCTTTCCTTTGG

TGGGATACTTTTTATTACTGGCTCAATCTCTTTTCTTGTTATTGGCTTATTCAGATTTGTTTCT

TCATGATTCACTCTTTGTAGGTTGTATATGTCTAGGAATTTATTCATTTCTTTAGGTCATCCAA

TTTGATGGTGCATAACTTCATAGTAGTTTCTTATAATCCTTTGTATTTTGGTGATATCAGTAGT

AAATGTCTCCTCTTTCATTTCTGATCTTATTTGAGTACTCTTTTTTTCTCCTAGTCTAGGTAAG

-continued

AATTTGTTGATTTTATCTTTCAAAAAAAAAAAAAACCAACTCTTAGCAACTCTTAGTTTTGTTC

ATTTTTTTCCAGTCTTTATTTCAACTGTGATCTTTGTTACTTACTTCTTTATGCTAACTTTCGG

GCTTAGTCTGTTCTTTTCCTAGTTCCTTTAGGTGAAAAGTGAGATTGTGATCCTTCTTCTTTAT

TGGCGTAGGTTTGTATCGCTATAAATTTCCATTAGGACTGATTTTGCTGCATCACATAAGTTTT

GTTTCCATTTTCATTTGTCTCAAGGTAATTTTTTATTTACTTTTTGACTTCTTCTGTGAACTAT

TAGTTGTTTGGGAGCATATTGTTTAATTTCCACATATTGCTGTATTTTCCACCAGAATTGATTC

TTGTTCTTGATTTCTAGTTTCACGCCATTGTAATCAGAAAAGGGATTTGATATGATTTCTGTCC

ACTTAAACTTAAGATTAGTTTTGTGGACTAACATATATCCTGGAGAATGTTCCATGGGCATTTG

AGAACAAAATGTATTTTGCTGCTTCTGGATGGAATGTTTCATATATGCCTGTTAAGTCCGTTTG

GTCTAAAGTGTAATTGAAATCCATTGTTTCTTTATTGATTTTCTGTCTAGGTGATCAATCTGCC

CATGGTGAAAAGTAGAGTATTGAGGTCCCGTATTATAGTATTGCAGCCTATCTCCCTCTTCACA

TCATTTAAAAATTGCTTTATGTATTTAGGTGGGTCAATGTTGGGTGCATATACTTTTACAATTG

TTATGTCTTCTTGGTGAATTAATCCCTTTATCATTATATAACAAACTTCTTTCTTTTTATAGTA

TTGACTTAAAGTCTATTTTGTCTGATAGAAGTATAGCTACCCCTGCTCTCAATTTCCATTTATA

TAGAATATCTTTTTCCATCCCTTCACTTTCAGTCTATGTGTATGTTTAGTAGAAAAGTGAATCT

CTTGCCGGGCGCAGTGGCTCACTCCTGTAATCCCAGCACTTTGGGAGGCCAAGGCGGCGGGATC

ACCAGAGGTTGGGAGTTAGAGACCAGCCTGACCAACATGGAGAAAACCTGTCTCTATTAAAAAT

ACAAAATTAGCCAGGCGTGGTTGTGGGCCCTTGTAATCCCAGCTACTCGAGAGGCTGAGGCAGG

AGAATTGCTTAAACCCGGGAGGTGGAGGTTGCGGTGAGCTGAGATCATGCCATTGCACTCCAGC

CTTGACAATAGCAAAACTCCGTCTCAAAAAAAGAAAAAGAAAAAGAAAAAAAAGTGAGTCTCTT

ATAGGCAGTATGTGGTTGTGACTTAAAAAAAAAAAAAAATCCATTCTGTCATTCTATGTCTTTT

TGTTGGAGAATCTAATCCGTTTACATTCAAGGTAACTATTGGTAAGAAACTGCTAGTGTCATTT

TGTAATTTGTTTTCTGATTGTTTTGTAGGTCCCTTGTTTCTTTTTTCCCTATTGCTACCTTCCT

TTGTGGTTTGGTGGTTTTCTGTGGTGGTGTGCTTTGAATCCTTTCTTTTATAGTATATGCGATT

ACCATTGTATTTGCTGTAAGGCTAACTTAAAACATTTTATCCTTAGGCTACTTTAAGCGATAAA

AACTTGCCTTTAGTTGCATACAAAAACTCTACGCTTTCACAACCCCCCCGCCTTTCGTGATTTT

GATGTCAAAGTTTACACTTTTTTAAATTTGTATCTCTTATTGTAGCTACAGTTACAATTACTTC

TTGTAGCTACAACTTATTGTAGCTACAGTTGTTTTTAATAGTTTCATCTTTTAAACCTCCTAAT

AGGAATAACATTGCTTTACCTGCCACCTTTACAATACTAGAGAATTCTGACTATGAATTACTTA

TACCATTTAGTTTTTTACTTTTATGTTTCTCATTAACTAGCAGTCTTTTATTTAAGCCTAAAGA

ACTCCCTTTTAGTAATTCCAGTAGAGCAGGCCTAGTAGTGACAAACTCCCTTAGGCATTGTTTA

TCTGGAAAAGTGTTTATTTCTCCCTTTGCCAAGTAAAGTATTCTTAATTAACAGCTTTGTTTCC

TTCAGCACTTTGAATATACCATCCCACTCTCTACTGGCCTGTAAGGCTTTTGCTGATAAAGCCA

CTGAATCTGTATTGGGGCTACCTTGAATGTGATGTTTCTTATCTTTGCTGCTTTCAGTATTCTT

TGTCTTTGATTTTTGATAACTTGGTTGTGATGTGTCTTGGTGAACTCTTTAGGTTGAATCTGAT

CGGTGACCTCAGCTTCCTGTTCCTGAATTTTGTCATCTTTTCTCAGATTTGGGAATTTTTCAGC

TATTACTTCCTTAAATATGCTTTCTAGGCCTTTTTCTTTCTTTTCTCCTTAAGGACCTCCTATT

ATGCAAAAGTTAGCTAGCTTGATGTGTCCTGTAATTCTTATAGGCATTCTTTTTTGTTTTTGTT

TCTCATTGGATAATTTCAAATGTCTTACCTTTGAGCTCATTGATTCTTCTGCTTGATCAAGTCT

GCTGTTGAAGCGTTCTACTTAGATTTTCAGTTCAGTTACTGTATTCTTTATCTTTAGAATTTCT

-continued

ATTGTTTTTGTTTATATTTGTTAAACTTCTCATTCTGTTCAGATGTTGTTTTCCAAATTTCATT

TTTCTATCCATATTTTCTTGTACTTTGTTGAACTTAAGAGGATTAGTCTAAATTATTTGTCATT

TCACAGGTCTCCATTTCTTCTGAGTCTGTTACTGGAGCTTTCATATCCAATGTACACCAGAAAC

TTTGCTAATTCCACAGTAAATGTTAGAAATGGGTTTTTATTGATAAAATCAGTGGCTTGCTAAT

TAGTATGTTAGAAGCTGGCTTGCATTGGTGAAGTTGAGGGTATTCGATATACGTATCCCGGCTA

AAATACTTCTAAAGAACCTCTCCAGCTTTGCAAGAATAGAGTATAGGAATCTGAGGAGGCCTTT

AACATGGCCCTCAGAAAGGACACACAGGGCTTGACCTCTAAACATATAAACATATACAGAAACG

AGGTCAGAACATGTTTTGACTGATGCCAGTAGTAACACAGCAGAGCCTATTGCTGGTCACTGTT

ACCAATACCTTGTGTAATAAACCTTTCATTTAAATTGAGAGGTTGTAAGCCCCGAAAAAGCAAA

GGGCTTACAGTACCTCTTGCCTGAACACTCCTGTGTGTGCTTTCTAAGAAATGCTTTTAAAATA

ATGCCTGTGGCACAAATTGATTTGACACTGGCTCTCTTTATAAGCTGCTATCAAGGTTGTGGGG

AATAGCTAACTCTTACCCACTTTCCCTGACAAATAGGAACCCGTAGTTACCTACCAAAAGTATG

TAAAAGCTATATCCGACCCAAAGGCCAGTTAGGTCAAAACACCTTGAAAGGAGCTCAGTTTAAG

GAAATCAGTGGTGTCACAGTGCCCCACTAGCGTGTAAAAGTTTTCATAGTTTGACTATCGGATG

TGCTTAGTTTCACAGCTGAGTCTTACCTTGTGATACTTTTAGAGCAAAAGTCAAATCAAAGATG

ATTTAAAAAAACATTTCAAAGATTCATAAAGAATAAATGCCTCCTCAGGAAGTCTTCTGGAGTT

CTGCCCACTTCCCTTAGGTGGCTCTTTACTGTGCCCATCTCATAGCCTGTCTCCTTCCACTTGG

TGTATTGCAGAGTAAAGCTCACTGTTTACAGGGGTGGTAGAAAGTGTGGTCCTTTCCCAGACTC

CTTTTTCCCTTCCTCTTCTCATTTTTCAGAAGATGTGTTTGATAATAAACGAAACAAAATGACT

AACACATTGAGCTGAGCTACATAAGCAGATGTCAGTTTGACGTGAAGAGTTTAAAAGATCTATG

CATTATCTGGGGACTCCTCCCCCAGACCTGAAGGATCAGGTGCTGCCTTCTATGCCACCTGTGC

AGACAGCAAAAGAGGAAAACCATACCCACGTTCAGTATGAACAAAGGGGACATTTGAACTCTGT

GTGGACCCCTCATTGGAAGGGTGTTTCTTCTCCTGCTGCATCCACAAAGAGCACTCCTTAGCCT

TGCCTTTTGTCAGTTCTCTCTCCAATAAGGCTTGAGCAGAGACAACCCAGTGCAGTTCAGAGAG

ACTGAAGTCTGGTGTTCCAGGTCTGAGTCCTAGCTCTAGCTCTCTGTGTAACTTTGGGATGTCC

CAAAGTAACTTTTCACAACTTGATAGGTGTTAACTTGAATTTTGGATACAGGTGACTCTTAGCC

CATCCCCTCTCTGTGCTTCAGATATGTCATCACTTGGGCCATATGACCTCTGGACACCTTTCCT

ACTTTCCACAATTTCAGAGCAGCAGAGCAGACTGGAGCTCCTGCTGCCTCTGAGCTTCAGTGAA

TTATCACTCGTTGGAGGGAAGCTTCAAGCATTTTGTTATCTTTCAAGAGCAAACACAGTGTCTG

TCAGCAAGAATATGTAGCAGATGCTAGTGAACAGCAGTGATTAGGGTTGAATGCTGGATTTAAA

TATGGAGCTTAGGCTGTGAAGGAAGCCTGAAGAACCTAGAGCCCCATGAAGCTGCCCTCTGTGA

GATCTGACACCATTTCCCACTGATGAGCCATGGGTCTAATGGGTAGCACTGATTCCACATACAG

TATGTGAGTGCAATACAGTGAAAGCAAAGAGAATAAAATGATGGCTAACATGATGTTCCAAACT

TTAAACAGGAGAAAAACACACAATTCCATTATGTATAAGAACCCACACAGAGATCAGGAGAATA

ACCTCATTGGAGAATGAATGACCTGTGTGGGGAATTTAGGGTAGAGTTGAGATTGAAAAAATGG

GCCGAAGTCAGGTGGCCAAGGGCCTTAATACCTTGTATACAAGATGTGTAGTCAAGGAAGACCA

TGCCTTACTTATGCATCAATTCCCTTGGGCCTACAAAGAGCTGCCTAGCCTGGGACTGTTGTAG

AGAAAAGCTACAGTGTTCCAATGACACAGGGACTCCTCCATGTATGTATGAGTGCCCAGCTGGC

TCTGTAATAAATCTTATTTTTATTTATTAACTTTTCTTGCGCATTGGCTTGATGCATCAGTTGG

AAGTCAGAGGCCAAACGAAGTGAACACTGAGCCAAAGGAAGTTCTCAGCCTTTAGGGAGGCAGA

ATTCACTTTAAACACAATAAACAAATGAACTCACATTATACAGGAGAGAGTCAGAAGATCCCAG

-continued

TGGCTGGTGTCATCGGGCCATATTTGCCCGAAGTGCCTATTCCTTATAGGAACCCACTCCCAGG

GTTGATGGGCTACATCCTTAGGAGGCTTTATGCCTATGTTCTCCTGACCACTGGCTCCTCCAGG

GCTGGCCTTTTTTAGTCTCTCTGTAGAGGTTCCTGTAGCTGGTTGGATATAGGCTTTCACAGAA

GGGTCAGTGCCTTGGGTCTGGTTACAGGACTGTTAATCTTGCTTTGTTAAGAGTAATGTTATTT

CCCCATTTCCAAATTCTCCAGGGAGATGGAATGTCAAAGATAGTATGACTGTAGCACCTAAATC

CTGGGTTCCAGAAGCAGAGAAGAGAATACACTGAAGCTGTAGAAAGGCCTATTAGTCCATGTCA

GAGATTAACTGGATGCGAGGACCATTTCTGGGATGGTGTATACAGAACTGGAGAACTGGATAGG

GAGTCAGAAACAAAGAGCTGAAGATGATGCCTTTGAAGTTTCCAACGTGGATAACTAGGTCAAC

AGAATATTACTCAAGAAAGTATTAACATAGGATTGAGATGCAGTCAGTAGTAATGGAATTGAAA

TTTCAAAGTATATACCTCATGGATCTCAGGGGGTGTTGAGCTGATCACCTGGGCTAACACTCCT

ATGACCCTGGGGAAAATCAAATGACCTGGTACTGTAGCCATGGTAGGGGTGTCATCACCTTAAT

CCAACTGGGACAGTGCTGTTTGATATTCATCTGGAACTTGGTGCAGACCCACATTTTGCTGGGT

TTCACCACAACCAAGGCTTTTTTGATTCTTTTCTCTTTTAACATCAGTACATCACTGCAAAGTT

AATCCTCATATAATAGGAGATGAAACTAATTGCTTATAAAAACAAGATTTTTACAACACTAAAA

TTGTTCAAGCATATGGGCATATTTATAGTTGCAGGCAGTGTTTCAGATGCAGACTGTTCTTGGC

TGCAGTGGTTGTTTACAGGCAGCATCTGTTCTGATTAAATATTTGATGATTATCCCCGAATGTT

TTAAAGCATAGTACTGGGCTCTGCTGACTGTACAACAAACTGGCATTTTTGACCTATAGGGCAC

TGGGCTAGGAGATACAGTTCTGAGGGAAGTGAAAGATAGTTAACAACTGCACAACTGACCCTTT

ATTAGTTGCAATAAAGCAATCCAACCACCCAACCCACTGTGATGGCTTTCCTACTATTTAAGGT

TGGTGGTGTCAAAGAGACACCCTCCTGTACAGTGTGCAGTGAATCAACATCATTTCCACAAAAC

CTCCTTCCTGCACAAAGGAATTATCATACTTTGTTACGAAGTAAAATTTTCCTGTATCAGTCAC

AGGAGTTCACCAGTTAAGATACTGTTAGTTGAAGACTTCTGGGGTGACTTAATGAAATAGCTCA

GCCATCTGGTTTAAAAACTGGATTCTTCTATCCCTCCACACAGCTGTCCATGCACCTGCATCAT

CTCAAGGCTGGTCTCCCTGGTGGTAGAAAGGCTGACAGTAAAAACTGGAGCCACATGATTCCTT

GCTTAGGCAGTGTTTCTTCATACTCTCACATGAGAGCAGGCATGTTCTTTCCCTAGGCTCACAG

TAAACACTCTGTCAAATCTCACAGGCCCAAAGTGCTTTTGGTTATCCCCATTCCAAGCCAATCT

GTGGCATGGAAGATAGCATTACCCTGACTGCCTTAGACTAATATACCTACTCCACTTCTGGGGC

TGGGAATAATTTTGAGGTCAACCATCCAAACTGCATGACAGCCATTCCATGGAAGAGGTATGGC

CTAAATCTTTGGGGCAACCTGAATTCATGAAAACTCTCTTAGATTTATGTAACTATTTTTAGAA

TTCACTTCTGTATCATTTAATTTTACTAATAAAAATACCACCTTTACCCTAAATGTCAGCCAAG

CGTAAGGCTCCGTTGGGACAGAAGGAACTATCAAAGCTTTGTGTTTTTATACATTAGCAGCATT

TGACAAAGAAATAACTCTGAAGGAAGGAGAATAACCAGGCAGAGTCTAGATGCATGGAAAAGAA

GTCTTTGAGAAGGCTTCGCAGGCTGAAGGAAAGGGCAGGACTACTTCAGGAATACAACGTTTAA

GTAAAAGAGGTTGGGGTCTGTTGATCTTGAGGAGAGATGAGGATGGACTGGAAAATAGGAGTGA

GATATAGTAGGAGAGGAAAGGATATGGATGATGTATATACTGTATGGGTAACCATCAGTCGACC

CTAAGAAGATAATAGTTGTTAAATGGTTAGCTATTTAATGAAAGAAACCTGAACAAGTAATAAT

CTTGAGTTGCAAAGTGGCTGGAGTCACACAACAGACTAAATTTCTGGTAGAACAAATCCAGCAG

CTTATGTGAAGGTTACCATGTCTGAAGCTGGATAGAAAAGGTCTAACTTCCAACCAAAGTCACA

GTTCTTGAGCTCGGTACACAGAGACAGACTGCTAACAGCTGATGTGTCCTCAGCGAGAGTGTCC

TCATTTATATCCTCGTTCTCTTCTGCCTCCTTTTTTTGTTTTAAACTTTTGGGAAGTCTCATCA

-continued
TTCAATACAGTTCTAATATATCACAATAACAGAGGCGGCCCAATTTCTACAAATTGACTAATTC

TATCCCTGAAAAGTTCATACAATAAAACTATACAAAGCATCATTTTCAACCATCCTATAGAAAA

ATTTCCCTATTAAATTTTAACTCTAAATCCTCTATCTCTGTTAATAACCTTACTAAAAACTTCC

CCATCACTGCCTGCCAGGGAGATCAAAAGAAACCAAATTTAAGAAACCTCCAACACCTGTACCT

GACTGAAAAGCAAACATACAGACCTTTCAGTCCTGCCCCTACTATTCAGCTCCTATCACAGAGA

CATGGTGGATGTCCCCTTGGGAAGCGGATAGCTCTTAGGTGGAAGCTAGGCCTGCAATAAGCAG

GCCAGGAAACATGTCTCCCAGGCCCCATACTCTTGGCAGAAGCACTTGGCCACCAGACAGCATG

TCCTGTCAACCTACAGAGTTCTTAAAAACAAACACTGGGACCCAGAATAGTACCCTGTGGTCAT

AGTGCCCACAGTTCACTAAGCACCCTCACAGGTCTTTGACAGAACACTGACTGCCAGGTCACCT

GGTGGGCAGAGAAATGGAAGATTCCCAGGCCCAACTAGCATCTCAGGGAAGAACCACAAGCAGA

GCAACTTTCAGAGCTGGTCGGCCAGCGTTGGCACCCAGGGAAGCAAGTGCTATTCCATATTTGG

AGAGAACATAAAACTCAAGGAAACAGAGAAGTCCTACTCAATACCGTTCTCAACTGAAAACAAG

AGAACTTGCAAAAAAGAAACCCAGTTTTCTGGAGTCCATGGAGAAATATGAAGCCAATGCTCGG

CTAACAGAGCAGAAAGCCTTTTATAAATAATGCCAGTCAAAGCTCCAAAGGTCAGAGCTGATGC

ATGCCGGATTGTTCTGACAATTTCTTAGGTTTCTAGGCAACAAGGAGCTGGTCAAACAGCTCAC

CTCCAAGGACATACTTTATAATACCACCCTGGTAGACGAGAGCGAGGCAGCAGTGAAGGCAATA

GTCAAGAACAGGAGAGGGAGGTAAAGAACAAGATGCTCTTCAGACAGTCTGGACAAAGACAGTC

CCTACCCAGCTCTCAGGAGTTGCCTCCTTAAGAAGGTGGAGGCCCAGGCAGCTCCCAGGGTGAC

CCTAAAGACAGACTCCAAGGAAAAGGGTGTGAGGGCAATGGTGAATATAAGGAGGTCCCCTTTC

AGTAGGCAGAGCAAGTCAGTTCAGGTCTTATTTTTAGAGTCTCTGAACAGTGAAGAGAAGCTTT

CTGTGGACAGCATTCCACCACCATGGGAGGGGAAAGGTGCCATGAGAGACTTCTCCAGTGGGGC

ATACAAGCATTGTGCAGTGATCCCCAAGATCCAGCCACTGGCAGGAAATCGAAAGGCAAGCTTC

TTAAATACATAGTATATGGAGACAGAAGTGTGGAGCACTCCCAAAATGAAAGGCCAAGACCCAG

GAACAACCTCCACAACCTGGAGTATATACAAATGAACCCAGCCCTGCTGACTCAGATCCACACC

ATCCTAAAGCAGGGGTTTCTCATGAATGAAAGGGCTAAGTATTTGGTGGAGAGAATGAGAAGTC

TCCCACTGCCCACACATTTTTTCTTCAGAGATTTCTTTTCCAAGAGCCCCTTGAATAAAGGAAG

GGAGGGAGCACTGAATGCCCCAGAAATCAGAATGCATGGTGCGGGAAGACGACAGGAAATAGTT

CTCAAAGAGATCAGAAAATAAATTGGAAGCAATTTCATTACCACAAAGAACAGACATTTTTTCT

AAGGCACCCCTCCCCTTTCCACCCAATTGTCATTCAGCAACTACTGAATACTTACCAATGAAAA

ACGTTACCCCTGACCTCAAGGCTGCTCCTGAGCTCTGGTAGAAAATGCTTTCCTTGTCTATAAA

ACATGGCAAGCAAGGCAGGATTTAACAGTAAGGGCACAGTAGCACTGCAAGCCTTCAAATGGAA

ACCTGGAGACAAGCAGTGAGAACAGGAAGCAAAAGCAGGGCAGGTGAAGCTAGGACCAGGGCAT

CTGGAACTTTCCACACAGGTTGGATCTCCATGCCAGACAACAGTTTTCAAGGAAAAATATCTAA

GAGGAACATGACTTTGGGAAACTTTTTGGCAGTACTGCTTACTGTATACTAGAGAGTAAAAGAA

TTTGGGGAACATTCACCAATTTGCTTCTTCAGGGGCTTGGGTAGGGAACGTGAACAGGAACCTG

GCTCTAATTTCTGAACTTTTTTATCAGTAAAAACAATCCAACAAACGAAAGCTAGTCAGTGAGA

GAACTGGGAGGGTCTGCCCTCCTTCCCTGAGTCAAGCCTTCTGGGGGGACCTCCTGACATTTAA

TTAAGCAAAGACAACGCCCACTGAAGGAAGCTGACCTGAAAGTGACACGCTACTGTGAAATGAG

CATGAAGTGGGAGCTTGTTACATATATGAAATGGCCAGCGATCCTGAGCAAAGCGCTTCAGAGC

TTGAGACCTAAGTCTTCTCATCTATATACTGAGGGCTGGACAAGATGATCTGTCAAGCCATTTT

TATCCCTAATCCACCAAAATCCAATGCTTTAGTTTATTGTCACAAAAGCAGGTATCGAATGGCT

-continued

ATCCTGCAGTGCCTCCAATCAACATTCAGACTTTTTCCCTGAGGCAATATAAGATAACAGTTAA

CATGTTTTTATCAATTAGGTGGTCATGAGATAAATATATATGGGAAGTGGTAGTTTTTCACTTA

AATGCATATAATAATGGTACAGCTCTCTTTGAATAGTATTTGTTTATTTCTTAAATATTTAAGT

TCCTAAAGACGGTAAGAATAACCCAAGGAAGTGAAATCAATGTCACAAAGCACATGGCTAAATA

ACTGCAGGTTTGCAGTGCCATGTGTGAGATCAGATGACAGAAGGGAGAACTACCTTTAGGCAGA

GGCTTCTCATGTCCCCTGGAGTGGCCATGTGCTGTTCTACATGACTACTTCCACTTCGGTTATG

TAGAAGCTATTTAAAGCACACAGATGTTTGTGATGAGAAAAAAGCCACCCTTAATTGAATAATG

GAAATTATAAGCATGATTTGAGGGTGGGGGTGGAGGTGGGAGTAGAGATGGGTAGAAAGGAGTG

CAATGGAAACAAAGGAGCCTTCATAAAATTCAAGTCACTTCTTAGGATAACGTGATTGATTTAC

TCACCACCTTCTTAGGAACATAAAGCAAACAAGTGGGTTTTCCTTTTACTGCTTTTCTGAAATG

AGCTACACTCAAGAAAGCAGCACGGGGGTTGTGCTGTCCCTGCACAGTGGCAGGAGAGTATGAG

GAGCAGGTGAATGCCACAACAGCTCCATCCAAGATCATTTTTCACATGCAGGAACCATTCTTAT

ACTACCCTTTACTGGTAATTTCTGTAGAAATCTGGAAGTCTGGTTGACACCCTCCTGTACAGTG

TGCAGTGAATCAACATCATTTCCCTTGGACTTTGCAATCACGGTGGCATTCATACATTCATTCA

ACAAGTATGTATGTACAGGACAGTGGAGTAAAGAAAACAGATAGTTCTTACTCTCACGAGGCTT

AAAATTTCAGGAGGGAACTAGGCAGTCATGAAGTAAACATAAAAACACAGATTGTAATAGGCAC

TAGAGAATAATGAAGACTTTGGGGAACACAATTTAAATTGGAAAAATATCTCAGTTCCGTTAAC

ACATGTTGAAGGGGAATAGCATTGTTTTGCTGGATTTGGGGCCTGGATGCAAGCATGTTGGGTA

TGCATTGTAGGGTAATGCATTTCCTTCCATTTGGGCCCAAGTGTATATTTACCACCCAGTTGTG

ATGAGCTGGGATCCTCCTGCTCAATCTCAGCTTGAAGCACTTGGAGGTTATCTGCCTGCTGTGG

GTGATTATTTTGGAGCAAGGTACTTCATTTGCCTCAAGAAACAGATTTGATACCACTACTGTGC

CCTTTTGGAACAGAGAAGTAGGCAAGACCCCAGTGTGAGGCAGAGTGATGGGATCTTTAGGGAC

ATAATTGATGATGTAACTGATGATGATTTTGGAGTTTATACATTTCCAAAGTTTCAAAATATTT

TCACTTGGTTGATTTATCTTTATGGTGATGACACTACGTAGATATATGCCCTTCTTAAAAGTTA

CAGTAAGAGGCTGGGAGCGGTGGCTCACGCCTATAATCCCAGCACTTTGGAAGGCCGAGGTGGG

CAGATCATGAGGTCAGGAGATTGAGACCATTCTGGCTAACACGGTGAAACTCCGTCTCTACTAA

AAATACAAAAAAATTAGCCGGGCGTGGTGGCGGGCGCCTGTAGTCCCAGCTACTCAGGAAGCTG

AGGCAGGAGAATGGCGTGAACCCGGGAGGCGGAGCTTGCAGTGAGCTGAGATTCCGCCACTGCA

CTCCAGCCAGGGCAATGAGCGAGACTCCGTCTAAAAAAAAAAAAAAAAAAAAAAAAAAAACGTTA

CAGTGAGAGTTGACATTGAGAAAAGGGAGGCCCAGCCAGGGTTATGCAAAGACACAGTAGGGAG

GAGGATGGGAAGTTTCTGAGACACCCCAGTAACTGCATGGGTCCACAAAGCACATGTACAGTCT

GCTCTATGCACTGCAGGTACAGCCACGAATAAGACAAAGTCTCTGCCCTCATGGAGCTTGGTGT

CTGTCTACTGGAGCAGACAAAAACAAACCTGCTTTTTCTCATTTGCCTCTACTGTGGGTTCCGT

GTATAACTCTCAAATGCTAGCATTTCCATGCATTCCATCCTTGTCCTTCTCTCCTCTCTGCCTT

TTCCAGGAGAATTTTCCTAGCCACAGGTTCAGCTATGGTCTATGTGCTGGAGTCATACATTTTT

ATCTTCTGTGTACGTTTTTCTCTAGACCCATATTTTTAATTGCCTTAGGACAGCTCTCCCTGGA

TATCCCTCAGACACAACTAAAACATCATTCAATTGTACTATTAATAATTTTCCCTTCAAAATCC

ACTCCTCTTCTCTATAGACCTAACAGCAACACTGTCCGTCCAGCTCTCAAAACCTGAAATGTGG

GAGTTGTCTTTGACTCTTATCTTTCCCATGCATGAGCACTGAATCAATCAGAGTCCCTAGCATG

TCTTGGACTGTGGCCTCCCTTCTATCTTCAGATTATCTGCCTTTTTAGAATTATGGCAATAACT

-continued

TAACTGCAAAGACCACATGTGCACTTGTGCTCTTTCAGTTTGTAATAAATATAAAATGAAAAGT

GATTATGTCTTTGCTTAACGTCTGCAAAATAAAAGTCCAAAGTCCTTGGTATGGTCTATAAGGC

CCTCATTATCTGACCTGCCTGCCTTCCCAATCTCATCTTAATCCCTTACAGCCTGACACTCAGA

CATACTAGACTTTCCACCTAACTCACTCACATACACCTATCCTGTATGTCAAGATTCGGCTTGA

CCTTCATCACCTACCTATCTGCAGTATTTTTGGATCTGAATTCTCTGCCCACATTGTACTTTCA

CATACTTCTTTTACCCTTAGTGGTTTGTACTTATGCCTGGTCTAACTAGATTGTCTCCCTGTAA

CAGACTTCTTGATTCAACAAAGCAGCTCTGAATCAGCCTGAAACCTATGGCACACTGCAAAATG

GCAAACATTCAATAGGTATTTGCCCAGTAAATGTTAATGAAAGGAAAAAAAATTCAAACTTCAGT

TGGAATAGGATTAGAGACAAGTTAAAAAAAAGTTTCCCATAGAAATCTTCCTCATCGTAAATAT

CATCATCCTAAATGTCCCGAGTCTTTCCATGGGTCTAATTTACCAAATCATGAAGACTCTCTTT

CTCACTGTGTATGTGTAGTGGGAGAGGCAGAGACAGAACGGTTTTTTTTTTTTTTTGCAAGTCT

GCTCTCTGGATTCGTTTTTCTGGGGATGAAATCTCAGGCTATGTAGCTTTTCTGGTCCCTTTTT

GGTAATCAACAAATCATCAGTTTCTCTAGGTATTAAAAAGCCTACACTTTTGAAACACCAAGAG

GCCAAACTCTCTCTTAATTGAAAACATAATTCTGCCTCTTACTGAGGTCTTTGGGTGGGAAGCT

TAAAGACAGCAGTGTTGGGGCAATTGGTTTTTCTTTTCCTCCCTCCACCTTCTTTCCCATTCAA

GAGCTGTTGCTGCCCTTTCTGGAGGGGAGGGAATTAGAAAAAAAGATCCTGCCTTACCCAGTCA

CTGTTAATTATTACTTTGAGCCAGGGTGGGGAATGACTTTCTTTCCTGGAATACACCCTGCTGG

AAACCACAGCTGAGATTCTCTAAGCTGGCAGCTTCCAACCTCTCCTCCCTCAACAGCTTCAACA

TTATATGGCACTCAGCTGCAGGGTGCCTGGCTCCAGGCCGGCAGTCCATTTGTGCAGGGTAGTT

TTCAAGATGGCTCATAGCCCATCTCTTTCAGTGACCAGCGTGGCCTATGGGAAACATACATCTT

GACTCCATTATTGGTAGGAGTACTCTTTAGTTAACTGCCACAGGCCAGTTCAGACACGTCTTAC

CCTGAGAGCCTTTTCAGAGTCAGGTACCATCCCTGTGTCCCCCAGCATCTGAAGATCACAGGTG

AAGGTCTCCAAGTAGTTCACTTAAAAAATACCTCAGTAGGTTTAAGAACAGGGAAAGCTCCCAA

TTCATTCTGTCAGGAGTATGACTCTCATCCCCAAACTGGACAGATATATAATATGAAAACTACA

GACCAATATTCCTTATGAATATAGATGCAAACATTCTAAACAAAATACTAGCAAACCAAATCCA

GCAGCATAGAACAAGGTTTATGTAGCATGGACAACTGAGATTATCCCAGGAATGCAAAGTTAAT

TCAATATACAAAAGTCCATTAATACAACATATTAATAAAGGACAAAACAACATGAAAATCTTGA

TACAGAAGAAGCATTTAACAAAACCCACAGCCCCTCCTTTTTTTTTTTTTGATTAAAAAACACT

CAGTAAACTAGGTTTAATAAAAGAATTTCCTCAACTTGAAGCAAACCCACAGCTAGCTAACATC

ATACTCAATGGTGAAAGACTGAATGCTTTCCCCTTAAAATCAGGAACAAGAAAAAGATGTCTGC

TCTTGTCACTTCTATCCAATATTGTACTGGAGGTGCTAGCCAGCACACTAAGGCAAGAAAATGA

AATAATAGGAATCTAGACTGGAAAGGAAGAAGTAAAAGTATTTCTGTTCACAGATGCATGATCT

CATATGCAAAAAATACTAAGTGACAAAAAAAGAATTTTAGAAAAGCTACAATATACAAAATCAA

TATACAAAAATTAATTTTATTTCTAACACCAGTGATGAATACAAAAATAAAAATTAGAAAATAA

TCATATAATTAAAGTGGCATCAGTAAAATACTTAGAAAAAAATTAAAGACGTCAAGACTTGCAC

ACTGAAATCTCTAAAACATCACTGAAATAAAGACCTAAGCAAATGCAAAGACATCCCACAGTCA

TGGAACAGAAAACCTAACACCATTAAAATAGCAGTTATTTCTCAAATTTATCTACCAATTCAAC

TAAATCCCTATCAAGATCCCAGCTGTTTTGCAGGAATTGACACAATGATCATATAAAAATTCAT

ATGCAATGCAAGGGACCCAAAACAGACAAAATGATTTTGGGGAAAAAAAAAAAAAAAAATGGAGG

ACTTGCACATCCCAAATCTAAACTTACTACCAAGCTACAGCCATCAAGACAGTGCGGTGCTGGT

ATAACGACAGACATATAGGGCAATGGAGTAAGACTGAGAATCCAGAAAGTCTTATATTTATGGT

-continued

CAACTGTTCTTTGACAAGGGTACCAGGACCATTCATGGGGAAATAATAGTCTTTTCAACAACTG
GTGCTTGGGCAGATGGATATACAGATACCAATGCACTTATGCAAAAAATGGATGAAATAGGAAA
CTTCACTACATTCTACTGCATGCTCGGTCATTTTCAATCATTTAGGTGGCAACACTGACAAGAT
AACAGAAAGATGGAGGTAATAACATGTGAAAGGCAAAATGGTTTGTTTTTTTTTTTAAAAATGA
CAGTCTCTATCATGAATTTACTTACACTCCAGGCAAAGGTTATTAGAAGAAAAAAAGATGTAAG
AAAATTCCTTAACTGAAATGTGGAAAGAGTATCAAGAGGAGACCCTAAGACACTCTGTAAGAAT
CCCAGTGACTCCTCACTGTTCAACTAAGAAATGTACCCCATTATGCTGTGCTACCACGGAAGCA
TTGGAGGCACTTTGGGGGTTGATGAAGTCTTCATGGATGAGGTACTTTAAATATCTGGTCATGA
AGAGTATTTGAGAAATATGACAAGTGAAGATGCTGGGTAGGAATGCAGCGAGGAAAGTGTGTAA
CACAAGGCCAAATTGGAAAGGTCAGTGAGGGGGCAATCTGTGGAGGCACTGAATGCAGAGGATA
TTAAAATTAGCAAGATAGTGTTCTAGCACAATGAAAAGGATTGGAAGAGGGAGATGAGAGTCAG
GGAGTGAAATTAGGCAGCTGCTAAGAATGTCCGGGTGAGTCAGAGGATCAGGACCTGTAAGGGC
AGTATAAAGAAGGAAGGAATGATGGGAGAGGTTTAGGGGGAAAGAAGTGACAACCTGTGACAAT
TGAGGAATGAGAGATTTTGATGATTGGGGTGAAGGTTACATTTCTTAAAAAGAAACAAAGAATG
GTCGGTCGATAGAGATGCAAGATGAAGAATTTTGTTTTTAGGACTACTGACTATGAGGTAACAA
AGAAATCCCAGAGACAGAGGTCTGAGCAAAAGATATGGGATTGGGGAAGAATCTTTGGGAGTGA
CTGAGGTTGACTAGAGGGAACTGGGCAAGAACAGGTAAGGACTTTAAGCAGAATTGGAGGAGTA
TCCATCTAAAATCTGGGTAAACTGGGATGGAAAAACAAGTAGCCAGAGAAGCAACAGCCCAAGC
TAGGGTGTTGTCAAGGTTATAGATGTTACTGATTTTGGCAATGAGGAGATTATAAGGATCCTTG
AAGACTGTACTTTCGGTGAAACTACCATGCATTAGTAGCCTTTCACAGTGATATCTACCCCACA
CCTGCATCAAAATCTTGCAGTGCCTATTAATAAATGCCAACCCACTAACGGGGAGGGGAGAAAA
GACTTGGGACTCTGTACTTGTAAAACCCTCTACCCTCCCCAGGCAATTCTTTACACACTAACAC
TGTTGAGGTAAAAGGAGACAAGTGAGGGAGCAAATGGAAGGTGTGTTTTTGGATTATACAGTGG
CTCATGGAAGGGTGGGAGGGGTACAGATGGCCCTTAGACACTGGCGGAAAGTCAGAGAAAAAAA
ATTACAGTAAGCAGGTAAAGGGATCAAGACTACACAGGGACTAGTCTTGGGACGACATTTCTTC
CTCTGACAGTTTGTATGGAATTCTTGAGAAAAATTCCTCGAAGGGGCCTGAAATCTCAGAATGG
TCATGTTTTTAATGGGAATAGGGAGTGATGCTGCCCCATTACAACCATCTGTTCTAACAGAATG
TCTGTACCGAGGAGGGATGAGTAACATCGGCAAGTTCTGTTCGAAGCCTTTTTCAAGTTTCTTT
TTGATATGTATCTATCTATCTATCATCTCCCTATACAAGCAAGCATCCCCAAAAGTAGTTGTCT
CAGGAAACCAGGGTTAGGATGACCAGCTCATTTGCTGGAGCTGCCAAGGTCCAGAAAAGTTTGG
CTGCAGGCTGTTTTCATGTTTTATGTATGTTTGAAATGTTCTATAATAATAAAAGGTTAAAAAA
GTTTACATTTATTTGGAAAACCAGTTACTTTAGTTTATGGTTCCTTTTTTTCCCTCCAGAGCTT
CCTGGAGATTGAGGTCTAATTCAAAGAAAACCAAAATATATAATAGAGTACCTGGGCAAAAAAA
GTACTTTTATAACATAACATTTGGGGTAGAGGAAGTATCCACTGTAGTCAAAATGTCTATGTTT
TGCTCTTCCTTATTGTTCAGGGACATTCCATTAAATAGTAATGAAAAGGCAGCAAAAGTAAGAG
GAGTGACAACATGCCCGGCATAATTAAGCAAGCTAGAGCAGCTATTCTGTGCAACCGACGATTT
TTTTTCTCTAAAATTTTAAGGGTAGGTTCATTCTGACTCTGTTAAAAGTCTACTTGATGTGAAC
AACTCTATATCTGATAACCTATTTCAATTACCACTTTAAAACTTGTCATATGGATACGTTATTA
CAATTGTAGAACTTTAATAAATACCATAATAATAAAACTTGAGAACTGAAGAGCACACATTTCT
TCACGAATTTATTATATATAAAACGCCCTCAGAGTATTTAATTTCTCCTCACTTTAATTACACATT

-continued

AAGAAGCACAGTGGATGAGAAGCCTTTAAGATGACTACAGTTGCACGAAGGTCCCTTTCATCAA

GGTAGCGTATGTACCCTAACAGTGTTCTAAAGGCTGGCCCAGAAAAACCCCATGTTACCTTATC

ACAATATGGAAAGCATTGTCTTCTTTTTCCACTAAATTAAATTATGGTGAAAAGTGCCACAGTT

TTATTTAGCATTATGGTACATAACAAACAGTTCTGTCTCAATTATGAAAAAAATTAATTAAAAT

AATCCTGAAAGACATCCTTTTTCTCCCCCCAATGATTTGAAAGCTGCATTTTTCCTGCCAATTT

CAAACAAACAAATCATCAGGTTGATCTACAGTAATCAGTTAAAACAATCAGTCAATCAATCAAT

CAATCACCAAGGCACAAGCTCAGCACATTAGCTATAGCTTGTAGCAAAAGGATATATCAATGTC

TCACCTTAGTTAAAAATACATAATCCTTTTATTTTATAATGCAATAAAAGAAATTAACAACATC

ACATACACAGAAGACTAGGAAAGGGGAAACTACTTACTTCTGGAAATCAGTAATGTAAACCTAC

TTGTACTTTTCCATAGTACATGAAAGTAACGTTTAACATGTTTTGAATTAATTAATTAAATTTA

ATCTGTGGGGCTATACAATGTAATTCTTAGGAGTAATAGTTTCATTCATTTCCAGGTCAGCTTA

CTGTATGATTAAGTAACACAAGGCACAGTAGCCATCTTTTTCATTATGTTGCAACACTGATCAC

GTGCCTCGATAAAATGGCTGATTCAACAAGATGATGGCAACACGAAGGGGAGACTTTGGATTGT

CTATTTAAAATCTAGGTAATAAGTAAGTAATTAATAAAAACTCTATCTTAAGTGCACTTTCACA

TGCTTTTTGTTTATAATAAACAAACAACAAACTTCCTAACTTTGTTGCAATAGGCTTGACTACC

ATTTCATTTGGCCAAATGCACTTTCCCCAGTAAACTTAAAACAACAACGAGAACAACAAGAACA

AAAATCCCTGTCCTTTCATATACTAAGAAAGAGGATTGGCTACTGAAACAGTTCATTGCAAGAC

ACATGAAGACGACATACTGTGGCATGAGTTGTTTTTGTTTTTAATTTGTTGTGCTGTTACTAAA

GTTCTGAGGGCTGCAGTTAAAACATTCCAATTTCTCCCTTCCTTCCATCTTTCTTTATTGATTG

ATTCTCAAGATTTTGCACAGAAAACTCTTTGGGGGCTAGAACAGCAGTAATTGCATCACACTGT

TTTCAAGACTTCAAGTTTCAAAAGCAAATCATTAAAAAAAAATACAGTTCCTGATTTGAGTTAGA

TACAGGGACAAAAAAGTAGCACATACTTGAAGGTTACGTGGTCTACAAATGGTGGCAATATTTT

CCTTGGGAGAGTAGTTCTGTTGGTATATATTTTTTAAATACTCAAAAGGCTCAACCTCAAGCAG

TAATAAACACAAGCAAAAGTGATTTAACCCTTAAAATAAATATTCAGAAAAACCTCTCTGTACA

TACAAGTGAAAGAATATGTAACACTTTCACGCAAAAAAATAATTATAATAATAATAAAGGATTT

GTTCATATATGTAGCTGAAATCTGCTGTTCCAGCCCACATGTCCCCAATAAAGAAGGGAGGCAC

AGACATAGGTGACTACTGTGGTTGACTATCTTACAGCCTTTTTGTACTGGGACACTATCACCAC

CAAAAATTTATCCCTCGTTATATTTTTAAAATTTTTTAAATTTTTTCTTTTTTTTTCCTTCCTT

TTTTTTGTTTTATTTTGTTTTGTTTTGTTTTACAGCATGCCAAATCCTTTGGCATACGTGATGG

CCTTCAACAATCTCTCTTTAAGTTTTTCTTTGCTTGAGTATTCCGGAAGTAAAAGCACATTAAA

GCAAGTATGAGATGTAGGTAACCTAAATAGAGAAAAGGGGAAAAAAACAGGAAAACTGTAAGTC

ATGGGAAATACACTTAGAATTAAATGCTCCTATTTTTAGATTGTATATAGTTGAGACGGTCTGC

AATGCAAACTATACATTAATGCAAATCATAAACTTTTTGTTGTGTAACTACCAAGTTGCCTTTA

TCCTATAAATTACTCAAAGCTAGTGACGATGATAAGATACTGTATCCATTGAGTTTTTACTACA

TAACAGATACCATTTTAGGTACTGAATTCTTACAGTTCATTTAACTAAATCTTTCCACAACAAA

ACCACAGAGAGGACATCAGTAAATGCACTTTAGAGGTTAGGTCACTGAGAAGTCAAGTAACTTC

CTCTAAGGTGGAGAAAATACTCAAACCTGTTTTACAAGACTGCAAAGTGTGTGCTCTTAAATGC

TTATTAGAAACACTGCTGGCAATATGACTAAGAAAATGATTTGATAACAGGATTCTAGCACAAT

CAAATGATAATCTTCCGAGCCTCAATGTAACCATTCTAAATAGATGATCATGTTATATGGCTTT

CAATTAACAAGCTGGGAATCAAAAAAGTAAATGAATCACACTAATTTGATTCCAAACCAATGTG

AGCCCCATAATAATTTTTAACTAGGGCAATTTCTTAAAAGTTTCCTCACACAATGACAGCAAAG

-continued

TATTTTCTCAATTGTCTAATATGATTTGGGGATTTGTATATAAAATCACGAATGTGCTCAGAAA

CTATAAAGACAGTTCATATGTATGTGACGAGGAATGCAAGGTTTTCGGTAGGTATACAGTCACA

AGTTAATAATTACCTACCTTTCTGTGTCTGGGCCATTTTTGGCTATAATCATCTTTAATTTTCC

TAGTCCTCCCACAGGTGCTCTGTCTGTGCCCGTTGTAAACTGCAAGAAGAGTCTTTTCTGTTCA

TCTGTAAATGAATGAACGATTTCCCAGAACTCCCTAATGAGAAAAAATACAATACTGGTTTCAG

TTTGGCATTCATTATGACTGGTACTAACATAAGCTTATGATTTGCATTAAAACTATATTAAGAG

ACAACTTGGAAGTTAATTATCAGGATAGTATCACTTCTGGTGATTTAAAAATTTCCAAGCAAAT

TTATCCTGAACAGCTCTGAATACGTAAAAATTTAGATTAGATTACAATATAGTAAAATATTAGT

ACTACAATAGTAAAAAATTGAGAAAACCCAAGTGTGTAGTAACAGGAAGTGACTATTTAAACTA

TGGTATAATCACATTATGCAGTCAGTAATGAGCAAAAGACAAAATCCTATGAATTGAAAAAGAC

TGAAATGAATATTTGGAAAAATTAACTCCAGGTGCCTTTGGGTATATATTTTATTTATCCTTTC

TCCTTTATTCTCCTGGTCTACTCATCCTTTAACTCAACTTTGGGAGGAAAAAGTGATACAGATT

AAGGACAAAAGAAAAAAAGACCCCCTGCCCCAACCAACTGGCCCCAAATGCAAACAACTACATA

CCTAATAGCAGTAATACAAAAGTTCAATTTTTATATGAACTAGAATACTTTAAACAAGTAATAT

GTGCTGTGTATGGAGGAGGAGAATTATTCTGACATTTCTGCCACCTGCAGTTATTTTAAGAGAA

TGATTTATCCTGTGGCATTCCTAAAATCTATGTAATAAAAGCTATGTTTTAATGACACTTATGT

TAGTTTGAGTTCTAAAAAACGAAATACAAGCTCATAAAGTGCAATCTTGAAGTTTATTTGAATA

ATCAGGCATCTATAAAACATATATACACTAGTTCATAGCTAAATAAATTTTTTTTTTTTTGAGA

CAGAGTCTTGCTCTGTCGCTCAGGCTGGAGTGCAGTGGCGCGATCTCGGCTCATTGCAAGCTCC

GCCTCCTGGGTTCGCGCCATTGTCCTGCCTCAGCCTCCCAAGTGGCTGGGACTATAGGTGCCTG

CCACCACGCCTGGCTAATTTTCTGTACGTTTAAGTAGAGGCAGGATTTCACCATGTTAGCCAGG

ATGGGTCTCGATCTCCTGACCTCGTGATCCGCCCACCTTGGCCTCCCAAAGTGCTGGGATTGCA

GGCATGAGCCACCGCGCCTGGCCTATAGCTAAATAATGTTAAGATTAAAAAATTAAAAAAAAAA

TTAAAAGTATTTTTAGTTGCTTATATAATATAAAATGCATTTTAATAGTTATTTAGAAAGTTCT

TTCCAGAGCCAGGTGTGGTGGCTCATGCCTGTAATCCCAGCACTTTGGGAGGCTGAGGCCAGTG

GATCACCTGAGGTCAGGGGTTCAAGATCAGCCTGACCAACGTGGTGAAACCCTGTCTCTACTAA

AATACAAAAATTAGCCGGGCGTGGTGGCAGATGCCTGTAATCTCAGCTACTTGGGAGGCCAAGG

CAGAAGAATTGCTTGAACATGGGAGGCGGAGGCTGCAATGAGCTGAGATCACACCATTGCACTC

TAGCCTGGGAAACATTTTGAGCCATCTCAAAAAAAAAAAAAAAATTTCATCTCAAAAAAAAAAA

AAAAAAAATTCCAGAATGTTAGCAGAGAACATCACACATCCCAAACCAGTAATTACAATTTTCT

ACCTTTTGATATTCTAATATCCCAACATACTATTTTTATTACCAAAATGCTGGCATTTTTGGTG

CTGCAACACCATTTATCTGAAATAACTTAAAAGTTTTATTAGAATTCTTGGCTTTCTCCAATCT

CTTGCCACTTCCCTTCCCTGCCCCTTTACAAATCCACCAGTCAGCAAGAGAAAACAAAAAAGAA

ACACACAACAACAGAAAACTGGACATGAAACTTGCAGGAGCATCTCTCAGGTAAGGAGGAGAGG

AATCGGACCCCAGTTCATGATACTCCTTTTGGGGAGGCTGACAAGAGAAAACAAGTCTGCTGTA

GCACAGAACCCTCCAACATAGCAGAAAAGCTGCCCTGCAGTGGGTGGTAATAAAGCCTCCTCAC

ACTGCAGGAGGGCTCTGAAGCTTAACTGAACCAGCTACACCTAAGGAGGTAGACCAAAGAGCAC

CACCGAAGAACAGAGACAGACCCTGCAGGAAGTGGCAGATCAGCAGTGGTCACAATGACCAGTC

TGGCTATATTATTACGGAGCTGTTTCTTTGGACTTTTAAACGAAACCTTTAAAAATTTTATACA

ATGAAAACAGGGAACAAAATGCATCTCTATTCCTATAAGTGTTATGTGTGTTACATTAACATTT

-continued

TGAATTAAACAAGAATGCATATATTTAGAAAGCTGAAGAAAACACGAAGAAGCTTCCAGGTTTC

CACATAAAAGTGGTGGCTGTATCGATCACATCCTACTCACATCTCTAAAAATCTACCCGGATCA

AAAAGGGGAAAATAAAAAAAAAACCTATGACTTAGGTCTAGAGTAAAACTAGGAGACAGAACAA

TAAACTCCAAATACCAAAGAAGTGGGGAAATGAGCAGGGTCCAGCAGGAGCTACATCGAAGAGT

GGCTTGTGCGGAATCATACTGATTAGGGATCACCCAAGGCCAGACCCCACCCCCTCCACCACCT

GCCCCTCAACAGAGCACTACTGAGTGTAGGTTAGAGCACTGGCAACAGGGTGGTTAAAGGAAGG

ACTACAGAAAAGTACTTGGGTCCAGCAATGGCAGGCTCAGGAAGGCACCATGCATGAAAGGAAG

GGGGGTACCTTCAAAAGCAGAAGTGTCCCTTAAGCGGCTGTAAAGGGGTGGAAGCAGCTAATGA

AAAAGAGTCTTCATTAAGCTACATGGAGCTGAAAAATCAGAAAGTGGTGATTCTGCCCTTACTA

AAGCAACAGAAGAGGGATCCCTTCAACCAAGACCCCTAAAGCCACACAATTCCTCCCTGCTCCA

CCATGAGGTCTAGTAATAACAGGTCCAGAAAAAAGTAACATCTGTTATAGAAACATAAACAAGA

AAAACAGAATTCGGAAGTCTAAATAAAGTTATTATGGGAAGAGTCTGGCGAATGAGAAGCAAAA

CTTTCCGGTAGACAAAAGTAGACCAGAAAAATTCAGTCATAAACAATGGGAAACTAGTAACACC

ACATTCCAACACAAAAGGAGAATGCAGCAGCAGACAAGACAGACCACCAGTGATGAGAAATACA

AATTCAGAAAGAAATGAGCACATCTTAAATAAAAATAAGAATACTAAAAAATACTGAAGAAATA

TGCAAGGTAACTTTGGAAATAAAGGCTAATTTTATTATAAGGTGACCAAAGAAGAAGCAGTATG

ACTAAAATTTCTACTGAGGACAGACTCTAGAAAATTAAAAAACAAAGAAAATGAATAAAATAAA

CATAACTAAAGAAATGCATATCAAAGCATAATAACGAAAAAGATTAATAGCTAACTACATAAAC

ATAAAACCTTTCATTTGGCAAAAAAATCCTATAAGCAAGGTTAAAAGACAAATGACAAACTGGG

AAAAAATATTTGCGAATTTACCAGCGTTAAAGGACTAATCTCCTTAACATATAAAGTTTCTAAA

AGTGAAGAAAACGACCAGCTGAGCAGCAAAATGAGCAAAAGACTATATAAAACTATAAACAGCT

CTACAAGAAAAAATGTCCATTATCATTCATAATTGAGGTAAGCTCAAAAATTGTAACTATAGTA

AAATACCATTTCTCAATTGGCAAATAAGTAAACATCCACATTTAACAACACATTCTGTTTGGAA

AGTTTTAAGAAAAGAGATACTGTTGTAAACTGCTGGTGGGAATGCAAAATGTTATTTTTCTGTG

AAGGAGGATTTGGCAGTATCTAGCAAAATTACACATGCATCTACCATTTGATGCAACAATCCCA

CTTCTAACAATTTATCTTAATGATACTTTACATATGTACGGAATAATGCATGAACATTAAGAGG

ATTCACTGTGACATTAGTACTAACAGCAAAAGGTTAAAAATAACCTCGATGCCCATAAATATTG

ATAAGCTATGCTGCATCCACACAAAGGAGCAGTATTCAGTCATACAAAACAAAATGGAAAACAC

CTCTGCAATAATGTGGGATGATTCTCAGGATACACTAGGAAGATTATTTTCCTAGTTCTGTCCT

CTGATAAGGCCTACAAGCAGTAACGTTCAAAAGCAAAGGCCATACTTTGCATCTAAAATCTGAC

TTCTAAATGCCATTCTCCAACAATTTATTGGAAAAATAACTTATTCCAGGCCTGAGAATGAATG

TTCGAGATTAGTTAGAAATCTCAAAATCTAATAGGGTCATTTTAAAAGCACACGATAGCTAAGC

AATTTGAATATCATTTAGAGTAATGACTGTGAAACGTATTAAATACAAAAACATTCATTAGTTC

GTAATATTCAAAAAGGCAGCAAAAACCAACCAAAAAACAAAATTAAATTGTCACTATTAAAATT

ATTACATTAACTCCTTACTCTAAAAACCTTAAATCTATTTTATCATGCCTTTTCTGTAGAACTG

TTTTTCAAGGTAATCAAATGGCACCCAATGATGAGAAAAAAGAATGCCAGGTATATATGTAGGA

CAAGCAGATGGAAATTTTTTTTCCCCAAACAGCCATTTTGCAATCCCCAATGAGATAACAGATT

AAGGTAATGATACTGATAAATACGAAAATCAGGTGAAGGGCAGGTAGCAGGTTCTGGAAAGATG

ATGATGGCAACGACATAGTTATTATTATTATTATTTTTTGTTTTATTCCCTCCCAACCTCCCCT

ACAAAAACAGCAAACTGAATGAGAAAACCAAAGACCCAGAGACATTATCTACAACAAAACCATG

AACCATTGCATATAATTGGACAGAAACAAAGCTCTGACAACTACAAGACTGGTTAGTAAGGAAG

-continued

CAGATGCAAGGTAACTGACTGGGTTTCTGACAGCCCTGAGAACACTGCCAACCCACTGGAAAGC

ACAGGCCAATCTGAAAACAGGGCTTAAAGTTTTAAAAAGTTCTACAGGATCTAATTTGCAGATG

ATTACAAAGGGATCATGATGTAGTAAGCTCTGGGCCCTTAAAACACCCGAATACCAAACCCCCA

CCAGAAACAAACCTTGTACCGAGGAAAAACTTCTGGGAATAACTTCCGAATGGACCAGGTCAGT

AATAAAAACCAAAAAAAAGTTCAAATATATGTGTGGGATAGAGGAGTAAAGAAGGCAGTTTCAG

AAAGCACAAGGGCATATTTTTGACCATTTTACAAAAACACAGACTTCTCCTCGTCCCTAAAAAG

CGAAAAAAGTTATCCTGGCCCATCTCTCCCTCGTCCAAGTATGAGAAACTCATTTCACTCACAC

ACACACACACACACACACAAATAAATAAATAACAGAACAGAGTGAAACAGTGTAATTATTAGAG

AAAAAGTATGTGCATATACATGAGAATGGTGTCCCTACAGAAAATCAAAGTACATGAAACAATA

TGCAAATAAAACATGAAAACTGTAAACAAATTTCAAACTGAGCTAAAAAGAATTTAAAAAATAA

CAAATCATTAGAAATGGGAAATTTCTGAATGAGGGTAACTGAAAAAAAGGAAGACATGACACAA

CTAAGGAGTAATTAGAAATGCAAGGAAAAAAATCCCATCAAATACAAAGAAACTAAAACTAAAC

TAGAAGAAACATAAAGGTGAATAAAACAGAACAATAATACCAGAACCTGAAGGCAGAAGAAAAA

TCTTAAAATCAAAAAGAAACAAACCCATGCTTGAGACTCTCCTTGCTGGTCCAGAGCCACAGTG

CTGCTGTGTACTGGCAGGAGGAATTCTGCTATAATTGGTCCTGGCAGTGTTCACCTTTCCTGCA

AGTGTTCCACAGCCCAGGGACACAATGTGGTCAGGAGCACTGCCAGGAACACCAGCAAGGGGGA

GCCTGCCACAACAGGCACAAGGCTCAGGAAGCACTCTCCAGCCCACGAAAATCTAGTGGGGGTC

CTCTTCCCTCACCCAAACACACTCTGCGCAGCT shRNA artificial/synthetic sequence.

SEQ ID NO: 2

5'- TGCTCTTCTTTCTACTTTATTCTCGAG*AATAAAGTAGAAAGAAGAGCA* -3'

551 Ribo 1 artificial/synthetic sequence.

SEQ ID NO: 3

5'- GAAATAATAATCTGATGAGGCCGAAAGGCCGAAACTAAAAG -3'

551 Ribo 2 artificial/synthetic sequence.

SEQ ID NO: 4

5'- GAAAGAAGCTGATGAGGCCGAAAGGCCGAAAAATAATAATG -3'

UBE3A-ATS artificial/synthetic target sequence.

SEQ ID NO: 5

5'- TGCTCTTCTTTCTACTTTATT -3'

UBE3A-ATS artificial/synthetic sequence.

SEQ ID NO: 6

5'- CTTTTAGTCATTATTATTTC -3'

UBE3A-ATS artificial/synthetic sequence.

SEQ ID NO: 7

5'- CATTATTATTTCCTTCTTTC -3' microRNA artificial/synthetic sequence.

SEQ ID NO: 8

5'- TCCT*GAATAAAGTAGAGAAGAGCA*GTCAGTCAGTGGCCAAAACTGCTCTTCTT

TCTACTTTATTCAG -3'

UBE3A-ATS artificial/synthetic sequence.

SEQ ID NOs: 9-508

9 TGTGGAGAATCATTGATATAT

10 GTGGAGAATCATTGATATATT

11 GTATATGAGAGTTCCATTATT

12 TGGCTGTGGAAACGCTTATTT

13 TGGATCGATGATGAGAATAAT

14 GGATCGATGATGAGAATAATT

-continued

15 GCCCTCCAATAGGACAAATAA

16 TGACCCAAGACTTGCTTTAAT

17 GACCCAAGACTTGCTTTAATT

18 TGTGCTGAAAGAAGGAAATAT

19 ATATGGCATGCCTCTATTAAA

20 TATGGCATGCCTCTATTAAAT

21 ATGGCATGCCTCTATTAAATA

22 TGGCATGCCTCTATTAAATAA

23 GGCATGCCTCTATTAAATAAT

24 GACAGTGGAACCAAGTTTATT

25 GAGACTCCATGGTTCATAATA

26 AGACTCCATGGTTCATAATAT

27 TTGTGGTCATACTACATTATA

28 TGTGGTCATACTACATTATAT

29 GTGGTCATACTACATTATATT

30 TTGCAACAAGGTAAGTTATAT

31 TGCAACAAGGTAAGTTATATA

32 TTGATTGATGCCCTCATAATA

33 TGAAGTTGGGTAAAGTATAAA

34 GTCAATACACAACTGATAAAT

35 CAAAGAGTTTCAGCCATAAAT

36 CATGCTTTCCAGAGGAAATAT

37 TCCAGAGGAAATATGTTTAAT

38 TTTAATCATCTGCCCTATATT

39 TTAATCATCTGCCCTATATTA

40 TGCAAGATACCATACATTTAT

41 GCAAGATACCATACATTTATA

42 GGTCCATGTGATTTCTTTAAT

43 TGCCATAACTATAGCATTTAT

44 GGATACCATCCACACTATAAA

45 TGTGTTTCCTTCCAGATAATT

46 GTGTTTCCTTCCAGATAATTT

47 GTGTGCTGAAAGGGCTATAAA

48 TTGAACCAACCACCCTATAAA

49 TAAACGTTGTATGGCTTATTT

50 ATCCCTGTGTACACAATATTT

51 ATGTGTGGTAAATCCATTATT

52 TGTGTGGTAAATCCATTATTT

53 ATGAGCATTTGGCAGTAATAT

54 TGAGCATTTGGCAGTAATATT

55 GAGCATTTGGCAGTAATATTA

-continued

56 AGCATTTGGCAGTAATATTAT

57 GCATTTGGCAGTAATATTATT

58 GAGACTCTGCTGAAGTTTATA

59 AGACTCTGCTGAAGTTTATAA

60 CAGTTATAGAAGTGCTAATTT

61 TATGATGACCTCCTGAATTAT

62 GGGTCTGGTGTTTCATTTATT

63 GGTCTGGTGTTTCATTTATTT

64 GGGTCTCATTATAGTTAATAT

65 TAACAGCATGTCAGGTAATAA

66 GCAGAGCCCTATTCCTTTAAA

67 CTCCTAAATGTTTGGAAATTT

68 TTAGCATTTCTGACCTATTTA

69 TAGCATTTCTGACCTATTTAT

70 AGCATTTCTGACCTATTTATT

71 ACAGGATATAGGGAATAATTT

72 CAGGATATAGGGAATAATTTA

73 TAGCACTGAAATGCCTATATT

74 AGCACTGAAATGCCTATATTA

75 GAGCAGAAATCAATGAAATAT

76 ACTTGTAACCAGACCAATTTA

77 CTTGTAACCAGACCAATTTAA

78 ACTCAGTGAACAAGTAAATAA

79 TAGCCCTGTATCAAGTAAATT

80 ACAAGATTCCAGAACATTTAA

81 CAAGATTCCAGAACATTTAAA

82 GAGAGTTACCCAAAGAATTTA

83 AGAGTTACCCAAAGAATTTAA

84 AGAAGAAAGGTTTGGAAATTT

85 AGCCCAATCTATAGGATTTAT

86 GCCCAATCTATAGGATTTATA

87 CCCAATCTATAGGATTTATAT

88 CACATACTACAGGGCATATAA

89 ACATACTACAGGGCATATAAA

90 TTAAAGAGTTGCCACATTATA

91 GTTGCCACATTATACATAATA

92 AGACATTGAACCAGCTATTAA

93 GACATTGAACCAGCTATTAAA

94 AGGGTTAAAGAAAGGTATAAA

95 ATACCCGAGATGACCAATAAA

-continued

96 CAAATCCACGAGAAGAAATAA

97 ACTTGTGTTGATGGTATTATA

98 CTTGTGTTGATGGTATTATAT

99 ATTCATTGGAAAGGGTATAAA

100 CAGTAACAAGAGCCCATTATT

101 AGTAACAAGAGCCCATTATTT

102 GCCCAAGAGATCCACTTTATT

103 CCCAAGAGATCCACTTTATTT

104 TTTCATCTCACCCAGAATATT

105 TGTTATGAGATCCAGTTATTT

106 ACTGAACTGTGAGCCAATTAA

107 CTGAACTGTGAGCCAATTAAA

108 AGTCTTAGGTAGTTCTTTATA

109 CAAAGGCAGCAGCACAATAAT

110 AGACTGGCTATTTGAAATTAT

111 GACTGGCTATTTGAAATTATT

112 CACCATCAAGAGAACTAATAT

113 ACCATCAAGAGAACTAATATA

114 CCATCAAGAGAACTAATATAA

115 GGAAAGTACATAGTCAAATTT

116 CAATGCATACTACAGTATAAA

117 AGTCCTTACGTGTCAATAATT

118 GTCCTTACGTGTCAATAATTA

119 GACACATACAGGCTGAAATTA

120 ACACATACAGGCTGAAATTAA

121 CACATACAGGCTGAAATTAAA

122 CAATATTGAAGCACCTAAATA

123 ATGGATCTAACAGACATTATA

124 CATTCTCCAGGATAGATTATA

125 ATTCTCCAGGATAGATTATAT

126 CAAGATGGAAACTGGAAATTT

127 TTCTATGAGGTAAGCTTATAT

128 TCTATGAGGTAAGCTTATATT

129 ACAAAGATCAGACAGAAATAA

130 CAAAGATCAGACAGAAATAAA

131 ATACCACAGACATACAAATTA

132 TGAAGACTGCCAACCATTTAA

133 GAAGACTGCCAACCATTTAAA

134 CTAATTCAGCAACACATTATA

135 GATGCAGGATAGTTCAATATA

136 ATGCAGGATAGTTCAATATAA

-continued

137 TGCAGGATAGTTCAATATAAT

138 GTGTCTGTTGGCTGCATAAAT

139 CTTTGTAGATTCTGGATATTA

140 GCAGAAGCTCTTTAGTTTAAT

141 CAGAAGCTCTTTAGTTTAATT

142 CATCCTGTTACTGGGTATATA

143 GTATATACCCAGAGGATTATA

144 TATATACCCAGAGGATTATAA

145 ATATACCCAGAGGATTATAAA

146 TATACCCAGAGGATTATAAAT

147 CCCTAGAACTTAAAGTATAAT

148 TGACAAACCTGGAGGTAATAT

149 GACAAACCTGGAGGTAATATA

150 GTCCATTCTCACCACTTATAT

151 TCCATTCTCACCACTTATATT

152 CCATTCTCACCACTTATATTT

153 CATTCTCACCACTTATATTTA

154 GTAGATGACATGATCTTATAT

155 GAATAGAGAGCCCAGAAATAA

156 ATGCTTGACATCACTAATAAT

157 TACACTGTTGGTGTGAATTTA

158 ACACTGTTGGTGTGAATTTAA

159 CACTGTTGGTGTGAATTTAAA

160 GGTATTTGCACACTCATATTT

161 GTATTTGCACACTCATATTTA

162 ATAAAGAGAACGTGGTATATA

163 AGACACAGTGGAATCTATTTA

164 GGTACAAACTTTCAGTTATAA

165 GAAGGCACTGATATGTTAATT

166 AGGCACTGATATGTTAATTAT

167 ATCCATTCAAGCTAGATTATT

168 TCCATTCAAGCTAGATTATTT

169 GGCATGGTGGCCCTCAATTAT

170 GCATGGTGGCCCTCAATTATA

171 CATGGTGGCCCTCAATTATAT

172 ATGGTGGCCCTCAATTATATA

173 TGGTGGCCCTCAATTATATAT

174 GGTGGCCCTCAATTATATATA

175 GTGGCCCTCAATTATATATAT

176 TGGCCCTCAATTATATATATA

-continued

177 GGCCCTCAATTATATATATAA

178 ATGAACAACAATGGGATTTAA

179 TGAACAACAATGGGATTTAAA

180 GAACAACAATGGGATTTAAAT

181 AGCAATAGTGGAGAAATATAA

182 GACCTAAACCCTATCTTATAA

183 ACCTAAACCCTATCTTATAAT

184 CCTAAACCCTATCTTATAATT

185 CTAGAGCAGCAATACTAATAT

186 CTGAAGTGCACATGGAATATT

187 TCTTCAGGATGACACATATTA

188 CACAATGATATGGAGATTTAA

189 CTCAATCCAATAACCTAATTT

190 GTAAACAGAAGGAAGAAATAA

191 GATATCACCTTACAGAAATTA

192 AGGTCCGTATTACCCTTATAT

193 CATCTAGCCTTTCTGATTTAT

194 ATCTAGCCTTTCTGATTTATA

195 TCTAGCCTTTCTGATTTATAT

196 CTAGCCTTTCTGATTTATATA

197 AGTCACAACTCAGATTTATTT

198 GGCCTCACAACTCAGATTTAA

199 GAACAGAGCCCTCAGAAATAA

200 GGAAAGGATTCCCTATTTAAT

201 GAAAGGATTCCCTATTTAATA

202 GACAAACGGGATCTCATTAAA

203 CATCTGACAAAGGGCTAATAT

204 ACAATGAACTCAGACAAATTT

205 CAATGAACTCAGACAAATTTA

206 GTTAGAATGGCGATCATTAAA

207 CAGCCATCCCATTGCTATATA

208 AGCCATCCCATTGCTATATAT

209 GCCATCCCATTGCTATATATA

210 CCATCCCATTGCTATATATAT

211 CATCCCATTGCTATATATATA

212 ATATACCCAAAGGACTATAAA

213 TATACCCAAAGGACTATAAAT

214 ATATGCACAGGTATGTTTATT

215 GAAAGACACTGATTGTATTTA

216 ACATAGCCCTAACCATATAAA

217 CCTCACACAAAGACCTATTAT

-continued

218 TGGCAGAGATTTGGCAATTAT

219 GGCAGAGATTTGGCAATTATA

220 AGAACAACAAGGAGGAAATTT

221 GAACAACAAGGAGGAAATTTA

222 GAATGGAGTGAAATGTTTAAA

223 TCTGATTTCCTTGGGTTTATT

224 CTGATTTCCTTGGGTTTATTT

225 TGCTCTTCTTTCTACTTTATT

226 GTAAGCATTTAGTGCTATAAA

227 TTAGTCACATCCCACAAATTT

228 ATGGTCTGTGCTGTGAATATT

229 TTGAAGTCTCCAACCATAATT

230 CAGTTTGTGCATCACATATTT

231 TGCCCTCTTGGTGGCTTATTT

232 TCCTAGGTCATAATGATAATT

233 CTCCACATCCTTACCAATATT

234 CGCTTATCAGATATGATTTAT

235 GGTCTATACATGTAGATTATT

236 TCATAGATGTATGGGATTATT

237 CATAGATGTATGGGATTATTT

238 CTTGTAACTCCTTGGTTAAAT

239 TTGTAACTCCTTGGTTAAATT

240 TGTAACTCCTTGGTTAAATTT

241 GTAACTCCTTGGTTAAATTTA

242 TCCTTTCTGATGCTGTTTAAA

243 CCTTTCTGATGCTGTTTAAAT

244 CTGAAACTTTGCTGCATTTAT

245 TGAAACTTTGCTGCATTTATT

246 GAAACTTTGCTGCATTTATTA

247 TTGCTCTGTGAATAGATAATT

248 TGCTCTGTGAATAGATAATTT

249 ATATGTTGATCCACCTTTATA

250 TATGTTGATCCACCTTTATAT

251 ATGTTGATCCACCTTTATATT

252 TCTTTGGCTACTTTGTATAAT

253 CTTTGGCTACTTTGTATAATA

254 TAAGTGCATAGAGCCAATAAA

255 ATGCACATGATCTTCTTAATT

256 TGCACATGATCTTCTTAATTT

257 TGGCTTAAACAAGAGAAATTT

-continued

258 GGCTTAAACAAGAGAAATTTA

259 ATATGTTGATCCACCTTTATA

260 TATGTTGATCCACCTTTATAT

261 ATGTTGATCCACCTTTATATT

262 TCTTTGGCTACTTTGTATAAT

263 CTTTGGCTACTTTGTATAATA

264 TAAGTGCATAGAGCCAATAAA

265 ATGCACATGATCTTCTTAATT

266 TGCACATGATCTTCTTAATTT

267 TGGCTTAAACAAGAGAAATTT

268 GGCTTAAACAAGAGAAATTTA

269 AGGTATCAGAGTAGTATATTT

270 AGTTCATCGTTAGTGTTATAT

271 GTTCATCGTTAGTGTTATATA

272 ACCACCATGCCCAGCTAATTT

273 ATGACCCATTTGAAGTTAATT

274 TGACCCATTTGAAGTTAATTT

275 ATGCTGGCCTCACTGAATAAA

276 TGCTGGCCTCACTGAATAAAT

277 GCTGGCCTCACTGAATAAATT

278 TGTTCCCTCCTCTTCAATTAT

279 GTTCCCTCCTCTTCAATTATT

280 TTCCCTCCTCTTCAATTATTT

281 TTGGTAGGTTGTGCGTATTTA

282 ATTAGTTGGCATGCAATTATT

283 ATTCGTAGTTCTCTGAATAAT

284 TTCCTTCTGTTGGCCTTTAAT

285 TCCTTCTGTTGGCCTTTAATT

286 CCTTCTGTTGGCCTTTAATTT

287 GAAAGCATTTAGAGCTATAAA

288 CTTTCACTACCTGCCATAAAT

289 TTTCACTACCTGCCATAAATT

290 TTCACTACCTGCCATAAATTT

291 TCCTTGACCTATTGGTTATTT

292 CCTTGACCTATTGGTTATTTA

293 CTTGACCTATTGGTTATTTAA

294 TTGTGATCACAGAAGATATTT

295 TGTATAATCGCAGTCTATTAA

296 TCGCAGTCTATTAACATTTAT

297 CGCAGTCTATTAACATTTATT

298 GAGTGGTAAAGTCTCTATTAT

-continued

299 AGTGGTAAAGTCTCTATTATT

300 AGCATAAGCTATGTCATTAAA

301 CTCTTCATTTCCTTCAATATT

302 TGAGATACCTAGAACAATATA

303 GAGATACCTAGAACAATATAA

304 CTCTTTCTCTGTGAGATTATA

305 ACAACAGCCTGGAAGTATAAT

306 CAACAGCCTGGAAGTATAATT

307 ACAGCCTGGAAGTATAATTAA

308 ATTCAAACTGATGCCAATTTA

309 TTCAAACTGATGCCAATTTAA

310 AGTCAACACACCAATATTAAA

311 AGCTCCTGTTTGAAGTAAATT

312 GCTCCTGTTTGAAGTAAATTT

313 GCCTTCCAAGGTTTCTATTAA

314 TGTGGGTCTCTTTGGATTTAT

315 TATGGTTCTGTAGAGATATTT

316 TGTTCTCAATTTCCCTATATA

317 GTTCTCAATTTCCCTATATAA

318 AGGTTGGAACATTTCAAATAA

319 TTACATGGGCTGTTCTATAAA

320 TACATGGGCTGTTCTATAAAT

321 TGTTACTTAAGGTGGTTAATA

322 GTTACTTAAGGTGGTTAATAA

323 GTTGCTCAAGTCTTCTATATT

324 CAACATGCAGGTTTGTTATAT

325 ACATGCAGGTTTGTTATATAT

326 ACGTGTGCATGTGTCTTTATA

327 CTTTATAGCAGCATGATTTAT

328 TGTGTCTTTGGCTGCATAAAT

329 CTTTGTAGATTCTGGATATTA

330 GCAGAAGCTCTTTAGTTTAAT

331 TTTCCCAGCACCATTTATTAA

332 TTCCCAGCACCATTTATTAAA

333 TCCCAGCACCATTTATTAAAT

334 CCCAGCACCATTTATTAAATA

335 GTTGTAGATGTGTGGTATTAT

336 TTGTAGATGTGTGGTATTATT

337 TGTAGATGTGTGGTATTATTT

338 GTTCTGTTCCATTGGTTTATA

-continued

339 TTCTGTTCCATTGGTTTATAT

340 GGATGGCATTGAATCTATAAA

341 GATGGCATTGAATCTATAAAT

342 CCTAATTGAATACCCTTTATT

343 GGCTGTGGGTTTGTCATAAAT

344 GCTGTGGGTTTGTCATAAATA

345 TGTCCCATCAATACCTAATTT

346 GTCCCATCAATACCTAATTTA

347 TCCCATCAATACCTAATTTAT

348 CCCATCAATACCTAATTTATT

349 TTGTCTTTGGTTCTGTTTATA

350 TGTCTTTGGTTCTGTTTATAT

351 AGCATGCTTTGCTGGTATTAA

352 GCATGCTTTGCTGGTATTAAT

353 CATGCTTTGCTGGTATTAATA

354 ATGCTTTGCTGGTATTAATAT

355 TGCTTTGCTGGTATTAATATA

356 GAGAGTTAGAACCTCAATATA

357 AGAGTTAGAACCTCAATATAT

358 CCACCACGCCTGGCTTTATAA

359 CACCACGCCTGGCTTTATAAT

360 ACCACGCCTGGCTTTATAATT

361 CCACGCCTGGCTTTATAATTT

362 GTCTAGCTCCAAGTGATATAT

363 TTTGCTTCTGTCTGAAATATA

364 TTGCTTCTGTCTGAAATATAT

365 TCTTAAGTCTGTGAGTTTATA

366 TCTCTGATTTCCACCTATATT

367 CTCTGATTTCCACCTATATTA

368 GTATATACTCCAGAGAAATAA

369 CACCAGAACTTGAACATTAAT

370 ACCAGAACTTGAACATTAATT

371 CCAGAACTTGAACATTAATTT

372 GTCTGGAACTCCTGGAATTAA

373 CTTTCTGTGCCTGGCTTATTT

374 CAGGATTTACCTTCCTTTAAA

375 TCTGTTGATGGGCACTTAAAT

376 CTGTTGATGGGCACTTAAATT

377 TCATAGCGGCTGTACTAATTT

378 CATAGCGGCTGTACTAATTTA

379 TTTACCCATTTCCAGATATAT

-continued

380 GTGTAAATAAGGGTCTAATTT

381 TGGTTATGTCATCAGTAATTA

382 CCTTGCATCCTAAGGATAAAT

383 GTGAATCCAGTTTGCTAATAT

384 TGAATCCAGTTTGCTAATATA

385 GAATCCAGTTTGCTAATATAT

386 CCATGTTCATCAGGGATATTA

387 GTGTCTTTCTCTGGCTTTAAT

388 TGTCTTTCTCTGGCTTTAATA

389 GTCTTTCTCTGGCTTTAATAA

390 TTGTGATCCTTCTTCTTTATT

391 GTAGGTTTGTATCGCTATAAA

392 TAGGTTTGTATCGCTATAAAT

393 AGGTTTGTATCGCTATAAATT

394 GGTTTGTATCGCTATAAATTT

395 TCATTTGTCTCAAGGTAATTT

396 TTTGGGAGCATATTGTTTAAT

397 TTGGGAGCATATTGTTTAATT

398 TGGGAGCATATTGTTTAATTT

399 TGGATGGAATGTTTCATATAT

400 AGTATTGAGGTCCCGTATTAT

401 GTATTGAGGTCCCGTATTATA

402 CTCCCTCTTCACATCATTTAA

403 TCCCTCTTCACATCATTTAAA

404 TATGTCTTCTTGGTGAATTAA

405 ATGTCTTCTTGGTGAATTAAT

406 CTGCTCTCAATTTCCATTTAT

407 TGCTCTCAATTTCCATTTATA

408 GCTCTCAATTTCCATTTATAT

409 TCCTTCAGCACTTTGAATATA

410 TCAGCTATTACTTCCTTAAAT

411 CAGCTATTACTTCCTTAAATA

412 TCCTTAAGGACCTCCTATTAT

413 GCTTGACCTCTAAACATATAA

414 CTTGACCTCTAAACATATAAA

415 ACCAATACCTTGTGTAATAAA

416 TTGACACTGGCTCTCTTTATA

417 TGACACTGGCTCTCTTTATAA

418 CAGAAGATGTGTTTGATAATA

419 GTTTGACGTGAAGAGTTTAAA

-continued

420 CTCTGAGCTTCAGTGAATTAT

421 AGGGTTGAATGCTGGATTTAA

422 GGGTTGAATGCTGGATTTAAA

423 GGTTGAATGCTGGATTTAAAT

424 GTTGAATGCTGGATTTAAATA

425 AGTGAAAGCAAAGAGAATAAA

426 CATGATGTTCCAAACTTTAAA

427 AGGTGGCCAAGGGCCTTAATA

428 GCCCAGCTGGCTCTGTAATAA

429 CCCAGCTGGCTCTGTAATAAA

430 CCAGCTGGCTCTGTAATAAAT

431 TGGTGTCATCGGGCCATATTT

432 TAACTAGGTCAACAGAATATT

433 GCAAAGTTAATCCTCATATAA

434 GCAGCATCTGTTCTGATTAAA

435 CAGCATCTGTTCTGATTAAAT

436 AGCATCTGTTCTGATTAAATA

437 GCATCTGTTCTGATTAAATAT

438 CTGCACAACTGACCCTTTATT

439 TGCACAACTGACCCTTTATTA

440 TGATGGCTTTCCTACTATTTA

441 GATGGCTTTCCTACTATTTAA

442 AGCTCAGCCATCTGGTTTAAA

443 CTGACTGCCTTAGACTAATAT

444 TGACTGCCTTAGACTAATATA

445 CAGCATTTGACAAAGAAATAA

446 AGGATATGGATGATGTATATA

447 GTCGACCCTAAGAAGATAATA

448 AGAAACCTGAACAAGTAATAA

449 GAAACCTGAACAAGTAATAAT

450 AGTCACACAACAGACTAAATT

451 GTCACACAACAGACTAAATTT

452 AGCGAGAGTGTCCTCATTTAT

453 GCGAGAGTGTCCTCATTTATA

454 CGAGAGTGTCCTCATTTATAT

455 ATCCTCTATCTCTGTTAATAA

456 AGCAAGTGCTATTCCATATTT

457 CTGGAGTCCATGGAGAAATAT

458 CCTCCAAGGACATACTTTATA

459 CTCCAAGGACATACTTTATAA

460 TCCAAGGACATACTTTATAAT

-continued

461 CCAAGGACATACTTTATAATA

462 GTGAGGGCAATGGTGAATATA

463 TGAGGGCAATGGTGAATATAA

464 CGAAAGGCAAGCTTCTTAAAT

465 GAAAGGCAAGCTTCTTAAATA

466 GGCAAGCAAGGCAGGATTTAA

467 ACAGGAACCTGGCTCTAATTT

468 GGGACCTCCTGACATTTAATT

469 GGACCTCCTGACATTTAATTA

470 GACCTCCTGACATTTAATTAA

471 GTGGGAGCTTGTTACATATAT

472 CTAAGTCTTCTCATCTATATA

473 TTAGGTGGTCATGAGATAAAT

474 TAGGTGGTCATGAGATAAATA

475 AGGTGGTCATGAGATAAATAT

476 GGTGGTCATGAGATAAATATA

477 GTGGTCATGAGATAAATATAT

478 CACAAAGCACATGGCTAAATA

479 ACAAAGCACATGGCTAAATAA

480 CGGTTATGTAGAAGCTATTTA

481 GGTTATGTAGAAGCTATTTAA

482 AGCCACCCTTAATTGAATAAT

483 ACTACCCTTTACTGGTAATTT

484 TAATAGGCACTAGAGAATAAT

485 ATTTGGGCCCAAGTGTATATT

486 TTTGGGCCCAAGTGTATATTT

487 TTGGGCCCAAGTGTATATTTA

488 TGCCTGCTGTGGGTGATTATT

489 GCCTGCTGTGGGTGATTATTT

490 GGGATCTTTAGGGACATAATT

491 GATGACACTACGTAGATATAT

492 TGCTCTTTCAGTTTGTAATAA

493 GCTCTTTCAGTTTGTAATAAA

494 GTCTTTCCATGGGTCTAATTT

495 TCTTTCCATGGGTCTAATTTA

496 ATCAGTTTCTCTAGGTATTAA

497 TCAGTTTCTCTAGGTATTAAA

498 AGGCCAAACTCTCTCTTAATT

499 CTTACCCAGTCACTGTTAATT

500 TTACCCAGTCACTGTTAATTA

-continued

501 ACCCAGTCACTGTTAATTATT

502 CCCAGTCACTGTTAATTATTA

503 CTCAACAGCTTCAACATTATA

504 TCAACAGCTTCAACATTATAT

505 ATACATCTTGACTCCATTATT

506 CCCAAACTGGACAGATATATA

507 CCAAACTGGACAGATATATAA

508 CAAACTGGACAGATATATAAT

Human UBE3A sequence.

SEQ ID NO: 509

CAATGAGAATAAACTCACTGTAGCTCCATGCTACAACATGGATACATCTCAAAAACAATTTTGA

TGAAAGAAGGTGGACACAAAAGAATACATGCTGTATGACTCCTTTTACATAATGTTCAAAAAAC

AAGAAAAAACTAAACCATAGTATTTAGCAATTCAAACTTAGATGGCAAAAGTATAAAGAAATGTA

GGGAAATTATTTTCGTAAATGTCTCCTCTAGGGAAAAGGGAGGATTAAGTCAAGCTCATCCATC

ACTCCATACTGGCCCTTCCTCGCCAGTGATCTCACATGTTTATTCCAACAAGAGAGCTGGAGAA

ACTGTGTTTGTGCTATATCAACAATTCTCAGTGAATGTCTTGTTGACTGGGAAAGCAATGTGGG

TCCTACTTTTCTTTCTTTCATTTTGTAAAACCATTTCTGATGAGCATGAATGAGTCCTCCATTT

CTTAAGTAACTGACAGCACAGGTTTGATATCAGCAATCAAAGATCTGCCAGGCCTTGTTTATCA

TGCCTCACCTCTGTTGCCACATGTTTCCCAGGGATCGATTGAATGTGACTATGAGTAGCTCTCC

ATGTACACCATCTAGTGTCACTTCTGGGACTTGGGGGTTTCTGACTTACAGTCCTCTTCCCTAT

CATTTATTTACATATTCAGTAAATAATCATGAACACCTACCTTATGCCAGACAGTGTTCTGGGT

GCTAAATATATAGTAGTAGAAGAGATAAAGTTTATGTTTTCATAGAACTTTCAATTCAGTACAT

GAGATGGAAAGGTGGACGGTGCCTGTAGTCCCAGCTACCCGGGAGGCTGAAGTGAGAGGACTGC

TTGAGCCCAGGAATTTGAGACCAGCCTGGACAACGTAGTGAGACCCTGTCTCTATTAAAGTTTT

TTTAAATTACTGATATAATTTAAGGTAGTGGTGAGTACTAGAAAAAATGTACCAGGAGAAAAAA

ACAGAAGCAAAAGTACATGTGGCCAATACTATTTTGATATGTAGAGGCCAGGAAAAGCTTCTCT

GAAGAGGTAAACACAAAGTTGAAGGATGTACCATCACAGAGAGATGGAAGTTTTCCATAATTTC

CTTGCATATACTATGGTGTGACTTCATTTTTTCACCCACGTCTGTTAGGCTGCTCAGATAAACT

GCTTTTTTTTTAAACGAGATCTAAAGACCACGTACATTCTTCATAGTCCCTGAATTAAGTATTA

CCCAAACCATAGCTCATGGGCCACCTACCTGTTAATTTAATGTCTATGTATGCCTTCACTCTAC

AATGGCAGGCTTAAGCAGCTGGGACAGAGACCACATAACCCAGAAAGCCTAAAACTTTTATTCT

CTGGCCCTTTACAGCAGCAGTCCCTAAACTTTTTGGCACCAGGGACTGGTTTCCCAGAAGACAA

TTTTTCCTCCTACTGGGGGTGAGGGATGGTTTCAGGATGATTCAAGCGCATTACTCTTACTGTG

TACTTTATTTCTATTATTATTACATTGTAACATATAAGGAAATAATTATACAGTTCACCATAAT

GTAGAATCAGTGGGAGCCATGAGCTTGTTTTCCTGAAACTAGACAGTCCCATCTAGGGGTGATG

GGAGACGTGACAGATCATCAGGCATTAGATTCTCATAAGGAGTGTGCAACCTAGATCCCTTGCA

TGTGCAGTTCACAATAGGGTTCGTGCTCCTATGAGAATCTAATGCTGCCACTGATCTGACAGGA

GGCGGAGCTCAGTAATGTGAGTGATGGGCAGCAGCTGTAAATACAGATGAAACTTCCTTGACTT

CCCTGCCCTCGCCTCCTGCTGTGCAGCAATTTCCAACAGGCCACGACAGGGGTTGGGGACCCCT

GCTTTACAGGAAATAATGTGCTGATCCCTGGTTTAGATAATTGATTTTGAAATTTGATTCTATT

TAAAACTATTAGTTTTCCTGTAAGCTCTTCTTTAGCTGCATTTAACTGGTTTTAATATGATATA

CTGCAGTATCATTCGATTCAAACTATTTTCTAAGATTCGAAGATTTGCTGTAACTTATCCTTTT

-continued

ACCAATGGGTTATTTAGAAGTGTGCTGCTTAATTGCTAAGCTATTGGAAATTTGTCTACTTACC

TTTCTGTTCTTAATTGTCAGTTTAAATTCACTGTGATGTGGTCAGAGAATACAACCTAAATGTT

ATCAATCATTTGAAAAAATTTTAGGACTTAAATTAGGGGCCAGCATACAGTATACTTTGGTAAC

TGTTCCCTGTGTAAATAAAAAGAAAATCTGATCTAGAACTGTTAACTGTGGTATCTTACATAGT

CAACTTGATTAATTTAATGAATCATGTTGTTCAAATATTTTATATTCCTGTTGATGCTTTGACA

GCTGTTCTAATACTGAGAAGTGTGTGTGAAAATCTCCAACTATTATTATATGATTTTGATGTTT

CCTCATCTAATTCTGTTACACTTTGAAATATAAATTTTGAAGCTATTAGGTGCATATAGGTGAA

ATATTACATACAGAATATTTTATGATTTTTCTGTTTAATTGACAGTTTTACTATTACAAAATGT

TCTTGTGTTCTTCTAGTGATTTTTCTTGCTTTAAAGTCTATTAACTTGATATTATATAATAATC

AACTTTCTTATAGCTATTGTTTGCATGTTATAACGTCTATCCTTTTACTCTCCATTTCACTGTG

TTCTTATATTTAAACTGCCTTTCTTATCAATAGCACATACTTGAGTCTTGTTTTTGTATGCAGT

GTGACAATCTGTCTTTAATTGAAATGTTTAGTTATACATATACAATATAACAAATAAAATAGAT

GGATTTATATCTGCAGTCTTGCTATTTATTTTCTATTAACTCCATCTATTTTCATTTCATATTT

TTTCTCTTCTGCCTTCTTTTGAATAATCAGCTTTTTTGCTATTCTATTATTCTCCTCTATTAGC

TATTCTTGAATATTTTAATAATTAGCTAGAGATTCAATACAAACTCCTTATGTTCTACAGTCTA

CCTTAAGCTAGTTGTTTTTACCACCTCCTGAGGGTGCAAGAACTTTACAACACATGTAATCAAT

TCACTGTCCTCAGTCTTTGTGCTATTGCTGGCATATATTTTTACTTCTCCATGTTATATATTTC

ACAATACATCATAATTATTTTTAACAGTTATTTGTTTATATTTTTCAGATATATTTACCCAATC

CAGTGCTCTTTATTTCTCTTTCTTGCAGTTTTATGCTTTCATCTGGGATAACTTTCTTTCAGCC

TGAAGAGTCTATTTTAAAATTTTTTCTAGAAAAAATCTGCTGGCCATGACTATTTTCAACTTAT

TTTTGTCTAAAACATTTTTATTTTACATTTATTTATGAAGAATATTTTCTCTGAGTATAAAATG

TTAGGTTGGCTGCTTTTTTTATTTCAGGTTTCAGAGATGCCTTTCTATTTTCTCCTGGCACCTA

TAATTTCTGATAAAAAGTCAGCTGTAAGTTTTATTGTTGTTCCTTTAAAGGTTATGTGTCTCAT

TTCTCTGACCATATTTAGGGTCATCTCATTCTCTTTGGTTTTCAGCAGTCTGACTGTGGTGTGC

TTCAGTGGGGTTTTCTTTTACTCTACGTAAGATTCACCAGTCTGCAGTCTGTGAGTTGATAGCC

ATTCAACAAAAGAAAAGAACAGCAGCTACCATTGAAATCTCCACCTGATTAGACTTACAATAAT

CCACACTGTCATTCTCTAATATCCATCTGATTTTTTGCACAAGCCAAACAACCAAGTTAAGTGG

GAGAGGTAGTAGAAAGCAACACCCCTATGTCTTCCCAATTTTAGGTGGTGGCACTAAATCACTA

ATATTCTCCTTGAGGCATGGTATTGCTTTTGGTTTATTTTTTTCAAATAGAGGACTACGTTCAT

AGGTTTATATCACGAGAGTCCCTCATTCTATGGGTCAGTGGAACAACTGAGGATCTTGTCAGAT

AACAAGTATGTCTATTACAACTCACATTCAGGATCTGAGGAATTAACAGGATGGCTCATGGACC

TACTGGACCCATTGAGAAATGATGTCAACTGATGTTCACAAGCCCTCATCAGGCTTGAAGGACC

AGAGTGTCTTTATGGTCGCCAGGAATTATTACATGTTAGCTCAGTGACAGTGCCCCCAAATCCC

TGAAAGATCTGGATATTTCCTTTCCCTTGGTGAACAGTTATTCTGCTAAACGATCGCGTAGCTC

CTTCAGGAGGGCTAGAAGGAAAATATACAGCATGAACTTATTGGGTTATCCTCAGCTGTACCCA

GACTCACCTTCACTCACATGACTCTGTGTCTATGAACTGACTGAGGTTTGGGATTTGGCAAGGG

GCTGTGAATCTCTATTGAGGTGGCTTAAGTCAAGCTTTGGTTTACTCAGAACTAGAATTGTACT

TATCTAAAAGGACACAGTAAACTGATTACCTATTTCAGTCCTTGGGACTTCATGACCAATTCAC

CTGTCAAAGATCCCTGTAGGCTAAACTATTCAGATTGCTACTCTAGCTCTTTTGTGCAAGATTT

CACCTCCTAAATTAGACTGCACGTGGCCTGCTTAATGACTTGAACCACAATCTCTTAAATCAAA

-continued

GTCTTTCCTTCAAAAGCTACTTTAGTCCAGCTGACTACAAAAGATCATTTAACTGTTTGGTCAC

TGTGTGCCATGGACCACTGTCCCACTGCCAGCACTACTTAGATACTTACTGTTTTCAAATCCAT

TTCAGACACTAGTCCCAGATTTCTATTTCTTTAAGGATCTTTTGTCATCAATTCTGTGTCAATA

ATACTTGTTGGTTGGAGACAACAGAATCCATAGTAACTAGTCTAGGCAGGCATGTCAGATGATC

CTAGATGACCCTTATGCTCAAGTATTTGCCGGAAGGACTCACAGGACTCAGAAAAGCTCTTACA

CTCATGGTTATAGTTCATTACAGCAAATGGATACAGATTAAAATCAGCAAAGGGAAAAGGTACA

TGGGATGAAATCCAGGAGAAACTAGGTCCAGGCTTCCAGATATCTTCTCTGCTGGAGTCACATG

GAGATACACTTAATTGTCTCTGCAATAATGTGTAACACATATGAAGTAGCTTCCTGGTTGGCAA

GACTTCATAAATTTTGCCATTATTTGAAGATAACCCACACCTTGGTGTCCAGGGTTTTCACAGG

TATTAGTGGTCAGTCACATAGGCATATAGTACCTGTATGACTTCTATTCCAGCCACCGCAAACT

TCTCCTCTCCCTGCTGGCTCCTGAGCCAAAAACAGGCATTTACCATAAATCACTTTGTTAGGAT

GAACTTATCTGGCCAAACTGATACAGCATGACCCACAGCCTCAGGTATATAAAACACTCTCATC

AGGCAGAATGTTTCAGGGTCTCAGAGGTTAGTCAGGGGCTAGTCAAGGACCAATCCTGAAGGCA

GGCCTTTTTTTTTTTTTTTTTTTTTTTTTGAGACGGGGTCTTGCTCTGTCGCCCAGGCTGGAGT

GCAGTGGCATGATCTCAGCTCACTGCAAGCTCTGCCTCCCAGGTTCACGCCATTCTCCTGCCTC

AGCCTCCTGAGTAGCTGGGACTACAGGCACCCGCCACCATGCCCAGCTAATTTTTTGTATTTTT

AGTAGAGACTGGGTTTCACCGTATTAGCCAGGATGGTCTCGATCTCCTGACCTGGTGTTCCACC

TGCCTCAGCCTCCCAAAGTGCTGGGATTACAGGCGTGAGCCACCATGCCCAGCCAAGGCAGGCC

TTTTTTTGGAACCTACAGGGTTTGACCAACCCAGGACTGCTGAGTTAACCCTTTCCTGTGCAGC

AAGAAAAGATTTATTTAAAAAAAAAAATGGAAAATCACAGTTTAATCAGAAGGGATGAAAAGACA

GCTTCTAGCTTGTATTTCTGAGAACATTTCCCAGAACCATATCATAAAACTGGCCTGCTAAGGA

AGATGTCTCTGCTAACCCAGAACAAGGTTAAATTGCATGTGGTTTATGGTTATATATGGGAATG

CCCTGGTTCTTATGGAAAAGATACAGGGATAAAGTGTTACAAAGTCTGTAACTTATGACAAATG

GGTCCATAGCTGGAGATAACAGATAAATGGATAGATAGAACAAATATGGCCAGATATAAACTAC

CAGGACATCTAGCTAAAGAAAATATGGTTATTGATTATACTATGCTCTAAACTTTTCTTTAGAT

TTAAAAAATGACCAAGAAATAAGGAAGTACAAAAAACTATGGCATGTTTCATATGAGAAGTGTT

TGACATAAAAGGGAAATTGGGAGGCTGGGTGTGGGGCTCACGCCTGTAATCTTAGCACTTTGGG

AGGCTGAAGTGGGAGGATCGCTTGAGCCCAGGAGTTCAAGACCAGTCTGGGTAACATAGTGAAA

CCTAATCTCTACTTAAATATATATATATATAAAATAAATTGAAAAAAAGAGAGAAATAGGAAAAAA

GCTACTGAGAACTAGATAGTAGGTTTAGTAGGTTTGAAAGTCATGAAGAAGTTCAGACTGAAGG

ACTTCTAGATGTGAGGAGATTACAATCAGGTAATAAAATATAGTACAGTTGACACTTGGCACAC

ATAGAAATGCCACAGAAATATGGAAAAAAAGGAAAATATGATTGCCTTTGGGTGTTAACCTGTT

GGCTTATTCACATATGGACCAAAGCAGAGTTTGTTATAAGTCACTTAAAAAAAAGAGAAATGGC

TTCCAGGCCTGCAAGATATAATGGAAGCCTGACATTTCTAAAGAAAAGGGCTAGTCATCAATGA

AAACACTGGATAAAATCAGACTAGGAAAGTCTGGCTGTAACTTCCTAGGGGATATTTGCCCAAA

AGCTTCAACATACTCTCATTCCCGTCAATGATGCTTCACGGAAGTTGAATGTATCAGGTATCAA

TTGTCCAGTTCTTTCAGTTCCTGTTCTGTCACTTCCCTTTGTCTAGATTTCAAGCTTCCTAAGA

AGCTTCTGTTATGTGGGGACCCTGTGTGTCTTCTTACAGGGAAAAAATGCTCTGGTCACCTGCA

TACCAGTCCTTTCCAGCATTCCAGTCCCTCTGATGGGTACTTTTCAATTTAAATCAATAAACTG

GCATTCCGATTTTATAATTCCATCTCTTGAGTTTGTTAAATGTGAGTTTGATTGGTGGGCTGGC

TTAAATCAGTTTCTAAGCCTGCAATCATGAGGGCCAGACCTGAACTCTAGTCAACTCACCAAGT

-continued

TTGGCTCGTTTGTTCATTTGTGTGGCAAATGCGATTGGTGCCCTGGATCTTCCTACTGTATTGT

ATGCCAGTCCTAGTTTCAATTGCCAGCTCCTGCATTTCTTGCTTAGGGCTCTCTCTGACCAGCT

GGAGCTGCTGTGTCCCAACCACAGCAAGCCAGCCAGATGAGGATAACAACATTATACACTCACA

GGATAATTGTGAAGTGTGTGTTCTACACTGGCTCCCAGAGTTCTTCAACATAAGCAAATTCCAG

TTGCCCAAAGTGGACACTTGATTGATAATACACCCTTTTTGGTTTCCTCCCTTCCGTAACTCAC

TTACTTTCTTACCAGTGTTTCTAGGGATCACCTCCCAAATAAATTACTTGCACTGAAATCATTG

TCTCAAGGTCTGTTTTCGTGAGAAACACAAACTAAGACAACTTCGTCCATTCATTCATCATTTA

TTGAGCTTAATCAATTATTAATAAGTCCTTAAGGCACAAAATAAGTCCTTAGCAACATGTTATC

TCTTTTCTCATCACAGTATTATCCCCTTTACAAATGAAGAAATCAAGGTTGAAATAAATTAAGT

AGCTGACTCAGTATCACATAATCAGGACAGAGTGCTGGAAAGGACTGATGGCAGATGAAGATGG

CTGAGACTCCCAGATGCCCAGTCTTGAATGGAGAGTATAAAAAATGAGTTTTCTGCTGGGGTAA

TAATTTGAGTATATTATAAGATTGCTACGAAGCAATGAAAAAAGGGATTATTGAATGAGGAAAC

ATTTCAATGAAATATATTTTTGAAATTTTTGTTTTCTAGGAAAGCAACATGCTACAATAAGAGC

GCACACACATACACCTGTGGGTTTAAATCCTAGCACTACTAGTTTTTAGCTGTAAGACATGGGC

AAGTTGCTTACTTACTCTAAGCTCAATTTTCTAATCCATAAAGTATATAATATCCAAGAATGTT

GTATGAATTAATGAGATTTATTTAAACAACTGGCACCTAATGAGTGTACAAATTTAATTTGCAG

AAATGTACTGTCCTTTCAGGAACTTTGTGGTAAGTACTGAAATATGGATGCAATCAGTACTATG

CTTAGCAGTAACTTAAAAAAAGAAGCAATATAAAATTTGTATGTCATAAATGATAACTATATTA

CTATCTTTAAAAATCTTGGTCTTTCCATATGTAGTATGCTAATTTAATGTTACAAAATAAAAGT

AAAATCAATAATTTTAAAAAGTCAGACTTTAAGTATAAAATTTTGTTTGAAGCAATGCCAAAGA

ATCCACATAGTAACATTTATCATTTTGATAACAGAATTTTGTGTTCTGTATGTGGGCCTCAAGC

AGTACTAAAACAAAATAGTGTATCAATTATAAATGATACTCATGATTCTTCCCTAGTCAGATGT

TTTTTTCAGTTGAGAGATTCTGAAGAAAAACAATAAGTGTAGAATGTCTGTACCATCTTTAATA

CTAAGATTTAATTGAATCAATGCATTTCCTTAGATTTAAAAATCATTTTGTTAGAGTCTGTGTT

AGAATCAGTATGATACGTATTTAAAATGGAATTAGAGATATGGACTGTAGTAGGAATGACTTCA

AATAACTCAAATGATGCGCATGTCAGAAAGAAACAATTTCTAAGGGCTGCTTCATTGATTCAAG

TGGAACTGTTTTATTCAGAACAGCTCAGATTAGCAGCAGCAGCAGCTGGTGTTCAATGAAATGC

TTCCCTTTTCCACCTACTCTCCAGCTGGGTTAAGACAGGCACAAAGAGATTGGGATGACCAAGG

TCAAAGCATGATTTGATAGACTTCCAGGTTTTTGCTCCAGTAACTTCTTGTGTAGTCTTGGCTA

TAGAGGCAATTCGTGAAATTGGTGGTTGAAAAAGTCATAGCTTTAGAAGGACTTCATAGATCAT

CTTGTTCAATATCTTAATTTTATACTTCATATACCACGGTTCTAATTAAAATACTTTATTGTTG

CATATTTATTGGAATTGACAAGAAGTTAAGATTTCTTACATTTATTTCATTTGCCTGATTTTTC

TGTTCCCACTGAATTGTATAAGCAGGCACTACTGCACTTTGTATCTCTACTTGACATAGCTGAA

AAATGAAACATTCAAAGATACACTACTTTATTACATGTTAGCTCAGTAAAGGGGCCCTCTATTA

GACATGCTGGTCTCAGTTCTTAACTTTTACACTCACAAAGCCCGATTCACTCATTCAAACCTTT

TTTGAGGAGTTACCAGGTTTTAGCCATTGAGATAGATACTGGGAACACAAGAAGTCAAGGGTGC

TCTCCTCTCTCAAGAAGCTTAAGAGAAGACAGAAGTGCTAAGCACATACATCGAGTATGCGGAG

GGCACACAGAGGTATAAGCAATGACCCTCCTTGAGTAGATCTGAAAGGCTTCTCAGAGGAGGAG

CTTGAACTTGTCTAAAAGGTAGAATAAACTGCATGCAAAAGAGCTCCAAATGACTCTCAAGCTT

AAGTATTGCCTAAGCAATACATTCATGTGGGAAGTGGGAGATGGGGCTGGAATGGAGGCAGAGG

-continued

CCACATCCAATGGGCCGTTTTTGGAGTTTAGACATTATTCAGAAGGCCATGGTGAGCCACTGAT

AGAGTTAAGAAAGGCAGCAAGGTGATAACACATGTTTCTTAAGAAAACATACTGTGATGAGGAC

ATTTGGCAGGAAAGTAGTATAATATGAACCAGCATTCTCTGAATGTTGGGGTTAAAATAGTGAA

TGAGGTAATATGATCTTACCCTTCTGGAACTTACAGTCTAGTTCAGAAACACAACGGGTCTAAA

CACTAAGGGTCTAAATTAAGGTAGTAGCAGTGGAAATATACAGAAGGAAATGGATGTTATGATA

ATGATGATGATGATATTGCTTATTACCATTTATTGAACACCTCCCATGTGTCAGGCACTAAACA

CCTCATATGCACTATCTTTGTCCATTCTCCACACAGTAGCTAGAGTTATTCTATGGATCTTGTC

ATAACTCTCTCAAACCCTTCCAGAGGCTTCCCACCTCATTCAGCACAAATACCTAAGTTCTTAG

GAAAAGCTAAAAAGTCCTCCAGGCTGTGACCCACTGTGACTTCTCTGAGCTCATCTTCAACTCC

TCCTTTCTCTCTCTAGCCACAACGCCTTGCTACTGTTCCTAGATGACTCTAGGCACCTTTCTGC

TTCAGGGCCCCCTCTGTCTAGAAGGTTGTTTCCTTTGTATTTCCACAGTTCATTCCTCACTTCT

GTCAAGCCTCTGATTAAACGAATTCTTTTCAATAAGATCTTCCCTGGCCACTCGGCATGACGGA

ACTCCTGTAGCACTCCCTATTCCCTTTGCCTTGCTTTGTATTTCTCCTTAACATATCATATTCT

GACATAACACATATGTGTTGGTTTTCTTCCTCCATGGATCACAAACTCCATGAAGGTAGACTGT

TTTTGTTCATTGCTGTATTCTCAGCACTGATAACAGTGCTCGCACATATCCATTCAATAAATAT

GTACTGAATAGATGAATGAAGGATTACAATGGTCCTATGAGGATGGTACTATTATTTTTTCCCA

CTTTCCTAAAGAGGAAACAGACACCAATTGAGGTACTCAAGGTTGTATTTCTGGTAACTGGCAG

AACTGGGATTTGCGTGGGGCGGGGGGAAGCCTGCCTTTGTTGAGTTGTACTATGTGCCCAGCAT

TATTCTAAGAACTTTATGTACATTAACACTTAATCCCTACACCTCCATTTTATAGATGAGGAAA

CTAAATCAGAAAGGGGTTTACAATCTTGCCTGGTATCTGTGCACTTGCCAGTAAGTTGGGGGCC

TGTGCTCTCAGCTACTTTGCTACACTAATTCTAAAGCCAATTCTTTAGAGAGATACAACTTTGC

CTCTTAATTGCCAGGAGAGTGAGGGAAAGGAAGAAATCCAGGATTGCTACCATTATTATGACTG

TGGACCGCCATAGATGGTAGAGTCACCAATCAAGTCAAAGAATGTAAGATGAGTTGGTTTCATT

CTCCTCTAACTCTAGACTTCCACATCCAACTGCCTCCTGATATCTTTGCTTGGATATTAAGACA

CAAGGTCAGCTGCAGTTAAAGGGATTTAGAATAACCATGGCAGATCATAGAAGTTAGTAGCTGT

CTTACATCAGAGTTGACCTGGTACACAGGACCTGCCCAATGAAGTCCTCAGGGCCCCAACTTGT

TGCTCTGCAATCCCTAGAATGTTTCCCAGTGTCTTAGTCTTGTTTATGCTGCTGTAACAAAATA

CCTGAAACTGGGAAATTTGTGAAGAACAGAAATATACTTTTTCACAGTTCTAAAGGCTGGGAAG

TACAAGCTCAAGACCCCCAGCAGGTTTAGTGTCTGGTGAGGGCTGCAGTTTCCAAGGTGGGACC

TTACTGCTATATCCTCTGGAGGGGGGTGAATGCTGTGTCCTCGTGTGGCTAAAGGGATGGAAGGG

CAAAAGAAGGCCTAAGCTAGTTCCCTCCAGTCCTTTTACAAGGTATTAATCCATCCATGAGGCA

GGGCCCTCATGATTTCATCAGCTGTTAGTATCATCACAATGGGGATTAAGTTTCAACATGAATT

TTGAAGGGGACACCATCATTGAAACCACAGCATCTTTCAACATGGTTTACTACCCCAACTATTT

AATACATACATTCATCAGAAAAGGACAAAAGAAAGGGCAAGTGACACCCAATTTCTTTTAGAAA

ATGATCTGGAAGTTGCATACATAATTTCTGCTCACATCCTACTGGCCAGAACTTAAGAGATATG

GCCACACTTAAGGGTGTATTATAGGCAACCATGTGTCTGGCTAGATGTTCTATTATCATGGATA

AAGAGCAGAATGCATAAGAGTCAGCTAGGAAGCAGTTTGTACAACAGATATCCAACAGGTATCT

CAAATTTAACATTACCAAAACTAAATTCCTGCTTGTTCTCCCAAAACCTGCTCCTTTGCACTGT

TATCACATCTCAGTCCATGGTGGAAGACAGAACAAACTCAGGGGTTTGATGTTAATCATGTTGA

GCTTGAGGTGCCTGTAGAACACCCAGTACAGGTTTCCAATAAGGGGTTGAAGATACTGTGTCTG

ATGCTTCTGACTGAGATCTGTGTTCAAGATTCAGACTTGATTCCTGACTGAAATAAGTGATAGA

-continued

AGAGTATACGTAAATGGTACTGTCAAAGATTATAACATGGTAGGCAGAGAACCAAGAATGGGGA

GGGAGGATTCTGCACAGGAGACCTGAGAAAGAGTGGCCTAAGACAAGGCAGAAGAGCAGAGAAT

GTAAGGTGACAGAACCAAGGGAGCAGTTTCCAGGAGGCAGTGGTCAGCAGTGTGGAAGGCTGCA

GAGAGATCAGATGTTATGAAAACTGAGAAGCAACCTTTCAATTTGGCCATTATGCCACAGTGAA

ATTGATACAAGCAATGTATACAGTAAAATGGAGGGAGCTGCTAAATTTCTGTAGTTGAAGAGGA

ATTTGGAAGGTAATAGCAATCTAAGTATAGACAGCTTTTCTAAATAGAAGGGACAAAGTAGAGG

GAGAATTTATGAACAGGAGTGGGAATATTTAAGGGAGTAAGAGTCTTGAGTCAATCTCTCTTCC

CTCAAGAAATAAAAATTACCTGTAGAAAGGACAGAAGGATGGCTTCTACCTTAAGACTCGAGGT

CAGAAAGAATGCAAATTTAGACAGGTCTGCAGGCATAAGGGTGGGGGTATGTAGGAGTTCATGC

CTGATGTGTGCAGTACTAAACAATGATACATATACTACTACTACTACCACTACTAAGCACTAAC

ATTTACTGAGCACTTATCATATGCCAGTGTTCTTCATGGAGCTAAGTTTGCTTAACAGTATTTC

TTAAATAATGGGAGCTATTCATATATTGAAAGCTTAGTGTTTTTCAGAAGTTGAGTGTGTAACA

TTTGGATGTGGCCTAAAAATAGCAACCGTGACTTCTATCCCACCATATCTGAATTTTGTCTCTT

CCATGCTCGACTTATTTCTGATCCTGGGGCATGCTGAGTAGTAAAAAAAGTTGTTCTTGCATTT

TGATTCATCTGTTATGACTGGCATCAATAAGAAATCTTCAGCAATAAAACAGCTCTGTCAAAAA

ACAACTTCACCAGCAATTTAGGGCAAAATGTTTCCTTTAAAAAAAAGTTTGTTGGCTGGGCATG

GTGGATCATGCCTGTAATCCCAGCACTTTGGGAGGCCGAGGCGGGCGGATCACGAGGTCAGGAG

ATCGAGCCCATCCTGGCTAACACGGTGAAACCCCGTCTCTACTAAAAATACAAAAAATTAGCCA

GGCGTGGTGGCGGGTGCCTGTAGTCCCAGCTACTTGGGAGGCTGAGGCAGGAGAATGGCATGAA

CCTGGGAGGTGGAGCTTGCAATGAGCCAAGATTGCGCCACTGCACTCCAGCATGGGCGACGGAG

CAAGACTCTGTCTCAAAAAAATAATAATAATAATAAAATAAAAAGTTTGTTAGTATTAGCAGAT

ACATATTACTAGGTACCCCCCATGCTCAATGAAGTGTTGGGTTACTCTGAAAAAGTGTCCAATC

TTACAGGTGTGACTTCCTCTGGAACTGCAAGTTCTTGAGGGCAGGGATAGAGATTGTTCATCTT

TTATTGTTTCCCAAGGTCTGGCACATAAATAGTAGTTCAAGTAGTCCAACATATGACACATAAA

TAGTTCTGGGTAAACATTAGCTCAAAGTTTGCTCAAGGCATTGATGCAGATGCTTATAAAATTA

AATTGCTCTTTTTACTGTATACCTGAAATGAGAAAATTATTAGAAACTACTGGGTCTCATTTGG

ACTAGAAAAGTCTGAAGAAATCACTGTTCACTTAGTAGATACAAAGTTGTTTTTCTGGGAAAAA

CACACCTAAAAAAAAAAAAACACATGGGTCTGATATGGGAGAATTTTTTTATTTTTCATATAAA

CAGGTGTATAGGGAAGTGGAACACTGCTAGTATCTTAAGGATTCCTGAAAGTATTTATGTTGGT

AAGTTTGATGAGCAAACATTTCTAAATTTGAAAATGGATAAAACAAAAAGCACAGTGAAATCTT

GAAAGAATTCTAATACTAATGTCACACATAAGAATACAGATTTAAAATTAATGAACTAAAACGG

ATATACGTAATTTCTCCAGGAGGAATTAAGATCCTCCTTGATCTCAGTAAAGCAATGAATAGTC

ATTCTGACATCTAGCTAAAAGCAGACTTATTTCCCTTCGGTCTTTAATCTTTTTGGAACTCAGG

GATTTCCGCCACACTTTGATACACCAGGCCATTATAAAATTACACTTAATTTATTGTCAATTTC

TACTTAAAAGGAAGAATACCTATAAGTATCTCCATATGCTAGATATAGTAGAAATGGTATGCTT

TAATTAGTCCAACAATAAAGTCCTTAAAGATTTACATTCTTTGTTGCCTATTTTGAAAACTTGC

GAAGATAAATTTTTTTAAAGATTATAATTCTTACTAGTCCTTTCCATGAAATATAACAGCAAAT

AGTTTCCAAATGTGGATGTGTAATGAGAGGAAATGAAAAGTGAGTAAAGAGCTGAGTTAAAACA

TCTTAAAATCGAATATGGCTTAATACTATCATTATCATCAGTTGTCCTGGAATAACTTAAATTC

TTCTAGCTTATTGTTGGTTTTTCAATGGTTGGTTATAGTTGTGAGGCGGATACACACACACACC

-continued

CACACACTTGGCTATACAAAAAAGATGTTCCGAGACTGACAGTTAAAAATTACACTGCTGGCCG

AGCACTGTGGCTCATGCCTGTAGTCCCAAAACTTTGGGAGGCCGAGGTGGGAGGATCACTTGAG

GCCAGGAGCTCGAGACCAGCCTGGGCCTAACATAGCAAGACACCATTTCTAAGTTTAAAAATAA

AAATAAATTTAAAAAAGATACACTGCTATGTACGACTGTTGATATAAAAAATCTGAATACTAGA

CATGGGTACTCATCTAGTACTTCAAGGGCTTATCAACAAAGTTGCAAGTTGTAACACTATGAAT

TGTTAGTGATACTCTTTTGGCTTTGCTAGCAAGTGTTGTAAAGCTATACACACACACACACACA

CACACACACATACACACACACACCTTTTAAAATGGTGACCCTGGTACCAAATATGACTTTAAAT

GGATTTAATTTTAATGGCTTTAACTACGTTCAGCTGTCATATGGATCAAAATTAGCCTCTATCC

AGCTGGGGTCAACCAGGGAGCCACTTTTCTTAACCGACGACCTACTGAACGTCAACAACTGCAG

GAGACGGGACTTTACCTTCGTCTCTGGTAAACTAGTTGACACATCCTGTGTTGGCAAGAGGCCT

AAGTAGATGACCTTGGTCCTCTAAAATCTGGCCTGCACTCTCGGGGCACCCCTGCAACATCTAC

AAAGGCAGCTCCAGATAGAAAAGGGTTGGGGTCGAAAAGCCAATAACGGCAGGCACCTGCCCCG

CCTCGGGGCTGGGGGGCTATTCCAGCGGCTTCAGCTAACTTTCAGAGCCATTCGTTTCCCAACA

AAGTCTGAGGCGTTCCTCTGCTGGGTACACCAAGGGGCTCTGCAACCCTCCTGGGGGGGGGGGT

GCCCAGAGGGCTTCCGGAAGTCCCAGGTTTATTCTTTCGGGTCACAGACAGCAGAAACTAAAAA

GAGGGATTACCCTTTCTGTCCAGTCGCAAGATGGCGACCGAGCCTGGTGGGACTCCGAGGGGCC

GCAGGCCACCTCCTCTTCCCAATGGCCCGTGCGCCGGCGGCGACGGCAAGCGGGAGGGAGGCGG

GGCCGGCGAAGGAAGGAGGGGCGGAGCGCGGCGCCCTCCCGCGCGTCTTGGCCCCGCCCCACGT

CCCCGCGTCCCGGCCTGGAGCCCTCGCCCGGCCGGGCGGCGCGCGCTGCCTGCCGGGATACTCG

GCCCGCCCAGCCAGTCCTCCCGTCTTGCGCCGCGGCCGCGAGATCCGTGTGTCTCCCAAGATGG

TGGCGCTGGGCTCGGGGTGACTACAGGAGACGACGGGGCCTTTTCCCTTCGCCAGGACCCGACA

CACCAGGCTTCGCTCGCTCGCGCACCCCTCCGCCGCGTAGCCATCCGCCAGCGCGGGCGCCCGC

CATCCGCCGCCTACTTACGCTTCACCTCTGCCGACCCGGCGCGCTCGGCTGCGGGCGGCGGCGC

CTCCTTCGGCTCCTCCTCGGAATAGCTCGCGGCCTGTAGCCCCTGGCAGGAGGGCCCCTCAGCC

CCCCGGTGTGGACAGGCAGCGGCGGCTGGCGACGAACGCCGGGATTTCGGCGGCCCCGGCGCTC

CCTTTCCCGGCCTCGTTTTCCGGATAAGGAAGCGCGGGTCCCGCATGAGCCCCGGCGGTGGCGG

CAGCGAAAGAGAACGAGGCGGTGGCGGGCGGAGGCGGCGGGCGAGGGCGACTACGACCAGTGAG

GCGGCCGCCGCAGCCCAGGCGCGGGGGCGACGACAGGTCAGTGTTGCCGCGGCCTGCGCCAGGC

GGCGCTGGCTCCCCTCCGTCACTCGGCCGGCCTTCGGGGCCCGCTGTGGCGAGGTCGACACCCC

CCTTCCCCGCCCCCCGCCGCCGAGGCGAGTGTTTGGGGGCGCGTGGTCCGAAGGGGCTGGTGCC

AGAAGTAGGCCCCTGGTGGCCGCGGCTGCTGCAGCCGTAACTGTCAGTCCTGGCTGAGCGACGG

CGGGAGGGTTTTGTCGCCCGAGGGGACGCGAGCGGGCCCGGGGCGGGGCGGGACGTGCGAGGCG

TCGAGATTTGGGCCTCCTAGGAGCCAGGCTCTTCGAGCCAGCCGGGGCCCCAGACAGGGAAGGG

CAGGCCCTTTCCTTCAAAGGGGAGCCCTTTCTCGGCGTTTTCAAGGTTTTTGGCTCTCTTGGGG

AAGACATATTTAGCCGTGTGCTTGGTGGGTTGGGGTTTTGGGGGTGGATTGATGGGAAGGGAGG

GCGGATGAAGTGGTATGTCAAGCCCAAGGGTTGTGCGCACAGGTTACTCTGTGTTACCGGCCAC

CAGGATTTCTGAAGTTGAACGTGAGTTATTGGCTTTGCCAGAGACTGCTGTGTTATATGCAGAC

CTGTATGCAAGCAGTTGGCCTTTTTTCCCCCCCCTTTTCAGTGTAGAAAATGAAAAGGATGCTT

TCCTCATCTTGGTGGTAAAGGCTTTTGTTGGTAAAGGTAGAATTGAATGTACCAAATGCCTTAG

TCCGTAAAATTTTAGAAATAATTTTAATACAGACACTGGTGAAGCTTGGCAACCTTGAAAGAGA

ATTTAGCGTCTACATTTTTTAAATGACTTTTTATGGATATGCTAAATTAGTAACAGTCCAAAAT

-continued

CTGTTTGAGATTATTAAGTGGCGAGGGTGCTGTTGAAAATGTAAACTAATAGCATATGGGGTTT

ACAGTGCACAGTTAACCTCAATCATGAAGAAATGTGGATATGACCCGTAATTTTGGATCATTTT

ACTGCCTGCAATATTGAGAGAAGCAGCAAATTATTACAGTTTTTTTTGGGAGACGACCTAAAGT

TTAAGAAATACAACTGTTGAAAGTTACCTGTCAGAGACACAAAGGTACCCAATCAATCTTGTTG

AATAAATTGGACAAGTGGGATAAGGTGTTTGTCTCACACTTCTGATCAATAAGTACTCTTACTT

AAGAAGTGATTTGGTAAATCATGTAAAATTTAGAATTTAGGAGAGATAAGAAAGTTGTAACTTG

GTGTGTATAGTGGAAATAGCTTTGAAATTAGATCCTGTTTTTAAATCCAAGCTACTTACCACAT

TTTTAGTGAAATGAATACATTATTAATGATGCTACTGATAAGCCCTAAGGATGACCAGAAGCCC

TTTTAAGAAACACTAATACAGTTGACCAAAAAAATAAAAAAGGAAATAGCTTCAAGAAATAATTT

TCAATCTTTGTGTATTTATAATATACACAGGAGAAATAAAAGAACAGAATATGAAGAGGTAACT

TATAATCTTTACAAAATTAGAATGTAAACTATGCTAGTCTTACTGTGTCAATATTTATTAACCT

GCATTAGTTTGCTAAGTAGTATGCTCACTATCCTCTGGACATTGCCCCTGTCCCTGAGGAGCTT

AACTTTATACAGAGATACAAAATACTGTGTTTTGATTTCCTTTCAGAGGATTTATAAGCTACTT

ATGTTTTATCTGTCCTAAATTCTGCCCTTTTTTTTCCCATGGCTGAAAAAATAACTTCCTAAGA

AAGGTACATACTAGTCAGAGGTGTGGGGAAAACGTGTTCTCATCCCACTTGTGCAGTCCATTTA

ACAGGATTTATTGGGTACCTACAGTGTCTTTGACATGTAACATTTAATCAGTTGTATTTCTTAA

ACTTTAGATAATTTCTATTTCGATCATTTCTATTTCAATCTCCTCCCTCTCCCCTCCAAAAAAA

TTTACTGTGTAAACTGTGATAATACACTGTTTCTCTCAGTGTCAGTCAGTGGAATGATCCAGAT

TTATAGGTCATAGCAAAATTTTTCATCCCAAGCTCTTGAAATGATGTTTCCAAATGTCCATTTT

CTTAAATGACTGCTAGTTATGTTCTCCAATCATGTTACACATATTTTGTTTAGACTTATAATTG

TGTAGGTCTAAATGTAGAAACATTACATTATGTACATATGCAGCTGCTGAAAGAAAATTAGTTT

TCTAATTTTTAGATCGGGGTGAAGACAAACTTTTAGAAGTGATCTTTCGGTAAAATACTGGATG

AAGTCTTAGGTGCTCTTTTTATGTTGGTTCAGGACAAAAGTTTTTTGACTGCTTTTTGAGTTTT

CCCCTCACTGCCAAATGTAAGGATAAAATGTAGTAACAAGACATCTTGGTATGTATAGTGGTAA

TATCTTTGGAATTAGACCCTAATTTTAATTCTGGCCTTATTAATCTTGGTAAGCCACAGTTTTG

TCATCTGTAAAATGGGTTGGTGAAACTTCCCCAGAGTTGTGAGGCTTAAAGTATGTAAAACGCC

TAACACGTAGGCACTCAATAAGTATTACCTTAGAAATCTTCCTATCCAGTTTTTCTGAATGGTC

TGGAAGCACCTTGTATGTAGTGGACTACAGCATGTTATCCTTTATGTTGTTTATTTCTTTTCTC

ATTAGCTATGAACTTTTTAAGGCCAGGAATTCCTAGTGTTTACCAGAGAATGTGTTACTAGATG

TCTTAGTCTGTTCTGGCTGCTATTACAAAACACCACAGACAGCATGGCTTATAAACAACAGAAG

TTTATTTCTCACGGTTCTGGGGGCTGAGAAGTCCAAGATCAAGGTACCAACAAATTTGACATCT

TAGTGAGGGCCCTCTTCCCTTGTTCATAGATAGCTAGCTGTCTTTTCACCATTACCTCATGTAG

TAGAAGAGTAGACGGGGCTCTATAGGGCCTCTTTTATAGAGGCATTAATTCCATTAATGATGGC

AAAGCTTCCCAAAGGCCCCACCTCTTAATACTATCACCTTGGAGGTTAGGCTTTCAACATGAAT

TTTGGGGGACACATTCAGACCACAGCACTAGAGCAGGCATGAATTGGTTATTGGTAAATCAGTA

AATGATCAACTAACATTTATTAGGTTCCTCCTGTGGCTTCTATGAGCTGAGCTAAGTACAGGAC

CCACAAAGACAAGAAAGATGTCTGTCTTTTTTGAATGCTTATAGTTGAGTGACTTTCTCACATT

TGTGTGTGTGTGTGTGTGTGTGTGTGTGTAAAACCCTATCACATAATGGAACTTCATTTTCCCA

TGCCCTTCCAATCTAAGAGCAGTTCTATGGACTCAATACCTCCTACCCACCAGCTGCTACTGTA

AAGATTTACTTTTTTACTCCTTTTAAAAAGTTCAACCCTCTGGCACATGCATTACTTCATTCCT

-continued

TGGTCCCAGCCCACCACCCCAGTATCTGGCACGTAGTGTATTAGTATTTGTGTGTGTGTGTG

TGTGTGTGTGTGTGTGTGTGTGTGTGTGTGTGTATGTATATAGAATTTAAAATTTTTACTCC

GGCAGTTGTCTTCAAATACTCTAATTTTGGGGGGCATGATTATCATTCTGTCTTCTGGCAGTAC

ATGGATAGATGCTACCTGAGTAGGATTGTCTATGAGGTCAGCTGCTCCAGTCATTTTATACAAG

AGGAAATTGGAGTGCAAAGCTTTAAAATGATTTTCTTAAAGTCACCCAGGTGTCAGAACCAGAA

CCAGAGTCCATGTCTCTAGTTCAGGACTCTGCACACATTGGCACATGTTCTGTCCTACCTTTTG

GGATGAATAGTTATACTTGCTTTGTGATTACTCACCCACCTTTTTGGAGACATATGAGTGTTTT

GTACACTATTAATAGAAGGCAGCCTTCACAAAATGCCATCTGCAGATCTGTTATTTCTTCTAAT

AAAGGAAATGATGTAAAATTACCTTAAATAGAAATAGTGTTAATTCTTCTGGAGACATATTCCA

TAATCCAAACACGAAATGTTTGAAATACTTGAAGATGCCATATAAATAAGTCCTTTGTAAAAAG

ATAATATTAAAAATTTTTGTTTTATAGAGATGGGGGTCTCACTGTGTTGCCCAGGCTGGTCTTG

AACTCCTCAGCTTTTACTTTAGCTTCCCAGTGTGTTGGGATTACAGGCATGAGCCACAATACCT

GGCCAAGTCCTTTTTTTTAATCAAATGACTTATTAATACACAGTTTCTTTGCCAGCTTTTGTTT

TCATTTGCTATCAAAAATGTTGCTTAGTAGTGCTTTGATCTGAGTTATCAATAACAGGTAAATG

CCATTATGGATAATAATTCAAAAAGAAGCTTATTAATTATTAGGCCTATCTGAGAGTGAAGTAA

AGTTAGCATTTTCTTTTTGTTTATTTTACTTATTGTTTATTTGTTTAGAGACAGGGTCTCGCTG

TGTTGCCCAAGTTGGAGTGCAGTGGTGCTGTCATAACTCATTGCAGTCTCAGGCTGGAGTGATC

CTCCCATCTCACCCTCCTGAGTAGGTGGGATTAGCATATGCCACCATGCCTGGCTAATTTTTTT

ATTTTTTAATTTTTTTGTGGAGATGGGGTCTTGCCGTGTTCAGGTTGGTTTCAAACTCCTGGTC

TCAAGCGGCTTGGCCTCCCAAGGTGCTAGGATTACAGGTGTGAGCTACCATGCCCAGCTGAGCA

TTTTTAAAAAATACTGGTCTTTGTACATGAGTCGTTACTATTTGATTCTAAGCCTTATGACTGA

TATCCCTAAAAATTATTTATAAAATTTTAAGTGCATCAGAGTCATTGAAATGGAATGAGCACTG

TCTTTTGGTCTTGAGGTTGTTTTAACTAGCTTCGTAATGGTCATGAGCAGGTTATTTAGCTTTT

GAAGCCTTCGTTCCTTCTTTTGTCAAATGAAAGTGATAGTTGCTTTGTTTTAAAAGAGTATGCT

TTTCAAACGTGATCATTCTTGAAAATGTAGATTAAGAGCTTTTTAGAGGCCAAGTGCCATGGCT

CACGCCTGTCATCCCAGCACTTTGGGAAGCCGAGGCGGGCGGATCACGAGATCAGGAGATCGAG

ACCATCCTGGCCAACACGGTGAAACCTCATCTCTACTAAAATACAAAAAAAAAATTAGCCGGAC

GTGGTGGCGCATGCCTGTAGTCCCAACTACTCAGGAGGCTGAGGCAGGGGAAACGCTTGAACAC

GGGAGGCGGAGGTTGCAGTGAGCCAAGATCATGCTACTGCCTGGCGACAGAGTGAGACTGCCTC

TCAAAGAAAAAAAAAAAAAACTTTTAGAAACGTTGTTTTGGGGAATTTTTAGTGTGTGAATTCA

TTTTAAATATGTGAACTCCATTTGACATGGACAATGGATCTTAATAGTTTGTGATACATTATTC

AGTGTATTAATCAAAAGTCAAATCTCTTTTGTAATTTGCTGTACCAGACCTGTTGTGTTAATCT

GATCAATGGCAAGTGAATCATAAGATTGACCTGAAAGGAAAAGATATTTTTAGGGGACATAGAA

TCATATTGGATAAGATTATTCCTATAGTTCATTTTCAGGAAATCTGAACAGGAATCTCGTGTAA

GGAATCACATGTGAATTATAGAAGAGAGTCTGATGTAAGACTTTATTTATTAAGGTCTGCATCT

GTGTTTCAAGTAAGAGCATAGAGGTAGTATATGAGCCCTGAACACTCATACAAGTAGGATAAAA

TTTTTCTTAAAACTGTTGGCTGGACAGTGTAGAGTCTAATGCTGTGACTCTTAACAGTTTTGTG

TGTTCCAGAAGTTCATCTCCTCAGGATCAATTGAGGTTAGTCTAGCACAGACTTTAGTTATAGA

AACCAAACATGAGAAAAAATTTTTTGACCCATGTCTTCGTAGCATGCAGGCTTGGTAGCTCTTTC

CTAGTTCTGGATGTGTGCCCGTTGTATATACTTTCAGCAATTCAGGATGTTCCTTTTCATATTT

AAGACAAGCACTCTTGCATACAAATTACATAGCTGTGGGCTGAATGAAGATGCTACCATTGCTG

-continued

TACTTCTACACAGGTTCTTTTCATGTAATGAAATCAGAAGGGATGGCTTTTCCATTTCAAGCTT

CTGTTAATAAGTAGTCTTAGAATTGCCTTTGTGTACTGTAGCCAACACCCCAACTCATATATTT

TTATAATCTTTGTGATGCAGAATAAATTCTGAAACTTTCCACCTCCTAATTAAATATAGAAATA

CTGAAAACAATAAAGCACCATGTATTCACTATGGACATATGTCACATTTTGTCACTTTCTTGCA

CTCTTGTAATCCCTCTCTAAAGCTCATGTTAAACTCATGTTCTTTATTTTCTTCTCAGATGATT

CCTTTGGCACTGCATGTAACAGTACAGGAATTTCTTCCTTTCGTACTTCCAACAAATACTTTTT

TGTCTCTTAACAGATGTGAACCATAATGCTGTTCTTTAGAAAGCAAAGGATGAAGTGCACAGCA

GTGTTTTCTATATAAAGCTAATGGGTCATAAGGGGAAATATGGGTTATTTCCAGCTTGTTAATT

GTCTTAATACATTTTTCCTAAGAATTCTATTGTGCCTCTGTGGTTATATGCACCAATATTGATA

ATCTTACAGCGTGCCATAAATAAGGATTTTTATATTATCTTTGCTAAATATTTTAAGTTTTTGT

TTTGGGAATTGAAAAAATCTTTTGTGCATCTATGGTATGTGATACGTATACTAATGGATAAATC

CTGTTTCACACAAAGATTAATTGGGTAACATTTTTCTTTCCTAGTTTTCTGAAGTCAGTGGTCA

TGTTGTGTGTTGGTGATTGAAAATATGCTGTTTAGGCTGGGCGCCTTGGCTCACTCCTGTAATC

CCAGCACTTTGGGAGGCCGAGGCACACGGATCACCTGAGGTCAGGAGTTCGAGACCAGCCTGGC

CAACATGGTGAAACCCTGTCTCTACTAAAAATACAAAAATTAGCTAGGCGTGGTGGCACACGTC

TGTAATCCCAGTTACTTGGGAGGCTGAGGCACGAGAATCGCTTGAACCTGGGAGGCAGAGGTTG

CAGTGAGCTGAGATCACACCATTGCACTCCAGCCTGGGCAAGCAAGATTTCATCTCAAAAAAGA

AAAGAAAAGAAAAGAAAATATGCTGTTTAAGATCATTCAAATTCAGTTTCTAAGAAGTGTAAAG

TTTTCCTAATTACTTAAGCTGCTTCATTCTCATTCCCTTTTGTAACACATTTTGCCATCTCTGT

AACATGTTGAACATGTTTAAAGAACAGAGTGGGAGAATAGGAAGTTACGTGGATAAAGTTTGGT

AATCAAGGTAGGAATACATCCTGCTTCACAGAATGGGAATATTTCTGAAAAGTTGACTGTAGTA

TTGAAGAACACTTAAGTGTAGTGTATTAGACGAACTGAGCTAATTTTGGTCTTTTATACACATA

AATCAAGATTTCTGCATTTCAAATCATGCATATTTCTTTAAATTTATTGCTCAGTGTACTGTAT

TTCAAATATTGTAAAAATGAAAAGATCTTGTGGTCTTATTTAACTCAGTATGGGATAAGTCCTT

CCCACCTTCCCATTCTTATTCCCTCTTTTAGGCTGAATGAAAGGCTGGGGGAGTGAATTTAAAA

ATAGATGGATCTCAGCTGGAGAATGGGTTGGTCACGTATCTCAACTGATATTAAATAATTTCTT

AAATCCTGGATTGAAGATTATAAGAAAACAGTAAATGTTTGCTCTCAGTTCATTTCTTTGTTTT

GTTTTTTCATGTACAGTTTTAGGCACTTGTAACTGCTGGATGCATGAACTACTTTCTAGTTCTT

TCAGGCCTACTTTTAGATATCTGCTGTGGGGACAGTCCTCAACACTTAAAGTAATTTTAAATAG

TGATAGGCAGAACTAGGGGTCAGTTTTACTGCCTATGCCTGTGCTGAATTTGACATGGCATTCC

TAGGAGGGGAGGTGGAACGAGGGCGGTGCACACATTGTCCATATTGCTAGTCAGTGCCAGATTT

TGAGAAACTGGGGCTAATCTCTCTCTTAAATGGTCAAGATCTAATTCCCCAAAGTGCTGTTTCA

GATAACCTAGTATTTGTCCAAAATTGCCCTGCTACAATAGTATTTATCTTATATATATGTATTA

TATATATAATATATATATAATCTTATATATATGTATTATATATATTATATATATAATCTTATAT

ATGTATTATATATATAATATATATATAATCTTATATATATGTATTATATATATAATATATATAT

AATCTTATATATATGTATTATATATATAATATATATATAATCTTATATATATGTATTATATATA

TAATATATATATAATCTTATATATATGTATTATATATATAATATATATATAATCTTATATATAT

GTATTATATATATATAATACATATAAATATATATATATATATATATATAGGTTTTTTTTTGTTT

TTCCTCCTGAGATGTAGTCTCGCCCTGTTGCCCAGGCTGGTGTGCAATGGTGCAGTCTTAGCTC

ACTGCAGCCTCCGCCTCCTGGGTTCAAGTGATTCTCCTGCCTCAGCCTCCTGAGTAGCAGAGAC

-continued

TACAGGTGTGCACTACCACGCCCGGCTAATTTTTGTATTTTTAGTAGATACAGGGTTTCACCAT

GTTGGCCATGCTGGTTTCAAACTCCTAACCTCAGGTGATCTGCCTGCCTCAACCTCTGAAAGCA

CTGGGATTACAGGCATGAGCCACCACACCAATCCTATTACATTCTTAAAAAAATGTTTGTTTGT

TTGTTTTTGTAGAGATGAAGTTTCACTATATTACCCAGCCTGGTCTTGACTCCTGGGCTCAAGT

GATCCTCCTGCCTTGGCGTCCCAAAGTGCTGGGATTATAGACATGAGCCACTGCGTCCAGCCTG

TATCATATTTTTATTCTGATATCTTTTGTAATTTTGTTTTTAGTGAAGTAGGGAGGTTTATATT

AGATAATCTTCCAAGGTAATTATCAGCTTGGACATTATATGCTAATATGTCTTTTGTTTGTTTT

TAAAATAAGTGTATATGTTTTAATTGTAAAATTTTTAAAACATCCAGAAAATGACATAGCAAGT

GCCTATTTATCCACCACCTGGAAATATAAATTATGTCCATTTTTATCCCTTGGGGGAAAGGATG

CAGTTATATAATCACTTTTAACAACCCCAACTGTTCAAGTCCTGTTACCCGTCTCTACACAAAG

TAACAACTGTCTTGAGATTCTTAAGTAAATTTCACATCCTTGTTTTATACTTTTACTATACATG

TGTACATGTATCTGTAAGTGATATGTGGTGTTGGTTTTTGTATTAAATTTTTACAGACATGTAT

AACGCTGTCTTTCAATAGCTTGATTTTTTTAAACTCAGTATCAAGTTTTTGAGGTGTATATGTT

GATGCGTGTACATGTAGTTTATTCAGTTTCACTGCTGTATGGCACTTCATTTTATGCATAGATA

AAATGTATGTGTCCCACTATTGATGGATATTTTGAGTTGTTTTCTTTTTGCTATTATAAATAAT

GCTGCAGTGTTTATTTTTACATGAGTGTATGTGCAGGTGTTTTGGGAAAAAACCGTAGAAGTGAA

ATTGCTGGTTACTAGATATTGGTAAATTCTTTTCCTAAATGGATATGCCCATGTATACTTTATC

AGCATTATGTGGGCATTTCTAGCATCCTCACCCATACTTGGGATTGTCAGATTTTAAAATAGTT

ACTAATTTGAGGCATGTGAAATGCTATCTCATTTTAATTTACAGTTGCTTGATTATTCTGAATC

GTAGGTAAAAGGATAGGAAATTTATTATTTTCTGTATGTTTTAAATATCTCAAAAATAAATGTT

TTTAAAGGAAAGGCACACTATCGTACAACATTTATGTTGAAAAGGACCATGAAGATCATTTCAT

CCAACCTTCTTACTTTACAGTGCAGCCAAAGAAAGTTACCAGAATAAGAGTAAAATATAAAATC

CTGCCCATTGTAGTATTCTCTGGTAGTATGAGCCTTAATTTTTGATGTAAAAATCATGTCTTTT

TCTTTATGATTGTGCTTTTTGTTTAAGAAATCCTCTTTTTATATTGTCTGCTAATAGTTGAGGA

TTTTTTGTTACTCTTTGTTATTTGCATTTAGGTTCATCTGAAAGGAGTTAGGATTTTTTATTTT

AAATATGAAAAGCTAGTTGTTCCAGCATTAAGTATTGAATTTTTAAAATTTTGTATTGAGGTTA

AATATACATACATAATTTACCATCTTTTTTAAGTGTACAGTTCATTTTTTAATGATTTTTTAAGT

GTACAGTTTTTTAAGTGTACAGTTCAGCAATAATAAATACAGTTATGTTCTTCTGCCTTTGTCC

TCTCACTCCCCACTTCGGCTGCTAGTAACCACCAGTCTATGCTTATCTTCTTGAGATATACTTT

TTTAGCCCATGTATGAGTGAGAACATGTGGTATTTGTCTTTCTGTGTTTGGCTTATTTCACTTA

ACATAATGGCTTCTTGTTCCATCCGTGTTCCTGCAAATTACAGGGTTTTATTCTTATTTTTATA

GCTGAGTAGTATTCCACTGTGTGTATAAACTACATTTTAAAGTCTATTCGTCCTAATTATTGAA

TTCTCCCCACCCCACCCACCTTTTTTTTTTTTTTTTTTTTTCCAGGAGACAGGGTCTCCCTCTC

TTCCCCAGGCTGGAGTGCAGTGCCATGATCATAGCTCCCTGCATCCTTGAACCCCCTGGCCTCA

AGCGATAGTCTTGCCTCAGCCTCCCAAGTAGCTGGGACTGCAGGCAGGCACCTCCAGGCCCTGC

TAAGTTTTGTGGGTTTTTTTTTTTTTTTTTTTTTTTTTTTTTTTTGTAGAGATGGGGTCTTCCTATG

TTGCCCACTTTGGTTTGTTAGTTTTAGTAGTTTATAATTCCTTTGTATTATTGTGAACAAATAA

CAGTTATTTTGAAATAGAAGAGTGCTTTCTATTTAAAATTTTGCTTTGATAGGGTTCTGTCTAC

TTTCTGAGCCTTACCTTCCTGTGCATTCCCCTTTGGTCAGTACCATCTTACCACACAGGCTGCT

TTTAGTTTCTTGAGTTATCCATCTTCCTTCTATCTTATAGGGCTCAACCTAAATATTACTCAGG

GAAGCCTTCCTTGAGAGTCTTTCTTTTTGCACTCATTGGTTTGGGGCTTCTTTATATTATACTG

-continued

TTAATTGAATTCTGAGTCGTGTTTATCTCAACTGAGATTAGGTAATTTATTTTGAGAACAGTAA

ATGTTTATCATCTGTCATTCTTTTTTTCATGCCCACATTCAGTTATTTGTAAGTGCTGAATGTA

TAAGTGTTCATCTACAGATAAGGATCAGTTCTTTTTTCCCCAACTAGAAATGTTACTCCAGTTG

ATAATAACAGCTCAAACGGAAATATAAGGCAGAGGTGAGAGAGTCACTTGAGGCCACGAATTGG

AGACCAGCCTGGGCAACAAAGTGAGACCTTATCCCTATGAAAAATAAAATTAGCCCAGCTTGGG

AGGCTGAGGTGGGGGGATTGCTTGAACCCTGGAGTTCCAGGCTGCAGTGAGTTGTTATCACACC

ACTGCACTCCAGCCGCGGTGACAGACCCTGTCCCTTAAAAAAAAAAAAATTATAACCAGCCACA

TTGAAATATTTTGTAAGACATTAATAGAAGACTAAATGTTCTCATATGTTTACTGTTTGTGTTA

AGTACGTATGGTTTTTAGAACAACAGTTTTCTATCAAGTGTGGTCTGGTTCACTTAGAATTAGA

TGGGGTAGATTTTTTGAAAAGCGTTTTGAAGTTAAATTAGAAGCTAATGGTTTTTTGTCACTAA

ATCAAATTTTGTTTTATGCGTTTAAGTGCTACATTTATTTGATAGGCAGGTGAATGTAACAGAT

TAAACTTGAAAATAATGTAGCTATGATTCCTTCAAGGAAAAACCCACCTACCTTTAGTTCTTTT

AGTATATTGCATTATAAGTCTTTTGTGTGTGCATATATAGCAGGCATAAATTGGCATAATTCTG

GGTTTAATTTTAGGCTAGGCGCTATGGAAGTTTGAACTCTAATTACAGTGTAAAAATAACCCAG

AGGAAAATTTCAGAATAATAAATCATTGGGACTATATGGTACAGATGTCCCTGTTTTCAGATTG

TAGAATTGTTGACCAGTAGGAATGCTTTATGATTAAAAGCCAGGAAATTAAAGTAATTCTGATG

ATTTGGTATTTCTAAAGATTTTCATAGATGACAGTTGAGAACTACTCTCAGATGAGATTCTTCC

ATTGCTGGTAAGTCATGTAATAAAACACTTAAGTAAATATTTTAATGAGGAATGATAACATTTT

AATATTGGCACATTGTGAGTCTACCTTCTGTAGTTAGTAGGTAAATAAGAAATAAACATACCTT

ATTTAAAAAAAAAATTTCAAAGAACCCAAGGGAGGGGAGAGCCAAGGTGCACATTAGAAGGAGA

TTACAGTACTCTTCCAGTGCACAGTGGATGTGTTGTGATTCCAGAGTTCTATGTATGTATGACT

GTGTAGCCCAGATTTACCAGCATGGGCTCAGTTTTAAATGTTAGGTTAGGCTCATAAATCATGA

AAAGTTCCTAGGAATTCTAACATTTTTACATTTCCAGAAGAGAGCCTCTTGTATTTTGTGGTAG

TTGCCCCACCATCCCTCAAATATTGGTGTGTAGAATCTATTTTTGAGGATGAGGAAATACAGAA

AAGAAAAATAAAAAGCTATTTTTTTTTAAGTATAAGAAGAAATGAAAGGTTTCTCTTCGCTTCA

TAGCCAATTCTAAAACTTAACAGTTGTTAAGTGTGTTTAACTGTAGAGGGAAAAAAATGCCTGG

AAGGAAATTACCAATCAAATATAAAATGTAAGATAGCTGTAAAAGTACTGATATACATACAGCT

TTTTTCCTTTTGGGGAGGCAGTATTTAAAAAAAATCCTACCAAACATATTCTCTAACTTTCAAA

ACTGTTAATAGCTTTATTGAGATAATTCACATACTATAAAATTCACCCTTTTAAAGTTTTTAGT

ATATTCACAGTTCTGCAGCCATCACCACTATTGAATTTTAGAACATTTTCATCATCCCCAAAAT

AAATCCTAACCTGTTAGCAGCCATTCCCCATTCTTTCCTGGCCTCTGGAAACCACTAATCTGCT

TTGTCTCTATGAATTTATTTATTCTGGATATTTCATATAAATGGGAATCATACAGTATGTGTCC

TTTTGTGTGTGGGTTCTTTTACTTACCATGGTATTTTCAAGGTATGTTCATTGACATGTATGTC

TGTTTTTTTTGGGTAACACACACTCTTGATTACTGTAGCTTTGTAGTAAGTCTTGAAACCAGGA

AATGTGAGTATTCTAACTTATTCTTTTTCAAAATTGTTTTGGGTCTCTGGGTTTCTCAAATTTC

CATAGAATTTTAGGGTTAGCTTGCAAAAAAATGCAACTGGGATTTTAATAGGACTTGGATTTGT

GTTGAATCTGTAGGTCTATTTGGGAAGTATTGCTACCTTAATACTGTCTTCTCATTCATGAGCA

TGGGATATCTTTCCATTTATTAAGGTGTTCTTTAATTTCTTTCATGTTTTGTAGTTTTCAGTAT

ACAGGTCTTGTACTTATTACTTTAAAAATTTATTTCTAAGAATTTTATGTTTTGATGGTATTGC

AAATTGAATTTTTTAAAATTTCATTTCAGGTTTTTAATTCCTTGTGCATAGATTTTTGTGTACT

-continued

AAAACTTGTGTTTCATATAATTTTTTTTTCCTCTTAACTGTGTTATAGGAATCTTTCAAATGGT

TGGCTACATACACATCCATCTGATTCACTTAGTAAACATTTCTTGAACACCTACTGTGTAGTGG

GCCTTTTTTTCTAGGTCCTGGTAGAGACAGCAGTGTATAAAACCCACTCAGTCCTTTGCTTTCA

TGGCACTTAAATCCTAAAAAGAGATCATAAAGATAGGTAAAATATATGTTACATAGTGCTAAGG

AGAAGAAACAAATAAGGGAAGTGTTTGCAGGTGAAAAGGATGATGGGAAATTTTAGATAGGGTA

GGTAGAGAAAACTTCACTGAAATGGTAACTTGGGTGAAGAACTGAGGGAGATGAGAGAGCTAGC

CATGTGGATATTTGGGGGAAGAGCATTTCAGGCAGAGTGTAGTGAATAGGGAAACCCCAAAGTG

AGAGTGCCTGATGTGTTTGAAGAACTCGAGGTGTGGCCAGTGTAGCTTTAGAAAAGTAATTGAT

GGGAAATAGAGAGAATGGAGGGTACAGATATTTTGATCATAATAAGGTGTTTGATTTTTACCTA

TAAGTGAGATGGGAAGCTATTGGAAGTCTTTGAGCAGAGTAGTGAAAAAGTATGACTTATGTTT

AGCAAGGTCACTCTGGTTGCTGTGTTAATCATAGACTGAAAAAGGGGACAAGGGCAGAAACAGA

CCAATTGGTAGACCATTAGTACAGATTAAGACGTGACTGAAATGGACAGAGTGGTCACAGTGAG

GGTGGTGAGAAGTGGTTGAATTCTTGATATATGTTGAAATAGAGTCCATAGGATTTGGTAGTAG

ACCAGATGAAAGTGGGAAATAAAGGGAGGAGTAAAACATGATGCCAAAGTTTTTTGACCAGAGC

AGCTGAGAGAATGGAGTTGGATAATTCTTATAAATTATTGCATTAAATCTGTGCATCATATCAC

ATGCCCACTTAACTACAGGTAATTTTACCATATAAGCTTGTGGGGGGAAAAGAGGAAAAACAGA

AAAAAGGATGGAAAAGCATGTTTTAAAATATAATAAATTAGGCCTTAATGAAAAATTGTCCTTG

AGAAACCTGAGATGGAATACTCTAAATCTGATGTGTTCTCTCAATCTTTAGAACTGAACTAGGA

ATTAACTCTGAGAGTTCATGATGTTATGAGACCCTTTGCCTGTTTTGGAAATTCGGTTGTTTTC

AATATTTGCTTTTGCAATGATGGTACCTGTTATTTTTTCTGTAAGGTAGATTCCTACAAATAAG

ATGTCAGGCCATTAGATCATGTCAATCTAAATATTTGATAGGTTTTGCCAATTACCTTTTAAAA

AATAATTTTAGCAAGTTTCATTCCTTAAAATATATTAGGGACTGCTCATTTACCTTGTTTTGAT

TCATGTATATATAAAATCTGTTTAAGTCTTTATAAATAACCTGGGAAATTGCCTGGTTTTTTGG

TCCATTTCTATTGTGGTGTTTGTTTTTTAAATTTGTAAGCATTCTTTATATATCATTTAATTCT

TTATTATAATTTGCAAATATTATCTCTACCTACCTTTAATTTTATAGTATCTAGTCATGTGAAA

TTTTAAAGTTTTTATGTAGGCAAATCTGTCCATCTTTTATGGTTTCTGGGTTTCAGCATGCTAA

CAAAGTTGATATAAATATGATCTCATATATATATTACAAAAACTTTTTAGAGATAGGATCTCAC

TCTGTCACCCGGGCTGGAGCAACCATAGCTCCCTGCAACCTCAAACTCCTGGGCTCAAGTGATC

CTCCTGCCTCAGCTTCCCAAGTAGCTAAGATTATAGACATGTGCCACTATAGCTAGTTGGTTTT

TTTTTGGTTGGTTGGTTTTTTTTTTTTTTTTTGGTAGAGAACGTATCTCAGTGTGTTGCCCAGA

CTGGTCTCAAACTTCTGGCCTCAAGCTATCCTCCCACCTCAGCCTCCCAAAGTGCTGGGATTAC

AGGCATGAGCTACTATACCTGGCCAATCTCTTGTATTTTCTTCTGATACTTTTGTGATTTTACT

TTATAGACTTTAATTTAGAAAGTTAGATATGAGCATTCAGCATATTTTTGGATATGGTATGATA

TGGTTTAGATCTGGATTGCATTTGTCATGGTTTGGGAATTATATCTACCTTTTATTTTCTTCCA

CTTGGGTAGCTGATTGTCTTGTAAGGCATCCTTTCCCCACTGATAATGCCACCTTTTTCTATAT

TAAGTTCTCACAAACTTTGAAAAAAATCAAGTTTATTGATGTATAATTGATACACAATGAAATG

CACCCATTTTAACTATATAGTTTTATTGATTTTGATAAATATATACACTATCACTGCTACTACA

ATCAAGCTTTAGAACAATTGAATTACCTCCAAAAAGTTCCTTCCTGTCTGTAGTCATTTCTCCC

TCTTGGCCCCAGGCAACCACTGATCTGTTTATTAGTTTTCCTACTCTAGAATTGCATATCCATG

GAATCAAGTAACATGTACTCTTCCATGCCTGGTTTCTTTCACTTGGCATGTTTTTGAGATTCAT

CCAATTTGTGTTTGTCACAGATTTTTGTTTGTTTCGTTTTTTTAAATACAATATGACTATACCA

-continued

CAGTTCATTCATTTTCTGGTGAACATTTAAATTGTTTTCAGTTTTAGGCTGTTGCGAATAAAGG

TACTGTTTTGTGTGCATGTTTTTGTGTGAACATATGTTTTCATTTTTCTAGGGTAAATACCTTA

AATTGGAATTACTGGGTCACATGGTAAGTTTATGTTTAAATGTATAAGGAACTGCCAAACTATT

TTCCAGATGATTATACTACTTTACATTCCCATCATCAGTGTATGAGAGTTCCAGTTCTCCAAAT

GTCAGCATTTGATGTTCTCAGTCTTTAATTGCACACGTTCTGAGAGGTGTGTAGTGGTATCCCA

TTGCAGTGTTTTTTTTTAAGTGGTACTAAAATACACAACATCAAATATACCATTTTAACTATTT

TTAAGTGTACAGTTCAGTGACATAAAGTACATTCACATTATTCTGCAGCCATCACCACTATCCA

TCTCTGAAACTTTTTCATCTTCTCAGTCTGAAACCCTATCCATTAAACAGTAACTCTTCATTGC

CTACTCTCCCTATCTGCTGGTAATCACTGTTCTACTTCATATGTGAATTTGACTCTTCCAGGTA

CTTCATATAAGTGGAATCATACGATTTTTGTCCTTTTGTGTCTGGCACATTTCATTTAATAATA

ATAATGTCCTTGCGTTAGGCCATTCTTGCGTTGCCTTAAATGAATATCTGAGACTGGGTAATTT

AAAAAGAAAAGAAGTTTATTTGGCCCCTGGTGCTGCAGGCTGTACAAGCATGGCGCCACCATCT

GCTCAGCTTCTGGGGAGCCCTCATGGTGAGTTTACTCATGGTGGAAGGCAAAGGGGGAGCAGGC

GTGTCATATGGCGAGAGCAGGAGCAAGAGAGAGGGTGGGGAAGTGGCACACCCTTTTTAAACGA

CCACATCTGCGAACTCACTCTGTATCCCAAGGAGAGCACCAAGCTATGAGGGATTGCTCCCATG

ACCCAGTTACCTCCCACCAGGCCCCACCCCCAACATTGGGGATTATATTTTAACATGAGATTTG

GGCAGGACAAATATTCAAACCGTATCAGTCATCAAAGTTCATTCATGTTGTAGCATGTATCCAA

ATTTGATTCTTTAAGGTTGAGTAATATTTCATTGTGTGCATATATCACTTTTTGTTTTATTTAT

TTATTTGTCAGTGGACATTTGGACTCTTTGTAACTTTTAACTATGTGAATGATGCTGCTATGAA

CATTGGTATATAAGTATCTGTTTGAGTCCCTTCTTTTAATTCTTTTGGTTATGTACTTAGGAGT

GGAATTGCTGGGTCATGTGGTAATTGTATGTTTAATTTTTTTAGAGACTGCCATACTGTTTTCC

ACAGTGACTGCACCATTTTACATTCCCACCAGCAGTGAATAAGGGTTCCAATTTCTCTGCATCT

TTTCTAACACTTGGTAATTTCTGTTTTTTATTTAAAATAATTGCCATTCTAATGGGTGTAAAAA

GTCATTATGGTCTTAATTTACATTTTCTTCATGACTGCTGTTGAGAAGTTTTCTTTTGTGTGTC

TGTTCAAATATTTTCACATTCTTTTCAGAACATATGTTCTTTGTCAGATAGATAAATGTATTTC

TTCTGTATCCTTACTGATTTTCTGTCCACTTACTAATTACCGAGAGAGGAATGTTGAAATCTTC

AACTATAATTTTGAGTTTATCTTCCTTCTGCTCTGTTCATTTTTTCTTCATATGCTTTGAAGCA

AAGTCTTTAAAGTTGTGTCCTTAGGTGTGTTCACATTTAGGACTGTTAGATCTCCTTGATTAAT

TGATGTCTTTATCATTATGAAATGTCTCTGTTTATCGCTGGTAATGTTCCTTATCTAAAGTCTA

CTTTGATATTAGTGTATCCATTCCTTTCTTATGATTAATTTTTGCACATTATATCATTTTGCTG

TGTTTTTATTTTCAGCTTATTGGTCATTTAATGTCTTTCTTTTAGATAGCATATAGTTGCATCT

TGCTTTCAGATTGACTTTTTACGATCGTTGCTTTTTGATTAAGTCCATTTACATTTATTGCAGT

TGGCAATATAATTGTGTTTAAGACACTATTTGTTTTCTATTTGTCTAATCTTTTCTTCCTTTTC

TGCCTTCTTTTCGGTTAATGGAGCATTTTTGGAATTTTGTATTGTCTCCATTATTAGCTTGTCC

CTCTGTTTTTTTTCCCCCCAGTGATACTTCTAGGATTTACAATATGCACCTTTAACTTACCTCA

ATCTACCTTCAAAAATATTATTCCTCTTAATGTATAATGTAAGAATTTTGGAATAGTATACATC

CATTTACTCTCCCTCATTCTTTTTGGTATTATGATCTTAACATTTTACTTCTATATGTGTTATA

GATTCCACAGCAGCGTTTGAAACTATTTCTTTCAAAGGCCAGTTGTCTTACGAAGAAACTTAAA

AACTAAGAATAACATTCCTTTATATTTACCTTCATATTTACCATTTTTATTTATTTTTCTTTGT

GGAGATTCCTTTTTGTAGATCCAAGTTTGTTGCTGGTGTTATTTTCCTTTTACTTGAAAAAATT

-continued

TCTTAAACATTTCTAAAGTATAGGTCTACTGGCTACAAAATCTTTCAGCTTTTGTTTGTATGGA

AATGTCTTTATTTCACTCTTCATTTTATCGTACAATTTTTCAAACCACACAGACTTTAAAATAA

TTGTAGAATATAATTTCACAACATTTTGTTCTATTTGTTATTGTCTTCTATCTTGTCCATCTAT

CCATCCTGTCTTCTTCTAGTGTCTTTTTTTATGCTTTTCAAAGTAAGTTGCAGTTGTTAGTATA

CCACACCCTTAACTTGAGCATGTATGTTAACTAAAACTTAGTAGTTTAGTATTTTTAACTAGAA

TTTACTATGCTGTTCCAGTTATTTATTGCTGTGTAATACATTGCCCCAAACTTAGTGCCTTAAA

TATCAGCAACTATTTATTTTGCTCATGAATCTCTCATTTGGTCAGGGATTGGCAAGGAGAGCTT

GTCTTTGACAATACATTGTAACAACTGTTTACATAGCATTACATTGTATTTGGTATTATAAGTA

ATCTAGAGATGGTTTAACATATTTGAAGATGCATGTAGGTTATATGCAAATACCATGCCATTTT

ATATAAGGGATTCGAAGCATCCTTGGATTTTGGGATCCATGGGAGTCCTGGAACCAGTCCTCTG

TAGATAGTTGAGGTATGACTGTAGTCTTTGGATTGAAAGACTCACTAATTTCACTCAGATTCAA

GGAGAAGGGCCATAGACTCCACCACCTGATGAAAAAATGACAGTGTTACATTGTTAAGAGCATG

TGGAATGGCTTCTATTGTGACCATCTTTGGAAAATACAGTTGACCACATATACCATTTCATGAG

CTGTGACAAATGTATACACCTTTGCCAGAAAGTTCTATCAGGGTATAGAACCTACACCTCTTCC

TAGTTATTCCTTCCCCCCACACCACCCCTAGAACCTAACATTGTTCAGATTGTTTTCATCTTAG

TTTAGCTTGCGCAGAACTTTATGTAAGTAGAGTCATACAATACTTATATGTTGTAAAAAGTTTC

TTTTTGCTCAACATAATGTTTTTGAGATTCATCCATATTGTTGAATGTTTCGGTGGTTTGTGAC

TTCATCTGTTAAGGGACACCTGGGCTGTTTTCAGTTCCAGGCTGTTTTCAGTTCCCAGCTATTA

TAAAAAGGTACAATGAACATTTGTGTAAAAAAAGAAGTCTCTGTGTGGACATATATGTTTCTTT

TTTCTTGGTTAGTTGATGTGTTTTTCTTTCAGCATTTGTTTTTGATGAGAAGTCTGGTTATACA

GTCATGTGCCGCATGCTGACATTTCAGTCAACGAGATCATAGTTGACAATAGTCATTTAAGATT

ATACCACCATATTTTCACTGTACCTTTTCTAGGTTTAGATGTATAAATACTTACACTTTGTTAC

AGTTGCTTACAGTATTCATTCAGTATAGTAACATGCTGTACAGCTTTATAACCTAGGAGCACCC

GGGCTATACCATGTATCCTAGTTCTGTAGTAAGCTATACCATCTAATCTAGATTTGTGTAAGTA

CGTTCTATGATATTTGCACAATGATTACCATGCTGAGAGTTGTTGGGGTTTTGTTTTTTTTTTC

TTTTTGAATCTGTACATTTATGGTTTTCCTTAAATTTGGAAGATTGTTGCCATTGTTTCTTCTA

TATATATATTTTTTACCACCTTTACTCCTCTTTCATCATTTCCTCTTTTTCTGGGACTCCAGTT

ACACATATGTTAGACTGTTTGGTATTATCCACAGGTCATTAACATCATATTCATTATTTTTCAG

TCTTTTTATTTCCCTGTGCTTCAGTTTGCTTTGTCTTCTATTTTACTGTTTTTTCTCCTCCCTT

GTTAAATAATTTCAGATATTTCGCTTTATATTTCAAGAAATTCCATTTGATTCATTTTATTCAT

GTATTTTTTTGAATTCTTGAGCATATTTGTAATAGCTGTTTGAAAATCAGGTTACTTATTGATT

TCTTGAATTTTTTCACTCTGAATTTGTTGGTTGGTTTTTTCTCTTGGTCATGGGTTGTATTTTC

CTAGTATTTATTTTATTTTATTTTTTGTTTTTTACATATTTAATGATTTTTTAAGATTGGATGC

TGGACATTGTAATATTTTGTTGTTGGGTGTCTAGATTTTGTTTTCTTTTAGAGTGTTTTGTTTT

GTAGCCACCTAAATAACTTGCTGGTCAGTTTTATCCCTTCAGGGCTACATTGGAGTTTGTCTAG

AGAAGGCTTTGCTTTAATGGTAGTAGCTCCTACCTAAGGCATGATCCTTCTGAGTCTTTACTAA

ATGCTCCCAGTGTCACCGTGTTCTCTTCACTCAGGTTAGAGAGAATTTTAGGAGTCTCCCAGTC

CTTTATAAGTACTGGGAATATTTCAGCTTACTGCCCCTCTTTCACTAGCTTCATGGAGTCACTT

ACCTTAATCGTGTACAGTTAGTACTCAGCAGTGGACTCTCAAATGGCAGATTTCTGAAGCCATT

TCTCTGCCTTCTCAGACAAGCACTTGTCTGGCACTTGTCATCAATTTTACCCACTTCAGCTTTC

TCAGCTCTGATCTCTTGATTCTGAACTCAGTAAAACTGCTGTCTTCTCACTGGATTTCCCCTCC

-continued

ATTGACTGCAGGTTGGAAATTACCTCCAGGCAGACATCCAAGCAGTGGATGGCTCACCTCCTTT

GTTTTTGTCCTTTCATGCATTATAGTCCTCTGCTGCCTGTTATCCAAGGTCTGAAAATTCTCGT

TTGAGAAGGAGCAACTGTCAGATACTTTCGGATCTTTCTCTGAAATTAGCTTTCTGTTGTGCTT

GTTGTGCTTACCTCTTTGTCTAATGCTAATACCATATGAGGTTTTTTTTTTTTTTTTTAGAATG

TTTTAAGCTATACACTTCTAAGTGTATAGCTTGTTGCACTTTCACACACTGAGCACCCGTTTAG

CTAGCATTCAGATCAAAAAACAGCAGCAGCTCCTGCGTAGCCCCTTGTGCTCTGTGTCACTACC

CCTTTTCTTCCATGTGTAACCACTGTCCTGACTTCTCATAGCATAGATTAGATTTGCCTGTTTT

CATCCTTTAACTAGAATCAAGCACATTTAGTTGTGTCTGACTTCTTTTAATGTATTTGTGAGAT

TTATTCACATTGTTGGTTGTAGTAATTGTTTATGATAGTCGCTGTATATTCCATTTTAAGAATG

GAAGTGATATTCCATTTTAAGAATATGCCATAGTTTAATCTGCTGTTACGGACATTTAATCATT

TTTGGTTTGGAACTGTTAAGAATATTGCTGCTGCTCTAAACATTTCAGTGATTGTCTTCTTGTG

AATATGTTTACTTCTGTTTGGTATACTTAAGAGTGAAATTTTTAAGTCATAAGGTATGCATATA

TTTAGTGTATACTCAGTTTTTTAAAGGCATGCCGATTTTAATTATTCCATTTAAGTTAATATGT

TTTAATATCTGGTAGAGAAAGGAACATTATTAGAAACAATTGTTTTGGTTATTCTTACATATTT

AGTCTTTGAAAAAACGTTTCTTAAATTGGCATTTACTTATATTTGTGTTAATTTGGGAAGAAAT

GGTATCTTTGTTCATCTATGAGTCACATTTGGAACTAGCTCAAAGGCCATGGGTCCTGATTCCT

TTTTTTTTTTTTTTTTTTTCTTGTAGAGGGGAGGTATGGTGTCAAGAAAACATAGTCACCATTA

TTACGAAAAGTAAAATATGGAAGAGATGATCCCTACCATCAATCAGCTTACAACTAGAGGCACT

GACAAATGTATACAGATAGCTGTAATGTAAGGTATAACATAATAAATATAAGGAGAAATTAATA

AATTATTTTATGGTATTAAGAATGTATAATAAGACATGAAGGAGATGGTGATTATGTATAAGAG

TTTAGATAACCCTGTGAGATACAGTGTTTAGAATGAGGCCAGTTTTTAACATGGCATGATAGGT

GGGTGGGGGATAGAGGTTAGTAATGGATAGAGGACCATTTCCGAGTGAAGTCTCCTCAGAAGCA

AAAGCATTGAAGTCAGAAACACAAATATCCAGTACATTATAGCCAATAGTCAAATGATGGGACT

AGATCTGGTAACTGGTGATGATGTCATATAGTGGGCAGTAGTGCTGGGATGGCTGGGGTCAGGG

CCACATGGCAGGGGCCTCAAATAAAATGTGAAGGAGTTAGAAATTTATTCTGTTGGCATGAGAA

AGTGTTAAAGCTTTTGAATATAGAATGATATGTGTAACTTTGAGTTTTTAGGAAGATAATTCTA

GTGGCAAAGTTGAGGATAAAGGCAAAAGGGAAACCAGATGAAATAATGGGGCACTGTAGTAGGA

CAGTGTTGGTAAGTTTGAGGAAAAAAGGAGTAAGAGATATTTTTAAGGAAATTCATAGGGTTTG

AGTATAAATTAGAAGGCAAGTACAAGGGAATAAGCGTGGTCTTTAGAATCAGACAAATTAGGGT

TTGAATCTTAACCTTGCATTTACTAAAGGACTGAAAGCTAGTTCCCTAAGAGAAAAATTTTCTC

TTTTGTAAGATGCTTATTCTATAAACATTTGCAAGCACTGGAAGTATAAAAGCAAATGATACAC

ATGTTCTCTTGAAGTCTGGTCTAGTCTGTAAGAAGAGGCTGCACTGGCAGGTTTTGACCAAATT

GTGTAGAATCTCATCTGACGTGATTGGGAGCTTTGGCTTTATTCTGGAAGCAACTAAAAGCAAT

CAAAAAAGACTGGGGAATAATGTGAGAATGTAGAAATGTAGGGGAATTTCTAAGGATGAATTGG

TAGCAATTGGTAAACAATTTGATATACTGGGAAAGAGAGAGACTCTTTAGAATATGACTGAGAA

TCTTCCAATTTGAGCAGCTGGACTGATAGTGCTACCATCATTACCTCACAGGGTTTTTCTTAGT

GTGTCTTGTAAATCTTGCTTGTCCCTCATAAAGAATGGTTTTCCTTTTCTTCAGACTAAGGACT

TTTTATTACAGTACACAACTTAACACCCCCTGTATCTCTCCATCACAACACTTAACTGTGCATT

GTTATTGCATAATTAATTGTGGTTTTTATTTGTGCCCATTTCCTTCACCACATGAGGGCAAGAA

ATTATGTCTAGTTTTTCTACCTCTGCATCTTCATCCACCTAGTAGGCACTCAAAATCTAGTAGA

-continued
CAGTTTTTGAATTAATGATTATGAAGAATTTGAAGGCTGAACAAGTATCAACCTACACAGTGGT

TAGGGCAAATAAAAATGAGGGGGAGAAAGTAATGAATGGCACCAATTTTTTTAGTCCTTAACCA

GGACAGTGAGATTAGGCAGAGTGAGTTCTTTGGGAAAATAATTGAGTTTGATATTAGATACGTT

GAATGTAGATGTTAATGAGACATCCAAATGGATGTGTACCGTTGGTAATATGTAGTTGCAGGCA

TACCATGCCAGACATAAGGACTTAAAGATACAGAGTTAGGGGTTTGTAAGCATAGAGGTGCTAT

GGGAATGGATGACATTGCGCAGAAAATTGGTTTAGGTTAAGAAAAGTGGCTATTGACAGAAACT

TGGAGAGAGGCCATGTATGAGGTAGGAAGATGAACTAGCAGAAGACCTTATTGCCTTTAGAGAG

ATGGAAGAAAATGAGTGGATACAACATTAGGGAAGCCAGAGGAGGTGAGGAGTCATTAGCAGTC

TTAAAAGCTACAAAAATTAAGTAGGATTAAGGGGCCAAAGCACTGGGAATATACAGAAATGATG

GAAACTTTACAAGAAAAATTTCAGTAGATAGAAAAATAGCAGCTGAGCTAGTGGTTTTCACGTC

TTTTTGGCAGTAAAAGGAAAGAAGATAAAGAAATGGTACTCTGAGGAGCTAATGGAGTTGAGGG

AATTATGTTGCAAGTATTATTTGAAAGCAGTATTTAAAACTTTTTAAGTCTTAACTGCAGAATG

GACTGGAATAAGGAGAAACTAAAGCAGGAGGACTTAGGAAAATTGTTGTAGTAGTCCTTTAATT

GTGAAATGTGTAAACGGACAAAACTTAGACAGTTTTAATAAGTAGCATTATCCATAAATATAAG

ACACCATAAACATGATGCAAAGGAGAACAGAAGTGTTGGGTGTTATAATAAAAAGTGATAGAAA

AAAACAGTTTGTGAAATTAAGTTTTGAAACAGCTTTAGAAGGAGGTGAAGGAAAAAATAGAAATG

AATAAAATGAAAATTTTAGGGAGGTAGATATAGATCAACATAGGCATTTATTATTAGACTATAC

TTATTTATAAGATTATTAGACTGAGCCCTCTGTTGAAGAGATAAAGTAAGAGAACTATGTCTGG

TATTAGGATTCTTATGGTTAAATTGGCAAGTGAGTGTGCCTAATATTTGTAGTGCTTACAGTTT

TTGTTATTCTGTATTTTTATAGATTTGGTATATTTCCTCCATGATTATGTGTTCCTAACTCATA

ATTTGGAAGGCAGGGCTTCTTAAAATGAGATCTGTGTGTCATGTGAAGTATATGTTAAAATGCA

AATTCATTTCTGCGTTCTTGGGTTGGTCTGAAAAAAATTAAAAAAAAAATTCATTTACCCCTAC

TTCATGCACTGAATGAAAATCTTTGCGAGTAGAGCCCAAGTAGTTGCATTTTTAGATTTCCCCA

GGTAATTCTATTATAGACTGAAGTTTGAAAGTCAGTCTCTAAAACCTTAAAAGTTGGTTAATTT

TATTTCAAAATGTTTTATATGCAGTGTATTCACTTTCTACCATCAACCTCTAGGACACTGGATA

GGTTTCTTAACCTTTGAGATTTGCTTTCTTTATATGTAATGCAGTACATGAAAGGACTTTATTT

TTGTTCCATTGAGGAATGTTCTGATTGTATACAAACAAGTTAAGAATTTACAGTGATAATTTAG

GGGCTTGCTTTAAGCTTCAGGATTTTTTTTTAAGAGTTAAGTTTTGATATATATTAAGTGGTTG

ATTTAATAAATTATAATTATCGTCGTATATTGAAGTCCTGTTTTGTGCCAGGTAGGCATTATAC

TATAACTTTTTAACGCATTTTCTCTGCTACAATAACCTGACATTGGAGACTCAAGGGTCAGAGG

GTCGGCCCAAGGCTGCTACTCTAGAAAGTGGTAGATGCCCAGATTTGTACCTAACATAGCCGAT

GCTTAGCATATAGAATTTAATTAAAAACAAAATTGCTATAGGTATTTGAAAGGATTAGAGGGAT

ATAGTCAAATAGTTTTCATATGTGTTTAGCCCTTTTGGAGGGAGGATAGAGTAAATAAATAGAA

GGCACTAAGCTTTATGGATGAATATGGGAAATATGGCTTTGCCTGCTGAAAGCACTCAGGCCAC

AGGGCCTGCCTACCTATGCTTTCCTCATCCCGGCAACAGCAGTAATTTGTTTCTTGATACGTTT

TTGGATGTTCATAATTATAGAAAATAAATTTGCCTTTATGATGAAATTTAGTACCTTTTTTTTT

GAAAGTTCATCCAGTTGTTTATGTAAAAAGAATTGAGTGAGGTGTTTTATATTTTAGGTTAAAA

ATCTGTAAGAGCCTGATTTTAGAATTCACCAGCTCCTCAGAAGTTTGGCGAAATATGGTATGTT

TTTGTTTTATTTTTTGGAATTCGTATTGCATGTGTATCTTAATGTCATAATAATGACAGATGTG

TTCAGCAAATTTGGGCCCCTGCCATTTTTAAAGCATTGTGTCAGGTGCTCACTAACTACACTTC

CAAGACTGTATGAGGGACCCAGGTAGGGTGCTGAAAAAATTTACAAGAGATTAGTGTGCTATGA

-continued

GAGGTAAAATAATATGCATAAAAAGATTGAGAGGGCAGGTTTGGATTTTGGGCTATGAGTATTA

ATAATAGCTTTCATTTGTTGTTGTTGTTGCTGCTGCTGCTGCTGCTGTTGTTTTTGAGACAGAG

TCTTGCTCTGTTGCCCAGGCTGGAGTGCAGTGGCACCTTCTTGACTCACTGCAACGTCCATCTC

CCAGGTTCAAGTGATTCTCATGCCTTGGCCTCCCAGGTAGCTGGGATTACAGGCGTGTGCCACC

ACACCTGGCTAAGTTTTGTATTTTTAGTAGAGACGGGGTTTCACCGTGTTGGCCAGGCTAGTCT

CGAACTCCTGGCCTCAAGTGATCCACCCGCCTTGGCCTCCCAAAGTGCTGGGATTACAGGCGTT

AGCCACCACGCCCAGCCATTTGTGAGCACATTATGTCAGGCACTGTTCTGAGATACTTAGATGT

TAGCTTGTTTATCCATGACAGCTCTATGGAATAGGTACTATTATCCTAGTTCTACCTATAAGGA

AACTGAGACTCGGAGAGGTTAAGTAACTTGCCCAAGATTTCTCAGCTAGTGAATGACCAAACAG

AGACATAAGTCCAGCCTGGCCTTGGAGCCTTTTGAGCACCGGATCTCATAAAAGAGGGGACTGG

AAGAGAGGACTTGACTCTAGTTTTCAAAATACATATAGCTCTTTAATTACATTGAGGTCAATTA

GTCAATTAAAAGATATTTTAACTTTATTATTTTTGTGTTTACAAGATGGAAAGTTAGACTTGTT

TGAATCTTCTAATTCCACATACCATTAGTCTCTTGAGAACCCAAGGGGAAGCTGTATCATGACC

ACATTGTTTATTTTAGGGAAGGTGGTGTTTCCCATATGACCTCAGCAATGTCTAAGTTCTTATT

AGGCAATGTATAGTTAGGATAGGAGTATCTGGGAGATTGCGTTATTTCTTACAGATACTATAAA

TCCCATTTATTGGAATCCCCTGCAATTATTTTTATATATTCAGGCCAATCCTCACCTAATCTGG

ATTTTGAAGCCCTGCGTTCATAGCTGCATAGGTATGGGCTCAAACATTCATGTTTTAACCGTTG

GTATTCGCAGATACCTTGCTGTTTTATATTGGGTTCTGAATCCACACTGGTAACCACCTTTTAC

GCTTGACTATTGTTGCTTTGAGGATGTTAATTATGAAAGGTTTCTTCCTCCTAATTTCCTCATC

TTTCCGTAGTTGATGCCTCAGATTTGGCCTGGATAGGGGAATCGTGAGGGGAAAGAACTAGTTG

CACAAAATGATCTTTTGATACTGGGATATTTCAGATGTATGGTATCTTTGCCAGAACTACAGTG

TCAGTAAAGAGGCCTGCTAAATTTGAACTGTGACAATCAGAAAAGTTCAGCTAAGGCCATGTAA

GGGGTTAAAAAGATATTTGGTTGAGGGAGGAGGATATGCTTTCATCTTTTGCCATACTTTTTCA

TGAAATTAAATCTTAGTAGATTTATGGCCAAGAAAGAGTAGAATATATTTTTATGCAGTACTTA

AGGGGTTTTGACTGATGTTTTTTATTATTATTATACTTTAAGTTTTAGGGTACATGTGCACAAT

GTGCAGGTTAGTTACATATGTATACATGTGCCATGCTGGTGTGCTGCACCCATTAACTCGTCAT

TTAGCATTAGGTATATTTCCTAATGCTATCCCTCCCCTTCCCCCCACCCCACAACAGTCCCCAG

AGTGTGATGTTCCCCTTCCTGTGTCCATGTGTTCTCATTGTTCAGTTCCCACCTGTGAGTGAGA

ACATGCGGTGACTGATGTTAAATGACTTTACGTACATACAGAATTAGTGGGACTAGACTTTGTG

TTTATGTGTGTGTGTTTATGTGTATGTATATAACTATTCCATTAAGCAGTTGCCCTCCTTGGTG

ACTGATTGCTCTATCAGCTTAGGAATCTTTTGACTGAATTTGTCCGTATTTGAAAGATCTCAAT

CTGTGTTCTGAATCTTTACTCATTTACATATACTTAAATCTTGAAACCCAGTATAGCAAAACTA

AGCCAAAACAAACAAAAAAATCCATCCCTTGATAGGAAGTCAGTATATCTGGGTTTTAGTCAGT

CCTTCAACACTAGTTCCAAAATCTTGGGCAAGTCAGTTAATCACTCGGAGGCTGCTTAATTTTT

TTTTTTTTTAATTCTTAGTATATTATCTGTCTTGATTAGGTAAAGCCAAAGTTGTTATAAGACT

CAAGGTACTATTGACCAAAATGCTTCAGAAACTATAACATTACATAAAAGTACAAGGAATTATT

ACATTTTCTCAAATGAAGAGATCATTTAAGAAAAACAAAATGCTGGAAAATAGTCCTTAAAAAC

TTTTCTATAATAATTACTCTTCTGATGAATTTTACATTGACACCTAATTTGAAGCTTTGAATAT

TATTTTTTGAACAATGAATTGGGTTTATATATTAAAGTGTTCTAACCAAAGGTTTGTTTAATTT

ATTAGAGTTATTAAGCCTACGCTCAGATCAAGGTAGCAGCTAGACTGGTGTGACAACCTGTTTT

-continued

TAATCAGTGACTCAAAGCTGTGATCACCCTGATGTCACCGAATGGCCACAGCTTGTAAAAGGTA

ATTTTGAATTATTTTACAGCCTTTAAAAGGCTGTCATTGTAAAGTGAAATACATACTGTAAAAA

TGAAGACAATGTATAGTTGGCAGGAATACTGCTAAGAATAGTGGGCCTGAGAGTTGACCTACTT

CATTTAATCTCCTTAAAATATTTTAGTGTCTTTTTTTCTCATTAAAAATATCAGTAGCCACTAT

CAAAGACCTATCTGTATGTATAAACAGGAAAGTATTTCTCAAAAAAACTTCAAGGTTTTAAACA

TTTTACTATAAACATTATAGAAAACATTAAAAATTTCTTAATATGCATTTTAAAGTATGCCTTT

TATGTGGTGAACGTTTTAACTAAACATTTCTCTAGAAGTTTTTATAACATTAATAAAACTAGTA

TACTTTTCTCTCCTAGAGAGTTACAGTGGAGGTAAAAGGAGTGGCTTGCAGGATGGAGAAGCTG

CACCAGTGTTATTGGAAGTGAGCCACCATTTGAATTTGCTAGCTCATGCTGCAGTATTCAGATT

AGTGGGTGTTTTGTGATCATATTTTCTGCGATTCAAATCAAGACCTAAAATTGATTCTCATTCT

GAGATTTACATTTTATTATCCAATGTTATTTGGTTATTGTTTCAGTTTTAAAATTTCTGACTTG

TTATTCTGACACACTTTAGGATAACCTAAGTCAATAGTTTAATACAAAAATTTCCCTTTGGTTA

TATGTTTTGAATTAGGTTATATGTTCTGCATTTACAAGCACATACAGGATTCTTACTTCCAGCA

ACTTGGCAGTAAAAGAATAAGTAGACTCTTTAGGAGCCAAAGTCAAGCTTGGGAACTGTTGCTA

GGTGGTATATATTTCATAGTTTATGTTTGTTTCCAAGACAAGGTCTCACTCCATCGCCCAGGCT

GGAGTGCAGTGGCACGATCACAGTTCACTGCAACTTTGACCTTCTGGGCTCAAGTGACCCTCCC

ACCTCAGCCTCCCAAGTTGCTGGGACTAAAGGCACCCACCACCACACCCGGCTAAGAGACGAGG

TTTCATCATGTTGCCCAGGTTGACCTTGAACTCCTGAGCTCAAGTGGTCCTTATGTCTTGACCT

CCCAAAGTGCTGAGATTACAGACATGAACTACCACACCTGGCATATGTCATAGTTTTGAGAGTT

TGAATTCTAACCTCGGGACTTTGGTAACTTATTTATAATATTCTAGAAATATACTGTTATTAGG

ATGAGTAGAAATTCATTCAGACAGAAACTATTATAAATTACTGCAAGAAAAAATGTCTGCTAGTT

CTGCATATATTCATTTTTCTCTTGATTAAAAAACAATTTCCAATTTGAGTAGAACAACTTTGCT

ATGTTTAATAGACCCAGGACAGATTTATTTTAAGGTAATAATCTTTCAATCCTTCTTCTTCTAT

ACTGGATTGGTTTAAATTACTTAGCTTGTCTTATCAATGGTTTTTAATAGCCTACTTTAATATA

TGTAAAAAGTAGTAATTAATATGTTACAGTTTGGTGGCAAACATTTTGATGCCAAAGTTCACAT

ATTCTCTTGCTTAGGGAACAGAAATTGGGAAGATAGATGTAGTTATCATTTGATAATGTATTTA

AACTCTATCCCATTTCAGGATCTCAAAACTTTGTAACAGTTACATATTGTACTTCTAAGACTTA

GATTTGTTTTTCTTCTTGTGTCTTACCTTTTTGCAGTAATATTTTTATTTTCCTATCATCATGT

CCTCATTTTTTCCCTCTCTTCTCTTTCCCTGTTAATTTTGAAAGTTTTGCTGCCTACGTGTTTG

AAAACTTCTAATCTGCCTCTCTTCCCTCAGTGCCAGCAGGTTTATTTTTTGTTTTGCAAGCCAG

CTCTGCCTCCTTACAGTATGACATCTGATGCTGGAGGGTCGCACTTTCAAAAATGAGTCAGCTG

GTACATGGGGTTATCATCAATTTTTAGCTCTTCTGTCTGGGAGATACAAGTTTGGAAGCAATCT

TGGGGTACTTACCCACAAGGCTGGTGGAGACCAGGTGTGTCACATAGGTGATTTGCTTGCTCCC

TGGGGGAGAGGGTGGAGTGAAATTTTTGCATTTGTGTCACAGCCAAGTCACTGCCACCTCCAGC

ATGCCCCAGTTTTTAGTTGTTATGTAATTTTGTGCAAAATTGAAAATTTAAATACATTGCAAAG

AAGATCTAAAATAAATATTTGAGCTGCTGGAGTCTTTTTTTTTTTTTTTTTTTCCTTTTCCATTC

TTGTCCTTGGAATCTGAATGAATTGCAGTGAGGGTAATTTTGAGAGTCTGATAAAGAAGTGAGG

GGTTGTTTTTTTGTTTTTGTTTTTGTTTTTAGCTAAGAAATTTAGAAAACAGGTTTGTGTGTGTG

CGTGTGTGTGTGTGTGTGTGTGTGTGTGACTGATTTTAAGATTCTTGTTAGAGTTGCTTAAAGT

TGGAAGCCTAAAGTCAGTGAGAAGTTCACAAATCAGGACTTTGTAATGCCAATTTGAAAATTTA

GCTTTTGACCTCAAAAAACATTTTTTATCTAGTTTGGGAATTTCTAAGTGTTAGAAATCAATAT

-continued

TATATTGACTCATTCATTGTTGCTGATGCTGTTTATAAAAGTGAATAGATAGGGAAATACTGAT

TCATATCTCGTGAAATGAAAATGAAAGGCTTTTTAGTGACTTAGAATTTTAAATATTTCTACAT

GAGAGAGCAGTAGTATATTTAGAAATAACAAAGTAACTGGCAACTGTTTAAAACTGAAGTTAAT

TCACAGCTATCCAGTGCAAAACTTCACCTCAGGTGATACACTTTTGACAGGTAATACATACAGT

AAGTGTATTTTTAGGGAAACAGTTTCATTGTTGAACCAAGATAATCATCATTAGAATGTTGTAT

CTGATTTAAGTGTCTTTAAACTTACCAAGGTATTAGATTTTAGTTTGAATTGTCTGGAGTAGCG

GTAGCGGTTGGCACATTTGTTCTTAAAGGGCCAGAAAATAAATATTTTAGGCTTTATGGGCCAT

GTGGTTTCTGCCACAAGTCCTCAGCTCTGTTCTTTTAGTGTGAAAGCAGCCATAGATGATACCT

AAATGAATGAGTATGGCTGCATCCCAATAAAACTTCATTTACAAAACTACATGGCTGGCCTAAG

CTTTAGTCTGTCTGCCTAGGGAGTAGTTTACTGAGCCACTAATCTAAAGTTTAATACTGTGAGT

GAATACCAGTGAGTACCTTTGTTAATGTGGATAACCAATACTTGGCTATAGGAAGTTTTTTAGT

TGTGTGTTTTATTACACGTATTTGACTTTGTGAATAATTATGGCTTATAATGGCTTGTCTGTTG

GTATCTATGTATAGCGTTTACAGTTTCCTTTAAAAAACATGCATTGAGTTTTTTAATAGTCCAA

CCCTTAAAATAAATGTGTTGTATGGCCACCTGATCTGACCACTTTCTTTCATGTTGACATCTTT

AATTTTAAAACTGTTTTATTTAGTGCTTAAATCTTGTTTACAAAATTGTCTTCCTAAGTAATAT

GTCTACCTTTTTTTTTGGAATATGGAATATTTTGCTAACTGTTTCTCAATTGCATTTTACAGAT

CAGGAGAACCTCAGTCTGACGACATTGAAGCTAGCCGAATGTAAGTGTAACTTGGTTGAGACTG

TGGTTCTTATTTTGAGTTGCCCTAGACTGCTTTAAATTACGTCACATTATTTGGAAATAATTTC

TGGTTAAAAGAAAGGAATCATTTAGCAGTAAATGGGAGATAGGAACATACCTACTTTTTTTCCT

ATCAGATAACTCTAAACCTCGGTAACAGTTTACTAGGTTTCTACTACTAGATAGATAAATGCAC

ACGCCTAAATTCTTAGTCTTTTTGCTTCCCTGGTAGCAGTTGTAGGGAAATAGGGAGGTTGAGG

AAAGAGTTGAGTTTAACAGTCTCAACGCCTACCATATTTAAGGCATCAAGTACTATGTTATAGA

TACAGAGATGCGTAATAATTAGTTTTCACCCTACAGAAATTTATATTATACTCAAGAGTGAAAG

ATGCAGAAGCAAATAATTTCAGTCACTGAGGTAGAATGGTATCCAAAATACAATAGTAACATGA

AGGAGTACTGGAGTACCCAGGTATGCAATAGGAATCTAGTGTAGATGGCAGGGAAGTAAGAGTG

GCCAGGAAATGCTAAGTTCAGTCTTGAAATGTGACTGGGAATCAGGCAGCTAGAAGCATGAGCG

GCTTATTCCAGGCAGAAGTATGAGCCAAAGTTAGAAGCAGCATAGGGAGTAGGGGACAATAGGC

AGTTGAGGACTTTTAGATCATAAACTAGCTGAGAGGTAGGAAAATGAAGAAGATAAGATGTGAT

AGAAGGTATTAGGGAGTCAGCAAAGAATTTGCTCAGTAGGTAGATAGTAAGTTTGTCAAACGTG

TATTTTTAATAACCTTGCAAGAGAGAAAGGATTGAAGAGAAACGTGTGGTGGTAAGGTAGTTCA

GTCAGTGAGAGCCTTGACAATGACAGTGGTATAATAGGAATTCAAAATAAATTTTTCTGGATTT

AAGACAAATATTTAGGACATGAAGTAAGTAAGACTTTAGTGATTTATTGTGAAGACTAAAGATG

TTTCAGATAATAGAGGTAGTAATTATCAAAGCAAAGTTTTTCGAGGTATTAAGGGTTGGAATGA

AAAATACAGGTGTATCTCTCATACAGGTAATATAAAAAAAGAAAAATGCAGATATAGTGATTGA

CCTTGAATAAGAGGAAAGATGCCCATCTAATGAAATTAGAACAAGGAAGTAAAGATGGATGTGT

GATATTAATTGTAATTGTGGGTGAGGGTGGAAAAATCAAGATTTTTTTACTGAAAATATTGGAA

CCTTATTTAAATGCCGGTATATATTGTGAATCTGCAAGAAACGACTATAAAATGTATTTCTCAA

ATTTATGTGACCCAACCATGTGACTTGTCTTTTAAGCTTTAAAAAAATTGTAGTAAAATACACAT

AATGTAAAATTTTCCATTTCACCATTTTTAAGTATTTGGCTCAATGGTATTAAGTATATTAATA

TTGTTGCACAGTCACGATCAGAACTCTCTGTTTTGCAGAACTGAAACTCTGTACCCATTAAACA

-continued

ATAATTCCTCATTTCCTTATCTTCACAGCCTCTGACAACCATTATTCTACTTTGTGTCTAATTT

TGACTGCTCTAAGTACCCCCTATAAGTGCAATCATACAGTTTTTGCCCTTTTATGATTGGCTTA

TTTTACTTCGCAGTGTCATCAAGTTTCATCCATCTTTAGCATGTTTCAAAATTTGCATCCTTTT

TCAGGCTGAATAATGTTTTATTGTATGTATATACCACATTTTGCTTATCCATTTACCTGTTGAT

GAGCGCTCAGGTTGCTTCCATGTTGTAGCTATTACAGATAATGTTGCTATGAACAGGAGTGTAC

AAATATCTTTTTGAGACCCTGCTTTGAATTGTTTTCCCAGAAGTGGAATTGTTGGATCATATGG

TAATTTTATTTTTAAAATTTTGAGAAACTGCCATACTCTTCCAGAGCAACTGTACCTATTTGCG

TTTCTACCACTAGTGCACAAGGGGTCCAGTTTCTCTACATCCTTGCCATCACATATTGTGTGAG

AGTGTGTGTGTGTGTGTACTTCAATAGTAGTCATTGTAGTGGATATAAGGTAGTATGTTACTGT

AGGTTAGTGACCACGAAACTTTTTATGAAACATTTTTTAATAATATTTTGTGGAATACAAGGTT

TGTTTAGAGGTTTTGAGAAGACTGAAAACTTAGGAAGCTACTGAGGGGAATGGGTGAAGAAGTG

GATCAGAAGTTGAGAGTCTTGACTGGCTGGCTACCTGAAATCAGAAACCGTATCAGAGTAGGAG

AATCTCATTCCACTGAGTGACTAGTTAAGATTAAAGACTTTATCACATTTGAAATTTAAAGACT

TTTCTCCAATAGCCAGAAGATTATGCATGGTATTTTAGGGTTGGATATTAGCAGAGCTGATGGA

ACAGAATCATTAGTGGCATGTGCATAAGATGTTAACATTGGAGTATTTGAATTTATATGCTGTG

GATGATGGCCATGATTGGAAAGGTTGGGATGCCAGACCAAAGTGTTGAGTTGTTTTAAGAAAAG

CCTGAGGTCTAGATAACAGCAAGATGGCAGACTAGCACTTTGCAGCACTCATCTCATTGTAGAA

CCATCAATTTGAACAACTGTCTACACACAAAAATATAAGAGCTAAGAAACCAGACGAGAGATTA

CCTGAATGTGGCACACAGATAAGAAAAGACACATTGAAAAGGGTAAGAAGGACAGTTTTACATT

ACTTGTGTCACACCTCCCTCAGTCCCTGAGATCCCAGCATGGAGAGAGAGACTGTTCACCTGGG

GGAAGGAGGGGAAGTGTACACCAGACTTAGACCCTAACATTGAGCTCGCCCCAGTAAAACTCAA

TGCTAGGCAGGCCCCCATGGCCCCAAACTTCAGGCCAATACCCACAAACCAAGCTTGGAGGCCC

ACCCCAGCACCAAGCTGGATCCCACAGCCCTAGGCTCTAAGCCTGTCTAGTGCTAGGGTGGTCC

CTGCAGCCCTGCCCTCTAGATCGGCCCCTGTGGCCTCACATCACTGCAGAACAAGGGTCCAAAC

CCAGTACTTGGCCAGCCCCTTGTGATCCAAATTCTAGGCCAACATCCACCTACCCAGCCTTCAC

ACTGGTCCTTGCAGATCCAAGGTTCAGGCTCACTCTAGTAGACCAGGATGCCAGGCCAGCAGCA

CCTGTGTACCAAGGCTCCAGGACCTACCCTGCTGACCCAGACTCCAGGCCAGCCCCGGTAGACT

CAGGCTGCATAATCTCTGGACAGGCTGACTGGTGAAGGGCTTTACCCAATAAAGTCACTCTGCA

AAGACTGGAACAAGTCTCAGCTTCTTCAAATGTGCAGGTGCCAACACATGACTACAGGGATCAA

GAACAGTCAGGGAAACGTGACACCAGTCAAAGGAACACAATAAGGCACCTGAACCAACCATAAA

GAAATGGAGATATATGAACTGCCTGACAAAGAATTCAAAGTAATTGTTTAAGGAAGCTCAATGA

ATTTCAAGAAAATGCAGATAAACAATTCAACAAAATCAGGAAAACAGCAATCAAAATGAGAAAT

TTTGAGATTGAAATTATTTTTTAACAAATTCTGAAGCTGAAAATGCAATAAATGGAATGAAAAA

TGCAAAAGAGCATTAAAAGCAGAATTGAGCAAGCAGACAAAAGAATCTGAACTCAAAAGACAGG

TTATTTGGCTAGACTAAGGAAAAAAGAGATGACTCAAGATAAAAAAAATAAAGAGTTGTGTTTT

TTGATGATAAAAGCAACAAGTCTTTAGCTAGACTAAGAAAAAAAGAGATGACTCAAGTTAAATC

AGAAATGAAAGAGGAACCATTGCAGCTGATACCAGAGAAGTACAAGAAATAAGAGGATCATAAG

AGACTGAACAATTATATGCCAACAAATTGATTACCATAGAAGAAATGGATAAATTCCTAGACAC

ATGCAACTTGTCCAAGCTTAATCATGAAATGAAAAATGTGAACAGTCCAGTGACAAGGATTGTA

TCAGTCATAAAAAATATCTCCCACCAAAGGAAGCCCAAGACTTGGTGACTTTACTGCTGAATTCT

AGCAGACATTTAAAGAAGAACTAGTACAGATTGTTCTCATAATTTTATGAGAAATTTAAGAAGA

-continued

GGGAGTAATTTCAAACTCATTTTGGGAGATGAGCATTACCTAGATACCAAAGCCAGACAAGAAC

TCTCCAGGAAAAGAAAATTACAGACCCGTATTCTTAATTTAGATGCAGAAATTCTGAAGAAAAT

AATAACTAAATTCAACAGTGTATTAGAAGGATCATTTACTGTGATCATATGGGATTTACCTCAA

GGGTACAAGGATTATCCAACAGACCTGAATCCATAAAATGTGATATACAACATTAGGAGAACAA

AGGCCAAAACCATGTTATCATTTCAATAGATAATTGAGATAATTGAGAAAAAGCATTTGACAGA

ATTCAGTATTCTCTTGTGCTACAAAATTTTAAAAAATTAAGTATAGAAGGAATGTACCTCTATA

AAATAAAGGCCATATTGACAAACACACTGCTAACGTTATACTGAATGTTGAAAAGTTAAAAGCT

TTTCTTTTGAGATCAGGAAGAAAACGAGAATGCCCACTTTTGCCATTTCTATTCAGCACAGTAC

CGGAAGTCCTTGCAAGAGCAATTAGGCAAGAGAAAGAAAAGGCATCCCAGTAGGAAAGGAAGAC

ATTGTTGTCCCTGTTTGAAGATGACATGATCTTGTATATAGAAAAACCTAAAGACTCCACCAGA

GAATTGTTAGAACTGATAAATTCAGTAAAGTTGTAAGATATAAAATCAAGATACAAAAATCCGT

AGAATTTCTGTACATTAATGACAAATTATCTAAAAGAAAAATCAAGAAGACAATTCCATGTATA

ATAGGTACCAAAAACAAAACATGCAGTGGCTCCCAGTATCAGTGGTTCTGCATTTGCAAATTGA

ACCAACATTTGGATGAAAATATTTGAGAAAAAAATACAACAATAAAAATACTGTTTTCTTATAC

AATAAGGAAACTACAGTATAGCAACTATTTACATAGCATTTACGTTGTATTAGGTACTAAGTAA

TGATTTAAAGTATACACGAGGATGTGTGTAGGTTGTATGCAAATACTATACCATTTTATATAAT

GGACTTGAGCATCCATGGATTTTGGTATCTACAGGAGATCCTGGAACCAATATCCTGCAGATAC

CGAGGGATGATTGTACTTAGAAATAACTTTAACCAAAGAGTTGAAAACTATGTAACATTGATTA

AAGAAATTGAAGATGATACAAATAATGGAAAGTTATCTTGTGTTTATGGATTGGAAGAATTAAT

ATTGTAAAATGTTTTTATTATCCAAAGCAATCTGCAGTTTTAATGCAATCCTGATCAAAATTCC

AATGTTAAATTTCACAGAACTAGAAAACAGTGCTAAAATTTATATGGAACCACATAAGATCCTA

AATAGCCAAAGCTGTCATGAGTGAAAAGAACAAAGCTGGAGACATCACACTATCTGATTTCAAA

ATATAGTTCAAAGCTACAGTAATTATAACAGCATGATAGTCACATAGAAGTAGACAGGCCAGGC

ACAGTTGCTCACACGTGTATTCCCACACTCTGGGAGACTGAGGCAGAAGGATTACTTGAAACCA

GGAGTTCGAGAGCAGCCTGGGCAACATAGTGAGACCCTGTCTCTAAAATTAAAAAAAAAAAAAA

TTTTTAAAGCCAGGCGCGGTGCTGTGTATCTGTAGTCCTAGCTACCCGAGAGGCTGAAGAAGGA

GGATTGCTTGAGCTCAGGAGCTTAAGGTGGCAGTGAACTGTGATTGCATCACTGCACTCCAGCC

TGGATGACAGCGTGAGACCCTGTCTTTTAAAAACAAAAGAAACAAAAAAACAGACACATCGACC

CACAAAACAGAATGGAGAGCACAGAAATAAATTCGTGTACTATCAGTTGATTTTGGACAGGGTG

CAAAGAACACAGCGGGGAAAGGGAAGTCTGTTCAATAGGTGGTGTTGGGAAAATGGAATATCTA

CATGCATGAGAATGAAATCAGACCTGTATCTCACATCATATACCAAATTCAAGTTAAAATGGAT

TAAGGTCTTAAATATAAGACCTGAAACTGTAGAACTACCAGAATAAAGTATAGGAGAAATGTAC

ATGACATTGGTTTGGACAGTGATTTTTTTGGATATGACCCCCTCGAAGCACAGGCAACAAAAAT

AAAAATTGATGAATGAGATCACATCAAACTAAAAAGCTTCTGCATGGCAAAAAGAAAAAATCTA

CAGAATGAAAAAACTCACAGAATGGAAGATAGTATTTCCAAACCATATATCTGGTAAGGGGTTA

ATATGCAAAATATATAAGGAACTCAGACATCTCAATAGTAAGAAAGCACCTCACTTAAGAAATG

GGCAAAGGACTTGAATAGACATTTCTCAAAATAAGACATACAAATGGCCATTAGAATGGCTATT

AAAGTATGATGAGGATTTGCAGACAAGAGATATATTGCGCATGGCAGGAATGTAAATTAGTACA

GCATTTATGGAAAATAGCATGACGTTTGCTCAGAAATTAAAAAATAGAACTACCATATGATTCA

GCAGTCACACTTGGATATATATGTATTTTTATATATATATATATATATATATATATATATATAT

-continued

ATATATATAAATAAAAGAATAAAATCAGTGCGCTGAAGAGATCTGTACTCCCATGTTCCTTTCG

GTATCATTTGCAATACCCATGATACAGCATCAGCCTAAGTGTTCATGGATAAAGAAAATGTGGT

ATGTATACACAGTGGAATATACTTCAGCCATAAAAAGGAGGAAATGCTGTCATTTGTGACAGCA

GGGATGAACCTGGAGGGCATTGTTGAAAGTAAGCCAGCCACAGAAAGGCAAATACTACATCTCT

CTTAAATGTGGAATCTTAACTCAGGGATGTAAAATGGTGGTTACCAGGGGCTGGGGGTGAGTGG

ACTGGGTTGCAGAGGTGTTGGTCAGAGGACACAAAATTTCAATTAAGAGGAATTTGTTCAAGGT

ATCTATTGTACAACATGGAAACTAGTTAATAACAGTGTATTTTTGGAAATCACTGAGAGTAGAT

TTTAAATGTTCTGCCATAAAATATAAGTATGTGAGGTATTGCATGTATTAATTAGCTTGATCTA

GCCATTCCACAGTGTATACATATTTGGAACATCATGTGAATACAATAAATATGTATCCTTTTT

TTTGTTTTTTGTGTTTTTTTTTTTTTTTTTTTTTTTTTGAGACAGAGTCTTGCTTTGTCACCCAG

GCTGGAGTGTAGTAGCATGATCTTGGCCACTGCATCCTCTGCTTCCTGGGTTCAAATGATTCTC

CTGCCTCAGCCTCCCAAATACGTATCATTTTTATTTGTCACCAAACCTGGTGTCTTGACAGGTG

AAAGGAGATATGAGTATGAGTGAAACTCTTACAAAGATAGCTGAGATGATCATTGTCAGAGGTT

TTAGTATGTCTAACAAAGACAAGGGAGTGATTTGCTGAAATGAGGAGGTGAAGATGTCTCAAAT

TTAGAAAGGCAAATATTTTGGGGGCCTAGAGTATTGGGATAGAACCATGTACAGGGACATTGAA

GTCACTTTGCTGATGATGTAACTGGGGGCAAAGTGGAGGCTTAAATATGTGGGTTTAATTGACC

AGAACAGGGAGGGAAAGAGAAGGCATTCGGTTAGATGACATGAGTTTCAAATTACAAGCTGTTT

TTTTGTTGTTTTTAATACAGGGAATTTTGCCGTTTATTTTTAATACAGGGAATTAGAAGAATAA

TGGTGGACTTAGGAGTTTTAGGAGTCACATAAAAGGGTTGCATGATAGGCAGTGCCTTTGGGGA

GGAGCCAGGCTTTCATGAAAGCTAAGAAGTTGAGGGGCCATTATGTAAAGTAGTTGAAGATGGG

GGATAGCCTATGGGTCTTCAGAAAGCCTCTGGGTTTCTAGAGATCTTTCTGGAAGAGGTTAGGA

GGATGAGTCAAGTTTAGAATGGAAGAGGATAGATGAAGCTTGCATTTGGTAGTAAAAACCAAGG

ATGAATGTGTGAGGCATGATTATTTGTCACAAGTTTCCAGGTGACACTCTGGCACTCAGTCCTT

GTTGAATTAAGCAAGCTTTCTTACTGTTTTACTTGGCTGTGTTAAAGTAGAGTAACAGGAAATT

AGACTTCCCATAATGTCTCAATAGAGCTGTTTTAAGTTTCTAGCCATAATTGGTATGGGAATAT

AGCTCTAAACCTTCAAGGCTGCTACCATTTCTCACATTCCTATATCTAGAAACTGTAGCCAGGC

AGCACTTTCAGTGAGGTGAGTGGGTCCAGGTTTGTTCAATTACTTTTGTACCAACCTAATACCT

TAATAGTATTTGTCCTAATTTACAAAAATAGGTAATGAAGGATTCTTGGTTTTACCTCAGAGCT

AACTGTCCATTAATGGCAACATCCCACATTTGTTGAAGCATGATTTTGTTGTTTGTACTTTGAC

ATGCATTTGATATTTTAAGTAACGCCTTGAATGCATCTTAAATAATAATTTATATACAGTTAAC

ACTCCTGTTTGTTTTTAGGAATTCTTAGTGTTGCCAATTTCCTAGGATGTAGAAGAGCATAGTA

AAAAAAAAAATTATTAATACTCTTAAACAAGTGTTTTTAACAACTGGACACCATTTTGTAGTTA

AGCCTAGAAACAGAACTAATGCAATAACCCAGATCTTTTCATTTATTCGTATGTTTATTTTACC

TGGATTTACTTTAGTTTTTTGTTTTGTTTGCTTGTTGTTTGAGATATTGTCTTGCTCTGTCATA

AGTGATACAGCTAGAGTGCAGTGGTGTGATCAGAGCTCACTACAACTTTGAATTCCTGGGCTCA

AGTGATCCTCATGCCTCAGCCTCCTGAGTAGCTGGGACTACAGGCATGTGCCACCATGCCAGGC

TAAAACAGTGTTTTTGTTTGTTTGTTTGTTTTTTGTAGAGACAGGGTCTCACTATGTTGCCCAG

GCTGGTCTTGAACTCTTGGCCCCAAAGTAATCCTTCTGCCTTGGCCTCACAAAGTGCTGGGACT

ACAGACGTGAGCCACCGTGCCTGGCCATGGATTTTGTTTAAATTTATAAATACCGTGTTGTAGA

ATCTCTTTGTATGTATTAATTTAGACACCTTAGTTTTCTTAATGATTTCATACCAGTTTCTCAG

TAACTTCAGATTTTTTTTTTGAGATGGAATCTTGCTCTGTCACCCAGGCTGGAGTGCAGTGGCG

-continued

CAATTTGGCTCACTGCAACCCCTGCCTCCCAGGATGAAGCAATTCTCCTGCCTCAGCCACCCGA

GTAGCTGAGATTACAGGCATGTGCCACCATGCCTGGCTAATTTTGTATTTTTAGTAGAGACAGA

GTTTCACCATATTGGCCAGGCTGGTCTTGAACTCCTGACCTCGTGATCTGCCTGCCTCGGCCTT

CCAGAGCGCTGGGATTACAGGCTTGAGCCACCGCACCCAACCAGATCAGATTTTTTATGTTTGG

TATTTACTCTTTACCTCTAACACTAAGGCTATGTTTCCAGATGTATAACTATAAATGGAGCAGG

GGTAAATACAACAAGTGATTTATGGTTCAGTAAAGCAAGTTAGTTTTAATAAATGCTCAGTTTA

CTGTAAATGTCAGAAATGCCCCAGGACTCTGTCTATTGACAACTCTTCTATTTCCATCGTCAGC

TCTTGCCCTCTGAACTGTAGACTGATTTATCCAACAGTTAAGTCTGGTTCTCAAACTTAACCTG

TCCTAAGTGGAGCTCCTGATTTTCATCATCCCAAACCTACGTCTCTCATAATATTTTGCCATCT

CAGTCAATAACAGCTTTTTTCCCCTCCTGTGCAGCCAGAAGCCTTGGAAGCATCTTTTAATTTC

TCTATGTCACATACTCAAATTATTGGTAAATCTTGTTGGCTACACCTTCCAAATACCCATAATT

CATTTTATTTTTTTTAACCATTATACTTCTGTTTACTCTGTTTAAAGGCATCATCTTTTGGCAA

AAGAAAGAAATTGTTTCCCAGGAGTCTTGTGCTTTACAGTGTATTCTCTAGTAGCAGCCGGAAT

GATCTTTTTAAAATCTGAGTTAAACCATGTTATTTACTATGCACAGAACTTTTCAGAGGCTTCC

CATCTTAAAAGTAAAATCTGGAGATTTACATGGCCCTGTGTGAACTGGCTTCCTTTCATTTCTG

TGATCTCTCTACCGCACTTGCTCATCTCTGTCTAAAATGGCTGTATCTTTGTCATCTTAAGGCT

TGTAACTATTGTCTGTGACCCTGTGACCCTTCTCTGTGATAATCCATGTGGCTTCCTTCCTCAC

TTGATTCAGAGAGCTCTCTGCTCAAATGATGCTTTTCCTGACCGGCTGCATCAAAGAATGATCA

TGTTCTTCTGCATTCCCCTTAACTTGCTGCATTTTTCTTCATGGGATTTAATGTCATTTGACTT

CTTGCATATTGATTTCTTTGTTGTTTTGCTTCTTTACCACTAGAATGGAAGCCTAATGACAGTG

CCTGGCATACAGTAGGTAGTCAGTAACTACTTCCTACATGAAAGAATGAAGCTAGTAAATTTAT

GCAAAATGTTTGTTTCTGCCTTTTTAATTATCTTGCAGAAATGTAGGAAGAATTTTTTAGGATC

AGTTTATGTATATATATAAACTGATAAGTATGTACACAGCCTGTAGAATGTGGGTAATACCACC

TATCATCTTTTTGAGCATTTACCATGTAGCAAGTGACTGTGCTCCATAATCCACATGCATTATC

TTGAATTTGATAGGAGAGCTGAGCTTTTTAATCAGAGTAGACCATAGAAATATAGCTTGGATGC

TTTTATTTCCTATATGACTTCTTCGGTGTACTTACACATCTATAAGCATTTATGGGTCAAGTAA

CATACTGAAATATTTTCTGAAGTAAAAGAAATCTCTTTAATCAAATAAGTGGTTCTCCTATAGG

TTCTCATATCATATTCTTGGTCTCCAGATTGAGAAGGTCCTTTTGTATGCTTCCAGTATACTCG

AAACCAGGAGGTAGTCTGACATCTATTTCCCTTCAAGGTCAAATAATTAGAGAAAGGTTTAATT

GACACTGTTATCGAGACAGTATCAGAAGAGAAATTGAAAAATCTCTGTTGAGACTCTGTAATTT

GCTAGGTTCTGAGGATACGACAGTAAATAAGTTATTAGGTCATATACCTCAGCTTCCCATTTAA

TTAATAGGCAGTTATTATATATAATAGAATAGGTACTGGTTGGTATGAGACTACAGAGGAAGAA

TACCTAATTATCTTAAAAGTGGTATATAAGCTGAAACCTTGAGGATGCTTGGGAATAGCTAAGA

ATCATAGTGTTCTAGGCAGGAAGAATAACACCTGGAATCAGAGAAGACAGCAGAACAAGTCCAC

TGAGTAGTAAGAAGTTCCGTATTGCAGTAATGTAGAGTTAGCTGATGGGAGAAGGTGTGAAAAA

ATGCATTTGGATATAGAAAGCCAGGAGCACGCTAAGGCCCTTTGCTTTCTTCTGACAGACACAG

GAGCCCATGAAAGGCATCACGTGTGGAAGGAAGTGACACGAGTCATAGTCTGCCCTGCTTTTCT

ACCACCTGAAGCATCATATAAACCTATATCTTCTGTTTCAAATGTAAGGAAACATACTTCTAGT

TCACAGTAGGGATAGTTGAATGGATGAACTGTTTCTGGCTGAATCTTCTCAAAGTAGAATGAGC

AAAACATGGCTATATTATGAGATTATCTAAGGAAAGATTTTTATAATCATGTGAATTTTGAATT

-continued

```
TCTTTATATCTTAATTATTCCAAGAGATTTTTGGGAACATTAATGAGAATAGTTTACCTTTAGT

ACATAGAACTTCTTGTCAGCTATAAATGAGGATCAAACCCAAAAGAGATTAACAAAAATAAAAG

GGATGCTATTTCCCCAAATTAGCAGAACTTTTTGATTCACCGAGTTCTTTGTTTTTTAACTGCT

GTCTGCCTCTTAACATAATTGAGTATTCAGTGATATAATATAAATAAATCACTTACTAAATGCT

GATGAACGCTTGTTTTTACTAACATCTCAGCTTGTAGCATATCTTGTTGCCCATACCAGAAACC

CTACCCATTACCTCTGGCTCTTCCAGCTTATTTACCTCTTACAAACTACTTATTTTAAATATTT

CCTGGGTCAATTTCATCTTTTTTTTTCTTCCTACTGCTACATTATTTGTCCGGACTATTACAGT

AGTCATTACCTAACTGGATTGCTTGCCTCCAGTTTTGCCCACTTTGGTTTCAGTTATTGAAAAG

GCAAATTTTGTCAGTCACTTAACCTGCTTAAAACCCTTCAGTGACTCCTTGTGTTTTAGTTCTT

ATCTAATGGTTTATGAATGTAGTGGGTTACGAATCTTCCGGAAGAGTGCATTTGCACTCCTGAA

GTGTGCATGTATTTTTATGAGGAGAAGATCTTTAGCTTTTATTAGATTACTCCTCTTTTGGCTA

AAAAAAGAATTACTTATCATGGCTATTGAGGTCTTCCATGATCTGGCTTTTCCCTGCCTCTCCA

TTTTCATATTTTTGAAACTTTTCTTGAACTTTAGGCTCTTGAAGTGCTTGGAATTGTCTTATAA

TATCATGTTTTCAGGCCCCTGTGCTTTTACTCATTTTCCTCTATCTGAAACATTCTTCCCCTGT

CTGAAACATTCTTCCCACCCATAGTGTCATCAGCTCCTAGTCATCTTTTGTGATTCACCTCTCC

TAAGTTGCCTCTCTTTTTATTGCTATTCCTCTGTAGTCATCTCTGTGATATTGAAATCGTGGCT

TTCTCTTTCTTTAGACATCATAATTCCTTGAAGAGCCCTTTTTATGTAGCCTGACAAGCAGAAT

TTATACTGAAGTAGACATTTGGAAGTCATTTAGTTATTGCTCAATCCTTGAAAGATGAAACTGT

CCAAAGGGAAATTTAAAAGGGAAAGTATCTAATAGCTGATCCCTGGAGAATACAAATGTCTCTA

GATTTGGAAGGGAAGTCTCTGAAAAACAGCCAGAGAGAAGGGAGGAAACCAAGAAATAGTGTCC

TAGACCCAAAAGTCAATAATTTCCAAAAGGTCTATATTTCTTAGGAAGGCCAAGTAAAATAAGT

AGTGAAAAGTGATGACCTGACTAGAGCAGATTCTTCATTTCCAGTTACAGAAGCTAGGTTATAG

GTACAGTAAGCTCTGGACATGTTCTTTTCCCACATGGAACGTTATTCGTGTTCTCCACTGCTGC

TTTGAACTATTCCTTTTACTCTCTCAGCATAAAAATCCCTGCTCCTTTGAAGCTTATGCCTTCT

GGTTTTGTCTTCCTCTGTCTGCCTTCAGTGAGCTATCAGTTTCTTCTCGGTTTTTGAGGACTGC

TACCTGAACTTATTCTTCTTCACTCTTTCCCAAATCTGCTGCCATCTTTATTTATATGATTAAC

CCCTCAGTCCCTAGCAAGTCAAATTCCCATCCGTTTTTATCTACAGTAATGTTCACCTCTGCAT

CACTGCTGCTTCCCATGTCTACAGGCATGCCAACTCAAAACTGTTTTACCCCAAAAGCTTCAGT

GAAAACACCTTACCTCAGGTTGCCGTCTTTGAATGCTTTTCTACTATCTTAAACTTGTTTTCTT

TCATTGCGCCTTTTCTTCCTTCTCTTAGAGACTTGTCCTATGGCTCTTCTACTGTCTTCCAGCT

ACAATTCCCTCTTGTTCCTGACATGTACTGCTCAGAGCCAGGAGATGGATAAGTAGTAGTATTT

CACATGCACTTTTTTCTCTGGGGAGCAGTAGTCATACAATAATTGATTAAGATAAAACAGGTTT

TTATCAGTTTATATAAGAGGTAAAGAAAACAATGGGGTAGAGTTTTAAAAATTGTCAAAAACAA

CACATTTTACCATATTAATGATTTGAAGTGTACGGTACAATTGTGGTAACTGTGCACATTGTTG

TGCAGCAGATCTCTAGAACTTTTTCATCTTGTAAAACAGAAACTCTACATTCATTGAACAACTC

TTCTTTTCCCCCTTCTTCCTATTCCTTGGCAAATGCCATTCTACTTTTTGCCTCTAAAATTTGA

CTGTTTTGGCTACTTCATGTCAGTGGAATCATTAAGTATTTGTCTTTTGTTGACTGGCCTATTT

CACATAGCAATGTCCTCAAGGTTCATTTGTGTTGTAGCATATTACAGAATTTCTTTCTTTTCTT

TTAGGCTGAATAACATTTTGTTATATATGTATACCACATTTTCTTTAACCATTTGTTGATGGAT

GTTTAGGTTCCTTCCACTTCTTGAATATTGTAATGTTGAAATAAACATGGGTATACAAATATTT

TTTTGAGAACCTGTTTTTAATATATTTGGAAGTATACCCAGGTGTAGGATTACTGGATCATATG
```

TATTCTATTTTTTTTTAGATTTTTTTTTTTTTTTACAGGAGTTCTAGGTTCACAGAATTGAGAGG

AAGGTACAGAGATTTCCCCTGTACCTCCTTCCACACACATGTATGGATTCTCTCATAGCCAGTG

TGCATCTCCCACCAGAGTGGTACATGTCTTTCTGATGAACCTATATTGATACATCATAATTACC

CAAAGTCCGTAGTTTATATTAGGGATCATTCTTAGTGCTGTACGTTCTGTGGCTTTGAACAAAG

TACAATGACATGTATCTACCATTATATCATACAGAATGTTTTCACTGCCCCAAAATCCTCTGTG

TTCTGCCTATTTATCTTTCCTTCCCTCCCACTCCTTGGCAATCACCGATCCTTTTACTGTGTCT

CTAACTTTGCCTTTTCCAGCATATTATATACTTGTAATCATACAGTATATAGCCCTTTCAGCTT

GACTATTTTTACTTACTAATATGCATTAAAGTTTCTTCCATGTCTTTTCATAGGTTGTTAGTAC

CTCTCTTTTTCCATTTTCTGGACATATCACAGTTTGTGAATGAATATTCACCTAATGAAGGACA

TTGTGGTTGCTTCCACATTTTGCTAATTATGAATAAAACTGCTGTAGATATCGGTGTGCAGGTT

TTTGTGTGGACTTAGGTTTTCAGCGACTTTCTGTAAATACTAGGGAGTGCAATTGCTGGATCTT

ATGGTAAAAGTGTTTAGTTTTGTAGGAAACATCCAAACTGTCTTCTAATATGACGCTATCCTTT

TACATTTTTCACCAGCAATGAGTGAGTGTTTCTTTTGCTCTACATCTTCACCAGTATTTGGTGT

TATCAGTGTTCTGAATTTTGTCCATTCTGATAGGTGTGTAGAGGTATCTTATAATTTTAATTTG

TGTTTCTCTGATGCCATATGATGTGTGGGACATCTTTTCATATGCTGAATTGCCATCTGTATAT

CTTTGGTGAGGTGTCTGTTAAGGTTGTTGGCCAATTTTTTAATTGGGTTGTTTGTTTTCTTGTG

GAATTTTAAGAGTTCCTTACACTGTCTCTGTCTGTCTTGTCTGTCTGTCTGTCTGTCTGTTGAG

ACAGAGCCTCGCTCTGTCACCCAGGTTGCAGTACAGTGGCACAGTCTTGGCTCCCTGCAACCTC

TGCCACCTGGGTTCAAGTGATTCTCCTGCGTCAGCCTCCCGAGTAGCTGGGATTATACCCGTGC

ACCACCACACCTGGCTAATTTTTGTATTTTTAGTAGACACGGGGTTTCACTATGTTAGCCAGGC

TGGTCTCGACCTCCTGACCTCAGGTGATCCACCCACCTTGGCCTCCCAAAGTGCTGGGATGTGA

GCCACCACACCCAGCCTCCTTACACATTTAGTTAATAGTTCTTTATCAGATGTGTCTTATGTA

AATATTTCCTCCCTATCTGTGGCTTGTCTTTTCATACTCTTGACATTGTCTTTTGCAAAAGACA

ACAATTTTTAAGAAACAAGTAGACAATTTTAATGAAGTCTGGCTTATCAGTTCTTTTCTTCATG

GTTGGTACCTTTGGTGCCGTATCTAAAAGTCATCACCAAACCCAAGATCTAGATTTTTTCTTAT

GTTATCCTCTAGGAGTTTTATAGTTTTGAGTTTTACATTTAATTCTCTGGTTTATTTTGAGTTT

ATTTTTGTGAAGGGTGTAAGACCTGTGTCTAGACTCTTTTTTTTTTTGCATGTGGATGTTCAGT

TATTACCACTGTTTATTGAAAAAGACTATTTTCTTCATTGTATTGCCTTTGCCTCTTTGTCAAA

TACTGCCATTGCTCCTTTGACTATGTGGGTCCATTTCTGGGCTCTCTATTCTGTTTCGTTGGTC

TGTTTTGTCAGTTCTTTTGTCAGTACCACACCATCTTGACTACTGTAGCTTTACAGTAAATCTT

GAAATCAGTAGTGTCCATCTGACTTTTTCTGTCAATATTGAGTTGTCTCTCACGGGTCATGGAA

TAGCTCTTCATTATTTAGTTATTTGATTTCTTTCATCAGAGTTCTAAAACATTTTTCCTCATAT

ATCTTGTACTAATTTTGTTAGATCTGTACTTAAATATTTCATTTTGGGACACGCTAATGTAAAA

TGGTATTGTGTTTTTAATTTCAAATTCAACTTATGCATTGCTGGTTTACAGGAAAGCTATTAAC

TTTTTTATATGAACCTTGTATCCTGCAGCTTTGCTATAATCACTTATTAGTTCTAGGAGGTTTT

TGTTGTTTTTCTTTTTCTTTTTTTCAATTCCTGTCTATGTTCTACACATATAGTCATTTCATCT

GCAAACAAAGGCAGTTGTATTTTTTTGTTCCCCGTTAGTATACCCTTTATTTCCTTTTCTTGTC

TTAGCTAGGACTTCCAGTATGGAGTGGTGAGGTGGGGATATTCTTTTCTTGTTCCTGATCTTAG

TAAGAAAGTTTCTAGTTTCTCATCATTAAGGATGGTGTTAGCTGTATGTTTTTTGTAAACGTTC

TTTATCAAGTTGAAGGTGTTCCCTCTATTCCTAGTTTACTAGTTTCTATCATGAGTGGGTGTTA

-continued

AATTTTGTCACATACTTCTCTCCATCTATGGTATGGTCATGTGATTTTTCTTCTTTAGTCTGTT

GATATGGTGAATTGCATTAATTGATTTTCCAATATTGAACCAGTCTTGCATACCTGGGATAAAT

CCTACTTTGTGCTGGTGTATACTTCTTTTTATACATTGTAGTAAAATTTAGTTTGCTAATACTT

TGCTAATACAAAGATTTTTGCATCTTTGTTCATGACAAATATGGGTCTGTAGTTTTCTTTTCTG

ATAATGTCTTTGTCTGGTTTGGGTATTAGAGTAATGCTGACTTCATACAATGAGATAGGAGCAT

CTCCTTTGCTTCTGTCTTCTGAAGGAGATTGTAGAGAACTGGTGTGGTTTCTTCCTTAAATGTT

TAGTAGAATTCATCAGAGAATCCATCTGGGCCTGATGCCTTCTCTTTTAGAACATTATTAATTA

TGGATTTAATTTCTTTAATATATGCTTTTTAATCAAGATTATTTCTTCTTAGAGTTCTAATAGA

TTGTGTCTTTTAAGGAATTGATTCATTTCATCTAGGTTACCAAATTCGTGGCCGTAAAGTTGTT

CATAATATCCCTTGATTATCCTTTTAATGTCCATGAGATCTGTAATGATGTCCACTCTTTTCAT

TCTGATATTAGTTATTTTGTCCTTTGTCTCTTTTTCTTAGCCTGGCTAGAGGCTTATTGATTTT

ATTGATCTTTTCAGAGAACTAGTTGATTTCTTTGATTTTTCTCTATTGATATCTTGTTTTCAAT

TTCATTGATTTCTGCTCTAATTTTTATTACTTCTATTTGGATTTAATTTGCTTTTTCTAGTTTC

ATAAGTTGGTAGCTCAGATAATTGATTTTTAGATCATTCTTTTCTTTTCTTTTTTTTTTGAGAT

GGAGTCTCGCTTTGTCGCCCAGGCTGGAGTGCAGTGGCTCGATCTCGGCTCACCGCAAGCTCCG

CCTCCCGGGTTCACGCCATTCTCTTGCCTCAGCCTCCCAAGTAGCTGGGACTACAGGCGCCTGC

CACCACGTGTGGCTAATTTTTTTGTATTTTTAGTAGAGACGGGGTTTCACTGTGTTAGCCAGGA

TGGTCTTGATCTCCTGACCATGTGATCCACCCGCCTCAGCCTCCCAAAGTGCTGGGATTACAGG

CGTGAGCCACAGCGCCCGGCCTAGATAATTCTTTTCTAATAAATGCATCAGTGTTGTATGTTTC

TTTCTAAGCGCTGCTTTCACTGTATCCCACAAATTTGGATAAGTTGTGTTTTCATGATATTTTC

AATTTATAATGGTATTGGGACACAACCCAATAAGTAAGTTTAGGAGCATTTGTATGCATAAGCA

CAATTGTTGACATTATTTTGAACAAATTCTTATTTGTTAGATCAATTAAGTATAAGAAAAAATAA

AAGGTTTTATTTTACTTTCAGTGTTTCCTTCTTTTGATGCTCTATATATGTAGATTTCAGTTTC

TGAACTTCCCAACACTTATTGCAAGGCAGGTGTACTGACAACAAATTTCCTTAATTTTTGTCTG

AGAAAGTGTTTCTTTTTAACTTTTGAATAATAATCTCACAAGGTAGAGTGCTAGGTTTATGGTT

TTTTTTTCTCTCAACACTATGAATATTTCACTCTTTTTCTTGTTGGAAGTCACATGTATTTTTT

CTTTTTTTTCTTTTTTTCCTCTACAGGTAAGGTGATTTTTTCCCTCTGGCTTACTTCGGATTTT

TTTCTTATCCTTGAATTTCTGTAATTACAACGTTTTATGCCCAGATGTAGTTTTTTGGCATATT

TTCAAGCTCAGAGATTCTTCATCCATGCCCAGCCTACTAATAAGCCCATCAAAGGCATTCTTCA

TTTCTCTTACAGTGTTCTGTTTTTTGTTTTTGTTTGTGTTTTATCTCTAGCACTTCCTTTTGGT

TCTTAGGATTTTCATCTCTACTTTTTTAACATGTTGTTTACTCAGTTCGTTAGGGCCCTTAGCA

TATTAATCATAGTTGTTTTAGATTCCAAGTTTGATAATTCCAAATCCCTGCTGTATCTGGTCCT

GGTGCTTGTTTTTTACCTTTTATTATGCCCTGTAATTTTTTTCTTGATAGCTTGGACATGATGT

ACTAGGTAAAAGGAACTGTTGTAAATGAGCATTTAGTAATGTGGTTGTAAGGTGTAGGGAGAGG

AGAAGAGTTCTGTAGTCTTATGATTAGGTCAGTCTTTTTAGTGAGCTTATGCCTCTGGACTGTG

AACTTCACAAGTGTTTCTCAATCCCACCCCTCCCTCATTCCCTTAGTTAGAACAAGATAGCTAT

AATGGCCTGAAGTTGGGTTATTTCTCTTCCCCCACATCATTTTGGCTTTGCTACAACCCCAGCA

GGTTAGGCTCTGGTTAACTAGTTTCTCCTGAGGACAAACCTTGTTAAGACTGGAATAGTCTAGT

GTACTTGAAAATCATTTCTCTTTGCCTCCCCTGCTGAGGGTTGAGGATTTTTCTCCTATATTTA

CTGTGAGAAGCTGGTCAATTGCCTGGATGTAAAACTTAGAAAATTGTAGGGCTCCCCCTATAAT

TGGGTAACTCTGGAGTTTTTAGCTTTCAGAGTTGTCCACACTGAGCCTTCATCAATTTGTCTAT

-continued

TACACTTCAGGATTTCCTACCCCGTGGAGGTTTCTGCTTGTGTTTTTCATCTCAGATAAATGGT

GATGCTATGTGTTCACCTGTTCTCTGCTCTCACAGGCAGTCATTTGCCCTGTGACCTCACTTAT

CCTATCTCAGATTTGTTTATTTTTAAGTTTGTCATTTTTTACTTGTTGTTAGGATGGAGTGGTG

ACTTCCAAGCTCTTCATATGTGGAACTGGAGGTAATTCTATTTCAAATTTTTTGAGGGACCTTC

ATGTTGTTTTCCACAGTGCCTGGCACCATTTTACATTTTCACCAGTGGTGCATAAGGGTTCCAG

TTTCTCCATATCTTCACCAATACTTATTTTCTGTTTTTTTAATGGTGGCCATCCTAATGGTTTC

AGATGATGTATCATTGCAGTTTTAATTGACATTTCTCCCTACTGATCAGTGATGGTGAGAATCT

TTTCATGGGCTTATTGCCCATTTGTATATATTCTTTGGAAAAATGACTATTCAAGTCCTTTGTC

CACTTTTTAACTAGATTTTTTGTTGTTGAATTGTAGGAGTTATTTATATATTCTGGATATTAAC

CAAATAACAGATACATGGTATAGAAATATTTTCTCCTGTTTTGTAGGTTGCCATTTTACTCCAT

TTACTGTTTGCTTTGTAGAAATTTTTGAGTTTATGTATCCCCAGTTTGTCTATTTTTGCTTTGG

TTGCTTGTGCTTTTGGTGATCTATTCAAGAAATCATTGCCAAGTCCAATGTCATGAAGCTTTTT

CTCCATGTTTTCTTGTAGTAGTTTTATAATTCGATGTTTTAAGTTTAGGTCTGTAATCCAGCTT

GAGTTCATCTTTGTATATGGTGTGAGATAAGGCTCCAACTTCATTCTTTTGCATGTTAGATTCC

AGATTTCCCAATACAGTTTGTTGAAGAACCTCTTTTCCCTATTTCTGTGTTCTCTCTTCTGCTC

ACTTGGTCTGTATATCTGTCTTTATGCCAGCACCATAGTGTTTTGATTACTATAGCTTTGCAAT

ATCTTTAGAAATCAGGGAATGTGAGGCCTCTAGCTTTGTTTTTTGTCCAGATTGTTACGGCTAT

TCAGGGTCCTTCAAGATTCTGTATTAATTTTAAGATTTTTTTTTTCTGTTTCTGTAGAAAATGC

CATTGGGATTTTGATAGGGATTGCTTTGAATTTGCAGATTGCTTTGGGTAGTATTGCCATCTTA

ACAGTACTAAATCTTCCAATTCATAAACTTGGATGTCTTTCCATTTATTTGTATTGTCTTTAAT

TTCTTTCAGCATTGTTGTATAATTTTCTTTTTCTTTTTTTTTTTTTTTTGAGACAGAGTCTCAC

TCTGTCACCAGGCTGGAGTAGAGTGGCGTGATCTTGGCTCACTGCACCTCTGCCTCCCAAATTC

AAGTGACAACTCCTGCCTCAGCCTCCCGAGTGGCTGGGATTACAGGCGCGCGCCACCAAGCCCA

GCTAATTTATTTTGTATTTTTAGTAGAGACAGGGTTTCACCATGTTGGCCAGGATGGTCTCAAT

CTCTTGACCTCGTGATCAGCCCACCTTGGCCTCCCAAACTGCTGGGGTTACAGGCGTGAGCCAC

CACGTCCGGCCTATGTTGTTTAATTTTCAATGTACATGTCTTTCATTTGCTTGGTGAAAATATT

CCCTAAGTATTTTTTACTCTTTGATTTCATTTTAAATGGGTTTAAAAAATTAATTTCCTTTTTG

GATTCTTCATTTTTAGTATTTAGAAATGCAACTCTTTTCTTAATATTGGTTTTTATATCCTGTA

ACTTTACTGAATTCCTTTATTCTAACGGTTTTTTTTCTTTTTGGTAGGCTAGAGTTTTCAACAT

AAAAGATCATGTCATTTGCTAACAGAAGTAATTTTACTTCTTACTTTTCTCATTTAATACCTTT

CATTTCTTTTTCTTGCCCAGTTGCTAACTCTGGCAGGATGTCTAACAGTATGTTGAATAGAAGT

GGTGAATGTGTGCATTCTTGTTCCATTTGTGATCTTAGAGGGAAAACTTTCAGTTTTTCATCAT

TGAATAACATTAGCTGTGGTCTTTCTATATATGGCCTTCATTATGTTGAAGTAATTTCCATATC

TTTCTAGCGAATTGAGCGTTTTTGTTTTTGTTTTTTTGAGACAGAATCTTGCTCTTGTCACCCA

GGCTGGAGTGCAATGATGCTATCTCACCTCACTGCCAGCTCCGCCTCCCGGGTTCTCAAGTGAT

TGTCCTGCCTCAGCCTCCCGAGTAGCTGGAATTACAGGCGCCCACCACCATGCCCGATTAGTTT

TTGTATTTTTAGTAGAGACAGGGTTTCACTGTGTTGGCCAGGCTGGTCTCACACTCCTGACCTC

AGGTGATCCACCCACCTTGCCCTTCTAAAGTGCTGGGATTACAGGCATGAGCCACCCTGTCTGG

CCTTTTTTTAAATCCTAAAAGGGTGTTGATTTTTGTCAAATGCTTCTTCTGAGTCAGTTGAGAT

TATTGGTTTTTGTCCTAAGAATGCAGTGTATTAAAGTGATTTTTTTGTATGTTGAACCATCCTT

-continued

GGATTTTATGAATAAATTCCAGTTGAGAATTTATGAAATATAATCTTTTTAATGCATTGTTGAA

TTCTGTTTCTTGGTATTTTGTTGATTTTTTTTGCATCAGTATTTATTAGGGATTCTTTTTTCTT

GTAAATTTGTCTGATTTCGATATCTAAGTAATGCTTACCTCATAAAATGATTTTGAAAGTGTTC

TGTCCTCTAGTTTTTTCAAAGAGTTTGAGAAGGGTTGTTAGTTTTTAAATGTTTGGTAGAGTTT

TCAGTGAAGCCCTGGCGTTGTTGGACAGTTACTGATTCAATCTCTAATAGTTATAGGTCCATTC

AGAAGTTGTATGTATTTGTGGCTCAGTCTTGGTGGGTTTGATGTGTCTATCCGTTCTCAAAGGT

TATCAAATTTTTTTGGGTCATAGTTGTTCATATTAGTCTTTTAAGGTCCTATTTATTTCTGTGG

CAGCAGTTGTTGTATCGCCTTTCTAATTTCCAGTTGTTGCTGTTTGTGTCTATTCTCTTCATTT

CTTAATCTAAGAATTTGCCAGTTTTGTTGATCTTTTCAATAAAACAGCTACTCCTAATTTTGTT

GATTTTTTTTCTATTGCAAAAATTTTCTATTTTTCTCTATTTTATTTTAGCTGTAATTTATTTT

TATTTTTTTTATTTTTTGGTAAGTTTGAGTCTCATTTGTTCTTCATTTCCTAATTCCATAAGAT

GTAAAGTTAATTTGTTGATTTAAGGTTTTTCTTCCTTTCTAACTGTGAAATATGACACTGTAAA

ACAGATTTTCATTTTACAGATGAATTATGTAAATATTTAGTTCTACAATTTTACTTTTTTTTTT

ATCATATATCACGCATTCTGGATATTGAGACTATAAAAATGAAAAAAACAGTTCTTTTCTTTTC

TTTTTTTTTTTTGAGACAGAGTCTCGCTCTTTTGCCCAGGCCACAGTGCAGTGGCTCTGTCTCG

GCTCACTGCAAGCTCCGCCTCCCGGGTTCATGCCATTCTTCTGCATCAGCCTCCCAAGTAGCTG

GGACTATAGGCGCCCACCACGGCGCCCAGCTAATTTTTTTTTGTATTTTTAGTAGGGACGTAGT

TTCACCATGTTAGCCAGGATGGTCTCGATCTCCTGACCTCATGATCCGCCTGCCTCGGCCTCCC

AAAGTGCTGGGATTAGAGGCGTGGCGTGAGCCACTGCACCCGGCCATAAAACAGTAATTGAAGG

TTAACCTATATTTCAAACAACTGAAAATACTGATTTGTTCATATTTATTTTTTCATGAAAATCG

TCTTGTTCTATATTTAATAGGTTTTTGTTCGGTTCATGGTACTAATGAGTTCACAATTGTAGGT

TTAGTCTTGAAATAATCTAAATTCACTTCATCCCATTGTAACAGACCCTACATCATACTGAATA

TAGTTGTGTCACAGATGTCTCTTACAGTCTATTTCTACAAGGCCTAGAACTATTTAGGATACCG

TTGCTCACTCTTACAAATTTTAACATTAAAAATAACTTTGAGATGGAATGGAGTTTTGCAACGT

CTCAGAACAAAGAGACTCCACTTACGAGAAATTACTAAGCAGTGGTTCCTAGCTTTATAGACTA

ATTATATAAGCCTTCAGTTGTTTCTATTTTATATCTGTTTTTTAGATTCCTCACATGTTCATTC

TGCTTTACCTTCTGTATAATATAAAGGTCACTCTACTTACAGTCACATTTTCCTTTTAATCTTT

CCGTTTTTATTTTTTATTCTTTGCTTTGTTCACCATTAGTTTTTATATTGCATCTCACAGTTCA

TGTTTCTTTTTTGTCATTTCTGATTCTAATTGTAATTCTAATCTTACTTGTTTGGCGTTCACTG

TCACATCTTCACTTTCTGGCAGCTGTTTCTATGGCTTCATCTTCTTAGTGCTTGTATTCATTGC

TTATATTCCAGTTGTCTTGTAAATTCATTTTTTTAGTGAACTAAGCCAGACACGGAAAGACAGA

TATCACATGTTCTCACTGATATGTGGGAACTAAAAAAACATTGAACACAAATTTTACAGCTGAC

ACACATATGCCTGCCACCTAGATTCTGCCATTAATACTTACATTGCTTTATCGTATAACCATCC

TTGTATCCATCAATCCATCTTAATTTTTATGCCTTTCAAAGTTAATTGCTAACATTAGTACACA

TCCCTCTAGGTGAAACCATTTTTAAACTGATTGCTGTCAAGTTGTCTAGAGTAAACTCTGATCT

TCCAAGTATGACTTATTCCATAGGACTTCTGTTTGTAGCACTGTCCCATTAATTCAATCATAGA

AATAAATAATTGGAAAGTATTGTCTGTTTTAAATGGATAAGTATTTTCATGTGTCTGACTTTAG

AGGACTTTTACTAGAAGGTCTCACTTGACCTTCATTGCTGACTAAATAAGAAAAGTTTGTTTTA

TTTTAAAAATCAACACATTATAACATACTTTGTTTTTTGAGTAATAAGAAAAGTCAATGGAATG

TGAAGAAATTATAGCAAGTAAGCTGTTGTTCCTCTTCTAGGAATTTTGATTATGAACAGCTGAT

AAGGTATTACTAAGGGATCTCATCAGGGAAATTCCTTTCTTTCCTTCTTTTTCTTTTGCATCCT

-continued

CTCCCTTTCCTCACTTTCTTTTCCCCTTTTTCCCTTTTCCCCTCTCCTCTTCTTTTCTTTAATA

GTACTTGGGGAAAGGTATACCTTTTATTTTACGGATTTGCTCAGGGTAAAGAGAGAGTTAAGAG

GCCAAATGATTAGATGGCAGGGTCACTGGAGGGCAGAGATAAATAATAGATCCTAAACTAAGGG

TTGGCAAACATTTTCTGTAAAGGGCAGGTGGTATTTGTTTTAGGTTTTGCAGGCCTAAAGTACT

CAACTCTGCCATTGTAGTATGAAAAACAGCCATAAACTATATAGTATATTGTATTAGTCCTTTT

TCACGCTGCTGATAAAGACGTACCTGAGACTGGGAAAAAAAAAAGAAGTTTAATTGGACTTACA

CTTCCACATGGCTGGGAAGGCTTCAGAATCATGGCGAAAGGTGAAAGACACTTCTTGCATGGCA

GTGACAAGAGAAAATGAGAAGGATGCAAAAGCGGAAACCCCTGATAAAACCATCAGATCTCGTG

AGACTTACTACCACAAGAACAGCATGTGGGAAACTGCCCCCATGATTCAGATTATCTCCCAGGG

GGTCACTCCTACAACACATGAGAATTATGGGAGTACAATTCAAGATGAGATTTGGGTGGGGACA

CAGAGCCAAAGCATTATCATATATAGTATATTTATAAATCAATGAACTTGGGTATGTTCCAGTA

CACTTGATGGATACTGGAACTTGAATTTCTTATAATTTTCACGTTACAAACTATTATTATTTTT

CAAACTTTTTCCAGCCATTTAAAAATGTAAAATATTCTAAGCTTGAGAGACATAAACAGGTGGT

GGACTCGATTTGACTTACGAGCTATGATTTGGTGACCCATATGGTACAAGGATTTCCCTTGCGC

AGGAACTATACCAAAAAGTCGTTATTAGTGTATACTTTTCCAACGTAGAGGCCCTTTTATGTGC

TCTAAATTTTGTATGCCTTTTACATATCCTAAATTAGATAGTGATGCAGATGAGGTCAGATAAA

TTAAGGTGTCATTGGAGTGAGGAAAAAAGAAGAATGCTTAATATAGTTGATTCCACCATTAACT

TGGAGGTTCTGGCATGGCTTCCTTTAGTCCTGTCTCATCAGTGTAGCTGCTATTTGTTAAACTT

GGCACAGAAAGGCAGATCAAATATAGAGGGCTACTTTCAGATCCTCCTCTTAATAGTTATTAAA

AGCTCAAGTTTAGTAGCTGAGTTCAAATCTCTTATTAGATGTATGACTTATGTAATTTCTCTGA

GCATCAGCAGAATGAAGGTTTATAGTGCTAACTCATACACTTGTGAGGGTGATAGTAACAATTA

CAACAATAATAGTAGTAGCTAACACTTTCATAGTGCTTAGTATGTGCCAGGCAATGTTCTAAGC

ACTTTATATATATTAACACATTTAATTTTCTCACAATTGGTAATGTGAAGAAGAATAATACTCT

CACCATGATAATGCTCGTAGATACTACCATTTAAATTACGAGGAAACTTACGTCCAGAAAGATC

AAGTAATTCATTCAGGGTCACATAGTTAATTAAGAGGTAGAGCCATTATGTGAACTTGGGCATC

TGGCCTCAGAATGCGAGCTCTTAACTGTTAAGGTTTATTCCCCTCTAAAGTGGGAATGTCTATA

AAATGCATAGCACATAGGTCCTCAACAAATTAGAGAGAAATTAACTTTGCAGAATATAGTGGTT

CCATTTCCTCAAGAAACTTGGTCTGCCTTTGTGGTACCAGATAGATGCATAAATGTGAGGTTCA

CGTTATGATTCTTCAGATTTTTTTCCCAGTTGCACATTAGTTATGAGATTTTTTTCCATAGAAT

TCTTCAGTATTACTCATGTTAAAAAATAATTATTTTGAAATGAATCACCTTCTGCAAAACAATA

TAGTCAAAATGACTTAGACTCTGAAGCTGAAAGACTCCTGGACTCCTATTCTTGTCTTGGTTCT

GTACTTTCTTTGAGATCTTGGTTTCGTGATTTGACTCCAGTTCTATTTCTCTCTTTGGCTGTGG

ACTGAAGATAATCCTCAATGTCATGGTATTCAAATGAGATAACCCATGTCAAAGTGCCCCGCAG

TGTGTGTAATAAGTTATCAGGCATCCAGCAAATACTAGTTTCTTGCTCACCTCCCTATTACATA

AAATAACTTTAAAATTAGAACTGAAGGGACTCATAAAGCTGGGAAAACTGAGGCCCAGACAATT

GTTTCCCTAGGATCCTACAGCTGCTTAGGGACAGAAGGATGACACTTAATGCAGATCTTCTGAT

TTTTCAGTCTCGTTCTGTTTGTGCTGATCACTCTCCTCCTATGTAGTATATAAAGAAGTACTAT

GTATCTGACAAGTTTTGGGGAGGTTATTTTAGTATAAAAGCTCACATTAAAAATATCTATTTTG

GTATTTTGACTTTTGTAATTTTTTTAAAAATCAGAGACAATTTAGTAAATCTCGGGGCCATTCA

AATCATGTATATGAAGTTTTATAACTGCTATTGTTTTCCCCTTATAGTTATTAATTTTTAATAT

-continued

GCAAGTAGCATCCTTACTATGGAAAGAATAAATAAGAAATCAAAAGATGGAAGAAGTTTTAAAA

CTCACTTAATCACATCATCCAGAGAAAATGCTATTAATGCTTTGAAATAACAATGGGTTCATCC

TACACCTGCTACTTTTTAACTGACTTTTGTCAGTTAGTGATATATCAGGAAGACTAGGCAGTTC

TTTGTCGAATTCAAATCTTGATAGTTTTTATTTTATTGTGTGACCTATTATCAGTTCATTTAAG

TAATCTTTTATTAGACATGTTTTTTTCAGATATAGAAACAATGCATTTTTGTAAAATTGTCAAA

TTATTTTCCACAAGTAGGATCTCATTCACACGGTATTCGTGTTTTTAAGACTTTCGATACATGT

TCACTGTTTTCCTCCAGAAAGGAAATACCTACTTACATTTTCACCAGGGAAGTCACTGTAGTTT

GGGAGAACATGACATTATCTCCCTTTCTTTACTGAAGGGTAGCAATATATATTTTAAATTTTCT

AGATTCTGCATTTCCATTTTATTTTTACATGTTTTCACTTTCATATTTTGCATAGTGCTAAATC

TGTGATAACAGTTTTTAATTTTCAGGTGGGGTTTATAGCTTCATAGATAGCAAAATGTCTTTAA

GTCATGTTTATGCAATTTTTACATGTGCTTTGTGGGTTTTCTTTTTTCTCTGTTTGCATGCAGT

GAGTGGTAAATTTGCATGGAACATTTGAAAAATAAGCACCAGAATGAATTGAATGTGTGTGAAT

TATCACTTTTTGTCACCTACCTGGACAGAGAGTGAAAGTTCTTCTGTTGAGACAAAATTGGATC

TCGTGTGTTTCTTCACTTACTTGCTGCCTTGTTAATTGTTGAGTTTCTCATGATTAGCAAGATG

TAAACTCTGGCATTGGTCATCTAGTCCTACATGTTAGATAATTCTGTGAATGTTTTGAAAATCA

GCTGAACTATTTTTCTTATAATTTTGATTCTTTGTAGTTGTTATTTCCATGCTTGTGAATTTGG

GACCAAAAGGAATGGCTATGACTTATGTTTCTTTGGATCCAGTAGTTTATTCTACTGAAATTAT

GGTAATTTTATCAGTTAGTAGAAGCATAGACTCTTTAGTGTTGAATATAATGTCATCTAACTTC

TTACATGGTCACATAATTCCTCCCTCAGTTTTGGTAGCTCTCCTGAAACAGCCATAATAGGACA

TTAATCTGTGTACTTTAAGTTGACAGAGTAAAAGGAATATAAGATTTCACGTGATGGAACTTAA

AATATTCCATCTTGTGACGTGGAACTAATGAGGAGGTTTAGTGACAAGTTTTAGATTTAAGATT

CTACACTTTGGAGCCTCTTTTTCTTTTTCTTTTTGGTTTTTGTTTGTTTGTTTGTTTTTGAGAC

AAAGTCTAGCTCTGTTGCCCAGGCTGGAGTGCAGTGGTGCAATTTCAGCTTATGGCAGCCTTGA

CTCTCAGGCTCAAGTGATCCTCAGCCTCCCAAGTAGCTGGGACTACAGGTGCATGCCACCACAC

TTGGCTAATTTTTTTTAAAAAAGTTTGTAGAGAGTAGCCTCACTATGTTGCCCAGGCTGGTGTT

GACCTCCTGGGCTCAAGTAGTCGGCCTGCCTCAGCCTCCCACAGTTATGGGATTGATTACAGTC

ATGATCTGCCTCACTCAGGCTGCAGCCGCTTTCTTTCAGTGTAACACTATCTTTGGATATTCCA

CTTACAAATTTATTTTTAAGTCTCCCATGTTGTTGATAATTGGGAAAAAATAGTTTTTATTCCAG

ATAGATATTCTGTGTTAACTATAAGTCAAATGTTTACAAGCTGTTAAAAATGAAATACTGATTA

TGTAAAAGAAAACCGGATTGATGCTTTAAATAGACTCATTTTCCTAATGCTAATTTTTAAAATG

ATAGAATCCTACAACTCTTAGCTGTAAACCTTGTGATTTTTCAGCTGTTGTACTAAACAACTTA

AGCACATATACCATCAGACAAGCCCCCCTCCCCCCTTTTAAACCAAAGGAATGTATACTCTGTT

AATACAGTCAGTAAGCATTGACATTCTTTATCATAATATCCTAGAAAATATTTATTAACTATTT

CACTAGTCAGGAGTTGTGGTAAATAGTGCATCTCCATTTTCTACTTCTCATCTTCATACACAGG

TTAATCACTTCAGTGCTTGACTAACTTTTGCCTTGATGATATGTTGAGCTTTGTACTTGAGAGC

TGTACTAATCACTGTGCTTATTGTTTGAATGTTTGGTACAGGAAGCGAGCAGCTGCAAAGCATC

TAATAGAACGCTACTACCACCAGTTAACTGAGGGCTGTGGAAATGAAGCCTGCACGAATGAGTT

TTGTGCTTCCTGTCCAACTTTTCTTCGTATGGATAATAATGCAGCAGCTATTAAAGCCCTCGAG

CTTTATAAGATTAATGCAAAACTCTGTGATCCTCATCCCTCCAAGAAAGGAGCAAGCTCAGCTT

ACCTTGAGAACTCGAAAGGTGCCCCCAACAACTCCTGCTCTGAGATAAAAAATGAACAAGAAAGG

CGCTAGAATTGATTTTAAAGGTAAGATGTTTTATTTTCAATTGAGAATTGTTGCCTGAAAACCA

-continued

TGTGGGAGATTTAAATGTATTAGTTTTTATTTGTTTTTTCTTCTGTGACATAAAGACATTTTGA

TATCGTAGAACCAATTTTTTATTGTGGTAACGGACAGGAATAATAACTACATTTTACAGGTCTA

ATCATTGCTAATTAGAAGCAGATCATATGCCAAAAGTTCATTTGTTAATAGATTGATTTGAACT

TTTTAAAATTCTTAGGAAAAAATGTATTAAGTGGTAGTGAATCTCCAAAACTAGGCCACAACATC

TATTTAAGTTATAGAATAACTGGACTAAGTATCTGGCATGAGTTCTGGAACCTCAGGATGATGT

GATGAAAGAAGCAGAAAGAGGAAACAGTGGGTTTTTTCCATTTTTGAAGGCAAGACAAAATTTT

GTGATAGTTATGTGAGAATTCTACGTTTCCTTCAGATATATGCTTCTCACTCTCCTTCCGGACA

TTTGGTACAGTCATGCTGCCAAGGATCATGACCTACCAATGACAGTCTTCACTCAGGTCTTTTG

TTTTCTAAATGGTCCTACGTCCAAAATTCAGAATTCGATTACCTTGTCGCTAATACTAAAACTC

CAAGTTATTTTCTTCAGTGAAGGTAATTAGTAACAAAGTAATCAAATTTTTGAATGACTACCAG

GGCTTAGCGCCCCTCCACTCTCACCCCTACACACACCCAGAGGCAATTGTATTTTAAGAGAGAA

AGCTTTTTTTTTATGACATACAAGTCAGAGAATTTTAGAGGCATTTGCCTCTAAAACTTTCACT

AACATCATTTGAATCAAGTTTGAAAGAATTAGTGAAGTGGCATTGTGTTATAACCTCTACTCTG

TTTCCACAATAAAATTATTTTCGTCACTTTACACAACTTTGTTGCTTCAGAGTGTATAATTCTG

TTTCATGAATTAGTTCACACACTATGGGAAAATAGGTAAATGTTGTCTGTATATATAGTGTGTC

AGTATAATGTGGAAGCTGCATTGACTTTATTGTACACAGTTCTCCAGTAAGTGTGCACCAGAGA

GTACCAGTAACTGAATGTAGAGTGCTGGCACAGTGGAATGCAGCCAGCTGCGGGGGATGTGGTA

CATGAGGAATGTGCTCATCTGCTCTTTTGGCCACGTGCTCCATCTTAGAGGTGCTTATTGTGTG

GCTTTATCCAGTCTTTATGCCCCCTCCTCTTTTTGCTCAAGTCTGCATTATAGCAGTTGTGACC

TTTCCTTATCCCTGTTTTCTAATATGCTACTGTTACTGTTCCCTGTTCGTTACTGGTTTTTTTG

TTTTTGTTTTTGCATTGTTCTATAGTTACTATTGTATATTGGAAATTAGAGATGCTTTCTGTAC

ACTAGTACTCTTATTTTGATTATTAATTATGTTTGTTAACACTAATTACAAAGTTGCATAAGTA

TTAAGTAGTCTGCACCAAACTGTTTTTGCGTAGGAGGTTTTTAAGTGCAAAATTTAAAAGATTG

AGTATTTTCAGGGACACATTTATCACAAGAAATCTTATAAAAATGTCTTTCTCAGTAGAACACC

TGTATCAATAAACCAAACTTTTTGAATGTTCATATCTAATTACAGTGTTTTTTGACTAATTTTT

ATCTATATACCTGAAAAATTCAGTTTAACATATTAAACACTACAGGCCAGGCACAGTGGCTCAC

GCCTGTAATCCCAGCACTTTGGGAGGCTGAGGCGGGCGAATCACGACGTCAAGAGATCGAGACC

AACCTGGCCAACGTGGTGAAACCCCCTCTCTACTAAAAATACAAAAAAATTAGCCAGTTGTGGT

GGCGTGCATCTGTAGTCCCAGCTACTTGGGAGGCTGAGGTAGGAGAATCGTTTGAACCCGGGAG

GCAGAAGTTGCAGTGAGCCGAAATGGTGCCACTGCATTCCAACCTGGCAACAGAGTGAGACTCC

ATGTCAAAAAACAACAACAAAAAACACTCCTTGGAAAAAGTATAGGTACATTCTATATAGGATT

AGTAGACTGTCAGAATCACTTGAAGATGTTCCGAAAGCATGACATATCAACAAAGGACATGTGA

GTCTAGAATGGTGATCCCTAGGACAGGCCATATTACTGCATGCAAAGCAAGTCTTTGTTAACCT

TATGACTTGCTCAGGAAGCAAAGTGTTTCATGTCCTAATAGGATAGTAGTATTTTCTGTTATGT

TACATTTTAGGAAATTAGGAGTTTTGCATTGTCTTGTAAGAAGGTATTTTAAAAATTTTCAATG

AAAATAATGAGAAATAGGTTTCCAGTGGTTTTATGCTTTTGGGGAAGAGGTTACTGATGTTTAG

CAAAAGATGCTTATATATTCTTAATAGAACAAACCTGAGAATTAGTTCTTAAAGAGTTAAGGCC

CATAAAAGAAACTGTAAGTGTTGGTACTCTTGTAGCTGGGCCACAGATCAGATCCTTAGTATGA

TAAAATTTGGTATTTTTGTGCTTCAATTTTTGGAGACCATTCAATGATCACTTACATTTTATAT

TGTCTTTCATTGTGAAACATATATTATAGCAGAGGTGGGAGTCATTAAAAATTCTACATGTTGT

-continued

ACACTACATGTATAAGGGTATATTTGGCGCAATGGAGGTAGGATTGTCTGTGTGCCTCTAAAAT

TAACCTCTCAAGTAGTTAATCTGATGATGACAAGTATGTCACTTTATTGATAAAAGGGAGAATT

AAGACTATTCTCAGTATTATGTTGGTCAGTACACAAAATATATCATTTGTTTTTACCTGTGAAA

TGAAATATCTTTCATCCTATTAGCCAGAAGGGAGAAAGCCTTGGCCTGAAAATAACACTTATCT

CAAAAAGTTGGGAAATGTGGTCCAACTCTGTGCCCAGGAAAAGAGGAAATAGATTTTGATGACT

ACATAGTCTCTGCACTGCTTGCCAGCTCATAAGTTTACTTCTTTGCACTGTTTGTTTTCATTGC

TCAAAAACTATTTTCTGTCACTCTATGAGATTTAGTCTAACCTGATTCCTGGCTGTGGAAAGCA

GTTTCTACTTAAGAGCCGATGAGAAATGGTATATTCTTCTCAATCACTCACAGAATGACTACCC

TGGAACAAACTAGGAAGACCCAAAATGAACCAGTTTGATTTTAATACATACATAGATGCTGAAG

GAGCCTTTTTTTAAGACCTTGCCTTCTTAGTCTTTGGAGAACAGAGTACTGAAACAAGAAAACT

CACAGATTAGTAGTATTTCTGTGTGTTCTACAGTGAGGTTTTAAGAGCTGTATTATGATTAATC

AGTACATGACATATTGGTTCATATTTATAATTAAAGCTATACATTAATAGATATCTTGATTATA

AAGAAAGTTTAAACTCATGATCTTATTAAGAGTTATACATTGTTGAAAGAATGTAAAAGCATGG

GTGAGGTCATTGGTATAGGTAGGTAGTTCATTGAAAAAAATAGGTAAGCATTAAATTTTGTTTG

CTGAATCTAAGTATTAGATACTTTAAGAGTTGTATATCATAAATGATATTGAGCCTAGAATGTT

TGGCTGTTTTACTTTTAGAACTTTTTGCAACAGAGTAAACATACATATTATGAAAATAAATGTT

CTCTTTTTTCCTCTGATTTTCTAGATGTGACTTACTTAACAGAAGAGAAGGTATATGAAATTCT

TGAATTATGTAGAGAAAGAGAGGATTATTCCCCTTTAATCCGTGTTATTGGAAGAGTTTTTTCT

AGTGCTGAGGCATTGGTACAGAGCTTCCGGAAAGTTAAACAACACACCAAGGAAGAACTGAAAT

CTCTTCAAGCAAAAGATGAAGACAAAGATGAAGATGAAAAGGAAAAAGCTGCATGTTCTGCTGC

TGCTATGGAAGAAGACTCAGAAGCATCTTCCTCAAGGATAGGTGATAGCTCACAGGGAGACAAC

AATTTGCAAAAATTAGGCCCTGATGATGTGTCTGTGGATATTGATGCCATTAGAAGGGTCTACA

CCAGATTGCTCTCTAATGAAAAAATTGAAACTGCCTTTCTCAATGCACTTGTATATTTGTCACC

TAACGTGGAATGTGACTTGACGTATCACAATGTATACTCTCGAGATCCTAATTATCTGAATTTG

TTCATTATCGTAATGGAGAATAGAAATCTCCACAGTCCTGAATATCTGGAAATGGCTTTGCCAT

TATTTTGCAAAGCGATGAGCAAGCTACCCCTTGCAGCCCAAGGAAAACTGATCAGACTGTGGTC

TAAATACAATGCAGACCAGATTCGGAGAATGATGGAGACATTTCAGCAACTTATTACTTATAAA

GTCATAAGCAATGAATTTAACAGTCGAAATCTAGTGAATGATGATGATGCCATTGTTGCTGCTT

CGAAGTGCTTGAAAATGGTTTACTATGCAAATGTAGTGGGAGGGGAAGTGGACACAAATCACAA

TGAAGAAGATGATGAAGAGCCCATCCCTGAGTCCAGCGAGCTGACACTTCAGGAACTTTTGGGA

GAAGAAAGAAGAAACAAGAAAGGTCCTCGAGTGGACCCCCTGGAAACTGAACTTGGTGTTAAAA

CCCTGGATTGTCGAAAACCACTTATCCCTTTTGAAGAGTTTATTAATGAACCACTGAATGAGGT

TCTAGAAATGGATAAAGATTATACTTTTTTCAAAGTAGAAACAGAGAACAAATTCTCTTTTATG

ACATGTCCCTTTATATTGAATGCTGTCACAAAGAATTTGGGATTATATTATGACAATAGAATTC

GCATGTACAGTGAACGAAGAATCACTGTTCTCTACAGCTTAGTTCAAGGACAGCAGTTGAATCC

ATATTTGAGACTCAAAGTTAGACGTGACCATATCATAGATGATGCACTTGTCCGGGTAAGTTGG

GCTGCTAGATTAAAAACCTAATAATGGGGATATCATGATACAGTTCAGTGAATTCATTTTAAAA

GTGACTGAAAAAAATGATACCATATAGCATAGGAACACATGGACATTTCTGATCTTATATAAGT

ATTATACTTTTGTTGTTCCTGTGCAAGTTTATAGATGTGTTCTACAAAGTATCGGTTGTATTAT

ATAATGGTCATGCTATCTTTGAAAAAGAATGGGTTTTCTAAATCTTGAAAACTAAATCCAAAGT

TTCTTTCATTCAGAAGAGAATAGAGTGTTGGACAAAGACCAGAACAAGAGAAATGTGGAGATAC

-continued

CCAATAATAAGTGTGGATGTGCAGTCTTGAACTGGGAGTAATGGTACAGTAAAACCATACCATA

AAATTATAGGTAGTGTCCAAAAAATTCCATCGTGTAAAATTCAGAGTTGCATTATTGTGGACTT

GATGAAGTGACCATGGCAGATCAGTGCCTGTTGCCAGTAAGAGTTGAGTCCTGCTGGGCCACTT

AGAATATCCCTGTGTGGACGGCACTGCCTGGCTGTGGTAGTTTCTTCCCACTTAAAAATTCATA

GAGACAACTCTGGGTCTTGGAACTTCTGGAAAACAGCAGCTATTCCAAAAATCTGGGGATTAGT

GGTGCCTGTAACATCAAGTCCAGGGAGATTGAGCAGGGAAATACTGGAAACTCAGGTACTCATC

CTAACTTCCTGGTTTTCCAGATGGGGTTGCCATTTGTTCCTTTTCTTTCCTCCACAAGATAATT

TTAGTGTATCTGTTTAAGAATATAAGAGTGGCCAGAAGACAGAAAGCAGTCGTCAGTCACATTT

CACCAAAATTTACATTTGTCTCAGGTGCATTATCGCAGAGCTTTATTGTATTTCTAGTATTAGC

TATCCCTGTCATTGCTGCTACTTTTTTATCATCTTCAAGTAAAATTTAATGTCAACAAAAATTA

AGGTAGTTAATAATACTATAGTATACTAGTAAAGTTGTCTGACACAGACAACTAGGAAATGTGA

TTTTTACTTTAAAATGTATTTTAGTTTTAGAATGTCTAAATTTTAGTTTTAGAATTGTCTAAAT

TCGAGAATTCATAAAGCTGTAGCCCGGTGGAAAAAGTTATTTGACATCTCAGAAATTAAAAATT

GCAGAGATTTTGTGTGTTTTTTTTTTTTTTGTTACTGGTTTGTTTTTTTTTTTTAATGTCAGAT

ATGTTTATAGTGTTGGAGAAAGATTCTGCATTATTTAAGCAACTCAGGTGGTTTTCTAGCAGAG

ACAAAAGGGGGCTTTAACTGCCTGAAGTCATTATTATTGCTTGCTTTCTGGTACCCTTTTTATT

TCACTTACATAGTTTTGAGACACATGAATAATTAATACACTTAATGACTGATCATAAGGCAGCC

AGCACCTTACTTTACATAGTTTAGCAGAATGATAGGGTATTTTATAAGAATGTGAGTGATGTTT

TATGAAAGGTATGTTGAGGTCTGTCTATGACTATCCATTGTTGGAGCAGAACTGCAAATGCCAA

AGCTACATACTTTATGTTTGGCTTCTTGAGGTGAGATCCCTTCAGCTGTCTTCATCAAAAGCTA

TGTCTAGCCTTTAAAAGGCAATGAAATTACACTGTAAGAATCATTCCAGGGTTCAAAAAATTGT

CTACCTTCCTTATCTGTCTTTCGCTCAGAAGTCTACTCAGTCTTATTTTCCTCAGTCCCCCATT

TTTTTCTCTAGTAAAGCAAGACTAAAAACAAAAGTTTAAGTACTTGGTATATACTTTATTCTAT

ATTTTAAATTCTATTCTAGAATTTTAAGGAAACAACTGCTTTTAAAGCCTTAGGTGTTAGTGTA

AAATTAACTGTGAGCTCTTTAATTATGGTAACTTGTTTTTAGCAAGTTCTGCTTAATTATATCA

AAATTAGATAATATAGTGTGGCCTATCATAAATCAGGATTCACTAGATAGTATATGTACTTGAA

TATTGCCAGCCCACAAAAGCAGTTCACTTCAGAAATCATGTGTGTTAGGCAGTTTAATAAACTG

TGAAAATAGAAAGAGATGATGCTTACAGAGAAGCTTCCTTAGGGGCTCTGAATGCTCACACTAA

GCAGATTTTACTCTTAACTTTCTTTCTCCCTTGCTTTTTCTTCCTTTTCTTTTTTTTAAAAAAA

TAACAGAATGTGAAAAGACTAGAAAAACCAGCATCGAAATAGGTCTTATAAGTAAAATTGATAA

CCTGTGTAATTTTTTGAAGTAAGTATTCACAGCAGGTGATGATTATGATAAAGCCACATATTTT

AGTAACACATAGTAGAAGTTCTATAATAGAAAGTGGTTTAAGATTATTCTCTCATATGAAAGCT

CAAAAGTGATGAATTTTTCAAGATCTTATTTCCCAAGGATCTCTGCTTTTTAAGCCTCATTCTT

ATATATCACAGTGAACAAACTAGTGGCCACTTTTTTATGACTTGCTAATTTTGGAATTGTATAG

CAGGGTTGGGTGGAAAAGAAGAAATGAGAAACTTTGTGGTAAGCTTAATATTGATAAATAAAAT

TATGGGATCCTAGGCTTTAAGAGCTAAAAGAAACCTTAGAGTTATCCACTCCTTAGTTTAGAAA

TCAAGCCCAGAAAATAGTGACTTCATATATGAGACTCTTGTATGTTTTCTGTTGAGGAGTGGTA

ACTTGAATTAATAATTGTGGATTTTTTTAAAAAAGAAAAATATATTCATTGCTTTTATATATTG

TGAAATTCAAACCAGACTAGCAGCTTTTTTCCTGAGGTTTTTAGAGAAATTGTCTTTGATGACA

AGAGAAGAATTCATGTTGATAGTATTTTCACTAATCTCTGATTGTAGGAAACACTATCATTTTA

-continued

TTACTGCTAAGACAGAAAAATACCAGCAATTCATTGTAAGATGCTATCATTTGTATGGTGTAAT

CTGATTTCAGAGATAATGTGAAAAAAGTGAATTTTAGAATCAATAGAATATAAGTTGTCTCTTC

ACAAATACCTTAGAACTGCTTAAGAACACCCCCACCCTACCCGTTTAACTTACTGCCATAGTTC

CCCTAGGACTTATTTTCAGTATTTTTTCGTTATTGTTCCTTAGAAAACAGTACAGTGATAAACA

TGAGCTTAGACTTCACCTTTCATTTGAATGACATTCCTAATGTGATGAGGTTTTTACAAATATG

TAAAACCATATTTACAAATTTACATTTTTAATATAAATATGTAATTTAATTTAATATGTAAATT

AATTTAATTTAAATATGTAAATATTTACATATTTACAAATATGCAAATATTTACATATTTACAA

ATATGTAAATATTTACATATTTACAAATATGTAAATATTTACATATTTACAAATATGTAAATAT

ACCCATTTGTGTGTTCTTTTACAAGTAGATAATTTCTCATTTTTCTTAGATGAAGCACTTCCAA

TGATAGTATGTATTAAGATTTTTTAAATTACTTCTTAAAGGAGAAGATAGAGGTTATAAGTTTA

TGGAAGAATATAGTATTGCCATCATGAGGTCCCTCAAACTGCCTTCACATCTGAATGGGAAAAT

TGTTTAAAAAAAATAAATAAATAAATAAATAAAATCCAGGGCCCTAACCTCTAGAGGTTTAGAT

TAGAAGCTGTATTGTAGAGCCTATGAATCTGAACTTCTGGTAATACTCCACAAATATTTTGATA

AAGCCAGACTCCAATATTTGGGAAGATGGCCTTTGGTTCAGCTCAGGTGGGGGTGTGTGTGCAT

GTGTGTTTATGTGTGTATGTGTGCATATATAGAGAGAAAGAGAAAGGCCATTTTGATATACAAG

TATGTTTATGTGTTTTGGAAACTCAGATTTTTAAGAGGATCATGGGGACAGCAAGCTTGGAATA

GAGGATGATGATGATGTGAAACTTGGTTCCAATTAGTCAGGGAGTTCTAGCATTTCACATAAAT

ATCTAAAAACCAAAAGGAATGGCTGAGATGTGGAATTGAATAGGGAAGTTCAAAAATAGGAATT

AGCACAGATAAAGGTGATTGGCACAGATAAAAAGCCCCACTACCAGGAGGTTCTGCAAAATCCC

CTCTAAAAGTCACTGGCCCTTTTTATCTGGTTTCTAATAGCCTAGTCTAACCCAGCTTCCAGCA

TTTTCAGCTCCCAGCTTCCAGCATTGGTGAACACTCTTACTAGTGAAACATGAACGTAATTCTT

TTATTTATTCATTGACTCACAGAGCTTTAAAAATGAGATTATTCTGTGCTGCACTAGGTATGTT

TAATTTTGTCTTACACATACACTATATTGTGGTTAACATGTAATTTCCATTGTTCTTTCTTGTG

ATTTATTCTAATTGAAATCAAAAATGAAACCAAGAAATATGCTTGGTTTATGCCCTCAAAGTAA

TTTCTCAGAAACTGAATGAGAGAATGAAGCCTATATATACATAGATCCTCAGCATTATATAATA

ATTTAAGACAATGAAACATCAAACTTAGTATTACATGTGAGGAAAATGAAATCTAAAAGAGATT

CCAGCCTACATAAATTAATGGCAGAATTGGAAATAGAAGTCAGGATTCCAGGTCTCATGGACGA

ACGTGATTATGTGATTTGGTGTTACCCAAACATTTAAACTACATTTGAGATATAACAGACTTTT

CTTCATGTGTTTATCGTGAACATGAAAAAATTAATTTGGATAATCTGGAAATCTCAAGCAATAG

TTTAAGCCTCAAGTTGACTGAAGTAGTTGAAGCTAGCCTTTCTTTCTTTTTCCTCTTTTTTTTT

TTTTTTTTTTAGACGGAGTCTTGCTCTGTCACCCAGGCTGGAGTGCAGTGGCGCAATCTTGGCT

CACTGCAAGCCCCGCCTCCCAGGTTCATGCCATTCTCCTGCCTCAGCCTCCCGAGTAGCTGGGA

CTACAGGCGCCTGCCACCATGCCCAGCTAATTTTTTTGTATTTTTAGTAGAGATGGGGTTCACC

GTGTTAGCCAGGATGGTCTCAATCTCCTGACCTCGTGATCCGCCCGCCTCGGCCTCCCAGAGTG

CCGGGATTACAGGCATGAGCCACCACGCCCGGCCTTGAAGCTAGCCTTTCTTAGAAATCCCAGG

CATTCTTAAGTATTAGAGGTCTCTTTTATCTGATTATTGCTTCTACTTAAATATTCATGGTATT

AAGGAATTTTTTTAAAAAATTATGAATTGATTTGATGTAATAGCTCAGAAAACTATAAGATTTT

AAGTGATAAGGTTTTCCTTTTGATTCCTGTAAGTCTAGTAATATCATATTTTGATATTAAGATG

TCATCCTGCTAGGTATTCTGCAAATGCTTTGATATCAGGTCAGATTTTTTTTTTAAAAAATGAA

CTCCCTAGGATTTCATCATCATGGCCAATTAAAAAGTTCAGAAATTAAAAATCATTTTATCCAG

CAATTGATGAAATCAAGAGTCTTAAAGAAGAGGAAGTTACGCAGTGAAGAGGTAGATATGATTA

-continued

TATCCAGGATATTTTTGTTTATTTTTCCCCAGTAATCTCTGTCTGTTGCTAGTCTCCATGTTAA

ATAAATACAACATACACTGTACTTTTAAATATACCTAAAAATTGGCCTGGCGCGGTGGCTCACA

CCTGTAATCCCAGCACTTTGGGAGGCCAAGGCGGGCAGATCACAAGGTCAGGAGACCGAAACCA

TCCTGGCTAACACAGTGAAACCCCATCTCTACTAAAAAATACAAAAAAAAATAGCCAGGCGCGG

TGGCAGGCGCCTGTAGTCCCAGCTACTCGGGAGGCTGAGGCAGGAGAATGGCATGAACCTGGGA

GGCGGGGCTTGCAGTGCGCCAAGATTGCGCCACTGCACTCCAGCCTGGGCGACAGAGCGAGACT

CCGTCTCAAAAAAAAAAAAAAAACAAACAAAAAAAACCCTAAAAATCCACGTGTGTATTGTAAA

TAAATTCAGGCATGCATGCACGTTCTCCTTTTCAGAATGTTTAGACATAGTCCTCCAAATTTCA

AATATCCTAATGCATTTAAAACAACTTCTGACTTAAAAAATACAGTTTTATGGTGAGGTTTGGG

TTTAAACAACAACATACAATTTTAAATAATATAGCTATTATGTAAAGAATACACCTTTACAGTT

TATTTGTTAAATCTTTTTTAAATTGACCGAACAATTGATGGAGGTTATTTTTAAGAAAAAGAAT

TATCAGTACAGCTGTTTATGCAATAATGGCCTTTATCAAAATGGTTATTGCTAAATTTTATGTG

TTAATAATTTAAAATAAAATAGTTTTAAAGGCTATTTATGTATTCTGTTTTTACTATTTTATTT

ATTTTAATTTTTGAGACAGGGTCTTAACTCTGTCACCCAGGCCTGGAGTACAGTGGCACGATCT

CTACTGACTGCAGCCTTGACCTCCCACCTCAGCCTCCCAAGTAGCTGGGATGACAGGCGCATGC

CACCACCCCCCACTATTTTTTATTTATTTATTTATTTATTTATTTATTTATTTATTAGTTTTTT

GTAGAAACAAGGTTTCATCATGTTGCCCAGGCTGATCTCAAACTGCTGGGCTCAGGCAATCTGC

CTGCATTGGCCTCCCAAAGTGGTGGGATTACAGGTGTGAGCCACGGCGCCCAGCCTTTATTCTT

AAGTGGTACAGTATTTTATGAAATCACTTATGTGTACCAGAATGGTAATCTAAAATAGGTAATA

ACAAAATTTTTGCCTACAGAATTCAGTTACCAACTACTTTTCAAATTATTCTTTTTACATATTT

ATATTTGAACACATTCTGACTCTGAAAAATGTATTTGTTGTAAAAAATGGAAAAATATGGAAAA

GAATAAGGAAAATAAAAATCACTCATAATCCTAAAAAAAAAATTTTTGGTCGTCATTGAAGAGA

GTGAGTAAAGCATAGTAGTTAAGAGCTTGTTTCCTGGATTAGTATCTCTGTTCCACAACTTACT

GTGACTTACTGTGACTTGAAGTTATTTCACCTTTCAGTATCTTGGGGTCCTTATCTGTAAAGTG

GAGTTAATGTTTCCTTCCTCATAAGGGTGTTGTGAAGATTAAATTAGTTGCTATGTGTGAAATG

CTACAAAAGTGCTATATATTATTGTTGCTGTATTCATGGAATATTTTTGTTCTATAATGCTATG

GTAGGTTTTCAGAAAATATTTTAGAACCAATAAAATAACAGCAACAACAGCTAGTACTTTTAAG

CACTAACTTTATGCAGGGAATTAATCTAAGCAGTTCATACATTAATTTATTACTATATTATTAT

GGTTATTTTACAGATGAAATAAGAGAGGTAAAGTTGTATGTTTGCATTTACAATAGAACATATT

GCATTGCATTACATTCTTTTGGCACCAAGGTGGGGAGCATAGAATAGAGATCAGTGGAAGTGGA

CAGACATGTAATATTTTATGGAGAATAAAGATAAATTTGCTTCAGTTATCATTTGACATGTCTT

AGGTAGAGCTAAGACTAGATAGAACACAGGGCCTCTCAATCCTGTAGAAATTCACCACCACATC

CTTTAAAAGGTTTTACATTGATAAGGAGTCAGCTCTCATCTATGAATGTTAGTGGGGAAAAGCT

GTAGAATGCACAGTCTAAATACCAGATAACCTTTTTTTTCCCCACTTTGGAATACATTATATTT

GATAAAAGCAAGTATACCTTTGGATGTAAAGGTAAATATAAACACTGACTTACATCTTTAACAC

CTAGCCAGTTGGGAACTGGCATAAGGAAACTCAGAATGGATTACATGGCAATATGGAATGTTGG

CCTGGTCCCACATTTGAGCTAAGATGTTAATTCTAATTTTAGTCTCCTCAGAATTCTGTATACT

CCGTAGCTTGAAACAGGTTTCCAACTGAAACTATTTTTTTCCCCAAGGTTATTTTCACATCTAC

ATTTGTTTGACTCTAGATCTTGGAACTAGTCTATATCAAGTTCCTTTGGGGACACAAAATTGCA

AATCTGTTGTTCAGAGAGCAAAACTATTTTAAAAGGTAACACTCGTTCTCATATATTCTTAATA

-continued

AGCCTTCACAACTTACAGTATGTTGAGGAAACTGAGGCTTAATTGAATCGCGTGCTAAAGTTTA

AAGGTTAAAAGTTATGGTAAGTGAGAGTTGGGACTAGTAAGGTGAATTCTGACTGACTCTTGGT

CTTTCCATAACAAAACATTGTCTAAAAGTAAACTGTGTGGCCTAAAAATGATTTTGTAAATATT

AGAGATCGGTGTTGAACAACAACAGACATTATTTAAAGCTAAAGACTAAATTCACAGAATAGGA

CCCTAAAGTTGAAGATACCCAGAAGATAATTTCAGCTAGTTTTGTCAAACTCTTTGACTGCAAT

CCCTAGTATTTTACATAGCATCCCAGTACATGCTTATCCATCTGTACATCTAATTGAAACAAAA

GTTTCACAAAACAGTAGGTTCCATTACTATGTGGAATGCATTCTGATTTTCCCATTGCTGATTG

CAAACCACTAAATGGATTAGACTACCCACTAATGAGTTGCAGGTGACAAGTTTGAAAAAACAAT

GCTCTCGGGCAACCTGACCTGATGCGTTAATTTATGAGATTTTATTTTTTGTAGACAGACTAGA

TTGTCCAAATGAGTATTATTACTTTAACTACTATAGTGCTGTGTTACAGTTGTTTCAGTGATTA

TTGCATTTTTCAAAACCATTTTTAAAATTCTGTTTGAAATAGTTGGAATAACCTGAAAACATTT

AATATCCTGTTTTGGTAAATTTTCATCTCCAAGATTAAATTTTTTTAACCAGCCAACAGATGTT

TGAAGGCAAGTTAGGAGATATGATGGATACTGGATACAGTATCCATCCATGTACTAGATACAGT

ATCCATCCATGTACTGGATACAGTCATACTGTTAGCAAATTTTAGATACATAAAGTAAAACAAA

CAAAATGCAGTATAAACAGTTAATATTGGAATCTAGTGTTGATTTTATGATTAATCTCAATGAG

GTTACTGTATATTCATAATTCTATAGGTACACAAAAATATTTGGTAAAAGATTTATAGTTGAGA

AAATGCTAGACACTAAAGTTTGTTAACTTACAATTTAAGAATAAGGGCTGGGTGCAGTTGCTCA

CGCCTGTAATCCCAGCACTTTGAGAGGCTGAGGTGGGCGGATCATGAGGTCAGGAGTTCAAGAC

CATCCTGGCAAACGTAGTGAAACCCCATCTCTACTAAAAATAAAAAATTTAGCCAGGCGTAGTG

GCGCCTGCCTGTAATCCCAGCTACTCAGGAGGCTGAGGCAGGAGAATTGCTTGAACCCAGGAGG

CGGAGGTTGCAGTGAGCTGAGATCGCGCCACTGCACTCCAGCCTAGGCGACAGAGTGAGATTTC

ATGTCAAAAAAAAAAAAAAAAAAGAGTAAGGACATGAGTAAGGTTATGTCTCACCTGTTTTTAAG

GAAATGTGGATATAAGATGGGTTCTAGTCCATTAAAAGGTGGTAATTTATACTAAGTCTTACTG

TGAGAGACCATAAACTGCTTTAGTATTCAGTGTATTTTTCTTAATTGAAATATTTTACTTATGA

CTTAGTAGATACTAAGACTTAACCCTTGAGTTTCTATTCTAATAAAGGACTACTAATGAACAAT

TTTGAGGTTAGACCTCTACTCCATTGTTTTTGCTGAAATGATTTAGCTGCTTTTCCATGTCCTG

TGTAGTCCAGACTTAACACACAAGTAATAAAATCTTAATTAATTGTATGTTAATTTCATAACAA

ATCAGTAAAGTTAGCTTTTTACTATGCTAGTGTCTGTTTTGTGTCTGTCTTTTTGATTATCTTT

AAGACTGAATCTTTGTCTTCACTGGCTTTTTATCAGTTTGCTTTCTGTTTCCATTTACATACAA

AAAGTCAAAAATTTGTATTTGTTTCCTAATCCTACTCCTTGTTTTTATTTTGTTTTTTTCCTGA

TACTAGCAATCATCTTCTTTTCATGTTTATCTTTTCAATCACTAGCTAGAGATGATCGCTATGG

AAAATCCTGCAGACTTGAAGAAGCAGTTGTATGTGGAATTTGAAGGAGAACAAGGAGTTGATGA

GGGAGGTGTTTCCAAAGAATTTTTTCAGCTGGTTGTGGAGGAAATCTTCAATCCAGATATTGGT

AAATACATTAGTAATGTGATTATGGTGTCGTATCATCTTTTGAGTTAGTTATTTGTTTATCTTA

CTTTGTAAATATTTTCAGCTATGAAGAGCAGCAAAAGAAGGATTTGGTATGGATTACCCAGAAT

CACACATCATGACTGAATTTGTAGGTTTTAGGAACTGATTTGTATCACTAATTTATTCAAATTC

TTTTATTTCTTAGAAGGAATATTCTAATGAAGGAAATTATCTCTTTGGTAAACTGAATTGAAAG

CACTTTAGAATGGTATATTGGAACAGTTGGAGGGATTTCTTTGCTTTTTGTTGTCTAAAACCAT

CATCAAACTCACGGTTTTCCTGACCTGTGAACTTCAAAGAACAATGGTTTGAAGAGTATTGAGA

GACTGTCTCACAAGTATGTCATGCTCAAAGTTCAGAAACACTAGCTGATATCACATTAATTAGG

TTTATTTGCTATAAGATTTCTTGGGGCTTAATATAGGTAGTGTTTCCCCCAAACTTTTTGAACT

-continued

CCAGAACTCTTTTTCTGCCCTAACAGAAGAGTTGTTATTGAACACAGTTTGGGAAAGGCTGATG

GGATTTGGAAATTTGAAAGTGAAGGATCAGAATTTTAGTTTTTTCCCTTTTGTGATAAAGTAGA

ACAGGGAAAAGATGCAGTCTTTTGGGTAGTCTACTTAACTTCATAATTCTGAACTGGTTCAGTT

TCTACTGTAAATATAACCACTTAGTAACTGAGCTTGCTTACGTTTAAAATTGAGTACATGACAA

TTACAGGAAAAGGTTTCCACTGAAGGTACCATCAGAATTGTGAGGAGTGTGCATAGAATAATGT

ATGTCATTTCCCTTCAGCTTTGAGATTTGAGCTGTTATAGCCTGTTGATTCTAATTGAGTTGAC

CTTTCTGTTACTGTTCTTAGTCACACACACACACACACACACACACACACACACACACACACAC

ACGCATCCCTTATCTATAATCTAGCTAGTGTTTTATTAATAACTAAAAAGCTATGCCATTTGTA

TGTAGTTTGTTCTAAGTAAATCAGAGATACATAAGACGACGCCCTTTTTGAGATAGAAAATTAT

AAACTTCATAAAGTTCTTAAATTTGGTAAACCTTAGCTCTAGCTTTTGATGTATCTAGAAATGT

TAAACCTTAGCTATAAAGCATACTTGCATTATATGCAGAAATACTTGTAAGAAAAAACATAGAT

TAAGCAGTTCCAGTAAGATAACTGAAGTGATGGCAGTAGAAGTATCAAAAAGGAGTATTTTACC

AGGAGGTTATGGTGCTTTTCTCCCTGGAACATGAGAAAATGTGCCTAAAATGGAACTTCAGAGT

TATATTCTGATTAACTTATAGCTTGTTGCTCTTGGTTCCAAGGAAGGGCATTTGTGACATTTTA

TTAAATTCATTAATTTTTTAGACACACCATTGTCAGCTTGAACAAATTTATTAATTGTAATTAT

TTGTCAGCTGTTCTTGATCCTGTTAATACCATACTTATAACTAAAAGCATTTCCATGGATGTTG

TAACTTGGCCTGTAAAAAAAATGTTTAGATAGAAACCATGAAACTCAAATATGAATTGTTTAAT

TTTCAAACCATTTTGCATTCAGAAAATGTCCTAAGCTTAATTCATACTCCTAGTGATCAAGGAA

ACATGTTAAAGCTCCTTATTTTTAAACTTAAAGTGACAATGACATTTTCAAAGATTTTAAAATT

CTTATAAACAGGTTAAAATACTTATATACTGTATAATTTGATTTCTGATTTCTAAGCTCTACTT

TTCTATTGGAAATTACAGATTTTTTTCAGACTTAATTCTTAAGATGTTTTCATTGTTTCACAGT

AGCAACTAAACATGTAGTAAAATGATTTAAATTCAATTAAAATTTTTTTCCTTAGTCATTTAAA

AGGGAAGAAATCAATTTTTAGTAGTACTCATTCCAAAGATTCCAATTTTCCTTTTTTTTAATCT

TTTATTTTTTGGTGGAGGGAGGCAGGATCTGGCTCTGAGGCCCAGGCTGGAGTGTAGTGGTTCT

GTCTCGGCTCACTGCAACCTCCACCTCCCAGGCTGAAGACTCAAACCATCCCCATGCATCACCC

TCTCAAGTAGCTGAGACTATAGGCACATGCTACCACACCCAGCTTATTTTTTGTGTTTTTGTAG

AGATGGGGTTTCTCCATCTTGCCCAGGCTGGTCTTGAACTCCTGAGCTCAAGTGATCTGCCTGC

CTCAGCCTCCCCAAAGTGCTGGGATTACAGGTGTGAACTACCACACCGGGCCCCAATTTTCCAA

TGAGTGATATAAAAAAGGCCTCCACGCAGGCGCCTGTAGTCCCAACTACTCCGGAGGCTGAGGC

CAGAGAATGGCATGAACCCGGGAGGCGGAGCTTGCACTAAGCTGAGTGCTGCTGCACTCCAGCT

TGGGCGACAGAGCGAGACCGTCTCAAAAAAAAAAAAAAAAAAAAAAAGCCTCCATGATTGGGGCT

TGCATAGTGAAGACCATGTGAAATTGAAAGACTACGAAACTACTTTTCTTTTACGTATTGGCCC

ATAATTAACATGTGTATTGAATAGCTTTGTTTATCTAAGTTCATCAGATTTATCCAGGTTTATG

TATTTCAGATCATCTGATTTTATTAGGAAAATGCTAGAAAAAATTTCATGGCACCATTGTCTAAT

TTTGAAAAAACGAACCTTTCTTTACTGTGATTAAAAATTGTTTTTTAGGCCAGGTGTGGTGGCT

CACGCCTGTAATCCCAGCACTTTGGGAGGCTGAGGCTGGCAGATCACGAGGTCAAGAGGTTGAG

ACCATCCTGGCAAACATGGTGAAACCCCTTCTCTACTAAAAATACAAAAATTAGCTGGCGTGGT

GGTGCACACCTGTAGTCCTAGCTACTCAGGAGGCTGAGGCAGGAGAATTGTTTGAACCTAGGAG

GCAGAGGTTGCAGTGAGCTGAGATCGTGCCACTCCAGCCCACCCTGGGTAACAGAGCGAGACTC

CATCTCAAGGAAAAAAATGAAAAATTGTTTTCAAAAATAGTACGTGTGGTACAGATATAAGTAA

-continued

TTATATTTTTATAAATGAAACACTTTGGAAATGTAGCCATTTTTTGTTTTTTTATGTTTATTTT

TCAGCTATGGGTGGATAAAGCATGAATATAACTTTTCTTATGTGTTAGTAGAAAATTAGAAAGC

TTGAATTTAATTAACGTATTTTTCTACCCGATGCCACCAAATTACTTACTACTTTATTCCTTTG

GCTTCATAAAATTACATATCACCATTCACCCCAATTTATAGCAGATATATGTGGACATTGTTTT

CTCAAGTGCTAATATAATAGAAATCAATGTTGCATGCCTAATTACATATATTTTAAATGTTTTA

TATGCATAATTATTTTAAGTTTATATTTGTATTATTCATCAGTCCTTAATAAAATACAAAAGTA

ATGTATTTTTAAAAATCATTTCTTATAGGTATGTTCACATACGATGAATCTACAAAATTGTTTT

GGTTTAATCCATCTTCTTTTGAAACTGAGGGTCAGTTTACTCTGATTGGCATAGTACTGGGTCT

GGCTATTTACAATAACTGTATACTGGATGTACATTTTCCCATGGTTGTCTACAGGAAGCTAATG

GGGAAAAAAGGAACTTTTCGTGACTTGGGAGACTCTCACCCAGTAAGTTCTTTGTCATTTTTTT

AATTCAGTCTCTTAGATTTTATTTAAATGCAAAAATTTAATTTATGTCAAAATTTTAAAGTTTT

TGTTTAGAATCTTTGTTGATACTCTTATCAATAAGATAAAAATGTTTTAATCTGACCGAAGTAC

CAGAAACACTTAAAAACTCAAAGGGGGACATTTTTATATATTGCTGTCAGCACGAAGCTTTTGT

AAGATTGATTTCATAGAGAAGTGTTTCTAAACATTTTGTTTGTGTTTTAGTGAAATCTTAAGAG

ATAGGTAAAAATCAGAGTAGCCCTGGCTAAGGGTCTTGGTAGTTACAACGAGTGTGCCTGCTCC

TACCACCCCCACCCCCACCTTGAGACACCACAGAATTTCTCATAGAGCACAGTGTGAATTCTAT

TGCTAAATTGGTGGTATGGGGTTTCTCAGCAGAGAATGGGACATCACAGTGACTGACAATCTTT

CTTTTATAGGTTGGAAACTATTTGGGGGACTGGAGGGATACTGTCTACACTTTTTACAATTTTT

ATTGATAAGATTTTTGTTGTCTTCTAAGAAGAGTGATATAAATTATTTGTTGTATTTTGTAGTT

CTATGGTGGCCTCAATTTACCATTTCTGGTTGCTAGGTTCTATATCAGAGTTTAAAAGATTTAT

TGGAGTATGAAGGGAATGTGGAAGATGACATGATGATCACTTTCCAGATATCACAGACAGATCT

TTTTGGTAACCCAATGATGTATGATCTAAAGGAAAATGGTGATAAAATTCCAATTACAAATGAA

AACAGGAAGGTAATAAATGTTTTTATGTCACATTTTGTCTCTTCATTAACACTTTCAAAGCATG

TATGCTTATAATTTTTAAAGAAGTATCTAATATAGTCTGTACAAAAAAAAAACAAGTAACTAAG

TTTATGTAAATGCTAGAGTCCACTTTTCTAAATCTTGGATATAAGTTGGTATGAAAGCACACAG

TTGGGCACTAAAGCCCCTTTTAGAGAAAGAGGACATGAAGCAGGAGATAGTTAATAGCTAAGTG

TGGTTGTAGTATAAAGCAAGAAGCAGGGTGTTTCTTGTATTAAGCTGTAAGCAGGAACCTCATG

ATTAAGGTCTTTATCACAGAACAAATAAAAATTACATTTAATTTACACATGTATATCCTGTTTG

TGATAAAAAATACATTTCTGAAAAGTATACTTTACGTCAGATTTGGGTTTCTATTGACTAAAATG

TGTTCATCGGGAATGGGAATAACCCAGAACATAACAAGCAAAAAATTATGACAAATATATAGTA

TACCTTTAAGAAACATGTTTATATTGATATAATTTTTTGATTAAATATTATACACACTAAGGGT

ACAAAGCACATTTTCCTTTTATGATTTGATACAGTAGTTTATGTGTCAGTCAGTACTTCCACAT

TTTTGCTGAACTGGATACAGTAGGCAGCTTACCAAATATTCTATGGTAGAAAACTTGGGACTTC

CTGGTTTGCTTAAATCAAATATATTGTACTCTCTTAAAACGGTTGGCATTTATAAATAGATGGA

TACATGGTTTAAATGTGTCTGTTTACATACCTAGTTGAGAGAACCTAAAGAATTTTCTGCGTCT

CCAGCATTTATATTCAGTTCTGTTTAATACATTATCGAAATTGACATTTATAAGTATGACAGTT

TTGTGTATATGGCCTTTTCATAGCTTAATATTGGCTGTAACAGAGAATTGTGAAATTGTAAGAA

GTAGTTTTCTTTGTAGGTGTAAAATTGAATTTTTAAGAATATTCTTGACAGTTTTATGTATATG

GCCTTTTCATAGCTTAATATTGGCTATAACAGAGAATTGTGAAATTGTTAAGAAGTAGGTGTAA

AATTGAATTTTTAAGAATATTCTTGAATGTTTTTTTCTTGGAAAAATTAAAAAGCTATGCAGCC

CAATAACTTGTGTTTTGTTTGCATAGCATATTATAAGAAGTTCTTGTGATTAATGTTTTCTACA

-continued

GGAATTTGTCAATCTTTATTCTGACTACATTCTCAATAAATCAGTAGAAAAACAGTTCAAGGCT

TTTCGGAGAGGTTTTCATATGGTGACCAATGAATCTCCCTTAAAGTACTTATTCAGACCAGAAG

AAATTGAATTGCTTATATGTGGAAGCCGGGTAAGAAAGCAGGTGTCTGCAAAAAGTCATGTATC

GATTTATTGTTTGTAATGATACAGTAGTATAGCAGATAACTAAGACATATTTTCTTGAATTTGC

AGAATCTAGATTTCCAAGCACTAGAAGAAACTACAGAATATGACGGTGGCTATACCAGGGACTC

TGTTCTGATTAGGTGAGGTACTTAGTTCTTCAGAGGAAGATTTGATTCACCAAAGGGGTGTGTG

ATTTTGCTTCAGACCTTTATCTCTAGGTACTAATTCCCAAATAAGCAAACTCACAAATTGTCAT

CTATATACTTAGATTTGTATTTGTAATATAATCACCATTTTTCAGAGCTAATCTTGTGATTTAT

TTCATGAATGAAGTGTTGTTATATATAAGTCTCATGTAATCTCCTGCATTTGGCGTATGGATTA

TCTAGTATTCCTCACTGGTTAGAGTATGCTTACTGCTGGTTAGAAGATAATTAAAATAAGGCTA

CCATGTCTGCAATTTTTCCTTTCTTTTGAACTCTGCATTTGTGAACTGTTACATGGCTTCCCAG

GATCAAGCACTTTTTGAGTGAAATGGTAGTCTTTTATTTAATTCTTAAGATAATATGTCCAGAT

ACATACTAGTATTTCCATTTTACACCCTAAAAAACTAAGCCCTGAATTCTCACAGAAAGATGTA

GAGGTTCCCAGTTCTATCTGCTTTTAAGCAAATGCCCTTACTACTCTACTGTCTACTTCTGTGT

ACTACATCATCCAATTCTGAAAGACATAGGCTTCCCCATCCCCTGCTAAGACTGGTTCAAGTGG

CAGCTACTGATGGATTGCAGTGAGAAGGCATGCAAACACGTACCTTCCTGGAAGTTGTCTCCAA

AGGCTATTGCTCTAAGACTCAAGTATATAAACACTAGAATGAATATCAACTCTATCTAGCAATA

AATGTTATTTTTATATTACAGTTGACCCTTGAACAACACAGCTGTGAACTTCATGGGCCCTCTG

ACATGCAGATTTTTTTTCTCAACTAAGAGCAGATTCAGTATTGGTGGGACTCAGAACCTGCATA

TACAGAGGGCTGACTTTCATACATGCCAGTTTCACAGGGCCAACTGCAGAACTTGAGCGTGCAT

GGATTTTGGTATACACACGTGGTCCTGGAACCAATCCCTGTCACATATACCAAGGGATGGCTGT

ATGTTACTTTATATTCATTTGTTCTGTTATTTTATAAGGTTGTTCGTCGTGGTATGTGGGAATT

CACCAGTATTTCTTCTTTCTGGTGCACCGTTGGTCATTTCTGGCAGCAGTGGTGAATGTATTTA

CTCTTAGCAACCTCTGTGCTGCTACCTGTTCTGAGTTTCAAAGGTGATTCATTAAAGGGTTGGG

ATAACATGGTGATAGGAAAAACCCCCCTCATCAGTCACAAGGAGTATAACAGCAATATCTCTGT

AATATGATTGATCATAGATATAATTTCTAGTAGGAAAAAAAGTCATATCTTGATGCATCTCTGA

GAATAGTTGAACATATCTTGTGCTATTCTTTATAGAGAAATTATCTTTGAAATTAAAGTCTTAA

TTTTACTTCTAGCTTTTTATAACAACATAATCCCTACTTGGTATGTATCTTAAGATCATTTTTA

AATGTATGATTTGAAGGGCAAACTAGTGTTATGTGAAAAATGACAGATAAAGTAGCTTCCAACT

CATCCTCAAGAGTTGATGATATTCTAAACCTTTTCTAACTAAATTCAGCTTCTTAATTTTCTCA

ATATAAATATGATGAAAATATTAATTCATTAAATAGTCTACAAGTATTCGGTAGTTGAAGACTT

AAAGTAGTGCTTGTAATAACAGAAGAGAAAAAAGACATTACAGGCGTATCTCACTTTATTGCAC

TTTGCAGATACTGAGTTTTTTTGGTGGCAACCCTGCATCAAGCAGGTCTACCAGCACCATTTTT

CCAACAAAATGTGCTCACTTCATTAGCATTTTTAGCAATGATTTTAAATTAAGATAATGTACTT

ATTTTTAGACAATGCTGTTACACACTTGACTACAGTATAATGTAAACGTAACTTTTATAAGCAC

TGGGAAACAAAAAAATTTGTGTGACTCACTTTACTGCCATAATCACTTTATTTGCCATGGTCTG

AAACTGAACCGGCAGTATCTCTGGGGTATGCCTGTATAGATATTTTGGTTGGTATTTATTTATT

GTATGCAGAATTCATAAAAATAAAAACTGCGAGGCTGTTTAATACATTTCAACTAAAAGTTGCC

AGCATCATTAATATGTAAACCACTAGAAATAAGATTTTGTTAATTTTTTGTTTGTTTGTTTAAA

CAGTCTTGCTCTGTCACTGAGGCTGGAGTGCAGTGGCGCAGTCTCAGTTCACTGCAACCTCCGC

-continued

TTCCTGGGTTCAAGTGATTCTCCTGCCTCAGCCTCCTGAGTAGCTGGGGTTACAGGTGCACACC

ACTACACCTGGCTAATGTTTGTATTTTTAGTAGAGATAAGGGTTTTGCCATGTTGGCCAGGCTG

GTCTCAAACTCCTGACCTCTGGTGATCCGCCCGCCTCGGCCTCCCAAAGTGCTGGGATTACAGG

CGTGAGCCACCATACCTAGCAAAATCAACTCTGAATCTGAATCAAACCTTTGAAACAAAAATTA

CCAATCAAAAAAACGTGCAATCCCTGCTCCTAACTTTGAAAAAGTGACAAGGAAGGACATTTGG

AAAGATGTCTCTAAGCAGTCAACAAGAAATGAAATCAGGGAGAGCTTTTTCAGCACCTGAAAAA

ATACATGCAAAAACGCCCGAGGCGGGCAGATCACCGGAAGCCAGGAGTTTGAGACCAGCCTGGC

AAACATGGGGGAAACCCCGTCTCTACTAAAAATACAAAAATTAGCTGGGTTTGGTGGCAGGCAG

CTGTAATCCCAGCTCCTCGGGAGGCTGAGGCAGGAGAATCGCTTGAACCTGGGAGGCGGAGGTT

GCAGTGAGCCTAGATCGTGCCACTGCACTCCAGCCTGGGCAACAGAGTGAGATTCCATCTCAAA

AAAACGAAAAACAGATTCAGAGTTTATTTCCTTCCCAAATACTTCATAGATGTTGGTTTGTAGG

AATAACTTAAAAGTCTCACTCGCTTTCTGTCTTTTCTAGTAATTTTTATCGTGGATTCTGATTG

CCTAGATCTGCTAATTCATTGAGGGTTACAAAATTGTGATACTCGAATTCTTTATTCCTCCTTC

CTTTATTACCTGTAATACTTCTTAAGAAAAACTCTTTCTCATCAACTCTATGACTACCCTAAAT

TACAGATCCACATATAGGATCTGTATACATGTATATAAATATGTACATATCATATACGATAATG

CTTAATTCTTTCCCATTACTTACTAATTTTCAAAATAATGTGATTCCCTAACTGCTCTCTGAAT

GTTATCAATGTGGTGGTAATAATGGTGGTGTCGATGTTGTGTGGGGTAAAATTTGAATACAGTG

AAATACCCAGGGCTTAATTGGGTTAGTTTTTAAAAATTACATTTATGTAACCATATTTCAGTCA

AGGTGTAGACTATGTCCATCAGCACAGAGTTCCCATGTTTTCCCTTCCAGTGAATCTCCATCCC

CCATTAGAACAGACAATAACTGTCCTAATTACTGTCACTGTAGCTTACTTTTGTCTGCTCTAGA

ATTTCTTATGAATGGAATCTTATGTACTTGTACTGCATGAAGACTCTTTAGATTCATCCATGTT

ATTGCATTGATTTATAGTGCCTTTTAAAAAATTATAGAGTAGTGTTGCATTATATGAATACGCA

AAGTGTTTTTTTTTTACCTGTTGGTGGACAGTTGGATTGTTTCCAGTTTGGGACTATTGTGAAT

AAAGCTGTGTAGTCTTATTGTGGAAATGTTTTATTTCTCCTGGGCAAACATGTAGGAGTGGAGT

TTCCAAAGCATATAGCAGGTGCATATTTAACTAAAAGTGTCTTTTCCTCATTTTTAATATTGGA

TTTTTGTATTTCTATTGACTATAGATATTTTCTTAAAATATAGCAGTATGTCTTATCCTTAGTT

TTGCTTTTTTTTGGTTTCAGTTATCTTTGGTCAGCAGTGGTCCAAAAATATTTATTAAGTAGAA

AATTCCATGAATAATTCAGGGTTTTTGATGTATGTGTGTGTTGGCGGGTGCAGGGCAGGGAGAG

TTGGTTGGTTGGTTCGTTGGTTTTTTTTTTTTTTAAAGAGACAAAGTCTCTGTCATCCAGGCTGG

AGTGCAGTAGCATGACTACAGATTGTTATAAACTGAAACTCCTGGGCTCATGCAATCTTCTTAC

CTCAGTCCTCTGAGTATCTGGGCTCATGCAATCTTCTTACGTCAGCCCTCTGAGTAGCTGGTAC

TACAGGTGTGCAGCTAATTTTTAGTTGGTTATTTTTTTGTAGAAACAGGGTCTCACTATGTTGC

CCAGGCTGGTTTCAAACCCCTGGACTCTAGCAATTCTTCCACTTCAGCCTTCCAAAGTGCTGGG

ATTACAGGCGTGAGCCACTGCACCCAGCCAACAACTCTTAAGTTTTAAATTACATGCTATTCTG

AGTAACATGGTGAAATCTCCCACCTTTCCACCCAGGGCATGAATTATCCCTTTTTCCAGTATAT

CGTTGTTGTCTAGACTACCCACCACTTTTAGTCTACTGGTTATCAGATCGACTGTTGCAGTATC

ACATGCTTGTGTTCAAGTAACCCTTATTTTACTTAATAATGGCCCTAAAGCACAAGAGCAGTGA

TGTTGGAAATTCGAATATATATGCCAAAGAGAAGCTGGAAAGTGCTTCCTTTAAGGAAAGAATT

TAAAAATCATATGTTGAGGTTGCTAAAATCTATGGTAAAAATGAGTATTGTATCTATGAAATTG

TGAAGAAGGAAAAATAAATCATGCATAGTATATACAGGGTTCAGTACTATTTGCAATTTCAGAC

ATCACTGGAGGTCTTGGAACGTATTCCCCATGGGTAAGTGGGGAATACTGTATATTCTATATAA

-continued

AAGGCCCATTTCTGATAAGTAGTTTATGATTATTTTCTCCAAGTTTTCATTTTCTTAAGTGTCT

TCTGGTGAGCAGAAATTATTCATTTTTTGAGGTCTAATTTATTTTTTCTTTTATGGTTTTTTAT

GTCCTTTTATATCTTTGCCTAGCCCAAAGCCACAAATATCTTATGTTTTCTTCTAATTGTGTAA

TATAGGTTTAACTTTTATGTGTAAATCTGTGATCCACCACCAATAAAATTTTGTGATGCTGTTA

GACAGTGGATGTCATTCATTTTCTAAATAGTTTTATTTATTTGTTCCAGTACCATTTGTTAAAG

AGACTTTTCTTTCCCCATTGAATTGCCTTTGCACCTTTGTTGAAAATCAATCTGTGTGTGAGCC

GTGTTTCTGGATTCTCCATTCTGTTCTATTAATTTGTTTTGTCCTTTTGCCAAAATGACACTGT

TATGGTTACTGCAGCTTCAAATCAGATGCTGTGAGTCCCACAACTTTTTCATTAGGTTGCTTTG

ACTTTTATTTGCATATAAATATTAGAATCAGTTAATTTTTACAAACAAAAGGGCAAAGCCTGCA

GAGATTTTGATTTGGGTTGCCTTGACTGGGGCAGGTCAATTTGGAGAGAATTCACATTTTAACA

ATATATTCTTCCAATCCTTGAACACCGTACGTCTCTCCATTTATTTAGATGTTTGTTAGTTTAT

CTCAGCACTGTTTTATAGTTTTTAATGTTGAAATCATGTACTCTTTGGTTAGGAATAAACTTAA

AATATGTTTCTAATGCTATTAGTGGTATTTTTTAAATACTGCTTTTCACTTGTTTATTACTATC

TTGAAATAAAATCGATTTTTATATATTGATCTTATATCCTATAACCTTTCTAAATTGACTTATT

CTAGTAGTTATTTAGTAGATTTCATAGGGTTTTCTAGTAAACAGCTATGTCATCTACAAATCAA

GACAGGTTTCTTTCTTTCCAATGTTTATGTTATTTATTACTGTTCCTCTATTGCACTGGCTAGA

ACCTTTGGTAGAAGGTATTCTTACTTTATTCCTCATTTTATTGAGAGAGACTATAATATTTACC

ATTAACTGTGATGTTACTTGTAAACAAAAAGTTTGTATTTCTCTGGGATTAAAAACCAAGAGTC

CATTTGGTTTTTTACTGTTGAGTTTTAAGGGTTCCTTATGTATTTTCTAGGTATGTTCTTCCTT

CATTGAATTGTTTTTTTCACATACGTTAAAAATCACTTGAGAATATTTATATAGGTCTGCTTCT

GAGATTTATCTGTTTATCAGGTTTTGTTTCATTTATTTTGAGGCTCTATCATTTGGTTCATACC

CATTTAGAATTACTATGTCTTGGTGATTGGTCCTTTATCATTATATAAGTTTTTTCTGTTTTGC

GATTTTCTTTGCTCTGAATCTGATATGAGTGTAACCATTTGTTTTTTTTTAAATTAATGTTTGC

ATGATCTGTCTTTTACTATCATTTTACTTTCATCCTGTGTTGCTGAATTTGAAACGAATCTCTT

GTAAACAGCATATAGTTGTCATTTTAATAAAAACTGTTAGTCTCTGCCTTTTAATTTTTTTATT

TAGACCATTTATATTTAAGGTAATTATTGATATGTTAGGGAGAGGTCTGCCATTTTATTATTTG

TTTTCTGTTTCTGTCTTCTGTTTATGGTTATTTATTTATTGCCTTCCATGATTACTTGAACATT

TTTTAAGATTTTTAAGACCCTTGATTTATTTAGTGTTTGGGTTTTGTTTTGTTTGTTTGTTTGT

TTTTGTTTCGAGACACAGTCTCGCTCTGTTGCCCAGGCTGGAGTGCAGTGGCACAATCTCAGCT

CACTGCAACATCGGCTTCCCAGGTTCAAGCAATCCTCCCGCCTCAGCCTCCTGGGTAGCTGGGA

CTACAGGCACATGCCACCACACCTGGCTAATTTTTGTATTTTTATTAGAGATGAGGTTTCACCA

TATTGGCCAGGCTGGTCTCGAACTCTTGACCTTGTGATCTGTCCACCTCAGCCTCCCAAAGTGC

TGGAATTACAGGCATGAGCCACCATGCCTGGCCTTCTATGTGTTTTTTATAGTTGTTTTCACGG

TCATTGTGGGTATCACATTATAGATAATGTGACTTACCACCATTCACTGCCATCAATACCATTA

CATGGAATGAGATATGGAAACCTTAATTTCAGTTGGGTCTCTTTCCCCACTTTTAAATAGTATT

GTTTTGAGGATTAATGCTATTACAGTTTTTGTATCAGTTATCCAATATGACTTATAGAACTTAT

CAAGGGAGTGATGCTCTGTTGTATGTACCCATGTTTCTGCTATTTCCATTATTTTTTCCAAGAT

TCCATCTTTTATTACTTCCATTAGCCAGTCTTCAAAGGCAGTTCTGCTAGTGAGAAATTCTTTT

TGTTTTTCTCTTTCTGAAGATGACTTTATTTTCCCTTTATTCCCAAAGAATAGTTTTATTTGTG

CTATTTGGGGTTCGCTCAGCTTCTTGAAGCTGTAAGTTTGTGTCTTTTGCCAAACATGGAAAAT

-continued

TTTCAACCATTATTTCTTCAGGTGTTCTTTCAGCGTCACTCTTTTCTCCATTCTAGGCCTCTAA

TGATACAAATGTTGAGTCATTTGTTACTGTTCCACATGGACCTGAGGCATGGTTCATTTTTCAG

TCTATTTTCTCTCTTTTGTTCAGATTTCTCTCCTTTGTCATCTTCACTCTACTGTTGAGCCCAT

CTAATGATTATTTTTCTCCTATTGTATTTTTTAGGTCTATAATTTCCATTTGCTTTTTTTTCCT

TGTATCTTGTTTCCTTGCTGAGATTTTCTATTGTTTCGTTTTTGAAACAGTAGAACTTGTAATT

GCTTGTCAAATCATTTCTCTGATGGCAGCATTAAGATCCTTGCCAGATAATTTCAGCATCTTAC

TCATCCCAGTGTTGGCGTTTTCTTTCCTTCATGTAATTTTCCTGGTTCTTGGTATGACAGATAA

TTTTTGGATTGTGTCTCGGACATTTTAGTTATTATATCAGGAGACTCTGTACTTTTTAAAAATT

TTAACTTCAGTAGTAACCTGTTAAGGTATAGCATGTAGGTACTAGCATATATTTGTGAGCTGTG

GTTCCAGTGACCATTTTTCAGAGGCTTTATGGTGCTGTTTTGGTTTGTTGCTTTTATCTCAGTC

CACTGGGGCTCGCACTGGTTCCTAGTAGTGCTGCTTGAGGGGCCTTCTCCAGGCTGAGCTGCGC

AGAGTGTGTTTGGGTGAGGGAAGAGGACCCCCACTAGATTTTCGTGGGCTGGAGAGTGCTTCCT

GAGCCTTGTGCCTGTTGTGGCAGGCTCCCCCTTGCTGGTGTTCCTGGCAGTGCTCCTGACCACA

TTGTGTCCCTGGGCTGTGGAACACTTGCAGGAAAGGTGAACACTGCCAGGACCAATTATAGCAG

AATTCCTCCTGCCAGTACACAGCAGCACTGTGGCTCTGGACCAGCAAGGAGAGTCTCAAGCATG

GGTTTGTTTCTTTTTGATTTTAAGATTTTTCTTCTGCCTTCAGGTTCTGGTATTATTGTTCTGT

TTTATTCACCTTTATGTTTCTTCTAGTTTAGTTTTAGTTTCTTTGTATTTGATGGGATTTTTTT

CCTTGCATTTCTAATTACTCCTTAGTTGTGTCATGTCTTCCTTTTTTTCAGTTACCCTCATTCA

GAAATTTCCCATTTCTAATGATTTGTTATTTTTTAAATTCTTTTTAGCTCAGTTTGAAATTTGT

TTACAGTTTTCATGTTTTATTTGCATATTGTTTCATGTACTTTGATTTTCTGTAGGGACACCAT

TCTCATGTATATGCACATACTTTTTCTCTAATAATTACACTGTTTCACTCTGTTCTGTTATTTA

TTTATTTGTGTGTGTGTGTGTGTGTGTGTGAGTGAAATGAGTTTCTCATACTTGGACGAGGGAG

AGATGGGCCAGGATAACTTTTTTCGCTTTTTAGGGACGAGGAGAAGTCTGTGTTTTTGTAAAAT

GGTCAAAAATATGCCCTTGTGCTTTCTGAAACTGCCTTCTTTACTCCTCTATCCCACACATATA

TTTGAACTTTTTTTTGGTTTTTATTACTGACCTGGTCCATTCGGAAGTTATTCCCAGAAGTTTT

TCCTCGGTACAAGGTTTGTTTCTGGTGGGGGTTTGGTATTCGGGTGTTTTAAGGGCCCAGAGCT

TACTACATCATGATCCCTTTGTAATCATCTGCAAATTAGATCCTGTAGAACTTTTTAAAACTTT

AAGCCCTGTTTTCAGATTGGCCTGTGCTTTCCAGTGGGTTGGCAGTGTTCTCAGGGCTGTCAGA

AACCCAGTCAGTTACCTTGCATCTGCTTCCTTACTAACCAGTCTTGTAGTTGTCAGAGCTTTGT

TTCTGTCCAATTATATGCAATGGTTCATGGTTTTGTTGTAGATAATGTCTCTGGGTCTTTGGTT

TTCTCATTCAGTTTGCTGTTTTTGTAGGGGAGGTTGGGAGGGAATAAAACAAAAAATAATAATA

ATAATAACTATGTCGTTGCCATCATCATCTTTCCAGAACCTGCTACCTGCCCTTCACCTGATTT

TCGTATTTATCAGTATCATTACCTTAATCTGTTATCTCATTGGGGATTGCAAAATGGCTGTTTG

GGGAAAAAAAAATTTCCATCTGCTTGTCCTACATATATACCTGGCATTCTTTTTTCTCATCATTG

GGTGCCATTTGATTACCTTGAAAAACAGTTCTACAGAAAAGGCATGATAAAATAGATTTAAGGT

TTTTAGAGTAAGGAGTTAATGTAATAATTTTAATAGTGACAATTTAATTTTGTTTTTTGGTTGG

TTTTTGCTGCCTTTTTGAATATTACGAACTAATGAATGTTTTTGTATTTAATACGTTTCACAGT

CATTACTCTAAATGATATTCAAATTGCTTAGCTATCGTGTGCTTTTAAAATGACCCTATTAGAT

TTTGAGATTTCTAACTAATCTCGAACATTCATTCTCAGGCCTGGAATAAGTTATTTTTCCAATA

AATTGTTGGAGAATGGCATTTAGAAGTCAGATTTTAGATGCAAAGTATGGCCTTTGCTTTTGAA

CGTTACTGCTTGTAGGCCTTATCAGAGGACAGAACTAGGAAAATAATCTTCCTAGTGTATCCTG

-continued

AGAATCATCCCACATTATTGCAGAGGTGTTTTCCATTTTGTTTTGTATGACTGAATACTGCTCC

TTTGTGTGGATGCAGCATAGCTTATCAATATTTATGGGCATCGAGGTTATTTTTAACCTTTTGC

TGTTAGTACTAATGTCACAGTGAATCCTCTTAATGTTCATGCATTATTCCGTACATATGTAAAG

TATCATTAAGATAAATTGTTAGAAGTGGGATTGTTGCATCAAATGGTAGATGCATGTGTAATTT

TGCTAGATACTGCCAAATCCTCCTTCACAGAAAAATAACATTTTGCATTCCCACCAGCAGTTTA

CAACAGTATCTCTTTTCTTAAAACTTTCCAAACAGAATGTGTTGTTAAATGTGGATGTTTACTT

ATTTGCCAATTGAGAAATGGTATTTTACTATAGTTACAATTTTTGAGCTTACCTCAATTATGAA

TGATAATGGACATTTTTTCTTGTAGAGCTGTTTATAGTTTTATATAGTCTTTTGCTCATTTTGC

TGCTCAGCTGGTCGTTTTCTTCACTTTTAGAAACTTTATATGTTAAGGAGATTAGTCCTTTAAC

GCTGGTAAATTCGCAAATATTTTTTCCCAGTTTGTCATTTGTCTTTTAACCTTGCTTATAGGAT

TTTTTTGCCAAATGAAAGGTTTTATGTTTATGTAGTTAGCTATTAATCTTTTTCGTTATTATGC

TTTGATATGCATTTCTTTAGTTATGTTTATTTTATTCATTTTCTTTGTTTTTTAATTTTCTAGA

GTCTGTCCTCAGTAGAAATTTTAGTCATACTGCTTCTTCTTTGGTCACCTTATAATAAAATTAG

CCTTTATTTCCAAAGTTACCTTGCATATTTCTTCAGTATTTTTTAGTATTCTTATTTTTATTTA

AGATGTGCTCATTTCTTTCTGAATTTGTATTTCTCATCACTGGTGGTCTGTCTTGTCTGCTGCT

GCATTCTCCTTTTGTGTTGGAATGTGGTGTTACTAGTTTCCCATTGTTTATGACTGAATTTTTC

TGGTCTACTTTTGTCTACCGGAAAGTTTTGCTTCTCATTCGCCAGACTCTTCCCATAATAACTT

TATTTAGACTTCCGAATTCTGTTTTTCTTGTTTATGTTTCTATAACAGATGTTACTTTTTTCTG

GACCTGTTATTACTAGACCTCATGGTGGAGCAGGGAGGAATTGTGTGGCTTTAGGGGTCTTGGT

TGAAGGGATCCCTCTTCTGTTGCTTTAGTAAGGGCAGAATCACCACTTTCTGATTTTTCAGCTC

CATGTAGCTTAATGAAGACTCTTTTTCATTAGCTGCTTCCACCCCTTTACAGCCGCTTAAGGGA

CACTTCTGCTTTTGAAGGTACCCCCCTTCCTTTCATGCATGGTGCCTTCCTGAGCCTGCCATTG

CTGGACCCAAGTACTTTTCTGTAGTCCTTCCTTTAACCACCCTGTTGCCAGTGCTCTAACCTAC

ACTCAGTAGTGCTCTGTTGAGGGGCAGGTGGTGGAGGGGGGTGGGGTCTGGCCTTGGGTGATCCC

TAATCAGTATGATTCCGCACAAGCCACTCTTCGATGTAGCTCCTGCTGGACCCTGCTCATTTCC

CCACTTCTTTGGTATTTGGAGTTTATTGTTCTGTCTCCTAGTTTTACTCTAGACCTAAGTCATA

GGTTTTTTTTTTATTTTCCCCTTTTTGATCCGGGTAGATTTTTAGAGATGTGAGTAGGATGTGA

TCGATACAGCCACCACTTTTATGTGGAAACCTGGAAGCTTCTTCGTGTTTTCTTCAGCTTTCTA

AATATATGCATTCTTGTTTAATTCAAAATGTTAATGTAACACACATAACACTTATAGGAATAGA

GATGCATTTTGTTCCCTGTTTTCATTGTATAAAATTTTTAAAGGTTTCGTTTAAAAGTCCAAAG

AAACAGCTCCGTAATAATATAGCCAGACTGGTCATTGTGACCACTGCTGATCTGCCACTTCCTG

CAGGGTCTGTCTCTGTTCTTCGGTGGTGCTCTTTGGTCTACCTCCTTAGGTGTAGCTGGTTCAG

TTAAGCTTCAGAGCCCTCCTGCAGTGTGAGGAGGCTTTATTACCACCCACTGCAGGGCAGCTTT

TCTGCTATGTTGGAGGGTTCTGTGCTACAGCAGACTTGTTTTCTCTTGTCAGCCTCCCCAAAAG

GAGTATCATGAACTGGGGTCCGATTCCTCTCCTCCTTACCTGAGAGATGCTCCTGCAAGTTTCA

TGTCCAGTTTTCTGTTGTTGTGTGTTTCTTTTTTGTTTTCTCTTGCTGACTGGTGGATTTGTAA

AGGGGCAGGGAAGGGAAGTGGCAAGAGATTGGAGAAAGCCAAGAATTCTAATAAAACTTTTAAG

TTATTTCAGATAAATGGTGTTGCAGCACCAAAAATGCCAGCATTTTGGTAATAAAAATAGTATG

TTGGGATATTAGAATATCAAAAGGTAGAAAATTGTAATTACTGGTTTGGGATGTGTGATGTTCT

CTGCTAACATTCTGGAATTTTTTTTTTTTTTTTTTTTGAGATGAAATTTTTTTTTTTTTTTGAG

-continued

ATGGCTCAAAATGTTTCCCAGGCTAGAGTGCAATGGTGTGATCTCAGCTCATTGCAGCCTCCGC

CTCCCATGTTCAAGCAATTCTTCTGCCTTGGCCTCCCAAGTAGCTGAGATTACAGGCATCTGCC

ACCACGCCCGGCTAATTTTTGTATTTTAGTAGAGACAGGGTTTCACCACGTTGGTCAGGCTGAT

CTTGAACCCCTGACCTCAGGTGATCCACTGGCCTCAGCCTCCCAAAGTGCTGGGATTACAGGCA

TGAGCCACCACACCTGGCTCTGGAAAGAACTTTCTAAATAACTATTAAAATGCATTTTATATTA

TATAAGCAACTAAAAATACTTTTAATTTTTTTTTTAATTTTTTAATCTTAACATTATTTAGCTA

TAGGCCAGGCGCGGTGGCTCATGCCTGCAATCCCAGCACTTTGGGAGGCCAAGGTGGGCGGATC

ACGAGGTCAGGAGATCGAGACCCATCCTGGCTAACATGGTGAAATCCTGCCTCTACTTAAACGT

ACAGAAAATTAGCCAGGCGTGGTGGCAGGCACCTATAGTCCCAGCCACTTGGGAGGCTGAGGCA

GGACAATGGCGCGAACCCAGGAGGCGGAGCTTGCAATGAGCCGAGATCGCGCCACTGCACTCCA

GCCTGAGCGACAGAGCAAGACTCTGTCTCAAAAAAAAAAAAAATTTATTTAGCTATGAACTAGTG

TATATATGTTTTATAGATGCCTGATTATTCAAATAAACTTCAAGATTGCACTTTATGAGCTTGT

ATTTCGTTTTTTAGAACTCAAACTAACATAAGTGTCATTAAAACATAGCTTTTATTACATAGAT

TTTAGGAATGCCACAGGATAAATCATTCTCTTAAAATAACTGCAGGTGGCAGAAATGTCAGAAT

AATTCTCCTCCTCCATACACAGCACATATTACTTGTTTAAAGTATTCTAGTTCATATAAAAATT

GAACTTTTGTATTACTGCTATTAGGTATGTAGTTGTTTGCATTTGGGGCCAGTTGGTTGGGGCA

GGGGGTCTTTTTTTCTTTTGTCCTTAATCTGTATCACTTTTTCCTCCCAAAGTTGAGTTAAAGG

ATGAGTAGACCAGGAGAATAAAGGAGAAAGGATAAATAAAATATATACCCAAAGGCACCTGGAG

TTAATTTTTCCAAATATTCATTTCAGTCTTTTTCAATTCATAGGATTTTGTCTTTTGCTCATTA

CTGACTGCATAATGTGATTATACCATAGTTTAAATAGTCACTTCCTGTTACTACACACTTGGGT

TTTCTCAATTTTTTACTATTGTAGTACTAATATTTTACTATATTGTAATCTAATCTAAATTTTT

ACGTATTCAGAGCTGTTCAGGATAAATTTGCTTGGAAATTTTTAAATCACCAGAAGTGATACTA

TCCTGATAATTAACTTCCAAGTTGTCTCTTAATATAGTTTTAATGCAAATCATAAGCTTATGTT

AGTACCAGTCATAATGAATGCCAAACTGAAACCAGTATTGTATTTTTTCTCATTAGGGAGTTCT

GGGAAATCGTTCATTCATTTACAGATGAACAGAAAAGACTCTTCTTGCAGTTTACAACGGGCAC

AGACAGAGCACCTGTGGGAGGACTAGGAAAATTAAAGATGATTATAGCCAAAAATGGCCCAGAC

ACAGAAAGGTAGGTAATTATTAACTTGTGACTGTATACCTACCGAAAACCTTGCATTCCTCGTC

ACATACATATGAACTGTCTTTATAGTTTCTGAGCACATTCGTGATTTTATATACAAATCCCCAA

ATCATATTAGACAATTGAGAAAATACTTTGCTGTCATTGTGTGAGGAAACTTTTAAGAAATTGC

CCTAGTTAAAAATTATTATGGGGCTCACATTGGTTTGGAATCAAATTAGTGTGATTCATTTACT

TTTTTGATTCCCAGCTTGTTAATTGAAAGCCATATAACATGATCATCTATTTAGAATGGTTACA

TTGAGGCTCGGAAGATTATCATTTGATTGTGCTAGAATCCTGTTATCAAATCATTTTCTTAGTC

ATATTGCCAGCAGTGTTTCTAATAAGCATTTAAGAGCACACACTTTGCAGTCTTGTAAAACAGG

TTTGAGTATTTTCTCCACCTTAGAGGAAGTTACTTGACTTCTCAGTGACCTAACCTCTAAAGTG

CATTTACTGATGTCCTCTCTGTGGTTTTGTTGTGGAAAGATTTAGTTAAATGAACTGTAAGAAT

TCAGTACCTAAAATGGTATCTGTTATGTAGTAAAAACTCAATGGATACAGTATCTTATCATCGT

CACTAGCTTTGAGTAATTTATAGGATAAAGGCAACTTGGTAGTTACACAACAAAAAGTTTATGA

TTTGCATTAATGTATAGTTTGCATTGCAGACCGTCTCAACTATATACAATCTAAAAATAGGAGC

ATTTAATTCTAAGTGTATTTCCCATGACTTACAGTTTTCCTGTTTTTTTCCCCTTTTCTCTATT

TAGGTTACCTACATCTCATACTTGCTTTAATGTGCTTTTACTTCCGGAATACTCAAGCAAAGAA

AAACTTAAAGAGAGATTGTTGAAGGCCATCACGTATGCCAAAGGATTTGGCATGCTGTAAAACA

-continued

AAACAAAACAAAATAAAACAAAAAAAAGGAAGGAAAAAAAAAGAAAAAATTTAAAAAATTTTAA
AAATATAACGAGGGATAAATTTTTGGTGGTGATAGTGTCCCAGTACAAAAAGGCTGTAAGATAG
TCAACCACAGTAGTCACCTATGTCTGTGCCTCCCTTCTTTATTGGGGACATGTGGGCTGGAACA
GCAGATTTCAGCTACATATATGAACAAATCCTTTATTATTATTATAATTATTTTTTTGCGTGAA
AGTGTTACATATTCTTTCACTTGTATGTACAGAGAGGTTTTTCTGAATATTTATTTTAAGGGTT
AAATCACTTTTGCTTGTGTTTATTACTGCTTGAGGTTGAGCCTTTTGAGTATTTAAAAAATATA
TACCAACAGAACTACTCTCCCAAGGAAAATATTGCCACCATTTGTAGACCACGTAACCTTCAAG
TATGTGCTACTTTTTTGTCCCTGTATCTAACTCAAATCAGGAACTGTATTTTTTTTAATGATTT
GCTTTTGAAACTTGAAGTCTTGAAAACAGTGTGATGCAATTACTGCTGTTCTAGCCCCCAAAGA
GTTTTCTGTGCAAAATCTTGAGAATCAATCAATAAAGAAAGATGGAAGGAAGGGAGAAATTGGA
ATGTTTTAACTGCAGCCCTCAGAACTTTAGTAACAGCACAACAAATTAAAAACAAAAACAACTC
ATGCCACAGTATGTCGTCTTCATGTGTCTTGCAATGAACTGTTTCAGTAGCCAATCCTCTTTCT
TAGTATATGAAAGGACAGGGATTTTTGTTCTTGTTGTTCTCGTTGTTGTTTTAAGTTTACTGGG
GAAAGTGCATTTGGCCAAATGAAATGGTAGTCAAGCCTATTGCAACAAAGTTAGGAAGTTTGTT
GTTTGTTTATTATAAACAAAAAGCATGTGAAAGTGCACTTAAGATAGAGTTTTTATTAATTACT
TACTTATTACCTAGATTTTAAATAGACAATCCAAAGTCTCCCCTTCGTGTTGCCATCATCTTGT
TGAATCAGCCATTTTATCGAGGCACGTGATCAGTGTTGCAACATAATGAAAAAGATGGCTACTG
TGCCTTGTGTTACTTAATCATACAGTAAGCTGACCTGGAAATGAATGAAACTATTACTCCTAAG
AATTACATTGTATAGCCCCACAGATTAAATTTAATTAATTAATTCAAAACATGTTAAACGTTAC
TTTCATGTACTATGGAAAAGTACAAGTAGGTTTACATTACTGATTTCCAGAAGTAAGTAGTTTC
CCCTTTCCTAGTCTTCTGTGTATGTGATGTTGTTAATTTCTTTTATTGCATTATAAAATAAAAG
GATTATGTATTTTTAACTAAGGTGAGACATTGATATATCCTTTTGCTACAAGCTATAGCTAATG
TGCTGAGCTTGTGCCTTGGTGATTGATTGATTGATTGACTGATTGTTTTAACTGATTACTGTAG
ATCAACCTGATGATTTGTTTGTTTGAAATTGGCAGGAAAAAATGCAGCTTTCAAATCATTGGGGG
GAGAAAAAGGATGTCTTTCAGGATTATTTTAATTAATTTTTTTCATAATTGAGACAGAACTGTT
TGTTATGTACCATAATGCTAAATAAAACTGTGGCACTTTTCACCATAATTTAATTTAGTGGAAA
AAGAAGACAATGCTTTCCATATTGTGATAAGGTAACATGGGGTTTTTCTGGGCCAGCCTTTAGA
ACACTGTTAGGGTACATACGCTACCTTGATGAAAGGGACCTTCGTGCAACTGTAGTCATCTTAA
AGGCTTCTCATCCACTGTGCTTCTTAATGTGTAATTAAAGTGAGGAGAAATTAAATACTCTGAG
GGCGTTTTATATAATAAATTCGTGAAGAAATGTGTGCTCTTCAGTTCTCAAGTTTTATTATTAT
GGTATTTATTAAAGTTCTACAATTGTAATAACGTATCCATATGACAAGTTTTAAAGTGGTAATT
GAAATAGGTTATCAGATATAGAGTTGTTCACATCAAGTAGACTTTTAACAGAGTCAGAATGAAC
CTACCCTTAAAATTTTAGAGAAAAAAAAATCGTCGGTTGCACAGAATAGCTGCTCTAGCTTGCTT
AATTATGCCGGGCATGTTGTCACTCCTCTTACTTTTGCTGCCTTTTCATTACTATTTAATGGAA
TGTCCCTGAACAATAAGGAAGAGCAAAACATAGACATTTTGACTACAGTGGATACTTCCTCTAC
CCCAAATGTTATGTTATAAAAGTACTTTTTTTGCCCAGGTACTCTATTATATATTTTGGTTTTC
TTTGAATTAGACCTCAATCTCCAGGAAGCTCTGGAGGGAAAAAAAGGAACCATAAACTAAAGTA
ACTGGTTTTCCAAATAAATGTAAACTTTTTTAACCTTTTATTATTATAGAACATTTCAAACATA
CATAAAACATGAAAACAGCCTGCAGCCAAACTTTTCTGGACCTTGGCAGCTCCAGCAAATGAGC
TGGTCATCCTAACCCTGGTTTCCTGAGACAACTACTTTTGGGGATGCTTGCTTGTATAGGGAGA

-continued

TGATAGATAGATAGATACATATCAAAAAGAAACTTGAAAAAGGCTTCGAACAGAACTTGCCGAT

GTTACTCATCCCTCCTCGGTACAGACATTCTGTTAGAACAGATGGTTGTAATGGGGCAGCATCA

CTCCCTATTCCCATTAAAAACATGACCATTCTGAGATTTCAGGCCCCTTCGAGGAATTTTTCTC

AAGAATTCCATACAAACTGTCAGAGGAAGAAATGTCGTCCCAAGACTAGTCCCTGTGTAGTCTT

GATCCCTTTACCTGCTTACTGTAATTTTTTTTCTCTGACTTTCCGCCAGTGTCTAAGGGCCATC

TGTACCCCTCCCACCCTTCCATGAGCCACTGTATAATCCAAAAACACACCTTCCATTTGCTCCC

TCACTTGTCTCCTTTTACCTCAACAGTGTTAGTGTGTAAAGAATTGCCTGGGGAGGGTAGAGGG

TTTTACAAGTACAGAGTCCCAAGTCTTTTCTCCCCTCCCCGTTAGTGGGTTGGCATTTATTAAT

AGGCACTGCAAGATTTTGATGCAGGTGTGGGGTAGATATCACTGTGAAAGGCTACTAATGCATG

GTAGTTTCACCGAAAGTACAGTCTTCAAGGATCCTTATAATCTCCTCATTGCCAAAATCAGTAA

CATCTATAACCTTGACAACACCCTAGCTTGGGCTGTTGCTTCTCTGGCTACTTGTTTTTCCATC

CCAGTTTACCCAGATTTTAGATGGATACTCCTCCAATTCTGCTTAAAGTCCTTACCTGTTCTTG

CCCAGTTCCCTCTAGTCAACCTCAGTCACTCCCAAAGATTCTTCCCCAATCCCATATCTTTTGC

TCAGACCTCTGTCTCTGGGATTTCTTTGTTACCTCATAGTCAGTAGTCCTAAAAACAAAATTCT

TCATCTTGCATCTCTATCGACCGACCATTCTTTGTTTCTTTTTAAGAAATGTAACCTTCACCCC

AATCATCAAAATCTCTCATTCCTCAATTGTCACAGGTTGTCACTTCTTTCCCCCTAAACCTCTC

CCATCATTCCTTCCTTCTTTATACTGCCCTTACAGGTCCTGATCCTCTGACTCACCCGGACATT

CTTAGCAGCTGCCTAATTTCACTCCCTGACTCTCATCTCCCTCTTCCAATCCTTTTCATTGTGC

TAGAACACTATCTTGCTAATTTTAATATCCTCTGCATTCAGTGCCTCCACAGATTGCCCCCTCA

CTGACCTTTCCAATTTGGCCTTGTGTTACACACTTTCCTCGCTGCATTCCTACCCAGCATCTTC

ACTTGTCATATTTCTCAAATACTCTTCATGACCAGATATTTAAAGTACCTCATCCATGAAGACT

TCATCAACCCCCAAAGTGCCTCCAATGCTTCCGTGGTAGCACAGCATAATGGGGTACATTTCTT

AGTTGAACAGTGAGGAGTCACTGGGATTCTTACAGAGTGTCTTAGGGTCTCCTCTTGATACTCT

TTCCACATTTCAGTTAAGGAATTTTCTTACATCTTTTTTTCTTCTAATAACCTTTGCCTGGAGT

GTAAGTAAATTCATGATAGAGACTGTCATTTTTAAAAAAAAAAACAAACCATTTTGCCTTTCAC

ATGTTATTACCTCCATCTTTCTGTTATCTTGTCAGTGTTGCCACCTAAATGATTGAAAATGACC

GAGCATGCAGTAGAATGTAGTGAAGTTTCCTATTTCATCCATTTTTTGCATAAGTGCATTGGTA

TCTGTATATCCATCTGCCCAAGCACCAGTTGTTGAAAAGACTATTATTTCCCCATGAATGGTCC

TGGTACCCTTGTCAAAGAACAGTTGACCATAAATATAAGACTTTCTGGATTCTCAGTCTTACTC

CATTGCCCTATATGTCTGTCGTTATACCAGCACCGCACTGTCTTGATGGCTGTAGCTTGGTAGT

AAGTTTAGATTTGGGATGTGCAAGTCCTCCATTTTTTTTTTTTTTTTCCCCAAAATCATTTTGT

CTGTTTTGGGTCCCTTGCATTGCATATGAATTTTTATATGATCATTGTGTCAATTCCTGCAAAA

CAGCTGGGATCTTGATAGGGATTTAGTTGAATTGGTAGATAAATTTGAGAAATAACTGCTATTT

TAATGGTGTTAGGTTTTCTGTTCCATGACTGTGGGATGTCTTTGCATTTGCTTAGGTCTTTATT

TCAGTGATGTTTTAGAGATTTCAGTGTGCAAGTCTTGACGTCTTTAATTTTTTTCTAAGTATTT

TACTGATGCCACTTTAATTATATGATTATTTTCTAATTTTTATTTTTGTATTCATCACTGGTGT

TAGAAATAAAATTAATTTTTGTATATTGATTTTGTATATTGTAGCTTTTCTAAAATTCTTTTTT

TGTCACTTAGTATTTTTTGCATATGAGATCATGCATCTGTGAACAGAAATACTTTTACTTCTTC

CTTTCCAGTCTAGATTCCTATTATTTCATTTTCTTGCCTTAGTGTGCTGGCTAGCACCTCCAGT

ACAATATTGGATAGAAGTGACAAGAGCAGACATCTTTTTCTTGTTCCTGATTTTAAGGGGAAAG

CATTCAGTCTTTCACCATTGAGTATGATGTTAGCTAGCTGTGGGTTTGCTTCAAGTTGAGGAAA

-continued

TTCTTTTATTAAACCTAGTTTACTGAGTGTTTTTAATCAAAAAAAAAAAAAGGAGGGGCTGTG
GGTTTTGTTAAATGCTTCTTCTGTATCAAGATTTTCATGTTGTTTTGTCCTTTATTAATATGTT
GTATTAATGGACTTTTGTATATTGAATTAACTTTGCATTCCTGGGATAATCTCAGTTGTCCATG
CTACATAAACCTTGTTCTATGCTGCTGGATTTGGTTTGCTAGTATTTTGTTTAGAATGTTTGCA
TCTATATTCATAAGGAATATTGGTCTGTAGTTTTCATATTATATATCTGTCCAGTTTGGGGATG
AGAGTCATACTCCTGACAGAATGAATTGGGAGCTTTCCCTGTTCTTAAACCTACTGAGGTATTT
TTTAAGTGAACTACTTGGAGACCTTCACCTGTGATCTTCAGATGCTGGGGGACACAGGGATGGT
ACCTGACTCTGAAAAGGCTCTCAGGGTAAGACGTGTCTGAACTGGCCTGTGGCAGTTAACTAAA
GAGTACTCCTACCAATAATGGAGTCAAGATGTATGTTTCCCATAGGCCACGCTGGTCACTGAAA
GAGATGGGCTATGAGCCATCTTGAAAACTACCCTGCACAAATGGACTGCCGGCCTGGAGCCAGG
CACCCTGCAGCTGAGTGCCATATAATGTTGAAGCTGTTGAGGGAGGAGAGGTTGGAAGCTGCCA
GCTTAGAGAATCTCAGCTGTGGTTTCCAGCAGGGTGTATTCCAGGAAAGAAAGTCATTCCCCAC
CCTGGCTCAAAGTAATAATTAACAGTGACTGGGTAAGGCAGGATCTTTTTTTCTAATTCCCTCC
CCTCCAGAAAGGGCAGCAACAGCTCTTGAATGGGAAAGAAGGTGGAGGGAGGAAAAGAAAAACC
AATTGCCCCAACACTGCTGTCTTTAAGCTTCCCACCCAAAGACCTCAGTAAGAGGCAGAATTAT
GTTTTCAATTAAGAGAGAGTTTGGCCTCTTGGTGTTTCAAAAGTGTAGGCTTTTTAATACCTAG
AGAAACTGATGATTTGTTGATTACCAAAAAGGGACCAGAAAAGCTACATAGCCTGAGATTTCAT
CCCCAGAAAAAACGAATCCAGAGAGCAGACTTGCAAAAAAAAAAAAAAAACCGTTCTGTCTCTGCC
TCTCCCACTACACATACACAGTGAGAAAGAGAGTCTTCATGATTTGGTAAATTAGACCCATGGA
AAGACTCGGGACATTTAGGATGATGATATTTACGATGAGGAAGATTTCTATGGGAAACTTTTTT
TTAACTTGTCTCTAATCCTATTCCAACTGAAGTTTGAATTTTTTTCCTTTCATTAACATTTACT
GGGCAAATACCTATTGAATGTTTGCCATTTTGCAGTGTGCCATAGGTTTCAGGCTGATTCAGAG
CTGCTTTGTTGAATCAAGAAGTCTGTTACAGGGAGACAATCTAGTTAGACCAGGCATAAGTACA
AACCACTAAGGGTAAAAGAAGTATGTGAAAGTACAATGTGGGCAGAGAATTCAGATCCAAAAAT
ACTGCAGATAGGTAGGTGATGAAGGTCAAGCCGAATCTTGACATACAGGATAGGTGTATGTGAG
TGAGTTAGGTGGAAAGTCTAGTATGTCTGAGTGTCAGGCTGTAAGGGATTAAGATGAGATTGGG
AAGGCAGGCAGGTCAGATAATGAGGGCCTTATAGACCATACCAAGGACTTTGGACTTTTATTTT
GCAGACGTTAAGCAAAGACATAATCACTTTTCATTTTATATTTATTACAAACTGAAAGAGCACA
AGTGCACATGTGGTCTTTGCAGTTAAGTTATTGCCATAATTCTAAAAAGGCAGATAATCTGAAG
ATAGAAGGGAGGCCACAGTCCAAGACATGCTAGGGACTCTGATTGATTCAGTGCTCATGCATGG
GAAAGATAAGAGTCAAAGACAACTCCCACATTTCAGGTTTTGAGAGCTGGACGGACAGTGTTGC
TGTTAGGTCTATAGAGAAGAGGAGTGGATTTTGAAGGGAAAATTATTAATAGTACAATTGAATG
ATGTTTTAGTTGTGTCTGAGGGATATCCAGGGAGAGCTGTCCTAAGGCAATTAAAAATATGGGT
CTAGAGAAAAACGTACACAGAAGATAAAAATGTATGACTCCAGCACATAGACCATAGCTGAACC
TGTGGCTAGGAAAATTCTCCTGGAAAAGGCAGAGAGGAGAGAAGGACAAGGATGGAATGCATGG
AAATGCTAGCATTTGAGAGTTATACACGGAACCCACAGTAGAGGCAAATGAGAAAAAGCAGGTT
TGTTTTTGTCTGCTCCAGTAGACAGACACCAAGCTCCATGAGGGCAGAGACTTTGTCTTATTCG
TGGCTGTACCTGCAGTGCATAGAGCAGACTGTACATGTGCTTTGTGGACCCATGCAGTTACTGG
GGTGTCTCAGAAACTTCCCATCCTCCTCCCTACTGTGTCTTTGCATAACCCTGGCTGGGCCTCC
CTTTTCTCAATGTCAACTCTCACTGTAACTTTTTTTTTTTTTTTTTTTTTTTTTTGAGACGGA

-continued

GTCTCGCTCATTGCCCTGGCTGGAGTGCAGTGGCGGAATCTCAGCTCACTGCAAGCTCCGCCTC

CCGGGTTCACGCCATTCTCCTGCCTCAGCTTCCTGAGTAGCTGGGACTACAGGCGCCCGCCACC

ACGCCCGGCTAATTTTTTTGTATTTTTAGTAGAGACGGAGTTTCACCGTGTTAGCCAGAATGGT

CTCAATCTCCTGACCTCATGATCTGCCCACCTCGGCCTTCCAAAGTGCTGGGATTATAGGCGTG

AGCCACCGCTCCCAGCCTCTTACTGTAACTTTTAAGAAGGGCATATATCTACGTAGTGTCATCA

CCATAAAGATAAATCAACCAAGTGAAAATATTTTGAAACTTTGGAAATGTATAAACTCCAAAAT

CATCATCAGTTACATCATCAATTATGTCCCTAAAGATCCCATCACTCTGCCTCACACTGGGGTC

TTGCCTACTTCTCTGTTCCAAAAGGGCACAGTAGTGGTATCAAATCTGTTTCTTGAGGCAAATG

AAGTACCTTGCTCCAAAATAATCACCCACAGCAGGCAGATAACCTCCAAGTGCTTCAAGCTGAG

ATTGAGCAGGAGGATCCCAGCTCATCACAACTGGGTGGTAAATATACACTTGGGCCCAAATGGA

AGGAAATGCATTACCCTACAATGCATACCCAACATGCTTGCATCCAGGCCCCAAATCCAGCAAA

ACAATGCTATTCCCCTTCAACATGTGTTAACGGAACTGAGATATTTTTCCAATTTAAATTGTGT

TCCCCAAAGTCTTCATTATTCTCTAGTGCCTATTACAATCTGTGTTTTTATGTTTACTTCATGA

CTGCCTAGTTCCCTCCTGAAATTTTAAGCCTCGTGAGAGTAAGAACTATCTGTTTTCTTTACTC

CACTGTCCTGTACATACATACTTGTTGAATGAATGTATGAATGCCACCGTGATTGCAAAGTCCA

AGGGAAATGATGTTGATTCACTGCACACTGTACAGGAGGGTGTCAACCAGACTTCCAGATTTCT

ACAGAAATTACCAGTAAAGGGTAGTATAAGAATGGTTCCTGCATGTGAAAAATGATCTTGGATG

GAGCTGTTGTGGCATTCACCTGCTCCTCATACTCTCCTGCCACTGTGCAGGGACAGCACAACCC

CCGTGCTGCTTTCTTGAGTGTAGCTCATTTCAGAAAAGCAGTAAAAGGAAAACCCACTTGTTTG

CTTTATGTTCCTAAGAAGGTGGTGAGTAAATCAATCACGTTATCCTAAGAAGTGACTTGAATTT

TATGAAGGCTCCTTTGTTTCCATTGCACTCCTTTCTACCCATCTCTACTCCCACCTCCACCCCC

ACCCTCAAATCATGCTTATAATTTCCATTATTCAATTAAGGGTGGCTTTTTTCTCATCACAAAC

ATCTGTGTGCTTTAAATAGCTTCTACATAACCGAAGTGGAAGTAGTCATGTAGAACAGCACATG

GCCACTCCAGGGGACATGAGAAGCCTCTGCCTAAAGGTAGTTCTCCCTTCTGTCATCTGATCTC

ACACATGGCACTGCAAACCTGCAGTTATTTAGCCATGTGCTTTGTGACATTGATTTCACTTCCT

TGGGTTATTCTTACCGTCTTTAGGAACTTAAATATTTAAGAAATAAACAAATACTATTCAAAGA

GAGCTGTACCATTATTATATGCATTTAAGTGAAAAACTACCACTTCCCATATATATTTATCTCA

TGACCACCTAATTGATAAAAACATGTTAACTGTTATCTTATATTGCCTCAGGGAAAAAGTCTGA

ATGTTGATTGGAGGCACTGCAGGATAGCCATTCGATACCTGCTTTTGTGACAATAAACTAAAGC

ATTGGATTTTGGTGGATTAGGGATAAAAATGGCTTGACAGATCATCTTGTCCAGCCCTCAGTAT

ATAGATGAGAAGACTTAGGTCTCAAGCTCTGAAGCGCTTTGCTCAGGATCGCTGGCCATTTCAT

ATATGTAACAAGCTCCCACTTCATGCTCATTTCACAGTAGCGTGTCACTTTCAGGTCAGCTTCC

TTCAGTGGGCGTTGTCTTTGCTTAATTAAATGTCAGGAGGTCCCCCCAGAAGGCTTGACTCAGG

GAAGGAGGGCAGACCCTCCCAGTTCTCTCACTGACTAGCTTTCGTTTGTTGGATTGTTTTTACT

GATAAAAAAGTTCAGAAATTAGAGCCAGGTTCCTGTTCACGTTCCCTACCCAAGCCCCTGAAGA

AGCAAATTGGTGAATGTTCCCCAAATTCTTTTACTCTCTAGTATACAGTAAGCAGTACTGCCAA

AAAGTTTCCCAAAGTCATGTTCCTCTTAGATATTTTTCCTTGAAAACTGTTGTCTGGCATGGAG

ATCCAACCTGTGTGGAAAGTTCCAGATGCCCTGGTCCTAGCTTCACCTGCCCTGCTTTTGCTTC

CTGTTCTCACTGCTTGTCTCCAGGTTTCCATTTGAAGGCTTGCAGTGCTACTGTGCCCTTACTG

TTAAATCCTGCCTTGCTTGCCATGTTTTATAGACAAGGAAAGCATTTTCTACCAGAGCTCAGGA

GCAGCCTTGAGGTCAGGGGTAACGTTTTTCATTGGTAAGTATTCAGTAGTTGCTGAATGACAAT

-continued

TGGGTGGAAAGGGGAGGGGTGCCTTAGAAAAAATGTCTGTTCTTTGTGGTAATGAAATTGCTTC

CAATTTATTTTCTGATCTCTTTGAGAACTATTTCCTGTCGTCTTCCCGCACCATGCATTCTGAT

TTCTGGGGCATTCAGTGCTCCCTCCCTTCCTTTATTCAAGGGGCTCTTGGAAAAGAAATCTCTG

AAGAAAAAAATGTGTGGGCAGTGGGAGACTTCTCATTCTCTCCACCAAATACTTAGCCCTTTCAT

TCATGAGAAACCCCTGCTTTAGGATGGTGTGGATCTGAGTCAGCAGGGCTGGGTTCATTTGTAT

ATACTCCAGGTTGTGGAGGTTGTTCCTGGGTCTTGGCCTTTCATTTTGGGAGTGCTCCACACTT

CTGTCTCCATATACTATGTATTTAAGAAGCTTGCCTTTCGATTTCCTGCCAGTGGCTGGATCTT

GGGGATCACTGCACAATGCTTGTATGCCCCACTGGAGAAGTCTCTCATGGCACCTTTCCCCTCC

CATGGTGGTGGAATGCTGTCCACAGAAAGCTTCTCTTCACTGTTCAGAGACTCTAAAAATAAGA

CCTGAACTGACTTGCTCTGCCTACTGAAAGGGGACCTCCTTATATTCACCATTGCCCTCACACC

CTTTTCCTTGGAGTCTGTCTTTAGGGTCACCCTGGGAGCTGCCTGGGCCTCCACCTTCTTAAGG

AGGCAACTCCTGAGAGCTGGGTAGGGACTGTCTTTGTCCAGACTGTCTGAAGAGCATCTTGTTC

TTTACCTCCCTCTCCTGTTCTTGACTATTGCCTTCACTGCTGCCTCGCTCTCGTCTACCAGGGT

GGTATTATAAAGTATGTCCTTGGAGGTGAGCTGTTTGACCAGCTCCTTGTTGCCTAGAAACCTA

AGAAATTGTCAGAACAATCCGGCATGCATCAGCTCTGACCTTTGGAGCTTTGACTGGCATTATT

TATAAAAGGCTTTCTGCTCTGTTAGCCGAGCATTGGCTTCATATTTCTCCATGGACTCCAGAAA

ACTGGGTTTCTTTTTTGCAAGTTCTCTTGTTTTCAGTTGAGAACGGTATTGAGTAGGACTTCTC

TGTTTCCTTGAGTTTTATGTTCTCTCCAAATATGGAATAGCACTTGCTTCCCTGGGTGCCAACG

CTGGCCGACCAGCTCTGAAAGTTGCTCTGCTTGTGGTTCTTCCCTGAGATGCTAGTTGGGCCTG

GGAATCTTCCATTTCTCTGCCCACCAGGTGACCTGGCAGTCAGTGTTCTGTCAAAGACCTGTGA

GGGTGCTTAGTGAACTGTGGGCACTATGACCACAGGGTACTATTCTGGGTCCCAGTGTTTGTTT

TTAAGAACTCTGTAGGTTGACAGGACATGCTGTCTGGTGGCCAAGTGCTTCTGCCAAGAGTATG

GGGCCTGGGAGACATGTTTCCTGGCCTGCTTATTGCAGGCCTAGCTTCCACCTAAGAGCTATCC

GCTTCCCAAGGGGACATCCACCATGTCTCTGTGATAGGAGCTGAATAGTAGGGGCAGGACTGAA

AGGTCTGTATGTTTGCTTTTCAGTCAGGTACAGGTGTTGGAGGTTTCTTAAATTTGGTTTCTTT

TGATCTCCCTGGCAGGCAGTGATGGGGAAGTTTTTAGTAAGGTTATTAACAGAGATAGAGGATT

TAGAGTTAAAATTTAATAGGGAAATTTTTCTATAGGATGGTTGAAAATGATGCTTTGTATAGTT

TTATTGTATGAACTTTTCAGGGATAGAATTAGTCAATTTGTAGAAATTGGGCCGCCTCTGTTAT

TGTGATATATTAGAACTGTATTGAATGATGAGACTTCCCAAAAGTTTAAAACAAAAAAAGGAGG

CAGAAGAGAACGAGGATATAAATGAGGACACTCTCGCTGAGGACACATCAGCTGTTAGCAGTCT

GTCTCTGTGTACCGAGCTCAAGAACTGTGACTTTGGTTGGAAGTTAGACCTTTTCTATCCAGCT

TCAGACATGGTAACCTTCACATAAGCTGCTGGATTTGTTCTACCAGAAATTTAGTCTGTTGTGT

GACTCCAGCCACTTTGCAACTCAAGATTATTACTTGTTCAGGTTTCTTTCATTAAATAGCTAAC

CATTTAACAACTATTATCTTCTTAGGGTCGACTGATGGTTACCCATACAGTATATACATCATCC

ATATCCTTTCCTCTCCTACTATATCTCACTCCTATTTTCCAGTCCATCCTCATCTCTCCTCAAG

ATCAACAGACCCCAACCTCTTTTACTTAAACGTTGTATTCCTGAAGTAGTCCTGCCCTTTCCTT

CAGCCTGCGAAGCCTTCTCAAAGACTTCTTTTCCATGCATCTAGACTCTGCCTGGTTATTCTCC

TTCCTTCAGAGTTATTTCTTTGTCAAATGCTGCTAATGTATAAAAACACAAAGCTTTGATAGTT

CCTTCTGTCCCAACGGAGCCTTACGCTTGGCTGACATTTAGGGTAAAGGTGGTATTTTTATTAG

TAAAATTAAATGATACAGAAGTGAATTCTAAAAATAGTTACATAAATCTAAGAGAGTTTTCATG

-continued

AATTCAGGTTGCCCCAAAGATTTAGGCCATACCTCTTCCATGGAATGGCTGTCATGCAGTTTGG

ATGGTTGACCTCAAAATTATTCCCAGCCCCAGAAGTGGAGTAGGTATATTAGTCTAAGGCAGTC

AGGGTAATGCTATCTTCCATGCCACAGATTGGCTTGGAATGGGGATAACCAAAAGCACTTTGGG

CCTGTGAGATTTGACAGAGTGTTTACTGTGAGCCTAGGGAAAGAACATGCCTGCTCTCATGTGA

GAGTATGAAGAAACACTGCCTAAGCAAGGAATCATGTGGCTCCAGTTTTTACTGTCAGCCTTTC

TACCACCAGGGAGACCAGCCTTGAGATGATGCAGGTGCATGGACAGCTGTGTGGAGGGATAGAA

GAATCCAGTTTTTAAACCAGATGGCTGAGCTATTTCATTAAGTCACCCCAGAAGTCTTCAACTA

ACAGTATCTTAACTGGTGAACTCCTGTGACTGATACAGGAAAATTTTACTTCGTAACAAAGTAT

GATAATTCCTTTGTGCAGGAAGGAGGTTTTGTGGAAATGATGTTGATTCACTGCACACTGTACA

GGAGGGTGTCTCTTTGACACCACCAACCTTAAATAGTAGGAAAGCCATCACAGTGGGTTGGGTG

GTTGGATTGCTTTATTGCAACTAATAAAGGGTCAGTTGTGCAGTTGTTAACTATCTTTCACTTC

CCTCAGAACTGTATCTCCTAGCCCAGTGCCCTATAGGTCAAAAATGCCAGTTTGTTGTACAGTC

AGCAGAGCCCAGTACTATGCTTTAAAACATTCGGGGATAATCATCAAATATTTAATCAGAACAG

ATGCTGCCTGTAAACAACCACTGCAGCCAAGAACAGTCTGCATCTGAAACACTGCCTGCAACTA

TAAATATGCCCATATGCTTGAACAATTTTAGTGTTGTAAAAATCTTGTTTTTATAAGCAATTAG

TTTCATCTCCTATTATATGAGGATTAACTTTGCAGTGATGTACTGATGTTAAAAGAGAAAAGAA

TCAAAAAAGCCTTGGTTGTGGTGAAACCCAGCAAAATGTGGGTCTGCACCAAGTTCCAGATGAA

TATCAAACAGCACTGTCCCAGTTGGATTAAGGTGATGACACCCCTACCATGGCTACAGTACCAG

GTCATTTGATTTTCCCCAGGGTCATAGGAGTGTTAGCCCAGGTGATCAGCTCAACACCCCCTGA

GATCCATGAGGTATATACTTTGAAATTTCAATTCCATTACTACTGACTGCATCTCAATCCTATG

TTAATACTTTCTTGAGTAATATTCTGTTGACCTAGTTATCCACGTTGGAAACTTCAAAGGCATC

ATCTTCAGCTCTTTGTTTCTGACTCCCTATCCAGTTCTCCAGTTCTGTATACACCATCCCAGAA

ATGGTCCTCGCATCCAGTTAATCTCTGACATGGACTAATAGGCCTTTCTACAGCTTCAGTGTAT

TCTCTTCTCTGCTTCTGGAACCCAGGATTTAGGTGCTACAGTCATACTATCTTTGACATTCCAT

CTCCCTGGAGAATTTGGAAATGGGGAAATAACATTACTCTTAACAAAGCAAGATTAACAGTCCT

GTAACCAGACCCAAGGCACTGACCCTTCTGTGAAAGCCTATATCCAACCAGCTACAGGAACCTC

TACAGAGAGACTAAAAAAGGCCAGCCCTGGAGGAGCCAGTGGTCAGGAGAACATAGGCATAAAG

CCTCCTAAGGATGTAGCCCATCAACCCTGGGAGTGGGTTCCTATAAGGAATAGGCACTTCGGGC

AAATATGGCCCGATGACACCAGCCACTGGGATCTTCTGACTCTCTCCTGTATAATGTGAGTTCA

TTTGTTTATTGTGTTTAAAGTGAATTCTGCCTCCCTAAAGGCTGAGAACTTCCTTTGGCTCAGT

GTTCACTTCGTTTGGCCTCTGACTTCCAACTGATGCATCAAGCCAATGCGCAAGAAAAGTTAAT

AAATAAAAATAAGATTTATTACAGAGCCAGCTGGGCACTCATACATACATGGAGGAGTCCCTGT

GTCATTGGAACACTGTAGCTTTTCTCTACAACAGTCCCAGGCTAGGCAGCTCTTTGTAGGCCCA

AGGGAATTGATGCATAAGTAAGGCATGGTCTTCCTTGACTACACATCTTGTATACAAGGTATTA

AGGCCCTTGGCCACCTGACTTCGGCCCATTTTTTCAATCTCAACTCTACCCTAAATTCCCCACA

CAGGTCATTCATTCTCCAATGAGGTTATTCTCCTGATCTCTGTGTGGGTTCTTATACATAATGG

AATTGTGTGTTTTTCTCCTGTTTAAAGTTTGGAACATCATGTTAGCCATCATTTTATTCTCTTT

GCTTTCACTGTATTGCACTCACATACTGTATGTGGAATCAGTGCTACCCATTAGACCCATGGCT

CATCAGTGGGAAATGGTGTCAGATCTCACAGAGGGCAGCTTCATGGGGCTCTAGGTTCTTCAGG

CTTCCTTCACAGCCTAAGCTCCATATTTAAATCCAGCATTCAACCCTAATCACTGCTGTTCACT

AGCATCTGCTACATATTCTTGCTGACAGACACTGTGTTTGCTCTTGAAAGATAACAAAATGCTT

-continued

GAAGCTTCCCTCCAACGAGTGATAATTCACTGAAGCTCAGAGGCAGCAGGAGCTCCAGTCTGCT

CTGCTGCTCTGAAATTGTGGAAAGTAGGAAAGGTGTCCAGAGGTCATATGGCCCAAGTGATGAC

ATATCTGAAGCACAGAGAGGGGATGGGCTAAGAGTCACCTGTATCCAAAATTCAAGTTAACACC

TATCAAGTTGTGAAAAGTTACTTTGGGACATCCCAAAGTTACACAGAGAGCTAGAGCTAGGACT

CAGACCTGGAACACCAGACTTCAGTCTCTCTGAACTGCACTGGGTTGTCTCTGCTCAAGCCTTA

TTGGAGAGAGAACTGACAAAAGGCAAGGCTAAGGAGTGCTCTTTGTGGATGCAGCAGGAGAAGA

AACACCCTTCCAATGAGGGGTCCACACAGAGTTCAAATGTCCCCTTTGTTCATACTGAACGTGG

GTATGGTTTTCCTCTTTTGCTGTCTGCACAGGTGGCATAGAAGGCAGCACCTGATCCTTCAGGT

CTGGGGGAGGAGTCCCCAGATAATGCATAGATCTTTTAAACTCTTCACGTCAAACTGACATCTG

CTTATGTAGCTCAGCTCAATGTGTTAGTCATTTTGTTTCGTTTATTATCAAACACATCTTCTGA

AAAATGAGAAGAGGAAGGGAAAAAGGAGTCTGGGAAAGGACCACACTTTCTACCACCCCTGTAA

ACAGTGAGCTTTACTCTGCAATACACCAAGTGGAAGGAGACAGGCTATGAGATGGGCACAGTAA

AGAGCCACCTAAGGGAAGTGGGCAGAACTCCAGAAGACTTCCTGAGGAGGCATTTATTCTTTAT

GAATCTTTGAAATGTTTTTTAAATCATCTTTGATTTGACTTTTGCTCTAAAAGTATCACAAGG

TAAGACTCAGCTGTGAAACTAAGCACATCCGATAGTCAAACTATGAAAACTTTTACACGCTAGT

GGGGCACTGTGACACCACTGATTTCCTTAAACTGAGCTCCTTTCAAGGTGTTTTGACCTAACTG

GCCTTTGGGTCGGATATAGCTTTTACATACTTTTGGTAGGTAACTACGGGTTCCTATTTGTCAG

GGAAAGTGGGTAAGAGTTAGCTATTCCCCACAACCTTGATAGCAGCTTATAAAGAGAGCCAGTG

TCAAATCAATTTGTGCCACAGGCATTATTTTAAAAGCATTTCTTAGAAAGCACACACAGGAGTG

TTCAGGCAAGAGGTACTGTAAGCCCTTTGCTTTTTCGGGGCTTACAACCTCTCAATTTAAATGA

AAGGTTTATTACACAAGGTATTGGTAACAGTGACCAGCAATAGGCTCTGCTGTGTTACTACTGG

CATCAGTCAAAACATGTTCTGACCTCGTTTCTGTATATGTTTATATGTTTAGAGGTCAAGCCCT

GTGTGTCCTTTCTGAGGGCCATGTTAAAGGCCTCCTCAGATTCCTATACTCTATTCTTGCAAAG

CTGGAGAGGTTCTTTAGAAGTATTTTAGCCGGGATACGTATATCGAATACCCTCAACTTCACCA

ATGCAAGCCAGCTTCTAACATACTAATTAGCAAGCCACTGATTTTATCAATAAAAACCCATTTC

TAACATTTACTGTGGAATTAGCAAAGTTTCTGGTGTACATTGGATATGAAAGCTCCAGTAACAG

ACTCAGAAGAAATGGAGACCTGTGAAATGACAAATAATTTAGACTAATCCTCTTAAGTTCAACA

AAGTACAAGAAAATATGGATAGAAAAATGAAATTTGGAAAACAACATCTGAACAGAATGAGAAG

TTTAACAAATATAAACAAAAACAATAGAAATTCTAAAGATAAAGAATACAGTAACTGAACTGAA

AATCTAAGTAGAACGCTTCAACAGCAGACTTGATCAAGCAGAAGAATCAATGAGCTCAAAGGTA

AGACATTTGAAATTATCCAATGAGAAACAAAAACAAAAAGAATGCCTATAAGAATTACAGGAC

ACATCAAGCTAGCTAACTTTTGCATAATAGGAGGTCCTTAAGGAGAAAAGAAAGAAAAAGGCCT

AGAAAGCATATTTAAGGAAGTAATAGCTGAAAAATTCCCAAATCTGAGAAAAGATGACAAAATT

CAGGAACAGGAAGCTGAGGTCACCGATCAGATTCAACCTAAAGAGTTCACCAAGACACATCACA

ACCAAGTTATCAAAAATCAAAGACAAAGAATACTGAAAGCAGCAAAGATAAGAAACATCACATT

CAAGGTAGCCCCAATACAGATTCAGTGGCTTTATCAGCAAAAGCCTTACAGGCCAGTAGAGAGT

GGGATGGTATATTCAAAGTGCTGAAGGAAACAAAGCTGTTAATTAAGAATACTTTACTTGGCAA

AGGGAGAAATAAACACTTTTCCAGATAAACAATGCCTAAGGGAGTTTGTCACTACTAGGCCTGC

TCTACTGGAATTACTAAAAGGGAGTTCTTTAGGCTTAAATAAAAGACTGCTAGTTAATGAGAAA

CATAAAAGTAAAAAACTAAATGGTATAAGTAATTCATAGTCAGAATTCTCTAGTATTGTAAAGG

-continued

TGGCAGGTAAAGCAATGTTATTCCTATTAGGAGGTTTAAAAGATGAAACTATTAAAAACAACTG

TAGCTACAATAAGTTGTAGCTACAAGAAGTAATTGTAACTGTAGCTACAATAAGAGATACAAAT

TTAAAAAAGTGTAAACTTTGACATCAAAATCACGAAAGGCGGGGGGGTTGTGAAAGCGTAGAGT

TTTTGTATGCAACTAAAGGCAAGTTTTTATCGCTTAAAGTAGCCTAAGGATAAAATGTTTTAAG

TTAGCCTTACAGCAAATACAATGGTAATCGCATATACTATAAAAGAAAGGATTCAAAGCACACC

ACCACAGAAAACCACCAAACCACAAAGGAAGGTAGCAATAGGGAAAAAAGAAACAAGGGACCTA

CAAAACAATCAGAAAACAAATTACAAAATGACACTAGCAGTTTCTTACCAATAGTTACCTTGAA

TGTAAACGGATTAGATTCTCCAACAAAAAGACATAGAATGACAGAATGGATTTTTTTTTTTTTT

TAAGTCACAACCACATACTGCCTATAAGAGACTCACTTTTTTTTCTTTTTCTTTTTCTTTTTTT

GAGACGGAGTTTTGCTATTGTCAAGGCTGGAGTGCAATGGCATGATCTCAGCTCACCGCAACCT

CCACCTCCCGGGTTTAAGCAATTCTCCTGCCTCAGCCTCTCGAGTAGCTGGGATTACAAGGGCC

CACAACCACGCCTGGCTAATTTTGTATTTTTAATAGAGACAGGTTTTCTCCATGTTGGTCAGGC

TGGTCTCTAACTCCCAACCTCTGGTGATCCCGCCGCCTTGGCCTCCCAAAGTGCTGGGATTACA

GGAGTGAGCCACTGCGCCCGGCAAGAGATTCACTTTTCTACTAAACATACACATAGACTGAAAG

TGAAGGGATGGAAAAAGATATTCTATATAAATGGAAATTGAGAGCAGGGGTAGCTATACTTCTA

TCAGACAAAATAGACTTTAAGTCAATACTATAAAAAGAAAGAAGTTTGTTATATAATGATAAAG

GGATTAATTCACCAAGAAGACATAACAATTGTAAAAGTATATGCACCCAACATTGACCCACCTA

AATACATAAAGCAATTTTTAAATGATGTGAAGAGGGAGATAGGCTGCAATACTATAATACGGGA

CCTCAATACTCTACTTTTCACCATGGGCAGATTGATCACCTAGACAGAAAATCAATAAAGAAAC

AATGGATTTCAATTACACTTTAGACCAAACGGACTTAACAGGCATATATGAAACATTCCATCCA

GAAGCAGCAAAATACATTTTGTTCTCAAATGCCCATGGAACATTCTCCAGGATATATGTTAGTC

CACAAAACTAATCTTAAGTTTAAGTGGACAGAAATCATATCAAATCCCTTTTCTGATTACAATG

GCGTGAAACTAGAAATCAAGAACAAGAATCAATTCTGGTGGAAAATACAGCAATATGTGGAAAT

TAAACAATATGCTCCCAAACAACTAATAGTTCACAGAAGAAGTCAAAAAGTAAATAAAAAATTA

CCTTGAGACAAATGAAAATGGAAACAAAACTTATGTGATGCAGCAAAATCAGTCCTAATGGAAA

TTTATAGCGATACAAACCTACGCCAATAAAGAAGAAGGATCACAATCTCACTTTTCACCTAAAG

GAACTAGGAAAAGAACAGACTAAGCCCGAAAGTTAGCATAAAGAAGTAAGTAACAAAGATCACA

GTTGAAATAAAGACTGGAAAAAAATGAACAAAACTAAGAGTTGCTAAGAGTTGGTTTTTTTTTT

TTTTGAAAGATAAAATCAACAAATTCTTACCTAGACTAGGAGAAAAAAAGAGTACTCAAATAAG

ATCAGAAATGAAAGAGGAGACATTTACTACTGATATCACCAAAATACAAAGGATTATAAGAAAC

TACTATGAAGTTATGCACCATCAAATTGGATGACCTAAAGAAATGAATAAATTCCTAGACATAT

ACAACCTACAAAGAGTGAATCATGAAGAAACAAATCTGAATAAGCCAATAACAAGAAAAGAGAT

TGAGCCAGTAATAAAAAGTATCCCACCAAAGGAAAGCCCAGGATTAGGCAGCTTCACTACTGAA

TTTTACCAGACATTTAAAGAACTAATAAAAATTCTCAAACTTTTCCAAAACAATGAAGCAGAGG

GAATACTTCTAAATTCATTTTACAAGGGTAGTGTTACACTGTTATTAAAGCCAGAGAAAGACAC

TTTAAGGACAGAAACTTACAAAGTAATATCCCTGATGAACATGGATGCAAAAATCCTCAACAAT

ATATTAGCAAACTGGATTCACGAATACAAAGAATGATTCACCATGATGAAGTGGGATTTATCCT

TAGGATGCAAGGGTGGTTCAACATATGCACATCAAAAAGTGTGATATACCACATAACAAAATGG

AGGGTGTAAATCAAATCATATGATCATCTCAATGGATGCAGAAAAAGCATTTGACAAAATTCAA

CCTGGTTTCATGGTAAAAACTCTCAACAGATTAGGTATGGAGGCCATGTACGACCCTCATCACT

TTTTGACATAGTACTAGAAGTCCTAACCAGAGCAGTTGGACAAGAGAAAGAAAAAAAAGGCATC

-continued

CTAATAGGAAAGGAATAGGTTAAATCATCTGTAATTACTGATGACATAACCATATACAAAAAC

TGTAATGTCTCCACCAGAACAAAACTAAAACCTGGTAGAACTGATACACAAACTCAGTAAAGTT

CCGTAATACAAAATCATCTTACAGAAATCAGTAGTGTTTCCATCTACTATTAATGAGCTATCTG

AAAAGGAAATTATGAAAATCTCATAATAGCAACAAATATTAAATACTGAGGTGTAAATTTAAGG

AGGTAAAAGATCTGCATACTGAAAAGTATAAAAGGACAGGGTCTTCAATAAATGGTGTTGGGAA

AACTGGATATCCACATGCAAAAGAATTAAATTAGACCCTTATTTACACCATATAAAAAAATAGA

TTTAAAACTTAACATATAAGACCTAAAACTGTACACCTACTGAAGAAAACATAGGGGGAAATCT

CCACAGCATTGGTCTTGGGAATGATTTTTTTGGATATGACTGCAAAAGCATGGCAAAAATAGAC

AATGG

We claim:

1. A polynucleotide comprising a nucleotide sequence encoding a short hairpin RNA (shRNA), wherein the shRNA is capable of inhibiting the silencing of paternal UBE3A gene, and wherein the nucleotide sequence encoding the shRNA consists of SEQ ID NO: 2.

2. The polynucleotide of claim 1, wherein the shRNA increases the expression of the paternal UBE3A gene.

3. The polynucleotide of claim 1, wherein the paternal UBE3A gene comprises a nucleotide sequence of SEQ ID NO: 509.

4. The polynucleotide of claim 1, wherein the silencing of the paternal UBE3A gene is by the RNA transcript encoded by SEQ ID NO: 1.

5. An expression vector comprising the polynucleotide of claim 1 and a promoter.

6. The expression vector of claim 5, wherein the promoter is a U6 promoter.

7. The expression vector of claim 5, wherein the polynucleotide is a DNA polynucleotide.

8. The expression vector of claim 5, wherein the expression vector is an adeno-associated viral (AAV) vector or a lentiviral vector.

9. A viral particle comprising the polynucleotide of claim 1.

10. The viral particle of claim 9, wherein the particle is an AAV particle or a lentiviral particle.

11. The viral particle of claim 10, wherein the particle is an AAV particle with specific neurotopism.

12. The viral particle of claim 10, wherein the particle is an AAV9 or an AAV10 particle.

13. A pharmaceutical composition comprising the polynucleotide of claim 1 and a pharmaceutically acceptable carrier.

14. A method of treating Angelman's syndrome comprising administering to a patient in need thereof, a therapeutically effective amount of the viral particle of claim 9.

15. A method of activating or increasing expression of paternal UBE3A gene expression comprising administering to a patient in need thereof, a therapeutically effective amount of the viral particle of claim 9.

16. A method of inhibiting the silencing of paternal UBE3A gene by the RNA antisense transcript encoded by SEQ ID NO: 1 comprising administering to a patient in need thereof, an amount of the viral particle of claim 9 effective to cut the RNA antisense transcript encoded by SEQ ID NO: 1.

17. The method of any of claim 14, 15 or 16, wherein the viral particle or the pharmaceutical composition is administered to the brain of the patient.

18. The method of any of claim 14, 15 or 16, wherein the viral particle or the pharmaceutical composition is administered to neurons of the patient.

19. The method of any of claim 14, 15 or 16, wherein the patient is a human.

20. The method of any of claim 14, 15 or 16, wherein the shRNA inhibits the silencing of paternal UBE3A gene by the RNA antisense transcript encoded by SEQ ID NO: 1.

21. The method of any of claim 14, 15 or 16, wherein the shRNA terminates transcription of a polynucleotide comprising the sequence of SEQ ID NO: 1.

22. The method of any of claim 14, 15 or 16, wherein the shRNA reduces the levels of the RNA antisense transcript encoded by SEQ ID NO: 1.

23. The method of any of claim 14, 15 or 16, wherein the shRNA cuts the RNA antisense transcript encoded by SEQ ID NO: 1.

24. A shRNA encoded by the polynucleotide of claim 1.

25. A pharmaceutical composition comprising the polynucleotide of claim 9 and a pharmaceutically acceptable carrier.

26. A method of treating Angelman's syndrome comprising administering to a patient in need thereof, a therapeutically effective amount of the pharmaceutical composition of claim 13.

27. A method of activating or increasing expression of paternal UBE3A gene expression comprising administering to a patient in need thereof, a therapeutically effective amount of the pharmaceutical composition of claim 13.

28. A method of inhibiting the silencing of paternal UBE3A gene by the RNA antisense transcript encoded by SEQ ID NO: 1 comprising administering to a patient in need thereof, an amount of the pharmaceutical composition of claim 13 effective to cut the RNA antisense transcript encoded by SEQ ID NO: 1.

* * * * *

SEQUENCE LISTING

<160> NUMBER OF SEQ ID NOS: 509

<210> SEQ ID NO 1
<211> LENGTH: 68641
<212> TYPE: DNA
<213> ORGANISM: Homo sapiens

<400> SEQUENCE: 1
tgagatgacc taaacaactg tggagaatca ttgatatatt tccttttttc actgttcatg 60
ttgggtgaaa ataatcttgt agtgaaattc acatgttcta aatattgttt ttttacatct 120
ttatctggca cattcataac atagatgttt ctatacatat tagtactgta atcataccat 180
atattattct gttaccccac ttactcctta aacttttagt taattaaaga gtttttataa 240
agtcccccaa tagatttttt ttttttgaga catagtctca ctctgttgcc caggctggag 300
tgcagtggcg tgattttggc tcactgcaac ctccccatcc tgggttcaag caattctcct 360
gcctcagcct gccaagtagc tgggattaca ggtgcctgcc accacgcccg actaattttt 420
gtattttcag tagtgacagg gtttcaccat cttggccagg ctggtcttga actcctgacc 480
tcgtgatcca cccgccttgg cctctcagag tgctaggatt acaggcttga gccactgcac 540
ccggccagat tttaatctaa ttttattaga acaattcagt catatgtttt ttcatgctat 600
gtatatgaga gttccattat tcagatacta aacaaatgtc tactgtacat ttactgttct 660
cactgatgat gcattagata accatgcaca aaataagcct ggctgtggaa acgcttattt 720
gttgggaggg tgcttgtttg gatcgatgat gagaataatt gtctgaggat gctgagggac 780
tcattccaga tgtcaatctg aggtccagat gtgcggccct ccaataggac aaataagact 840
ctcagagcct ggctctattt ggggatccct cagtgacaac atagtacccc tgtgagcgtg 900
ccttttctat ctcttcgaag agggcagtgg catcctgtct tatgagtcag tgtgcacttt 960
agtgtgccta gtgacccaag acttgcttta attgtagata gatacttaca tataggaaat 1020
atttcttaag taacaaatga aaaactttag aagattgaat taagggtcaa gcaactgtga 1080
tatgtctgaa aatctcatta gtgttgtgct gaaagaagga aatatggcat gcctctatta 1140
aataatgaca gtggaaccaa gtttattgct ttgttatttt tactgtggag tattttctaa 1200
gattattttt gcttttttttt tctttcatgt tttgctgaga tagaaggcct ggaatctgat 1260
cctccacttc agagaacagg ggtgagtagc taagccatta tcttttgaaa ttcatatgtc 1320
atgtgctctt tgctaggtct ttaggtcgtt ttgtacatct tttcagaagc ttattggagg 1380
acattttcat gatatgtcct tttcctcatt gagaccctca ccatgtcacc tacactattg 1440

```
aatccttatc atttctcttt taattttaac tctcttttgc ttttatggaa aaatgtagaa   1500
tttaagagaa tttttggcaa tttcatattg gatcaaaatg tattgtagtg aaatccaggt   1560
gtgccaaaat attaacagat tttccccatc tgtttaatta ttggggtttc agaatagaga   1620
ctccatggtt cataatatct ttgtggtcat actacattat atttctgctt ctaatttaat   1680
tattaaatat tgacttgaat tagtcttttc ctcattgttg caacaaggta agttatatag   1740
gaaattttct tctcttgatg gcatgtctga gataatcata gatataagac acctggctgg   1800
tttctagaat gcatgtaatt tttatttctt gatctgtgtg ttgagtactt gctgtgattg   1860
catcatgcaa atacattgag ctttacaatt ttagtgtatg cacttttcta catgtatatt   1920
attcttcgat agaaagtaaa aaaaacttat cgaactagtc aaaatattgg ttaatacata   1980
aaaaaagtct caagtagatt gtgtattaca tggtgcttgt tgattgatgc cctcataata   2040
gatcaagtgg gttctctctt tagcacaggg ctttttagca aatcatgtca tgagtagtta   2100
ctcaagtatt tttattttaa cacatttata ttttttctat gtatattctt aaattctctt   2160
atactttttt ctctgttata aaaacatgct gaacaatctc aagtcttaag gattgcagta   2220
ttgtccccac atattcatgt attttggtac tcaattcttt atactttctt tgacagatca   2280
cttgaactgg cacatgtctc ttgttttgca gagagggaat taatgtgata ccttcatgct   2340
tttctattct atgtgctaca taattgaata tacaagcaaa tatagttgtt aagatttagt   2400
gtgattattt ctacaccaca tgcaaagaag tttctcatag atcttaatag aggcccacat   2460
gcattgtaca gtttagaatt tggggaaata ttgatgaagt tgggtaaagt ataaagccaa   2520
aagtcagaac agtgaactcc ttgcttaagg atttccttgg agattactta gtcaatacac   2580
aactgataaa tttaagtgct tttcaccttt tgagttctcg acatactaaa gctaaaatgt   2640
gtttcaactt ttaatcctgc ttccctgatt ttcccttttt tagtctgaga tcaaagagtt   2700
tcagccataa attactgcca agagtaatca cttcatttta agaaagctta acaatataga   2760
agaatataaa attatttatg acagatgtat ttttaacctt ttccccatgc tttccagagg   2820
aaatatgttt aatcatctgc cctatattag ggaaaaactt tctatgctaa tacaagtatc   2880
tatcaatcca tttatctttc tatataagat gtattgatca taaccaatta actttactgt   2940
aaatgagctt tagatttgac attttggtag taatatatgt tgtacaatct cctgaggtcc   3000
tataggtctt gaggtctcta tgtcaaaaac tatagatgtg ccagtgtcct cagtgaatgt   3060
gaaggacacc acattttcct tagccatttc ttgttttcag aataatggtt atcaacattt   3120
tgctactgca agataccata catttataat cggaatatgc cagtttttat gcactcatgc   3180
ctctgtttct gtagagcatt cccagaatga gtaatgcttg aaaattaggt ccatgtgatt   3240
tctttaatga gttatagtca aatcatgaaa tattcaggtt accattattt cagtaatgta   3300
ttagaatgtc aaggtaaagt tatctacatt gtatatatac acacaacata gatataattt   3360
atacaacatc tatatttata caacagatat atatttatgt atatatttat acaacataaa   3420
atatatttta ttatttaaac ataaaatata ttttattatt taatatagat tcttaagtga   3480
taaatatgtt taatattatt aaaataggtt aaaataggtt atagttagta cagtgaaaat   3540
tggcagccct tttacaaaac atatgccata actatagcat ttatcactga cagtcatacc   3600
aggatagtct tttatttcca atcacttaaa tattcctaat tgcaaaagaa atttgaagac   3660
taaaattcag aagttttgaa agagccattg cctgggtaaa ctatacaggt ttcagtttta   3720
tttataataa ttatgaggcc aggcgcagtg gctcacacct gtaatcccaa cactttggga   3780
```

-continued

```
ggccgaggcg ggtggatcac gaggtcagga gatcgagacc atcctggcta acacggtgaa   3840
accccatctc tactaaaaat acaaaaaatt agccgggcgt ggtggcgggc gcctgtagtc   3900
ccagctactc gggaggctga ggcaggagaa tggcgtgaac ctggtaggcg gagcttgcag   3960
tgagccgaga tcgcgccact gccctccagc ctgggagaca gtgcgagact ccgtctcaaa   4020
aaaaaaaatt atgtatatat ttataaatta atacttaata aattaataac ttgtgatagg   4080
caatgcaaag atgacagtaa aaggacaaaa ttgattagat tgataaagtc ctgttaacat   4140
gaagaaattg accaggatac catccacact ataaagttag agaaatttat caggacaatt   4200
ccctaaaata ctcttctcaa ttttaacatt gtaacaggaa tttttaaaat tttggtatta   4260
tgtgtgtttc cttccagata atttgaacag attcatattt ggtattttta aaagccatat   4320
ctttgtcctt agtgctggca atgtattctt gagaatgaac aaataagaga tacgtaaaag   4380
cataagagaa ggtatcaggt tgaagtagtc aatcagttat acagaacaca aagaatttta   4440
tcttgtataa tgtttatata gctttataga agtgtgctga aagggctata aaacatggac   4500
attattatct cattgaaagg tccaatacgt actgaaatac atgcttttat tttgaaccaa   4560
ccaccctata aacgttgtat ggcttattta gatgagagcc caggttgtgt gtgtctgtgt   4620
gtgtgtgtgt gtgtgtgtgt gtgtgtgtgt gtgtgtgtgt acctgacagg gaagcaagaa   4680
catcgagttg ccaatgcact ctgtctatgg ttagaatcat gctgaaaaca tggctccccc   4740
agttctggaa tgagcccaca gatcaagcat tccccaaaga catagcaggc tcaaatccct   4800
gtgtacacaa tattttatga ttatcttatg tcagtacttt caaagtatac agtttgtgtg   4860
aagacaaatc caatgtcatt tttcttggct agcctatatg tgtggtaaat ccattattta   4920
cttacttgct tcctgaaaat tacaattaga ttaacaaact gcagcaaagt gggcatgatg   4980
agatagagat tgaagtgtaa gcttatgtta atgatgccct tggtttggat aaacacatct   5040
aagagaaaaa tggaaaaaca cacatggcag ggaagccttg atagagccaa aatataggat   5100
tgtatgtagt aatgcaatcc atagatgagc atttggcagt aatattattt ttcagatatg   5160
gataaaaatt gcttaggaga gtaaagagag acaaagttga aagcaggttt atagtaggtg   5220
ttgttttagt gttgatccct ttttgctcca ataatcaaag tgataaatat tgaaaattga   5280
ttcatgcagc attacttact ccattctaat ttttatatat gtcaaaagtg ccatctccca   5340
aactgtgcta tccccttcag gagaagagac tctgctgaag tttataaggt tgacatattg   5400
ccagcttcaa taatgtaaag atgaagtgta tactgaattc ttaatgcaaa taacaactct   5460
attggaaagt aacccagtta tagaagtgct aatttgtcag gagctgcctt accaagatca   5520
tgatgagtac agttatctca ggattctgaa agattgtttt ccgatttcaa ctagtctagc   5580
tgaatgttcc ttgatagaaa gagaggactt ttagaattgg ttcaatatga tgacctcctg   5640
aattatctca catagcccgt ttgtacatgc ctttcttttc tctcagaaaa tggcactatc   5700
ataatagctt tcttacacag acttcacctt agggttttac attaagggag gggtctggtg   5760
tttcatttat tttgaagtat ttgttgttga ttgtgtacag tgcttgagta aaaaattgaa   5820
tatagaaaca tctagaatat ttttttaaag gatcagtgtt tataaagtga attattagtg   5880
tcaataatgt tgggaaagtt ttaagagaat ataggaaact tgaacattac acaactacaa   5940
tgggaccaaa ttgtggggtc tcattatagt taatatttat gtattttttt ccaattgatt   6000
tgtgtgcttt ttttctgcat gtttttggca gatagaatgg ctataacaag taacagcatg   6060
tcaggtaata aaaataagca gagccctatt cctttaaaaa tcttcactga tgggagggcc   6120
ataaaataag tcttaataca tttaaagaat taaattcatg taaaccatgt taatttaatt   6180
```

```
ccacaatgat attgaattag aaataagagg aatatctctt gaacatctcc taaatgtttg   6240
gaaatttaaa ttagcatttc tgacctattt attggttaaa aaagatacaa agaaaggaaa   6300
attgaaaagt cttttgaact gaataaaaat aaaaatatag aatctaaaac tttatgggat   6360
actgacaaaa caggatatag ggaataattt atagcactga aatgcctata ttagaaaaga   6420
aaaaaggttt taaatcagta aatttgtatt ttaccttaag aaacttagaa aagaacaaat   6480
taacccagac ttaagtaaaa taaaggcact aataaagata agagcagaaa tcaatgaaat   6540
ataaaacaac aaaacacaga gaaaaattga gaaaatttaa aaatagccta gtgagaagat   6600
attgataaac ttgtaaccag accaatttaa gaaaaaaagt caaaacacaa ataccaatat   6660
ttgaaaatgt aggagggcaa atcattacag attctatgaa tactaaaatg ataataagga   6720
aaaattattt aaaaggggca tgtcagccag gcatggtggc ttacccctgt aatcccagca   6780
ctttggcagg ccgaggtggg aggattgcta gagctcaggc attcgagacc agcctgggca   6840
acatgttgaa accttgtcta cacaaaaagt acaaaaatta gctgggtgtg gtgttgcaca   6900
cttgtagtcc cagtcacttg ggaggctgag gcgagaggat cacttgagcc caggaggttg   6960
aggctgcagt gagccatgtt tgtaccactg ccctccagcc tgggtgacaa agtaagaccc   7020
tatgtaaaaa aaaaaaaatg tatgccaaca tttttcaata acttaaatga aatggaaaaa   7080
ttccttgaaa gacacgaact acaaaaactc agtgaacaag taaataacct gaatagccct   7140
gtatcaagta aattgaattt gtagttaaaa gccttccaac agagaaaact tcaggtacct   7200
atagcttcat atgaaatgaa aaaaaaaata ccaatcctct acaagattcc agaacattta   7260
aaagaaggga atatttccca acttattcca tttggacagc aatacccagg taagaaaaag   7320
agacacagaa atttaaaaag aagaatatac attattcctt aggaacataa atgcaaagaa   7380
atctaatcaa aattttggca aatgaaatgt agaaatactt tatgaccaag tgagagttac   7440
ccaaagaatt taaggttggt tttatatgta aagatcaacc aatataggaa aatcacttct   7500
ggaaagtcag agtaagaaac tccaaaaatc tactcctcca taaaaccaat aacagccttg   7560
atagaaatag ttgaaattaa ttttccaaaa ctttggaaat taaccaaagg cttacaaaat   7620
tccagagaac attaattcaa gaaaaatggc tgaatcagta agaacagcca gctttgtggc   7680
attttaatat gacccccttcc catgcttttc tccctagtgc tgagatagtc ttaaaaatta   7740
gcaggatagc aaccactgga gaagaaaggt ttggaaattt cccaaaaagt tccatcccca   7800
tagaattatc actatttgac ctctaaagcc caatctatag gatttatatt catttggact   7860
gactcagagc tcactcagta aggaaatctc aatttcaagg tattggtcaa aaagaatcca   7920
tggcaattgt tgactatcac aactgcctga agtcttggta acagttggga taaacaagaa   7980
gctgatcaaa aactgaaaac taaaatcttg ggaatgagat atctacagga tgcttcaaaa   8040
agctttgata cattcctgtt tatctagaaa gctacatgca ggctgggtgc agtggctcac   8100
acctgtaatc ccagcacttt gggaggccga ggcgtgcgga tcatgaggtc aggagtttga   8160
ggccagcctg accaacatgg tctctactaa aaacacaaaa attagccagg cgtggtggcg   8220
tgcatctgta atcctagcta ctcaggaggc tgagacagga gaatcgcttg aacccgggag   8280
gcggaggttg cagtgagcca agattgtgcc actgcactcc agcctgggcg acagagcaag   8340
gctctgtctc aaaaaaaaaa aaaaaaaaag ccacatgcat gtaattgttt acctctggct   8400
ttccttttat gctctgggca agctaaggaa gagttgtgaa ctacctaagt gctgaatggg   8460
aaccataaca cacacacaca cacacacaca cacacacaca gcaccttagt aaagggtgag   8520
```

```
aggcatgtta gttagaagca ttaaaggaaa tctctttcta gtcattatct gtgcactaac   8580
ctaactgagc agagacttca gtatccacat actacagggc atataaactt tacagaatta   8640
gtccaggaaa atcatatcta aaaaaaaaaa aaagcagtaa caaaaataaa ctctgggaaa   8700
ggggagaata tgatttaaag agttgccaca ttatacataa tatgtctagt gttcaacaaa   8760
aaattacgag acatgcaaag aaatagaaaa atatggcaca aagaggataa gatgaagtca   8820
gtgaaactat cctcgaggaa gaccagatgt tggtcttact agacacagac attgaaccag   8880
ctattaaaaa tacgtacaca gaactaagaa aaacatgtca aaagggttaa agaaaggtat   8940
aaaaatagtg tcttaccaaa tatagactac caataaagag atagaaatta taagaaaaga   9000
caacatgaaa aaatataaag caaaaaaatt agacaattga aacaagaggg cctctattcg   9060
cagatttgag caggcagaag aaagaatcag tgaacttgaa gatatgtcaa ctgagattat   9120
ccagtctgag caacaaaggt gggaaaaaat gaagaaaact gagcaacaaa gaactgtaga   9180
acagcatctc tcataccaat ggatacataa actggagccc tagaaggatg aaaaaaggag   9240
aaggaaagaa aacttcccaa attttaagaa aaacattaat ttatataccc gagatgacca   9300
ataaaatcca attaagataa tctcaaagag accaacacct atacacatca tagtcagcgt   9360
gtcaaaagac aaacataagg agagaattct tgaagatagt aagaaaaaaa ttattcataa   9420
catacacacc atcctcaata agtctgacaa ttgacttctc actgtaaacc atgcaggcta   9480
aaaaggcaat gtacataacc aaagtgatga aataaaaacc ttcaaccaat cattctagat   9540
ccaacaaaac tattgttcaa aaagaagaaa tgaagacatt cctaaacaaa atctcagaga   9600
aatgttctct ataagacttg tcctaataga aatgctaaag gaactccttc ggtctgaaat   9660
agaaaggcac tggagagtaa atcaaatcca cgagaagaaa taaagagaac cagtataagt   9720
aactacatgt gtaagtttaa aacaaagtat aaatttattt tgtttgtaac atttgtcttt   9780
tcctatttga tttaaaatat aatctcaatt ataaacttgt gttgatggta ttatataaag   9840
atgtaatttt gggttatagc accaaaatgg cagaatagga attttctgta ggtgtttccc   9900
acataagtat caattttgac aaccatccat gggcaagagt accttgtggg agttcaggag   9960
ttgacagtaa aacttcagca caccagagga gtaaagaaat ctaagaatag attcattgga  10020
aagggtataa acagtttcac tttacctgca tcaccaaccc ccaaaagtgg cacagctcag  10080
taacaagagc ccattatttc ttccacagag gaaaaggaga gtataataag taagtgtcca  10140
gtttctcaag acatacaggc ccctgcccaa gagatccact ttattttcat ctcacccaga  10200
atattgaggt gatcagcaag gtggagtggt tgggagaggg taaaagcagg aaagagagat  10260
ggggactcaa acagcagccc atacttggaa ctgccataga tcctaccagt tacttcatgg  10320
actccatcag gaacccacct ataagccaca ggggatgcat ccctcccatc ttgccaacaa  10380
aaccccgaat gctccaaatg cctcacccac tctttggctg gctcccaagt gcgctcctgt  10440
gaaaagcgag tgagtatctc tgcagatggc ttgcaagcac atgttgacag ctggctccac  10500
tctgtagaac tggaaaaaag ctcacataca tgagaatttc aggacactac cctaaaaaaa  10560
aaaatgagac ttcagcacct ggcctggctt tatgcaacct agagaaggtg atatgatttg  10620
gctctgtgtc cccacgtaaa tctcatgtca aattgtaatc cccacgtgtt ggacaaggga  10680
cttggtggga ggtgattgaa tcatgcgggt ggacttccct cttgctgttc ttgtgataga  10740
gttgttatga gatccagtta tttgaaagta tgtagcatgt ccccccttcac tctcttgcac  10800
tcctgctcca ccttggtaag acttgcttgc taccccctttg ccttctgcca tgattgtaag  10860
tttcctgagg cctcccagct atgcttcctg tatggcctgc agaactgaac tgtgagccaa  10920
```

```
ttaaacctct tttcttcata aattatccag tcttaggtag ttctttatag cagtgtgaga  10980
atggactaat gcagaaggca tacaaccttt agaatttgcc cccttgaggg aacaagatgt  11040
gtgaagcagg ttcatccata gaaaatgtct gagagaacct caaaatccct aacctgacta  11100
actgatgaaa gtgtttctct cctaaggcca gtcagtaaag accagagggg gtgactgttt  11160
ctttaaatgc aaaggcagca gcacaataat tcaagaaaca tgaaaaatca agaaaacatg  11220
acaccaccag aagaacacaa tcattttcca ataaccaact ccccaaaaat ggagatttac  11280
aaattggttt ataatgaatt cagaacaatt atgttaagga agctcagcaa actaaaagga  11340
acaccaatag actactctgt gaagtcaggc aaacaattca tgaacaaaac tagaaattca  11400
aaaaagagaa aaattatctt aaaagaaaac ccagaagtta tggagctaaa gaatacaatg  11460
catgaaatga aggagcgtat caacagcaaa gttgatcaag cataagaaaa aaaaaatctg  11520
tgaaactgaa gactggctat ttgaaattat tcatcagagg attaaaaaaa aaagaatgaa  11580
aagaaataaa gaaagcctac aggatgtata aaacaccatc aagagaacta atataaggat  11640
tattggagtc ataaaggaga agagagaaaa gggtagaaaa cttatttaag aaataatggc  11700
tgaaaactct ccaaatctag gaaaagatat gagcatccag gtatatgaag ctcaaagatc  11760
cccgtacagg atacattcca aaaagacttc accaaaacac atgataatca aactgtcaaa  11820
agcaaaatca agacgatgaa taaaccacca atcactaaga gggagacagg attcttatgt  11880
tgtcattatt atttacatat aatttcagta aatgttattg gaaaatttat aatgttttaa  11940
aaaaagaaat ttgaaagcac cgaaagaaaa gagactcatc acatacaggg aaccctttta  12000
aggcattcaa gagatttctc agtagaaacc ttacaaaata ggagagagtg ggatgaacta  12060
tacaagtgct gcaaggaaaa aaatgccaac caacgcttta cctggcaaat ctgttcctca  12120
gaaatgaagg agagagaaga actttcctag acaaacaaaa gctgaggcag ttcatcacca  12180
ctagacctgc cttacaagac atactaaggg gagttcttca agctgaaatg atatggcaat  12240
agttagtaat atgaaatgat aaacctcact ggtaaaggaa agtacatagt caaatttaga  12300
acactttgat actataatga tggtgtataa ataattttac tgtgctatga aggttaaaag  12360
acaaaagtat taaaaaaaac ccatagctgc aatagcttgt caatgcatac tacagtataa  12420
aaagatgtaa attagaacat taaaaacata gcatgcaagg gtagggaagt aaaagtgtag  12480
ttttcatatg taatcaaatt taatttgtta tcagcttaaa ataaattgtt atacctatgt  12540
tttatgtaag tgtcatggta actataaagg aaaaacctct agtagataca caaaagaaaa  12600
agagaaagga atcaaaacat aacactacag aaaattatca aattacaaag gaagacagca  12660
agggaggaac aaagtaaaaa gagcaagaaa aaatttaaca taatgaaaac agtaagtcct  12720
tacgtgtcaa taattacttt aaatgtaaat ggattaaatt atccaaacaa aaaaacagac  12780
tggacaaatg gattttagaa acaacaacaa caacaaacac cgcacacaca cacacacaca  12840
cacaaaccac ccagccccaa ctatgtgctg cctacaagag atttacttcc actttaagga  12900
cacatacagg ctgaaattaa aagaacagaa aaagatattg catgcagata gaaaccagaa  12960
gagaggagag gcatctatac ttacagcata cagaaaagat tttaagttaa aaactatatc  13020
aaaaggctaa gaaggtcaaa atggtgaagc agttaattgt tcaagaagac ataaaaattg  13080
taaatattta tacacccaat attgaagcac ctaaatatat aaggcaaata ttaatacata  13140
taaaaggaga aatatacagc aatacagtaa tagtagtgaa cttcagtgcc tccctttcaa  13200
aaatggataa tccagacata aaatcaataa ggaaacattt aacttaaact tcactttaga  13260
```

```
ccaaatggat ctaacagaca ttatactgaa catttcatcc aacagtggta gaattcacat  13320
tcttctcaag cacacatgga acattctcca ggatagatta tatgttagct cacaaaataa  13380
tattacaaaa tttaataaag ctgaaatatc aattattttg caccacaata gtataacact  13440
agaaatcaat aacaagatgg aaactggaaa tttacaaata tatagcatta acatattcct  13500
gaacaaccaa tgggtcaaag aaaaaaatca aaataatttt gtgacagcaa agtagaaaca  13560
caacatacca aaacatacag gacacagcaa aagcagttct atgaggtaag cttatattga  13620
taaacacatt taaaaaaaga ttttaaataa acaacattac acctcaagga actacaagga  13680
agaaaaaaaa acaagcccca tgttatcaaa gggaaggaac taacaaagat cagacagaaa  13740
taaatgaaac atagactaga aaaacaatag agactattaa taaaacttag agttagtttt  13800
ttaaaaaata aaatcaacaa acctttagct agactaaaaa aagagaagac tcaaataaaa  13860
taaaaaatga aagaggagac attacaactg ataccacaga catacaaatt aagagaaaac  13920
tatatgccaa catattagtt aacttgcaat gggtaaatcc ctagaaacat acaacctaca  13980
aaaactgaat catgaagaaa tggaagatct gaacagatca ataatgaata agggaattga  14040
atcaatattc aaaaatctca caaaaagaaa agctcaggat cagatggctt cactggtgaa  14100
gactgccaac catttaaaaa aattaatacc actctttatt aagctcttcc aaaaaaattg  14160
aagaggagaa aacactttca aattcattat aagaggccag ttttaccttg atatcaaaga  14220
tttaaaaaga acactttgag aaaggaaaat tacaggccaa aacccttgat aaatatagat  14280
gcaaaaatgc tcagcaaaat actagcaaac ctaattcagc aacacattat aatggcatac  14340
atcatgacca agtgagattc atgcctcgga tgcaggatag ttcaatataa tcaaatcaac  14400
aaatgttaca ctactttaac agaatgaagg ataaaaatca tatgatcatc tcgatggttg  14460
aactagttta cagtcccacc aacagtgtaa aaatgttcct atttctccac atcctctgca  14520
gcacctgttg tttcctaact ttttacagat caccattcta actggtgtga gatggtatct  14580
tattgtggtt ttgatttgca tttctctgat ggccagtgat ggtgagcatt tttcaagtgt  14640
ctgttggctg cataaatgtc ttcttttgag acgtgtctgt tcatatcctt cacctacttt  14700
ttgatggggt tgtttgtttt tttcttgtaa atttgtttga gttctttgta gattctggat  14760
attagccctt tgtcagatga gtagattgca aaaattttct cccattctgt aggttgtctg  14820
ttcactctga tggtagtttc ttttgctgtg cagaagctct ttagtttaat tagaccccat  14880
ttgtcaattt tgtcttttgt tgccattgct tttggtgttt tagacatgaa gacagtgtgg  14940
tgattcctca aggatctaga actagaaata ccatttgacc cagccatcct gttactgggt  15000
atatacccag aggattataa atcacgctgc tataagccat aaaaaatgat gagttcatgt  15060
cctttgtagg gacatggatg aagctggaaa ccatcattct cagcaaacta tcacaaggac  15120
aaaaaaccaa acaccgcatg ttctcactca taggtgggaa ttgaacaatg agaacacatg  15180
gacccaggaa ggggaacatc acacactggg gatggttgtg gggtgggggg aggggagagg  15240
gatagcatta ggagatatac ctaatgctaa atgacgagtt aatgggtgca gcacaccaac  15300
acggcacatg tgcacatatg taacaaacct gcacgttgtg cacatgtacc ctaaaactta  15360
aagtataatt aaaaaaaata atgctgctat aaagacacgt gcacacgtat gttcattgcg  15420
gcactattca caatagcaaa gacttggaac caacccaaat gtccatcaat gatagactgg  15480
attaagaaaa tgtggcacat atacaccatg gaatactatg cagccataaa aaagatgagt  15540
tcatgtcctt tgtagggaca tggatgaagc tggaaaccat cattctcagc aaactatcac  15600
aaggacaaaa aaccaaacac tgcatgttct cactcatagg tgggaattga acaatgagaa  15660
```

```
cacttggaca caggaagggg aacatcacac actggggcct gtcgtggggt cagggtaggg  15720
ggagggatag cattaggaga tatacctaat gtaaatgacg agttaatggg tgcagcacac  15780
caacacagca catgtgtgca catgtaccct agaacttaaa gtataataaa aaataaatca  15840
tatcatcatc tcagtagatt tagaaaagca tttaacaata ttcaacatcc tttcagaact  15900
aaaaactctc aataaatcag gtatagaaag aatgtgcctc aacactataa aagccacata  15960
tgacaaacct ggaggtaata tactcaatgg tgaaaagtaa aaagctttga ctctaagatc  16020
agaaccaaaa caaggatgtc cattctcacc acttatattt aacatagtag ttgaaattct  16080
agctagagca attaggcaag aaaaaaggca cccaagttgg aaagaatgaa gttaaattgt  16140
ctctgtagat gacatgatct tatatataga aaacactaaa gactccacca aaatgctgtt  16200
ttaattagag cttaaaaaaa taattcacta aagttgcagg atacaaaatc agtatacaaa  16260
aatcagttgc atttctaaac accaaaaaca agttatccaa aaaattaaga aaacaatcct  16320
atttgtgata tcatcaaaaa ataaaatact aaagaatacc aaagaaactg aaaataaatg  16380
gaaataaatg gaaagatagc ccatgttcat ggattagatg aattaatact gttaaaatgt  16440
tcatactacc caaagcaacc tacagattaa gtgcaattcc tactaaaatt ccaatgacat  16500
ttttcacaga aatagaaaac acactcctaa agtttgcatg gaaccgcaaa agactcaaat  16560
agatgaagca attttgagca agaacagtaa agctggagac atcacactac ctaacttcaa  16620
aattttatta atcaaaacag catgacataa aaacagacag aaaagaccaa tggaacagaa  16680
tagagagccc agaaataaac tcacgtttat agagtcaact aatattcaac gaaggtgcca  16740
agagtacaca atggggaaag tatagtctct acaataaaca gcactgggaa gacaatatcc  16800
aaatgcaaaa gaatgaaatt acacccttat cttataccat acacacaaat caaatcaaaa  16860
ttgataaaga cttaaatata agacctgaaa ccatacaatc tttaggcaaa aactcattga  16920
cattggtctt ggcaatgatt tttttgatat gacaccagaa gcacaggcaa caaaagcaaa  16980
cctaaacaag tgggacccta acaaactaaa aagtttctgc acagcaaagg aaacaatcaa  17040
tcatcagaat taaaaggcaa tttatgaaat gggagaaaat gtttgcaaac cacatatctg  17100
ataaagggtt aatatccaaa aatatataag gaatgcataa aattcaatag aaataaacaa  17160
acaaataatc caattttaaa atgggtgaag aacctgaata gacatttttt caaagaagac  17220
ttacagatag gcaacaggca tatgaaaaaa tgcttgacat cactaataat cagggaaatg  17280
caaatcaaag ctccagtgaa ataccacctc caactattag gatggctatt atcaaaaact  17340
caaaagaaaa caagctgggg gaatgtagag aaaagggaaa agaagatcct tatacactgt  17400
tggtgtgaat ttaaactgga atagccctta tggaaaacag catggaggtt cctcaaaaaa  17460
ttaaaaatag aactactata tgatccagca atttcactat tgagtatata tccaaatgaa  17520
ttaaaatcac tgtcttgaag aggtatttgc acactcatat ttatttcagc attattcaca  17580
atagccaaga catggaatca acctaagtgt tcatcagtag atgattagat aaagagaacg  17640
tggtatatag acacagtgga atctatttag tgttcaaaaa gaaggaaatc caacttttaa  17700
aatcctttaa aaagttaaac tcataaaaac agagaggaga atggcggttt ccaggaactg  17760
gagggtggga gaatggggag atgttggtca aaaggtacaa actttcagtt ataaaatgaa  17820
taagttctag agatctagtg tacaacagca ttactatagt taataataat attttttata  17880
cttgaaattt gctaagagta aatatcaata ttctcaatac acacaaaaca gaactatctg  17940
aaggcactga tatgttaatt atcttcatta tagtaatcat ttcacaatgt ataatgaata  18000
```

```
tcaaaacaat agtgtacatc ttaaatatat acagttttga tttgttaatc atacatcaat  18060
gaagctagaa aaaatgttgt aatttttaaa acaatagtaa tataaattag gggtgaagga  18120
attgacctat gttggagaaa agtttttgta aactatttaa attaattggt atccattcaa  18180
gctagattat ttttaattgt taatttaatt gtaatactaa ggcaaccact aaaaaagcct  18240
ttaaaaaaat atagcacttg aggctgggca tggtggccct caattatata tataatatat  18300
ataaaatata tattatatat atagtagatg aacaacaatg ggatttaaat ggtacactag  18360
aaaatatctg tttaacaaaa agaaagcaat agtggagaaa tataagaaca aaaccatgta  18420
agatttatag aaaatgaata gcaaattggt tgacctaaac cctatcttat aattatatta  18480
aagataaatg aaataaatac tacatcaaaa ggcagagatt atcagaatag agaagaaaaa  18540
tccaaaccat aattcaacct tatgttatct gtatttagaa tatttagagt caagacacaa  18600
atagatagag ttccatttgg gcgtgaaaat atttaccatg caaaatgtaa ttaaaataga  18660
gctagagcag caatactaat atctgacaaa atatacttta acaaaaattg ttgctaaaga  18720
caaaaaagaa cattttataa taagacacaa caattataaa catatacacc aaacaataga  18780
gcccaaaata tacaaagcaa aaactgctag aattgaagaa agatagaaaa atcaatgatt  18840
acagttggag gtgtcaatac caaactttca gtaatacaca gaacaacaag tcaaaagcaa  18900
aaaggaaata aaaaactaca cattatcata caacacctta atacgatatc caacaatagc  18960
agaatacaca ttattctgaa gtgcacatgg aatattcttc aggatgacac atattaggct  19020
gtaaaacata tcttaataat ttaaaagaat tgaaataata cagcacatat tctctgactg  19080
caaaatatta aaccaattac agaagaaaat gtgggaaatt cacaatgata tggagattta  19140
aaaatacttc aaagtaacca atgaatcaaa gaacaaatca caagagaaat tagaaaatat  19200
tttagatgaa taaaactgaa gaaacaacat accaaaattt tgtggttgta gctaaagcag  19260
tgcttcaagg gaaatgtata acagtatatc cctaaatttt aaaaaaatct caatccaata  19320
acctaatttt tcaccttaag aaatgagagt gaaagagcag acttaaccca aagtaaacag  19380
aaggaagaaa taataaagat tagcatggag ataagtagtg aaaataaaaa caatagagaa  19440
aattaataaa cttgaaagtt ggttcttctg atatatcagt aaaattgacg tattattagt  19500
ttgaccgaga aagaacaaaa gagagaagat tcaagttact agacataaat gaaagtatag  19560
atatcacctt acagaaatta aaagaattct aacagaatat tgtgaaaaag tgaatgtcaa  19620
aaaattaaat tatatgagat acacaaatcc ctctaaaggc acaaactacc acagctggtg  19680
taaaaacatg aatacaccat ttacagttaa aaagactgaa tagataaaaa ttttaagaag  19740
aaattgagta agtaatttaa ttttcaaact ataatcccaa gaccagatgt tttcattggt  19800
gaattctacc aaactttaaa aggattaata tctatttttc atacactctt tccagaaaat  19860
agaaaaggag ggaacactct ataactcact gtatgaggtc cgtattaccc ttatatcaag  19920
accaaacatc ataagaaaag aagactaaag acttatggtt tctgctctga tatgtttgga  19980
agtcatcact actattgtca caaggaaaaa tctgaacaaa ctaaagtcaa cgatttctta  20040
aactaaccat agaattgagg taacgggcga aaactggaga tgtaggcaaa tacaaaaaaa  20100
atcacagttt atcaggagca gaaactgctg aaaccagcaa ctcgtatgaa catgttaagt  20160
ggtaattgac aaatttctgg agattgaatg tggactggat tgagagttag gaactcctaa  20220
gtgcccagtt tttgatgacc ccacacactt ttgtaaacta gacttccaag agccccagca  20280
agtttcttac agtgaagact gcagaaaaat cccctgatgc ttcagatagg aggaagggaa  20340
aagcaactat tttgaaataa gcccagggga caagtagtta tttctaaaca ctctcagagc  20400
```

```
attttctttc acacggcagg gggctccctg caagggaagc tactttgcct gagccttgtc  20460
tgatgtagga gaaaaggaat tggatggctc aagctccatc tagcctttct gatttatata  20520
agggaagcaa aaaataggtt aagaaactct tctgaaagtc acaactcaga tttattttat  20580
atttatttat ttatttatat tttttgagac ggagtctcgc tctgttgccc aggctggagt  20640
gcagtggcgc gatctcggct cactgcaagc tccacctccc gggttcacgc cattcttctg  20700
cctcagcctc ctgagtagct gggactacag gcgcccagct aattttttgt atttttagta  20760
gagacggggt ttcaccacgt tagccaggat ggtctcgatc tcctgacctc gtgatccacc  20820
tgcctctgcc tcccaaagtg ctgggattac aggcgtgagc caccgcacct ggcctcacaa  20880
ctcagattta accataagat tatagaacac ttctcctccc aaaacagaga tatagatcaa  20940
tggaacagaa cagagccctc agaaataacg ccgcatatct acaactatct gatctttgac  21000
aaacccgaga aaaacaagca atggggaaag gattccctat ttaataaatg gtgctgggaa  21060
aactggctag ccatatgtaa aaagctgaaa ctggatccct tccttacacc ttacacaaaa  21120
attaattcaa gatggattaa agacttaaac gttaggccta aaaccataaa aaccctagaa  21180
gaaaacctag gcattaccat tcaggacata ggcatgggca aggacttcat gtctaaaaca  21240
ccaaaagcaa tggcaacaaa agacaaaatt gacaaacggg atctcattaa actaaagagc  21300
ttctgcacag caaaagaaac taccatcaga gtgaacaggc aacctacaaa attttcacaa  21360
cctactcatc tgacaaaggg ctaatatcca gaatctacaa tgaactcaga caaatttaca  21420
agaaaaaaac aaacaacctc atcaaaaagt gggcaaagga tataagcaga cacttctcaa  21480
aagaagacat ttatgcagcc aacagacaca tgaaaaaatg ctcatcatca ctggccgtca  21540
gagaaatgca aatcaaaacc acaatgagat accatctcac accagttaga atggcgatca  21600
ttaaaaagtc aggaaacaac aggtgctgga gaggatgtgg agaaatagga acacttttac  21660
actgttggtg ggactgtaaa ctagttcaac cattgtggaa gtcagtgtgg cgattcctca  21720
gggatctaga actagaaata ccatttgacc cagccatccc attgctatat atatatatat  21780
atacccaaag gactataaat catgctgcta taaagacata tgcacaggta tgtttattgc  21840
agcactattc acaatagcaa agacttggaa ccaacccaaa tgtccaacaa tgatagactg  21900
gattaagaaa atgtggcaca tatacaccat ggaatactat gcagccataa aaaagatgag  21960
ttcatgtctt ttgtagggac atggatgaaa ttggaaatca tcattctcag taaactatcg  22020
caaggacaaa aaaccaaaca ctgcatgttc tcactcatag atgggaattg aacaatgaga  22080
acacatggac acaggaaggg gaacatcaca ctctggggac tgttgtgggg tcgggggagg  22140
ggggagggat agcattagga gatataccta atggtaaatg acgagttaat gggtgtagca  22200
caccagcatg gcacatgtat acatatgtaa caaacctgca cattgtgcac atgtacccta  22260
aaacttaaag tataataata ataaaaaaag gctacctaaa aaaaaaaaaa agaacacttc  22320
tcctcccaac accatatcac cacatcaacc aggactccag tgtaatagca gtgaattcta  22380
actgaaagag gtgaaagaca ctgattgtat ttaagaaaga tcttctaagg aaatccaaaa  22440
atagtagggg agatcaaaac aaagatacta gaggaaattg aatatgtgac acctatagct  22500
acaaaaaaat taaacataac atagccctaa ccatataaac ataaaacctc acacaaagac  22560
ctattatctg agattctgtt gcctgataca ttgcgtttta tttcaataaa aaaattagag  22620
ggtatgttaa aaagcaggaa aagttagtct aaagagacaa attgagcctc agaagtaggc  22680
tcagatatgg cagagatttg gcaattatac ctagagttta atataaatga ttaatataat  22740
```

```
aagtgttcta acagaaaaag gcaacatgca agaacggatg ggtaatgtga tcagcaagaa  22800
ggaaactcta agaaagaagt caaaaggaaa tgctaggaat aaaaacctac aagaaataaa  22860
gaatgcctgt gatgggttcc tcagtagact ggacaaggtc aaagaatcag tggatttgaa  22920
aatatgtcaa caaaaactgc cccactgaaa tacaaaagaa aaatagaatt ttaaaaacgt  22980
aacacaatct ccaaaacagt gggacaatta caaaagatgt aatgtgccta atgcaaatga  23040
cagtaggagt ataaagggag aaaggaatag aaaatctgaa gtaataatgg cagagagttt  23100
tccaaaatta atgctaaacc acagatacag caagcccaga gaacaacaag gaggaaattt  23160
agtaaagcgt ctgcaaccaa gtatgtcata ttcagactga caaaaccaaa ggtgaagaga  23220
aaatattgaa agaagacaaa gaggaaaata aatatcaaga aaatacatac gaaatacatc  23280
atacatacat aagaaataca tcagaccata caagcaagaa gagaatggag tgaaatgttt  23340
aaaatgttga aaaaaaaact atcaatttgc aattctgtat ccagtgagat tatctttcaa  23400
aagtgaagag ggaaatggca gagaagtcat ctccaagacc tatggtttcc cttcacagaa  23460
acactgaaaa atatgaacaa aagtggtcag aattaacttt ctaagaattc tataaaatgg  23520
taaaatgttt acaccagtaa agcaaatgct gaattgagaa ggcaacttaa aaaggtgaag  23580
aaaacttcgt attattttta tgtgtccttg ccccacgtcc ttccctacct tagtcttgaa  23640
gatggcagcc cacatttcta ctgtggggct ctggtttctg tttcctggtt caagagggag  23700
aataacagac cttactttta gtcattatta tttccttctt tctgatttcc ttgggtttat  23760
tttgctcttc tttctacttt attgaaatga gaactaagat tatgatttga gacatttttc  23820
taatgtaagc atttagtgct ataaatttcc atctcaacac tgctttagtc acatccccaca  23880
aatttttata tgttgtaatt tcactttcat ttagttctat ttttaaattt tttcttttta  23940
tacttcctct gactcacaga ttacttagaa ttgtgttgtt cagttttcaa ggatattgta  24000
gattttcctg tttctctgtt gtctaatagt tctgttccat tttgtacaga tagctcacgc  24060
tgtatgattt caatttttta aaaaattgtg ctttgtttta tggcccagat atggtctgtg  24120
ctgtgaatat tccatgttat tataaagtat gcctgttata ttattatata tatataatat  24180
atataattat aaagcatgcc cgttttgtat tgttagcaga gtattctaga aatgtcaatg  24240
agatcttgtt ggttgatggt gcttttcagt tctatatctt tgctaatttt tttttttttt  24300
gcttagtagc tatatgagat tctgagagag gaaattgaag tctccaacca taattgtgga  24360
tttgtctatt tctcctatca gttctatcag tttgtgcatc acatatttga ggctctgttg  24420
tttggtgcat acacaagtgg aatcattgtg ccctcttggt ggcttatttt atgattatat  24480
agtgcctatc tttgtggtat ttttatttgc tcttaaatct actttgtgtt atattcatat  24540
acccattctt ttttaaaaaa aattgtttgc gtgatacatc ttttccattc ttttaatctc  24600
agcctatctg tgccattgaa tttgaagtga gttttcatat agagaacata ttattgaatc  24660
atcattttaa aaattccttt tgccaatctt ttttatactg aggtaaaatt gacataaaat  24720
ttatcatttt aaagtgtaca atacagtggc atttggtaat acacatgtta tgcaacgtta  24780
actctacctg gctcctaaat gttttcatca tccccaaaag gaaacttcat actcattaag  24840
cagttaattc ccattccttc tctcggccac tggcatccgc aaacctactt ttctgtctct  24900
atgaatttac ctattatgga tattttgtat aaattgaatt atacaataag tgacctttat  24960
gtttggcttc gttcgcttcg catactattt ttcgatattc aaccatgttg tagtatgtat  25020
cagttttatt tgaataactc aattcttttt gttgtatagc taaaagttga ttcctaggtc  25080
ataatgataa ttctatgttt agtttattga atagctgcca aagtttttcc acagtggctc  25140
```

```
tgtcatttta aaatcccact agcaatggat gagagttcca atatctccac atccttacca  25200
atattgttat tttatatttt tataattata attttcctag tgaatacgca atggtatctc  25260
attgtgtttt tggtttgcct ttccctaatg actaatgatg ttgagcatct tacaatgtac  25320
ttgttaacta tttgtgttct ttagagaaat gtctattcaa gtgccttgtc cattttaaaa  25380
atcgagttgt cttgttgact tatgagttct ttaatacagt aaacgcttat cagatatgat  25440
ttataagtat tttaacccat tctgaaggtc accttttcac ttttgtggta gaccattatg  25500
cacaaaggtt ttaattttga taaatccaat ttatccgctt ttgttgttgt ttttgttgtt  25560
cgtgcttttg caaaacctag tgtcatgagg ttttctcatt atctttggag aatttttatag  25620
tttgggtcta tacatgtaga ttattgatct aatttccatt aatttgtgtg tatgctacga  25680
ggtaggggtc caaattcaat ttttgcattg aattgaaaat tcatattttc agtttcaaat  25740
ttcaactgca tattcagttg ttgcagcaca atttgttgaa gagatcattc tttaccacag  25800
ggaatgatct gggacccttg tcaaaaatca attgatcata gatgtatggg attatttcag  25860
actttagatc ttgttccatg aatatgccta tttttatgcc agcactgcag tattttcatt  25920
actgtagctt tatcataaat tttgaaatca ggaagtatgt atcctccaag tgtgattttc  25980
atttgctaga gtgttttgac tatttggggt ctttgcaatt ccatatgaat ttcagaattg  26040
gcttttcatt taaaaaaatg gtagttgaga ttttcatagg aattatattg aatctacaga  26100
tcactttggg tagtattgcc atcttaacaa tattgtattc caatccataa acacggatgt  26160
attgccattc atatcttttt ttcttttctt tcggcaacat ttagtatatg acacttgtaa  26220
ctccttggtt aaatttatac ctaagcattt tatcctttct gatgctgttt aaatggaatt  26280
attttattaa tttctctttt agatggcttg ttgcaggtgt atagaaatag aactgattat  26340
tgtgctttta ttgaattatc tgaaactttg ctgcatttat taactctagt aggtttttttt  26400
tttctttaaa gttgtctata tatcttgctc tgtgaataga taattttact tcttgatctc  26460
caatatggat gcctttcttt ctttttctta cctaattgct gtagctagaa ttttcagtat  26520
aatgtatgat agaagttgtt cacaactatc cttgtcttct ttctgatcct aggggtatag  26580
ctttcagtct ttcaccatta agcacaatgt tagctgtggg gttttcttag atgccattta  26640
atatattaag gaagtgctct gctatttcta attggttgag tatttttatt ataaaatggt  26700
gttagatttt atgactttat gtactgcata attgagatta tcatgtggtc ttttcattcg  26760
attaatgtgg tatattttat gattttcata tgttgatcca cctttatatt cttggggcaa  26820
atcccactgt gtacacgggt tttttagggt ctcctaattt tcttcattct ttttcttttc  26880
tctccctgag actgaataac gttaactgac ctatcttcaa gtttactatt ttttcttctg  26940
ctgttcaaat ctgcttgaac ctatagagtg aatttttcat tttacttatt gaacttttca  27000
gctccaaaat ttctctttgg ctactttgta taatatctat ctctctatag atattctcta  27060
tttggaaaga catttttctc ctggttttct ttacttattt gtattttttta aagtctttaa  27120
gcatatttga gacagttgat ttaagtattt gtgtactaag tccattgcct aagcttttgc  27180
atagagattt tatattaatt tcttttttttt ctgtgaacag gtcttttttt tttttttttt  27240
tttttttttt tttttagaaa actggacatt ttgagtagta taaacgtggc tattttagaa  27300
ataattttcc tccctcctta ggttttgttt ccacttgttg catgttgctg ttgtttgctc  27360
attagtgact tttctaaagt attttgaaaa gtctgtgttc ttgatcatgt gggtccattg  27420
aattctgtat tctgttaatt tcatagtcag ctagtgttct gaaagttccc ttaagtgcat  27480
```

```
agagccaata aaagaaaaag aaaagaaaca cagaaaaaga aaagaggaaa aaaggaggga  27540
aagagattta aaaaaataat gtcggttggg catggtggct catgcctgta atcccagcac  27600
ttttgggagg ccgaggcagg caaatcactt aaggttgacc atcctggcca acacggagaa  27660
accttgtctc tactgaaaat ataaaattag ccgggcatgg tggcacatgc ctgtaatccc  27720
agctactcgg gaggctgaga ggtaggagaa tcacttgaac tcgggaggtg gaggttgcag  27780
tgaactgaga tcacaccact gcactccagc ctgggcaaca agaatgaaac tccatctcaa  27840
aaaaaaataa taataataat gcctttgccg atttgctctg tgtttgggcc ctcattcaat  27900
gcctagtcag gccatttaca actctctctt aactttcact acctgcttgt gtactgactg  27960
aaggccacct ataggtgaaa gcttaacatc atctcagatc tttttggacc atgaatccta  28020
ccctgggtat gcacatgatc ttcttaattt cccagtagat gcaagagttt tagtgtttta  28080
aaagtcctta ttccctcatc tatcttcttt tctgaccttt ttcagtctgc ttattgttca  28140
tctgaactga catcctttgc cccaagcggc tgtggcaaaa acttttacct ttaaatgctt  28200
tcaccacaag ccacttggga agctgcccca gacctgggac tgctctgacc ctgatgaaac  28260
aaagacaaga ccttgtacag ccaggcagcc ataagacaag tccataccca aaccacagtt  28320
ctttcagaat aaggtctata ttggattctc tggccctagt aaccagcatg agtctgggct  28380
tgccatcttc atggccactt gtcttagttt gctagggctg ccataacaaa atatgagaga  28440
ctgagtggct taaacaagag aaatttattt tttcacaatt ctgaagacca gaagtccatt  28500
actctgaaat ctctctcctt ggcttgcaga tactgccttc ttgccgtgtc ctcacacagc  28560
cttttctctg tgtacacatc cctggtgttt tttaagcctg tccaaatttt ctgttcttct  28620
gaggacacca atcagattgg attagcgacc acccatatga tcattttacc ttaagtacct  28680
cttcaaaggt atcagagtag tatatttgct acagttgatg aacctgcata caacatcatc  28740
acttgaggtc tgcagtttac attagagttc atcgttagtg ttatatattc tagggtttgt  28800
tttgttttga gacagaacag agtcttgctg tgttacccag gctggagcgc agtggtacaa  28860
tctcattgct acctctgctt cccagattca agcaattctc atacctcagc ctcctaagta  28920
gctggaacta caggcgcaca ccaccatgcc cagctaattt tcgtattttt agtggagatg  28980
gggtttcacc atgttggcca ggcaggtctt gaactccttg cctcaagtga tctgcccgcc  29040
tcagcctccc ccagtgttgg gataacaggc atgagtcacc atgcctggcc ttattctatg  29100
ggttttgaaa tgtataatga catgtatcca tcgttgtagt attagataga atagcttcat  29160
taccctaaaa gtcttctttg cactgggttg agttttaaaa gctctttgat tattttatga  29220
cagttcctta ttagatatat cttttgcaag tatttttatc agtctgtggt tatcttgtct  29280
tttacagagc agtaattttt aattttaata aaatccaatt tgtcaattac ttatctcata  29340
tgactctggt gttacatcta aaatgttacc accatactca aggtcaccta ggtttctct  29400
aggaatttta tggttttgca ttttacattt ggtgtatgac ccatttgaag ttaatttttg  29460
tgaggttgta aggtctgtgc ctagattcat tttttttttt tttggcatgt tacttcagta  29520
ttcataagaa acattgttct gtaatcttct ttcttatagt atcttagtct tgctttagtt  29580
tttgggcaat gctggcctca ctgaataaat tcaaagtgtt ccctcctctt caattatttg  29640
gaaaagtttg agaaagacta ttgttaactg ttttctaaat ttttggtgga atttaccagt  29700
gaaccaactg gtcctaggct tttctccagt aggtggtttt gattatgctt tcaatctctt  29760
tacaagttac acatctatac agacttttat aattcagtct tggtaggttg tgcgtattta  29820
ggaatctgac cacttcatct aagttatcca attagttggc atgcaattat tcgtagttct  29880
```

```
ctgaataatc atttttattt ccacaaaatt ggtaatatcc cagtttccat tttttatttc  29940
attgaatctt ctttttttctt agctaatcta gctaaatgtt tgccaatttt gttgatcttt  30000
tggaagaacc aacttttgat ttattaattt tctctactct ttttctgttc tttatattat  30060
ttatttccac actaatcttt actattttct tccttctgtt ggcctttaat tttttttttt  30120
taatttttaa ggtgtaaatt taggttgaga aattttttaa atgaaagcat ttagagctat  30180
aaattttcct tctggtgttc ctttcactac ctgccataaa ttttgatatg ttgagttttt  30240
gtttgtcttg gagtattttc taatttgtct tctaatttct tccttgacct attggttatt  30300
taaatgtatt taatttttgc atattgtgga tttcccagtt ttccttctgt tattgatttc  30360
tagttttatt ccattgtgat cacagaagat attttgtata atcgcagtct attaacattt  30420
attaagtctt gtggcctaac agaggatcta tgttggagaa tgttccaagt gcaattgaga  30480
atactattct ggtgctatta ggtgaagtat tctctatatg tctgttaagt ccaattcatc  30540
tatagtgttg acgtttcctg ttccttactg attttctgac ttattattct atccattatt  30600
aaaagtggag tggtaaagtc tctattattg tagaactctc tgtttttcaa gtctatcaat  30660
atctgtttca tatattttgg agctctgttt gctgcatatg tgtttacaat tgttatatct  30720
tcttggcaaa ttgaccagtt tcatcaacat aaaatataat tcttattgtc ttctaacagt  30780
ttatttttct ttttacataa agcctatttt atctgatctt agattccctc acactccacc  30840
ccagcacgct tttggttaca tttacataat atatcttttc catcctttca ttttcaacct  30900
gtttgtgtct ttagatctaa agtgaatgtc ttacagacag cataagctat gtcattaaaa  30960
aaatccattc tgcttatctc tgccttttga ctggggagtt taatccattt gcatttaaag  31020
taatcactga tcattaaata ctttcagtat tttgttgttt tatgtatgtc ttataactct  31080
tttgctcttc atttccttca atattgcctt tgtgtttagc ttatcttttt gtgtcacact  31140
ttgatcccct tctcatttct tttttatatt ttctttgtgg ttaccaggag gacaatgtat  31200
caacttttaa agttattaca attttatttt tttaaatctc tcccattcgg ggattttagg  31260
aaggttaaat aataatgtaa atgagatacc tagaacaata taagcattca ggaattatta  31320
actcaattcc aatccttcct ccacctccac ctctttctct gtgagattat agaaaagatg  31380
acaaaaagga tgttttctga gccctttaat tgttgagaat gatctttgag aaaaagaaaa  31440
aaaatgaaag cactaggaat gtacaacagc ctggaagtat aattaagtgt aaattaaata  31500
gataaaagtt ataagcagag gaaagtatag tagaactcag tatttaaaag agaatcaatg  31560
tgaaaattat ataaatttat gtaaaataaa actaccagac aaatctgata tccttaggat  31620
ttttctttct ttcatgtgat ttctaattgc tacatatgac actaaaccat tgatctgagc  31680
tgtaagagaa actggaaatt gttctgttat cttttgtaag atttctagaa cattttgccc  31740
tcagacttaa atgccaacgt atttctcact tattgtttac tgcttttgga tttacatatg  31800
atttgattct ttcttatctc ttatccttac aatgtaattc aaactgatgc caatttaagt  31860
tcaattgcgt acaaaaactc tactcctatg cagctccgcc ccatctaatt tacattattg  31920
atgtcgcaaa ttccatcttt gtacatagtt tacatattaa catggattta tacattttta  31980
tgtatttggt ttttaaatcc tgtagaaaat aaaaagtcaa cacaccaata ttaaaataat  32040
actggttttt atatttgtcc atgtgcttac ctttatcagt gttctttaca tctttatacg  32100
ggtttgagtt actgtcttgt gtcctttagt tccaacctaa agaactccct ttagcatttt  32160
tatagggcag gtctagtggt aatgaactct ctgagttttt atttagggat gtcttaattt  32220
```

ctagctcctg tttgaagtaa atttttctgg atatacaatt ctctgttgat tgatttttgt 32280
tcattttccc ttcagctctt ttaaatacat tatcccactt tcttctgcct tccaaggttt 32340
ctattaacaa aattcagctt ataatcttat taaagatctc atgtacatga gtggcttctc 32400
tcttgctgtt ttcaagattc tgtgactttg gtttctgata gtttaaatat aatgtgtctt 32460
attgtgggtc tctttggatt tatcctagag tttcttggtc ttcttacgtt ggtatatcca 32520
tgtatttcaa gacatttgag tagttttcag ccattatttc ttcaaacaat ctctcctctt 32580
tggggacttc cattttacct atattggttc ttttgatggt gtggcaccag tcccctagac 32640
tttgttcact tttttccagt cttttatttc tgcttctcag actcaacagc ttcaagtgtt 32700
ctgtattcaa gtctgctgac tctttcttct tccagctcaa atctgctgtt ggatcccccc 32760
ttgtaaaatt tttaattcca ttttagtgtt tttcaagtta agtattttta ttaggttcct 32820
ttttataatt tctttttgtt gatattctca ttttattaca cataatttgt ctgatttcca 32880
ttagtttttt tctttgtttt cctttagctc tttgaaaata tttaagacat tttaaaagtc 32940
tttatccaag ttcaatttct atggttctgt agagatattt tctgccagtt tatgttcttc 33000
ttttccatgg gccatgtttt cctgtttctt tgtatacttt ctaatttttg gttgaaaact 33060
gagcatttga aaatagagcc aactttccca gtttctgcag agagtcttta tgccacagta 33120
ttcgttcact gattaactgg gtatatctaa gcttagggag cagctgagtc aaaagtttaa 33180
ggtcttctca ggtcttttct gagtatacat gtttcctatg cctgtgtgaa atgttctcaa 33240
tttccctata taaacagcta cttcttcttt tttttttttt tttgagatgg agtctcgctc 33300
tgtcacccag gctggagtgc agtcatctca gctcactgca tcctccacct cccaggttca 33360
aacaattctc ctatacaggt gtgtgccacc acgtctggcc aatttttgta tttttagtag 33420
agacagggtt tcgccgtgtt ggccaggctg gtctcaatct cctgacctca ggaggattac 33480
aggcttgagc cacagtgtcc agcctaaaca gctacttttg aatgctttaa tttcctgaat 33540
agtctcaacc cagtttttcc ttgaggtctt aggtggtcca ttgtatgtct ccacccatag 33600
ttgcttgccc caggcatctg tgggtctgtg gtaccactgc agctttcacc acctgtagct 33660
gccacctttc cctatctgag atccaggtta ggtgagagag atcattcctt cacgcagtcc 33720
catgacaggt tggaacattt caaataaggt ctgttctgct cctctggttg aagggagaaa 33780
attgggaacc ggtttcccac cttctacaaa ccaagatctc atgttgccac gggagtggca 33840
gggcaagtgc aagtgaaaat gccatacaat tttctaccat tttgaacgcg ggtttttctt 33900
caatggtcat ttgcttggtt gctgtaggcc tttcactgtt ttccagagct cccataagat 33960
tactttagcc agtttttgt tctttcctga tgcttccctg gcagagtaag ggttggaact 34020
tccaccattt tgctgattca taactctgta gtcagtttta aatatattga tacttgagtt 34080
tgttttatgg cccagaatat ggtcttggta aatgtttcac atatactcag aaagaatgtg 34140
tattctgatg ttgttacatg ggctgttcta taaatgttac ttaaggtggt taataatgtt 34200
gctcaagtct tctatattct tgctgatttt cttttattta tttattttat tttttttatt 34260
atacttttaa gttctagggt acatgtgcac aacatgcagg tttgttatat atgtatacat 34320
gtgccatgtt ggtgtgctgc atccattaac tcatcattta cattaggtat atctcctaat 34380
gctgtccctc cctgctcccc ccaccccatg acaggcccca gtgtgtgatg ttcccctttc 34440
ctgtgtccaa gcgttctcat tgttcaattc ccacctatga gtgagaactt gcggtgtttg 34500
tttttttgtc cttgtgatag tttgctgaga atgatggttt ccagcttcat ccatgtccct 34560
acaaaggacg tgaactcatc ctttttatg actgcatagt attccatggt gtatatgtgc 34620
tacattttct taatccagtc tatcattgat ggacatttgg gttggttcca agtctttgct 34680
attgtgaaca gtgctgcaat gaacatacgt gtgcatgtgt ctttatagca gcatgattta 34740
taatcctttg agtatatact cagtaatggg atgggtgggt caaatggtat ttctagttct 34800
agatcttgag gaatcaccac actgtcttcc acaatggttg aactagttta cagtcccacc 34860
aacagtgtaa aagtgttcct atttcttcac atcctctcca gcacctgttg tttcctgact 34920
ttttaatgat cgccattcta actggtgtga gatgggatct cattgtggtt ttgatctgca 34980
tttttctgat ggccagtgat gatgagcatt ttttcatgtg tctttggctg cataaatgtc 35040
ttcttttgag aagtgtctgt tcatatcctt tgcccacttt ttgatggggt tgttttgttc 35100
ttgtatattt gtttgagttc tttgtagatt ctggatatta gccctttgtc agatgaggag 35160
attgcaaaaa ttttctccca ttctgtaggt tggctgttca ctctgatggt agtttctttt 35220
gctgtgcaga agctctttag tttaatgaga ccccatttgt caattttggc ttttgttgcc 35280
attgcttttg gtgttttaga catgaagtcc tcgcccatgc ctatgtcctg aatggtattg 35340
cctaggtttt cttctagggt tttttatggt tttaggtcta acatttaagt ctttaatcca 35400
tcttgaatta atttttgtat aaggtgtaag gaagggatcc agtttcagct tttacatat 35460 ggctagccag ttttcccagc accatttatt aaatagggaa tcctttcccc atttcttgtt 35520
tttgtcaggt ttgtcaaaga tcagatggtt gtagatgtgt ggtattattt ctgagggctc 35580
tgttctgttc cattggttta tatctgtttt ggtaccagta ccatgctgtt ttggttactg 35640
tagcctcgta gtatagtttg aagtcaggta gtatgatgcc tccagatttg tccttttggc 35700
ttaggattgt cttggcaata caggctcttt tttggttcca tatgaatttt aaagtagttt 35760
tttccaattc tgtgaaggaa gtcattggta acttaatggg gatggcattg aatctataaa 35820
ttaccttggg cagtatggcc attttcacga tactgattct tcctatccat gagcacggaa 35880
tgttcttcca tttgtttgtg tcctcttcta tttcgttgag cagtggtttg tatttctgct 35940
tgaagaggtc cttcacgtcc cttgtaagtt ggattcctag gtattttgtt ctctttgacg 36000
caactgtgaa tgggagttca ctcatgattt ggctctctgt tagtctgtta ctggtgtata 36060
agaatgcttg tgatttttgc acattgattt tgtatcctga gactttgctg aagttgctta 36120
tcagcttaag gagattttgg gctgagacga tggggttttc taaatataca atcatgtcat 36180
ctgcaaacag ggacaatttg acttcctctt ttcctaattg aatacccttt atttctttct 36240
cctgcctgat tgccctggcc agaacttcca acactatgtt gaataggagc ggtgagagag 36300
ggcattcctg tcttgtgcca gttttcaaag ggaatgcttc cagtttttgc ccattcagta 36360
tgacattggc tgtgggtttg tcataaatag ctcttattat tttgagatat gtcccatcaa 36420
tacctaattt attgagagtt tttagcatga agggctgctg aattttgtcg aaggcctttt 36480
ctgcatctat tgagataaac atatggtttt tgtctttggt tctgtttata tgatggatta 36540
tgtttattga tttgtgtatg ttgaaccagc cttgcaaccc agggatgaag cccacttgat 36600
catggtggat aagctttttg atgtgctgct ggattcagtt tgccagtatt ttactgagga 36660
tttttgcatc aatgttcatc agggaaattg gtctaaaatt ctcttttttt gttgtgtctc 36720
tgccaggctt tggtatcagg atgatgctgg cctcataaaa tgagttaggg aggattctct 36780
ctttttccta tttactgtac atttattcca ccagtgacta aaacaggtgt atcaataaaa 36840
tctgttccct caggttttgc ttcaggtatt ttgagggtct gttatcaggt gcataaacaa 36900
gattgttatg tcctattctt aaattaatct ccttataatt atgaagttaa ttttttttt 36960

```
cttgagatgc agttttgctc tgtcgcccag gctggagtgc agtggcacaa tctcggctca  37020
gtgcaacctc tgcctcctgg gttcaagcat ttctttgcct cagcctcccg agtagctggg  37080
gttacaggta cctgccacca cgcccggcta attttttgt atttttagta gagatggggt  37140
ttcaccatct tggccaagct ggtcttgaac tcctgaactc ttgatccacc caccttggcc  37200
tcccaaggtg ctgggattac aggtgtgagc cactgcgcct ggacctggcc cgaagtaaac  37260
ttctttaccc ttgctaatga tctttgctct gaagcatgct ttgctggtat taatatagtc  37320
attccttctt tctttgattc atgtttgcag ggtatatctg tttccattct tttactttta  37380
acctattgtc tttatattta aagtgcattt cttgtaagta taattggttt cttaaaatcc  37440
aattatctgc cttttaaatg tcatttttat atgatttgca taaatatgat tattattaca  37500
gctaaattga aatctgtcat cttgctattt ggtttctatt tatcccattt ttttcccctc  37560
tttttttgct ttccttgaga ttgaacattg tattagtttt ctagggttgc tgtaagaaag  37620
tgacataaag tggatggctt aaaacaacag aaatttattg tttcagtttg gaggctagtc  37680
atctgaaacc aaggtgtcat cagggccgta ttctctctga aacctgtagg gaagaattct  37740
ttcctgcctg ttctagcttc tagcattttc cagcaattct tggcattcct ttgcttgtag  37800
atgtatccct ccaatctctg cctctatcat aacatagcca tcttctccct ttatctgtct  37860
attcttctca tcttataaga acattaatta ctgaattggg gcccagcata gattaggcct  37920
aatctcatct tgaataggtt acatctgcca aagattcttc ttccaaataa gatcactttt  37980
acagctttta caggtactga gagttagaac ctcaatatat cctttggtgg ggaccgacct  38040
cttacccata aaaagtattt tatatgattc cattttatct ccttttttagg ttattaacta  38100
caattttttt ttcttttttt tgagatggag ttttgctctt gtagcccagg ctggagcgcg  38160
attttggctc actgaaacct ctgcctcccg ggttcaagtg attgtcctgc ctcagcctcc  38220
tgagtagctg ggattacagg catgtgccac cgtgcctggc caatttttgt atttttagta  38280
gaaacagggt ttcaccatgt tggctagggt gggtctcaaa ttcctgacct taggtgatcc  38340
acccacctcg gcctcccaaa gtgctgggat tacaggcgag agccaccacg cctggcttta  38400
taattttttt ttaattcagt ggatgtttta gggtttatag tatacatctt tatcacagtc  38460
tagctccaag tgatatatcc ctttatgtat agtacatgac ccttacagta gtgcatttcc  38520
atttttcctc tctggcattt aggctattgc acacacatac actcaattca tccctttgtg  38580
tagatccgta tttccagctg ctatcttttg cttctgtctg aaatatatgt atgatttctt  38640
ttatgactat tttgagaaat ttggttatgt gcatttgtct atttttctta tgtactttta  38700
gctcatcaat cttaagtctg tgagtttata gtttttaaaa acaaatttga aattatttgg  38760
ctattatttc ctcaaatatt tttttctgcc gcccctgctt tccctttcct tagggatctc  38820
tgatttccac ctatattact ctgattgaag ttgttccacg tctcttttga aaatctctga  38880
aaaatctttt atcatttgga taatctgtat ttgtacatct tcaagtacat taatattttc  38940
ttttgcaatg tttaatctgc tgttaatccc atgtagtgga ttcttcatct caggtattgc  39000
tgttttaatc tctagaaatt ccattgaagt cttacttgat gaaaaaggca gataaaaaca  39060
aatgttggca aagatatgga gaaatcagaa tctgcacaca ctgatgatgg gaatgtaaaa  39120
tggtcaaggc aatttggaaa gcagtctggc agtttctcaa aaggctaaac gtagttccca  39180
tatgacagca atcattcatc taggtatata ctccagagaa ataaaaaacat atccacacca  39240
gaacttgaac attaattttc atagcaacat tattcctagg ggtttaaaat tttttacatt  39300
atttttattt aaaatagaga cagggtctca ctacgttgca taggctggtc tggaactcct  39360
```

```
ggaattaagc attcctcctg cctttgtcct gttttctcca ctggaaaaga ataaaacttt  39420
gtacacttgg actaacaact cccgattccc tcctttacca acatgcccca cagcctctag  39480
taacttactc tctactttca tgaattcaac ttttttaaga ttccacatat aagtgagatc  39540
atacaatatt tgtctttctg tgcctggctt atttctctta gcataatgtc ctccagattc  39600
atacatgttg tcttaaatga caggatttac cttcctttaa aggctgacta gtacttcatt  39660
gtgtatatgt atcacatttt ctttatccac ttatctgttg atgggcactt aaattgtttc  39720
aatgtcttgg ctactgtaag taatgcttca ataaacatgg gaatgaagat atcccttcaa  39780
catattgatt tctgttcttt tggataatac tcagaagtga gattactgga tcatatggtt  39840
gttctatttt tttcagaaac ctccatactg tttttcatag cggctgtact aatttacatt  39900
cccactaaca atgcatgagt tcacttttct ggacatcctc cccaacactt gttatctttc  39960
atctttttca taaaagccat tatataatag gtgtgaagtg acatctcact gtggttttga  40020
tttgcattac tctaataatt agtgtgagca tttttttttt ttcatgtacc gaatgtcttt  40080
tgagaaaggt ctcttcattc ctttgcccat tttaaaatca ggtggttttc ttgctcttga  40140
gttgtttgag ttccttatgt attttagata tttacccatt tccagatata tcatttatat  40200
tttttcctat tctttgagtt ccctcttcac tgtgttgttt ccattgctgt gcaggtcttt  40260
tattttgatg ccaccccatt tgtctatttt tgccatgctt ttgcagtcat atccaaaaaa  40320
atcattccca agaccaatgc tgtggagatt tccccctatg ttttcttcag taggtgtaca  40380
gttttaggtc ttatatgtta agttttaaat ctattttttt atatggtgta aataagggtc  40440
taatttaatt cttttgcatg tggatatcca gttttcccaa caccatttat tgaagaccct  40500
gtccttttat acttttcagt atgcagatct tttacctcct taaatttaca cctcagtatt  40560
taatatttgt tgctattatg agattttcat aatttccttt tcagatagct cattaatagt  40620
agatggaaac actactgatt tctgtaagat gatttgtat tacggaactt tactgagttt  40680
gtgtatcagt tctaccaggt tttagttttg ttctggtgga gacattacag tttttgtat  40740
atggttatgt catcagtaat tacagatgat ttaacctatt cctttcctat taggatgcct  40800
tttttttctt tctcttgtcc aactgctctg gttaggactt ctagtactat gtcaaaaagt  40860
gatgagggtc gtacatggcc tccataccta atctgttgag agtttttacc atgaaaccag  40920
gttgaatttt gtcaaatgct ttttctgcat ccattgagat gatcatatga tttgatttac  40980
accctccatt ttgttatgtg gtatatcaca ctttttgatg tgcatatgtt gaaccaccct  41040
tgcatcctaa ggataaatcc cacttcatca tggtgaatca ttctttgtat tcgtgaatcc  41100
agtttgctaa tatattgttg aggatttttg catccatgtt catcagggat attactttgt  41160
aagtttctgt ccttaaagtg tctttctctg gctttaataa cagtgtaaca ctacccttgt  41220
aaaatgaatt tagaagtatt ccctctgctt cattgttttg gaaaagtttg agaattttta  41280
ttagttcttt aaatgtctgg taaaattcag tagtgaagct gcctaatcct gggctttcct  41340
ttggtgggat actttttatt actggctcaa tctcttttct tgttattggc ttattcagat  41400
ttgtttcttc atgattcact ctttgtaggt tgtatatgtc taggaattta ttcatttctt  41460
taggtcatcc aatttgatgg tgcataactt catagtagtt tcttataatc ctttgtattt  41520
tggtgatatc agtagtaaat gtctcctctt tcatttctga tcttatttga gtactctttt  41580
tttctcctag tctaggtaag aatttgttga ttttatcttt caaaaaaaaa aaaaaccaac  41640
tcttagcaac tcttagtttt gttcattttt ttccagtctt tatttcaact gtgatctttg  41700
```

```
ttacttactt ctttatgcta actttcgggc ttagtctgtt cttttcctag ttcctttagg  41760
tgaaaagtga gattgtgatc cttcttcttt attggcgtag gtttgtatcg ctataaattt  41820
ccattaggac tgattttgct gcatcacata agttttgttt ccattttcat ttgtctcaag  41880
gtaatttttt atttactttt tgacttcttc tgtgaactat tagttgtttg ggagcatatt  41940
gtttaatttc cacatattgc tgtattttcc accagaattg attcttgttc ttgatttcta  42000
gtttcacgcc attgtaatca gaaaagggat ttgatatgat ttctgtccac ttaaacttaa  42060
gattagtttt gtggactaac atatatcctg gagaatgttc catgggcatt tgagaacaaa  42120
atgtattttg ctgcttctgg atggaatgtt tcatatatgc ctgttaagtc cgtttggtct  42180
aaagtgtaat tgaaatccat tgtttcttta ttgattttct gtctaggtga tcaatctgcc  42240
catggtgaaa agtagagtat tgaggtcccg tattatagta ttgcagccta tctccctctt  42300
cacatcattt aaaaattgct ttatgtattt aggtgggtca atgttgggtg catatacttt  42360
tacaattgtt atgtcttctt ggtgaattaa tccctttatc attatataac aaacttcttt  42420
ctttttatag tattgactta aagtctattt tgtctgatag aagtatagct acccctgctc  42480
tcaatttcca tttatataga atatcttttt ccatcccttc actttcagtc tatgtgtatg  42540
tttagtagaa aagtgaatct cttgccgggc gcagtggctc actcctgtaa tcccagcact  42600
ttgggaggcc aaggcggcgg gatcaccaga ggttgggagt tagagaccag cctgaccaac  42660
atggagaaaa cctgtctcta ttaaaaatac aaaattagcc aggcgtggtt gtgggccctt  42720
gtaatcccag ctactcgaga ggctgaggca ggagaattgc ttaaacccgg gaggtggagg  42780
ttgcggtgag ctgagatcat gccattgcac tccagccttg acaatagcaa aactccgtct  42840
caaaaaaaga aaaagaaaaa gaaaaaaaag tgagtctctt ataggcagta tgtggttgtg  42900
acttaaaaaa aaaaaaaaat ccattctgtc attctatgtc tttttgttgg agaatctaat  42960
ccgtttacat tcaaggtaac tattggtaag aaactgctag tgtcattttg taatttgttt  43020
tctgattgtt ttgtaggtcc cttgtttctt ttttccctat tgctaccttc ctttgtggtt  43080
tggtggtttt ctgtggtggt gtgctttgaa tcctttcttt tatagtatat gcgattacca  43140
ttgtatttgc tgtaaggcta acttaaaaca ttttatcctt aggctacttt aagcgataaa  43200
aacttgcctt tagttgcata caaaaactct acgctttcac aaccccccccg cctttcgtga  43260
ttttgatgtc aaagtttaca ctttttttaaa tttgtatctc ttattgtagc tacagttaca  43320
attacttctt gtagctacaa cttattgtag ctacagttgt ttttaatagt ttcatctttt  43380
aaacctccta ataggaataa cattgcttta cctgccacct ttacaatact agagaattct  43440
gactatgaat tacttatacc atttagtttt ttacttttat gtttctcatt aactagcagt  43500
cttttattta agcctaaaga actccctttt agtaattcca gtagagcagg cctagtagtg  43560
acaaactccc ttaggcattg tttatctgga aaagtgttta tttctccctt tgccaagtaa  43620
agtattctta attaacagct ttgtttcctt cagcactttg aatataccat cccactctct  43680
actggcctgt aaggcttttg ctgataaagc cactgaatct gtattggggc taccttgaat  43740
gtgatgtttc ttatctttgc tgctttcagt attctttgtc tttgattttt gataacttgg  43800
ttgtgatgtg tcttggtgaa ctctttaggt tgaatctgat cggtgacctc agcttcctgt  43860
tcctgaattt tgtcatcttt tctcagattt gggaattttt cagctattac ttccttaaat  43920
atgctttcta ggcctttttc tttcttttct ccttaaggac ctcctattat gcaaaagtta  43980
gctagcttga tgtgtcctgt aattcttata ggcattcttt tttgtttttg tttctcattg  44040
gataatttca aatgtcttac ctttgagctc attgattctt ctgcttgatc aagtctgctg  44100
```

```
ttgaagcgtt ctacttagat tttcagttca gttactgtat tctttatctt tagaatttct  44160
attgtttttg tttatatttg ttaaacttct cattctgttc agatgttgtt ttccaaattt  44220
catttttcta tccatatttt cttgtacttt gttgaactta agaggattag tctaaattat  44280
ttgtcatttc acaggtctcc atttcttctg agtctgttac tggagctttc atatccaatg  44340
tacaccagaa actttgctaa ttccacagta aatgttagaa atgggttttt attgataaaa  44400
tcagtggctt gctaattagt atgttagaag ctggcttgca ttggtgaagt tgagggtatt  44460
cgatatacgt atcccggcta aaatacttct aaagaacctc tccagctttg caagaataga  44520
gtataggaat ctgaggaggc ctttaacatg gccctcagaa aggacacaca gggcttgacc  44580
tctaaacata taaacatata cagaaacgag gtcagaacat gttttgactg atgccagtag  44640
taacacagca gagcctattg ctggtcactg ttaccaatac cttgtgtaat aaacctttca  44700
tttaaattga gaggttgtaa gccccgaaaa agcaaagggc ttacagtacc tcttgcctga  44760
acactcctgt gtgtgctttc taagaaatgc ttttaaaata atgcctgtgg cacaaattga  44820
tttgacactg gctctcttta taagctgcta tcaaggttgt ggggaatagc taactcttac  44880
ccactttccc tgacaaatag gaacccgtag ttacctacca aaagtatgta aaagctatat  44940
ccgacccaaa ggccagttag gtcaaaacac cttgaaagga gctcagttta aggaaatcag  45000
tggtgtcaca gtgccccact agcgtgtaaa agttttcata gtttgactat cggatgtgct  45060
tagtttcaca gctgagtctt accttgtgat acttttagag caaaagtcaa atcaaagatg  45120
atttaaaaaa acatttcaaa gattcataaa gaataaatgc ctcctcagga agtcttctgg  45180
agttctgccc acttccctta ggtggctctt tactgtgccc atctcatagc ctgtctcctt  45240
ccacttggtg tattgcagag taaagctcac tgtttacagg ggtggtagaa agtgtggtcc  45300
tttcccagac tcctttttcc cttcctcttc tcatttttca gaagatgtgt ttgataataa  45360
acgaaacaaa atgactaaca cattgagctg agctacataa gcagatgtca gtttgacgtg  45420
aagagtttaa aagatctatg cattatctgg ggactcctcc cccagacctg aaggatcagg  45480
tgctgccttc tatgccacct gtgcagacag caaaagagga aaaccatacc cacgttcagt  45540
atgaacaaag gggacatttg aactctgtgt ggacccctca ttggaagggt gtttcttctc  45600
ctgctgcatc cacaaagagc actccttagc cttgcctttt gtcagttctc tctccaataa  45660
ggcttgagca gagacaaccc agtgcagttc agagagactg aagtctggtg ttccaggtct  45720
gagtcctagc tctagctctc tgtgtaactt tgggatgtcc caaagtaact tttcacaact  45780
tgataggtgt taacttgaat tttggataca ggtgactctt agcccatccc ctctctgtgc  45840
ttcagatatg tcatcacttg ggccatatga cctctggaca cctttcctac tttccacaat  45900
ttcagagcag cagagcagac tggagctcct gctgcctctg agcttcagtg aattatcact  45960
cgttggaggg aagcttcaag cattttgtta tctttcaaga gcaaacacag tgtctgtcag  46020
caagaatatg tagcagatgc tagtgaacag cagtgattag ggttgaatgc tggatttaaa  46080
tatggagctt aggctgtgaa ggaagcctga agaacctaga gccccatgaa gctgccctct  46140
gtgagatctg acaccatttc ccactgatga gccatgggtc taatgggtag cactgattcc  46200
acatacagta tgtgagtgca atacagtgaa agcaaagaga ataaaatgat ggctaacatg  46260
atgttccaaa ctttaaacag gagaaaaaca cacaattcca ttatgtataa gaacccacac  46320
agagatcagg agaataacct cattggagaa tgaatgacct gtgtggggaa tttagggtag  46380
agttgagatt gaaaaaatgg gccgaagtca ggtggccaag ggccttaata ccttgtatac  46440
```

```
aagatgtgta gtcaaggaag accatgcctt acttatgcat caattccctt gggcctacaa  46500
agagctgcct agcctgggac tgttgtagag aaaagctaca gtgttccaat gacacaggga  46560
ctcctccatg tatgtatgag tgcccagctg gctctgtaat aaatcttatt tttatttatt  46620
aacttttctt gcgcattggc ttgatgcatc agttggaagt cagaggccaa acgaagtgaa  46680
cactgagcca aaggaagttc tcagccttta gggaggcaga attcacttta aacacaataa  46740
acaaatgaac tcacattata caggagagag tcagaagatc ccagtggctg gtgtcatcgg  46800
gccatatttg cccgaagtgc ctattcctta taggaaccca ctcccagggt tgatgggcta  46860
catccttagg aggctttatg cctatgttct cctgaccact ggctcctcca gggctggcct  46920
tttttagtct ctctgtagag gttcctgtag ctggttggat ataggctttc acagaagggt  46980
cagtgccttg ggtctggtta caggactgtt aatcttgctt tgttaagagt aatgttattt  47040
ccccatttcc aaattctcca gggagatgga atgtcaaaga tagtatgact gtagcaccta  47100
aatcctgggt tccagaagca gagaagagaa tacactgaag ctgtagaaag gcctattagt  47160
ccatgtcaga gattaactgg atgcgaggac catttctggg atggtgtata cagaactgga  47220
gaactggata gggagtcaga aacaaagagc tgaagatgat gcctttgaag tttccaacgt  47280
ggataactag gtcaacagaa tattactcaa gaaagtatta acataggatt gagatgcagt  47340
cagtagtaat ggaattgaaa tttcaaagta tatacctcat ggatctcagg gggtgttgag  47400
ctgatcacct gggctaacac tcctatgacc ctggggaaaa tcaaatgacc tggtactgta  47460
gccatggtag gggtgtcatc accttaatcc aactgggaca gtgctgtttg atattcatct  47520
ggaacttggt gcagacccac atttgctgg gtttcaccac aaccaaggct tttttgattc  47580
ttttctcttt taacatcagt acatcactgc aaagttaatc ctcatataat aggagatgaa  47640
actaattgct tataaaaaca agatttttac aacactaaaa ttgttcaagc atatgggcat  47700
atttatagtt gcaggcagtg tttcagatgc agactgttct tggctgcagt ggttgtttac  47760
aggcagcatc tgttctgatt aaatatttga tgattatccc cgaatgtttt aaagcatagt  47820
actgggctct gctgactgta caacaaactg gcatttttga cctatagggc actgggctag  47880
gagatacagt tctgagggaa gtgaaagata gttaacaact gcacaactga ccctttatta  47940
gttgcaataa agcaatccaa ccacccaacc cactgtgatg gctttcctac tatttaaggt  48000
tggtggtgtc aaagagacac cctcctgtac agtgtgcagt gaatcaacat catttccaca  48060
aaacctcctt cctgcacaaa ggaattatca tactttgtta cgaagtaaaa ttttcctgta  48120
tcagtcacag gagttcacca gttaagatac tgttagttga agacttctgg ggtgacttaa  48180
tgaaatagct cagccatctg gtttaaaaac tggattcttc tatccctcca cacagctgtc  48240
catgcacctg catcatctca aggctggtct ccctggtggt agaaaggctg acagtaaaaa  48300
ctggagccac atgattcctt gcttaggcag tgtttcttca tactctcaca tgagagcagg  48360
catgttcttt ccctaggctc acagtaaaca ctctgtcaaa tctcacaggc ccaaagtgct  48420
tttggttatc cccattccaa gccaatctgt ggcatggaag atagcattac cctgactgcc  48480
ttagactaat atacctactc cacttctggg gctgggaata attttgaggt caaccatcca  48540
aactgcatga cagccattcc atggaagagg tatggcctaa atctttgggg caacctgaat  48600
tcatgaaaac tctcttagat ttatgtaact atttttagaa ttcacttctg tatcatttaa  48660
ttttactaat aaaaatacca cctttaccct aaatgtcagc caagcgtaag gctccgttgg  48720
gacagaagga actatcaaag ctttgtgttt ttatacatta gcagcatttg acaaagaaat  48780
aactctgaag gaaggagaat aaccaggcag agtctagatg catggaaaag aagtctttga  48840
```

```
gaaggcttcg caggctgaag gaaagggcag gactacttca ggaatacaac gtttaagtaa  48900
aagaggttgg ggtctgttga tcttgaggag agatgaggat ggactggaaa ataggagtga  48960
gatatagtag gagaggaaag gatatggatg atgtatatac tgtatgggta accatcagtc  49020
gaccctaaga agataatagt tgttaaatgg ttagctattt aatgaaagaa acctgaacaa  49080
gtaataatct tgagttgcaa agtggctgga gtcacacaac agactaaatt tctggtagaa  49140
caaatccagc agcttatgtg aaggttacca tgtctgaagc tggatagaaa aggtctaact  49200
tccaaccaaa gtcacagttc ttgagctcgg tacacagaga cagactgcta acagctgatg  49260
tgtcctcagc gagagtgtcc tcatttatat cctcgttctc ttctgcctcc tttttttgtt  49320
ttaaactttt gggaagtctc atcattcaat acagttctaa tatatcacaa taacagaggc  49380
ggcccaattt ctacaaattg actaattcta tccctgaaaa gttcatacaa taaaactata  49440
caaagcatca ttttcaacca tcctatagaa aaatttccct attaaatttt aactctaaat  49500
cctctatctc tgttaataac cttactaaaa acttccccat cactgcctgc cagggagatc  49560
aaaagaaacc aaatttaaga aacctccaac acctgtacct gactgaaaag caaacataca  49620
gacctttcag tcctgcccct actattcagc tcctatcaca gagacatggt ggatgtcccc  49680
ttgggaagcg gatagctctt aggtggaagc taggcctgca ataagcaggc caggaaacat  49740
gtctcccagg ccccatactc ttggcagaag cacttggcca ccagacagca tgtcctgtca  49800
acctacagag ttcttaaaaa caaacactgg gacccagaat agtaccctgt ggtcatagtg  49860
cccacagttc actaagcacc ctcacaggtc tttgacagaa cactgactgc caggtcacct  49920
ggtgggcaga gaaatggaag attcccaggc ccaactagca tctcagggaa gaaccacaag  49980
cagagcaact ttcagagctg gtcggccagc gttggcaccc agggaagcaa gtgctattcc  50040
atatttggag agaacataaa actcaaggaa acagagaagt cctactcaat accgttctca  50100
actgaaaaca agagaacttg caaaaaagaa acccagtttt ctggagtcca tggagaaata  50160
tgaagccaat gctcggctaa cagagcagaa agccttttat aaataatgcc agtcaaagct  50220
ccaaaggtca gagctgatgc atgccggatt gttctgacaa tttcttaggt ttctaggcaa  50280
caaggagctg gtcaaacagc tcacctccaa ggacatactt tataatacca ccctggtaga  50340
cgagagcgag gcagcagtga aggcaatagt caagaacagg agagggaggt aaagaacaag  50400
atgctcttca gacagtctgg acaaagacag tccctaccca gctctcagga gttgcctcct  50460
taagaaggtg gaggcccagg cagctcccag ggtgacccta aagacagact ccaaggaaaa  50520
gggtgtgagg gcaatggtga atataaggag gtcccctttc agtaggcaga gcaagtcagt  50580
tcaggtctta tttttagagt ctctgaacag tgaagagaag ctttctgtgg acagcattcc  50640
accaccatgg gaggggaaag gtgccatgag agacttctcc agtggggcat acaagcattg  50700
tgcagtgatc cccaagatcc agccactggc aggaaatcga aaggcaagct tcttaaatac  50760
atagtatatg gagacagaag tgtggagcac tcccaaaatg aaaggccaag acccaggaac  50820
aacctccaca acctggagta tatacaaatg aacccagccc tgctgactca gatccacacc  50880
atcctaaagc aggggtttct catgaatgaa agggctaagt atttggtgga gagaatgaga  50940
agtctcccac tgcccacaca ttttttcttc agagatttct tttccaagag ccccttgaat  51000
aaaggaaggg agggagcact gaatgcccca gaaatcagaa tgcatggtgc gggaagacga  51060
caggaaatag ttctcaaaga gatcagaaaa taaattggaa gcaatttcat taccacaaag  51120
aacagacatt ttttctaagg cacccctccc ctttccaccc aattgtcatt cagcaactac  51180
```

```
tgaatactta ccaatgaaaa acgttacccc tgacctcaag gctgctcctg agctctggta  51240
gaaaatgctt tccttgtcta taaaacatgg caagcaaggc aggatttaac agtaagggca  51300
cagtagcact gcaagccttc aaatggaaac ctggagacaa gcagtgagaa caggaagcaa  51360
aagcagggca ggtgaagcta ggaccagggc atctggaact ttccacacag gttggatctc  51420
catgccagac aacagttttc aaggaaaaat atctaagagg aacatgactt tgggaaactt  51480
tttggcagta ctgcttactg tatactagag agtaaaagaa tttggggaac attcaccaat  51540
ttgcttcttc aggggcttgg gtagggaacg tgaacaggaa cctggctcta atttctgaac  51600
ttttttatca gtaaaaacaa tccaacaaac gaaagctagt cagtgagaga actgggaggg  51660
tctgccctcc ttccctgagt caagccttct ggggggacct cctgacattt aattaagcaa  51720
agacaacgcc cactgaagga agctgacctg aaagtgacac gctactgtga aatgagcatg  51780
aagtgggagc ttgttacata tatgaaatgg ccagcgatcc tgagcaaagc gcttcagagc  51840
ttgagaccta agtcttctca tctatatact gagggctgga caagatgatc tgtcaagcca  51900
tttttatccc taatccacca aaatccaatg ctttagttta ttgtcacaaa agcaggtatc  51960
gaatggctat cctgcagtgc ctccaatcaa cattcagact tttccctga ggcaatataa  52020
gataacagtt aacatgtttt tatcaattag gtggtcatga gataaatata tatgggaagt  52080
ggtagttttt cacttaaatg catataataa tggtacagct ctctttgaat agtatttgtt  52140
tatttcttaa atatttaagt tcctaaagac ggtaagaata acccaaggaa gtgaaatcaa  52200
tgtcacaaag cacatggcta aataactgca ggtttgcagt gccatgtgtg agatcagatg  52260
acagaaggga gaactacctt taggcagagg cttctcatgt cccctggagt ggccatgtgc  52320
tgttctacat gactacttcc acttcggtta tgtagaagct atttaaagca cacagatgtt  52380
tgtgatgaga aaaaagccac ccttaattga ataatggaaa ttataagcat gatttgaggg  52440
tgggggtgga ggtgggagta gagatgggta gaaaggagtg caatggaaac aaaggagcct  52500
tcataaaatt caagtcactt cttaggataa cgtgattgat ttactcacca ccttcttagg  52560
aacataaagc aaacaagtgg gttttccttt tactgctttt ctgaaatgag ctacactcaa  52620
gaaagcagca cgggggttgt gctgtccctg cacagtggca ggagagtatg aggagcaggt  52680
gaatgccaca acagctccat ccaagatcat ttttcacatg caggaaccat tcttatacta  52740
ccctttactg gtaatttctg tagaaatctg gaagtctggt tgacaccctc ctgtacagtg  52800
tgcagtgaat caacatcatt tcccttggac tttgcaatca cggtggcatt catacattca  52860
ttcaacaagt atgtatgtac aggacagtgg agtaaagaaa acagatagtt cttactctca  52920
cgaggcttaa aatttcagga gggaactagg cagtcatgaa gtaaacataa aaacacagat  52980
tgtaataggc actagagaat aatgaagact ttggggaaca caatttaaat tggaaaaata  53040
tctcagttcc gttaacacat gttgaagggg aatagcattg ttttgctgga tttggggcct  53100
ggatgcaagc atgttgggta tgcattgtag ggtaatgcat ttccttccat ttgggcccaa  53160
gtgtatattt accacccagt tgtgatgagc tgggatcctc ctgctcaatc tcagcttgaa  53220
gcacttggag gttatctgcc tgctgtgggt gattattttg gagcaaggta cttcatttgc  53280
ctcaagaaac agatttgata ccactactgt gccctttttgg aacagagaag taggcaagac  53340
cccagtgtga ggcagagtga tgggatcttt agggacataa ttgatgatgt aactgatgat  53400
gattttggag tttatacatt tccaaagttt caaaatattt tcacttggtt gatttatctt  53460
tatggtgatg acactacgta gatatatgcc cttcttaaaa gttacagtaa gaggctggga  53520
gcggtggctc acgcctataa tcccagcact ttggaaggcc gaggtgggca gatcatgagg  53580
```

```
tcaggagatt gagaccattc tggctaacac ggtgaaactc cgtctctact aaaaatacaa  53640
aaaaattagc cgggcgtggt ggcgggcgcc tgtagtccca gctactcagg aagctgaggc  53700
aggagaatgg cgtgaacccg ggaggcggag cttgcagtga gctgagattc cgccactgca  53760
ctccagccag ggcaatgagc gagactccgt ctcaaaaaaa aaaaaaaaaa aaaaaaaaaa  53820
gttacagtga gagttgacat tgagaaaagg gaggcccagc cagggttatg caaagacaca  53880
gtagggagga ggatgggaag tttctgagac accccagtaa ctgcatgggt ccacaaagca  53940
catgtacagt ctgctctatg cactgcaggt acagccacga ataagacaaa gtctctgccc  54000
tcatggagct tggtgtctgt ctactggagc agacaaaaac aaacctgctt tttctcattt  54060
gcctctactg tgggttccgt gtataactct caaatgctag catttccatg cattccatcc  54120
ttgtccttct ctcctctctg ccttttccag gagaattttc ctagccacag gttcagctat  54180
ggtctatgtg ctggagtcat acatttttat cttctgtgta cgtttttctc tagacccata  54240
tttttaattg ccttaggaca gctctccctg gatatccctc agacacaact aaaacatcat  54300
tcaattgtac tattaataat tttcccttca aaatccactc ctcttctcta tagacctaac  54360
agcaacactg tccgtccagc tctcaaaacc tgaaatgtgg gagttgtctt tgactcttat  54420
ctttcccatg catgagcact gaatcaatca gagtccctag catgtcttgg actgtggcct  54480
cccttctatc ttcagattat ctgccttttt agaattatgg caataactta actgcaaaga  54540
ccacatgtgc acttgtgctc tttcagtttg taataaatat aaaatgaaaa gtgattatgt  54600
ctttgcttaa cgtctgcaaa ataaaagtcc aaagtccttg gtatggtcta taaggccctc  54660
attatctgac ctgcctgcct tcccaatctc atcttaatcc cttacagcct gacactcaga  54720
catactagac tttccaccta actcactcac atacacctat cctgtatgtc aagattcggc  54780
ttgaccttca tcacctacct atctgcagta tttttggatc tgaattctct gcccacattg  54840
tactttcaca tacttctttt acccttagtg gtttgtactt atgcctggtc taactagatt  54900
gtctccctgt aacagacttc ttgattcaac aaagcagctc tgaatcagcc tgaaacctat  54960
ggcacactgc aaaatggcaa acattcaata ggtatttgcc cagtaaatgt taatgaaagg  55020
aaaaaaattc aaacttcagt tggaatagga ttagagacaa gttaaaaaaa agtttcccat  55080
agaaatcttc ctcatcgtaa atatcatcat cctaaatgtc ccgagtcttt ccatgggtct  55140
aatttaccaa atcatgaaga ctctctttct cactgtgtat gtgtagtggg agaggcagag  55200
acagaacggt tttttttttt ttttgcaagt ctgctctctg gattcgtttt tctggggatg  55260
aaatctcagg ctatgtagct tttctggtcc ctttttggta atcaacaaat catcagtttc  55320
tctaggtatt aaaaagccta cacttttgaa acaccaagag gccaaactct ctcttaattg  55380
aaaacataat tctgcctctt actgaggtct ttgggtggga agcttaaaga cagcagtgtt  55440
ggggcaattg gtttttcttt tcctccctcc accttctttc ccattcaaga gctgttgctg  55500
ccctttctgg aggggaggga attagaaaaa aagatcctgc cttacccagt cactgttaat  55560
tattactttg agccagggtg gggaatgact ttctttcctg gaatacaccc tgctggaaac  55620
cacagctgag attctctaag ctggcagctt ccaacctctc ctccctcaac agcttcaaca  55680
ttatatggca ctcagctgca gggtgcctgg ctccaggccg gcagtccatt tgtgcagggt  55740
agttttcaag atggctcata gcccatctct ttcagtgacc agcgtggcct atgggaaaca  55800
tacatcttga ctccattatt ggtaggagta ctctttagtt aactgccaca ggccagttca  55860
gacacgtctt accctgagag ccttttcaga gtcaggtacc atccctgtgt cccccagcat  55920
```

```
ctgaagatca caggtgaagg tctccaagta gttcacttaa aaaatacctc agtaggttta  55980
agaacaggga aagctcccaa ttcattctgt caggagtatg actctcatcc ccaaactgga  56040
cagatatata atatgaaaac tacagaccaa tattccttat gaatatagat gcaaacattc  56100
taaacaaaat actagcaaac caaatccagc agcatagaac aaggtttatg tagcatggac  56160
aactgagatt atcccaggaa tgcaaagtta attcaatata caaaagtcca ttaatacaac  56220
atattaataa aggacaaaac aacatgaaaa tcttgataca gaagaagcat ttaacaaaac  56280
ccacagcccc tccttttttt ttttttgatt aaaaaacact cagtaaacta ggtttaataa  56340
aagaatttcc tcaacttgaa gcaaacccac agctagctaa catcatactc aatggtgaaa  56400
gactgaatgc tttcccctta aaatcaggaa caagaaaaag atgtctgctc ttgtcacttc  56460
tatccaatat tgtactggag gtgctagcca gcacactaag gcaagaaaat gaaataatag  56520
gaatctagac tggaaaggaa gaagtaaaag tatttctgtt cacagatgca tgatctcata  56580
tgcaaaaaat actaagtgac aaaaaaagaa ttttagaaaa gctacaatat acaaaatcaa  56640
tatacaaaaa ttaattttat ttctaacacc agtgatgaat acaaaaataa aaattagaaa  56700
ataatcatat aattaaagtg gcatcagtaa aatacttaga aaaaaattaa agacgtcaag  56760
acttgcacac tgaaatctct aaaacatcac tgaaataaag acctaagcaa atgcaaagac  56820
atcccacagt catggaacag aaaacctaac accattaaaa tagcagttat ttctcaaatt  56880
tatctaccaa ttcaactaaa tccctatcaa gatcccagct gttttgcagg aattgacaca  56940
atgatcatat aaaaattcat atgcaatgca agggacccaa aacagacaaa atgattttgg  57000
ggaaaaaaaa aaaaaaaatg gaggacttgc acatcccaaa tctaaactta ctaccaagct  57060
acagccatca agacagtgcg gtgctggtat aacgacagac atatagggca atggagtaag  57120
actgagaatc cagaaagtct tatatttatg gtcaactgtt ctttgacaag ggtaccagga  57180
ccattcatgg ggaaataata gtcttttcaa caactggtgc ttgggcagat ggatatacag  57240
ataccaatgc acttatgcaa aaaatggatg aaataggaaa cttcactaca ttctactgca  57300
tgctcggtca ttttcaatca tttaggtggc aacactgaca agataacaga aagatggagg  57360
taataacatg tgaaaggcaa aatggtttgt tttttttttt aaaaatgaca gtctctatca  57420
tgaatttact tacactccag gcaaaggtta ttagaagaaa aaaagatgta agaaaattcc  57480
ttaactgaaa tgtggaaaga gtatcaagag gagaccctaa gacactctgt aagaatccca  57540
gtgactcctc actgttcaac taagaaatgt accccattat gctgtgctac cacggaagca  57600
ttggaggcac tttgggggtt gatgaagtct tcatggatga ggtactttaa atatctggtc  57660
atgaagagta tttgagaaat atgacaagtg aagatgctgg gtaggaatgc agcgaggaaa  57720
gtgtgtaaca caaggccaaa ttggaaaggt cagtgagggg gcaatctgtg gaggcactga  57780
atgcagagga tattaaaatt agcaagatag tgttctagca caatgaaaag gattggaaga  57840
gggagatgag agtcagggag tgaaattagg cagctgctaa gaatgtccgg gtgagtcaga  57900
ggatcaggac ctgtaagggc agtataaaga aggaaggaat gatgggagag gtttaggggg  57960
aaagaagtga caacctgtga caattgagga atgagagatt ttgatgattg gggtgaaggt  58020
tacatttctt aaaaagaaac aaagaatggt cggtcgatag agatgcaaga tgaagaattt  58080
tgtttttagg actactgact atgaggtaac aaagaaatcc cagagacaga ggtctgagca  58140
aaagatatgg gattggggaa gaatctttgg gagtgactga ggttgactag agggaactgg  58200
gcaagaacag gtaaggactt taagcagaat tggaggagta tccatctaaa atctgggtaa  58260
actgggatgg aaaaacaagt agccagagaa gcaacagccc aagctagggt gttgtcaagg  58320
```

```
ttatagatgt tactgatttt ggcaatgagg agattataag gatccttgaa gactgtactt  58380
tcggtgaaac taccatgcat tagtagcctt tcacagtgat atctacccca cacctgcatc  58440
aaaatcttgc agtgcctatt aataaatgcc aacccactaa cggggagggg agaaaagact  58500
tgggactctg tacttgtaaa accctctacc ctccccaggc aattctttac acactaacac  58560
tgttgaggta aaaggagaca agtgagggag caaatggaag gtgtgttttt ggattataca  58620
gtggctcatg gaagggtggg aggggtacag atggccctta gacactggcg gaaagtcaga  58680
gaaaaaaaat tacagtaagc aggtaaaggg atcaagacta cacagggact agtcttggga  58740
cgacatttct tcctctgaca gtttgtatgg aattcttgag aaaaattcct cgaaggggcc  58800
tgaaatctca gaatggtcat gtttttaatg ggaataggga gtgatgctgc cccattacaa  58860
ccatctgttc taacagaatg tctgtaccga ggagggatga gtaacatcgg caagttctgt  58920
tcgaagcctt tttcaagttt ctttttgata tgtatctatc tatctatcat ctccctatac  58980
aagcaagcat ccccaaaagt agttgtctca ggaaaccagg gttaggatga ccagctcatt  59040
tgctggagct gccaaggtcc agaaaagttt ggctgcaggc tgttttcatg ttttatgtat  59100
gtttgaaatg ttctataata ataaaaggtt aaaaaagttt acatttattt ggaaaaccag  59160
ttactttagt ttatggttcc tttttttccc tccagagctt cctggagatt gaggtctaat  59220
tcaaagaaaa ccaaaatata taatagagta cctgggcaaa aaaagtactt ttataacata  59280
acatttgggg tagaggaagt atccactgta gtcaaaatgt ctatgttttg ctcttcctta  59340
ttgttcaggg acattccatt aaatagtaat gaaaaggcag caaaagtaag aggagtgaca  59400
acatgcccgg cataattaag caagctagag cagctattct gtgcaaccga cgattttttt  59460
tctctaaaat tttaagggta ggttcattct gactctgtta aaagtctact tgatgtgaac  59520
aactctatat ctgataacct atttcaatta ccactttaaa acttgtcata tggatacgtt  59580
attacaattg tagaacttta ataaatacca taataataaa acttgagaac tgaagagcac  59640
acatttcttc acgaatttat tatataaaac gccctcagag tatttaattt ctcctcactt  59700
taattacaca ttaagaagca cagtggatga gaagccttta agatgactac agttgcacga  59760
aggtcccttt catcaaggta gcgtatgtac cctaacagtg ttctaaaggc tggcccagaa  59820
aaaccccatg ttaccttatc acaatatgga aagcattgtc ttctttttcc actaaattaa  59880
attatggtga aaagtgccac agttttattt agcattatgg tacataacaa acagttctgt  59940
ctcaattatg aaaaaaatta attaaaataa tcctgaaaga catccttttt ctccccccaa  60000
tgatttgaaa gctgcatttt tcctgccaat ttcaaacaaa caaatcatca ggttgatcta  60060
cagtaatcag ttaaaacaat cagtcaatca atcaatcaat caccaaggca caagctcagc  60120
acattagcta tagcttgtag caaaaggata tatcaatgtc tcaccttagt taaaaataca  60180
taatcctttt attttataat gcaataaaag aaattaacaa catcacatac acagaagact  60240
aggaaagggg aaactactta cttctggaaa tcagtaatgt aaacctactt gtacttttcc  60300
atagtacatg aaagtaacgt ttaacatgtt ttgaattaat taattaaatt taatctgtgg  60360
ggctatacaa tgtaattctt aggagtaata gtttcattca tttccaggtc agcttactgt  60420
atgattaagt aacacaaggc acagtagcca tctttttcat tatgttgcaa cactgatcac  60480
gtgcctcgat aaaatggctg attcaacaag atgatggcaa cacgaagggg agactttgga  60540
ttgtctattt aaaatctagg taataagtaa gtaattaata aaaactctat cttaagtgca  60600
ctttcacatg ctttttgttt ataataaaca aacaacaaac ttcctaactt tgttgcaata  60660
```

-continued

```
ggcttgacta ccatttcatt tggccaaatg cactttcccc agtaaactta aaacaacaac  60720
gagaacaaca agaacaaaaa tccctgtcct ttcatatact aagaaagagg attggctact  60780
gaaacagttc attgcaagac acatgaagac gacatactgt ggcatgagtt gtttttgttt  60840
ttaatttgtt gtgctgttac taaagttctg agggctgcag ttaaaacatt ccaatttctc  60900
ccttccttcc atctttcttt attgattgat tctcaagatt ttgcacagaa aactctttgg  60960
gggctagaac agcagtaatt gcatcacact gttttcaaga cttcaagttt caaaagcaaa  61020
tcattaaaaa aaatacagtt cctgatttga gttagataca gggacaaaaa agtagcacat  61080
acttgaaggt tacgtggtct acaaatggtg gcaatatttt ccttgggaga gtagttctgt  61140
tggtatatat tttttaaata ctcaaaaggc tcaacctcaa gcagtaataa acacaagcaa  61200
aagtgattta acccttaaaa taaatattca gaaaaacctc tctgtacata caagtgaaag  61260
aatatgtaac actttcacgc aaaaaaataa ttataataat aataaaggat ttgttcatat  61320
atgtagctga aatctgctgt tccagcccac atgtccccaa taaagaaggg aggcacagac  61380
ataggtgact actgtggttg actatcttac agccttttg tactgggaca ctatcaccac  61440
caaaaattta tccctcgtta tatttttaaa atttttttaaa ttttttcttt ttttttcctt  61500
ccttttttt gttttatttt gttttgtttt gttttacagc atgccaaatc ctttggcata  61560
cgtgatggcc ttcaacaatc tctctttaag tttttctttg cttgagtatt ccggaagtaa  61620
aagcacatta aagcaagtat gagatgtagg taacctaaat agagaaaagg ggaaaaaaac  61680
aggaaaactg taagtcatgg gaaatacact tagaattaaa tgctcctatt tttagattgt  61740
atatagttga gacggtctgc aatgcaaact atacattaat gcaaatcata aactttttgt  61800
tgtgtaacta ccaagttgcc tttatcctat aaattactca aagctagtga cgatgataag  61860
atactgtatc cattgagttt ttactacata acagatacca ttttaggtac tgaattctta  61920
cagttcattt aactaaatct ttccacaaca aaaccacaga gaggacatca gtaaatgcac  61980
tttagaggtt aggtcactga gaagtcaagt aacttcctct aaggtggaga aaatactcaa  62040
acctgtttta caagactgca aagtgtgtgc tcttaaatgc ttattagaaa cactgctggc  62100
aatatgacta agaaaatgat ttgataacag gattctagca caatcaaatg ataatcttcc  62160
gagcctcaat gtaaccattc taaatagatg atcatgttat atggctttca attaacaagc  62220
tgggaatcaa aaaagtaaat gaatcacact aatttgattc caaaccaatg tgagccccat  62280
aataattttt aactagggca atttcttaaa agtttcctca cacaatgaca gcaaagtatt  62340
ttctcaattg tctaatatga tttggggatt tgtatataaa atcacgaatg tgctcagaaa  62400
ctataaagac agttcatatg tatgtgacga ggaatgcaag gttttcggta ggtatacagt  62460
cacaagttaa taattaccta cctttctgtg tctgggccat ttttggctat aatcatcttt  62520
aattttccta gtcctcccac aggtgctctg tctgtgcccg ttgtaaactg caagaagagt  62580
cttttctgtt catctgtaaa tgaatgaacg atttcccaga actccctaat gagaaaaaat  62640
acaatactgg tttcagtttg gcattcatta tgactggtac taacataagc ttatgatttg  62700
cattaaaact atattaagag acaacttgga agttaattat caggatagta tcacttctgg  62760
tgatttaaaa atttccaagc aaatttatcc tgaacagctc tgaatacgta aaaatttaga  62820
ttagattaca atatagtaaa atattagtac tacaatagta aaaaattgag aaaacccaag  62880
tgtgtagtaa caggaagtga ctatttaaac tatggtataa tcacattatg cagtcagtaa  62940
tgagcaaaag acaaaatcct atgaattgaa aaagactgaa atgaatattt ggaaaaatta  63000
actccaggtg cctttgggta tatattttat ttatcctttc tcctttattc tcctggtcta  63060
```

ctcatccttt aactcaactt tgggaggaaa aagtgataca gattaaggac aaaagaaaaa 63120
aagacccccct gccccaacca actggcccca aatgcaaaca actacatacc taatagcagt 63180
aatacaaaag ttcaattttt atatgaacta gaatacttta aacaagtaat atgtgctgtg 63240
tatggaggag gagaattatt ctgacatttc tgccacctgc agttatttta agagaatgat 63300
ttatcctgtg gcattcctaa aatctatgta ataaaagcta tgttttaatg acacttatgt 63360
tagtttgagt tctaaaaaac gaaatacaag ctcataaagt gcaatcttga agtttatttg 63420
aataatcagg catctataaa acatatatac actagttcat agctaaataa attttttttt 63480
ttttgagaca gagtcttgct ctgtcgctca ggctggagtg cagtggcgcg atctcggctc 63540
attgcaagct ccgcctcctg ggttcgcgcc attgtcctgc ctcagcctcc caagtggctg 63600
ggactatagg tgcctgccac cacgcctggc taattttctg tacgtttaag tagaggcagg 63660
atttcaccat gttagccagg atgggtctcg atctcctgac ctcgtgatcc gcccaccttg 63720
gcctcccaaa gtgctgggat tgcaggcatg agccaccgcg cctggcctat agctaaataa 63780
tgttaagatt aaaaaattaa aaaaaaaatt aaaagtattt ttagttgctt atataatata 63840
aaatgcattt taatagttat ttagaaagtt ctttccagag ccaggtgtgg tggctcatgc 63900
ctgtaatccc agcactttgg gaggctgagg ccagtggatc acctgaggtc aggggttcaa 63960
gatcagcctg accaacgtgg tgaaaccctg tctctactaa aatacaaaaa ttagccgggc 64020
gtggtggcag atgcctgtaa tctcagctac ttgggaggcc aaggcagaag aattgcttga 64080
acatgggagg cggaggctgc aatgagctga gatcacacca ttgcactcta gcctgggaaa 64140
cattttgagc catctcaaaa aaaaaaaaaa atttcatctc aaaaaaaaaa aaaaaaaaaa 64200
ttccagaatg ttagcagaga acatcacaca tcccaaacca gtaattacaa ttttctacct 64260
tttgatattc taatatccca acatactatt tttattacca aaatgctggc atttttggtg 64320
ctgcaacacc atttatctga aataacttaa aagttttatt agaattcttg gctttctcca 64380
atctcttgcc acttcccttc cctgcccctt tacaaatcca ccagtcagca agagaaaaca 64440
aaaaagaaac acacaacaac agaaaactgg acatgaaact tgcaggagca tctctcaggt 64500
aaggaggaga ggaatcggac cccagttcat gatactcctt ttggggaggc tgacaagaga 64560
aaacaagtct gctgtagcac agaaccctcc aacatagcag aaaagctgcc ctgcagtggg 64620
tggtaataaa gcctcctcac actgcaggag ggctctgaag cttaactgaa ccagctacac 64680
ctaaggaggt agaccaaaga gcaccaccga agaacagaga cagaccctgc aggaagtggc 64740
agatcagcag tggtcacaat gaccagtctg gctatattat tacggagctg tttctttgga 64800
cttttaaacg aaacctttaa aaattttata caatgaaaac agggaacaaa atgcatctct 64860
attcctataa gtgttatgtg tgttacatta acattttgaa ttaaacaaga atgcatatat 64920
ttagaaagct gaagaaaaca cgaagaagct tccaggtttc cacataaaag tggtggctgt 64980
atcgatcaca tcctactcac atctctaaaa atctacccgg atcaaaaagg ggaaaataaa 65040
aaaaaaacct atgacttagg tctagagtaa aactaggaga cagaacaata aactccaaat 65100
accaaagaag tggggaaatg agcagggtcc agcaggagct acatcgaaga gtggcttgtg 65160
cggaatcata ctgattaggg atcacccaag gccagacccc accccctcca ccacctgccc 65220
ctcaacagag cactactgag tgtaggttag agcactggca acagggtggt taaaggaagg 65280
actacagaaa agtacttggg tccagcaatg gcaggctcag gaaggcacca tgcatgaaag 65340
gaagggggt accttcaaaa gcagaagtgt cccttaagcg gctgtaaagg ggtggaagca 65400

```
gctaatgaaa aagagtcttc attaagctac atggagctga aaaatcagaa agtggtgatt  65460
ctgcccttac taaagcaaca gaagagggat cccttcaacc aagaccccta aagccacaca  65520
attcctccct gctccaccat gaggtctagt aataacaggt ccagaaaaaa gtaacatctg  65580
ttatagaaac ataaacaaga aaaacagaat tcggaagtct aaataaagtt attatgggaa  65640
gagtctggcg aatgagaagc aaaactttcc ggtagacaaa agtagaccag aaaaattcag  65700
tcataaacaa tgggaaacta gtaacaccac attccaacac aaaaggagaa tgcagcagca  65760
gacaagacag accaccagtg atgagaaata caaattcaga aagaaatgag cacatcttaa  65820
ataaaaataa gaatactaaa aaatactgaa gaaatatgca aggtaacttt ggaaataaag  65880
gctaatttta ttataaggtg accaaagaag aagcagtatg actaaaattt ctactgagga  65940
cagactctag aaaattaaaa aacaaagaaa atgaataaaa taaacataac taaagaaatg  66000
catatcaaag cataataacg aaaaagatta atagctaact acataaacat aaaacctttc  66060
atttggcaaa aaaatcctat aagcaaggtt aaaagacaaa tgacaaactg ggaaaaaata  66120
tttgcgaatt taccagcgtt aaaggactaa tctccttaac atataaagtt tctaaaagtg  66180
aagaaaacga ccagctgagc agcaaaatga gcaaaagact atataaaact ataaacagct  66240
ctacaagaaa aaatgtccat tatcattcat aattgaggta agctcaaaaa ttgtaactat  66300
agtaaaatac catttctcaa ttggcaaata agtaaacatc cacatttaac aacacattct  66360
gtttggaaag ttttaagaaa agagatactg ttgtaaactg ctggtgggaa tgcaaaatgt  66420
tatttttctg tgaaggagga tttggcagta tctagcaaaa ttacacatgc atctaccatt  66480
tgatgcaaca atcccacttc taacaattta tcttaatgat actttacata tgtacggaat  66540
aatgcatgaa cattaagagg attcactgtg acattagtac taacagcaaa aggttaaaaa  66600
taacctcgat gcccataaat attgataagc tatgctgcat ccacacaaag gagcagtatt  66660
cagtcataca aaacaaaatg gaaaacacct ctgcaataat gtgggatgat tctcaggata  66720
cactaggaag attattttcc tagttctgtc ctctgataag gcctacaagc agtaacgttc  66780
aaaagcaaag gccatacttt gcatctaaaa tctgacttct aaatgccatt ctccaacaat  66840
ttattggaaa aataacttat tccaggcctg agaatgaatg ttcgagatta gttagaaatc  66900
tcaaaatcta atagggtcat tttaaaagca cacgatagct aagcaatttg aatatcattt  66960
agagtaatga ctgtgaaacg tattaaatac aaaaacattc attagttcgt aatattcaaa  67020
aaggcagcaa aaaccaacca aaaaacaaaa ttaaattgtc actattaaaa ttattacatt  67080
aactccttac tctaaaaacc ttaaatctat tttatcatgc cttttctgta gaactgtttt  67140
tcaaggtaat caaatggcac ccaatgatga gaaaaaagaa tgccaggtat atatgtagga  67200
caagcagatg gaaatttttt ttccccaaac agccattttg caatccccaa tgagataaca  67260
gattaaggta atgatactga taaatacgaa aatcaggtga agggcaggta gcaggttctg  67320
gaaagatgat gatggcaacg acatagttat tattattatt attttttgtt ttattccctc  67380
ccaacctccc ctacaaaaac agcaaactga atgagaaaac caaagaccca gagacattat  67440
ctacaacaaa accatgaacc attgcatata attggacaga aacaaagctc tgacaactac  67500
aagactggtt agtaaggaag cagatgcaag gtaactgact gggtttctga cagccctgag  67560
aacactgcca acccactgga aagcacaggc caatctgaaa acagggctta aagttttaaa  67620
aagttctaca ggatctaatt tgcagatgat tacaaaggga tcatgatgta gtaagctctg  67680
ggcccttaaa acacccgaat accaaacccc caccagaaac aaaccttgta ccgaggaaaa  67740
acttctggga ataacttccg aatggaccag gtcagtaata aaaaccaaaa aaaagttcaa  67800
```

```
atatatgtgt gggatagagg agtaaagaag gcagtttcag aaagcacaag ggcatatttt  67860

tgaccatttt acaaaaacac agacttctcc tcgtccctaa aaagcgaaaa aagttatcct  67920

ggcccatctc tccctcgtcc aagtatgaga aactcatttc actcacacac acacacacac  67980

acacacaaat aaataaataa cagaacagag tgaaacagtg taattattag agaaaaagta  68040

tgtgcatata catgagaatg gtgtccctac agaaaatcaa agtacatgaa acaatatgca  68100

aataaaacat gaaaactgta aacaaatttc aaactgagct aaaaagaatt taaaaaataa  68160

caaatcatta gaaatgggaa atttctgaat gagggtaact gaaaaaaagg aagacatgac  68220

acaactaagg agtaattaga aatgcaagga aaaaaatccc atcaaataca aagaaactaa  68280

aactaaacta gaagaaacat aaaggtgaat aaaacagaac aataatacca gaacctgaag  68340

gcagaagaaa aatcttaaaa tcaaaaagaa acaaacccat gcttgagact ctccttgctg  68400

gtccagagcc acagtgctgc tgtgtactgg caggaggaat tctgctataa ttggtcctgg  68460

cagtgttcac ctttcctgca agtgttccac agcccaggga cacaatgtgg tcaggagcac  68520

tgccaggaac accagcaagg gggagcctgc cacaacaggc acaaggctca ggaagcactc  68580

tccagcccac gaaaatctag tgggggtcct cttccctcac ccaaacacac tctgcgcagc  68640

t                                                                  68641
```

```
<210> SEQ ID NO 2
<211> LENGTH: 48
<212> TYPE: DNA
<213> ORGANISM: Artificial Sequence
<220> FEATURE:
<223> OTHER INFORMATION: Synthetic

<400> SEQUENCE: 2

tgctcttctt tctactttat tctcgagaat aaagtagaaa gaagagca               48
```

```
<210> SEQ ID NO 3
<211> LENGTH: 41
<212> TYPE: DNA
<213> ORGANISM: Artificial Sequence
<220> FEATURE:
<223> OTHER INFORMATION: Synthetic

<400> SEQUENCE: 3

gaaataataa tctgatgagg ccgaaaggcc gaaactaaaa g                      41
```

```
<210> SEQ ID NO 4
<211> LENGTH: 41
<212> TYPE: DNA
<213> ORGANISM: Artificial Sequence
<220> FEATURE:
<223> OTHER INFORMATION: Synthetic

<400> SEQUENCE: 4

gaaagaagct gatgaggccg aaaggccgaa aaataataat g                      41
```

```
<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5

tgctcttctt tctactttat t                                            21
```

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
cttttagtca ttattatttc 20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
cattattatt tccttctttc 20

<210> SEQ ID NO 8
<211> LENGTH: 67
<212> TYPE: DNA
<213> ORGANISM: Artificial Sequence
<220> FEATURE:
<223> OTHER INFORMATION: Synthetic

<400> SEQUENCE: 8
tcctgaataa agtagagaag agcagtcagt cagtggccaa aactgctctt ctttctactt 60
tattcag 67

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
tgtggagaat cattgatata t 21

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
gtggagaatc attgatatat t 21

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
gtatatgaga gttccattat t 21

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
tggctgtgga aacgcttatt t 21

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
tggatcgatg atgagaataa t 21

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
ggatcgatga tgagaataat t 21

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
gccctccaat aggacaaata a 21

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
tgacccaaga cttgctttaa t 21

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
gacccaagac ttgctttaat t 21

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
tgtgctgaaa gaaggaaata t 21

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
atatggcatg cctctattaa a 21

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
tatggcatgc ctctattaaa t 21

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
atggcatgcc tctattaaat a 21

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
tggcatgcct ctattaaata a 21

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
ggcatgcctc tattaaataa t 21

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
gacagtggaa ccaagtttat t 21

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
gagactccat ggttcataat a 21

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
agactccatg gttcataata t 21

<210> SEQ ID NO 27
<211> LENGTH: 21
<212> TYPE: DNA
<213> ORGANISM: Artificial Sequence
<220> FEATURE:
<223> OTHER INFORMATION: Synthetic

<400> SEQUENCE: 27
ttgtggtcat actacattat a 21

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
tgtggtcata ctacattata t 21

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
gtggtcatac tacattatat t 21

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
ttgcaacaag gtaagttata t 21

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
tgcaacaagg taagttatat a 21

<210> SEQ ID NO 32

<211> LENGTH: 21
<212> TYPE: DNA
<213> ORGANISM: Artificial Sequence
<220> FEATURE:
<223> OTHER INFORMATION: Synthetic

<400> SEQUENCE: 32
ttgattgatg ccctcataat a 21

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
tgaagttggg taaagtataa a 21

<210> SEQ ID NO 34
<211> LENGTH: 21
<212> TYPE: DNA
<213> ORGANISM: Artificial Sequence
<220> FEATURE:
<223> OTHER INFORMATION: Synthetic

<400> SEQUENCE: 34
gtcaatacac aactgataaa t 21

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
caaagagttt cagccataaa t 21

<210> SEQ ID NO 36
<211> LENGTH: 21
<212> TYPE: DNA
<213> ORGANISM: Artificial Sequence
<220> FEATURE:
<223> OTHER INFORMATION: Synthetic

<400> SEQUENCE: 36
catgctttcc agaggaaata t 21

<210> SEQ ID NO 37
<211> LENGTH: 21
<212> TYPE: DNA
<213> ORGANISM: Artificial Sequence
<220> FEATURE:
<223> OTHER INFORMATION: Synthetic

<400> SEQUENCE: 37
tccagaggaa atatgtttaa t 21

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
tttaatcatc tgccctatat t 21

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
ttaatcatct gccctatatt a 21

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
tgcaagatac catacattta t 21

<210> SEQ ID NO 41
<211> LENGTH: 21
<212> TYPE: DNA
<213> ORGANISM: Artificial Sequence
<220> FEATURE:
<223> OTHER INFORMATION: Synthetic

<400> SEQUENCE: 41
gcaagatacc atacatttat a 21

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
ggtccatgtg atttctttaa t 21

<210> SEQ ID NO 43
<211> LENGTH: 21
<212> TYPE: DNA
<213> ORGANISM: Artificial Sequence
<220> FEATURE:
<223> OTHER INFORMATION: Synthetic

<400> SEQUENCE: 43
tgccataact atagcattta t 21

<210> SEQ ID NO 44
<211> LENGTH: 21
<212> TYPE: DNA
<213> ORGANISM: Artificial Sequence
<220> FEATURE:
<223> OTHER INFORMATION: Synthetic

<400> SEQUENCE: 44
ggataccatc cacactataa a 21

<210> SEQ ID NO 45
<211> LENGTH: 21
<212> TYPE: DNA

<213> ORGANISM: Artificial Sequence
<220> FEATURE:
<223> OTHER INFORMATION: Synthetic

<400> SEQUENCE: 45
tgtgtttcct tccagataat t 21

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
gtgtttcctt ccagataatt t 21

<210> SEQ ID NO 47
<211> LENGTH: 21
<212> TYPE: DNA
<213> ORGANISM: Artificial Sequence
<220> FEATURE:
<223> OTHER INFORMATION: Synthetic

<400> SEQUENCE: 47
gtgtgctgaa agggctataa a 21

<210> SEQ ID NO 48
<211> LENGTH: 21
<212> TYPE: DNA
<213> ORGANISM: Artificial Sequence
<220> FEATURE:
<223> OTHER INFORMATION: Synthetic

<400> SEQUENCE: 48
ttgaaccaac caccctataa a 21

<210> SEQ ID NO 49
<211> LENGTH: 21
<212> TYPE: DNA
<213> ORGANISM: Artificial Sequence
<220> FEATURE:
<223> OTHER INFORMATION: Synthetic

<400> SEQUENCE: 49
taaacgttgt atggcttatt t 21

<210> SEQ ID NO 50
<211> LENGTH: 21
<212> TYPE: DNA
<213> ORGANISM: Artificial Sequence
<220> FEATURE:
<223> OTHER INFORMATION: Synthetic

<400> SEQUENCE: 50
atccctgtgt acacaatatt t 21

<210> SEQ ID NO 51
<211> LENGTH: 21
<212> TYPE: DNA
<213> ORGANISM: Artificial Sequence
<220> FEATURE:
<223> OTHER INFORMATION: Synthetic

<400> SEQUENCE: 51
atgtgtggta aatccattat t 21

<210> SEQ ID NO 52
<211> LENGTH: 21
<212> TYPE: DNA
<213> ORGANISM: Artificial Sequence
<220> FEATURE:
<223> OTHER INFORMATION: Synthetic

<400> SEQUENCE: 52
tgtgtggtaa atccattatt t 21

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
atgagcattt ggcagtaata t 21

<210> SEQ ID NO 54
<211> LENGTH: 21
<212> TYPE: DNA
<213> ORGANISM: Artificial Sequence
<220> FEATURE:
<223> OTHER INFORMATION: Synthetic

<400> SEQUENCE: 54
tgagcatttg gcagtaatat t 21

<210> SEQ ID NO 55
<211> LENGTH: 21
<212> TYPE: DNA
<213> ORGANISM: Artificial Sequence
<220> FEATURE:
<223> OTHER INFORMATION: Synthetic

<400> SEQUENCE: 55
gagcatttgg cagtaatatt a 21

<210> SEQ ID NO 56
<211> LENGTH: 21
<212> TYPE: DNA
<213> ORGANISM: Artificial Sequence
<220> FEATURE:
<223> OTHER INFORMATION: Synthetic

<400> SEQUENCE: 56
agcatttggc agtaatatta t 21

<210> SEQ ID NO 57
<211> LENGTH: 21
<212> TYPE: DNA
<213> ORGANISM: Artificial Sequence
<220> FEATURE:
<223> OTHER INFORMATION: Synthetic

<400> SEQUENCE: 57
gcatttggca gtaatattat t 21

<210> SEQ ID NO 58
<211> LENGTH: 21
<212> TYPE: DNA
<213> ORGANISM: Artificial Sequence
<220> FEATURE:

<223> OTHER INFORMATION: Synthetic

<400> SEQUENCE: 58
gagactctgc tgaagtttat a 21

<210> SEQ ID NO 59
<211> LENGTH: 21
<212> TYPE: DNA
<213> ORGANISM: Artificial Sequence
<220> FEATURE:
<223> OTHER INFORMATION: Synthetic

<400> SEQUENCE: 59
agactctgct gaagtttata a 21

<210> SEQ ID NO 60
<211> LENGTH: 21
<212> TYPE: DNA
<213> ORGANISM: Artificial Sequence
<220> FEATURE:
<223> OTHER INFORMATION: Synthetic

<400> SEQUENCE: 60
cagttataga agtgctaatt t 21

<210> SEQ ID NO 61
<211> LENGTH: 21
<212> TYPE: DNA
<213> ORGANISM: Artificial Sequence
<220> FEATURE:
<223> OTHER INFORMATION: Synthetic

<400> SEQUENCE: 61
tatgatgacc tcctgaatta t 21

<210> SEQ ID NO 62
<211> LENGTH: 21
<212> TYPE: DNA
<213> ORGANISM: Artificial Sequence
<220> FEATURE:
<223> OTHER INFORMATION: Synthetic

<400> SEQUENCE: 62
gggtctggtg tttcatttat t 21

<210> SEQ ID NO 63
<211> LENGTH: 21
<212> TYPE: DNA
<213> ORGANISM: Artificial Sequence
<220> FEATURE:
<223> OTHER INFORMATION: Synthetic

<400> SEQUENCE: 63
ggtctggtgt ttcatttatt t 21

<210> SEQ ID NO 64
<211> LENGTH: 21
<212> TYPE: DNA
<213> ORGANISM: Artificial Sequence
<220> FEATURE:
<223> OTHER INFORMATION: Synthetic

<400> SEQUENCE: 64
gggtctcatt atagttaata t 21

<210> SEQ ID NO 65
<211> LENGTH: 21
<212> TYPE: DNA
<213> ORGANISM: Artificial Sequence
<220> FEATURE:
<223> OTHER INFORMATION: Synthetic

<400> SEQUENCE: 65
taacagcatg tcaggtaata a 21

<210> SEQ ID NO 66
<211> LENGTH: 21
<212> TYPE: DNA
<213> ORGANISM: Artificial Sequence
<220> FEATURE:
<223> OTHER INFORMATION: Synthetic

<400> SEQUENCE: 66
gcagagccct attcctttaa a 21

<210> SEQ ID NO 67
<211> LENGTH: 21
<212> TYPE: DNA
<213> ORGANISM: Artificial Sequence
<220> FEATURE:
<223> OTHER INFORMATION: Synthetic

<400> SEQUENCE: 67
ctcctaaatg tttggaaatt t 21

<210> SEQ ID NO 68
<211> LENGTH: 21
<212> TYPE: DNA
<213> ORGANISM: Artificial Sequence
<220> FEATURE:
<223> OTHER INFORMATION: Synthetic

<400> SEQUENCE: 68
ttagcatttc tgacctattt a 21

<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69
tagcatttct gacctattta t 21

<210> SEQ ID NO 70
<211> LENGTH: 21
<212> TYPE: DNA
<213> ORGANISM: Artificial Sequence
<220> FEATURE:
<223> OTHER INFORMATION: Synthetic

<400> SEQUENCE: 70
agcatttctg acctatttat t 21

<210> SEQ ID NO 71
<211> LENGTH: 21
<212> TYPE: DNA
<213> ORGANISM: Artificial Sequence
<220> FEATURE:
<223> OTHER INFORMATION: Synthetic

<400> SEQUENCE: 71
acaggatata gggaataatt t 21

<210> SEQ ID NO 72
<211> LENGTH: 21
<212> TYPE: DNA
<213> ORGANISM: Artificial Sequence
<220> FEATURE:
<223> OTHER INFORMATION: Synthetic

<400> SEQUENCE: 72
caggatatag ggaataattt a 21

<210> SEQ ID NO 73
<211> LENGTH: 21
<212> TYPE: DNA
<213> ORGANISM: Artificial Sequence
<220> FEATURE:
<223> OTHER INFORMATION: Synthetic

<400> SEQUENCE: 73
tagcactgaa atgcctatat t 21

<210> SEQ ID NO 74
<211> LENGTH: 21
<212> TYPE: DNA
<213> ORGANISM: Artificial Sequence
<220> FEATURE:
<223> OTHER INFORMATION: Synthetic

<400> SEQUENCE: 74
agcactgaaa tgcctatatt a 21

<210> SEQ ID NO 75
<211> LENGTH: 21
<212> TYPE: DNA
<213> ORGANISM: Artificial Sequence
<220> FEATURE:
<223> OTHER INFORMATION: Synthetic

<400> SEQUENCE: 75
gagcagaaat caatgaaata t 21

<210> SEQ ID NO 76
<211> LENGTH: 21
<212> TYPE: DNA
<213> ORGANISM: Artificial Sequence
<220> FEATURE:
<223> OTHER INFORMATION: Synthetic

<400> SEQUENCE: 76
acttgtaacc agaccaattt a 21

<210> SEQ ID NO 77
<211> LENGTH: 21
<212> TYPE: DNA
<213> ORGANISM: Artificial Sequence
<220> FEATURE:
<223> OTHER INFORMATION: Synthetic

<400> SEQUENCE: 77
cttgtaacca gaccaattta a 21

<210> SEQ ID NO 78
<211> LENGTH: 21

<212> TYPE: DNA
<213> ORGANISM: Artificial Sequence
<220> FEATURE:
<223> OTHER INFORMATION: Synthetic

<400> SEQUENCE: 78
actcagtgaa caagtaaata a 21

<210> SEQ ID NO 79
<211> LENGTH: 21
<212> TYPE: DNA
<213> ORGANISM: Artificial Sequence
<220> FEATURE:
<223> OTHER INFORMATION: Synthetic

<400> SEQUENCE: 79
tagccctgta tcaagtaaat t 21

<210> SEQ ID NO 80
<211> LENGTH: 21
<212> TYPE: DNA
<213> ORGANISM: Artificial Sequence
<220> FEATURE:
<223> OTHER INFORMATION: Synthetic

<400> SEQUENCE: 80
acaagattcc agaacattta a 21

<210> SEQ ID NO 81
<211> LENGTH: 21
<212> TYPE: DNA
<213> ORGANISM: Artificial Sequence
<220> FEATURE:
<223> OTHER INFORMATION: Synthetic

<400> SEQUENCE: 81
caagattcca gaacatttaa a 21

<210> SEQ ID NO 82
<211> LENGTH: 21
<212> TYPE: DNA
<213> ORGANISM: Artificial Sequence
<220> FEATURE:
<223> OTHER INFORMATION: Synthetic

<400> SEQUENCE: 82
gagagttacc caaagaattt a 21

<210> SEQ ID NO 83
<211> LENGTH: 21
<212> TYPE: DNA
<213> ORGANISM: Artificial Sequence
<220> FEATURE:
<223> OTHER INFORMATION: Synthetic

<400> SEQUENCE: 83
agagttaccc aaagaattta a 21

<210> SEQ ID NO 84
<211> LENGTH: 21
<212> TYPE: DNA
<213> ORGANISM: Artificial Sequence
<220> FEATURE:
<223> OTHER INFORMATION: Synthetic

<400> SEQUENCE: 84
agaagaaagg tttggaaatt t 21

<210> SEQ ID NO 85
<211> LENGTH: 21
<212> TYPE: DNA
<213> ORGANISM: Artificial Sequence
<220> FEATURE:
<223> OTHER INFORMATION: Synthetic

<400> SEQUENCE: 85
agcccaatct ataggattta t 21

<210> SEQ ID NO 86
<211> LENGTH: 21
<212> TYPE: DNA
<213> ORGANISM: Artificial Sequence
<220> FEATURE:
<223> OTHER INFORMATION: Synthetic

<400> SEQUENCE: 86
gcccaatcta taggatttat a 21

<210> SEQ ID NO 87
<211> LENGTH: 21
<212> TYPE: DNA
<213> ORGANISM: Artificial Sequence
<220> FEATURE:
<223> OTHER INFORMATION: Synthetic

<400> SEQUENCE: 87
cccaatctat aggatttata t 21

<210> SEQ ID NO 88
<211> LENGTH: 21
<212> TYPE: DNA
<213> ORGANISM: Artificial Sequence
<220> FEATURE:
<223> OTHER INFORMATION: Synthetic

<400> SEQUENCE: 88
cacatactac agggcatata a 21

<210> SEQ ID NO 89
<211> LENGTH: 21
<212> TYPE: DNA
<213> ORGANISM: Artificial Sequence
<220> FEATURE:
<223> OTHER INFORMATION: Synthetic

<400> SEQUENCE: 89
acatactaca gggcatataa a 21

<210> SEQ ID NO 90
<211> LENGTH: 21
<212> TYPE: DNA
<213> ORGANISM: Artificial Sequence
<220> FEATURE:
<223> OTHER INFORMATION: Synthetic

<400> SEQUENCE: 90
ttaaagagtt gccacattat a 21

<210> SEQ ID NO 91
<211> LENGTH: 21
<212> TYPE: DNA
<213> ORGANISM: Artificial Sequence
<220> FEATURE:
<223> OTHER INFORMATION: Synthetic

<400> SEQUENCE: 91
gttgccacat tatacataat a 21

<210> SEQ ID NO 92
<211> LENGTH: 21
<212> TYPE: DNA
<213> ORGANISM: Artificial Sequence
<220> FEATURE:
<223> OTHER INFORMATION: Synthetic

<400> SEQUENCE: 92
agacattgaa ccagctatta a 21

<210> SEQ ID NO 93
<211> LENGTH: 21
<212> TYPE: DNA
<213> ORGANISM: Artificial Sequence
<220> FEATURE:
<223> OTHER INFORMATION: Synthetic

<400> SEQUENCE: 93
gacattgaac cagctattaa a 21

<210> SEQ ID NO 94
<211> LENGTH: 21
<212> TYPE: DNA
<213> ORGANISM: Artificial Sequence
<220> FEATURE:
<223> OTHER INFORMATION: Synthetic

<400> SEQUENCE: 94
agggttaaag aaaggtataa a 21

<210> SEQ ID NO 95
<211> LENGTH: 21
<212> TYPE: DNA
<213> ORGANISM: Artificial Sequence
<220> FEATURE:
<223> OTHER INFORMATION: Synthetic

<400> SEQUENCE: 95
atacccgaga tgaccaataa a 21

<210> SEQ ID NO 96
<211> LENGTH: 21
<212> TYPE: DNA
<213> ORGANISM: Artificial Sequence
<220> FEATURE:
<223> OTHER INFORMATION: Synthetic

<400> SEQUENCE: 96
caaatccacg agaagaaata a 21

<210> SEQ ID NO 97
<211> LENGTH: 21
<212> TYPE: DNA
<213> ORGANISM: Artificial Sequence
<220> FEATURE:
<223> OTHER INFORMATION: Synthetic

<400> SEQUENCE: 97
acttgtgttg atggtattat a 21

<210> SEQ ID NO 98
<211> LENGTH: 21
<212> TYPE: DNA
<213> ORGANISM: Artificial Sequence
<220> FEATURE:
<223> OTHER INFORMATION: Synthetic

<400> SEQUENCE: 98
cttgtgttga tggtattata t 21

<210> SEQ ID NO 99
<211> LENGTH: 21
<212> TYPE: DNA
<213> ORGANISM: Artificial Sequence
<220> FEATURE:
<223> OTHER INFORMATION: Synthetic

<400> SEQUENCE: 99
attcattgga aagggtataa a 21

<210> SEQ ID NO 100
<211> LENGTH: 21
<212> TYPE: DNA
<213> ORGANISM: Artificial Sequence
<220> FEATURE:
<223> OTHER INFORMATION: Synthetic

<400> SEQUENCE: 100
cagtaacaag agcccattat t 21

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
agtaacaaga gcccattatt t 21

<210> SEQ ID NO 102
<211> LENGTH: 21
<212> TYPE: DNA
<213> ORGANISM: Artificial Sequence
<220> FEATURE:
<223> OTHER INFORMATION: Synthetic

<400> SEQUENCE: 102
gcccaagaga tccactttat t 21

<210> SEQ ID NO 103
<211> LENGTH: 21
<212> TYPE: DNA
<213> ORGANISM: Artificial Sequence
<220> FEATURE:
<223> OTHER INFORMATION: Synthetic

<400> SEQUENCE: 103
cccaagagat ccactttatt t 21

<210> SEQ ID NO 104
<211> LENGTH: 21
<212> TYPE: DNA
<213> ORGANISM: Artificial Sequence
<220> FEATURE:
<223> OTHER INFORMATION: Synthetic

<400> SEQUENCE: 104
tttcatctca cccagaatat t 21

<210> SEQ ID NO 105
<211> LENGTH: 21
<212> TYPE: DNA
<213> ORGANISM: Artificial Sequence
<220> FEATURE:
<223> OTHER INFORMATION: Synthetic

<400> SEQUENCE: 105
tgttatgaga tccagttatt t 21

<210> SEQ ID NO 106
<211> LENGTH: 21
<212> TYPE: DNA
<213> ORGANISM: Artificial Sequence
<220> FEATURE:
<223> OTHER INFORMATION: Synthetic

<400> SEQUENCE: 106
actgaactgt gagccaatta a 21

<210> SEQ ID NO 107
<211> LENGTH: 21
<212> TYPE: DNA
<213> ORGANISM: Artificial Sequence
<220> FEATURE:
<223> OTHER INFORMATION: Synthetic

<400> SEQUENCE: 107
ctgaactgtg agccaattaa a 21

<210> SEQ ID NO 108
<211> LENGTH: 21
<212> TYPE: DNA
<213> ORGANISM: Artificial Sequence
<220> FEATURE:
<223> OTHER INFORMATION: Synthetic

<400> SEQUENCE: 108
agtcttaggt agttctttat a 21

<210> SEQ ID NO 109
<211> LENGTH: 21
<212> TYPE: DNA
<213> ORGANISM: Artificial Sequence
<220> FEATURE:
<223> OTHER INFORMATION: Synthetic

<400> SEQUENCE: 109
caaaggcagc agcacaataa t 21

<210> SEQ ID NO 110
<211> LENGTH: 21
<212> TYPE: DNA
<213> ORGANISM: Artificial Sequence
<220> FEATURE:
<223> OTHER INFORMATION: Synthetic

<400> SEQUENCE: 110
agactggcta tttgaaatta t 21

<210> SEQ ID NO 111

<211> LENGTH: 21
<212> TYPE: DNA
<213> ORGANISM: Artificial Sequence
<220> FEATURE:
<223> OTHER INFORMATION: Synthetic

<400> SEQUENCE: 111
gactggctat ttgaaattat t 21

<210> SEQ ID NO 112
<211> LENGTH: 21
<212> TYPE: DNA
<213> ORGANISM: Artificial Sequence
<220> FEATURE:
<223> OTHER INFORMATION: Synthetic

<400> SEQUENCE: 112
caccatcaag agaactaata t 21

<210> SEQ ID NO 113
<211> LENGTH: 21
<212> TYPE: DNA
<213> ORGANISM: Artificial Sequence
<220> FEATURE:
<223> OTHER INFORMATION: Synthetic

<400> SEQUENCE: 113
accatcaaga gaactaatat a 21

<210> SEQ ID NO 114
<211> LENGTH: 21
<212> TYPE: DNA
<213> ORGANISM: Artificial Sequence
<220> FEATURE:
<223> OTHER INFORMATION: Synthetic

<400> SEQUENCE: 114
ccatcaagag aactaatata a 21

<210> SEQ ID NO 115
<211> LENGTH: 21
<212> TYPE: DNA
<213> ORGANISM: Artificial Sequence
<220> FEATURE:
<223> OTHER INFORMATION: Synthetic

<400> SEQUENCE: 115
ggaaagtaca tagtcaaatt t 21

<210> SEQ ID NO 116
<211> LENGTH: 21
<212> TYPE: DNA
<213> ORGANISM: Artificial Sequence
<220> FEATURE:
<223> OTHER INFORMATION: Synthetic

<400> SEQUENCE: 116
caatgcatac tacagtataa a 21

<210> SEQ ID NO 117
<211> LENGTH: 21
<212> TYPE: DNA
<213> ORGANISM: Artificial Sequence
<220> FEATURE:
<223> OTHER INFORMATION: Synthetic

<400> SEQUENCE: 117
agtccttacg tgtcaataat t 21

<210> SEQ ID NO 118
<211> LENGTH: 21
<212> TYPE: DNA
<213> ORGANISM: Artificial Sequence
<220> FEATURE:
<223> OTHER INFORMATION: Synthetic

<400> SEQUENCE: 118
gtccttacgt gtcaataatt a 21

<210> SEQ ID NO 119
<211> LENGTH: 21
<212> TYPE: DNA
<213> ORGANISM: Artificial Sequence
<220> FEATURE:
<223> OTHER INFORMATION: Synthetic

<400> SEQUENCE: 119
gacacataca ggctgaaatt a 21

<210> SEQ ID NO 120
<211> LENGTH: 21
<212> TYPE: DNA
<213> ORGANISM: Artificial Sequence
<220> FEATURE:
<223> OTHER INFORMATION: Synthetic

<400> SEQUENCE: 120
acacatacag gctgaaatta a 21

<210> SEQ ID NO 121
<211> LENGTH: 21
<212> TYPE: DNA
<213> ORGANISM: Artificial Sequence
<220> FEATURE:
<223> OTHER INFORMATION: Synthetic

<400> SEQUENCE: 121
cacatacagg ctgaaattaa a 21

<210> SEQ ID NO 122
<211> LENGTH: 21
<212> TYPE: DNA
<213> ORGANISM: Artificial Sequence
<220> FEATURE:
<223> OTHER INFORMATION: Synthetic

<400> SEQUENCE: 122
caatattgaa gcacctaaat a 21

<210> SEQ ID NO 123
<211> LENGTH: 21
<212> TYPE: DNA
<213> ORGANISM: Artificial Sequence
<220> FEATURE:
<223> OTHER INFORMATION: Synthetic

<400> SEQUENCE: 123
atggatctaa cagacattat a 21

<210> SEQ ID NO 124
<211> LENGTH: 21
<212> TYPE: DNA

<213> ORGANISM: Artificial Sequence
<220> FEATURE:
<223> OTHER INFORMATION: Synthetic

<400> SEQUENCE: 124
cattctccag gatagattat a 21

<210> SEQ ID NO 125
<211> LENGTH: 21
<212> TYPE: DNA
<213> ORGANISM: Artificial Sequence
<220> FEATURE:
<223> OTHER INFORMATION: Synthetic

<400> SEQUENCE: 125
attctccagg atagattata t 21

<210> SEQ ID NO 126
<211> LENGTH: 21
<212> TYPE: DNA
<213> ORGANISM: Artificial Sequence
<220> FEATURE:
<223> OTHER INFORMATION: Synthetic

<400> SEQUENCE: 126
caagatggaa actggaaatt t 21

<210> SEQ ID NO 127
<211> LENGTH: 21
<212> TYPE: DNA
<213> ORGANISM: Artificial Sequence
<220> FEATURE:
<223> OTHER INFORMATION: Synthetic

<400> SEQUENCE: 127
ttctatgagg taagcttata t 21

<210> SEQ ID NO 128
<211> LENGTH: 21
<212> TYPE: DNA
<213> ORGANISM: Artificial Sequence
<220> FEATURE:
<223> OTHER INFORMATION: Synthetic

<400> SEQUENCE: 128
tctatgaggt aagcttatat t 21

<210> SEQ ID NO 129
<211> LENGTH: 21
<212> TYPE: DNA
<213> ORGANISM: Artificial Sequence
<220> FEATURE:
<223> OTHER INFORMATION: Synthetic

<400> SEQUENCE: 129
acaaagatca gacagaaata a 21

<210> SEQ ID NO 130
<211> LENGTH: 21
<212> TYPE: DNA
<213> ORGANISM: Artificial Sequence
<220> FEATURE:
<223> OTHER INFORMATION: Synthetic

<400> SEQUENCE: 130
caaagatcag acagaaataa a 21

<210> SEQ ID NO 131
<211> LENGTH: 21
<212> TYPE: DNA
<213> ORGANISM: Artificial Sequence
<220> FEATURE:
<223> OTHER INFORMATION: Synthetic

<400> SEQUENCE: 131
ataccacaga catacaaatt a 21

<210> SEQ ID NO 132
<211> LENGTH: 21
<212> TYPE: DNA
<213> ORGANISM: Artificial Sequence
<220> FEATURE:
<223> OTHER INFORMATION: Synthetic

<400> SEQUENCE: 132
tgaagactgc caaccattta a 21

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
gaagactgcc aaccatttaa a 21

<210> SEQ ID NO 134
<211> LENGTH: 21
<212> TYPE: DNA
<213> ORGANISM: Artificial Sequence
<220> FEATURE:
<223> OTHER INFORMATION: Synthetic

<400> SEQUENCE: 134
ctaattcagc aacacattat a 21

<210> SEQ ID NO 135
<211> LENGTH: 21
<212> TYPE: DNA
<213> ORGANISM: Artificial Sequence
<220> FEATURE:
<223> OTHER INFORMATION: Synthetic

<400> SEQUENCE: 135
gatgcaggat agttcaatat a 21

<210> SEQ ID NO 136
<211> LENGTH: 21
<212> TYPE: DNA
<213> ORGANISM: Artificial Sequence
<220> FEATURE:
<223> OTHER INFORMATION: Synthetic

<400> SEQUENCE: 136
atgcaggata gttcaatata a 21

<210> SEQ ID NO 137
<211> LENGTH: 21
<212> TYPE: DNA
<213> ORGANISM: Artificial Sequence
<220> FEATURE:

<223> OTHER INFORMATION: Synthetic

<400> SEQUENCE: 137
tgcaggatag ttcaatataa t 21

<210> SEQ ID NO 138
<211> LENGTH: 21
<212> TYPE: DNA
<213> ORGANISM: Artificial Sequence
<220> FEATURE:
<223> OTHER INFORMATION: Synthetic

<400> SEQUENCE: 138
gtgtctgttg gctgcataaa t 21

<210> SEQ ID NO 139
<211> LENGTH: 21
<212> TYPE: DNA
<213> ORGANISM: Artificial Sequence
<220> FEATURE:
<223> OTHER INFORMATION: Synthetic

<400> SEQUENCE: 139
ctttgtagat tctggatatt a 21

<210> SEQ ID NO 140
<211> LENGTH: 21
<212> TYPE: DNA
<213> ORGANISM: Artificial Sequence
<220> FEATURE:
<223> OTHER INFORMATION: Synthetic

<400> SEQUENCE: 140
gcagaagctc tttagtttaa t 21

<210> SEQ ID NO 141
<211> LENGTH: 21
<212> TYPE: DNA
<213> ORGANISM: Artificial Sequence
<220> FEATURE:
<223> OTHER INFORMATION: Synthetic

<400> SEQUENCE: 141
cagaagctct ttagtttaat t 21

<210> SEQ ID NO 142
<211> LENGTH: 21
<212> TYPE: DNA
<213> ORGANISM: Artificial Sequence
<220> FEATURE:
<223> OTHER INFORMATION: Synthetic

<400> SEQUENCE: 142
catcctgtta ctgggtatat a 21

<210> SEQ ID NO 143
<211> LENGTH: 21
<212> TYPE: DNA
<213> ORGANISM: Artificial Sequence
<220> FEATURE:
<223> OTHER INFORMATION: Synthetic

<400> SEQUENCE: 143
gtatataccc agaggattat a 21

<210> SEQ ID NO 144
<211> LENGTH: 21
<212> TYPE: DNA
<213> ORGANISM: Artificial Sequence
<220> FEATURE:
<223> OTHER INFORMATION: Synthetic

<400> SEQUENCE: 144
tatataccca gaggattata a 21

<210> SEQ ID NO 145
<211> LENGTH: 21
<212> TYPE: DNA
<213> ORGANISM: Artificial Sequence
<220> FEATURE:
<223> OTHER INFORMATION: Synthetic

<400> SEQUENCE: 145
atatacccag aggattataa a 21

<210> SEQ ID NO 146
<211> LENGTH: 21
<212> TYPE: DNA
<213> ORGANISM: Artificial Sequence
<220> FEATURE:
<223> OTHER INFORMATION: Synthetic

<400> SEQUENCE: 146
tatacccaga ggattataaa t 21

<210> SEQ ID NO 147
<211> LENGTH: 21
<212> TYPE: DNA
<213> ORGANISM: Artificial Sequence
<220> FEATURE:
<223> OTHER INFORMATION: Synthetic

<400> SEQUENCE: 147
ccctagaact taaagtataa t 21

<210> SEQ ID NO 148
<211> LENGTH: 21
<212> TYPE: DNA
<213> ORGANISM: Artificial Sequence
<220> FEATURE:
<223> OTHER INFORMATION: Synthetic

<400> SEQUENCE: 148
tgacaaacct ggaggtaata t 21

<210> SEQ ID NO 149
<211> LENGTH: 21
<212> TYPE: DNA
<213> ORGANISM: Artificial Sequence
<220> FEATURE:
<223> OTHER INFORMATION: Synthetic

<400> SEQUENCE: 149
gacaaacctg gaggtaatat a 21

<210> SEQ ID NO 150
<211> LENGTH: 21
<212> TYPE: DNA
<213> ORGANISM: Artificial Sequence
<220> FEATURE:
<223> OTHER INFORMATION: Synthetic

<400> SEQUENCE: 150
gtccattctc accacttata t 21

<210> SEQ ID NO 151
<211> LENGTH: 21
<212> TYPE: DNA
<213> ORGANISM: Artificial Sequence
<220> FEATURE:
<223> OTHER INFORMATION: Synthetic

<400> SEQUENCE: 151
tccattctca ccacttatat t 21

<210> SEQ ID NO 152
<211> LENGTH: 21
<212> TYPE: DNA
<213> ORGANISM: Artificial Sequence
<220> FEATURE:
<223> OTHER INFORMATION: Synthetic

<400> SEQUENCE: 152
ccattctcac cacttatatt t 21

<210> SEQ ID NO 153
<211> LENGTH: 21
<212> TYPE: DNA
<213> ORGANISM: Artificial Sequence
<220> FEATURE:
<223> OTHER INFORMATION: Synthetic

<400> SEQUENCE: 153
cattctcacc acttatattt a 21

<210> SEQ ID NO 154
<211> LENGTH: 21
<212> TYPE: DNA
<213> ORGANISM: Artificial Sequence
<220> FEATURE:
<223> OTHER INFORMATION: Synthetic

<400> SEQUENCE: 154
gtagatgaca tgatcttata t 21

<210> SEQ ID NO 155
<211> LENGTH: 21
<212> TYPE: DNA
<213> ORGANISM: Artificial Sequence
<220> FEATURE:
<223> OTHER INFORMATION: Synthetic

<400> SEQUENCE: 155
gaatagagag cccagaaata a 21

<210> SEQ ID NO 156
<211> LENGTH: 21
<212> TYPE: DNA
<213> ORGANISM: Artificial Sequence
<220> FEATURE:
<223> OTHER INFORMATION: Synthetic

<400> SEQUENCE: 156
atgcttgaca tcactaataa t 21

<210> SEQ ID NO 157
<211> LENGTH: 21

<212> TYPE: DNA
<213> ORGANISM: Artificial Sequence
<220> FEATURE:
<223> OTHER INFORMATION: Synthetic

<400> SEQUENCE: 157
tacactgttg gtgtgaattt a 21

<210> SEQ ID NO 158
<211> LENGTH: 21
<212> TYPE: DNA
<213> ORGANISM: Artificial Sequence
<220> FEATURE:
<223> OTHER INFORMATION: Synthetic

<400> SEQUENCE: 158
acactgttgg tgtgaattta a 21

<210> SEQ ID NO 159
<211> LENGTH: 21
<212> TYPE: DNA
<213> ORGANISM: Artificial Sequence
<220> FEATURE:
<223> OTHER INFORMATION: Synthetic

<400> SEQUENCE: 159
cactgttggt gtgaatttaa a 21

<210> SEQ ID NO 160
<211> LENGTH: 21
<212> TYPE: DNA
<213> ORGANISM: Artificial Sequence
<220> FEATURE:
<223> OTHER INFORMATION: Synthetic

<400> SEQUENCE: 160
ggtatttgca cactcatatt t 21

<210> SEQ ID NO 161
<211> LENGTH: 21
<212> TYPE: DNA
<213> ORGANISM: Artificial Sequence
<220> FEATURE:
<223> OTHER INFORMATION: Synthetic

<400> SEQUENCE: 161
gtatttgcac actcatattt a 21

<210> SEQ ID NO 162
<211> LENGTH: 21
<212> TYPE: DNA
<213> ORGANISM: Artificial Sequence
<220> FEATURE:
<223> OTHER INFORMATION: Synthetic

<400> SEQUENCE: 162
ataaagagaa cgtggtatat a 21

<210> SEQ ID NO 163
<211> LENGTH: 21
<212> TYPE: DNA
<213> ORGANISM: Artificial Sequence
<220> FEATURE:
<223> OTHER INFORMATION: Synthetic

<400> SEQUENCE: 163
agacacagtg gaatctattt a 21

<210> SEQ ID NO 164
<211> LENGTH: 21
<212> TYPE: DNA
<213> ORGANISM: Artificial Sequence
<220> FEATURE:
<223> OTHER INFORMATION: Synthetic

<400> SEQUENCE: 164
ggtacaaact ttcagttata a 21

<210> SEQ ID NO 165
<211> LENGTH: 21
<212> TYPE: DNA
<213> ORGANISM: Artificial Sequence
<220> FEATURE:
<223> OTHER INFORMATION: Synthetic

<400> SEQUENCE: 165
gaaggcactg atatgttaat t 21

<210> SEQ ID NO 166
<211> LENGTH: 21
<212> TYPE: DNA
<213> ORGANISM: Artificial Sequence
<220> FEATURE:
<223> OTHER INFORMATION: Synthetic

<400> SEQUENCE: 166
aggcactgat atgttaatta t 21

<210> SEQ ID NO 167
<211> LENGTH: 21
<212> TYPE: DNA
<213> ORGANISM: Artificial Sequence
<220> FEATURE:
<223> OTHER INFORMATION: Synthetic

<400> SEQUENCE: 167
atccattcaa gctagattat t 21

<210> SEQ ID NO 168
<211> LENGTH: 21
<212> TYPE: DNA
<213> ORGANISM: Artificial Sequence
<220> FEATURE:
<223> OTHER INFORMATION: Synthetic

<400> SEQUENCE: 168
tccattcaag ctagattatt t 21

<210> SEQ ID NO 169
<211> LENGTH: 21
<212> TYPE: DNA
<213> ORGANISM: Artificial Sequence
<220> FEATURE:
<223> OTHER INFORMATION: Synthetic

<400> SEQUENCE: 169
ggcatggtgg ccctcaatta t 21

<210> SEQ ID NO 170
<211> LENGTH: 21
<212> TYPE: DNA
<213> ORGANISM: Artificial Sequence
<220> FEATURE:
<223> OTHER INFORMATION: Synthetic

<400> SEQUENCE: 170
gcatggtggc cctcaattat a 21

<210> SEQ ID NO 171
<211> LENGTH: 21
<212> TYPE: DNA
<213> ORGANISM: Artificial Sequence
<220> FEATURE:
<223> OTHER INFORMATION: Synthetic

<400> SEQUENCE: 171
catggtggcc ctcaattata t 21

<210> SEQ ID NO 172
<211> LENGTH: 21
<212> TYPE: DNA
<213> ORGANISM: Artificial Sequence
<220> FEATURE:
<223> OTHER INFORMATION: Synthetic

<400> SEQUENCE: 172
atggtggccc tcaattatat a 21

<210> SEQ ID NO 173
<211> LENGTH: 21
<212> TYPE: DNA
<213> ORGANISM: Artificial Sequence
<220> FEATURE:
<223> OTHER INFORMATION: Synthetic

<400> SEQUENCE: 173
tggtggccct caattatata t 21

<210> SEQ ID NO 174
<211> LENGTH: 21
<212> TYPE: DNA
<213> ORGANISM: Artificial Sequence
<220> FEATURE:
<223> OTHER INFORMATION: Synthetic

<400> SEQUENCE: 174
ggtggccctc aattatatat a 21

<210> SEQ ID NO 175
<211> LENGTH: 21
<212> TYPE: DNA
<213> ORGANISM: Artificial Sequence
<220> FEATURE:
<223> OTHER INFORMATION: Synthetic

<400> SEQUENCE: 175
gtggccctca attatatata t 21

<210> SEQ ID NO 176
<211> LENGTH: 21
<212> TYPE: DNA
<213> ORGANISM: Artificial Sequence
<220> FEATURE:
<223> OTHER INFORMATION: Synthetic

<400> SEQUENCE: 176
tggccctcaa ttatatatat a 21

<210> SEQ ID NO 177
<211> LENGTH: 21
<212> TYPE: DNA
<213> ORGANISM: Artificial Sequence
<220> FEATURE:
<223> OTHER INFORMATION: Synthetic

<400> SEQUENCE: 177
ggccctcaat tatatatata a 21

<210> SEQ ID NO 178
<211> LENGTH: 21
<212> TYPE: DNA
<213> ORGANISM: Artificial Sequence
<220> FEATURE:
<223> OTHER INFORMATION: Synthetic

<400> SEQUENCE: 178
atgaacaaca atgggattta a 21

<210> SEQ ID NO 179
<211> LENGTH: 21
<212> TYPE: DNA
<213> ORGANISM: Artificial Sequence
<220> FEATURE:
<223> OTHER INFORMATION: Synthetic

<400> SEQUENCE: 179
tgaacaacaa tgggatttaa a 21

<210> SEQ ID NO 180
<211> LENGTH: 21
<212> TYPE: DNA
<213> ORGANISM: Artificial Sequence
<220> FEATURE:
<223> OTHER INFORMATION: Synthetic

<400> SEQUENCE: 180
gaacaacaat gggatttaaa t 21

<210> SEQ ID NO 181
<211> LENGTH: 21
<212> TYPE: DNA
<213> ORGANISM: Artificial Sequence
<220> FEATURE:
<223> OTHER INFORMATION: Synthetic

<400> SEQUENCE: 181
agcaatagtg gagaaatata a 21

<210> SEQ ID NO 182
<211> LENGTH: 21
<212> TYPE: DNA
<213> ORGANISM: Artificial Sequence
<220> FEATURE:
<223> OTHER INFORMATION: Synthetic

<400> SEQUENCE: 182
gacctaaacc ctatcttata a 21

<210> SEQ ID NO 183
<211> LENGTH: 21
<212> TYPE: DNA
<213> ORGANISM: Artificial Sequence
<220> FEATURE:
<223> OTHER INFORMATION: Synthetic

<400> SEQUENCE: 183
acctaaaccc tatcttataa t 21

<210> SEQ ID NO 184
<211> LENGTH: 21
<212> TYPE: DNA
<213> ORGANISM: Artificial Sequence
<220> FEATURE:
<223> OTHER INFORMATION: Synthetic

<400> SEQUENCE: 184
cctaaaccct atcttataat t 21

<210> SEQ ID NO 185
<211> LENGTH: 21
<212> TYPE: DNA
<213> ORGANISM: Artificial Sequence
<220> FEATURE:
<223> OTHER INFORMATION: Synthetic

<400> SEQUENCE: 185
ctagagcagc aatactaata t 21

<210> SEQ ID NO 186
<211> LENGTH: 21
<212> TYPE: DNA
<213> ORGANISM: Artificial Sequence
<220> FEATURE:
<223> OTHER INFORMATION: Synthetic

<400> SEQUENCE: 186
ctgaagtgca catggaatat t 21

<210> SEQ ID NO 187
<211> LENGTH: 21
<212> TYPE: DNA
<213> ORGANISM: Artificial Sequence
<220> FEATURE:
<223> OTHER INFORMATION: Synthetic

<400> SEQUENCE: 187
tcttcaggat gacacatatt a 21

<210> SEQ ID NO 188
<211> LENGTH: 21
<212> TYPE: DNA
<213> ORGANISM: Artificial Sequence
<220> FEATURE:
<223> OTHER INFORMATION: Synthetic

<400> SEQUENCE: 188
cacaatgata tggagattta a 21

<210> SEQ ID NO 189
<211> LENGTH: 21
<212> TYPE: DNA
<213> ORGANISM: Artificial Sequence
<220> FEATURE:
<223> OTHER INFORMATION: Synthetic

<400> SEQUENCE: 189
ctcaatccaa taacctaatt t 21

<210> SEQ ID NO 190

<211> LENGTH: 21
<212> TYPE: DNA
<213> ORGANISM: Artificial Sequence
<220> FEATURE:
<223> OTHER INFORMATION: Synthetic

<400> SEQUENCE: 190
gtaaacagaa ggaagaaata a 21

<210> SEQ ID NO 191
<211> LENGTH: 21
<212> TYPE: DNA
<213> ORGANISM: Artificial Sequence
<220> FEATURE:
<223> OTHER INFORMATION: Synthetic

<400> SEQUENCE: 191
gatatcacct tacagaaatt a 21

<210> SEQ ID NO 192
<211> LENGTH: 21
<212> TYPE: DNA
<213> ORGANISM: Artificial Sequence
<220> FEATURE:
<223> OTHER INFORMATION: Synthetic

<400> SEQUENCE: 192
aggtccgtat taccettata t 21

<210> SEQ ID NO 193
<211> LENGTH: 21
<212> TYPE: DNA
<213> ORGANISM: Artificial Sequence
<220> FEATURE:
<223> OTHER INFORMATION: Synthetic

<400> SEQUENCE: 193
catctagcct ttctgattta t 21

<210> SEQ ID NO 194
<211> LENGTH: 21
<212> TYPE: DNA
<213> ORGANISM: Artificial Sequence
<220> FEATURE:
<223> OTHER INFORMATION: Synthetic

<400> SEQUENCE: 194
atctagcctt tctgatttat a 21

<210> SEQ ID NO 195
<211> LENGTH: 21
<212> TYPE: DNA
<213> ORGANISM: Artificial Sequence
<220> FEATURE:
<223> OTHER INFORMATION: Synthetic

<400> SEQUENCE: 195
tctagccttt ctgatttata t 21

<210> SEQ ID NO 196
<211> LENGTH: 21
<212> TYPE: DNA
<213> ORGANISM: Artificial Sequence
<220> FEATURE:
<223> OTHER INFORMATION: Synthetic

<400> SEQUENCE: 196
ctagcctttc tgatttatat a 21

<210> SEQ ID NO 197
<211> LENGTH: 21
<212> TYPE: DNA
<213> ORGANISM: Artificial Sequence
<220> FEATURE:
<223> OTHER INFORMATION: Synthetic

<400> SEQUENCE: 197
agtcacaact cagatttatt t 21

<210> SEQ ID NO 198
<211> LENGTH: 21
<212> TYPE: DNA
<213> ORGANISM: Artificial Sequence
<220> FEATURE:
<223> OTHER INFORMATION: Synthetic

<400> SEQUENCE: 198
ggcctcacaa ctcagattta a 21

<210> SEQ ID NO 199
<211> LENGTH: 21
<212> TYPE: DNA
<213> ORGANISM: Artificial Sequence
<220> FEATURE:
<223> OTHER INFORMATION: Synthetic

<400> SEQUENCE: 199
gaacagagcc ctcagaaata a 21

<210> SEQ ID NO 200
<211> LENGTH: 21
<212> TYPE: DNA
<213> ORGANISM: Artificial Sequence
<220> FEATURE:
<223> OTHER INFORMATION: Synthetic

<400> SEQUENCE: 200
ggaaaggatt ccctatttaa t 21

<210> SEQ ID NO 201
<211> LENGTH: 21
<212> TYPE: DNA
<213> ORGANISM: Artificial Sequence
<220> FEATURE:
<223> OTHER INFORMATION: Synthetic

<400> SEQUENCE: 201
gaaaggattc cctatttaat a 21

<210> SEQ ID NO 202
<211> LENGTH: 21
<212> TYPE: DNA
<213> ORGANISM: Artificial Sequence
<220> FEATURE:
<223> OTHER INFORMATION: Synthetic

<400> SEQUENCE: 202
gacaaacggg atctcattaa a 21

<210> SEQ ID NO 203
<211> LENGTH: 21
<212> TYPE: DNA

<213> ORGANISM: Artificial Sequence
<220> FEATURE:
<223> OTHER INFORMATION: Synthetic

<400> SEQUENCE: 203
catctgacaa agggctaata t 21

<210> SEQ ID NO 204
<211> LENGTH: 21
<212> TYPE: DNA
<213> ORGANISM: Artificial Sequence
<220> FEATURE:
<223> OTHER INFORMATION: Synthetic

<400> SEQUENCE: 204
acaatgaact cagacaaatt t 21

<210> SEQ ID NO 205
<211> LENGTH: 21
<212> TYPE: DNA
<213> ORGANISM: Artificial Sequence
<220> FEATURE:
<223> OTHER INFORMATION: Synthetic

<400> SEQUENCE: 205
caatgaactc agacaaattt a 21

<210> SEQ ID NO 206
<211> LENGTH: 21
<212> TYPE: DNA
<213> ORGANISM: Artificial Sequence
<220> FEATURE:
<223> OTHER INFORMATION: Synthetic

<400> SEQUENCE: 206
gttagaatgg cgatcattaa a 21

<210> SEQ ID NO 207
<211> LENGTH: 21
<212> TYPE: DNA
<213> ORGANISM: Artificial Sequence
<220> FEATURE:
<223> OTHER INFORMATION: Synthetic

<400> SEQUENCE: 207
cagccatccc attgctatat a 21

<210> SEQ ID NO 208
<211> LENGTH: 21
<212> TYPE: DNA
<213> ORGANISM: Artificial Sequence
<220> FEATURE:
<223> OTHER INFORMATION: Synthetic

<400> SEQUENCE: 208
agccatccca ttgctatata t 21

<210> SEQ ID NO 209
<211> LENGTH: 21
<212> TYPE: DNA
<213> ORGANISM: Artificial Sequence
<220> FEATURE:
<223> OTHER INFORMATION: Synthetic

<400> SEQUENCE: 209
gccatcccat tgctatatat a 21

<210> SEQ ID NO 210
<211> LENGTH: 21
<212> TYPE: DNA
<213> ORGANISM: Artificial Sequence
<220> FEATURE:
<223> OTHER INFORMATION: Synthetic

<400> SEQUENCE: 210
ccatcccatt gctatatata t 21

<210> SEQ ID NO 211
<211> LENGTH: 21
<212> TYPE: DNA
<213> ORGANISM: Artificial Sequence
<220> FEATURE:
<223> OTHER INFORMATION: Synthetic

<400> SEQUENCE: 211
catcccattg ctatatatat a 21

<210> SEQ ID NO 212
<211> LENGTH: 21
<212> TYPE: DNA
<213> ORGANISM: Artificial Sequence
<220> FEATURE:
<223> OTHER INFORMATION: Synthetic

<400> SEQUENCE: 212
atatacccaa aggactataa a 21

<210> SEQ ID NO 213
<211> LENGTH: 21
<212> TYPE: DNA
<213> ORGANISM: Artificial Sequence
<220> FEATURE:
<223> OTHER INFORMATION: Synthetic

<400> SEQUENCE: 213
tatacccaaa ggactataaa t 21

<210> SEQ ID NO 214
<211> LENGTH: 21
<212> TYPE: DNA
<213> ORGANISM: Artificial Sequence
<220> FEATURE:
<223> OTHER INFORMATION: Synthetic

<400> SEQUENCE: 214
atatgcacag gtatgtttat t 21

<210> SEQ ID NO 215
<211> LENGTH: 21
<212> TYPE: DNA
<213> ORGANISM: Artificial Sequence
<220> FEATURE:
<223> OTHER INFORMATION: Synthetic

<400> SEQUENCE: 215
gaaagacact gattgtattt a 21

<210> SEQ ID NO 216
<211> LENGTH: 21
<212> TYPE: DNA
<213> ORGANISM: Artificial Sequence
<220> FEATURE:

<223> OTHER INFORMATION: Synthetic

<400> SEQUENCE: 216
acatagccct aaccatataa a 21

<210> SEQ ID NO 217
<211> LENGTH: 21
<212> TYPE: DNA
<213> ORGANISM: Artificial Sequence
<220> FEATURE:
<223> OTHER INFORMATION: Synthetic

<400> SEQUENCE: 217
cctcacacaa agacctatta t 21

<210> SEQ ID NO 218
<211> LENGTH: 21
<212> TYPE: DNA
<213> ORGANISM: Artificial Sequence
<220> FEATURE:
<223> OTHER INFORMATION: Synthetic

<400> SEQUENCE: 218
tggcagagat ttggcaatta t 21

<210> SEQ ID NO 219
<211> LENGTH: 21
<212> TYPE: DNA
<213> ORGANISM: Artificial Sequence
<220> FEATURE:
<223> OTHER INFORMATION: Synthetic

<400> SEQUENCE: 219
ggcagagatt tggcaattat a 21

<210> SEQ ID NO 220
<211> LENGTH: 21
<212> TYPE: DNA
<213> ORGANISM: Artificial Sequence
<220> FEATURE:
<223> OTHER INFORMATION: Synthetic

<400> SEQUENCE: 220
agaacaacaa ggaggaaatt t 21

<210> SEQ ID NO 221
<211> LENGTH: 21
<212> TYPE: DNA
<213> ORGANISM: Artificial Sequence
<220> FEATURE:
<223> OTHER INFORMATION: Synthetic

<400> SEQUENCE: 221
gaacaacaag gaggaaattt a 21

<210> SEQ ID NO 222
<211> LENGTH: 21
<212> TYPE: DNA
<213> ORGANISM: Artificial Sequence
<220> FEATURE:
<223> OTHER INFORMATION: Synthetic

<400> SEQUENCE: 222
gaatggagtg aaatgtttaa a 21

<210> SEQ ID NO 223
<211> LENGTH: 21
<212> TYPE: DNA
<213> ORGANISM: Artificial Sequence
<220> FEATURE:
<223> OTHER INFORMATION: Synthetic

<400> SEQUENCE: 223
tctgatttcc ttgggtttat t 21

<210> SEQ ID NO 224
<211> LENGTH: 21
<212> TYPE: DNA
<213> ORGANISM: Artificial Sequence
<220> FEATURE:
<223> OTHER INFORMATION: Synthetic

<400> SEQUENCE: 224
ctgatttcct tgggtttatt t 21

<210> SEQ ID NO 225
<211> LENGTH: 21
<212> TYPE: DNA
<213> ORGANISM: Artificial Sequence
<220> FEATURE:
<223> OTHER INFORMATION: Synthetic

<400> SEQUENCE: 225
tgctcttctt tctactttat t 21

<210> SEQ ID NO 226
<211> LENGTH: 21
<212> TYPE: DNA
<213> ORGANISM: Artificial Sequence
<220> FEATURE:
<223> OTHER INFORMATION: Synthetic

<400> SEQUENCE: 226
gtaagcattt agtgctataa a 21

<210> SEQ ID NO 227
<211> LENGTH: 21
<212> TYPE: DNA
<213> ORGANISM: Artificial Sequence
<220> FEATURE:
<223> OTHER INFORMATION: Synthetic

<400> SEQUENCE: 227
ttagtcacat cccacaaatt t 21

<210> SEQ ID NO 228
<211> LENGTH: 21
<212> TYPE: DNA
<213> ORGANISM: Artificial Sequence
<220> FEATURE:
<223> OTHER INFORMATION: Synthetic

<400> SEQUENCE: 228
atggtctgtg ctgtgaatat t 21

<210> SEQ ID NO 229
<211> LENGTH: 21
<212> TYPE: DNA
<213> ORGANISM: Artificial Sequence
<220> FEATURE:
<223> OTHER INFORMATION: Synthetic

<400> SEQUENCE: 229
ttgaagtctc caaccataat t 21

<210> SEQ ID NO 230
<211> LENGTH: 21
<212> TYPE: DNA
<213> ORGANISM: Artificial Sequence
<220> FEATURE:
<223> OTHER INFORMATION: Synthetic

<400> SEQUENCE: 230
cagtttgtgc atcacatatt t 21

<210> SEQ ID NO 231
<211> LENGTH: 21
<212> TYPE: DNA
<213> ORGANISM: Artificial Sequence
<220> FEATURE:
<223> OTHER INFORMATION: Synthetic

<400> SEQUENCE: 231
tgccctcttg gtggcttatt t 21

<210> SEQ ID NO 232
<211> LENGTH: 21
<212> TYPE: DNA
<213> ORGANISM: Artificial Sequence
<220> FEATURE:
<223> OTHER INFORMATION: Synthetic

<400> SEQUENCE: 232
tcctaggtca taatgataat t 21

<210> SEQ ID NO 233
<211> LENGTH: 21
<212> TYPE: DNA
<213> ORGANISM: Artificial Sequence
<220> FEATURE:
<223> OTHER INFORMATION: Synthetic

<400> SEQUENCE: 233
ctccacatcc ttaccaatat t 21

<210> SEQ ID NO 234
<211> LENGTH: 21
<212> TYPE: DNA
<213> ORGANISM: Artificial Sequence
<220> FEATURE:
<223> OTHER INFORMATION: Synthetic

<400> SEQUENCE: 234
cgcttatcag atatgattta t 21

<210> SEQ ID NO 235
<211> LENGTH: 21
<212> TYPE: DNA
<213> ORGANISM: Artificial Sequence
<220> FEATURE:
<223> OTHER INFORMATION: Synthetic

<400> SEQUENCE: 235
ggtctataca tgtagattat t 21

<210> SEQ ID NO 236
<211> LENGTH: 21

<212> TYPE: DNA
<213> ORGANISM: Artificial Sequence
<220> FEATURE:
<223> OTHER INFORMATION: Synthetic

<400> SEQUENCE: 236
tcatagatgt atgggattat t 21

<210> SEQ ID NO 237
<211> LENGTH: 21
<212> TYPE: DNA
<213> ORGANISM: Artificial Sequence
<220> FEATURE:
<223> OTHER INFORMATION: Synthetic

<400> SEQUENCE: 237
catagatgta tgggattatt t 21

<210> SEQ ID NO 238
<211> LENGTH: 21
<212> TYPE: DNA
<213> ORGANISM: Artificial Sequence
<220> FEATURE:
<223> OTHER INFORMATION: Synthetic

<400> SEQUENCE: 238
cttgtaactc cttggttaaa t 21

<210> SEQ ID NO 239
<211> LENGTH: 21
<212> TYPE: DNA
<213> ORGANISM: Artificial Sequence
<220> FEATURE:
<223> OTHER INFORMATION: Synthetic

<400> SEQUENCE: 239
ttgtaactcc ttggttaaat t 21

<210> SEQ ID NO 240
<211> LENGTH: 21
<212> TYPE: DNA
<213> ORGANISM: Artificial Sequence
<220> FEATURE:
<223> OTHER INFORMATION: Synthetic

<400> SEQUENCE: 240
tgtaactcct tggttaaatt t 21

<210> SEQ ID NO 241
<211> LENGTH: 21
<212> TYPE: DNA
<213> ORGANISM: Artificial Sequence
<220> FEATURE:
<223> OTHER INFORMATION: Synthetic

<400> SEQUENCE: 241
gtaactcctt ggttaaattt a 21

<210> SEQ ID NO 242
<211> LENGTH: 21
<212> TYPE: DNA
<213> ORGANISM: Artificial Sequence
<220> FEATURE:
<223> OTHER INFORMATION: Synthetic

<400> SEQUENCE: 242
tcctttctga tgctgtttaa a 21

<210> SEQ ID NO 243
<211> LENGTH: 21
<212> TYPE: DNA
<213> ORGANISM: Artificial Sequence
<220> FEATURE:
<223> OTHER INFORMATION: Synthetic

<400> SEQUENCE: 243
cctttctgat gctgtttaaa t 21

<210> SEQ ID NO 244
<211> LENGTH: 21
<212> TYPE: DNA
<213> ORGANISM: Artificial Sequence
<220> FEATURE:
<223> OTHER INFORMATION: Synthetic

<400> SEQUENCE: 244
ctgaaacttt gctgcattta t 21

<210> SEQ ID NO 245
<211> LENGTH: 21
<212> TYPE: DNA
<213> ORGANISM: Artificial Sequence
<220> FEATURE:
<223> OTHER INFORMATION: Synthetic

<400> SEQUENCE: 245
tgaaactttg ctgcatttat t 21

<210> SEQ ID NO 246
<211> LENGTH: 21
<212> TYPE: DNA
<213> ORGANISM: Artificial Sequence
<220> FEATURE:
<223> OTHER INFORMATION: Synthetic

<400> SEQUENCE: 246
gaaactttgc tgcatttatt a 21

<210> SEQ ID NO 247
<211> LENGTH: 21
<212> TYPE: DNA
<213> ORGANISM: Artificial Sequence
<220> FEATURE:
<223> OTHER INFORMATION: Synthetic

<400> SEQUENCE: 247
ttgctctgtg aatagataat t 21

<210> SEQ ID NO 248
<211> LENGTH: 21
<212> TYPE: DNA
<213> ORGANISM: Artificial Sequence
<220> FEATURE:
<223> OTHER INFORMATION: Synthetic

<400> SEQUENCE: 248
tgctctgtga atagataatt t 21

<210> SEQ ID NO 249
<211> LENGTH: 21
<212> TYPE: DNA
<213> ORGANISM: Artificial Sequence
<220> FEATURE:
<223> OTHER INFORMATION: Synthetic

<400> SEQUENCE: 249
atatgttgat ccacctttat a 21

<210> SEQ ID NO 250
<211> LENGTH: 21
<212> TYPE: DNA
<213> ORGANISM: Artificial Sequence
<220> FEATURE:
<223> OTHER INFORMATION: Synthetic

<400> SEQUENCE: 250
tatgttgatc cacctttata t 21

<210> SEQ ID NO 251
<211> LENGTH: 21
<212> TYPE: DNA
<213> ORGANISM: Artificial Sequence
<220> FEATURE:
<223> OTHER INFORMATION: Synthetic

<400> SEQUENCE: 251
atgttgatcc acctttatat t 21

<210> SEQ ID NO 252
<211> LENGTH: 21
<212> TYPE: DNA
<213> ORGANISM: Artificial Sequence
<220> FEATURE:
<223> OTHER INFORMATION: Synthetic

<400> SEQUENCE: 252
tctttggcta ctttgtataa t 21

<210> SEQ ID NO 253
<211> LENGTH: 21
<212> TYPE: DNA
<213> ORGANISM: Artificial Sequence
<220> FEATURE:
<223> OTHER INFORMATION: Synthetic

<400> SEQUENCE: 253
ctttggctac tttgtataat a 21

<210> SEQ ID NO 254
<211> LENGTH: 21
<212> TYPE: DNA
<213> ORGANISM: Artificial Sequence
<220> FEATURE:
<223> OTHER INFORMATION: Synthetic

<400> SEQUENCE: 254
taagtgcata gagccaataa a 21

<210> SEQ ID NO 255
<211> LENGTH: 21
<212> TYPE: DNA
<213> ORGANISM: Artificial Sequence
<220> FEATURE:
<223> OTHER INFORMATION: Synthetic

<400> SEQUENCE: 255
atgcacatga tcttcttaat t 21

<210> SEQ ID NO 256
<211> LENGTH: 21
<212> TYPE: DNA
<213> ORGANISM: Artificial Sequence
<220> FEATURE:
<223> OTHER INFORMATION: Synthetic

<400> SEQUENCE: 256
tgcacatgat cttcttaatt t 21

<210> SEQ ID NO 257
<211> LENGTH: 21
<212> TYPE: DNA
<213> ORGANISM: Artificial Sequence
<220> FEATURE:
<223> OTHER INFORMATION: Synthetic

<400> SEQUENCE: 257
tggcttaaac aagagaaatt t 21

<210> SEQ ID NO 258
<211> LENGTH: 21
<212> TYPE: DNA
<213> ORGANISM: Artificial Sequence
<220> FEATURE:
<223> OTHER INFORMATION: Synthetic

<400> SEQUENCE: 258
ggcttaaaca agagaaattt a 21

<210> SEQ ID NO 259
<211> LENGTH: 21
<212> TYPE: DNA
<213> ORGANISM: Artificial Sequence
<220> FEATURE:
<223> OTHER INFORMATION: Synthetic

<400> SEQUENCE: 259
atatgttgat ccacctttat a 21

<210> SEQ ID NO 260
<211> LENGTH: 21
<212> TYPE: DNA
<213> ORGANISM: Artificial Sequence
<220> FEATURE:
<223> OTHER INFORMATION: Synthetic

<400> SEQUENCE: 260
tatgttgatc cacctttata t 21

<210> SEQ ID NO 261
<211> LENGTH: 21
<212> TYPE: DNA
<213> ORGANISM: Artificial Sequence
<220> FEATURE:
<223> OTHER INFORMATION: Synthetic

<400> SEQUENCE: 261
atgttgatcc acctttatat t 21

<210> SEQ ID NO 262
<211> LENGTH: 21
<212> TYPE: DNA
<213> ORGANISM: Artificial Sequence
<220> FEATURE:
<223> OTHER INFORMATION: Synthetic

<400> SEQUENCE: 262
tctttggcta ctttgtataa t 21

<210> SEQ ID NO 263
<211> LENGTH: 21
<212> TYPE: DNA
<213> ORGANISM: Artificial Sequence
<220> FEATURE:
<223> OTHER INFORMATION: Synthetic

<400> SEQUENCE: 263
ctttggctac tttgtataat a 21

<210> SEQ ID NO 264
<211> LENGTH: 21
<212> TYPE: DNA
<213> ORGANISM: Artificial Sequence
<220> FEATURE:
<223> OTHER INFORMATION: Synthetic

<400> SEQUENCE: 264
taagtgcata gagccaataa a 21

<210> SEQ ID NO 265
<211> LENGTH: 21
<212> TYPE: DNA
<213> ORGANISM: Artificial Sequence
<220> FEATURE:
<223> OTHER INFORMATION: Synthetic

<400> SEQUENCE: 265
atgcacatga tcttcttaat t 21

<210> SEQ ID NO 266
<211> LENGTH: 21
<212> TYPE: DNA
<213> ORGANISM: Artificial Sequence
<220> FEATURE:
<223> OTHER INFORMATION: Synthetic

<400> SEQUENCE: 266
tgcacatgat cttcttaatt t 21

<210> SEQ ID NO 267
<211> LENGTH: 21
<212> TYPE: DNA
<213> ORGANISM: Artificial Sequence
<220> FEATURE:
<223> OTHER INFORMATION: Synthetic

<400> SEQUENCE: 267
tggcttaaac aagagaaatt t 21

<210> SEQ ID NO 268
<211> LENGTH: 21
<212> TYPE: DNA
<213> ORGANISM: Artificial Sequence
<220> FEATURE:
<223> OTHER INFORMATION: Synthetic

<400> SEQUENCE: 268
ggcttaaaca agagaaattt a 21

<210> SEQ ID NO 269

<211> LENGTH: 21
<212> TYPE: DNA
<213> ORGANISM: Artificial Sequence
<220> FEATURE:
<223> OTHER INFORMATION: Synthetic

<400> SEQUENCE: 269
aggtatcaga gtagtatatt t 21

<210> SEQ ID NO 270
<211> LENGTH: 21
<212> TYPE: DNA
<213> ORGANISM: Artificial Sequence
<220> FEATURE:
<223> OTHER INFORMATION: Synthetic

<400> SEQUENCE: 270
agttcatcgt tagtgttata t 21

<210> SEQ ID NO 271
<211> LENGTH: 21
<212> TYPE: DNA
<213> ORGANISM: Artificial Sequence
<220> FEATURE:
<223> OTHER INFORMATION: Synthetic

<400> SEQUENCE: 271
gttcatcgtt agtgttatat a 21

<210> SEQ ID NO 272
<211> LENGTH: 21
<212> TYPE: DNA
<213> ORGANISM: Artificial Sequence
<220> FEATURE:
<223> OTHER INFORMATION: Synthetic

<400> SEQUENCE: 272
accaccatgc ccagctaatt t 21

<210> SEQ ID NO 273
<211> LENGTH: 21
<212> TYPE: DNA
<213> ORGANISM: Artificial Sequence
<220> FEATURE:
<223> OTHER INFORMATION: Synthetic

<400> SEQUENCE: 273
atgacccatt tgaagttaat t 21

<210> SEQ ID NO 274
<211> LENGTH: 21
<212> TYPE: DNA
<213> ORGANISM: Artificial Sequence
<220> FEATURE:
<223> OTHER INFORMATION: Synthetic

<400> SEQUENCE: 274
tgacccattt gaagttaatt t 21

<210> SEQ ID NO 275
<211> LENGTH: 21
<212> TYPE: DNA
<213> ORGANISM: Artificial Sequence
<220> FEATURE:
<223> OTHER INFORMATION: Synthetic

<400> SEQUENCE: 275
atgctggcct cactgaataa a 21

<210> SEQ ID NO 276
<211> LENGTH: 21
<212> TYPE: DNA
<213> ORGANISM: Artificial Sequence
<220> FEATURE:
<223> OTHER INFORMATION: Synthetic

<400> SEQUENCE: 276
tgctggcctc actgaataaa t 21

<210> SEQ ID NO 277
<211> LENGTH: 21
<212> TYPE: DNA
<213> ORGANISM: Artificial Sequence
<220> FEATURE:
<223> OTHER INFORMATION: Synthetic

<400> SEQUENCE: 277
gctggcctca ctgaataaat t 21

<210> SEQ ID NO 278
<211> LENGTH: 21
<212> TYPE: DNA
<213> ORGANISM: Artificial Sequence
<220> FEATURE:
<223> OTHER INFORMATION: Synthetic

<400> SEQUENCE: 278
tgttccctcc tcttcaatta t 21

<210> SEQ ID NO 279
<211> LENGTH: 21
<212> TYPE: DNA
<213> ORGANISM: Artificial Sequence
<220> FEATURE:
<223> OTHER INFORMATION: Synthetic

<400> SEQUENCE: 279
gttccctcct cttcaattat t 21

<210> SEQ ID NO 280
<211> LENGTH: 21
<212> TYPE: DNA
<213> ORGANISM: Artificial Sequence
<220> FEATURE:
<223> OTHER INFORMATION: Synthetic

<400> SEQUENCE: 280
ttccctcctc ttcaattatt t 21

<210> SEQ ID NO 281
<211> LENGTH: 21
<212> TYPE: DNA
<213> ORGANISM: Artificial Sequence
<220> FEATURE:
<223> OTHER INFORMATION: Synthetic

<400> SEQUENCE: 281
ttggtaggtt gtgcgtattt a 21

<210> SEQ ID NO 282
<211> LENGTH: 21
<212> TYPE: DNA

<213> ORGANISM: Artificial Sequence
<220> FEATURE:
<223> OTHER INFORMATION: Synthetic

<400> SEQUENCE: 282
attagttggc atgcaattat t 21

<210> SEQ ID NO 283
<211> LENGTH: 21
<212> TYPE: DNA
<213> ORGANISM: Artificial Sequence
<220> FEATURE:
<223> OTHER INFORMATION: Synthetic

<400> SEQUENCE: 283
attcgtagtt ctctgaataa t 21

<210> SEQ ID NO 284
<211> LENGTH: 21
<212> TYPE: DNA
<213> ORGANISM: Artificial Sequence
<220> FEATURE:
<223> OTHER INFORMATION: Synthetic

<400> SEQUENCE: 284
ttccttctgt tggcctttaa t 21

<210> SEQ ID NO 285
<211> LENGTH: 21
<212> TYPE: DNA
<213> ORGANISM: Artificial Sequence
<220> FEATURE:
<223> OTHER INFORMATION: Synthetic

<400> SEQUENCE: 285
tccttctgtt ggcctttaat t 21

<210> SEQ ID NO 286
<211> LENGTH: 21
<212> TYPE: DNA
<213> ORGANISM: Artificial Sequence
<220> FEATURE:
<223> OTHER INFORMATION: Synthetic

<400> SEQUENCE: 286
ccttctgttg gcctttaatt t 21

<210> SEQ ID NO 287
<211> LENGTH: 21
<212> TYPE: DNA
<213> ORGANISM: Artificial Sequence
<220> FEATURE:
<223> OTHER INFORMATION: Synthetic

<400> SEQUENCE: 287
gaaagcattt agagctataa a 21

<210> SEQ ID NO 288
<211> LENGTH: 21
<212> TYPE: DNA
<213> ORGANISM: Artificial Sequence
<220> FEATURE:
<223> OTHER INFORMATION: Synthetic

<400> SEQUENCE: 288
ctttcactac ctgccataaa t 21

<210> SEQ ID NO 289
<211> LENGTH: 21
<212> TYPE: DNA
<213> ORGANISM: Artificial Sequence
<220> FEATURE:
<223> OTHER INFORMATION: Synthetic

<400> SEQUENCE: 289
tttcactacc tgccataaat t 21

<210> SEQ ID NO 290
<211> LENGTH: 21
<212> TYPE: DNA
<213> ORGANISM: Artificial Sequence
<220> FEATURE:
<223> OTHER INFORMATION: Synthetic

<400> SEQUENCE: 290
ttcactacct gccataaatt t 21

<210> SEQ ID NO 291
<211> LENGTH: 21
<212> TYPE: DNA
<213> ORGANISM: Artificial Sequence
<220> FEATURE:
<223> OTHER INFORMATION: Synthetic

<400> SEQUENCE: 291
tccttgacct attggttatt t 21

<210> SEQ ID NO 292
<211> LENGTH: 21
<212> TYPE: DNA
<213> ORGANISM: Artificial Sequence
<220> FEATURE:
<223> OTHER INFORMATION: Synthetic

<400> SEQUENCE: 292
ccttgaccta ttggttattt a 21

<210> SEQ ID NO 293
<211> LENGTH: 21
<212> TYPE: DNA
<213> ORGANISM: Artificial Sequence
<220> FEATURE:
<223> OTHER INFORMATION: Synthetic

<400> SEQUENCE: 293
cttgacctat tggttattta a 21

<210> SEQ ID NO 294
<211> LENGTH: 21
<212> TYPE: DNA
<213> ORGANISM: Artificial Sequence
<220> FEATURE:
<223> OTHER INFORMATION: Synthetic

<400> SEQUENCE: 294
ttgtgatcac agaagatatt t 21

<210> SEQ ID NO 295
<211> LENGTH: 21
<212> TYPE: DNA
<213> ORGANISM: Artificial Sequence
<220> FEATURE:

<223> OTHER INFORMATION: Synthetic

<400> SEQUENCE: 295
tgtataatcg cagtctatta a 21

<210> SEQ ID NO 296
<211> LENGTH: 21
<212> TYPE: DNA
<213> ORGANISM: Artificial Sequence
<220> FEATURE:
<223> OTHER INFORMATION: Synthetic

<400> SEQUENCE: 296
tcgcagtcta ttaacattta t 21

<210> SEQ ID NO 297
<211> LENGTH: 21
<212> TYPE: DNA
<213> ORGANISM: Artificial Sequence
<220> FEATURE:
<223> OTHER INFORMATION: Synthetic

<400> SEQUENCE: 297
cgcagtctat taacatttat t 21

<210> SEQ ID NO 298
<211> LENGTH: 21
<212> TYPE: DNA
<213> ORGANISM: Artificial Sequence
<220> FEATURE:
<223> OTHER INFORMATION: Synthetic

<400> SEQUENCE: 298
gagtggtaaa gtctctatta t 21

<210> SEQ ID NO 299
<211> LENGTH: 21
<212> TYPE: DNA
<213> ORGANISM: Artificial Sequence
<220> FEATURE:
<223> OTHER INFORMATION: Synthetic

<400> SEQUENCE: 299
agtggtaaag tctctattat t 21

<210> SEQ ID NO 300
<211> LENGTH: 21
<212> TYPE: DNA
<213> ORGANISM: Artificial Sequence
<220> FEATURE:
<223> OTHER INFORMATION: Synthetic

<400> SEQUENCE: 300
agcataagct atgtcattaa a 21

<210> SEQ ID NO 301
<211> LENGTH: 21
<212> TYPE: DNA
<213> ORGANISM: Artificial Sequence
<220> FEATURE:
<223> OTHER INFORMATION: Synthetic

<400> SEQUENCE: 301
ctcttcattt ccttcaatat t 21

<210> SEQ ID NO 302
<211> LENGTH: 21
<212> TYPE: DNA
<213> ORGANISM: Artificial Sequence
<220> FEATURE:
<223> OTHER INFORMATION: Synthetic

<400> SEQUENCE: 302
tgagatacct agaacaatat a 21

<210> SEQ ID NO 303
<211> LENGTH: 21
<212> TYPE: DNA
<213> ORGANISM: Artificial Sequence
<220> FEATURE:
<223> OTHER INFORMATION: Synthetic

<400> SEQUENCE: 303
gagataccta gaacaatata a 21

<210> SEQ ID NO 304
<211> LENGTH: 21
<212> TYPE: DNA
<213> ORGANISM: Artificial Sequence
<220> FEATURE:
<223> OTHER INFORMATION: Synthetic

<400> SEQUENCE: 304
ctctttctct gtgagattat a 21

<210> SEQ ID NO 305
<211> LENGTH: 21
<212> TYPE: DNA
<213> ORGANISM: Artificial Sequence
<220> FEATURE:
<223> OTHER INFORMATION: Synthetic

<400> SEQUENCE: 305
acaacagcct ggaagtataa t 21

<210> SEQ ID NO 306
<211> LENGTH: 21
<212> TYPE: DNA
<213> ORGANISM: Artificial Sequence
<220> FEATURE:
<223> OTHER INFORMATION: Synthetic

<400> SEQUENCE: 306
caacagcctg gaagtataat t 21

<210> SEQ ID NO 307
<211> LENGTH: 21
<212> TYPE: DNA
<213> ORGANISM: Artificial Sequence
<220> FEATURE:
<223> OTHER INFORMATION: Synthetic

<400> SEQUENCE: 307
acagcctgga agtataatta a 21

<210> SEQ ID NO 308
<211> LENGTH: 21
<212> TYPE: DNA
<213> ORGANISM: Artificial Sequence
<220> FEATURE:
<223> OTHER INFORMATION: Synthetic

<400> SEQUENCE: 308
attcaaactg atgccaattt a 21

<210> SEQ ID NO 309
<211> LENGTH: 21
<212> TYPE: DNA
<213> ORGANISM: Artificial Sequence
<220> FEATURE:
<223> OTHER INFORMATION: Synthetic

<400> SEQUENCE: 309
ttcaaactga tgccaattta a 21

<210> SEQ ID NO 310
<211> LENGTH: 21
<212> TYPE: DNA
<213> ORGANISM: Artificial Sequence
<220> FEATURE:
<223> OTHER INFORMATION: Synthetic

<400> SEQUENCE: 310
agtcaacaca ccaatattaa a 21

<210> SEQ ID NO 311
<211> LENGTH: 21
<212> TYPE: DNA
<213> ORGANISM: Artificial Sequence
<220> FEATURE:
<223> OTHER INFORMATION: Synthetic

<400> SEQUENCE: 311
agctcctgtt tgaagtaaat t 21

<210> SEQ ID NO 312
<211> LENGTH: 21
<212> TYPE: DNA
<213> ORGANISM: Artificial Sequence
<220> FEATURE:
<223> OTHER INFORMATION: Synthetic

<400> SEQUENCE: 312
gctcctgttt gaagtaaatt t 21

<210> SEQ ID NO 313
<211> LENGTH: 21
<212> TYPE: DNA
<213> ORGANISM: Artificial Sequence
<220> FEATURE:
<223> OTHER INFORMATION: Synthetic

<400> SEQUENCE: 313
gccttccaag gtttctatta a 21

<210> SEQ ID NO 314
<211> LENGTH: 21
<212> TYPE: DNA
<213> ORGANISM: Artificial Sequence
<220> FEATURE:
<223> OTHER INFORMATION: Synthetic

<400> SEQUENCE: 314
tgtgggtctc tttggattta t 21

<210> SEQ ID NO 315
<211> LENGTH: 21

<212> TYPE: DNA
<213> ORGANISM: Artificial Sequence
<220> FEATURE:
<223> OTHER INFORMATION: Synthetic

<400> SEQUENCE: 315
tatggttctg tagagatatt t 21

<210> SEQ ID NO 316
<211> LENGTH: 21
<212> TYPE: DNA
<213> ORGANISM: Artificial Sequence
<220> FEATURE:
<223> OTHER INFORMATION: Synthetic

<400> SEQUENCE: 316
tgttctcaat ttccctatat a 21

<210> SEQ ID NO 317
<211> LENGTH: 21
<212> TYPE: DNA
<213> ORGANISM: Artificial Sequence
<220> FEATURE:
<223> OTHER INFORMATION: Synthetic

<400> SEQUENCE: 317
gttctcaatt tccctatata a 21

<210> SEQ ID NO 318
<211> LENGTH: 21
<212> TYPE: DNA
<213> ORGANISM: Artificial Sequence
<220> FEATURE:
<223> OTHER INFORMATION: Synthetic

<400> SEQUENCE: 318
aggttggaac atttcaaata a 21

<210> SEQ ID NO 319
<211> LENGTH: 21
<212> TYPE: DNA
<213> ORGANISM: Artificial Sequence
<220> FEATURE:
<223> OTHER INFORMATION: Synthetic

<400> SEQUENCE: 319
ttacatgggc tgttctataa a 21

<210> SEQ ID NO 320
<211> LENGTH: 21
<212> TYPE: DNA
<213> ORGANISM: Artificial Sequence
<220> FEATURE:
<223> OTHER INFORMATION: Synthetic

<400> SEQUENCE: 320
tacatgggct gttctataaa t 21

<210> SEQ ID NO 321
<211> LENGTH: 21
<212> TYPE: DNA
<213> ORGANISM: Artificial Sequence
<220> FEATURE:
<223> OTHER INFORMATION: Synthetic

<400> SEQUENCE: 321
tgttacttaa ggtggttaat a 21

<210> SEQ ID NO 322
<211> LENGTH: 21
<212> TYPE: DNA
<213> ORGANISM: Artificial Sequence
<220> FEATURE:
<223> OTHER INFORMATION: Synthetic

<400> SEQUENCE: 322
gttacttaag gtggttaata a 21

<210> SEQ ID NO 323
<211> LENGTH: 21
<212> TYPE: DNA
<213> ORGANISM: Artificial Sequence
<220> FEATURE:
<223> OTHER INFORMATION: Synthetic

<400> SEQUENCE: 323
gttgctcaag tcttctatat t 21

<210> SEQ ID NO 324
<211> LENGTH: 21
<212> TYPE: DNA
<213> ORGANISM: Artificial Sequence
<220> FEATURE:
<223> OTHER INFORMATION: Synthetic

<400> SEQUENCE: 324
caacatgcag gtttgttata t 21

<210> SEQ ID NO 325
<211> LENGTH: 21
<212> TYPE: DNA
<213> ORGANISM: Artificial Sequence
<220> FEATURE:
<223> OTHER INFORMATION: Synthetic

<400> SEQUENCE: 325
acatgcaggt ttgttatata t 21

<210> SEQ ID NO 326
<211> LENGTH: 21
<212> TYPE: DNA
<213> ORGANISM: Artificial Sequence
<220> FEATURE:
<223> OTHER INFORMATION: Synthetic

<400> SEQUENCE: 326
acgtgtgcat gtgtctttat a 21

<210> SEQ ID NO 327
<211> LENGTH: 21
<212> TYPE: DNA
<213> ORGANISM: Artificial Sequence
<220> FEATURE:
<223> OTHER INFORMATION: Synthetic

<400> SEQUENCE: 327
ctttatagca gcatgattta t 21

<210> SEQ ID NO 328
<211> LENGTH: 21
<212> TYPE: DNA
<213> ORGANISM: Artificial Sequence
<220> FEATURE:
<223> OTHER INFORMATION: Synthetic

<400> SEQUENCE: 328
tgtgtctttg gctgcataaa t 21

<210> SEQ ID NO 329
<211> LENGTH: 21
<212> TYPE: DNA
<213> ORGANISM: Artificial Sequence
<220> FEATURE:
<223> OTHER INFORMATION: Synthetic

<400> SEQUENCE: 329
ctttgtagat tctggatatt a 21

<210> SEQ ID NO 330
<211> LENGTH: 21
<212> TYPE: DNA
<213> ORGANISM: Artificial Sequence
<220> FEATURE:
<223> OTHER INFORMATION: Synthetic

<400> SEQUENCE: 330
gcagaagctc tttagtttaa t 21

<210> SEQ ID NO 331
<211> LENGTH: 21
<212> TYPE: DNA
<213> ORGANISM: Artificial Sequence
<220> FEATURE:
<223> OTHER INFORMATION: Synthetic

<400> SEQUENCE: 331
tttcccagca ccatttatta a 21

<210> SEQ ID NO 332
<211> LENGTH: 21
<212> TYPE: DNA
<213> ORGANISM: Artificial Sequence
<220> FEATURE:
<223> OTHER INFORMATION: Synthetic

<400> SEQUENCE: 332
ttcccagcac catttattaa a 21

<210> SEQ ID NO 333
<211> LENGTH: 21
<212> TYPE: DNA
<213> ORGANISM: Artificial Sequence
<220> FEATURE:
<223> OTHER INFORMATION: Synthetic

<400> SEQUENCE: 333
tcccagcacc atttattaaa t 21

<210> SEQ ID NO 334
<211> LENGTH: 21
<212> TYPE: DNA
<213> ORGANISM: Artificial Sequence
<220> FEATURE:
<223> OTHER INFORMATION: Synthetic

<400> SEQUENCE: 334
cccagcacca tttattaaat a 21

<210> SEQ ID NO 335
<211> LENGTH: 21
<212> TYPE: DNA
<213> ORGANISM: Artificial Sequence
<220> FEATURE:
<223> OTHER INFORMATION: Synthetic

<400> SEQUENCE: 335
gttgtagatg tgtggtatta t 21

<210> SEQ ID NO 336
<211> LENGTH: 21
<212> TYPE: DNA
<213> ORGANISM: Artificial Sequence
<220> FEATURE:
<223> OTHER INFORMATION: Synthetic

<400> SEQUENCE: 336
ttgtagatgt gtggtattat t 21

<210> SEQ ID NO 337
<211> LENGTH: 21
<212> TYPE: DNA
<213> ORGANISM: Artificial Sequence
<220> FEATURE:
<223> OTHER INFORMATION: Synthetic

<400> SEQUENCE: 337
tgtagatgtg tggtattatt t 21

<210> SEQ ID NO 338
<211> LENGTH: 21
<212> TYPE: DNA
<213> ORGANISM: Artificial Sequence
<220> FEATURE:
<223> OTHER INFORMATION: Synthetic

<400> SEQUENCE: 338
gttctgttcc attggtttat a 21

<210> SEQ ID NO 339
<211> LENGTH: 21
<212> TYPE: DNA
<213> ORGANISM: Artificial Sequence
<220> FEATURE:
<223> OTHER INFORMATION: Synthetic

<400> SEQUENCE: 339
ttctgttcca ttggtttata t 21

<210> SEQ ID NO 340
<211> LENGTH: 21
<212> TYPE: DNA
<213> ORGANISM: Artificial Sequence
<220> FEATURE:
<223> OTHER INFORMATION: Synthetic

<400> SEQUENCE: 340
ggatggcatt gaatctataa a 21

<210> SEQ ID NO 341
<211> LENGTH: 21
<212> TYPE: DNA
<213> ORGANISM: Artificial Sequence
<220> FEATURE:
<223> OTHER INFORMATION: Synthetic

<400> SEQUENCE: 341
gatggcattg aatctataaa t 21

<210> SEQ ID NO 342
<211> LENGTH: 21
<212> TYPE: DNA
<213> ORGANISM: Artificial Sequence
<220> FEATURE:
<223> OTHER INFORMATION: Synthetic

<400> SEQUENCE: 342
cctaattgaa taccctttat t 21

<210> SEQ ID NO 343
<211> LENGTH: 21
<212> TYPE: DNA
<213> ORGANISM: Artificial Sequence
<220> FEATURE:
<223> OTHER INFORMATION: Synthetic

<400> SEQUENCE: 343
ggctgtgggt ttgtcataaa t 21

<210> SEQ ID NO 344
<211> LENGTH: 21
<212> TYPE: DNA
<213> ORGANISM: Artificial Sequence
<220> FEATURE:
<223> OTHER INFORMATION: Synthetic

<400> SEQUENCE: 344
gctgtgggtt tgtcataaat a 21

<210> SEQ ID NO 345
<211> LENGTH: 21
<212> TYPE: DNA
<213> ORGANISM: Artificial Sequence
<220> FEATURE:
<223> OTHER INFORMATION: Synthetic

<400> SEQUENCE: 345
tgtcccatca atacctaatt t 21

<210> SEQ ID NO 346
<211> LENGTH: 21
<212> TYPE: DNA
<213> ORGANISM: Artificial Sequence
<220> FEATURE:
<223> OTHER INFORMATION: Synthetic

<400> SEQUENCE: 346
gtcccatcaa tacctaattt a 21

<210> SEQ ID NO 347
<211> LENGTH: 21
<212> TYPE: DNA
<213> ORGANISM: Artificial Sequence
<220> FEATURE:
<223> OTHER INFORMATION: Synthetic

<400> SEQUENCE: 347
tcccatcaat acctaattta t 21

<210> SEQ ID NO 348

<211> LENGTH: 21
<212> TYPE: DNA
<213> ORGANISM: Artificial Sequence
<220> FEATURE:
<223> OTHER INFORMATION: Synthetic

<400> SEQUENCE: 348
cccatcaata cctaatttat t 21

<210> SEQ ID NO 349
<211> LENGTH: 21
<212> TYPE: DNA
<213> ORGANISM: Artificial Sequence
<220> FEATURE:
<223> OTHER INFORMATION: Synthetic

<400> SEQUENCE: 349
ttgtctttgg ttctgtttat a 21

<210> SEQ ID NO 350
<211> LENGTH: 21
<212> TYPE: DNA
<213> ORGANISM: Artificial Sequence
<220> FEATURE:
<223> OTHER INFORMATION: Synthetic

<400> SEQUENCE: 350
tgtctttggt tctgtttata t 21

<210> SEQ ID NO 351
<211> LENGTH: 21
<212> TYPE: DNA
<213> ORGANISM: Artificial Sequence
<220> FEATURE:
<223> OTHER INFORMATION: Synthetic

<400> SEQUENCE: 351
agcatgcttt gctggtatta a 21

<210> SEQ ID NO 352
<211> LENGTH: 21
<212> TYPE: DNA
<213> ORGANISM: Artificial Sequence
<220> FEATURE:
<223> OTHER INFORMATION: Synthetic

<400> SEQUENCE: 352
gcatgctttg ctggtattaa t 21

<210> SEQ ID NO 353
<211> LENGTH: 21
<212> TYPE: DNA
<213> ORGANISM: Artificial Sequence
<220> FEATURE:
<223> OTHER INFORMATION: Synthetic

<400> SEQUENCE: 353
catgctttgc tggtattaat a 21

<210> SEQ ID NO 354
<211> LENGTH: 21
<212> TYPE: DNA
<213> ORGANISM: Artificial Sequence
<220> FEATURE:
<223> OTHER INFORMATION: Synthetic

<400> SEQUENCE: 354
atgctttgct ggtattaata t 21

<210> SEQ ID NO 355
<211> LENGTH: 21
<212> TYPE: DNA
<213> ORGANISM: Artificial Sequence
<220> FEATURE:
<223> OTHER INFORMATION: Synthetic

<400> SEQUENCE: 355
tgctttgctg gtattaatat a 21

<210> SEQ ID NO 356
<211> LENGTH: 21
<212> TYPE: DNA
<213> ORGANISM: Artificial Sequence
<220> FEATURE:
<223> OTHER INFORMATION: Synthetic

<400> SEQUENCE: 356
gagagttaga acctcaatat a 21

<210> SEQ ID NO 357
<211> LENGTH: 21
<212> TYPE: DNA
<213> ORGANISM: Artificial Sequence
<220> FEATURE:
<223> OTHER INFORMATION: Synthetic

<400> SEQUENCE: 357
agagttagaa cctcaatata t 21

<210> SEQ ID NO 358
<211> LENGTH: 21
<212> TYPE: DNA
<213> ORGANISM: Artificial Sequence
<220> FEATURE:
<223> OTHER INFORMATION: Synthetic

<400> SEQUENCE: 358
ccaccacgcc tggctttata a 21

<210> SEQ ID NO 359
<211> LENGTH: 21
<212> TYPE: DNA
<213> ORGANISM: Artificial Sequence
<220> FEATURE:
<223> OTHER INFORMATION: Synthetic

<400> SEQUENCE: 359
caccacgcct ggctttataa t 21

<210> SEQ ID NO 360
<211> LENGTH: 21
<212> TYPE: DNA
<213> ORGANISM: Artificial Sequence
<220> FEATURE:
<223> OTHER INFORMATION: Synthetic

<400> SEQUENCE: 360
accacgcctg gctttataat t 21

<210> SEQ ID NO 361
<211> LENGTH: 21
<212> TYPE: DNA

<213> ORGANISM: Artificial Sequence
<220> FEATURE:
<223> OTHER INFORMATION: Synthetic

<400> SEQUENCE: 361
ccacgcctgg ctttataatt t 21

<210> SEQ ID NO 362
<211> LENGTH: 21
<212> TYPE: DNA
<213> ORGANISM: Artificial Sequence
<220> FEATURE:
<223> OTHER INFORMATION: Synthetic

<400> SEQUENCE: 362
gtctagctcc aagtgatata t 21

<210> SEQ ID NO 363
<211> LENGTH: 21
<212> TYPE: DNA
<213> ORGANISM: Artificial Sequence
<220> FEATURE:
<223> OTHER INFORMATION: Synthetic

<400> SEQUENCE: 363
tttgcttctg tctgaaatat a 21

<210> SEQ ID NO 364
<211> LENGTH: 21
<212> TYPE: DNA
<213> ORGANISM: Artificial Sequence
<220> FEATURE:
<223> OTHER INFORMATION: Synthetic

<400> SEQUENCE: 364
ttgcttctgt ctgaaatata t 21

<210> SEQ ID NO 365
<211> LENGTH: 21
<212> TYPE: DNA
<213> ORGANISM: Artificial Sequence
<220> FEATURE:
<223> OTHER INFORMATION: Synthetic

<400> SEQUENCE: 365
tcttaagtct gtgagtttat a 21

<210> SEQ ID NO 366
<211> LENGTH: 21
<212> TYPE: DNA
<213> ORGANISM: Artificial Sequence
<220> FEATURE:
<223> OTHER INFORMATION: Synthetic

<400> SEQUENCE: 366
tctctgattt ccacctatat t 21

<210> SEQ ID NO 367
<211> LENGTH: 21
<212> TYPE: DNA
<213> ORGANISM: Artificial Sequence
<220> FEATURE:
<223> OTHER INFORMATION: Synthetic

<400> SEQUENCE: 367
ctctgatttc cacctatatt a 21

<210> SEQ ID NO 368
<211> LENGTH: 21
<212> TYPE: DNA
<213> ORGANISM: Artificial Sequence
<220> FEATURE:
<223> OTHER INFORMATION: Synthetic

<400> SEQUENCE: 368
gtatatactc cagagaaata a 21

<210> SEQ ID NO 369
<211> LENGTH: 21
<212> TYPE: DNA
<213> ORGANISM: Artificial Sequence
<220> FEATURE:
<223> OTHER INFORMATION: Synthetic

<400> SEQUENCE: 369
caccagaact tgaacattaa t 21

<210> SEQ ID NO 370
<211> LENGTH: 21
<212> TYPE: DNA
<213> ORGANISM: Artificial Sequence
<220> FEATURE:
<223> OTHER INFORMATION: Synthetic

<400> SEQUENCE: 370
accagaactt gaacattaat t 21

<210> SEQ ID NO 371
<211> LENGTH: 21
<212> TYPE: DNA
<213> ORGANISM: Artificial Sequence
<220> FEATURE:
<223> OTHER INFORMATION: Synthetic

<400> SEQUENCE: 371
ccagaacttg aacattaatt t 21

<210> SEQ ID NO 372
<211> LENGTH: 21
<212> TYPE: DNA
<213> ORGANISM: Artificial Sequence
<220> FEATURE:
<223> OTHER INFORMATION: Synthetic

<400> SEQUENCE: 372
gtctggaact cctggaatta a 21

<210> SEQ ID NO 373
<211> LENGTH: 21
<212> TYPE: DNA
<213> ORGANISM: Artificial Sequence
<220> FEATURE:
<223> OTHER INFORMATION: Synthetic

<400> SEQUENCE: 373
ctttctgtgc ctggcttatt t 21

<210> SEQ ID NO 374
<211> LENGTH: 21
<212> TYPE: DNA
<213> ORGANISM: Artificial Sequence
<220> FEATURE:

<223> OTHER INFORMATION: Synthetic

<400> SEQUENCE: 374
caggatttac cttcctttaa a 21

<210> SEQ ID NO 375
<211> LENGTH: 21
<212> TYPE: DNA
<213> ORGANISM: Artificial Sequence
<220> FEATURE:
<223> OTHER INFORMATION: Synthetic

<400> SEQUENCE: 375
tctgttgatg ggcacttaaa t 21

<210> SEQ ID NO 376
<211> LENGTH: 21
<212> TYPE: DNA
<213> ORGANISM: Artificial Sequence
<220> FEATURE:
<223> OTHER INFORMATION: Synthetic

<400> SEQUENCE: 376
ctgttgatgg gcacttaaat t 21

<210> SEQ ID NO 377
<211> LENGTH: 21
<212> TYPE: DNA
<213> ORGANISM: Artificial Sequence
<220> FEATURE:
<223> OTHER INFORMATION: Synthetic

<400> SEQUENCE: 377
tcatagcggc tgtactaatt t 21

<210> SEQ ID NO 378
<211> LENGTH: 21
<212> TYPE: DNA
<213> ORGANISM: Artificial Sequence
<220> FEATURE:
<223> OTHER INFORMATION: Synthetic

<400> SEQUENCE: 378
catagcggct gtactaattt a 21

<210> SEQ ID NO 379
<211> LENGTH: 21
<212> TYPE: DNA
<213> ORGANISM: Artificial Sequence
<220> FEATURE:
<223> OTHER INFORMATION: Synthetic

<400> SEQUENCE: 379
tttacccatt tccagatata t 21

<210> SEQ ID NO 380
<211> LENGTH: 21
<212> TYPE: DNA
<213> ORGANISM: Artificial Sequence
<220> FEATURE:
<223> OTHER INFORMATION: Synthetic

<400> SEQUENCE: 380
gtgtaaataa gggtctaatt t 21

<210> SEQ ID NO 381
<211> LENGTH: 21
<212> TYPE: DNA
<213> ORGANISM: Artificial Sequence
<220> FEATURE:
<223> OTHER INFORMATION: Synthetic

<400> SEQUENCE: 381
tggttatgtc atcagtaatt a 21

<210> SEQ ID NO 382
<211> LENGTH: 21
<212> TYPE: DNA
<213> ORGANISM: Artificial Sequence
<220> FEATURE:
<223> OTHER INFORMATION: Synthetic

<400> SEQUENCE: 382
ccttgcatcc taaggataaa t 21

<210> SEQ ID NO 383
<211> LENGTH: 21
<212> TYPE: DNA
<213> ORGANISM: Artificial Sequence
<220> FEATURE:
<223> OTHER INFORMATION: Synthetic

<400> SEQUENCE: 383
gtgaatccag tttgctaata t 21

<210> SEQ ID NO 384
<211> LENGTH: 21
<212> TYPE: DNA
<213> ORGANISM: Artificial Sequence
<220> FEATURE:
<223> OTHER INFORMATION: Synthetic

<400> SEQUENCE: 384
tgaatccagt ttgctaatat a 21

<210> SEQ ID NO 385
<211> LENGTH: 21
<212> TYPE: DNA
<213> ORGANISM: Artificial Sequence
<220> FEATURE:
<223> OTHER INFORMATION: Synthetic

<400> SEQUENCE: 385
gaatccagtt tgctaatata t 21

<210> SEQ ID NO 386
<211> LENGTH: 21
<212> TYPE: DNA
<213> ORGANISM: Artificial Sequence
<220> FEATURE:
<223> OTHER INFORMATION: Synthetic

<400> SEQUENCE: 386
ccatgttcat cagggatatt a 21

<210> SEQ ID NO 387
<211> LENGTH: 21
<212> TYPE: DNA
<213> ORGANISM: Artificial Sequence
<220> FEATURE:
<223> OTHER INFORMATION: Synthetic

<400> SEQUENCE: 387
gtgtctttct ctggctttaa t 21

<210> SEQ ID NO 388
<211> LENGTH: 21
<212> TYPE: DNA
<213> ORGANISM: Artificial Sequence
<220> FEATURE:
<223> OTHER INFORMATION: Synthetic

<400> SEQUENCE: 388
tgtctttctc tggctttaat a 21

<210> SEQ ID NO 389
<211> LENGTH: 21
<212> TYPE: DNA
<213> ORGANISM: Artificial Sequence
<220> FEATURE:
<223> OTHER INFORMATION: Synthetic

<400> SEQUENCE: 389
gtctttctct ggctttaata a 21

<210> SEQ ID NO 390
<211> LENGTH: 21
<212> TYPE: DNA
<213> ORGANISM: Artificial Sequence
<220> FEATURE:
<223> OTHER INFORMATION: Synthetic

<400> SEQUENCE: 390
ttgtgatcct tcttctttat t 21

<210> SEQ ID NO 391
<211> LENGTH: 21
<212> TYPE: DNA
<213> ORGANISM: Artificial Sequence
<220> FEATURE:
<223> OTHER INFORMATION: Synthetic

<400> SEQUENCE: 391
gtaggtttgt atcgctataa a 21

<210> SEQ ID NO 392
<211> LENGTH: 21
<212> TYPE: DNA
<213> ORGANISM: Artificial Sequence
<220> FEATURE:
<223> OTHER INFORMATION: Synthetic

<400> SEQUENCE: 392
taggtttgta tcgctataaa t 21

<210> SEQ ID NO 393
<211> LENGTH: 21
<212> TYPE: DNA
<213> ORGANISM: Artificial Sequence
<220> FEATURE:
<223> OTHER INFORMATION: Synthetic

<400> SEQUENCE: 393
aggtttgtat cgctataaat t 21

<210> SEQ ID NO 394
<211> LENGTH: 21

<212> TYPE: DNA
<213> ORGANISM: Artificial Sequence
<220> FEATURE:
<223> OTHER INFORMATION: Synthetic

<400> SEQUENCE: 394
ggtttgtatc gctataaatt t 21

<210> SEQ ID NO 395
<211> LENGTH: 21
<212> TYPE: DNA
<213> ORGANISM: Artificial Sequence
<220> FEATURE:
<223> OTHER INFORMATION: Synthetic

<400> SEQUENCE: 395
tcatttgtct caaggtaatt t 21

<210> SEQ ID NO 396
<211> LENGTH: 21
<212> TYPE: DNA
<213> ORGANISM: Artificial Sequence
<220> FEATURE:
<223> OTHER INFORMATION: Synthetic

<400> SEQUENCE: 396
tttgggagca tattgtttaa t 21

<210> SEQ ID NO 397
<211> LENGTH: 21
<212> TYPE: DNA
<213> ORGANISM: Artificial Sequence
<220> FEATURE:
<223> OTHER INFORMATION: Synthetic

<400> SEQUENCE: 397
ttgggagcat attgtttaat t 21

<210> SEQ ID NO 398
<211> LENGTH: 21
<212> TYPE: DNA
<213> ORGANISM: Artificial Sequence
<220> FEATURE:
<223> OTHER INFORMATION: Synthetic

<400> SEQUENCE: 398
tgggagcata ttgtttaatt t 21

<210> SEQ ID NO 399
<211> LENGTH: 21
<212> TYPE: DNA
<213> ORGANISM: Artificial Sequence
<220> FEATURE:
<223> OTHER INFORMATION: Synthetic

<400> SEQUENCE: 399
tggatggaat gtttcatata t 21

<210> SEQ ID NO 400
<211> LENGTH: 21
<212> TYPE: DNA
<213> ORGANISM: Artificial Sequence
<220> FEATURE:
<223> OTHER INFORMATION: Synthetic

<400> SEQUENCE: 400
agtattgagg tcccgtatta t 21

<210> SEQ ID NO 401
<211> LENGTH: 21
<212> TYPE: DNA
<213> ORGANISM: Artificial Sequence
<220> FEATURE:
<223> OTHER INFORMATION: Synthetic

<400> SEQUENCE: 401
gtattgaggt cccgtattat a 21

<210> SEQ ID NO 402
<211> LENGTH: 21
<212> TYPE: DNA
<213> ORGANISM: Artificial Sequence
<220> FEATURE:
<223> OTHER INFORMATION: Synthetic

<400> SEQUENCE: 402
ctccctcttc acatcattta a 21

<210> SEQ ID NO 403
<211> LENGTH: 21
<212> TYPE: DNA
<213> ORGANISM: Artificial Sequence
<220> FEATURE:
<223> OTHER INFORMATION: Synthetic

<400> SEQUENCE: 403
tccctcttca catcatttaa a 21

<210> SEQ ID NO 404
<211> LENGTH: 21
<212> TYPE: DNA
<213> ORGANISM: Artificial Sequence
<220> FEATURE:
<223> OTHER INFORMATION: Synthetic

<400> SEQUENCE: 404
tatgtcttct tggtgaatta a 21

<210> SEQ ID NO 405
<211> LENGTH: 21
<212> TYPE: DNA
<213> ORGANISM: Artificial Sequence
<220> FEATURE:
<223> OTHER INFORMATION: Synthetic

<400> SEQUENCE: 405
atgtcttctt ggtgaattaa t 21

<210> SEQ ID NO 406
<211> LENGTH: 21
<212> TYPE: DNA
<213> ORGANISM: Artificial Sequence
<220> FEATURE:
<223> OTHER INFORMATION: Synthetic

<400> SEQUENCE: 406
ctgctctcaa tttccattta t 21

<210> SEQ ID NO 407
<211> LENGTH: 21
<212> TYPE: DNA
<213> ORGANISM: Artificial Sequence
<220> FEATURE:
<223> OTHER INFORMATION: Synthetic

<400> SEQUENCE: 407
tgctctcaat ttccatttat a 21

<210> SEQ ID NO 408
<211> LENGTH: 21
<212> TYPE: DNA
<213> ORGANISM: Artificial Sequence
<220> FEATURE:
<223> OTHER INFORMATION: Synthetic

<400> SEQUENCE: 408
gctctcaatt tccatttata t 21

<210> SEQ ID NO 409
<211> LENGTH: 21
<212> TYPE: DNA
<213> ORGANISM: Artificial Sequence
<220> FEATURE:
<223> OTHER INFORMATION: Synthetic

<400> SEQUENCE: 409
tccttcagca ctttgaatat a 21

<210> SEQ ID NO 410
<211> LENGTH: 21
<212> TYPE: DNA
<213> ORGANISM: Artificial Sequence
<220> FEATURE:
<223> OTHER INFORMATION: Synthetic

<400> SEQUENCE: 410
tcagctatta cttccttaaa t 21

<210> SEQ ID NO 411
<211> LENGTH: 21
<212> TYPE: DNA
<213> ORGANISM: Artificial Sequence
<220> FEATURE:
<223> OTHER INFORMATION: Synthetic

<400> SEQUENCE: 411
cagctattac ttccttaaat a 21

<210> SEQ ID NO 412
<211> LENGTH: 21
<212> TYPE: DNA
<213> ORGANISM: Artificial Sequence
<220> FEATURE:
<223> OTHER INFORMATION: Synthetic

<400> SEQUENCE: 412
tccttaagga cctcctatta t 21

<210> SEQ ID NO 413
<211> LENGTH: 21
<212> TYPE: DNA
<213> ORGANISM: Artificial Sequence
<220> FEATURE:
<223> OTHER INFORMATION: Synthetic

<400> SEQUENCE: 413
gcttgacctc taaacatata a 21

<210> SEQ ID NO 414
<211> LENGTH: 21
<212> TYPE: DNA
<213> ORGANISM: Artificial Sequence
<220> FEATURE:
<223> OTHER INFORMATION: Synthetic

<400> SEQUENCE: 414
cttgacctct aaacatataa a 21

<210> SEQ ID NO 415
<211> LENGTH: 21
<212> TYPE: DNA
<213> ORGANISM: Artificial Sequence
<220> FEATURE:
<223> OTHER INFORMATION: Synthetic

<400> SEQUENCE: 415
accaatacct tgtgtaataa a 21

<210> SEQ ID NO 416
<211> LENGTH: 21
<212> TYPE: DNA
<213> ORGANISM: Artificial Sequence
<220> FEATURE:
<223> OTHER INFORMATION: Synthetic

<400> SEQUENCE: 416
ttgacactgg ctctctttat a 21

<210> SEQ ID NO 417
<211> LENGTH: 21
<212> TYPE: DNA
<213> ORGANISM: Artificial Sequence
<220> FEATURE:
<223> OTHER INFORMATION: Synthetic

<400> SEQUENCE: 417
tgacactggc tctctttata a 21

<210> SEQ ID NO 418
<211> LENGTH: 21
<212> TYPE: DNA
<213> ORGANISM: Artificial Sequence
<220> FEATURE:
<223> OTHER INFORMATION: Synthetic

<400> SEQUENCE: 418
cagaagatgt gtttgataat a 21

<210> SEQ ID NO 419
<211> LENGTH: 21
<212> TYPE: DNA
<213> ORGANISM: Artificial Sequence
<220> FEATURE:
<223> OTHER INFORMATION: Synthetic

<400> SEQUENCE: 419
gtttgacgtg aagagtttaa a 21

<210> SEQ ID NO 420
<211> LENGTH: 21
<212> TYPE: DNA
<213> ORGANISM: Artificial Sequence
<220> FEATURE:
<223> OTHER INFORMATION: Synthetic

<400> SEQUENCE: 420
ctctgagctt cagtgaatta t 21

<210> SEQ ID NO 421
<211> LENGTH: 21
<212> TYPE: DNA
<213> ORGANISM: Artificial Sequence
<220> FEATURE:
<223> OTHER INFORMATION: Synthetic

<400> SEQUENCE: 421
agggttgaat gctggattta a 21

<210> SEQ ID NO 422
<211> LENGTH: 21
<212> TYPE: DNA
<213> ORGANISM: Artificial Sequence
<220> FEATURE:
<223> OTHER INFORMATION: Synthetic

<400> SEQUENCE: 422
gggttgaatg ctggatttaa a 21

<210> SEQ ID NO 423
<211> LENGTH: 21
<212> TYPE: DNA
<213> ORGANISM: Artificial Sequence
<220> FEATURE:
<223> OTHER INFORMATION: Synthetic

<400> SEQUENCE: 423
ggttgaatgc tggatttaaa t 21

<210> SEQ ID NO 424
<211> LENGTH: 21
<212> TYPE: DNA
<213> ORGANISM: Artificial Sequence
<220> FEATURE:
<223> OTHER INFORMATION: Synthetic

<400> SEQUENCE: 424
gttgaatgct ggatttaaat a 21

<210> SEQ ID NO 425
<211> LENGTH: 21
<212> TYPE: DNA
<213> ORGANISM: Artificial Sequence
<220> FEATURE:
<223> OTHER INFORMATION: Synthetic

<400> SEQUENCE: 425
agtgaaagca aagagaataa a 21

<210> SEQ ID NO 426
<211> LENGTH: 21
<212> TYPE: DNA
<213> ORGANISM: Artificial Sequence
<220> FEATURE:
<223> OTHER INFORMATION: Synthetic

<400> SEQUENCE: 426
catgatgttc caaactttaa a 21

<210> SEQ ID NO 427

<211> LENGTH: 21
<212> TYPE: DNA
<213> ORGANISM: Artificial Sequence
<220> FEATURE:
<223> OTHER INFORMATION: Synthetic

<400> SEQUENCE: 427
aggtggccaa gggccttaat a 21

<210> SEQ ID NO 428
<211> LENGTH: 21
<212> TYPE: DNA
<213> ORGANISM: Artificial Sequence
<220> FEATURE:
<223> OTHER INFORMATION: Synthetic

<400> SEQUENCE: 428
gcccagctgg ctctgtaata a 21

<210> SEQ ID NO 429
<211> LENGTH: 21
<212> TYPE: DNA
<213> ORGANISM: Artificial Sequence
<220> FEATURE:
<223> OTHER INFORMATION: Synthetic

<400> SEQUENCE: 429
cccagctggc tctgtaataa a 21

<210> SEQ ID NO 430
<211> LENGTH: 21
<212> TYPE: DNA
<213> ORGANISM: Artificial Sequence
<220> FEATURE:
<223> OTHER INFORMATION: Synthetic

<400> SEQUENCE: 430
ccagctggct ctgtaataaa t 21

<210> SEQ ID NO 431
<211> LENGTH: 21
<212> TYPE: DNA
<213> ORGANISM: Artificial Sequence
<220> FEATURE:
<223> OTHER INFORMATION: Synthetic

<400> SEQUENCE: 431
tggtgtcatc gggccatatt t 21

<210> SEQ ID NO 432
<211> LENGTH: 21
<212> TYPE: DNA
<213> ORGANISM: Artificial Sequence
<220> FEATURE:
<223> OTHER INFORMATION: Synthetic

<400> SEQUENCE: 432
taactaggtc aacagaatat t 21

<210> SEQ ID NO 433
<211> LENGTH: 21
<212> TYPE: DNA
<213> ORGANISM: Artificial Sequence
<220> FEATURE:
<223> OTHER INFORMATION: Synthetic

<400> SEQUENCE: 433
gcaaagttaa tcctcatata a 21

<210> SEQ ID NO 434
<211> LENGTH: 21
<212> TYPE: DNA
<213> ORGANISM: Artificial Sequence
<220> FEATURE:
<223> OTHER INFORMATION: Synthetic

<400> SEQUENCE: 434
gcagcatctg ttctgattaa a 21

<210> SEQ ID NO 435
<211> LENGTH: 21
<212> TYPE: DNA
<213> ORGANISM: Artificial Sequence
<220> FEATURE:
<223> OTHER INFORMATION: Synthetic

<400> SEQUENCE: 435
cagcatctgt tctgattaaa t 21

<210> SEQ ID NO 436
<211> LENGTH: 21
<212> TYPE: DNA
<213> ORGANISM: Artificial Sequence
<220> FEATURE:
<223> OTHER INFORMATION: Synthetic

<400> SEQUENCE: 436
agcatctgtt ctgattaaat a 21

<210> SEQ ID NO 437
<211> LENGTH: 21
<212> TYPE: DNA
<213> ORGANISM: Artificial Sequence
<220> FEATURE:
<223> OTHER INFORMATION: Synthetic

<400> SEQUENCE: 437
gcatctgttc tgattaaata t 21

<210> SEQ ID NO 438
<211> LENGTH: 21
<212> TYPE: DNA
<213> ORGANISM: Artificial Sequence
<220> FEATURE:
<223> OTHER INFORMATION: Synthetic

<400> SEQUENCE: 438
ctgcacaact gaccctttat t 21

<210> SEQ ID NO 439
<211> LENGTH: 21
<212> TYPE: DNA
<213> ORGANISM: Artificial Sequence
<220> FEATURE:
<223> OTHER INFORMATION: Synthetic

<400> SEQUENCE: 439
tgcacaactg accctttatt a 21

<210> SEQ ID NO 440
<211> LENGTH: 21
<212> TYPE: DNA

<213> ORGANISM: Artificial Sequence
<220> FEATURE:
<223> OTHER INFORMATION: Synthetic

<400> SEQUENCE: 440
tgatggcttt cctactattt a 21

<210> SEQ ID NO 441
<211> LENGTH: 21
<212> TYPE: DNA
<213> ORGANISM: Artificial Sequence
<220> FEATURE:
<223> OTHER INFORMATION: Synthetic

<400> SEQUENCE: 441
gatggctttc ctactattta a 21

<210> SEQ ID NO 442
<211> LENGTH: 21
<212> TYPE: DNA
<213> ORGANISM: Artificial Sequence
<220> FEATURE:
<223> OTHER INFORMATION: Synthetic

<400> SEQUENCE: 442
agctcagcca tctggtttaa a 21

<210> SEQ ID NO 443
<211> LENGTH: 21
<212> TYPE: DNA
<213> ORGANISM: Artificial Sequence
<220> FEATURE:
<223> OTHER INFORMATION: Synthetic

<400> SEQUENCE: 443
ctgactgcct tagactaata t 21

<210> SEQ ID NO 444
<211> LENGTH: 21
<212> TYPE: DNA
<213> ORGANISM: Artificial Sequence
<220> FEATURE:
<223> OTHER INFORMATION: Synthetic

<400> SEQUENCE: 444
tgactgcctt agactaatat a 21

<210> SEQ ID NO 445
<211> LENGTH: 21
<212> TYPE: DNA
<213> ORGANISM: Artificial Sequence
<220> FEATURE:
<223> OTHER INFORMATION: Synthetic

<400> SEQUENCE: 445
cagcatttga caaagaaata a 21

<210> SEQ ID NO 446
<211> LENGTH: 21
<212> TYPE: DNA
<213> ORGANISM: Artificial Sequence
<220> FEATURE:
<223> OTHER INFORMATION: Synthetic

<400> SEQUENCE: 446
aggatatgga tgatgtatat a 21

<210> SEQ ID NO 447
<211> LENGTH: 21
<212> TYPE: DNA
<213> ORGANISM: Artificial Sequence
<220> FEATURE:
<223> OTHER INFORMATION: Synthetic

<400> SEQUENCE: 447
gtcgacccta agaagataat a 21

<210> SEQ ID NO 448
<211> LENGTH: 21
<212> TYPE: DNA
<213> ORGANISM: Artificial Sequence
<220> FEATURE:
<223> OTHER INFORMATION: Synthetic

<400> SEQUENCE: 448
agaaacctga acaagtaata a 21

<210> SEQ ID NO 449
<211> LENGTH: 21
<212> TYPE: DNA
<213> ORGANISM: Artificial Sequence
<220> FEATURE:
<223> OTHER INFORMATION: Synthetic

<400> SEQUENCE: 449
gaaacctgaa caagtaataa t 21

<210> SEQ ID NO 450
<211> LENGTH: 21
<212> TYPE: DNA
<213> ORGANISM: Artificial Sequence
<220> FEATURE:
<223> OTHER INFORMATION: Synthetic

<400> SEQUENCE: 450
agtcacacaa cagactaaat t 21

<210> SEQ ID NO 451
<211> LENGTH: 21
<212> TYPE: DNA
<213> ORGANISM: Artificial Sequence
<220> FEATURE:
<223> OTHER INFORMATION: Synthetic

<400> SEQUENCE: 451
gtcacacaac agactaaatt t 21

<210> SEQ ID NO 452
<211> LENGTH: 21
<212> TYPE: DNA
<213> ORGANISM: Artificial Sequence
<220> FEATURE:
<223> OTHER INFORMATION: Synthetic

<400> SEQUENCE: 452
agcgagagtg tcctcattta t 21

<210> SEQ ID NO 453
<211> LENGTH: 21
<212> TYPE: DNA
<213> ORGANISM: Artificial Sequence
<220> FEATURE:

<223> OTHER INFORMATION: Synthetic

<400> SEQUENCE: 453
gcgagagtgt cctcatttat a 21

<210> SEQ ID NO 454
<211> LENGTH: 21
<212> TYPE: DNA
<213> ORGANISM: Artificial Sequence
<220> FEATURE:
<223> OTHER INFORMATION: Synthetic

<400> SEQUENCE: 454
cgagagtgtc ctcatttata t 21

<210> SEQ ID NO 455
<211> LENGTH: 21
<212> TYPE: DNA
<213> ORGANISM: Artificial Sequence
<220> FEATURE:
<223> OTHER INFORMATION: Synthetic

<400> SEQUENCE: 455
atcctctatc tctgttaata a 21

<210> SEQ ID NO 456
<211> LENGTH: 21
<212> TYPE: DNA
<213> ORGANISM: Artificial Sequence
<220> FEATURE:
<223> OTHER INFORMATION: Synthetic

<400> SEQUENCE: 456
agcaagtgct attccatatt t 21

<210> SEQ ID NO 457
<211> LENGTH: 21
<212> TYPE: DNA
<213> ORGANISM: Artificial Sequence
<220> FEATURE:
<223> OTHER INFORMATION: Synthetic

<400> SEQUENCE: 457
ctggagtcca tggagaaata t 21

<210> SEQ ID NO 458
<211> LENGTH: 21
<212> TYPE: DNA
<213> ORGANISM: Artificial Sequence
<220> FEATURE:
<223> OTHER INFORMATION: Synthetic

<400> SEQUENCE: 458
cctccaagga catactttat a 21

<210> SEQ ID NO 459
<211> LENGTH: 21
<212> TYPE: DNA
<213> ORGANISM: Artificial Sequence
<220> FEATURE:
<223> OTHER INFORMATION: Synthetic

<400> SEQUENCE: 459
ctccaaggac atactttata a 21

<210> SEQ ID NO 460
<211> LENGTH: 21
<212> TYPE: DNA
<213> ORGANISM: Artificial Sequence
<220> FEATURE:
<223> OTHER INFORMATION: Synthetic

<400> SEQUENCE: 460
tccaaggaca tactttataa t 21

<210> SEQ ID NO 461
<211> LENGTH: 21
<212> TYPE: DNA
<213> ORGANISM: Artificial Sequence
<220> FEATURE:
<223> OTHER INFORMATION: Synthetic

<400> SEQUENCE: 461
ccaaggacat actttataat a 21

<210> SEQ ID NO 462
<211> LENGTH: 21
<212> TYPE: DNA
<213> ORGANISM: Artificial Sequence
<220> FEATURE:
<223> OTHER INFORMATION: Synthetic

<400> SEQUENCE: 462
gtgagggcaa tggtgaatat a 21

<210> SEQ ID NO 463
<211> LENGTH: 21
<212> TYPE: DNA
<213> ORGANISM: Artificial Sequence
<220> FEATURE:
<223> OTHER INFORMATION: Synthetic

<400> SEQUENCE: 463
tgagggcaat ggtgaatata a 21

<210> SEQ ID NO 464
<211> LENGTH: 21
<212> TYPE: DNA
<213> ORGANISM: Artificial Sequence
<220> FEATURE:
<223> OTHER INFORMATION: Synthetic

<400> SEQUENCE: 464
cgaaaggcaa gcttcttaaa t 21

<210> SEQ ID NO 465
<211> LENGTH: 21
<212> TYPE: DNA
<213> ORGANISM: Artificial Sequence
<220> FEATURE:
<223> OTHER INFORMATION: Synthetic

<400> SEQUENCE: 465
gaaaggcaag cttcttaaat a 21

<210> SEQ ID NO 466
<211> LENGTH: 21
<212> TYPE: DNA
<213> ORGANISM: Artificial Sequence
<220> FEATURE:
<223> OTHER INFORMATION: Synthetic

<400> SEQUENCE: 466
ggcaagcaag gcaggattta a 21

<210> SEQ ID NO 467
<211> LENGTH: 21
<212> TYPE: DNA
<213> ORGANISM: Artificial Sequence
<220> FEATURE:
<223> OTHER INFORMATION: Synthetic

<400> SEQUENCE: 467
acaggaacct ggctctaatt t 21

<210> SEQ ID NO 468
<211> LENGTH: 21
<212> TYPE: DNA
<213> ORGANISM: Artificial Sequence
<220> FEATURE:
<223> OTHER INFORMATION: Synthetic

<400> SEQUENCE: 468
gggacctcct gacatttaat t 21

<210> SEQ ID NO 469
<211> LENGTH: 21
<212> TYPE: DNA
<213> ORGANISM: Artificial Sequence
<220> FEATURE:
<223> OTHER INFORMATION: Synthetic

<400> SEQUENCE: 469
ggacctcctg acatttaatt a 21

<210> SEQ ID NO 470
<211> LENGTH: 21
<212> TYPE: DNA
<213> ORGANISM: Artificial Sequence
<220> FEATURE:
<223> OTHER INFORMATION: Synthetic

<400> SEQUENCE: 470
gacctcctga catttaatta a 21

<210> SEQ ID NO 471
<211> LENGTH: 21
<212> TYPE: DNA
<213> ORGANISM: Artificial Sequence
<220> FEATURE:
<223> OTHER INFORMATION: Synthetic

<400> SEQUENCE: 471
gtgggagctt gttacatata t 21

<210> SEQ ID NO 472
<211> LENGTH: 21
<212> TYPE: DNA
<213> ORGANISM: Artificial Sequence
<220> FEATURE:
<223> OTHER INFORMATION: Synthetic

<400> SEQUENCE: 472
ctaagtcttc tcatctatat a 21

<210> SEQ ID NO 473
<211> LENGTH: 21

<212> TYPE: DNA
<213> ORGANISM: Artificial Sequence
<220> FEATURE:
<223> OTHER INFORMATION: Synthetic

<400> SEQUENCE: 473
ttaggtggtc atgagataaa t 21

<210> SEQ ID NO 474
<211> LENGTH: 21
<212> TYPE: DNA
<213> ORGANISM: Artificial Sequence
<220> FEATURE:
<223> OTHER INFORMATION: Synthetic

<400> SEQUENCE: 474
taggtggtca tgagataaat a 21

<210> SEQ ID NO 475
<211> LENGTH: 21
<212> TYPE: DNA
<213> ORGANISM: Artificial Sequence
<220> FEATURE:
<223> OTHER INFORMATION: Synthetic

<400> SEQUENCE: 475
aggtggtcat gagataaata t 21

<210> SEQ ID NO 476
<211> LENGTH: 21
<212> TYPE: DNA
<213> ORGANISM: Artificial Sequence
<220> FEATURE:
<223> OTHER INFORMATION: Synthetic

<400> SEQUENCE: 476
ggtggtcatg agataaatat a 21

<210> SEQ ID NO 477
<211> LENGTH: 21
<212> TYPE: DNA
<213> ORGANISM: Artificial Sequence
<220> FEATURE:
<223> OTHER INFORMATION: Synthetic

<400> SEQUENCE: 477
gtggtcatga gataaatata t 21

<210> SEQ ID NO 478
<211> LENGTH: 21
<212> TYPE: DNA
<213> ORGANISM: Artificial Sequence
<220> FEATURE:
<223> OTHER INFORMATION: Synthetic

<400> SEQUENCE: 478
cacaaagcac atggctaaat a 21

<210> SEQ ID NO 479
<211> LENGTH: 21
<212> TYPE: DNA
<213> ORGANISM: Artificial Sequence
<220> FEATURE:
<223> OTHER INFORMATION: Synthetic

<400> SEQUENCE: 479
acaaagcaca tggctaaata a 21

<210> SEQ ID NO 480
<211> LENGTH: 21
<212> TYPE: DNA
<213> ORGANISM: Artificial Sequence
<220> FEATURE:
<223> OTHER INFORMATION: Synthetic

<400> SEQUENCE: 480
cggttatgta gaagctattt a 21

<210> SEQ ID NO 481
<211> LENGTH: 21
<212> TYPE: DNA
<213> ORGANISM: Artificial Sequence
<220> FEATURE:
<223> OTHER INFORMATION: Synthetic

<400> SEQUENCE: 481
ggttatgtag aagctattta a 21

<210> SEQ ID NO 482
<211> LENGTH: 21
<212> TYPE: DNA
<213> ORGANISM: Artificial Sequence
<220> FEATURE:
<223> OTHER INFORMATION: Synthetic

<400> SEQUENCE: 482
agccaccctt aattgaataa t 21

<210> SEQ ID NO 483
<211> LENGTH: 21
<212> TYPE: DNA
<213> ORGANISM: Artificial Sequence
<220> FEATURE:
<223> OTHER INFORMATION: Synthetic

<400> SEQUENCE: 483
actacccttt actggtaatt t 21

<210> SEQ ID NO 484
<211> LENGTH: 21
<212> TYPE: DNA
<213> ORGANISM: Artificial Sequence
<220> FEATURE:
<223> OTHER INFORMATION: Synthetic

<400> SEQUENCE: 484
taataggcac tagagaataa t 21

<210> SEQ ID NO 485
<211> LENGTH: 21
<212> TYPE: DNA
<213> ORGANISM: Artificial Sequence
<220> FEATURE:
<223> OTHER INFORMATION: Synthetic

<400> SEQUENCE: 485
atttgggccc aagtgtatat t 21

<210> SEQ ID NO 486
<211> LENGTH: 21
<212> TYPE: DNA
<213> ORGANISM: Artificial Sequence
<220> FEATURE:
<223> OTHER INFORMATION: Synthetic

<400> SEQUENCE: 486
tttgggccca agtgtatatt t 21

<210> SEQ ID NO 487
<211> LENGTH: 21
<212> TYPE: DNA
<213> ORGANISM: Artificial Sequence
<220> FEATURE:
<223> OTHER INFORMATION: Synthetic

<400> SEQUENCE: 487
ttgggcccaa gtgtatattt a 21

<210> SEQ ID NO 488
<211> LENGTH: 21
<212> TYPE: DNA
<213> ORGANISM: Artificial Sequence
<220> FEATURE:
<223> OTHER INFORMATION: Synthetic

<400> SEQUENCE: 488
tgcctgctgt gggtgattat t 21

<210> SEQ ID NO 489
<211> LENGTH: 21
<212> TYPE: DNA
<213> ORGANISM: Artificial Sequence
<220> FEATURE:
<223> OTHER INFORMATION: Synthetic

<400> SEQUENCE: 489
gcctgctgtg ggtgattatt t 21

<210> SEQ ID NO 490
<211> LENGTH: 21
<212> TYPE: DNA
<213> ORGANISM: Artificial Sequence
<220> FEATURE:
<223> OTHER INFORMATION: Synthetic

<400> SEQUENCE: 490
gggatcttta gggacataat t 21

<210> SEQ ID NO 491
<211> LENGTH: 21
<212> TYPE: DNA
<213> ORGANISM: Artificial Sequence
<220> FEATURE:
<223> OTHER INFORMATION: Synthetic

<400> SEQUENCE: 491
gatgacacta cgtagatata t 21

<210> SEQ ID NO 492
<211> LENGTH: 21
<212> TYPE: DNA
<213> ORGANISM: Artificial Sequence
<220> FEATURE:
<223> OTHER INFORMATION: Synthetic

<400> SEQUENCE: 492
tgctctttca gtttgtaata a 21

<210> SEQ ID NO 493
<211> LENGTH: 21
<212> TYPE: DNA
<213> ORGANISM: Artificial Sequence
<220> FEATURE:
<223> OTHER INFORMATION: Synthetic

<400> SEQUENCE: 493
gctctttcag tttgtaataa a 21

<210> SEQ ID NO 494
<211> LENGTH: 21
<212> TYPE: DNA
<213> ORGANISM: Artificial Sequence
<220> FEATURE:
<223> OTHER INFORMATION: Synthetic

<400> SEQUENCE: 494
gtctttccat gggtctaatt t 21

<210> SEQ ID NO 495
<211> LENGTH: 21
<212> TYPE: DNA
<213> ORGANISM: Artificial Sequence
<220> FEATURE:
<223> OTHER INFORMATION: Synthetic

<400> SEQUENCE: 495
tctttccatg ggtctaattt a 21

<210> SEQ ID NO 496
<211> LENGTH: 21
<212> TYPE: DNA
<213> ORGANISM: Artificial Sequence
<220> FEATURE:
<223> OTHER INFORMATION: Synthetic

<400> SEQUENCE: 496
atcagtttct ctaggtatta a 21

<210> SEQ ID NO 497
<211> LENGTH: 21
<212> TYPE: DNA
<213> ORGANISM: Artificial Sequence
<220> FEATURE:
<223> OTHER INFORMATION: Synthetic

<400> SEQUENCE: 497
tcagtttctc taggtattaa a 21

<210> SEQ ID NO 498
<211> LENGTH: 21
<212> TYPE: DNA
<213> ORGANISM: Artificial Sequence
<220> FEATURE:
<223> OTHER INFORMATION: Synthetic

<400> SEQUENCE: 498
aggccaaact ctctcttaat t 21

<210> SEQ ID NO 499
<211> LENGTH: 21
<212> TYPE: DNA
<213> ORGANISM: Artificial Sequence
<220> FEATURE:
<223> OTHER INFORMATION: Synthetic

<400> SEQUENCE: 499
cttacccagt cactgttaat t 21

<210> SEQ ID NO 500
<211> LENGTH: 21
<212> TYPE: DNA
<213> ORGANISM: Artificial Sequence
<220> FEATURE:
<223> OTHER INFORMATION: Synthetic

<400> SEQUENCE: 500
ttacccagtc actgttaatt a 21

<210> SEQ ID NO 501
<211> LENGTH: 21
<212> TYPE: DNA
<213> ORGANISM: Artificial Sequence
<220> FEATURE:
<223> OTHER INFORMATION: Synthetic

<400> SEQUENCE: 501
acccagtcac tgttaattat t 21

<210> SEQ ID NO 502
<211> LENGTH: 21
<212> TYPE: DNA
<213> ORGANISM: Artificial Sequence
<220> FEATURE:
<223> OTHER INFORMATION: Synthetic

<400> SEQUENCE: 502
cccagtcact gttaattatt a 21

<210> SEQ ID NO 503
<211> LENGTH: 21
<212> TYPE: DNA
<213> ORGANISM: Artificial Sequence
<220> FEATURE:
<223> OTHER INFORMATION: Synthetic

<400> SEQUENCE: 503
ctcaacagct tcaacattat a 21

<210> SEQ ID NO 504
<211> LENGTH: 21
<212> TYPE: DNA
<213> ORGANISM: Artificial Sequence
<220> FEATURE:
<223> OTHER INFORMATION: Synthetic

<400> SEQUENCE: 504
tcaacagctt caacattata t 21

<210> SEQ ID NO 505
<211> LENGTH: 21
<212> TYPE: DNA
<213> ORGANISM: Artificial Sequence
<220> FEATURE:
<223> OTHER INFORMATION: Synthetic

<400> SEQUENCE: 505
atacatcttg actccattat t 21

<210> SEQ ID NO 506

<211> LENGTH: 21
<212> TYPE: DNA
<213> ORGANISM: Artificial Sequence
<220> FEATURE:
<223> OTHER INFORMATION: Synthetic

<400> SEQUENCE: 506
cccaaactgg acagatatat a 21

<210> SEQ ID NO 507
<211> LENGTH: 21
<212> TYPE: DNA
<213> ORGANISM: Artificial Sequence
<220> FEATURE:
<223> OTHER INFORMATION: Synthetic

<400> SEQUENCE: 507
ccaaactgga cagatatata a 21

<210> SEQ ID NO 508
<211> LENGTH: 21
<212> TYPE: DNA
<213> ORGANISM: Artificial Sequence
<220> FEATURE:
<223> OTHER INFORMATION: Synthetic

<400> SEQUENCE: 508
caaactggac agatatataa t 21

<210> SEQ ID NO 509
<211> LENGTH: 137350
<212> TYPE: DNA
<213> ORGANISM: Homo sapiens

<400> SEQUENCE: 509
caatgagaat aaactcactg tagctccatg ctacaacatg gatacatctc aaaaacaatt 60
ttgatgaaag aaggtggaca caaaagaata catgctgtat gactcctttt acataatgtt 120
caaaaaacaa gaaaaactaa accatagtat ttagcaattc aaacttagat ggcaaaagta 180
taaagaaatg tagggaaatt attttcgtaa atgtctcctc tagggaaaag ggaggattaa 240
gtcaagctca tccatcactc catactggcc cttcctcgcc agtgatctca catgtttatt 300
ccaacaagag agctggagaa actgtgtttg tgctatatca acaattctca gtgaatgtct 360
tgttgactgg gaaagcaatg tgggtcctac ttttctttct ttcattttgt aaaaccattt 420
ctgatgagca tgaatgagtc ctccatttct taagtaactg acagcacagg tttgatatca 480
gcaatcaaag atctgccagg ccttgtttat catgcctcac ctctgttgcc acatgtttcc 540
cagggatcga ttgaatgtga ctatgagtag ctctccatgt acaccatcta gtgtcacttc 600
tgggacttgg gggtttctga cttacagtcc tcttccctat catttattta catattcagt 660
aaataatcat gaacacctac cttatgccag acagtgttct gggtgctaaa tatatagtag 720
tagaagagat aaagtttatg ttttcataga actttcaatt cagtacatga gatggaaagg 780
tggacggtgc ctgtagtccc agctacccgg gaggctgaag tgagaggact gcttgagccc 840
aggaatttga gaccagcctg gacaacgtag tgagaccctg tctctattaa agttttttta 900
aattactgat ataatttaag gtagtggtga gtactagaaa aaatgtacca ggagaaaaaa 960
acagaagcaa aagtacatgt ggccaatact attttgatat gtagaggcca ggaaaagctt 1020
ctctgaagag gtaaacacaa agttgaagga tgtaccatca cagagagatg gaagttttcc 1080
ataatttcct tgcatatact atggtgtgac ttcatttttt cacccacgtc tgttaggctg 1140

```
ctcagataaa ctgctttttt tttaaacgag atctaaagac cacgtacatt cttcatagtc   1200
cctgaattaa gtattaccca aaccatagct catgggccac ctacctgtta atttaatgtc   1260
tatgtatgcc ttcactctac aatggcaggc ttaagcagct gggacagaga ccacataacc   1320
cagaaagcct aaaactttta ttctctggcc ctttacagca gcagtcccta aactttttgg   1380
caccagggac tggtttccca gaagacaatt tttcctccta ctgggggtga gggatggttt   1440
caggatgatt caagcgcatt actcttactg tgtactttat ttctattatt attacattgt   1500
aacatataag gaaataatta tacagttcac cataatgtag aatcagtggg agccatgagc   1560
ttgttttcct gaaactagac agtcccatct aggggtgatg ggagacgtga cagatcatca   1620
ggcattagat tctcataagg agtgtgcaac ctagatccct tgcatgtgca gttcacaata   1680
gggttcgtgc tcctatgaga atctaatgct gccactgatc tgacaggagg cggagctcag   1740
taatgtgagt gatgggcagc agctgtaaat acagatgaaa cttccttgac ttccctgccc   1800
tcgcctcctg ctgtgcagca atttccaaca ggccacgaca ggggttgggg acccctgctt   1860
tacaggaaat aatgtgctga tccctggttt agataattga ttttgaaatt tgattctatt   1920
taaaactatt agttttcctg taagctcttc tttagctgca tttaactggt tttaatatga   1980
tatactgcag tatcattcga ttcaaactat tttctaagat tcgaagattt gctgtaactt   2040
atccttttac caatgggtta tttagaagtg tgctgcttaa ttgctaagct attggaaatt   2100
tgtctactta cctttctgtt cttaattgtc agtttaaatt cactgtgatg tggtcagaga   2160
atacaaccta aatgttatca atcatttgaa aaaattttag gacttaaatt aggggccagc   2220
atacagtata ctttggtaac tgttccctgt gtaaataaaa agaaaatctg atctagaact   2280
gttaactgtg gtatcttaca tagtcaactt gattaattta atgaatcatg ttgttcaaat   2340
attttatatt cctgttgatg ctttgacagc tgttctaata ctgagaagtg tgtgtgaaaa   2400
tctccaacta ttattatatg attttgatgt ttcctcatct aattctgtta cactttgaaa   2460
tataaatttt gaagctatta ggtgcatata ggtgaaatat tacatacaga atattttatg   2520
atttttctgt ttaattgaca gttttactat tacaaaatgt tcttgtgttc ttctagtgat   2580
ttttcttgct ttaaagtcta ttaacttgat attatataat aatcaacttt cttatagcta   2640
ttgtttgcat gttataacgt ctatcctttt actctccatt tcactgtgtt cttatattta   2700
aactgccttt cttatcaata gcacatactt gagtcttgtt tttgtatgca gtgtgacaat   2760
ctgtctttaa ttgaaatgtt tagttataca tatacaatat aacaaataaa atagatggat   2820
ttatatctgc agtcttgcta tttattttct attaactcca tctattttca tttcatattt   2880
tttctcttct gccttctttt gaataatcag cttttttgct attctattat tctcctctat   2940
tagctattct tgaatatttt aataattagc tagagattca atacaaactc cttatgttct   3000
acagtctacc ttaagctagt tgtttttacc acctcctgag ggtgcaagaa ctttacaaca   3060
catgtaatca attcactgtc ctcagtcttt gtgctattgc tggcatatat ttttacttct   3120
ccatgttata tatttcacaa tacatcataa ttatttttaa cagttatttg tttatatttt   3180
tcagatatat ttacccaatc cagtgctctt tatttctctt tcttgcagtt ttatgctttc   3240
atctgggata actttctttc agcctgaaga gtctatttta aaattttttc tagaaaaaat   3300
ctgctggcca tgactatttt caacttattt ttgtctaaaa catttttatt ttacatttat   3360
ttatgaagaa tattttctct gagtataaaa tgttaggttg gctgcttttt ttatttcagg   3420
tttcagagat gcctttctat tttctcctgg cacctataat ttctgataaa aagtcagctg   3480
```

-continued

```
taagttttat tgttgttcct ttaaaggtta tgtgtctcat ttctctgacc atatttaggg   3540
tcatctcatt ctctttggtt ttcagcagtc tgactgtggt gtgcttcagt ggggttttct   3600
tttactctac gtaagattca ccagtctgca gtctgtgagt tgatagccat tcaacaaaag   3660
aaaagaacag cagctaccat tgaaatctcc acctgattag acttacaata atccacactg   3720
tcattctcta atatccatct gattttttgc acaagccaaa caaccaagtt aagtgggaga   3780
ggtagtagaa agcaacaccc ctatgtcttc ccaattttag gtggtggcac taaatcacta   3840
atattctcct tgaggcatgg tattgctttt ggtttatttt tttcaaatag aggactacgt   3900
tcataggttt atatcacgag agtccctcat tctatgggtc agtggaacaa ctgaggatct   3960
tgtcagataa caagtatgtc tattacaact cacattcagg atctgaggaa ttaacaggat   4020
ggctcatgga cctactggac ccattgagaa atgatgtcaa ctgatgttca caagccctca   4080
tcaggcttga aggaccagag tgtctttatg gtcgccagga attattacat gttagctcag   4140
tgacagtgcc cccaaatccc tgaaagatct ggatatttcc tttcccttgg tgaacagtta   4200
ttctgctaaa cgatcgcgta gctccttcag gagggctaga aggaaaatat acagcatgaa   4260
cttattgggt tatcctcagc tgtacccaga ctcaccttca ctcacatgac tctgtgtcta   4320
tgaactgact gaggtttggg atttggcaag gggctgtgaa tctctattga ggtggcttaa   4380
gtcaagcttt ggtttactca gaactagaat tgtacttatc taaaaggaca cagtaaactg   4440
attacctatt tcagtccttg ggacttcatg accaattcac ctgtcaaaga tccctgtagg   4500
ctaaactatt cagattgcta ctctagctct tttgtgcaag atttcacctc ctaaattaga   4560
ctgcacgtgg cctgcttaat gacttgaacc acaatctctt aaatcaaagt ctttccttca   4620
aaagctactt tagtccagct gactacaaaa gatcatttaa ctgtttggtc actgtgtgcc   4680
atggaccact gtcccactgc cagcactact tagatactta ctgttttcaa atccatttca   4740
gacactagtc ccagatttct atttctttaa ggatcttttg tcatcaattc tgtgtcaata   4800
atacttgttg gttggagaca acagaatcca tagtaactag tctaggcagg catgtcagat   4860
gatcctagat gacccttatg ctcaagtatt tgccggaagg actcacagga ctcagaaaag   4920
ctcttacact catggttata gttcattaca gcaaatggat acagattaaa atcagcaaag   4980
ggaaaaggta catgggatga aatccaggag aaactaggtc caggcttcca gatatcttct   5040
ctgctggagt cacatggaga tacacttaat tgtctctgca ataatgtgta acacatatga   5100
agtagcttcc tggttggcaa gacttcataa attttgccat tatttgaaga taacccacac   5160
cttggtgtcc agggttttca caggtattag tggtcagtca cataggcata tagtacctgt   5220
atgacttcta ttccagccac cgcaaacttc tcctctccct gctggctcct gagccaaaaa   5280
caggcattta ccataaatca ctttgttagg atgaacttat ctggccaaac tgatacagca   5340
tgacccacag cctcaggtat ataaaacact ctcatcaggc agaatgtttc agggtctcag   5400
aggttagtca ggggctagtc aaggaccaat cctgaaggca ggcctttttt tttttttttt   5460
tttttttttg agacggggtc ttgctctgtc gcccaggctg gagtgcagtg gcatgatctc   5520
agctcactgc aagctctgcc tcccaggttc acgccattct cctgcctcag cctcctgagt   5580
agctgggact acaggcaccc gccaccatgc ccagctaatt ttttgtattt ttagtagaga   5640
ctgggtttca ccgtattagc caggatggtc tcgatctcct gacctggtgt tccacctgcc   5700
tcagcctccc aaagtgctgg gattacaggc gtgagccacc atgcccagcc aaggcaggcc   5760
tttttttgga acctacaggg tttgaccaac ccaggactgc tgagttaacc ctttcctgtg   5820
cagcaagaaa agatttattt aaaaaaaaaa tggaaaatca cagtttaatc agaagggatg   5880
```

```
aaaagacagc ttctagcttg tatttctgag aacatttccc agaaccatat cataaaactg   5940
gcctgctaag gaagatgtct ctgctaaccc agaacaaggt taaattgcat gtggtttatg   6000
gttatatatg ggaatgccct ggttcttatg gaaaagatac agggataaag tgttacaaag   6060
tctgtaactt atgacaaatg ggtccatagc tggagataac agataaatgg atagatagaa   6120
caaatatggc cagatataaa ctaccaggac atctagctaa agaaaatatg gttattgatt   6180
atactatgct ctaaactttt ctttagattt aaaaaatgac caagaaataa ggaagtacaa   6240
aaaactatgg catgtttcat atgagaagtg tttgacataa aagggaaatt gggaggctgg   6300
gtgtggggct cacgcctgta atcttagcac tttgggaggc tgaagtggga ggatcgcttg   6360
agcccaggag ttcaagacca gtctgggtaa catagtgaaa cctaatctct acttaaatat   6420
atatatataa aataaattga aaaaaagaga gaaataggaa aaaagctact gagaactaga   6480
tagtaggttt agtaggtttg aaagtcatga agaagttcag actgaaggac ttctagatgt   6540
gaggagatta caatcaggta ataaaatata gtacagttga cacttggcac acatagaaat   6600
gccacagaaa tatggaaaaa aaggaaaata tgattgcctt tgggtgttaa cctgttggct   6660
tattcacata tggaccaaag cagagtttgt tataagtcac ttaaaaaaaa gagaaatggc   6720
ttccaggcct gcaagatata atggaagcct gacatttcta aagaaaaggg ctagtcatca   6780
atgaaaacac tggataaaat cagactagga aagtctggct gtaacttcct aggggatatt   6840
tgcccaaaag cttcaacata ctctcattcc cgtcaatgat gcttcacgga agttgaatgt   6900
atcaggtatc aattgtccag ttctttcagt tcctgttctg tcacttccct ttgtctagat   6960
ttcaagcttc ctaagaagct tctgttatgt ggggaccctg tgtgtcttct tacagggaaa   7020
aaatgctctg gtcacctgca taccagtcct ttccagcatt ccagtccctc tgatgggtac   7080
ttttcaattt aaatcaataa actggcattc cgattttata attccatctc ttgagtttgt   7140
taaatgtgag tttgattggt gggctggctt aaatcagttt ctaagcctgc aatcatgagg   7200
gccagacctg aactctagtc aactcaccaa gtttggctcg tttgttcatt tgtgtggcaa   7260
atgcgattgg tgccctggat cttcctactg tattgtatgc cagtcctagt ttcaattgcc   7320
agctcctgca tttcttgctt agggctctct ctgaccagct ggagctgctg tgtcccaacc   7380
acagcaagcc agccagatga ggataacaac attatacact cacaggataa ttgtgaagtg   7440
tgtgttctac actggctccc agagttcttc aacataagca aattccagtt gcccaaagtg   7500
gacacttgat tgataataca cccttttggg tttcctccct tccgtaactc acttactttc   7560
ttaccagtgt ttctagggat cacctcccaa ataaattact tgcactgaaa tcattgtctc   7620
aaggtctgtt ttcgtgagaa acacaaacta agacaacttc gtccattcat tcatcattta   7680
ttgagcttaa tcaattatta ataagtcctt aaggcacaaa ataagtcctt agcaacatgt   7740
tatctctttt ctcatcacag tattatcccc tttacaaatg aagaaatcaa ggttgaaata   7800
aattaagtag ctgactcagt atcacataat caggacagag tgctggaaag gactgatggc   7860
agatgaagat ggctgagact cccagatgcc cagtcttgaa tggagagtat aaaaaatgag   7920
ttttctgctg ggtaataat ttgagtatat tataagattg ctacgaagca atgaaaaaag   7980
ggattattga atgaggaaac atttcaatga aatatatttt tgaaattttt gttttctagg   8040
aaagcaacat gctacaataa gagcgcacac acatacacct gtgggtttaa atcctagcac   8100
tactagtttt tagctgtaag acatgggcaa gttgcttact tactctaagc tcaattttct   8160
aatccataaa gtatataata tccaagaatg ttgtatgaat taatgagatt tatttaaaca   8220
```

```
actggcacct aatgagtgta caaatttaat ttgcagaaat gtactgtcct ttcaggaact   8280
ttgtggtaag tactgaaata tggatgcaat cagtactatg cttagcagta acttaaaaaa   8340
agaagcaata taaaatttgt atgtcataaa tgataactat attactatct ttaaaaatct   8400
tggtctttcc atatgtagta tgctaattta atgttacaaa ataaaagtaa aatcaataat   8460
tttaaaaagt cagactttaa gtataaaatt ttgtttgaag caatgccaaa gaatccacat   8520
agtaacattt atcattttga taacagaatt ttgtgttctg tatgtgggcc tcaagcagta   8580
ctaaaacaaa atagtgtatc aattataaat gatactcatg attcttccct agtcagatgt   8640
ttttttcagt tgagagattc tgaagaaaaa caataagtgt agaatgtctg taccatcttt   8700
aatactaaga tttaattgaa tcaatgcatt tccttagatt taaaaatcat tttgttagag   8760
tctgtgttag aatcagtatg atacgtattt aaaatggaat tagagatatg gactgtagta   8820
ggaatgactt caaataactc aaatgatgcg catgtcagaa agaaacaatt tctaagggct   8880
gcttcattga ttcaagtgga actgttttat tcagaacagc tcagattagc agcagcagca   8940
gctggtgttc aatgaaatgc ttccctttc cacctactct ccagctgggt taagacaggc   9000
acaaagagat tgggatgacc aaggtcaaag catgatttga tagacttcca ggtttttgct   9060
ccagtaactt cttgtgtagt cttggctata gaggcaattc gtgaaattgg tggttgaaaa   9120
agtcatagct ttagaaggac ttcatagatc atcttgttca atatcttaat tttatacttc   9180
atataccacg gttctaatta aaatacttta ttgttgcata tttattggaa ttgacaagaa   9240
gttaagattt cttacattta tttcatttgc ctgatttttc tgttcccact gaattgtata   9300
agcaggcact actgcacttt gtatctctac ttgacatagc tgaaaaatga aacattcaaa   9360
gatacactac tttattacat gttagctcag taaaggggcc ctctattaga catgctggtc   9420
tcagttctta acttttacac tcacaaagcc cgattcactc attcaaacct tttttgagga   9480
gttaccaggt tttagccatt gagatagata ctgggaacac aagaagtcaa gggtgctctc   9540
ctctctcaag aagcttaaga gaagacagaa gtgctaagca catacatcga gtatgcggag   9600
ggcacacaga ggtataagca atgaccctcc ttgagtagat ctgaaaggct tctcagagga   9660
ggagcttgaa cttgtctaaa aggtagaata aactgcatgc aaaagagctc caaatgactc   9720
tcaagcttaa gtattgccta agcaatacat tcatgtggga agtgggagat ggggctggaa   9780
tggaggcaga ggccacatcc aatgggccgt ttttggagtt tagacattat tcagaaggcc   9840
atggtgagcc actgatagag ttaagaaagg cagcaaggtg ataacacatg tttcttaaga   9900
aaacatactg tgatgaggac atttggcagg aaagtagtat aatatgaacc agcattctct   9960
gaatgttggg gttaaaatag tgaatgaggt aatatgatct taccettctg gaacttacag  10020
tctagttcag aaacacaacg ggtctaaaca ctaagggtct aaattaaggt agtagcagtg  10080
gaaatataca gaaggaaatg gatgttatga taatgatgat gatgatattg cttattacca  10140
tttattgaac acctcccatg tgtcaggcac taaacacctc atatgcacta tctttgtcca  10200
ttctccacac agtagctaga gttattctat ggatcttgtc ataactctct caaacccttc  10260
cagaggcttc ccacctcatt cagcacaaat acctaagttc ttaggaaaag ctaaaaagtc  10320
ctccaggctg tgacccactg tgacttctct gagctcatct tcaactcctc ctttctctct  10380
ctagccacaa cgccttgcta ctgttcctag atgactctag gcacctttct gcttcagggc  10440
cccctctgtc tagaaggttg tttcctttgt atttccacag ttcattcctc acttctgtca  10500
agcctctgat taaacgaatt cttttcaata agatcttccc tggccactcg gcatgacgga  10560
actcctgtag cactccctat tccctttgcc ttgctttgta tttctcctta acatatcata  10620
```

```
ttctgacata acacatatgt gttggttttc ttcctccatg gatcacaaac tccatgaagg  10680
tagactgttt ttgttcattg ctgtattctc agcactgata acagtgctcg cacatatcca  10740
ttcaataaat atgtactgaa tagatgaatg aaggattaca atggtcctat gaggatggta  10800
ctattatttt ttcccacttt cctaaagagg aaacagacac caattgaggt actcaaggtt  10860
gtatttctgg taactggcag aactgggatt tgcgtggggc ggggggaagc ctgcctttgt  10920
tgagttgtac tatgtgccca gcattattct aagaacttta tgtacattaa cacttaatcc  10980
ctacacctcc attttataga tgaggaaact aaatcagaaa ggggtttaca atcttgcctg  11040
gtatctgtgc acttgccagt aagttggggg cctgtgctct cagctacttt gctacactaa  11100
ttctaaagcc aattctttag agagatacaa ctttgcctct taattgccag gagagtgagg  11160
gaaaggaaga aatccaggat tgctaccatt attatgactg tggaccgcca tagatggtag  11220
agtcaccaat caagtcaaag aatgtaagat gagttggttt cattctcctc taactctaga  11280
cttccacatc caactgcctc ctgatatctt tgcttggata ttaagacaca aggtcagctg  11340
cagttaaagg gatttagaat aaccatggca gatcatagaa gttagtagct gtcttacatc  11400
agagttgacc tggtacacag gacctgccca atgaagtcct cagggcccca acttgttgct  11460
ctgcaatccc tagaatgttt cccagtgtct tagtcttgtt tatgctgctg taacaaaata  11520
cctgaaactg ggaaatttgt gaagaacaga aatatacttt ttcacagttc taaaggctgg  11580
gaagtacaag ctcaagaccc ccagcaggtt tagtgtctgg tgagggctgc agtttccaag  11640
gtgggacctt actgctatat cctctggagg gggtgaatgc tgtgtcctcg tgtggctaaa  11700
gggatggaag ggcaaaagaa ggcctaagct agttccctcc agtcctttta caaggtatta  11760
atccatccat gaggcagggc cctcatgatt tcatcagctg ttagtatcat cacaatgggg  11820
attaagtttc aacatgaatt ttgaagggga caccatcatt gaaaccacag catctttcaa  11880
catggtttac taccccaact atttaataca tacattcatc agaaaaggac aaaagaaagg  11940
gcaagtgaca cccaatttct tttagaaaat gatctggaag ttgcatacat aatttctgct  12000
cacatcctac tggccagaac ttaagagata tggccacact taagggtgta ttataggcaa  12060
ccatgtgtct ggctagatgt tctattatca tggataaaga gcagaatgca taagagtcag  12120
ctaggaagca gtttgtacaa cagatatcca acaggtatct caaatttaac attaccaaaa  12180
ctaaattcct gcttgttctc ccaaaacctg ctcctttgca ctgttatcac atctcagtcc  12240
atggtggaag acagaacaaa ctcaggggtt tgatgttaat catgttgagc ttgaggtgcc  12300
tgtagaacac ccagtacagg tttccaataa ggggttgaag atactgtgtc tgatgcttct  12360
gactgagatc tgtgttcaag attcagactt gattcctgac tgaaataagt gatagaagag  12420
tatacgtaaa tggtactgtc aaagattata acatggtagg cagagaacca agaatgggga  12480
gggaggattc tgcacaggag acctgagaaa gagtggccta agacaaggca gaagagcaga  12540
gaatgtaagg tgacagaacc aagggagcag tttccaggag gcagtggtca gcagtgtgga  12600
aggctgcaga gagatcagat gttatgaaaa ctgagaagca acctttcaat ttggccatta  12660
tgccacagtg aaattgatac aagcaatgta tacagtaaaa tggagggagc tgctaaattt  12720
ctgtagttga agaggaattt ggaaggtaat agcaatctaa gtatagacag cttttctaaa  12780
tagaagggac aaagtagagg gagaatttat gaacaggagt gggaatattt aagggagtaa  12840
gagtcttgag tcaatctctc ttccctcaag aaataaaaat tacctgtaga aaggacagaa  12900
ggatggcttc taccttaaga ctcgaggtca gaaagaatgc aaatttagac aggtctgcag  12960
```

-continued

```
gcataagggt gggggtatgt aggagttcat gcctgatgtg tgcagtacta aacaatgata  13020
catatactac tactactacc actactaagc actaacattt actgagcact tatcatatgc  13080
cagtgttctt catggagcta agtttgctta acagtatttc ttaaataatg ggagctattc  13140
atatattgaa agcttagtgt ttttcagaag ttgagtgtgt aacatttgga tgtggcctaa  13200
aaatagcaac cgtgacttct atcccaccat atctgaattt tgtctcttcc atgctcgact  13260
tatttctgat cctggggcat gctgagtagt aaaaaaagtt gttcttgcat tttgattcat  13320
ctgttatgac tggcatcaat aagaaatctt cagcaataaa acagctctgt caaaaaacaa  13380
cttcaccagc aatttagggc aaaatgtttc ctttaaaaaa aagtttgttg gctgggcatg  13440
gtggatcatg cctgtaatcc cagcactttg ggaggccgag gcgggcggat cacgaggtca  13500
ggagatcgag cccatcctgg ctaacacggt gaaaccccgt ctctactaaa aatacaaaaa  13560
attagccagg cgtggtggcg ggtgcctgta gtcccagcta cttgggaggc tgaggcagga  13620
gaatggcatg aacctgggag gtggagcttg caatgagcca agattgcgcc actgcactcc  13680
agcatgggcg acggagcaag actctgtctc aaaaaaataa taataataat aaaataaaaa  13740
gtttgttagt attagcagat acatattact aggtaccccc catgctcaat gaagtgttgg  13800
gttactctga aaaagtgtcc aatcttacag gtgtgacttc ctctggaact gcaagttctt  13860
gagggcaggg atagagattg ttcatctttt attgtttccc aaggtctggc acataaatag  13920
tagttcaagt agtccaacat atgacacata aatagttctg ggtaaacatt agctcaaagt  13980
ttgctcaagg cattgatgca gatgcttata aaattaaatt gctcttttta ctgtatacct  14040
gaaatgagaa aattattaga aactactggg tctcatttgg actagaaaag tctgaagaaa  14100
tcactgttca cttagtagat acaaagttgt ttttctggga aaaacacacc taaaaaaaaa  14160
aaaacacatg ggtctgatat gggagaattt ttttattttt catataaaca ggtgtatagg  14220
gaagtggaac actgctagta tcttaaggat tcctgaaagt atttatgttg gtaagtttga  14280
tgagcaaaca tttctaaatt tgaaaatgga taaaacaaaa agcacagtga aatcttgaaa  14340
gaattctaat actaatgtca cacataagaa tacagattta aaattaatga actaaaacgg  14400
atatacgtaa tttctccagg aggaattaag atcctccttg atctcagtaa agcaatgaat  14460
agtcattctg acatctagct aaaagcagac ttatttccct tcggtcttta atctttttgg  14520
aactcaggga tttccgccac actttgatac accaggccat tataaaatta cacttaattt  14580
attgtcaatt tctacttaaa aggaagaata cctataagta tctccatatg ctagatatag  14640
tagaaatggt atgctttaat tagtccaaca ataaagtcct taaagattta cattctttgt  14700
tgcctatttt gaaaacttgc gaagataaat ttttttaaag attataattc ttactagtcc  14760
tttccatgaa atataacagc aaatagtttc caaatgtgga tgtgtaatga gaggaaatga  14820
aaagtgagta aagagctgag ttaaaacatc ttaaaatcga atatggctta atactatcat  14880
tatcatcagt tgtcctggaa taacttaaat tcttctagct tattgttggt ttttcaatgg  14940
ttggttatag ttgtgaggcg gatacacaca cacacccaca cacttggcta tacaaaaaag  15000
atgttccgag actgacagtt aaaaattaca ctgctggccg agcactgtgg ctcatgcctg  15060
tagtcccaaa actttgggag gccgaggtgg gaggatcact tgaggccagg agctcgagac  15120
cagcctgggc ctaacatagc aagacaccat ttctaagttt aaaaataaaa ataaatttaa  15180
aaaagataca ctgctatgta cgactgttga tataaaaaat ctgaatacta gacatgggta  15240
ctcatctagt acttcaaggg cttatcaaca aagttgcaag ttgtaacact atgaattgtt  15300
agtgatactc ttttggcttt gctagcaagt gttgtaaagc tatacacaca cacacacaca  15360
```

```
cacacacaca tacacacaca caccttttaa aatggtgacc ctggtaccaa atatgacttt  15420
aaatggattt aattttaatg gctttaacta cgttcagctg tcatatggat caaaattagc  15480
ctctatccag ctggggtcaa ccagggagcc acttttctta accgacgacc tactgaacgt  15540
caacaactgc aggagacggg actttacctt cgtctctggt aaactagttg acacatcctg  15600
tgttggcaag aggcctaagt agatgacctt ggtcctctaa aatctggcct gcactctcgg  15660
ggcacccctg caacatctac aaaggcagct ccagatagaa aagggttggg gtcgaaaagc  15720
caataacggc aggcacctgc cccgcctcgg ggctgggggg ctattccagc ggcttcagct  15780
aactttcaga gccattcgtt tcccaacaaa gtctgaggcg ttcctctgct gggtacacca  15840
aggggctctg caaccctcct gggggggggg gtgcccagag ggcttccgga agtcccaggt  15900
ttattctttc gggtcacaga cagcagaaac taaaaagagg gattaccctt tctgtccagt  15960
cgcaagatgg cgaccgagcc tggtgggact ccgaggggcc gcaggccacc tcctcttccc  16020
aatggcccgt gcgccggcgg cgacggcaag cgggagggag gcggggccgg cgaaggaagg  16080
aggggcggag cgcggcgccc tcccgcgcgt cttggccccg ccccacgtcc ccgcgtcccg  16140
gcctggagcc ctcgcccggc cggcggcgc gcgctgcctg ccgggatact cggcccgccc  16200
agccagtcct cccgtcttgc gccgcggccg cgagatccgt gtgtctccca agatggtggc  16260
gctgggctcg gggtgactac aggagacgac ggggcctttt cccttcgcca ggacccgaca  16320
caccaggctt cgctcgctcg cgcacccctc cgccgcgtag ccatccgcca gcgcgggcgc  16380
ccgccatccg ccgcctactt acgcttcacc tctgccgacc cggcgcgctc ggctgcgggc  16440
ggcggcgcct ccttcggctc ctcctcggaa tagctcgcgg cctgtagccc ctggcaggag  16500
ggcccctcag ccccccggtg tggacaggca gcggcggctg gcgacgaacg ccgggatttc  16560
ggcggccccg gcgctccctt tcccggcctc gttttccgga taaggaagcg cgggtcccgc  16620
atgagccccg gcggtggcgg cagcgaaaga gaacgaggcg gtggcgggcg gaggcggcgg  16680
gcgagggcga ctacgaccag tgaggcggcc gccgcagccc aggcgcgggg gcgacgacag  16740
gtcagtgttg ccgcggcctg cgccaggcgg cgctggctcc cctccgtcac tcggccggcc  16800
ttcggggccc gctgtggcga ggtcgacacc ccccttcccc gccccccgcc gccgaggcga  16860
gtgtttgggg gcgcgtggtc cgaaggggct ggtgccagaa gtaggcccct ggtggccgcg  16920
gctgctgcag ccgtaactgt cagtcctggc tgagcgacgg cgggagggtt ttgtcgcccg  16980
aggggacgcg agcgggcccg gggcggggcg ggacgtgcga ggcgtcgaga tttgggcctc  17040
ctaggagcca ggctcttcga gccagccggg gccccagaca gggaagggca ggccctttcc  17100
ttcaaagggg agccctttct cggcgttttc aaggtttttg gctctcttgg ggaagacata  17160
tttagccgtg tgcttggtgg gttggggttt tgggggtgga ttgatgggaa gggagggcgg  17220
atgaagtggt atgtcaagcc caagggttgt gcgcacaggt tactctgtgt taccggccac  17280
caggatttct gaagttgaac gtgagttatt ggctttgcca gagactgctg tgttatatgc  17340
agacctgtat gcaagcagtt ggcctttttt ccccccccctt ttcagtgtag aaaatgaaaa  17400
ggatgctttc ctcatcttgg tggtaaaggc ttttgttggt aaaggtagaa ttgaatgtac  17460
caaatgcctt agtccgtaaa attttagaaa taattttaat acagacactg gtgaagcttg  17520
gcaaccttga aagagaattt agcgtctaca ttttttaaat gactttttat ggatatgcta  17580
aattagtaac agtccaaaat ctgtttgaga ttattaagtg gcgagggtgc tgttgaaaat  17640
gtaaactaat agcatatggg gtttacagtg cacagttaac ctcaatcatg aagaaatgtg  17700
```

-continued

```
gatatgaccc gtaattttgg atcattttac tgcctgcaat attgagagaa gcagcaaatt  17760
attacagttt tttttgggag acgacctaaa gtttaagaaa tacaactgtt gaaagttacc  17820
tgtcagagac acaaaggtac ccaatcaatc ttgttgaata aattggacaa gtgggataag  17880
gtgtttgtct cacacttctg atcaataagt actcttactt aagaagtgat ttggtaaatc  17940
atgtaaaatt tagaatttag gagagataag aaagttgtaa cttggtgtgt atagtggaaa  18000
tagctttgaa attagatcct gtttttaaat ccaagctact taccacattt ttagtgaaat  18060
gaatacatta ttaatgatgc tactgataag ccctaaggat gaccagaagc ccttttaaga  18120
aacactaata cagttgacca aaaaataaaa aaggaaatag cttcaagaaa taattttcaa  18180
tctttgtgta tttataatat acacaggaga aataaaagaa cagaatatga agaggtaact  18240
tataatcttt acaaaattag aatgtaaact atgctagtct tactgtgtca atatttatta  18300
acctgcatta gtttgctaag tagtatgctc actatcctct ggacattgcc cctgtccctg  18360
aggagcttaa ctttatacag agatacaaaa tactgtgttt tgatttcctt tcagaggatt  18420
tataagctac ttatgtttta tctgtcctaa attctgccct ttttttcccc atggctgaaa  18480
aaataacttc ctaagaaagg tacatactag tcagaggtgt ggggaaaacg tgttctcatc  18540
ccacttgtgc agtccattta acaggattta ttgggtacct acagtgtctt tgacatgtaa  18600
catttaatca gttgtatttc ttaaacttta gataatttct atttcgatca tttctatttc  18660
aatctcctcc ctctcccctc caaaaaaatt tactgtgtaa actgtgataa tacactgttt  18720
ctctcagtgt cagtcagtgg aatgatccag atttataggt catagcaaaa tttttcatcc  18780
caagctcttg aaatgatgtt tccaaatgtc cattttctta aatgactgct agttatgttc  18840
tccaatcatg ttacacatat tttgtttaga cttataattg tgtaggtcta aatgtagaaa  18900
cattacatta tgtacatatg cagctgctga aagaaaatta gttttctaat ttttagatcg  18960
gggtgaagac aaactttttag aagtgatctt tcggtaaaat actggatgaa gtcttaggtg  19020
ctctttttat gttggttcag gacaaaagtt ttttgactgc tttttgagtt ttcccctcac  19080
tgccaaatgt aaggataaaa tgtagtaaca agacatcttg gtatgtatag tggtaatatc  19140
tttggaatta gaccctaatt ttaattctgg ccttattaat cttggtaagc cacagttttg  19200
tcatctgtaa aatgggttgg tgaaacttcc ccagagttgt gaggcttaaa gtatgtaaaa  19260
cgcctaacac gtaggcactc aataagtatt accttagaaa tcttcctatc cagtttttct  19320
gaatggtctg gaagcacctt gtatgtagtg gactacagca tgttatcctt tatgttgttt  19380
atttcttttc tcattagcta tgaacttttt aaggccagga attcctagtg tttaccagag  19440
aatgtgttac tagatgtctt agtctgttct ggctgctatt acaaaacacc acagacagca  19500
tggcttataa acaacagaag tttatttctc acggttctgg gggctgagaa gtccaagatc  19560
aaggtaccaa caaatttgac atcttagtga gggccctctt cccttgttca tagatagcta  19620
gctgtctttt caccattacc tcatgtagta gaagagtaga cggggctcta tagggcctct  19680
tttatagagg cattaattcc attaatgatg gcaaagcttc ccaaaggccc cacctcttaa  19740
tactatcacc ttggaggtta ggctttcaac atgaattttg ggggacacat tcagaccaca  19800
gcactagagc aggcatgaat tggttattgg taaatcagta aatgatcaac taacatttat  19860
taggttcctc ctgtggcttc tatgagctga gctaagtaca ggacccacaa agacaagaaa  19920
gatgtctgtc ttttttgaat gcttatagtt gagtgacttt ctcacatttg tgtgtgtgtg  19980
tgtgtgtgtg tgtgtgtaaa accctatcac ataatggaac ttcattttcc catgcccttc  20040
caatctaaga gcagttctat ggactcaata cctcctaccc accagctgct actgtaaaga  20100
```

```
tttacttttt tactcctttt aaaaagttca accctctggc acatgcatta cttcattcct  20160
tggtcccagc ccaccacccc agtatctggc acgtagtgta ttagtatttg tgtgtgtgtg  20220
tgtgtgtgtg tgtgtgtgtg tgtgtgtgtg tgtgtgtgta tgtatataga atttaaaatt  20280
tttactccgg cagttgtctt caaatactct aattttgggg ggcatgatta tcattctgtc  20340
ttctggcagt acatggatag atgctacctg agtaggattg tctatgaggt cagctgctcc  20400
agtcatttta tacaagagga aattggagtg caaagcttta aaatgatttt cttaaagtca  20460
cccaggtgtc agaaccagaa ccagagtcca tgtctctagt tcaggactct gcacacattg  20520
gcacatgttc tgtcctacct tttgggatga atagttatac ttgctttgtg attactcacc  20580
caccttttttg gagacatatg agtgttttgt acactattaa tagaaggcag ccttcacaaa  20640
atgccatctg cagatctgtt atttcttcta ataaaggaaa tgatgtaaaa ttaccttaaa  20700
tagaaatagt gttaattctt ctggagacat attccataat ccaaacacga aatgtttgaa  20760
atacttgaag atgccatata aataagtcct ttgtaaaaag ataatattaa aaatttttgt  20820
tttatagaga tgggggtctc actgtgttgc ccaggctggt cttgaactcc tcagctttta  20880
ctttagcttc ccagtgtgtt gggattacag gcatgagcca caatacctgg ccaagtcctt  20940
tttttaatc aaatgactta ttaatacaca gtttctttgc cagcttttgt tttcatttgc  21000
tatcaaaaat gttgcttagt agtgctttga tctgagttat caataacagg taaatgccat  21060
tatggataat aattcaaaaa gaagcttatt aattattagg cctatctgag agtgaagtaa  21120
agttagcatt ttctttttgt ttattttact tattgtttat ttgtttagag acagggtctc  21180
gctgtgttgc ccaagttgga gtgcagtggt gctgtcataa ctcattgcag tctcaggctg  21240
gagtgatcct cccatctcac cctcctgagt aggtgggatt agcatatgcc accatgcctg  21300
gctaattttt ttattttttta attttttttgt ggagatgggg tcttgccgtg ttcaggttgg  21360
tttcaaactc ctggtctcaa gcggcttggc ctcccaaggt gctaggatta caggtgtgag  21420
ctaccatgcc cagctgagca tttttaaaaa atactggtct ttgtacatga gtcgttacta  21480
tttgattcta agccttatga ctgatatccc taaaaattat ttataaaatt ttaagtgcat  21540
cagagtcatt gaaatggaat gagcactgtc ttttggtctt gaggttgttt taactagctt  21600
cgtaatggtc atgagcaggt tatttagctt ttgaagcctt cgttccttct tttgtcaaat  21660
gaaagtgata gttgctttgt tttaaaagag tatgcttttc aaacgtgatc attcttgaaa  21720
atgtagatta agagcttttt agaggccaag tgccatggct cacgcctgtc atcccagcac  21780
tttgggaagc cgaggcgggc ggatcacgag atcaggagat cgagaccatc ctggccaaca  21840
cggtgaaacc tcatctctac taaaatacaa aaaaaaaatt agccggacgt ggtggcgcat  21900
gcctgtagtc ccaactactc aggaggctga ggcaggggaa acgcttgaac acgggaggcg  21960
gaggttgcag tgagccaaga tcatgctact gcctggcgac agagtgagac tgcctctcaa  22020
agaaaaaaaa aaaaactttt tagaaacgtt gttttgggga atttttagtg tgtgaattca  22080
ttttaaatat gtgaactcca tttgacatgg acaatggatc ttaatagttt gtgatacatt  22140
attcagtgta ttaatcaaaa gtcaaatctc ttttgtaatt tgctgtacca gacctgttgt  22200
gttaatctga tcaatggcaa gtgaatcata agattgacct gaaaggaaaa gatattttta  22260
ggggacatag aatcatattg gataagatta ttcctatagt tcattttcag gaaatctgaa  22320
caggaatctc gtgtaaggaa tcacatgtga attatagaag agagtctgat gtaagacttt  22380
atttattaag gtctgcatct gtgtttcaag taagagcata gaggtagtat atgagccctg  22440
```

aacactcata caagtaggat aaaatttttc ttaaaactgt tggctggaca gtgtagagtc 22500
taatgctgtg actcttaaca gttttgtgtg ttccagaagt tcatctcctc aggatcaatt 22560
gaggttagtc tagcacagac tttagttata gaaaccaaac atgagaaaaa ttttttgacc 22620
catgtcttcg tagcatgcag gcttggtagc tctttcctag ttctggatgt gtgcccgttg 22680
tatatacttt cagcaattca ggatgttcct tttcatattt aagacaagca ctcttgcata 22740
caaattacat agctgtgggc tgaatgaaga tgctaccatt gctgtacttc tacacaggtt 22800
cttttcatgt aatgaaatca gaagggatgg cttttccatt tcaagcttct gttaataagt 22860
agtcttagaa ttgcctttgt gtactgtagc caacacccca actcatatat ttttataatc 22920
tttgtgatgc agaataaatt ctgaaacttt ccacctccta attaaatata gaaatactga 22980
aaacaataaa gcaccatgta ttcactatgg acatatgtca cattttgtca ctttcttgca 23040
ctcttgtaat ccctctctaa agctcatgtt aaactcatgt tctttatttt cttctcagat 23100
gattcctttg gcactgcatg taacagtaca ggaatttctt cctttcgtac ttccaacaaa 23160
tacttttttg tctcttaaca gatgtgaacc ataatgctgt tctttagaaa gcaaaggatg 23220
aagtgcacag cagtgttttc tatataaagc taatgggtca taaggggaaa tatgggttat 23280
ttccagcttg ttaattgtct taatacattt ttcctaagaa ttctattgtg cctctgtggt 23340
tatatgcacc aatattgata atcttacagc gtgccataaa taaggatttt tatattatct 23400
ttgctaaata ttttaagttt ttgttttggg aattgaaaaa atcttttgtg catctatggt 23460
atgtgatacg tatactaatg gataaatcct gtttcacaca aagattaatt gggtaacatt 23520
tttctttcct agttttctga agtcagtggt catgttgtgt gttggtgatt gaaaatatgc 23580
tgtttaggct gggcgccttg gctcactcct gtaatcccag cactttggga ggccgaggca 23640
cacggatcac ctgaggtcag gagttcgaga ccagcctggc caacatggtg aaaccctgtc 23700
tctactaaaa atacaaaaat tagctaggcg tggtggcaca cgtctgtaat cccagttact 23760
tgggaggctg aggcacgaga atcgcttgaa cctgggaggc agaggttgca gtgagctgag 23820
atcacaccat tgcactccag cctgggcaag caagatttca tctcaaaaaa gaaaagaaaa 23880
gaaaagaaaa tatgctgttt aagatcattc aaattcagtt tctaagaagt gtaaagtttt 23940
cctaattact taagctgctt cattctcatt cccttttgta acacattttg ccatctctgt 24000
aacatgttga acatgtttaa agaacagagt gggagaatag gaagttacgt ggataaagtt 24060
tggtaatcaa ggtaggaata catcctgctt cacagaatgg gaatatttct gaaaagttga 24120
ctgtagtatt gaagaacact taagtgtagt gtattagacg aactgagcta attttggtct 24180
tttatacaca taaatcaaga tttctgcatt tcaaatcatg catatttctt taaatttatt 24240
gctcagtgta ctgtatttca aatattgtaa aaatgaaaag atcttgtggt cttatttaac 24300
tcagtatggg ataagtcctt cccaccttcc cattcttatt ccctctttta ggctgaatga 24360
aaggctgggg gagtgaattt aaaaatagat ggatctcagc tggagaatgg gttggtcacg 24420
tatctcaact gatattaaat aatttcttaa atcctggatt gaagattata agaaaacagt 24480
aaatgtttgc tctcagttca tttctttgtt ttgtttttttc atgtacagtt ttaggcactt 24540
gtaactgctg gatgcatgaa ctactttcta gttctttcag gcctactttt agatatctgc 24600
tgtggggaca gtcctcaaca cttaaagtaa ttttaaatag tgataggcag aactaggggt 24660
cagttttact gcctatgcct gtgctgaatt tgacatggca ttcctaggag gggaggtgga 24720
acgagggcgg tgcacacatt gtccatattg ctagtcagtg ccagattttg agaaactggg 24780
gctaatctct ctcttaaatg gtcaagatct aattccccaa agtgctgttt cagataacct 24840

```
agtatttgtc caaaattgcc ctgctacaat agtatttatc ttatatatat gtattatata  24900
tataatatat atataatctt atatatatgt attatatata ttatatatat aatcttatat  24960
atgtattata tatataatat atatataatc ttatatatat gtattatata tataatatat  25020
atataatctt atatatatgt attatatata taatatatat ataatcttat atatatgtat  25080
tatatatata atatatatat aatcttatat atatgtatta tatatataat atatatataa  25140
tcttatatat atgtattata tatatataat acatataaat atatatatat atatatatat  25200
aggttttttt ttgtttttcc tcctgagatg tagtctcgcc ctgttgccca ggctggtgtg  25260
caatggtgca gtcttagctc actgcagcct ccgcctcctg ggttcaagtg attctcctgc  25320
ctcagcctcc tgagtagcag agactacagg tgtgcactac cacgcccggc taatttttgt  25380
atttttagta gatacagggt ttcaccatgt tggccatgct ggtttcaaac tcctaacctc  25440
aggtgatctg cctgcctcaa cctctgaaag cactgggatt acaggcatga gccaccacac  25500
caatcctatt acattcttaa aaaaatgttt gtttgtttgt ttttgtagag atgaagtttc  25560
actatattac ccagcctggt cttgactcct gggctcaagt gatcctcctg ccttggcgtc  25620
ccaaagtgct gggattatag acatgagcca ctgcgtccag cctgtatcat atttttattc  25680
tgatatcttt tgtaattttg tttttagtga agtagggagg tttatattag ataatcttcc  25740
aaggtaatta tcagcttgga cattatatgc taatatgtct tttgtttgtt tttaaaataa  25800
gtgtatatgt tttaattgta aaatttttaa aacatccaga aaatgacata gcaagtgcct  25860
atttatccac cacctggaaa tataaattat gtccattttt atcccttggg ggaaaggatg  25920
cagttatata atcactttta acaaccccaa ctgttcaagt cctgttaccc gtctctacac  25980
aaagtaacaa ctgtcttgag attcttaagt aaatttcaca tccttgtttt atacttttac  26040
tatacatgtg tacatgtatc tgtaagtgat atgtggtgtt ggtttttgta ttaaattttt  26100
acagacatgt ataacgctgt ctttcaatag cttgattttt ttaaactcag tatcaagttt  26160
ttgaggtgta tatgttgatg cgtgtacatg tagtttattc agtttcactg ctgtatggca  26220
cttcatttta tgcatagata aaatgtatgt gtcccactat tgatggatat tttgagttgt  26280
tttctttttg ctattataaa taatgctgca gtgtttattt ttacatgagt gtatgtgcag  26340
gtgttttggg aaaaaccgta gaagtgaaat tgctggttac tagatattgg taaattcttt  26400
tcctaaatgg atatgcccat gtatacttta tcagcattat gtgggcattt ctagcatcct  26460
cacccatact tgggattgtc agattttaaa atagttacta atttgaggca tgtgaaatgc  26520
tatctcattt taatttacag ttgcttgatt attctgaatc gtaggtaaaa ggataggaaa  26580
tttattattt tctgtatgtt ttaaatatct caaaaataaa tgtttttaaa ggaaaggcac  26640
actatcgtac aacatttatg ttgaaaagga ccatgaagat catttcatcc aaccttctta  26700
ctttacagtg cagccaaaga aagttaccag aataagagta aaatataaaa tcctgcccat  26760
tgtagtattc tctggtagta tgagccttaa tttttgatgt aaaaatcatg tctttttctt  26820
tatgattgtg ctttttgttt aagaaatcct ctttttatat tgtctgctaa tagttgagga  26880
ttttttgtta ctctttgtta tttgcattta ggttcatctg aaaggagtta ggattttttta  26940
ttttaaatat gaaaagctag ttgttccagc attaagtatt gaatttttaa aattttgtat  27000
tgaggttaaa tatacataca taatttacca tcttttttaa gtgtacagtt catttttaat  27060
gatttttttaa gtgtacagtt ttttaagtgt acagttcagc aataataaat acagttatgt  27120
tcttctgcct ttgtcctctc actccccact tcggctgcta gtaaccacca gtctatgctt  27180
```

```
atcttcttga gatatacttt tttagcccat gtatgagtga gaacatgtgg tatttgtctt  27240

tctgtgtttg gcttatttca cttaacataa tggcttcttg ttccatccgt gttcctgcaa  27300

attacagggt tttattctta tttttatagc tgagtagtat tccactgtgt gtataaacta  27360

cattttaaag tctattcgtc ctaattattg aattctcccc accccaccca ccttttttt  27420

ttttttttt tttccaggag acagggtctc cctctcttcc ccaggctgga gtgcagtgcc  27480

atgatcatag ctccctgcat ccttgaaccc cctggcctca agcgatagtc ttgcctcagc  27540

ctcccaagta gctgggactg caggcaggca cctccaggcc ctgctaagtt ttgtgggttt  27600

ttttttttt ttttttttt ttttttgtag agatggggtc ttcctatgtt gcccactttg  27660

gtttgttagt tttagtagtt tataattcct ttgtattatt gtgaacaaat aacagttatt  27720

ttgaaataga agagtgcttt ctatttaaaa ttttgctttg atagggttct gtctactttc  27780

tgagccttac cttcctgtgc attccccttt ggtcagtacc atcttaccac acaggctgct  27840

tttagtttct tgagttatcc atcttccttc tatcttatag ggctcaacct aaatattact  27900

cagggaagcc ttccttgaga gtctttcttt ttgcactcat tggtttgggg cttctttata  27960

ttatactgtt aattgaattc tgagtcgtgt ttatctcaac tgagattagg taatttattt  28020

tgagaacagt aaatgtttat catctgtcat tcttttttc atgcccacat tcagttattt  28080

gtaagtgctg aatgtataag tgttcatcta cagataagga tcagttcttt tttccccaac  28140

tagaaatgtt actccagttg ataataacag ctcaaacgga aatataaggc agaggtgaga  28200

gagtcacttg aggccacgaa ttggagacca gcctgggcaa caaagtgaga ccttatccct  28260

atgaaaaata aaattagccc agcttgggag gctgaggtgg ggggattgct tgaaccctgg  28320

agttccaggc tgcagtgagt tgttatcaca ccactgcact ccagccgcgg tgacagaccc  28380

tgtcccttaa aaaaaaaaaa attataacca gccacattga aatattttgt aagacattaa  28440

tagaagacta aatgttctca tatgtttact gtttgtgtta agtacgtatg gtttttagaa  28500

caacagtttt ctatcaagtg tggtctggtt cacttagaat tagatggggt agattttttg  28560

aaaagcgttt tgaagttaaa ttagaagcta atggtttttt gtcactaaat caaattttgt  28620

tttatgcgtt taagtgctac atttatttga taggcaggtg aatgtaacag attaaacttg  28680

aaaataatgt agctatgatt ccttcaagga aaaacccacc tacctttagt tcttttagta  28740

tattgcatta taagtctttt gtgtgtgcat atatagcagg cataaattgg cataattctg  28800

ggtttaattt taggctaggc gctatggaag tttgaactct aattacagtg taaaaataac  28860

ccagaggaaa atttcagaat aataaatcat tgggactata tggtacagat gtccctgttt  28920

tcagattgta gaattgttga ccagtaggaa tgctttatga ttaaaagcca ggaaattaaa  28980

gtaattctga tgatttggta tttctaaaga ttttcataga tgacagttga gaactactct  29040

cagatgagat tcttccattg ctggtaagtc atgtaataaa acacttaagt aaatatttta  29100

atgaggaatg ataacatttt aatattggca cattgtgagt ctaccttctg tagttagtag  29160

gtaaataaga aataaacata ccttatttaa aaaaaaaatt tcaaagaacc caagggaggg  29220

gagagccaag gtgcacatta gaaggagatt acagtactct tccagtgcac agtggatgtg  29280

ttgtgattcc agagttctat gtatgtatga ctgtgtagcc cagatttacc agcatgggct  29340

cagttttaaa tgttaggtta ggctcataaa tcatgaaaag ttcctaggaa ttctaacatt  29400

tttacatttc cagaagagag cctcttgtat tttgtggtag ttgccccacc atccctcaaa  29460

tattggtgtg tagaatctat ttttgaggat gaggaaatac agaaaagaaa aataaaaagc  29520

tatttttttt taagtataag aagaaatgaa aggtttctct tcgcttcata gccaattcta  29580
```

```
aaacttaaca gttgttaagt gtgtttaact gtagagggaa aaaaatgcct ggaaggaaat  29640
taccaatcaa atataaaatg taagatagct gtaaaagtac tgatatacat acagcttttt  29700
tccttttggg gaggcagtat ttaaaaaaaa tcctaccaaa catattctct aactttcaaa  29760
actgttaata gctttattga gataattcac atactataaa attcaccctt ttaaagtttt  29820
tagtatattc acagttctgc agccatcacc actattgaat tttagaacat tttcatcatc  29880
cccaaaataa atcctaacct gttagcagcc attccccatt ctttcctggc ctctggaaac  29940
cactaatctg ctttgtctct atgaatttat ttattctgga tatttcatat aaatgggaat  30000
catacagtat gtgtcctttt gtgtgtgggt tcttttactt accatggtat tttcaaggta  30060
tgttcattga catgtatgtc tgtttttttt gggtaacaca cactcttgat tactgtagct  30120
ttgtagtaag tcttgaaacc aggaaatgtg agtattctaa cttattcttt ttcaaaattg  30180
ttttgggtct ctgggtttct caaatttcca tagaatttta gggttagctt gcaaaaaaat  30240
gcaactggga ttttaatagg acttggattt gtgttgaatc tgtaggtcta tttgggaagt  30300
attgctacct taatactgtc ttctcattca tgagcatggg atatctttcc atttattaag  30360
gtgttcttta atttctttca tgttttgtag ttttcagtat acaggtcttg tacttattac  30420
tttaaaaatt tatttctaag aattttatgt tttgatggta ttgcaaattg aattttttaa  30480
aatttcattt caggttttta attccttgtg catagatttt tgtgtactaa aacttgtgtt  30540
tcatataatt tttttttcct cttaactgtg ttataggaat ctttcaaatg gttggctaca  30600
tacacatcca tctgattcac ttagtaaaca tttcttgaac acctactgtg tagtgggcct  30660
ttttttctag gtcctggtag agacagcagt gtataaaacc cactcagtcc tttgctttca  30720
tggcacttaa atcctaaaaa gagatcataa agataggtaa aatatatgtt acatagtgct  30780
aaggagaaga aacaaataag ggaagtgttt gcaggtgaaa aggatgatgg gaaattttag  30840
atagggtagg tagagaaaac ttcactgaaa tggtaacttg ggtgaagaac tgagggagat  30900
gagagagcta gccatgtgga tatttggggg aagagcattt caggcagagt gtagtgaata  30960
gggaaacccc aaagtgagag tgcctgatgt gtttgaagaa ctcgaggtgt ggccagtgta  31020
gctttagaaa agtaattgat gggaaataga gagaatggag ggtacagata ttttgatcat  31080
aataaggtgt ttgattttta cctataagtg agatgggaag ctattggaag tctttgagca  31140
gagtagtgaa aaagtatgac ttatgtttag caaggtcact ctggttgctg tgttaatcat  31200
agactgaaaa aggggacaag ggcagaaaca gaccaattgg tagaccatta gtacagatta  31260
agacgtgact gaaatggaca gagtggtcac agtgagggtg gtgagaagtg gttgaattct  31320
tgatatatgt tgaaatagag tccataggat ttggtagtag accagatgaa agtgggaaat  31380
aaagggagga gtaaaacatg atgccaaagt tttttgacca gagcagctga gagaatggag  31440
ttggataatt cttataaatt attgcattaa atctgtgcat catatcacat gcccacttaa  31500
ctacaggtaa ttttaccata taagcttgtg gggggaaaag aggaaaaaca gaaaaaagga  31560
tggaaaagca tgttttaaaa tataataaat taggccttaa tgaaaaattg tccttgagaa  31620
acctgagatg gaatactcta aatctgatgt gttctctcaa tctttagaac tgaactagga  31680
attaactctg agagttcatg atgttatgag accctttgcc tgttttggaa attcggttgt  31740
tttcaatatt tgcttttgca atgatggtac ctgttatttt ttctgtaagg tagattccta  31800
caaataagat gtcaggccat tagatcatgt caatctaaat atttgatagg ttttgccaat  31860
tacctttttaa aaaataattt tagcaagttt cattccttaa aatatattag ggactgctca  31920
```

```
tttaccttgt tttgattcat gtatatataa aatctgttta agtctttata aataacctgg  31980
gaaattgcct ggttttttgg tccatttcta ttgtggtgtt tgttttttaa atttgtaagc  32040
attctttata tatcatttaa ttctttatta taatttgcaa atattatctc tacctacctt  32100
taattttata gtatctagtc atgtgaaatt ttaaagtttt tatgtaggca aatctgtcca  32160
tcttttatgg tttctgggtt tcagcatgct aacaaagttg atataaatat gatctcatat  32220
atatattaca aaaacttttt agagatagga tctcactctg tcacccgggc tggagcaacc  32280
atagctccct gcaacctcaa actcctgggc tcaagtgatc ctcctgcctc agcttcccaa  32340
gtagctaaga ttatagacat gtgccactat agctagttgg ttttttttg gttggttggt  32400
ttttttttt tttttggta gagaacgtat ctcagtgtgt tgcccagact ggtctcaaac  32460
ttctggcctc aagctatcct cccacctcag cctcccaaag tgctgggatt acaggcatga  32520
gctactatac ctggccaatc tcttgtattt tcttctgata cttttgtgat tttactttat  32580
agactttaat ttagaaagtt agatatgagc attcagcata tttttggata tggtatgata  32640
tggtttagat ctggattgca tttgtcatgg tttgggaatt atatctacct tttattttct  32700
tccacttggg tagctgattg tcttgtaagg catcctttcc ccactgataa tgccaccttt  32760
ttctatatta agttctcaca aactttgaaa aaaatcaagt ttattgatgt ataattgata  32820
cacaatgaaa tgcacccatt ttaactatat agttttattg attttgataa atatatacac  32880
tatcactgct actacaatca agctttagaa caattgaatt acctccaaaa agttccttcc  32940
tgtctgtagt catttctccc tcttggcccc aggcaaccac tgatctgttt attagttttc  33000
ctactctaga attgcatatc catggaatca agtaacatgt actcttccat gcctggtttc  33060
tttcacttgg catgtttttg agattcatcc aatttgtgtt tgtcacagat ttttgtttgt  33120
ttcgtttttt taaatacaat atgactatac cacagttcat tcattttctg gtgaacattt  33180
aaattgtttt cagttttagg ctgttgcgaa taaaggtact gttttgtgtg catgtttttg  33240
tgtgaacata tgttttcatt tttctagggt aaataccta aattggaatt actgggtcac  33300
atggtaagtt tatgtttaaa tgtataagga actgccaaac tattttccag atgattatac  33360
tactttacat tcccatcatc agtgtatgag agttccagtt ctccaaatgt cagcatttga  33420
tgttctcagt ctttaattgc acacgttctg agaggtgtgt agtggtatcc cattgcagtg  33480
ttttttttta agtggtacta aaatacacaa catcaaatat accattttaa ctatttttaa  33540
gtgtacagtt cagtgacata aagtacattc acattattct gcagccatca ccactatcca  33600
tctctgaaac tttttcatct tctcagtctg aaaccctatc cattaaacag taactcttca  33660
ttgcctactc tccctatctg ctggtaatca ctgttctact tcatatgtga atttgactct  33720
tccaggtact tcatataagt ggaatcatac gatttttgtc cttttgtgtc tggcacattt  33780
catttaataa taataatgtc cttgcgttag gccattcttg cgttgcctta aatgaatatc  33840
tgagactggg taatttaaaa agaaaagaag tttatttggc ccctggtgct gcaggctgta  33900
caagcatggc gccaccatct gctcagcttc tggggagccc tcatggtgag tttactcatg  33960
gtggaaggca aagggggagc aggcgtgtca tatggcgaga gcaggagcaa gagagagggt  34020
ggggaagtgg cacacccttt ttaaacgacc acatctgcga actcactctg tatcccaagg  34080
agagcaccaa gctatgaggg attgctccca tgacccagtt acctcccacc aggccccacc  34140
cccaacattg ggattatat tttaacatga gatttgggca ggacaaatat tcaaaccgta  34200
tcagtcatca aagttcattc atgttgtagc atgtatccaa atttgattct ttaaggttga  34260
gtaatatttc attgtgtgca tatatcactt tttgttttat ttatttattt gtcagtggac  34320
```

```
atttggactc tttgtaactt ttaactatgt gaatgatgct gctatgaaca ttggtatata  34380
agtatctgtt tgagtccctt cttttaattc ttttggttat gtacttagga gtggaattgc  34440
tgggtcatgt ggtaattgta tgtttaattt ttttagagac tgccatactg ttttccacag  34500
tgactgcacc attttacatt cccaccagca gtgaataagg gttccaattt ctctgcatct  34560
tttctaacac ttggtaattt ctgtttttta tttaaaataa ttgccattct aatgggtgta  34620
aaaagtcatt atggtcttaa tttacatttt cttcatgact gctgttgaga agttttcttt  34680
tgtgtgtctg ttcaaatatt ttcacattct tttcagaaca tatgttcttt gtcagataga  34740
taaatgtatt tcttctgtat ccttactgat tttctgtcca cttactaatt accgagagag  34800
gaatgttgaa atcttcaact ataattttga gtttatcttc cttctgctct gttcattttt  34860
tcttcatatg ctttgaagca aagtctttaa agttgtgtcc ttaggtgtgt tcacatttag  34920
gactgttaga tctccttgat taattgatgt ctttatcatt atgaaatgtc tctgtttatc  34980
gctggtaatg ttccttatct aaagtctact ttgatattag tgtatccatt cctttcttat  35040
gattaatttt tgcacattat atcattttgc tgtgttttta ttttcagctt attggtcatt  35100
taatgtcttt cttttagata gcatatagtt gcatcttgct ttcagattga ctttttacga  35160
tcgttgcttt ttgattaagt ccatttacat ttattgcagt tggcaatata attgtgttta  35220
agacactatt tgttttctat ttgtctaatc ttttcttcct tttctgcctt cttttcggtt  35280
aatggagcat ttttggaatt ttgtattgtc tccattatta gcttgtccct ctgttttttt  35340
tccccccagt gatacttcta ggatttacaa tatgcacctt taacttacct caatctacct  35400
tcaaaaatat tattcctctt aatgtataat gtaagaattt tggaatagta tacatccatt  35460
tactctccct cattcttttt ggtattatga tcttaacatt ttacttctat atgtgttata  35520
gattccacag cagcgtttga aactatttct ttcaaaggcc agttgtctta cgaagaaact  35580
taaaaactaa gaataacatt cctttatatt taccttcata tttaccattt ttatttattt  35640
ttctttgtgg agattccttt ttgtagatcc aagtttgttg ctggtgttat tttcctttta  35700
cttgaaaaaa tttcttaaac atttctaaag tataggtcta ctggctacaa aatctttcag  35760
cttttgtttg tatggaaatg tctttatttc actcttcatt ttatcgtaca atttttcaaa  35820
ccacacagac tttaaaataa ttgtagaata taatttcaca acattttgtt ctatttgtta  35880
ttgtcttcta tcttgtccat ctatccatcc tgtcttcttc tagtgtcttt ttttatgctt  35940
ttcaaagtaa gttgcagttg ttagtatacc acacccttaa cttgagcatg tatgttaact  36000
aaaacttagt agtttagtat ttttaactag aatttactat gctgttccag ttatttattg  36060
ctgtgtaata cattgcccca aacttagtgc cttaaatatc agcaactatt tattttgctc  36120
atgaatctct catttggtca gggattggca aggagagctt gtctttgaca atacattgta  36180
acaactgttt acatagcatt acattgtatt tggtattata agtaatctag agatggttta  36240
acatatttga agatgcatgt aggttatatg caaataccat gccattttat ataagggatt  36300
cgaagcatcc ttggattttg ggatccatgg gagtcctgga accagtcctc tgtagatagt  36360
tgaggtatga ctgtagtctt tggattgaaa gactcactaa tttcactcag attcaaggag  36420
aagggccata gactccacca cctgatgaaa aaatgacagt gttacattgt taagagcatg  36480
tggaatggct tctattgtga ccatctttgg aaaatacagt tgaccacata taccatttca  36540
tgagctgtga caaatgtata cacctttgcc agaaagttct atcagggtat agaacctaca  36600
cctcttccta gttattcctt ccccccacac caccccctaga acctaacatt gttcagattg  36660
```

-continued

```
ttttcatctt agtttagctt gcgcagaact ttatgtaagt agagtcatac aatacttata 36720
tgttgtaaaa agtttctttt tgctcaacat aatgtttttg agattcatcc atattgttga 36780
atgtttcggt ggtttgtgac ttcatctgtt aagggacacc tgggctgttt tcagttccag 36840
gctgttttca gttcccagct attataaaaa ggtacaatga acatttgtgt aaaaaaagaa 36900
gtctctgtgt ggacatatat gtttcttttt tcttggttag ttgatgtgtt tttctttcag 36960
catttgtttt tgatgagaag tctggttata cagtcatgtg ccgcatgctg acatttcagt 37020
caacgagatc atagttgaca atagtcattt aagattatac caccatattt tcactgtacc 37080
ttttctaggt ttagatgtat aaatacttac actttgttac agttgcttac agtattcatt 37140
cagtatagta acatgctgta cagctttata acctaggagc acccgggcta taccatgtat 37200
cctagttctg tagtaagcta taccatctaa tctagatttg tgtaagtacg ttctatgata 37260
tttgcacaat gattaccatg ctgagagttg ttggggtttt gttttttttt tctttttgaa 37320
tctgtacatt tatggttttc cttaaatttg gaagattgtt gccattgttt cttctatata 37380
tatatttttt accaccttta ctcctctttc atcatttcct ctttttctgg gactccagtt 37440
acacatatgt tagactgttt ggtattatcc acaggtcatt aacatcatat tcattatttt 37500
tcagtctttt tatttccctg tgcttcagtt tgctttgtct tctattttac tgtttttttct 37560
cctcccttgt taaataattt cagatatttc gctttatatt tcaagaaatt ccatttgatt 37620
cattttattc atgtattttt ttgaattctt gagcatattt gtaatagctg tttgaaaatc 37680
aggttactta ttgatttctt gaatttttttc actctgaatt tgttggttgg tttttttctct 37740
tggtcatggg ttgtattttc ctagtattta ttttatttta ttttttgttt tttacatatt 37800
taatgatttt ttaagattgg atgctggaca ttgtaatatt ttgttgttgg gtgtctagat 37860
tttgttttct tttagagtgt tttgttttgt agccacctaa ataacttgct ggtcagtttt 37920
atcccttcag ggctacattg gagtttgtct agagaaggct ttgctttaat ggtagtagct 37980
cctacctaag gcatgatcct tctgagtctt tactaaatgc tcccagtgtc accgtgttct 38040
cttcactcag gttagagaga attttaggag tctcccagtc ctttataagt actgggaata 38100
tttcagctta ctgcccctct ttcactagct tcatggagtc acttacctta atcgtgtaca 38160
gttagtactc agcagtggac tctcaaatgg cagatttctg aagccatttc tctgccttct 38220
cagacaagca cttgtctggc acttgtcatc aattttaccc acttcagctt tctcagctct 38280
gatctcttga ttctgaactc agtaaaactg ctgtcttctc actggatttc ccctccattg 38340
actgcaggtt ggaaattacc tccaggcaga catccaagca gtggatggct cacctccttt 38400
gtttttgtcc tttcatgcat tatagtcctc tgctgcctgt tatccaaggt ctgaaaattc 38460
tcgtttgaga aggagcaact gtcagatact ttcggatctt tctctgaaat tagctttctg 38520
ttgtgcttgt tgtgcttacc tctttgtcta atgctaatac catatgaggt ttttttttt 38580
ttttttagaa tgttttaagc tatacacttc taagtgtata gcttgttgca ctttcacaca 38640
ctgagcaccc gtttagctag cattcagatc aaaaaacagc agcagctcct gcgtagcccc 38700
ttgtgctctg tgtcactacc ccttttcttc catgtgtaac cactgtcctg acttctcata 38760
gcatagatta gatttgcctg ttttcatcct ttaactagaa tcaagcacat ttagttgtgt 38820
ctgacttctt ttaatgtatt tgtgagattt attcacattg ttggttgtag taattgttta 38880
tgatagtcgc tgtatattcc attttaagaa tggaagtgat attccatttt aagaatatgc 38940
catagtttaa tctgctgtta cggacattta atcatttttg gtttggaact gttaagaata 39000
ttgctgctgc tctaaacatt tcagtgattg tcttcttgtg aatatgttta cttctgtttg 39060
```

```
gtatacttaa gagtgaaatt tttaagtcat aaggtatgca tatatttagt gtatactcag  39120
tttttttaaag gcatgccgat tttaattatt ccatttaagt taatatgttt taatatctgg  39180
tagagaaagg aacattatta gaaacaattg ttttggttat tcttacatat ttagtctttg  39240
aaaaaacgtt tcttaaattg gcatttactt atatttgtgt taatttggga agaaatggta  39300
tctttgttca tctatgagtc acatttggaa ctagctcaaa ggccatgggt cctgattcct  39360
ttttttttt tttttttc ttgtagaggg gaggtatggt gtcaagaaaa catagtcacc  39420
attattacga aaagtaaaat atggaagaga tgatccctac catcaatcag cttacaacta  39480
gaggcactga caaatgtata cagatagctg taatgtaagg tataacataa taaatataag  39540
gagaaattaa taaattattt tatggtatta agaatgtata ataagacatg aaggagatgg  39600
tgattatgta taagagttta gataaccctg tgagatacag tgtttagaat gaggccagtt  39660
tttaacatgg catgataggt gggtggggga tagaggttag taatggatag aggaccattt  39720
ccgagtgaag tctcctcaga agcaaaagca ttgaagtcag aaacacaaat atccagtaca  39780
ttatagccaa tagtcaaatg atgggactag atctggtaac tggtgatgat gtcatatagt  39840
gggcagtagt gctgggatgg ctggggtcag ggccacatgg caggggcctc aaataaaatg  39900
tgaaggagtt agaaatttat tctgttggca tgagaaagtg ttaaagcttt tgaatataga  39960
atgatatgtg taactttgag tttttaggaa gataattcta gtggcaaagt tgaggataaa  40020
ggcaaaaggg aaaccagatg aaataatggg gcactgtagt aggacagtgt tggtaagttt  40080
gaggaaaaaa ggagtaagag atatttttaa ggaaattcat agggtttgag tataaattag  40140
aaggcaagta caagggaata agcgtggtct ttagaatcag acaaattagg gtttgaatct  40200
taaccttgca tttactaaag gactgaaagc tagttcccta agagaaaaat tttctctttt  40260
gtaagatgct tattctataa acatttgcaa gcactggaag tataaaagca aatgatacac  40320
atgttctctt gaagtctggt ctagtctgta agaagaggct gcactggcag gttttgacca  40380
aattgtgtag aatctcatct gacgtgattg ggagctttgg ctttattctg gaagcaacta  40440
aaagcaatca aaaaagactg gggaataatg tgagaatgta gaaatgtagg ggaatttcta  40500
aggatgaatt ggtagcaatt ggtaaacaat ttgatatact gggaaagaga gagactcttt  40560
agaatatgac tgagaatctt ccaatttgag cagctggact gatagtgcta ccatcattac  40620
ctcacagggt ttttcttagt gtgtcttgta aatcttgctt gtccctcata aagaatggtt  40680
ttccttttct tcagactaag gactttttat tacagtacac aacttaacac cccctgtatc  40740
tctccatcac aacacttaac tgtgcattgt tattgcataa ttaattgtgg tttttatttg  40800
tgcccatttc cttcaccaca tgagggcaag aaattatgtc tagtttttct acctctgcat  40860
cttcatccac ctagtaggca ctcaaaatct agtagacagt ttttgaatta atgattatga  40920
agaatttgaa ggctgaacaa gtatcaacct acacagtggt tagggcaaat aaaaatgagg  40980
gggagaaagt aatgaatggc accaattttt ttagtcctta accaggacag tgagattagg  41040
cagagtgagt tctttgggaa aataattgag tttgatatta gatacgttga atgtagatgt  41100
taatgagaca tccaaatgga tgtgtaccgt tggtaatatg tagttgcagg cataccatgc  41160
cagacataag gacttaaaga tacagagtta ggggtttgta agcatagagg tgctatggga  41220
atggatgaca ttgcgcagaa aattggttta ggttaagaaa agtggctatt gacagaaact  41280
tggagagagg ccatgtatga ggtaggaaga tgaactagca gaagacctta ttgcctttag  41340
agagatggaa gaaaatgagt ggatacaaca ttagggaagc cagaggaggt gaggagtcat  41400
```

```
tagcagtctt aaaagctaca aaaattaagt aggattaagg ggccaaagca ctgggaatat  41460
acagaaatga tggaaacttt acaagaaaaa tttcagtaga tagaaaaata gcagctgagc  41520
tagtggtttt cacgtctttt tggcagtaaa aggaaagaag ataaagaaat ggtactctga  41580
ggagctaatg gagttgaggg aattatgttg caagtattat ttgaaagcag tatttaaaac  41640
tttttaagtc ttaactgcag aatggactgg aataaggaga aactaaagca ggaggactta  41700
ggaaaattgt tgtagtagtc ctttaattgt gaaatgtgta aacggacaaa acttagacag  41760
ttttaataag tagcattatc cataaatata agacaccata aacatgatgc aaaggagaac  41820
agaagtgttg ggtgttataa taaaaagtga tagaaaaaaa cagtttgtga aattaagttt  41880
tgaaacagct ttagaaggag gtgaaggaaa aatagaaatg aataaaatga aaattttagg  41940
gaggtagata tagatcaaca taggcattta ttattagact atacttattt ataagattat  42000
tagactgagc cctctgttga agagataaag taagagaact atgtctggta ttaggattct  42060
tatggttaaa ttggcaagtg agtgtgccta atatttgtag tgcttacagt tttgttatt  42120
ctgtattttt atagatttgg tatatttcct ccatgattat gtgttcctaa ctcataattt  42180
ggaaggcagg gcttcttaaa atgagatctg tgtgtcatgt gaagtatatg ttaaaatgca  42240
aattcatttc tgcgttcttg ggttggtctg aaaaaaatta aaaaaaaaat tcatttaccc  42300
ctacttcatg cactgaatga aaatctttgc gagtagagcc caagtagttg catttttaga  42360
tttccccagg taattctatt atagactgaa gtttgaaagt cagtctctaa aaccttaaaa  42420
gttggttaat tttatttcaa aatgttttat atgcagtgta ttcactttct accatcaacc  42480
tctaggacac tggataggtt tcttaacctt tgagatttgc tttctttata tgtaatgcag  42540
tacatgaaag gactttattt ttgttccatt gaggaatgtt ctgattgtat acaaacaagt  42600
taagaattta cagtgataat ttaggggctt gctttaagct tcaggatttt tttttaagag  42660
ttaagttttg atatatatta agtggttgat ttaataaatt ataattatcg tcgtatattg  42720
aagtcctgtt ttgtgccagg taggcattat actataactt tttaacgcat tttctctgct  42780
acaataacct gacattggag actcaagggt cagagggtcg gcccaaggct gctactctag  42840
aaagtggtag atgcccagat ttgtacctaa catagccgat gcttagcata tagaatttaa  42900
ttaaaaacaa aattgctata ggtatttgaa aggattagag ggatatagtc aaatagtttt  42960
catatgtgtt tagccctttt ggagggagga tagagtaaat aaatagaagg cactaagctt  43020
tatggatgaa tatgggaaat atggctttgc ctgctgaaag cactcaggcc acagggcctg  43080
cctacctatg ctttcctcat cccggcaaca gcagtaattt gtttcttgat acgtttttgg  43140
atgttcataa ttatagaaaa taaatttgcc tttatgatga aatttagtac cttttttttt  43200
gaaagttcat ccagttgttt atgtaaaaag aattgagtga ggtgttttat attttaggtt  43260
aaaaatctgt aagagcctga ttttagaatt caccagctcc tcagaagttt ggcgaaatat  43320
ggtatgtttt tgttttattt tttggaattc gtattgcatg tgtatcttaa tgtcataata  43380
atgacagatg tgttcagcaa atttgggccc ctgccatttt taaagcattg tgtcaggtgc  43440
tcactaacta cacttccaag actgtatgag ggacccaggt agggtgctga aaaaatttac  43500
aagagattag tgtgctatga gaggtaaaat aatatgcata aaaagattga gagggcaggt  43560
ttggattttg ggctatgagt attaataata gctttcattt gttgttgttg ttgctgctgc  43620
tgctgctgct gttgtttttg agacagagtc ttgctctgtt gcccaggctg gagtgcagtg  43680
gcaccttctt gactcactgc aacgtccatc tcccaggttc aagtgattct catgccttgg  43740
cctcccaggt agctgggatt acaggcgtgt gccaccacac ctggctaagt tttgtatttt  43800
```

```
tagtagagac ggggtttcac cgtgttggcc aggctagtct cgaactcctg gcctcaagtg  43860
atccacccgc cttggcctcc caaagtgctg ggattacagg cgttagccac cacgcccagc  43920
catttgtgag cacattatgt caggcactgt tctgagatac ttagatgtta gcttgtttat  43980
ccatgacagc tctatggaat aggtactatt atcctagttc tacctataag gaaactgaga  44040
ctcggagagg ttaagtaact tgcccaagat ttctcagcta gtgaatgacc aaacagagac  44100
ataagtccag cctggccttg gagccttttg agcaccggat ctcataaaag aggggactgg  44160
aagagaggac ttgactctag ttttcaaaat acatatagct ctttaattac attgaggtca  44220
attagtcaat taaaagatat tttaacttta ttatttttgt gtttacaaga tggaaagtta  44280
gacttgtttg aatcttctaa ttccacatac cattagtctc ttgagaaccc aaggggaagc  44340
tgtatcatga ccacattgtt tattttaggg aaggtggtgt ttcccatatg acctcagcaa  44400
tgtctaagtt cttattaggc aatgtatagt taggatagga gtatctggga gattgcgtta  44460
tttcttacag atactataaa tcccatttat tggaatcccc tgcaattatt tttatatatt  44520
caggccaatc ctcacctaat ctggattttg aagccctgcg ttcatagctg cataggtatg  44580
ggctcaaaca ttcatgtttt aaccgttggt attcgcagat accttgctgt tttatattgg  44640
gttctgaatc cacactggta accacctttt acgcttgact attgttgctt tgaggatgtt  44700
aattatgaaa ggtttcttcc tcctaatttc ctcatctttc cgtagttgat gcctcagatt  44760
tggcctggat aggggaatcg tgaggggaaa gaactagttg cacaaaatga tcttttgata  44820
ctgggatatt tcagatgtat ggtatctttg ccagaactac agtgtcagta aagaggcctg  44880
ctaaatttga actgtgacaa tcagaaaagt tcagctaagg ccatgtaagg ggttaaaaag  44940
atatttggtt gagggaggag gatatgcttt catcttttgc catacttttt catgaaatta  45000
aatcttagta gatttatggc caagaaagag tagaatatat ttttatgcag tacttaaggg  45060
gttttgactg atgtttttta ttattattat actttaagtt ttagggtaca tgtgcacaat  45120
gtgcaggtta gttacatatg tatacatgtg ccatgctggt gtgctgcacc cattaactcg  45180
tcatttagca ttaggtatat ttcctaatgc tatccctccc cttcccccca ccccacaaca  45240
gtccccagag tgtgatgttc cccttcctgt gtccatgtgt tctcattgtt cagttcccac  45300
ctgtgagtga gaacatgcgg tgactgatgt taaatgactt tacgtacata cagaattagt  45360
gggactagac tttgtgttta tgtgtgtgtg tttatgtgta tgtatataac tattccatta  45420
agcagttgcc ctccttggtg actgattgct ctatcagctt aggaatcttt tgactgaatt  45480
tgtccgtatt tgaaagatct caatctgtgt tctgaatctt tactcattta catatactta  45540
aatcttgaaa cccagtatag caaaactaag ccaaaacaaa caaaaaaatc catcccttga  45600
taggaagtca gtatatctgg gttttagtca gtccttcaac actagttcca aaatcttggg  45660
caagtcagtt aatcactcgg aggctgctta attttttttt tttttaattc ttagtatatt  45720
atctgtcttg attaggtaaa gccaaagttg ttataagact caaggtacta ttgaccaaaa  45780
tgcttcagaa actataacat tacataaaag tacaaggaat tattacattt tctcaaatga  45840
agagatcatt taagaaaaac aaaatgctgg aaaatagtcc ttaaaaactt ttctataata  45900
attactcttc tgatgaattt tacattgaca cctaatttga agctttgaat attatttttt  45960
gaacaatgaa ttgggtttat atattaaagt gttctaacca aaggtttgtt taatttatta  46020
gagttattaa gcctacgctc agatcaaggt agcagctaga ctggtgtgac aacctgtttt  46080
taatcagtga ctcaaagctg tgatcaccct gatgtcaccg aatggccaca gcttgtaaaa  46140
```

```
ggtaattttg aattatttta cagcctttaa aaggctgtca ttgtaaagtg aaatacatac  46200
tgtaaaaatg aagacaatgt atagttggca ggaatactgc taagaatagt gggcctgaga  46260
gttgacctac ttcatttaat ctccttaaaa tattttagtg tcttttttc tcattaaaaa  46320
tatcagtagc cactatcaaa gacctatctg tatgtataaa caggaaagta tttctcaaaa  46380
aaacttcaag gttttaaaca ttttactata aacattatag aaaacattaa aaatttctta  46440
atatgcattt taaagtatgc cttttatgtg gtgaacgttt taactaaaca tttctctaga  46500
agtttttata acattaataa aactagtata cttttctctc ctagagagtt acagtggagg  46560
taaaaggagt ggcttgcagg atggagaagc tgcaccagtg ttattggaag tgagccacca  46620
tttgaatttg ctagctcatg ctgcagtatt cagattagtg ggtgttttgt gatcatattt  46680
tctgcgattc aaatcaagac ctaaaattga ttctcattct gagatttaca ttttattatc  46740
caatgttatt tggttattgt ttcagtttta aaatttctga cttgttattc tgacacactt  46800
taggataacc taagtcaata gtttaataca aaaatttccc tttggttata tgttttgaat  46860
taggttatat gttctgcatt tacaagcaca tacaggattc ttacttccag caacttggca  46920
gtaaaagaat aagtagactc tttaggagcc aaagtcaagc ttgggaactg ttgctaggtg  46980
gtatatattt catagtttat gtttgtttcc aagacaaggt ctcactccat cgcccaggct  47040
ggagtgcagt ggcacgatca cagttcactg caactttgac cttctgggct caagtgaccc  47100
tcccacctca gcctcccaag ttgctgggac taaaggcacc caccaccaca cccggctaag  47160
agacgaggtt tcatcatgtt gcccaggttg accttgaact cctgagctca agtggtcctt  47220
atgtcttgac ctcccaaagt gctgagatta cagacatgaa ctaccacacc tggcatatgt  47280
catagttttg agagtttgaa ttctaacctc gggactttgg taacttattt ataatattct  47340
agaaatatac tgttattagg atgagtagaa attcattcag acagaaacta ttataaatta  47400
ctgcaagaaa aatgtctgct agttctgcat atattcattt ttctcttgat taaaaaacaa  47460
tttccaattt gagtagaaca actttgctat gtttaataga cccaggacag atttatttta  47520
aggtaataat ctttcaatcc ttcttcttct atactggatt ggtttaaatt acttagcttg  47580
tcttatcaat ggtttttaat agcctacttt aatatatgta aaaagtagta attaatatgt  47640
tacagtttgg tggcaaacat tttgatgcca aagttcacat attctcttgc ttagggaaca  47700
gaaattggga agatagatgt agttatcatt tgataatgta tttaaactct atcccatttc  47760
aggatctcaa aactttgtaa cagttacata ttgtacttct aagacttaga tttgtttttc  47820
ttcttgtgtc ttaccttttt gcagtaatat ttttattttc ctatcatcat gtcctcattt  47880
tttccctctc ttctctttcc ctgttaattt tgaaagtttt gctgcctacg tgtttgaaaa  47940
cttctaatct gcctctcttc cctcagtgcc agcaggttta tttttttgttt tgcaagccag  48000
ctctgcctcc ttacagtatg acatctgatg ctggagggtc gcactttcaa aaatgagtca  48060
gctggtacat ggggttatca tcaattttta gctcttctgt ctgggagata caagtttgga  48120
agcaatcttg ggtacttac ccacaaggct ggtggagacc aggtgtgtca cataggtgat  48180
ttgcttgctc cctgggggag agggtggagt gaaatttttg catttgtgtc acagccaagt  48240
cactgccacc tccagcatgc cccagttttt agttgttatg taattttgtg caaaattgaa  48300
aatttaaata cattgcaaag aagatctaaa ataaatattt gagctgctgg agtctttttt  48360
tttttttttt ttccttttcc attcttgtcc ttggaatctg aatgaattgc agtgagggta  48420
attttgagag tctgataaag aagtgagggg ttgttttttg tttttgtttt tgtttttagc  48480
taagaaattt agaaaacagg tttgtgtgtg tgcgtgtgtg tgtgtgtgtg tgtgtgtgtg  48540
```

```
actgatttta agattcttgt tagagttgct taaagttgga agcctaaagt cagtgagaag  48600
ttcacaaatc aggactttgt aatgccaatt tgaaaattta gcttttgacc tcaaaaaaca  48660
tttttatct agtttgggaa tttctaagtg ttagaaatca atattatatt gactcattca  48720
ttgttgctga tgctgtttat aaaagtgaat agatagggaa atactgattc atatctcgtg  48780
aaatgaaaat gaaaggcttt ttagtgactt agaattttaa atatttctac atgagagagc  48840
agtagtatat ttagaaataa caaagtaact ggcaactgtt taaaactgaa gttaattcac  48900
agctatccag tgcaaaactt cacctcaggt gatacacttt tgacaggtaa tacatacagt  48960
aagtgtattt ttagggaaac agtttcattg ttgaaccaag ataatcatca ttagaatgtt  49020
gtatctgatt taagtgtctt taaacttacc aaggtattag attttagttt gaattgtctg  49080
gagtagcggt agcggttggc acatttgttc ttaaagggcc agaaaataaa tattttaggc  49140
tttatgggcc atgtggtttc tgccacaagt cctcagctct gttcttttag tgtgaaagca  49200
gccatagatg atacctaaat gaatgagtat ggctgcatcc caataaaact tcatttacaa  49260
aactacatgg ctggcctaag ctttagtctg tctgcctagg gagtagttta ctgagccact  49320
aatctaaagt ttaatactgt gagtgaatac cagtgagtac ctttgttaat gtggataacc  49380
aatacttggc tataggaagt tttttagttg tgtgttttat tacacgtatt tgactttgtg  49440
aataattatg gcttataatg gcttgtctgt tggtatctat gtatagcgtt tacagtttcc  49500
tttaaaaaac atgcattgag ttttttaata gtccaaccct taaaataaat gtgttgtatg  49560
gccacctgat ctgaccactt tctttcatgt tgacatcttt aattttaaaa ctgttttatt  49620
tagtgcttaa atcttgttta caaaattgtc ttcctaagta atatgtctac cttttttttt  49680
ggaatatgga atattttgct aactgtttct caattgcatt ttacagatca ggagaacctc  49740
agtctgacga cattgaagct agccgaatgt aagtgtaact tggttgagac tgtggttctt  49800
attttgagtt gccctagact gctttaaatt acgtcacatt atttggaaat aatttctggt  49860
taaaagaaag gaatcattta gcagtaaatg ggagatagga acatacctac tttttttcct  49920
atcagataac tctaaacctc ggtaacagtt tactaggttt ctactactag atagataaat  49980
gcacacgcct aaattcttag tctttttgct tccctggtag cagttgtagg gaaataggga  50040
ggttgaggaa agagttgagt ttaacagtct caacgcctac catatttaag gcatcaagta  50100
ctatgttata gatacagaga tgcgtaataa ttagttttca ccctacagaa atttatatta  50160
tactcaagag tgaaagatgc agaagcaaat aatttcagtc actgaggtag aatggtatcc  50220
aaaatacaat agtaacatga aggagtactg gagtacccag gtatgcaata ggaatctagt  50280
gtagatggca gggaagtaag agtggccagg aaatgctaag ttcagtcttg aaatgtgact  50340
gggaatcagg cagctagaag catgagcggc ttattccagg cagaagtatg agccaaagtt  50400
agaagcagca tagggagtag gggacaatag gcagttgagg acttttagat cataaactag  50460
ctgagaggta ggaaaatgaa gaagataaga tgtgatagaa ggtattaggg agtcagcaaa  50520
gaatttgctc agtaggtaga tagtaagttt gtcaaacgtg tatttttaat aaccttgcaa  50580
gagagaaagg attgaagaga aacgtgtggt ggtaaggtag ttcagtcagt gagagccttg  50640
acaatgacag tggtataata ggaattcaaa ataaattttt ctggatttaa gacaaatatt  50700
taggacatga agtaagtaag actttagtga tttattgtga agactaaaga tgtttcagat  50760
aatagaggta gtaattatca aagcaaagtt tttcgaggta ttaagggttg gaatgaaaaa  50820
tacaggtgta tctctcatac aggtaatata aaaaaagaaa aatgcagata tagtgattga  50880
```

ccttgaataa gaggaaagat gcccatctaa tgaaattaga acaaggaagt aaagatggat 50940
gtgtgatatt aattgtaatt gtgggtgagg gtggaaaaat caagattttt ttactgaaaa 51000
tattggaacc ttatttaaat gccggtatat attgtgaatc tgcaagaaac gactataaaa 51060
tgtatttctc aaatttatgt gacccaacca tgtgacttgt cttttaagct ttaaaaaatt 51120
gtagtaaaat acacataatg taaaattttc catttcacca tttttaagta tttggctcaa 51180
tggtattaag tatattaata ttgttgcaca gtcacgatca gaactctctg ttttgcagaa 51240
ctgaaactct gtacccatta aacaataatt cctcatttcc ttatcttcac agcctctgac 51300
aaccattatt ctactttgtg tctaattttg actgctctaa gtacccccta taagtgcaat 51360
catacagttt ttgccctttt atgattggct tattttactt cgcagtgtca tcaagtttca 51420
tccatcttta gcatgtttca aaatttgcat cctttttcag gctgaataat gttttattgt 51480
atgtatatac cacattttgc ttatccattt acctgttgat gagcgctcag gttgcttcca 51540
tgttgtagct attacagata atgttgctat gaacaggagt gtacaaatat ctttttgaga 51600
ccctgctttg aattgttttc ccagaagtgg aattgttgga tcatatggta attttatttt 51660
taaaattttg agaaactgcc atactcttcc agagcaactg tacctatttg cgtttctacc 51720
actagtgcac aaggggtcca gtttctctac atccttgcca tcacatattg tgtgagagtg 51780
tgtgtgtgtg tgtacttcaa tagtagtcat tgtagtggat ataaggtagt atgttactgt 51840
aggttagtga ccacgaaact ttttatgaaa catttttttaa taatattttg tggaatacaa 51900
ggtttgttta gaggttttga gaagactgaa aacttaggaa gctactgagg ggaatgggtg 51960
aagaagtgga tcagaagttg agagtcttga ctggctggct acctgaaatc agaaaccgta 52020
tcagagtagg agaatctcat tccactgagt gactagttaa gattaaagac tttatcacat 52080
ttgaaattta aagacttttc tccaatagcc agaagattat gcatggtatt ttagggttgg 52140
atattagcag agctgatgga acagaatcat tagtggcatg tgcataagat gttaacattg 52200
gagtatttga atttatatgc tgtggatgat ggccatgatt ggaaaggttg ggatgccaga 52260
ccaaagtgtt gagttgtttt aagaaaaagcc tgaggtctag ataacagcaa gatggcagac 52320
tagcactttg cagcactcat ctcattgtag aaccatcaat ttgaacaact gtctacacac 52380
aaaaatataa gagctaagaa accagacgag agattacctg aatgtggcac acagataaga 52440
aaagacacat tgaaaagggt aagaaggaca gttttacatt acttgtgtca cacctccctc 52500
agtccctgag atcccagcat ggagagagag actgttcacc tgggggaagg aggggaagtg 52560
tacaccagac ttagacccta acattgagct cgccccagta aaactcaatg ctaggcaggc 52620
ccccatggcc ccaaacttca ggccaatacc cacaaaccaa gcttggaggc ccaccccagc 52680
accaagctgg atcccacagc cctaggctct aagcctgtct agtgctaggg tggtccctgc 52740
agccctgccc tctagatcgg cccctgtggc ctcacatcac tgcagaacaa gggtccaaac 52800
ccagtacttg gccagcccct tgtgatccaa attctaggcc aacatccacc tacccagcct 52860
tcacactggt ccttgcagat ccaaggttca ggctcactct agtagaccag gatgccaggc 52920
cagcagcacc tgtgtaccaa ggctccagga cctaccctgc tgacccagac tccaggccag 52980
ccccggtaga ctcaggctgc ataatctctg gacaggctga ctggtgaagg gctttaccca 53040
ataaagtcac tctgcaaaga ctggaacaag tctcagcttc ttcaaatgtg caggtgccaa 53100
cacatgacta cagggatcaa gaacagtcag ggaaacgtga caccagtcaa aggaacacaa 53160
taaggcacct gaaccaacca taaagaaatg gagatatatg aactgcctga caaagaattc 53220
aaagtaattg tttaaggaag ctcaatgaat ttcaagaaaa tgcagataaa caattcaaca 53280

```
aaatcaggaa aacagcaatc aaaatgagaa attttgagat tgaaattatt ttttaacaaa  53340
ttctgaagct gaaaatgcaa taaatggaat gaaaaatgca aaagagcatt aaaagcagaa  53400
ttgagcaagc agacaaaaga atctgaactc aaaagacagg ttatttggct agactaagga  53460
aaaaagagat gactcaagat aaaaaaaata aagagttgtg ttttttgatg ataaaagcaa  53520
caagtcttta gctagactaa gaaaaaaaga gatgactcaa gttaaatcag aaatgaaaga  53580
ggaaccattg cagctgatac cagagaagta caagaaataa gaggatcata agagactgaa  53640
caattatatg ccaacaaatt gattaccata gaagaaatgg ataaattcct agacacatgc  53700
aacttgtcca agcttaatca tgaaatgaaa aatgtgaaca gtccagtgac aaggattgta  53760
tcagtcataa aaatatctcc caccaaagga agcccaagac ttggtgactt tactgctgaa  53820
ttctagcaga catttaaaga agaactagta cagattgttc tcataatttt atgagaaatt  53880
taagaagagg gagtaatttc aaactcattt tgggagatga gcattaccta gataccaaag  53940
ccagacaaga actctccagg aaaagaaaat tacagacccg tattcttaat ttagatgcag  54000
aaattctgaa gaaaataata actaaattca acagtgtatt agaaggatca tttactgtga  54060
tcatatggga tttacctcaa gggtacaagg attatccaac agacctgaat ccataaaatg  54120
tgatatacaa cattaggaga acaaaggcca aaaccatgtt atcatttcaa tagataattg  54180
agataattga gaaaaagcat ttgacagaat tcagtattct cttgtgctac aaaattttaa  54240
aaaattaagt atagaaggaa tgtacctcta taaaataaag gccatattga caaacacact  54300
gctaacgtta tactgaatgt tgaaaagtta aaagcttttc ttttgagatc aggaagaaaa  54360
cgagaatgcc cacttttgcc atttctattc agcacagtac cggaagtcct tgcaagagca  54420
attaggcaag agaaagaaaa ggcatcccag taggaaagga agacattgtt gtccctgttt  54480
gaagatgaca tgatcttgta tatagaaaaa cctaaagact ccaccagaga attgttagaa  54540
ctgataaatt cagtaaagtt gtaagatata aaatcaagat acaaaaatcc gtagaatttc  54600
tgtacattaa tgacaaatta tctaaaagaa aaatcaagaa gacaattcca tgtataatag  54660
gtaccaaaaa caaaacatgc agtggctccc agtatcagtg gttctgcatt tgcaaattga  54720
accaacattt ggatgaaaat atttgagaaa aaaatacaac aataaaaata ctgttttctt  54780
atacaataag gaaactacag tatagcaact atttacatag catttacgtt gtattaggta  54840
ctaagtaatg atttaaagta tacacgagga tgtgtgtagg ttgtatgcaa atactatacc  54900
attttatata atggacttga gcatccatgg attttggtat ctacaggaga tcctggaacc  54960
aatatcctgc agataccgag ggatgattgt acttagaaat aactttaacc aaagagttga  55020
aaactatgta acattgatta aagaaattga agatgataca aataatggaa agttatcttg  55080
tgtttatgga ttggaagaat taatattgta aaatgttttt attatccaaa gcaatctgca  55140
gttttaatgc aatcctgatc aaaattccaa tgttaaattt cacagaacta gaaaacagtg  55200
ctaaaattta tatggaacca cataagatcc taaatagcca aagctgtcat gagtgaaaag  55260
aacaaagctg gagacatcac actatctgat ttcaaaatat agttcaaagc tacagtaatt  55320
ataacagcat gatagtcaca tagaagtaga caggccaggc acagttgctc acacgtgtat  55380
tcccacactc tgggagactg aggcagaagg attacttgaa accaggagtt cgagagcagc  55440
ctgggcaaca tagtgagacc ctgtctctaa aattaaaaaa aaaaaaaatt tttaaagcca  55500
ggcgcggtgc tgtgtatctg tagtcctagc tacccgagag gctgaagaag gaggattgct  55560
tgagctcagg agcttaaggt ggcagtgaac tgtgattgca tcactgcact ccagcctgga  55620
```

```
tgacagcgtg agaccctgtc ttttaaaaac aaaagaaaca aaaaaacaga cacatcgacc  55680
cacaaaacag aatggagagc acagaaataa attcgtgtac tatcagttga ttttggacag  55740
ggtgcaaaga acacagcggg gaaagggaag tctgttcaat aggtggtgtt gggaaaatgg  55800
aatatctaca tgcatgagaa tgaaatcaga cctgtatctc acatcatata ccaaattcaa  55860
gttaaaatgg attaaggtct taaatataag acctgaaact gtagaactac cagaataaag  55920
tataggagaa atgtacatga cattggtttg gacagtgatt tttttggata tgaccccctc  55980
gaagcacagg caacaaaaat aaaaattgat gaatgagatc acatcaaact aaaaagcttc  56040
tgcatggcaa aaagaaaaaa tctacagaat gaaaaaactc acagaatgga agatagtatt  56100
tccaaaccat atatctggta aggggttaat atgcaaaata tataaggaac tcagacatct  56160
caatagtaag aaagcacctc acttaagaaa tgggcaaagg acttgaatag acatttctca  56220
aaataagaca tacaaatggc cattagaatg gctattaaag tatgatgagg atttgcagac  56280
aagagatata ttgcgcatgg caggaatgta aattagtaca gcatttatgg aaaatagcat  56340
gacgtttgct cagaaattaa aaaatagaac taccatatga ttcagcagtc acacttggat  56400
atatatgtat ttttatatat atatatatat atatatatat atatatatat atatataaat  56460
aaaagaataa aatcagtgcg ctgaagagat ctgtactccc atgttccttt cggtatcatt  56520
tgcaataccc atgatacagc atcagcctaa gtgttcatgg ataaagaaaa tgtggtatgt  56580
atacacagtg gaatatactt cagccataaa aaggaggaaa tgctgtcatt tgtgacagca  56640
gggatgaacc tggagggcat tgttgaaagt aagccagcca cagaaaggca aatactacat  56700
ctctcttaaa tgtggaatct taactcaggg atgtaaaatg gtggttacca ggggctgggg  56760
gtgagtggac tgggttgcag aggtgttggt cagaggacac aaaatttcaa ttaagaggaa  56820
tttgttcaag gtatctattg tacaacatgg aaactagtta ataacagtgt atttttggaa  56880
atcactgaga gtagatttta aatgttctgc cataaaatat aagtatgtga ggtattgcat  56940
gtattaatta gcttgatcta gccattccac agtgtataca tattttggaa catcatgtga  57000
atacaataaa tatgtatcct ttttttgtt ttttgtgttt ttttttttt ttttttttt  57060
tgagacagag tcttgctttg tcacccaggc tggagtgtag tagcatgatc ttggccactg  57120
catcctctgc ttcctgggtt caaatgattc tcctgcctca gcctcccaaa tacgtatcat  57180
ttttatttgt caccaaacct ggtgtcttga caggtgaaag gagatatgag tatgagtgaa  57240
actcttacaa agatagctga gatgatcatt gtcagaggtt ttagtatgtc taacaaagac  57300
aagggagtga tttgctgaaa tgaggaggtg aagatgtctc aaatttagaa aggcaaatat  57360
tttgggggcc tagagtattg ggatagaacc atgtacaggg acattgaagt cactttgctg  57420
atgatgtaac tgggggcaaa gtggaggctt aaatatgtgg gtttaattga ccagaacagg  57480
gagggaaaga gaaggcattc ggttagatga catgagtttc aaattacaag ctgttttttt  57540
gttgttttta atacagggaa ttttgccgtt tatttttaat acagggaatt agaagaataa  57600
tggtggactt aggagtttta ggagtcacat aaaagggttg catgataggc agtgcctttg  57660
gggaggagcc aggctttcat gaaagctaag aagttgaggg gccattatgt aaagtagttg  57720
aagatggggg atagcctatg ggtcttcaga aagcctctgg gtttctagag atctttctgg  57780
aagaggttag gaggatgagt caagtttaga atggaagagg atagatgaag cttgcatttg  57840
gtagtaaaaa ccaaggatga atgtgtgagg catgattatt tgtcacaagt ttccaggtga  57900
cactctggca ctcagtcctt gttgaattaa gcaagctttc ttactgtttt acttggctgt  57960
gttaaagtag agtaacagga aattagactt cccataatgt ctcaatagag ctgttttaag  58020
```

```
tttctagcca taattggtat gggaatatag ctctaaacct tcaaggctgc taccatttct  58080
cacattccta tatctagaaa ctgtagccag gcagcacttt cagtgaggtg agtgggtcca  58140
ggtttgttca attacttttg taccaaccta ataccttaat agtatttgtc ctaatttaca  58200
aaaataggta atgaaggatt cttggtttta cctcagagct aactgtccat taatggcaac  58260
atcccacatt tgttgaagca tgattttgtt gtttgtactt tgacatgcat ttgatatttt  58320
aagtaacgcc ttgaatgcat cttaaataat aatttatata cagttaacac tcctgtttgt  58380
ttttaggaat tcttagtgtt gccaatttcc taggatgtag aagagcatag taaaaaaaaa  58440
aattattaat actcttaaac aagtgttttt aacaactgga caccattttg tagttaagcc  58500
tagaaacaga actaatgcaa taacccagat cttttcattt attcgtatgt ttattttacc  58560
tggatttact ttagtttttt gttttgtttg cttgttgttt gagatattgt cttgctctgt  58620
cataagtgat acagctagag tgcagtggtg tgatcagagc tcactacaac tttgaattcc  58680
tgggctcaag tgatcctcat gcctcagcct cctgagtagc tgggactaca ggcatgtgcc  58740
accatgccag gctaaaacag tgtttttgtt tgtttgtttg tttttgtag agacagggtc  58800
tcactatgtt gcccaggctg gtcttgaact cttggcccca aagtaatcct tctgccttgg  58860
cctcacaaag tgctgggact acagacgtga gccaccgtgc ctggccatgg attttgttta  58920
aatttataaa taccgtgttg tagaatctct ttgtatgtat taatttagac accttagttt  58980
tcttaatgat ttcataccag tttctcagta acttcagatt tttttttga gatggaatct  59040
tgctctgtca cccaggctgg agtgcagtgg cgcaatttgg ctcactgcaa cccctgcctc  59100
ccaggatgaa gcaattctcc tgcctcagcc acccgagtag ctgagattac aggcatgtgc  59160
caccatgcct ggctaatttt gtatttttag tagagacaga gtttcaccat attggccagg  59220
ctggtcttga actcctgacc tcgtgatctg cctgcctcgg ccttccagag cgctgggatt  59280
acaggcttga gccaccgcac ccaaccagat cagatttttt atgtttggta tttactcttt  59340
acctctaaca ctaaggctat gtttccagat gtataactat aaatggagca ggggtaaata  59400
caacaagtga tttatggttc agtaaagcaa gttagtttta ataaatgctc agtttactgt  59460
aaatgtcaga aatgccccag gactctgtct attgacaact cttctatttc catcgtcagc  59520
tcttgccctc tgaactgtag actgatttat ccaacagtta agtctggttc tcaaacttaa  59580
cctgtcctaa gtggagctcc tgattttcat catcccaaac ctacgtctct cataatattt  59640
tgccatctca gtcaataaca gctttttttcc cctcctgtgc agccagaagc cttggaagca  59700
tcttttaatt tctctatgtc acatactcaa attattggta aatcttgttg gctacacctt  59760
ccaaataccc ataattcatt ttattttttt taaccattat acttctgttt actctgttta  59820
aaggcatcat cttttggcaa aagaaagaaa ttgtttccca ggagtcttgt gctttacagt  59880
gtattctcta gtagcagccg gaatgatctt tttaaaatct gagttaaacc atgttattta  59940
ctatgcacag aacttttcag aggcttccca tcttaaaagt aaaatctgga gatttacatg  60000
gccctgtgtg aactggcttc ctttcatttc tgtgatctct ctaccgcact tgctcatctc  60060
tgtctaaaat ggctgtatct ttgtcatctt aaggcttgta actattgtct gtgaccctgt  60120
gacccttctc tgtgataatc catgtggctt ccttcctcac ttgattcaga gagctctctg  60180
ctcaaatgat gcttttcctg accggctgca tcaaagaatg atcatgttct tctgcattcc  60240
ccttaacttg ctgcattttt cttcatggga tttaatgtca tttgacttct tgcatattga  60300
tttctttgtt gttttgcttc tttaccacta gaatggaagc ctaatgacag tgcctggcat  60360
```

```
acagtaggta gtcagtaact acttcctaca tgaaagaatg aagctagtaa atttatgcaa  60420
aatgtttgtt tctgcctttt taattatctt gcagaaatgt aggaagaatt ttttaggatc  60480
agtttatgta tatatataaa ctgataagta tgtacacagc ctgtagaatg tgggtaatac  60540
cacctatcat ctttttgagc atttaccatg tagcaagtga ctgtgctcca taatccacat  60600
gcattatctt gaatttgata ggagagctga gctttttaat cagagtagac catagaaata  60660
tagcttggat gcttttattt cctatatgac ttcttcggtg tacttacaca tctataagca  60720
tttatgggtc aagtaacata ctgaaatatt ttctgaagta aaagaaatct ctttaatcaa  60780
ataagtggtt ctcctatagg ttctcatatc atattcttgg tctccagatt gagaaggtcc  60840
ttttgtatgc ttccagtata ctcgaaacca ggaggtagtc tgacatctat ttcccttcaa  60900
ggtcaaataa ttagagaaag gtttaattga cactgttatc gagacagtat cagaagagaa  60960
attgaaaaat ctctgttgag actctgtaat ttgctaggtt ctgaggatac gacagtaaat  61020
aagttattag gtcatatacc tcagcttccc atttaattaa taggcagtta ttatatataa  61080
tagaataggt actggttggt atgagactac agaggaagaa tacctaatta tcttaaaagt  61140
ggtatataag ctgaaacctt gaggatgctt gggaatagct aagaatcata gtgttctagg  61200
caggaagaat aacacctgga atcagagaag acagcagaac aagtccactg agtagtaaga  61260
agttccgtat tgcagtaatg tagagttagc tgatgggaga aggtgtgaaa aaatgcattt  61320
ggatatagaa agccaggagc acgctaaggc cctttgcttt cttctgacag acacaggagc  61380
ccatgaaagg catcacgtgt ggaaggaagt gacacgagtc atagtctgcc ctgcttttct  61440
accacctgaa gcatcatata aacctatatc ttctgtttca aatgtaagga aacatacttc  61500
tagttcacag tagggatagt tgaatggatg aactgtttct ggctgaatct tctcaaagta  61560
gaatgagcaa aacatggcta tattatgaga ttatctaagg aaagattttt ataatcatgt  61620
gaattttgaa tttctttata tcttaattat tccaagagat ttttgggaac attaatgaga  61680
atagtttacc tttagtacat agaacttctt gtcagctata aatgaggatc aaacccaaaa  61740
gagattaaca aaaataaaag ggatgctatt tccccaaatt agcagaactt tttgattcac  61800
cgagttcttt gttttttaac tgctgtctgc ctcttaacat aattgagtat tcagtgatat  61860
aatataaata aatcacttac taaatgctga tgaacgcttg tttttactaa catctcagct  61920
tgtagcatat cttgttgccc ataccagaaa ccctacccat tacctctggc tcttccagct  61980
tatttacctc ttacaaacta cttattttaa atatttcctg ggtcaatttc atcttttttt  62040
ttcttcctac tgctacatta tttgtccgga ctattacagt agtcattacc taactggatt  62100
gcttgcctcc agttttgccc actttggttt cagttattga aaaggcaaat tttgtcagtc  62160
acttaacctg cttaaaaccc ttcagtgact ccttgtgttt tagttcttat ctaatggttt  62220
atgaatgtag tgggttacga atcttccgga agagtgcatt tgcactcctg aagtgtgcat  62280
gtatttttat gaggagaaga tctttagctt ttattagatt actcctcttt tggctaaaaa  62340
aagaattact tatcatggct attgaggtct tccatgatct ggcttttccc tgcctctcca  62400
ttttcatatt tttgaaactt ttcttgaact ttaggctctt gaagtgcttg gaattgtctt  62460
ataatatcat gttttcaggc ccctgtgctt ttactcattt tcctctatct gaaacattct  62520
tcccctgtct gaaacattct tcccacccat agtgtcatca gctcctagtc atcttttgtg  62580
attcacctct cctaagttgc ctctcttttt attgctattc ctctgtagtc atctctgtga  62640
tattgaaatc gtggctttct ctttctttag acatcataat tccttgaaga gccctttttta  62700
tgtagcctga caagcagaat ttatactgaa gtagacattt ggaagtcatt tagttattgc  62760
```

```
tcaatccttg aaagatgaaa ctgtccaaag ggaaatttaa aagggaaagt atctaatagc  62820
tgatccctgg agaatacaaa tgtctctaga tttggaaggg aagtctctga aaaacagcca  62880
gagagaaggg aggaaaccaa gaaatagtgt cctagaccca aaagtcaata atttccaaaa  62940
ggtctatatt tcttaggaag gccaagtaaa ataagtagtg aaaagtgatg acctgactag  63000
agcagattct tcatttccag ttacagaagc taggttatag gtacagtaag ctctggacat  63060
gttcttttcc cacatggaac gttattcgtg ttctccactg ctgctttgaa ctattccttt  63120
tactctctca gcataaaaat ccctgctcct ttgaagctta tgccttctgg ttttgtcttc  63180
ctctgtctgc cttcagtgag ctatcagttt cttctcggtt tttgaggact gctacctgaa  63240
cttattcttc ttcactcttt cccaaatctg ctgccatctt tatttatatg attaacccct  63300
cagtccctag caagtcaaat tcccatccgt ttttatctac agtaatgttc acctctgcat  63360
cactgctgct tcccatgtct acaggcatgc caactcaaaa ctgttttacc ccaaaagctt  63420
cagtgaaaac accttacctc aggttgccgt ctttgaatgc ttttctacta tcttaaactt  63480
gttttctttc attgcgcctt ttcttccttc tcttagagac ttgtcctatg gctcttctac  63540
tgtcttccag ctacaattcc ctcttgttcc tgacatgtac tgctcagagc caggagatgg  63600
ataagtagta gtatttcaca tgcacttttt tctctgggga gcagtagtca tacaataatt  63660
gattaagata aaacaggttt ttatcagttt atataagagg taaagaaaac aatggggtag  63720
agttttaaaa attgtcaaaa acaacacatt ttaccatatt aatgatttga agtgtacggt  63780
acaattgtgg taactgtgca cattgttgtg cagcagatct ctagaacttt ttcatcttgt  63840
aaaacagaaa ctctacattc attgaacaac tcttcttttc ccccttcttc ctattccttg  63900
gcaaatgcca ttctactttt tgcctctaaa atttgactgt tttggctact tcatgtcagt  63960
ggaatcatta agtatttgtc ttttgttgac tggcctattt cacatagcaa tgtcctcaag  64020
gttcatttgt gttgtagcat attacagaat ttctttcttt tcttttaggc tgaataacat  64080
tttgttatat atgtatacca cattttcttt aaccatttgt tgatggatgt ttaggttcct  64140
tccacttctt gaatattgta atgttgaaat aaacatgggt atacaaatat ttttttgaga  64200
acctgttttt aatatatttg gaagtatacc caggtgtagg attactggat catatgtatt  64260
ctattttttt ttagattttt ttttttttta caggagttct aggttcacag aattgagagg  64320
aaggtacaga gatttcccct gtacctcctt ccacacacat gtatggattc tctcatagcc  64380
agtgtgcatc tcccaccaga gtggtacatg tctttctgat gaacctatat tgatacatca  64440
taattaccca aagtccgtag tttatattag ggatcattct tagtgctgta cgttctgtgg  64500
ctttgaacaa agtacaatga catgtatcta ccattatatc atacagaatg ttttcactgc  64560
cccaaaatcc tctgtgttct gcctatttat ctttccttcc ctcccactcc ttggcaatca  64620
ccgatccttt tactgtgtct ctaactttgc cttttccagc atattatata cttgtaatca  64680
tacagtatat agccctttca gcttgactat ttttacttac taatatgcat taaagtttct  64740
tccatgtctt ttcataggtt gttagtacct ctctttttcc attttctgga catatcacag  64800
tttgtgaatg aatattcacc taatgaagga cattgtggtt gcttccacat tttgctaatt  64860
atgaataaaa ctgctgtaga tatcggtgtg caggtttttg tgtggactta ggttttcagc  64920
gactttctgt aaatactagg gagtgcaatt gctggatctt atggtaaaag tgtttagttt  64980
tgtaggaaac atccaaactg tcttctaata tgacgctatc cttttacatt tttcaccagc  65040
aatgagtgag tgtttctttt gctctacatc ttcaccagta tttggtgtta tcagtgttct  65100
```

```
gaattttgtc cattctgata ggtgtgtaga ggtatcttat aattttaatt tgtgtttctc  65160
tgatgccata tgatgtgtgg gacatctttt catatgctga attgccatct gtatatcttt  65220
ggtgaggtgt ctgttaaggt tgttggccaa ttttttaatt gggttgtttg ttttcttgtg  65280
gaattttaag agttccttac actgtctctg tctgtcttgt ctgtctgtct gtctgtctgt  65340
tgagacagag cctcgctctg tcacccaggt tgcagtacag tggcacagtc ttggctccct  65400
gcaacctctg ccacctgggt tcaagtgatt ctcctgcgtc agcctcccga gtagctggga  65460
ttatacccgt gcaccaccac acctggctaa tttttgtatt tttagtagac acggggtttc  65520
actatgttag ccaggctggt ctcgacctcc tgacctcagg tgatccaccc accttggcct  65580
cccaaagtgc tgggatgtga gccaccacac ccagcctcct tacacatttt agttaatagt  65640
tctttatcag atgtgtctta tgtaaatatt tcctccctat ctgtggcttg tcttttcata  65700
ctcttgacat tgtcttttgc aaaagacaac aatttttaag aaacaagtag acaattttaa  65760
tgaagtctgg cttatcagtt cttttcttca tggttggtac ctttggtgcc gtatctaaaa  65820
gtcatcacca aacccaagat ctagattttt tcttatgtta tcctctagga gttttatagt  65880
tttgagtttt acatttaatt ctctggttta ttttgagttt atttttgtga agggtgtaag  65940
acctgtgtct agactctttt ttttttgca tgtggatgtt cagttattac cactgtttat  66000
tgaaaaagac tattttcttc attgtattgc ctttgcctct ttgtcaaata ctgccattgc  66060
tcctttgact atgtgggtcc atttctgggc tctctattct gtttcgttgg tctgttttgt  66120
cagttctttt gtcagtacca caccatcttg actactgtag ctttacagta aatcttgaaa  66180
tcagtagtgt ccatctgact ttttctgtca atattgagtt gtctctcacg ggtcatggaa  66240
tagctcttca ttatttagtt atttgatttc tttcatcaga gttctaaaac atttttcctc  66300
atatatcttg tactaatttt gttagatctg tacttaaata tttcattttg ggacacgcta  66360
atgtaaaatg gtattgtgtt tttaatttca aattcaactt atgcattgct ggtttacagg  66420
aaagctatta actttttat atgaaccttg tatcctgcag ctttgctata atcacttatt  66480
agttctagga ggtttttgtt gtttttcttt ttcttttttt caattcctgt ctatgttcta  66540
cacatatagt catttcatct gcaaacaaag gcagttgtat ttttttgttc cccgttagta  66600
taccctttat ttcctttctt tgtcttagct aggacttcca gtatggagtg gtgaggtggg  66660
gatattcttt tcttgttcct gatcttagta agaaagtttc tagtttctca tcattaagga  66720
tggtgttagc tgtatgtttt ttgtaaacgt tctttatcaa gttgaaggtg ttccctctat  66780
tcctagttta ctagtttcta tcatgagtgg gtgttaaatt ttgtcacata cttctctcca  66840
tctatggtat ggtcatgtga tttttcttct ttagtctgtt gatatggtga attgcattaa  66900
ttgattttcc aatattgaac cagtcttgca tacctgggat aaatcctact ttgtgctggt  66960
gtatacttct ttttatacat tgtagtaaaa tttagtttgc taatactttg ctaatacaaa  67020
gatttttgca tctttgttca tgacaaatat gggtctgtag ttttcttttc tgataatgtc  67080
tttgtctggt ttgggtatta gagtaatgct gacttcatac aatgagatag gagcatctcc  67140
tttgcttctg tcttctgaag gagattgtag agaactggtg tggtttcttc cttaaatgtt  67200
tagtagaatt catcagagaa tccatctggg cctgatgcct tctcttttag aacattatta  67260
attatggatt taatttcttt aatatatgct ttttaatcaa gattatttct tcttagagtt  67320
ctaatagatt gtgtctttta aggaattgat tcatttcatc taggttacca aattcgtggc  67380
cgtaaagttg ttcataatat cccttgatta tccttttaat gtccatgaga tctgtaatga  67440
tgtccactct tttcattctg atattagtta ttttgtcctt tgtctctttt tcttagcctg  67500
```

```
gctagaggct tattgatttt attgatcttt tcagagaact agttgatttc tttgattttt  67560
ctctattgat atcttgtttt caatttcatt gatttctgct ctaattttta ttacttctat  67620
ttggatttaa tttgcttttt ctagtttcat aagttggtag ctcagataat tgatttttag  67680
atcattcttt tcttttcttt ttttttgag atggagtctc gctttgtcgc ccaggctgga  67740
gtgcagtggc tcgatctcgg ctcaccgcaa gctccgcctc ccgggttcac gccattctct  67800
tgcctcagcc tcccaagtag ctgggactac aggcgcctgc caccacgtgt ggctaatttt  67860
tttgtatttt tagtagagac ggggtttcac tgtgttagcc aggatggtct tgatctcctg  67920
accatgtgat ccacccgcct cagcctccca aagtgctggg attacaggcg tgagccacag  67980
cgcccggcct agataattct tttctaataa atgcatcagt gttgtatgtt tctttctaag  68040
cgctgctttc actgtatccc acaaatttgg ataagttgtg ttttcatgat attttcaatt  68100
tataatggta ttgggacaca acccaataag taagtttagg agcatttgta tgcataagca  68160
caattgttga cattattttg aacaaattct tatttgttag atcaattaag tataagaaaa  68220
ataaaaggtt ttattttact ttcagtgttt ccttcttttg atgctctata tatgtagatt  68280
tcagtttctg aacttcccaa cacttattgc aaggcaggtg tactgacaac aaatttcctt  68340
aatttttgtc tgagaaagtg tttcttttta acttttgaat aataatctca caaggtagag  68400
tgctaggttt atggtttttt tttctctcaa cactatgaat atttcactct ttttcttgtt  68460
ggaagtcaca tgtatttttt cttttttttc tttttttcct ctacaggtaa ggtgattttt  68520
tccctctggc ttacttcgga tttttttctt atccttgaat ttctgtaatt acaacgtttt  68580
atgcccagat gtagtttttt ggcatatttt caagctcaga gattcttcat ccatgcccag  68640
cctactaata agcccatcaa aggcattctt catttctctt acagtgttct gtttttttgtt  68700
tttgtttgtg ttttatctct agcacttcct tttggttctt aggattttca tctctacttt  68760
tttaacatgt tgtttactca gttcgttagg gcccttagca tattaatcat agttgtttta  68820
gattccaagt ttgataattc caaatccctg ctgtatctgg tcctggtgct tgttttttac  68880
cttttattat gccctgtaat ttttttcttg atagcttgga catgatgtac taggtaaaag  68940
gaactgttgt aaatgagcat ttagtaatgt ggttgtaagg tgtagggaga ggagaagagt  69000
tctgtagtct tatgattagg tcagtctttt tagtgagctt atgcctctgg actgtgaact  69060
tcacaagtgt ttctcaatcc cacccctccc tcattccctt agttagaaca agatagctat  69120
aatggcctga agttgggtta tttctcttcc cccacatcat tttggctttg ctacaacccc  69180
agcaggttag gctctggtta actagtttct cctgaggaca aaccttgtta agactggaat  69240
agtctagtgt acttgaaaat catttctctt tgcctcccct gctgagggtt gaggattttt  69300
ctcctatatt tactgtgaga agctggtcaa ttgcctggat gtaaaactta gaaaattgta  69360
gggctccccc tataattggg taactctgga gtttttagct ttcagagttg tccacactga  69420
gccttcatca atttgtctat tacacttcag gatttcctac cccgtggagg tttctgcttg  69480
tgtttttcat ctcagataaa tggtgatgct atgtgttcac ctgttctctg ctctcacagg  69540
cagtcatttg ccctgtgacc tcacttatcc tatctcagat ttgtttattt ttaagtttgt  69600
catttttttac ttgttgttag gatggagtgg tgacttccaa gctcttcata tgtggaactg  69660
gaggtaattc tatttcaaat tttttgaggg accttcatgt tgttttccac agtgcctggc  69720
accattttac attttcacca gtggtgcata agggttccag tttctccata tcttcaccaa  69780
tacttatttt ctgttttttt aatggtggcc atcctaatgg tttcagatga tgtatcattg  69840
```

```
cagttttaat tgacatttct ccctactgat cagtgatggt gagaatcttt tcatgggctt  69900
attgcccatt tgtatatatt ctttggaaaa atgactattc aagtcctttg tccacttttt  69960
aactagattt tttgttgttg aattgtagga gttatttata tattctggat attaaccaaa  70020
taacagatac atggtataga aatattttct cctgttttgt aggttgccat tttactccat  70080
ttactgtttg ctttgtagaa atttttgagt ttatgtatcc ccagtttgtc tatttttgct  70140
ttggttgctt gtgcttttgg tgatctattc aagaaatcat tgccaagtcc aatgtcatga  70200
agctttttct ccatgtttc ttgtagtagt tttataattc gatgttttaa gtttaggtct  70260
gtaatccagc ttgagttcat ctttgtatat ggtgtgagat aaggctccaa cttcattctt  70320
ttgcatgtta gattccagat ttcccaatac agtttgttga agaacctctt ttccctattt  70380
ctgtgttctc tcttctgctc acttggtctg tatatctgtc tttatgccag caccatagtg  70440
ttttgattac tatagctttg caatatcttt agaaatcagg gaatgtgagg cctctagctt  70500
tgtttttgt ccagattgtt acggctattc agggtccttc aagattctgt attaatttta  70560
agattttttt tttctgtttc tgtagaaaat gccattggga ttttgatagg gattgctttg  70620
aatttgcaga ttgctttggg tagtattgcc atcttaacag tactaaatct tccaattcat  70680
aaacttggat gtctttccat ttatttgtat tgtctttaat ttctttcagc attgttgtat  70740
aattttcttt ttcttttttt ttttttttg agacagagtc tcactctgtc accaggctgg  70800
agtagagtgg cgtgatcttg gctcactgca cctctgcctc ccaaattcaa gtgacaactc  70860
ctgcctcagc ctcccgagtg gctgggatta caggcgcgcg ccaccaagcc cagctaattt  70920
attttgtatt tttagtagag acagggtttc accatgttgg ccaggatggt ctcaatctct  70980
tgacctcgtg atcagcccac cttggcctcc caaactgctg ggttacagg cgtgagccac  71040
cacgtccggc ctatgttgtt taattttcaa tgtacatgtc tttcatttgc ttggtgaaaa  71100
tattccctaa gtatttttta ctctttgatt tcattttaaa tgggtttaaa aaattaattt  71160
ccttttttgga ttcttcattt ttagtattta gaaatgcaac tcttttctta atattggttt  71220
ttatatcctg taactttact gaattccttt attctaacgg tttttttttct ttttggtagg  71280
ctagagtttt caacataaaa gatcatgtca tttgctaaca gaagtaattt tacttcttac  71340
ttttctcatt taataccttt catttctttt tcttgcccag ttgctaactc tggcaggatg  71400
tctaacagta tgttgaatag aagtggtgaa tgtgtgcatt cttgttccat ttgtgatctt  71460
agagggaaaa ctttcagttt ttcatcattg aataacatta gctgtggtct ttctatatat  71520
ggccttcatt atgttgaagt aatttccata tctttctagc gaattgagcg tttttgtttt  71580
tgtttttttg agacagaatc ttgctcttgt cacccaggct ggagtgcaat gatgctatct  71640
cacctcactg ccagctccgc ctcccgggtt ctcaagtgat tgtcctgcct cagcctcccg  71700
agtagctgga attacaggcg cccaccacca tgcccgatta gtttttgtat ttttagtaga  71760
gacagggttt cactgtgttg gccaggctgg tctcacactc ctgacctcag gtgatccacc  71820
caccttgccc ttctaaagtg ctgggattac aggcatgagc caccctgtct ggcctttttt  71880
taaatcctaa aagggtgttg atttttgtca aatgcttctt ctgagtcagt tgagattatt  71940
ggtttttgtc ctaagaatgc agtgtattaa agtgattttt ttgtatgttg aaccatcctt  72000
ggattttatg aataaattcc agttgagaat ttatgaaata taatcttttt aatgcattgt  72060
tgaattctgt ttcttggtat tttgttgatt ttttttgcat cagtatttat tagggattct  72120
tttttcttgt aaatttgtct gatttcgata tctaagtaat gcttacctca taaaatgatt  72180
ttgaaagtgt tctgtcctct agttttttca aagagtttga gaagggttgt tagtttttaa  72240
```

```
atgtttggta gagttttcag tgaagccctg gcgttgttgg acagttactg attcaatctc  72300
taatagttat aggtccattc agaagttgta tgtatttgtg gctcagtctt ggtgggtttg  72360
atgtgtctat ccgttctcaa aggttatcaa atttttttgg gtcatagttg ttcatattag  72420
tcttttaagg tcctatttat ttctgtggca gcagttgttg tatcgccttt ctaatttcca  72480
gttgttgctg tttgtgtcta ttctcttcat ttcttaatct aagaatttgc cagttttgtt  72540
gatcttttca ataaaacagc tactcctaat tttgttgatt ttttttctat tgcaaaaatt  72600
ttctattttt ctctatttta ttttagctgt aatttatttt tatttttttt attttttggt  72660
aagtttgagt ctcatttgtt cttcatttcc taattccata agatgtaaag ttaatttgtt  72720
gatttaaggt ttttcttcct ttctaactgt gaaatatgac actgtaaaac agattttcat  72780
tttacagatg aattatgtaa atatttagtt ctacaatttt acttttttttt ttatcatata  72840
tcacgcattc tggatattga gactataaaa atgaaaaaaa cagttctttt cttttctttt  72900
tttttttga gacagagtct cgctcttttg cccaggccac agtgcagtgg ctctgtctcg  72960
gctcactgca agctccgcct cccgggttca tgccattctt ctgcatcagc ctcccaagta  73020
gctgggacta taggcgccca ccacggcgcc cagctaattt tttttgtat ttttagtagg  73080
gacgtagttt caccatgtta gccaggatgg tctcgatctc ctgacctcat gatccgcctg  73140
cctcggcctc ccaaagtgct gggattagag gcgtggcgtg agccactgca cccggccata  73200
aaacagtaat tgaaggttaa cctatatttc aaacaactga aaatactgat ttgttcatat  73260
ttatttttc atgaaaatcg tcttgttcta tatttaatag gtttttgttc ggttcatggt  73320
actaatgagt tcacaattgt aggtttagtc ttgaaataat ctaaattcac ttcatcccat  73380
tgtaacagac cctacatcat actgaatata gttgtgtcac agatgtctct tacagtctat  73440
ttctacaagg cctagaacta tttaggatac cgttgctcac tcttacaaat tttaacatta  73500
aaaataactt tgagatggaa tggagttttg caacgtctca gaacaaagag actccactta  73560
cgagaaatta ctaagcagtg gttcctagct ttatagacta attatataag ccttcagttg  73620
tttctatttt atatctgttt tttagattcc tcacatgttc attctgcttt accttctgta  73680
taatataaag gtcactctac ttacagtcac attttccttt taatctttcc gtttttattt  73740
tttattcttt gctttgttca ccattagttt ttatattgca tctcacagtt catgtttctt  73800
ttttgtcatt tctgattcta attgtaattc taatcttact tgtttggcgt tcactgtcac  73860
atcttcactt tctggcagct gtttctatgg cttcatcttc ttagtgcttg tattcattgc  73920
ttatattcca gttgtcttgt aaattcattt ttttagtgaa ctaagccaga cacggaaaga  73980
cagatatcac atgttctcac tgatatgtgg gaactaaaaa aacattgaac acaaatttta  74040
cagctgacac acatatgcct gccacctaga ttctgccatt aatacttaca ttgctttatc  74100
gtataaccat ccttgtatcc atcaatccat cttaattttt atgcctttca aagttaattg  74160
ctaacattag tacacatccc tctaggtgaa accattttta aactgattgc tgtcaagttg  74220
tctagagtaa actctgatct tccaagtatg acttattcca taggacttct gtttgtagca  74280
ctgtcccatt aattcaatca tagaaataaa taattggaaa gtattgtctg ttttaaatgg  74340
ataagtattt tcatgtgtct gactttagag gacttttact agaaggtctc acttgacctt  74400
cattgctgac taaataagaa aagtttgttt tattttaaaa atcaacacat tataacatac  74460
tttgtttttt gagtaataag aaaagtcaat ggaatgtgaa gaaattatag caagtaagct  74520
gttgttcctc ttctaggaat tttgattatg aacagctgat aaggtattac taagggatct  74580
```

```
catcagggaa attcctttct ttccttcttt ttcttttgca tcctctccct ttcctcactt  74640
tcttttcccc tttttccctt ttcccctctc ctcttctttt ctttaatagt acttggggaa  74700
aggtatacct tttattttac ggatttgctc agggtaaaga gagagttaag aggccaaatg  74760
attagatggc agggtcactg gagggcagag ataaataata gatcctaaac taagggttgg  74820
caaacatttt ctgtaaaggg caggtggtat ttgttttagg ttttgcaggc ctaaagtact  74880
caactctgcc attgtagtat gaaaaacagc cataaactat atagtatatt gtattagtcc  74940
tttttcacgc tgctgataaa gacgtacctg agactgggaa aaaaaaaaga agtttaattg  75000
gacttacact tccacatggc tgggaaggct tcagaatcat ggcgaaaggt gaaagacact  75060
tcttgcatgg cagtgacaag agaaaatgag aaggatgcaa aagcggaaac ccctgataaa  75120
accatcagat ctcgtgagac ttactaccac aagaacagca tgtgggaaac tgccccccatg  75180
attcagatta tctcccaggg ggtcactcct acaacacatg agaattatgg gagtacaatt  75240
caagatgaga tttgggtggg gacacagagc caaagcatta tcatatatag tatatttata  75300
aatcaatgaa cttgggtatg ttccagtaca cttgatggat actggaactt gaatttctta  75360
taattttcac gttacaaact attattattt ttcaaacttt ttccagccat ttaaaaatgt  75420
aaaatattct aagcttgaga gacataaaca ggtggtggac tcgatttgac ttacgagcta  75480
tgatttggtg acccatatgg tacaaggatt tcccttgcgc aggaactata ccaaaaagtc  75540
gttattagtg tatacttttc caacgtagag gccctttttat gtgctctaaa ttttgtatgc  75600
cttttacata tcctaaatta gatagtgatg cagatgaggt cagataaatt aaggtgtcat  75660
tggagtgagg aaaaaagaag aatgcttaat atagttgatt ccaccattaa cttggaggtt  75720
ctggcatggc ttcctttagt cctgtctcat cagtgtagct gctatttgtt aaacttggca  75780
cagaaaggca gatcaaatat agagggctac tttcagatcc tcctcttaat agttattaaa  75840
agctcaagtt tagtagctga gttcaaatct cttattagat gtatgactta tgtaatttct  75900
ctgagcatca gcagaatgaa ggtttatagt gctaactcat acacttgtga gggtgatagt  75960
aacaattaca acaataatag tagtagctaa cactttcata gtgcttagta tgtgccaggc  76020
aatgttctaa gcactttata tatattaaca catttaattt tctcacaatt ggtaatgtga  76080
agaagaataa tactctcacc atgataatgc tcgtagatac taccatttaa attacgagga  76140
aacttacgtc cagaaagatc aagtaattca ttcagggtca catagttaat taagaggtag  76200
agccattatg tgaacttggg catctggcct cagaatgcga gctcttaact gttaaggttt  76260
attcccctct aaagtgggaa tgtctataaa atgcatagca cataggtcct caacaaatta  76320
gagagaaatt aactttgcag aatatagtgg ttccatttcc tcaagaaact tggtctgcct  76380
ttgtggtacc agatagatgc ataaatgtga ggttcacgtt atgattcttc agattttttt  76440
cccagttgca cattagttat gagatttttt tccatagaat tcttcagtat tactcatgtt  76500
aaaaaataat tattttgaaa tgaatcacct tctgcaaaac aatatagtca aaatgactta  76560
gactctgaag ctgaaagact cctggactcc tattcttgtc ttggttctgt actttctttg  76620
agatcttggt ttcgtgattt gactccagtt ctatttctct ctttggctgt ggactgaaga  76680
taatcctcaa tgtcatggta ttcaaatgag ataacccatg tcaaagtgcc ccgcagtgtg  76740
tgtaataagt tatcaggcat ccagcaaata ctagtttctt gctcacctcc ctattacata  76800
aaataacttt aaaattagaa ctgaagggac tcataaagct gggaaaactg aggcccagac  76860
aattgtttcc ctaggatcct acagctgctt agggacagaa ggatgacact taatgcagat  76920
cttctgattt ttcagtctcg ttctgtttgt gctgatcact ctcctcctat gtagtatata  76980
```

```
aagaagtact atgtatctga caagttttgg ggaggttatt ttagtataaa agctcacatt  77040
aaaaatatct attttggtat tttgactttt gtaatttttt taaaaatcag agacaattta  77100
gtaaatctcg gggccattca aatcatgtat atgaagtttt ataactgcta ttgttttccc  77160
cttatagtta ttaattttta atatgcaagt agcatcctta ctatggaaag aataaataag  77220
aaatcaaaag atggaagaag ttttaaaact cacttaatca catcatccag agaaaatgct  77280
attaatgctt tgaaataaca atgggttcat cctacacctg ctacttttta actgactttt  77340
gtcagttagt gatatatcag gaagactagg cagttctttg tcgaattcaa atcttgatag  77400
tttttatttt attgtgtgac ctattatcag ttcatttaag taatctttta ttagacatgt  77460
ttttttcaga tatagaaaca atgcattttt gtaaaattgt caaattattt tccacaagta  77520
ggatctcatt cacacggtat tcgtgttttt aagactttcg atacatgttc actgttttcc  77580
tccagaaagg aaatacctac ttacattttc accagggaag tcactgtagt ttgggagaac  77640
atgacattat ctccctttct ttactgaagg gtagcaatat atattttaaa ttttctagat  77700
tctgcatttc cattttattt ttacatgttt tcactttcat attttgcata gtgctaaatc  77760
tgtgataaca gtttttaatt ttcaggtggg gtttatagct tcatagatag caaaatgtct  77820
ttaagtcatg tttatgcaat ttttacatgt gctttgtggg ttttcttttt tctctgtttg  77880
catgcagtga gtggtaaatt tgcatggaac atttgaaaaa taagcaccag aatgaattga  77940
atgtgtgtga attatcactt tttgtcacct acctggacag agagtgaaag ttcttctgtt  78000
gagacaaaat tggatctcgt gtgtttcttc acttacttgc tgccttgtta attgttgagt  78060
ttctcatgat tagcaagatg taaactctgg cattggtcat ctagtcctac atgttagata  78120
attctgtgaa tgttttgaaa atcagctgaa ctatttttct tataattttg attctttgta  78180
gttgttattt ccatgcttgt gaatttggga ccaaaaggaa tggctatgac ttatgtttct  78240
ttggatccag tagtttattc tactgaaatt atggtaattt tatcagttag tagaagcata  78300
gactctttag tgttgaatat aatgtcatct aacttcttac atggtcacat aattcctccc  78360
tcagttttgg tagctctcct gaaacagcca taataggaca ttaatctgtg tactttaagt  78420
tgacagagta aaaggaatat aagatttcac gtgatggaac ttaaaatatt ccatcttgtg  78480
acgtggaact aatgaggagg tttagtgaca agttttagat ttaagattct acactttgga  78540
gcctcttttt ctttttcttt ttggtttttg tttgtttgtt tgtttttgag acaaagtcta  78600
gctctgttgc ccaggctgga gtgcagtggt gcaatttcag cttatggcag ccttgactct  78660
caggctcaag tgatcctcag cctcccaagt agctgggact acaggtgcat gccaccacac  78720
ttggctaatt ttttttaaaa aagtttgtag agagtagcct cactatgttg cccaggctgg  78780
tgttgacctc ctgggctcaa gtagtcggcc tgcctcagcc tcccacagtt atgggattga  78840
ttacagtcat gatctgcctc actcaggctg cagccgcttt ctttcagtgt aacactatct  78900
ttggatattc cacttacaaa tttattttta agtctcccat gttgttgata attgggaaaa  78960
atagttttta ttccagatag atattctgtg ttaactataa gtcaaatgtt tacaagctgt  79020
taaaaatgaa atactgatta tgtaaaagaa aaccggattg atgctttaaa tagactcatt  79080
ttcctaatgc taatttttaa aatgatagaa tcctacaact cttagctgta aaccttgtga  79140
tttttcagct gttgtactaa acaacttaag cacatatacc atcagacaag ccccccctccc  79200
ccctttttaaa ccaaaggaat gtatactctg ttaatacagt cagtaagcat tgacattctt  79260
tatcataata tcctagaaaa tatttattaa ctatttcact agtcaggagt tgtggtaaat  79320
```

```
agtgcatctc cattttctac ttctcatctt catacacagg ttaatcactt cagtgcttga  79380
ctaacttttg ccttgatgat atgttgagct ttgtacttga gagctgtact aatcactgtg  79440
cttattgttt gaatgtttgg tacaggaagc gagcagctgc aaagcatcta atagaacgct  79500
actaccacca gttaactgag ggctgtggaa atgaagcctg cacgaatgag ttttgtgctt  79560
cctgtccaac ttttcttcgt atggataata atgcagcagc tattaaagcc ctcgagcttt  79620
ataagattaa tgcaaaactc tgtgatcctc atccctccaa gaaaggagca agctcagctt  79680
accttgagaa ctcgaaaggt gcccccaaca actcctgctc tgagataaaa atgaacaaga  79740
aaggcgctag aattgatttt aaaggtaaga tgttttattt tcaattgaga attgttgcct  79800
gaaaaccatg tgggagattt aaatgtatta gtttttattt gtttttcttt ctgtgacata  79860
aagacatttt gatatcgtag aaccaatttt ttattgtggt aacggacagg aataataact  79920
acattttaca ggtctaatca ttgctaatta gaagcagatc atatgccaaa agttcatttg  79980
ttaatagatt gatttgaact ttttaaaatt cttaggaaaa atgtattaag tggtagtgaa  80040
tctccaaaac taggccacaa catctattta agttatagaa taactggact aagtatctgg  80100
catgagttct ggaacctcag gatgatgtga tgaaagaagc agaaagagga aacagtgggt  80160
tttttccatt tttgaaggca agacaaaatt ttgtgatagt tatgtgagaa ttctacgttt  80220
ccttcagata tatgcttctc actctccttc cggacatttg gtacagtcat gctgccaagg  80280
atcatgacct accaatgaca gtcttcactc aggtcttttg ttttctaaat ggtcctacgt  80340
ccaaaattca gaattcgatt accttgtcgc taatactaaa actccaagtt attttcttca  80400
gtgaaggtaa ttagtaacaa agtaatcaaa tttttgaatg actaccaggg cttagcgccc  80460
ctccactctc accccctacac acacccagag gcaattgtat tttaagagag aaagcttttt  80520
ttttatgaca tacaagtcag agaattttag aggcatttgc ctctaaaact ttcactaaca  80580
tcatttgaat caagtttgaa agaattagtg aagtggcatt gtgttataac ctctactctg  80640
tttccacaat aaaattattt tcgtcacttt acacaacttt gttgcttcag agtgtataat  80700
tctgtttcat gaattagttc acacactatg ggaaaatagg taaatgttgt ctgtatatat  80760
agtgtgtcag tataatgtgg aagctgcatt gactttattg tacacagttc tccagtaagt  80820
gtgcaccaga gagtaccagt aactgaatgt agagtgctgg cacagtggaa tgcagccagc  80880
tgcgggggat gtggtacatg aggaatgtgc tcatctgctc ttttggccac gtgctccatc  80940
ttagaggtgc ttattgtgtg gctttatcca gtctttatgc cccctcctct ttttgctcaa  81000
gtctgcatta tagcagttgt gacctttcct tatccctgtt ttctaatatg ctactgttac  81060
tgttccctgt tcgttactgg ttttttgtt tttgtttttg cattgttcta tagttactat  81120
tgtatattgg aaattagaga tgctttctgt acactagtac tcttattttg attattaatt  81180
atgtttgtta acactaatta caaagttgca taagtattaa gtagtctgca ccaaactgtt  81240
tttgcgtagg aggtttttaa gtgcaaaatt taaaagattg agtattttca gggacacatt  81300
tatcacaaga aatcttataa aaatgtcttt ctcagtagaa cacctgtatc aataaaccaa  81360
actttttgaa tgttcatatc taattacagt gttttttgac taatttttat ctatatacct  81420
gaaaaattca gtttaacata ttaaacacta caggccaggc acagtggctc acgcctgtaa  81480
tcccagcact ttgggaggct gaggcgggcg aatcacgacg tcaagagatc gagaccaacc  81540
tggccaacgt ggtgaaaccc cctctctact aaaaatacaa aaaaattagc cagttgtggt  81600
ggcgtgcatc tgtagtccca gctacttggg aggctgaggt aggagaatcg tttgaacccg  81660
ggaggcagaa gttgcagtga gccgaaatgg tgccactgca ttccaacctg gcaacagagt  81720
```

```
gagactccat gtcaaaaaac aacaacaaaa aacactcctt ggaaaaagta taggtacatt  81780
ctatatagga ttagtagact gtcagaatca cttgaagatg ttccgaaagc atgacatatc  81840
aacaaaggac atgtgagtct agaatggtga tccctaggac aggccatatt actgcatgca  81900
aagcaagtct ttgttaacct tatgacttgc tcaggaagca aagtgtttca tgtcctaata  81960
ggatagtagt attttctgtt atgttacatt ttaggaaatt aggagttttg cattgtcttg  82020
taagaaggta ttttaaaaat tttcaatgaa aataatgaga aataggtttc cagtggtttt  82080
atgcttttgg ggaagaggtt actgatgttt agcaaaagat gcttatatat tcttaataga  82140
acaaacctga gaattagttc ttaaagagtt aaggcccata aaagaaactg taagtgttgg  82200
tactcttgta gctgggccac agatcagatc cttagtatga taaaatttgg tatttttgtg  82260
cttcaatttt tggagaccat tcaatgatca cttacatttt atattgtctt tcattgtgaa  82320
acatatatta tagcagaggt gggagtcatt aaaaattcta catgttgtac actacatgta  82380
taagggtata tttggcgcaa tggaggtagg attgtctgtg tgcctctaaa attaacctct  82440
caagtagtta atctgatgat gacaagtatg tcactttatt gataaaaggg agaattaaga  82500
ctattctcag tattatgttg gtcagtacac aaaatatatc atttgttttt acctgtgaaa  82560
tgaaatatct ttcatcctat tagccagaag ggagaaagcc ttggcctgaa aataacactt  82620
atctcaaaaa gttgggaaat gtggtccaac tctgtgccca ggaaaagagg aaatagattt  82680
tgatgactac atagtctctg cactgcttgc cagctcataa gtttacttct ttgcactgtt  82740
tgttttcatt gctcaaaaac tattttctgt cactctatga gatttagtct aacctgattc  82800
ctggctgtgg aaagcagttt ctacttaaga gccgatgaga aatggtatat tcttctcaat  82860
cactcacaga atgactaccc tggaacaaac taggaagacc caaaatgaac cagtttgatt  82920
ttaatacata catagatgct gaaggagcct ttttttaaga ccttgccttc ttagtctttg  82980
gagaacagag tactgaaaca agaaaactca cagattagta gtatttctgt gtgttctaca  83040
gtgaggtttt aagagctgta ttatgattaa tcagtacatg acatattggt tcatatttat  83100
aattaaagct atacattaat agatatcttg attataaaga aagtttaaac tcatgatctt  83160
attaagagtt atacattgtt gaaagaatgt aaaagcatgg gtgaggtcat tggtataggt  83220
aggtagttca ttgaaaaaaa taggtaagca ttaaattttg tttgctgaat ctaagtatta  83280
gatactttaa gagttgtata tcataaatga tattgagcct agaatgtttg gctgttttac  83340
ttttagaact ttttgcaaca gagtaaacat acatattatg aaaataaatg ttctcttttt  83400
tcctctgatt ttctagatgt gacttactta acagaagaga aggtatatga aattcttgaa  83460
ttatgtagag aaagagagga ttattcccct ttaatccgtg ttattggaag agtttttttct  83520
agtgctgagg cattggtaca gagcttccgg aaagttaaac aacacaccaa ggaagaactg  83580
aaatctcttc aagcaaaaga tgaagacaaa gatgaagatg aaaaggaaaa agctgcatgt  83640
tctgctgctg ctatggaaga agactcagaa gcatcttcct caaggatagg tgatagctca  83700
cagggagaca acaatttgca aaaattaggc cctgatgatg tgtctgtgga tattgatgcc  83760
attagaaggg tctacaccag attgctctct aatgaaaaaa ttgaaactgc ctttctcaat  83820
gcacttgtat atttgtcacc taacgtggaa tgtgacttga cgtatcacaa tgtatactct  83880
cgagatccta attatctgaa tttgttcatt atcgtaatgg agaatagaaa tctccacagt  83940
cctgaatatc tggaaatggc tttgccatta ttttgcaaag cgatgagcaa gctacccctt  84000
gcagcccaag gaaaactgat cagactgtgg tctaaataca atgcagacca gattcggaga  84060
```

```
atgatggaga catttcagca acttattact tataaagtca taagcaatga atttaacagt  84120
cgaaatctag tgaatgatga tgatgccatt gttgctgctt cgaagtgctt gaaaatggtt  84180
tactatgcaa atgtagtggg aggggaagtg gacacaaatc acaatgaaga agatgatgaa  84240
gagcccatcc ctgagtccag cgagctgaca cttcaggaac ttttgggaga agaaagaaga  84300
aacaagaaag gtcctcgagt ggacccccctg gaaactgaac ttggtgttaa aaccctggat  84360
tgtcgaaaac cacttatccc ttttgaagag tttattaatg aaccactgaa tgaggttcta  84420
gaaatggata aagattatac ttttttcaaa gtagaaacag agaacaaatt ctcttttatg  84480
acatgtccct ttatattgaa tgctgtcaca aagaatttgg gattatatta tgacaataga  84540
attcgcatgt acagtgaacg aagaatcact gttctctaca gcttagttca aggacagcag  84600
ttgaatccat atttgagact caaagttaga cgtgaccata tcatagatga tgcacttgtc  84660
cgggtaagtt gggctgctag attaaaaacc taataatggg gatatcatga tacagttcag  84720
tgaattcatt ttaaaagtga ctgaaaaaaa tgataccata tagcatagga acacatggac  84780
atttctgatc ttatataagt attatacttt tgttgttcct gtgcaagttt atagatgtgt  84840
tctacaaagt atcggttgta ttatataatg gtcatgctat ctttgaaaaa gaatgggttt  84900
tctaaatctt gaaaactaaa tccaaagttt ctttcattca gaagagaata gagtgttgga  84960
caaagaccag aacaagagaa atgtggagat acccaataat aagtgtggat gtgcagtctt  85020
gaactgggag taatggtaca gtaaaaccat accataaaat tataggtagt gtccaaaaaa  85080
ttccatcgtg taaaattcag agttgcatta ttgtggactt gatgaagtga ccatggcaga  85140
tcagtgcctg ttgccagtaa gagttgagtc ctgctgggcc acttagaata tccctgtgtg  85200
gacggcactg cctggctgtg gtagtttctt cccacttaaa aattcataga gacaactctg  85260
ggtcttggaa cttctggaaa acagcagcta ttccaaaaat ctggggatta gtggtgcctg  85320
taacatcaag tccagggaga ttgagcaggg aaatactgga aactcaggta ctcatcctaa  85380
cttcctggtt ttccagatgg ggttgccatt tgttcctttt ctttcctcca caagataatt  85440
ttagtgtatc tgtttaagaa tataagagtg gccagaagac agaaagcagt cgtcagtcac  85500
atttcaccaa aatttacatt tgtctcaggt gcattatcgc agagctttat tgtatttcta  85560
gtattagcta tccctgtcat tgctgctact tttttatcat cttcaagtaa aatttaatgt  85620
caacaaaaat taaggtagtt aataatacta tagtatacta gtaaagttgt ctgacacaga  85680
caactaggaa atgtgatttt tactttaaaa tgtattttag ttttagaatg tctaaatttt  85740
agttttagaa ttgtctaaat tcgagaattc ataaagctgt agcccggtgg aaaaagttat  85800
ttgacatctc agaaattaaa aattgcagag attttgtgtg tttttttttt ttttgttact  85860
ggtttgtttt ttttttttaa tgtcagatat gtttatagtg ttggagaaag attctgcatt  85920
atttaagcaa ctcaggtggt tttctagcag agacaaaagg gggctttaac tgcctgaagt  85980
cattattatt gcttgctttc tggtaccctt tttatttcac ttacatagtt ttgagacaca  86040
tgaataatta atacacttaa tgactgatca taaggcagcc agcaccttac tttacatagt  86100
ttagcagaat gatagggtat tttataagaa tgtgagtgat gttttatgaa aggtatgttg  86160
aggtctgtct atgactatcc attgttggag cagaactgca aatgccaaag ctacatactt  86220
tatgtttggc ttcttgaggt gagatccctt cagctgtctt catcaaaagc tatgtctagc  86280
ctttaaaagg caatgaaatt acactgtaag aatcattcca gggttcaaaa aattgtctac  86340
cttccttatc tgtctttcgc tcagaagtct actcagtctt attttcctca gtcccccatt  86400
tttttctcta gtaaagcaag actaaaaaca aaagtttaag tacttggtat atactttatt  86460
```

ctatatttta aattctattc tagaatttta aggaaacaac tgcttttaaa gccttaggtg 86520
ttagtgtaaa attaactgtg agctctttaa ttatggtaac ttgtttttag caagttctgc 86580
ttaattatat caaaattaga taatatagtg tggcctatca taaatcagga ttcactagat 86640
agtatatgta cttgaatatt gccagcccac aaaagcagtt cacttcagaa atcatgtgtg 86700
ttaggcagtt taataaactg tgaaaataga aagagatgat gcttacagag aagcttcctt 86760
aggggctctg aatgctcaca ctaagcagat tttactctta actttctttc tcccttgctt 86820
tttcttcctt ttcttttttt taaaaaaata acagaatgtg aaaagactag aaaaaccagc 86880
atcgaaatag gtcttataag taaaattgat aacctgtgta attttttgaa gtaagtattc 86940
acagcaggtg atgattatga taaagccaca tattttagta acacatagta gaagttctat 87000
aatagaaagt ggtttaagat tattctctca tatgaaagct caaaagtgat gaatttttca 87060
agatcttatt tcccaaggat ctctgctttt taagcctcat tcttatatat cacagtgaac 87120
aaactagtgg ccactttttt atgacttgct aattttggaa ttgtatagca gggttgggtg 87180
gaaaagaaga aatgagaaac tttgtggtaa gcttaatatt gataaataaa attatgggat 87240
cctaggcttt aagagctaaa agaaacctta gagttatcca ctccttagtt tagaaatcaa 87300
gcccagaaaa tagtgacttc atatatgaga ctcttgtatg ttttctgttg aggagtggta 87360
acttgaatta ataattgtgg attttttaa aaaagaaaaa tatattcatt gcttttatat 87420
attgtgaaat tcaaaccaga ctagcagctt ttttcctgag gtttttagag aaattgtctt 87480
tgatgacaag agaagaattc atgttgatag tattttcact aatctctgat tgtaggaaac 87540
actatcattt tattactgct aagacagaaa aataccagca attcattgta agatgctatc 87600
atttgtatgg tgtaatctga tttcagagat aatgtgaaaa aagtgaattt tagaatcaat 87660
agaatataag ttgtctcttc acaaatacct tagaactgct taagaacacc cccaccctac 87720
ccgtttaact tactgccata gttcccctag gacttatttt cagtattttt tcgttattgt 87780
tccttagaaa acagtacagt gataaacatg agcttagact tcacctttca tttgaatgac 87840
attcctaatg tgatgaggtt tttacaaata tgtaaaacca tatttacaaa tttacatttt 87900
taatataaat atgtaattta atttaatatg taaattaatt taatttaaat atgtaaatat 87960
ttacatattt acaaatatgc aaatatttac atatttacaa atatgtaaat atttacatat 88020
ttacaaatat gtaaatattt acatatttac aaatatgtaa atatacccat ttgtgtgttc 88080
ttttacaagt agataatttc tcatttttct tagatgaagc acttccaatg atagtatgta 88140
ttaagatttt ttaaattact tcttaaagga gaagatagag gttataagtt tatggaagaa 88200
tatagtattg ccatcatgag gtccctcaaa ctgccttcac atctgaatgg gaaaattgtt 88260
taaaaaaaat aaataaataa ataaataaaa tccagggccc taacctctag aggtttagat 88320
tagaagctgt attgtagagc ctatgaatct gaacttctgg taatactcca caaatatttt 88380
gataaagcca gactccaata tttgggaaga tggcctttgg ttcagctcag gtgggggtgt 88440
gtgtgcatgt gtgtttatgt gtgtatgtgt gcatatatag agagaaagag aaaggccatt 88500
ttgatataca agtatgttta tgtgttttgg aaactcagat ttttaagagg atcatgggga 88560
cagcaagctt ggaatagagg atgatgatga tgtgaaactt ggttccaatt agtcagggag 88620
ttctagcatt tcacataaat atctaaaaac caaaaggaat ggctgagatg tggaattgaa 88680
tagggaagtt caaaaatagg aattagcaca gataaaggtg attggcacag ataaaaagcc 88740
ccactaccag gaggttctgc aaaatcccct ctaaaagtca ctggcccttt ttatctggtt 88800

```
tctaatagcc tagtctaacc cagcttccag cattttcagc tcccagcttc cagcattggt  88860
gaacactctt actagtgaaa catgaacgta attcttttat ttattcattg actcacagag  88920
ctttaaaaat gagattattc tgtgctgcac taggtatgtt taattttgtc ttacacatac  88980
actatattgt ggttaacatg taatttccat tgttctttct tgtgatttat tctaattgaa  89040
atcaaaaatg aaaccaagaa atatgcttgg tttatgccct caaagtaatt tctcagaaac  89100
tgaatgagag aatgaagcct atatatacat agatcctcag cattatataa taatttaaga  89160
caatgaaaca tcaaacttag tattacatgt gaggaaaatg aaatctaaaa gagattccag  89220
cctacataaa ttaatggcag aattggaaat agaagtcagg attccaggtc tcatggacga  89280
acgtgattat gtgatttggt gttacccaaa catttaaact acatttgaga tataacagac  89340
ttttcttcat gtgtttatcg tgaacatgaa aaaattaatt tggataatct ggaaatctca  89400
agcaatagtt taagcctcaa gttgactgaa gtagttgaag ctagcctttc tttctttttc  89460
ctcttttttt tttttttttt ttagacggag tcttgctctg tcacccaggc tggagtgcag  89520
tggcgcaatc ttggctcact gcaagccccg cctcccaggt tcatgccatt ctcctgcctc  89580
agcctcccga gtagctggga ctacaggcgc ctgccaccat gcccagctaa tttttttgta  89640
tttttagtag agatggggtt caccgtgtta gccaggatgg tctcaatctc ctgacctcgt  89700
gatccgcccg cctcggcctc ccagagtgcc gggattacag gcatgagcca ccacgcccgg  89760
ccttgaagct agcctttctt agaaatccca ggcattctta agtattagag gtctctttta  89820
tctgattatt gcttctactt aaatattcat ggtattaagg aatttttttta aaaaattatg  89880
aattgatttg atgtaatagc tcagaaaact ataagatttt aagtgataag gttttccttt  89940
tgattcctgt aagtctagta atatcatatt ttgatattaa gatgtcatcc tgctaggtat  90000
tctgcaaatg ctttgatatc aggtcagatt ttttttttaa aaaatgaact ccctaggatt  90060
tcatcatcat ggccaattaa aaagttcaga aattaaaaat cattttatcc agcaattgat  90120
gaaatcaaga gtcttaaaga agaggaagtt acgcagtgaa gaggtagata tgattatatc  90180
caggatattt ttgtttattt ttccccagta atctctgtct gttgctagtc tccatgttaa  90240
ataaatacaa catacactgt acttttaaat atacctaaaa attggcctgg cgcggtggct  90300
cacacctgta atcccagcac tttgggaggc caaggcgggc agatcacaag gtcaggagac  90360
cgaaaccatc ctggctaaca cagtgaaacc ccatctctac taaaaaatac aaaaaaaaat  90420
agccaggcgc ggtggcaggc gcctgtagtc ccagctactc gggaggctga ggcaggagaa  90480
tggcatgaac ctgggaggcg gggcttgcag tgcgccaaga ttgcgccact gcactccagc  90540
ctgggcgaca gagcgagact ccgtctcaaa aaaaaaaaaa aaacaaacaa aaaaaaccct  90600
aaaaatccac gtgtgtattg taaataaatt caggcatgca tgcacgttct ccttttcaga  90660
atgtttagac atagtcctcc aaatttcaaa tatcctaatg catttaaaac aacttctgac  90720
ttaaaaaata cagttttatg gtgaggtttg ggtttaaaca acaacataca attttaaata  90780
atatagctat tatgtaaaga atacaccttt acagtttatt tgttaaatct tttttaaatt  90840
gaccgaacaa ttgatggagg ttatttttaa gaaaaagaat tatcagtaca gctgtttatg  90900
caataatggc ctttatcaaa atggttattg ctaaatttta tgtgttaata atttaaaata  90960
aaatagtttt aaaggctatt tatgtattct gtttttacta ttttatttat tttaattttt  91020
gagacagggt cttaactctg tcacccaggc ctggagtaca gtggcacgat ctctactgac  91080
tgcagccttg acctcccacc tcagcctccc aagtagctgg gatgacaggc gcatgccacc  91140
accccccact attttttatt tatttattta tttatttatt tatttattta ttagtttttt  91200
```

```
gtagaaacaa ggtttcatca tgttgcccag gctgatctca aactgctggg ctcaggcaat  91260
ctgcctgcat tggcctccca aagtggtggg attacaggtg tgagccacgg cgcccagcct  91320
ttattcttaa gtggtacagt attttatgaa atcacttatg tgtaccagaa tggtaatcta  91380
aaataggtaa taacaaaatt tttgcctaca gaattcagtt accaactact tttcaaatta  91440
ttctttttac atatttatat ttgaacacat tctgactctg aaaaatgtat ttgttgtaaa  91500
aaatggaaaa atatggaaaa gaataaggaa aataaaaatc actcataatc ctaaaaaaaa  91560
aatttttggt cgtcattgaa gagagtgagt aaagcatagt agttaagagc ttgtttcctg  91620
gattagtatc tctgttccac aacttactgt gacttactgt gacttgaagt tatttcacct  91680
ttcagtatct tggggtcctt atctgtaaag tggagttaat gtttccttcc tcataagggt  91740
gttgtgaaga ttaaattagt tgctatgtgt gaaatgctac aaaagtgcta tatattattg  91800
ttgctgtatt catggaatat ttttgttcta taatgctatg gtaggttttc agaaaatatt  91860
ttagaaccaa taaaataaca gcaacaacag ctagtacttt taagcactaa ctttatgcag  91920
ggaattaatc taagcagttc atacattaat ttattactat attattatgg ttattttaca  91980
gatgaaataa gagaggtaaa gttgtatgtt tgcatttaca atagaacata ttgcattgca  92040
ttacattctt ttggcaccaa ggtggggagc atagaataga gatcagtgga agtggacaga  92100
catgtaatat tttatggaga ataaagataa atttgcttca gttatcattt gacatgtctt  92160
aggtagagct aagactagat agaacacagg gcctctcaat cctgtagaaa ttcaccacca  92220
catcctttaa aaggttttac attgataagg agtcagctct catctatgaa tgttagtggg  92280
gaaaagctgt agaatgcaca gtctaaatac cagataacct ttttttttccc cactttggaa  92340
tacattatat ttgataaaag caagtatacc tttggatgta aaggtaaata taaacactga  92400
cttacatctt taacacctag ccagttggga actggcataa ggaaactcag aatggattac  92460
atggcaatat ggaatgttgg cctggtccca catttgagct aagatgttaa ttctaatttt  92520
agtctcctca gaattctgta tactccgtag cttgaaacag gtttccaact gaaactattt  92580
ttttccccaa ggttattttc acatctacat ttgtttgact ctagatcttg gaactagtct  92640
atatcaagtt cctttgggga cacaaaattg caaatctgtt gttcagagag caaaactatt  92700
ttaaaaggta acactcgttc tcatatattc ttaataagcc ttcacaactt acagtatgtt  92760
gaggaaactg aggcttaatt gaatcgcgtg ctaaagttta aaggttaaaa gttatggtaa  92820
gtgagagttg ggactagtaa ggtgaattct gactgactct tggtctttcc ataacaaaac  92880
attgtctaaa agtaaactgt gtggcctaaa aatgattttg taaatattag agatcggtgt  92940
tgaacaacaa cagacattat ttaaagctaa agactaaatt cacagaatag gaccctaaag  93000
ttgaagatac ccagaagata atttcagcta gttttgtcaa actctttgac tgcaatccct  93060
agtattttac atagcatccc agtacatgct tatccatctg tacatctaat tgaaacaaaa  93120
gtttcacaaa acagtaggtt ccattactat gtggaatgca ttctgatttt cccattgctg  93180
attgcaaacc actaaatgga ttagactacc cactaatgag ttgcaggtga caagtttgaa  93240
aaaacaatgc tctcgggcaa cctgacctga tgcgttaatt tatgagattt tattttttgt  93300
agacagacta gattgtccaa atgagtatta ttactttaac tactatagtg ctgtgttaca  93360
gttgtttcag tgattattgc atttttcaaa accattttta aaattctgtt tgaaatagtt  93420
ggaataacct gaaaacattt aatatcctgt tttggtaaat tttcatctcc aagattaaat  93480
ttttttaacc agccaacaga tgtttgaagg caagttagga gatatgatgg atactggata  93540
```

```
cagtatccat ccatgtacta gatacagtat ccatccatgt actggataca gtcatactgt  93600
tagcaaattt tagatacata aagtaaaaca aacaaaatgc agtataaaca gttaatattg  93660
gaatctagtg ttgattttat gattaatctc aatgaggtta ctgtatattc ataattctat  93720
aggtacacaa aaatatttgg taaaagattt atagttgaga aaatgctaga cactaaagtt  93780
tgttaactta caatttaaga ataagggctg ggtgcagttg ctcacgcctg taatcccagc  93840
actttgagag gctgaggtgg gcggatcatg aggtcaggag ttcaagacca tcctggcaaa  93900
cgtagtgaaa ccccatctct actaaaaata aaaaatttag ccaggcgtag tggcgcctgc  93960
ctgtaatccc agctactcag gaggctgagg caggagaatt gcttgaaccc aggaggcgga  94020
ggttgcagtg agctgagatc gcgccactgc actccagcct aggcgacaga gtgagatttc  94080
atgtcaaaaa aaaaaaaaaa aagagtaagg acatgagtaa ggttatgtct cacctgtttt  94140
taaggaaatg tggatataag atgggttcta gtccattaaa aggtggtaat ttatactaag  94200
tcttactgtg agagaccata aactgcttta gtattcagtg tatttttctt aattgaaata  94260
ttttacttat gacttagtag atactaagac ttaacccttg agtttctatt ctaataaagg  94320
actactaatg aacaatttg aggttagacc tctactccat tgtttttgct gaaatgattt  94380
agctgctttt ccatgtcctg tgtagtccag acttaacaca caagtaataa aatcttaatt  94440
aattgtatgt taatttcata acaaatcagt aaagttagct ttttactatg ctagtgtctg  94500
ttttgtgtct gtctttttga ttatctttaa gactgaatct ttgtcttcac tggcttttta  94560
tcagtttgct ttctgtttcc atttacatac aaaaagtcaa aaatttgtat ttgtttccta  94620
atcctactcc ttgtttttat tttgtttttt tcctgatact agcaatcatc ttcttttcat  94680
gtttatcttt tcaatcacta gctagagatg atcgctatgg aaaatcctgc agacttgaag  94740
aagcagttgt atgtggaatt tgaaggagaa caaggagttg atgagggagg tgtttccaaa  94800
gaattttttc agctggttgt ggaggaaatc ttcaatccag atattggtaa atacattagt  94860
aatgtgatta tggtgtcgta tcatcttttg agttagttat ttgtttatct tactttgtaa  94920
atattttcag ctatgaagag cagcaaaaga aggatttggt atggattacc cagaatcaca  94980
catcatgact gaatttgtag gttttaggaa ctgatttgta tcactaattt attcaaattc  95040
ttttatttct tagaaggaat attctaatga aggaaattat ctctttggta aactgaattg  95100
aaagcacttt agaatggtat attggaacag ttggagggat ttctttgctt tttgttgtct  95160
aaaaccatca tcaaactcac ggttttcctg acctgtgaac ttcaaagaac aatggtttga  95220
agagtattga gagactgtct cacaagtatg tcatgctcaa agttcagaaa cactagctga  95280
tatcacatta attaggttta tttgctataa gatttcttgg ggcttaatat aggtagtgtt  95340
tcccccaaac tttttgaact ccagaactct ttttctgccc taacagaaga gttgttattg  95400
aacacagttt gggaaaggct gatgggattt ggaaatttga aagtgaagga tcagaatttt  95460
agttttttcc cttttgtgat aaagtagaac agggaaaaga tgcagtcttt tgggtagtct  95520
acttaacttc ataattctga actggttcag tttctactgt aaatataacc acttagtaac  95580
tgagcttgct tacgtttaaa attgagtaca tgacaattac aggaaaaggt ttccactgaa  95640
ggtaccatca gaattgtgag gagtgtgcat agaataatgt atgtcatttc ccttcagctt  95700
tgagatttga gctgttatag cctgttgatt ctaattgagt tgacctttct gttactgttc  95760
ttagtcacac acacacacac acacacacac acacacacac acacacacac gcatccctta  95820
tctataatct agctagtgtt ttattaataa ctaaaaagct atgccatttg tatgtagttt  95880
gttctaagta aatcagagat acataagacg acgccctttt tgagatagaa aattataaac  95940
```

```
ttcataaagt tcttaaattt ggtaaacctt agctctagct tttgatgtat ctagaaatgt  96000
taaaccttag ctataaagca tacttgcatt atatgcagaa atacttgtaa gaaaaaacat  96060
agattaagca gttccagtaa gataactgaa gtgatggcag tagaagtatc aaaaaggagt  96120
attttaccag gaggttatgg tgcttttctc cctggaacat gagaaaatgt gcctaaaatg  96180
gaacttcaga gttatattct gattaactta tagcttgttg ctcttggttc caaggaaggg  96240
catttgtgac attttattaa attcattaat tttttagaca caccattgtc agcttgaaca  96300
aatttattaa ttgtaattat ttgtcagctg ttcttgatcc tgttaatacc atacttataa  96360
ctaaaagcat ttccatggat gttgtaactt ggcctgtaaa aaaaatgttt agatagaaac  96420
catgaaactc aaatatgaat tgtttaattt tcaaaccatt ttgcattcag aaaatgtcct  96480
aagcttaatt catactccta gtgatcaagg aaacatgtta aagctcctta tttttaaact  96540
taaagtgaca atgacatttt caaagatttt aaaattctta taaacaggtt aaaatactta  96600
tatactgtat aatttgattt ctgatttcta agctctactt ttctattgga aattacagat  96660
ttttttcaga cttaattctt aagatgtttt cattgtttca cagtagcaac taaacatgta  96720
gtaaaatgat ttaaattcaa ttaaaatttt tttccttagt catttaaaag ggaagaaatc  96780
aatttttagt agtactcatt ccaaagattc caattttcct ttttttaat cttttatttt  96840
ttggtggagg gaggcaggat ctggctctga ggcccaggct ggagtgtagt ggttctgtct  96900
cggctcactg caacctccac ctcccaggct gaagactcaa accatcccca tgcatcaccc  96960
tctcaagtag ctgagactat aggcacatgc taccacaccc agcttatttt ttgtgttttt  97020
gtagagatgg ggtttctcca tcttgcccag gctggtcttg aactcctgag ctcaagtgat  97080
ctgcctgcct cagcctcccc aaagtgctgg gattacaggt gtgaactacc acaccgggcc  97140
ccaattttcc aatgagtgat ataaaaaagg cctccacgca ggcgcctgta gtcccaacta  97200
ctccggaggc tgaggccaga gaatggcatg aacccgggag gcggagcttg cactaagctg  97260
agtgctgctg cactccagct tgggcgacag agcgagaccg tctcaaaaaa aaaaaaaaaa  97320
aaaaaagcct ccatgattgg ggcttgcata gtgaagacca tgtgaaattg aaagactacg  97380
aaactacttt tcttttacgt attggcccat aattaacatg tgtattgaat agctttgttt  97440
atctaagttc atcagattta tccaggttta tgtatttcag atcatctgat tttattagga  97500
aaatgctaga aaaatttcat ggcaccattg tctaattttg aaaaaacgaa cctttcttta  97560
ctgtgattaa aaattgtttt ttaggccagg tgtggtggct cacgcctgta atcccagcac  97620
tttgggaggc tgaggctggc agatcacgag gtcaagaggt tgagaccatc ctggcaaaca  97680
tggtgaaacc ccttctctac taaaaataca aaaattagct ggcgtggtgg tgcacacctg  97740
tagtcctagc tactcaggag gctgaggcag gagaattgtt tgaacctagg aggcagaggt  97800
tgcagtgagc tgagatcgtg ccactccagc ccaccctggg taacagagcg agactccatc  97860
tcaaggaaaa aaatgaaaaa ttgttttcaa aaatagtacg tgtggtacag atataagtaa  97920
ttatattttt ataaatgaaa cactttggaa atgtagccat tttttgtttt tttatgttta  97980
tttttcagct atgggtggat aaagcatgaa tataactttt cttatgtgtt agtagaaaat  98040
tagaaagctt gaatttaatt aacgtatttt tctacccgat gccaccaaat tacttactac  98100
tttattcctt tggcttcata aaattacata tcaccattca ccccaattta tagcagatat  98160
atgtggacat tgttttctca agtgctaata taatagaaat caatgttgca tgcctaatta  98220
catatatttt aaatgtttta tatgcataat tattttaagt ttatatttgt attattcatc  98280
```

agtccttaat aaaatacaaa agtaatgtat ttttaaaaat catttcttat aggtatgttc 98340
acatacgatg aatctacaaa attgttttgg tttaatccat cttcttttga aactgagggt 98400
cagtttactc tgattggcat agtactgggt ctggctattt acaataactg tatactggat 98460
gtacattttc ccatggttgt ctacaggaag ctaatgggga aaaaaggaac ttttcgtgac 98520
ttgggagact ctcacccagt aagttctttg tcattttttt aattcagtct cttagatttt 98580
atttaaatgc aaaaatttaa tttatgtcaa aattttaaag tttttgttta gaatctttgt 98640
tgatactctt atcaataaga taaaaatgtt ttaatctgac cgaagtacca gaaacactta 98700
aaaactcaaa gggggacatt tttatatatt gctgtcagca cgaagctttt gtaagattga 98760
tttcatagag aagtgtttct aaacattttg tttgtgtttt agtgaaatct taagagatag 98820
gtaaaaatca gagtagccct ggctaagggt cttggtagtt acaacgagtg tgcctgctcc 98880
taccaccccc acccccacct tgagacacca cagaatttct catagagcac agtgtgaatt 98940
ctattgctaa attggtggta tggggtttct cagcagagaa tgggacatca cagtgactga 99000
caatctttct tttataggtt ggaaactatt tgggggactg gagggatact gtctacactt 99060
tttacaattt ttattgataa gatttttgtt gtcttctaag aagagtgata taaattattt 99120
gttgtatttt gtagttctat ggtggcctca atttaccatt tctggttgct aggttctata 99180
tcagagttta aaagatttat tggagtatga agggaatgtg gaagatgaca tgatgatcac 99240
tttccagata tcacagacag atctttttgg taacccaatg atgtatgatc taaaggaaaa 99300
tggtgataaa attccaatta caaatgaaaa caggaaggta ataaatgttt ttatgtcaca 99360
ttttgtctct tcattaacac tttcaaagca tgtatgctta taatttttaa agaagtatct 99420
aatatagtct gtacaaaaaa aaaacaagta actaagttta tgtaaatgct agagtccact 99480
tttctaaatc ttggatataa gttggtatga aagcacacag ttgggcacta aagccccttt 99540
tagagaaaga ggacatgaag caggagatag ttaatagcta agtgtggttg tagtataaag 99600
caagaagcag ggtgtttctt gtattaagct gtaagcagga acctcatgat taaggtcttt 99660
atcacagaac aaataaaaat tacatttaat ttacacatgt atatcctgtt tgtgataaaa 99720
atacatttct gaaaagtata ctttacgtca gatttgggtt tctattgact aaaatgtgtt 99780
catcgggaat gggaataacc cagaacataa caagcaaaaa attatgacaa atatatagta 99840
tacctttaag aaacatgttt atattgatat aattttttga ttaaatatta tacacactaa 99900
gggtacaaag cacattttcc ttttatgatt tgatacagta gtttatgtgt cagtcagtac 99960
ttccacattt ttgctgaact ggatacagta ggcagcttac caaatattct atggtagaaa 100020
acttgggact tcctggtttg cttaaatcaa atatattgta ctctcttaaa acggttggca 100080
tttataaata gatggataca tggtttaaat gtgtctgttt acatacctag ttgagagaac 100140
ctaaagaatt ttctgcgtct ccagcattta tattcagttc tgtttaatac attatcgaaa 100200
ttgacattta taagtatgac agttttgtgt atatggcctt ttcatagctt aatattggct 100260
gtaacagaga attgtgaaat tgtaagaagt agtttttcttt gtaggtgtaa aattgaattt 100320
ttaagaatat tcttgacagt tttatgtata tggccttttc atagcttaat attggctata 100380
acagagaatt gtgaaattgt taagaagtag gtgtaaaatt gaatttttaa gaatattctt 100440
gaatgttttt ttcttggaaa aattaaaaag ctatgcagcc caataacttg tgttttgttt 100500
gcatagcata ttataagaag ttcttgtgat taatgttttc tacaggaatt tgtcaatctt 100560
tattctgact acattctcaa taaatcagta gaaaaacagt tcaaggcttt tcggagaggt 100620
tttcatatgg tgaccaatga atctccctta aagtacttat tcagaccaga agaaattgaa 100680
ttgcttatat gtggaagccg ggtaagaaag caggtgtctg caaaaagtca tgtatcgatt 100740
tattgtttgt aatgatacag tagtatagca gataactaag acatattttc ttgaatttgc 100800
agaatctaga tttccaagca ctagaagaaa ctacagaata tgacggtggc tataccaggg 100860
actctgttct gattaggtga ggtacttagt tcttcagagg aagatttgat tcaccaaagg 100920
ggtgtgtgat tttgcttcag acctttatct ctaggtacta attcccaaat aagcaaactc 100980
acaaattgtc atctatatac ttagatttgt atttgtaata taatcaccat ttttcagagc 101040
taatcttgtg atttatttca tgaatgaagt gttgttatat ataagtctca tgtaatctcc 101100
tgcatttggc gtatggatta tctagtattc ctcactggtt agagtatgct tactgctggt 101160
tagaagataa ttaaaataag gctaccatgt ctgcaatttt tcctttcttt tgaactctgc 101220
atttgtgaac tgttacatgg cttcccagga tcaagcactt tttgagtgaa atggtagtct 101280
tttatttaat tcttaagata atatgtccag atacatacta gtatttccat tttacaccct 101340
aaaaaactaa gccctgaatt ctcacagaaa gatgtagagg ttcccagttc tatctgcttt 101400
taagcaaatg cccttactac tctactgtct acttctgtgt actacatcat ccaattctga 101460
aagacatagg cttccccatc ccctgctaag actggttcaa gtggcagcta ctgatggatt 101520
gcagtgagaa ggcatgcaaa cacgtacctt cctggaagtt gtctccaaag gctattgctc 101580
taagactcaa gtatataaac actagaatga atatcaactc tatctagcaa taaatgttat 101640
ttttatatta cagttgaccc ttgaacaaca cagctgtgaa cttcatgggc cctctgacat 101700
gcagattttt tttctcaact aagagcagat tcagtattgg tgggactcag aacctgcata 101760
tacagagggc tgactttcat acatgccagt ttcacagggc caactgcaga acttgagcgt 101820
gcatggattt tggtatacac acgtggtcct ggaaccaatc cctgtcacat ataccaaggg 101880
atggctgtat gttactttat attcatttgt tctgttattt tataaggttg ttcgtcgtgg 101940
tatgtgggaa ttcaccagta tttcttcttt ctggtgcacc gttggtcatt tctggcagca 102000
gtggtgaatg tatttactct tagcaacctc tgtgctgcta cctgttctga gtttcaaagg 102060
tgattcatta aagggttggg ataacatggt gataggaaaa accccccctca tcagtcacaa 102120 ggagtataac agcaatatct ctgtaatatg attgatcata gatataattt ctagtaggaa 102180
aaaaagtcat atcttgatgc atctctgaga atagttgaac atatcttgtg ctattcttta 102240
tagagaaatt atctttgaaa ttaaagtctt aattttactt ctagcttttt ataacaacat 102300
aatccctact tggtatgtat cttaagatca tttttaaatg tatgatttga agggcaaact 102360
agtgttatgt gaaaaatgac agataaagta gcttccaact catcctcaag agttgatgat 102420
attctaaacc ttttctaact aaattcagct tcttaatttt ctcaatataa atatgatgaa 102480
aatattaatt cattaaatag tctacaagta ttcggtagtt gaagacttaa agtagtgctt 102540
gtaataacag aagagaaaaa agacattaca ggcgtatctc actttattgc actttgcaga 102600
tactgagttt ttttggtggc aaccctgcat caagcaggtc taccagcacc atttttccaa 102660
caaaatgtgc tcacttcatt agcattttta gcaatgattt taaattaaga taatgtactt 102720
atttttagac aatgctgtta cacacttgac tacagtataa tgtaaacgta acttttataa 102780
gcactgggaa acaaaaaaat ttgtgtgact cactttactg ccataatcac tttatttgcc 102840
atggtctgaa actgaaccgg cagtatctct ggggtatgcc tgtatagata ttttggttgg 102900
tatttattta ttgtatgcag aattcataaa aataaaaact gcgaggctgt ttaatacatt 102960
tcaactaaaa gttgccagca tcattaatat gtaaaccact agaaataaga ttttgttaat 103020

```
tttttgtttg tttgtttaaa cagtcttgct ctgtcactga ggctggagtg cagtggcgca 103080
gtctcagttc actgcaacct ccgcttcctg ggttcaagtg attctcctgc ctcagcctcc 103140
tgagtagctg ggttacagg tgcacaccac tacacctggc taatgtttgt atttttagta 103200
gagataaggg ttttgccatg ttggccaggc tggtctcaaa ctcctgacct ctggtgatcc 103260
gcccgcctcg gcctcccaaa gtgctgggat tacaggcgtg agccaccata cctagcaaaa 103320
tcaactctga atctgaatca aacctttgaa acaaaaatta ccaatcaaaa aaacgtgcaa 103380
tccctgctcc taactttgaa aaagtgacaa ggaaggacat ttggaaagat gtctctaagc 103440
agtcaacaag aaatgaaatc agggagagct ttttcagcac ctgaaaaaat acatgcaaaa 103500
acgcccgagg cgggcagatc accggaagcc aggagtttga gaccagcctg gcaaacatgg 103560
gggaaacccc gtctctacta aaaatacaaa aattagctgg gtttggtggc aggcagctgt 103620
aatcccagct cctcgggagg ctgaggcagg agaatcgctt gaacctggga ggcggaggtt 103680
gcagtgagcc tagatcgtgc cactgcactc cagcctgggc aacagagtga gattccatct 103740
caaaaaaacg aaaaacagat tcagagttta tttccttccc aaatacttca tagatgttgg 103800
tttgtaggaa taacttaaaa gtctcactcg ctttctgtct tttctagtaa tttttatcgt 103860
ggattctgat tgcctagatc tgctaattca ttgagggtta caaaattgtg atactcgaat 103920
tctttattcc tccttccttt attacctgta atacttctta agaaaaactc tttctcatca 103980
actctatgac taccctaaat tacagatcca catataggat ctgtatacat gtatataaat 104040
atgtacatat catatacgat aatgcttaat tctttcccat tacttactaa ttttcaaaat 104100
aatgtgattc cctaactgct ctctgaatgt tatcaatgtg gtggtaataa tggtggtgtc 104160
gatgttgtgt ggggtaaaat ttgaatacag tgaaataccc agggcttaat tgggttagtt 104220
tttaaaaatt acatttatgt aaccatattt cagtcaaggt gtagactatg tccatcagca 104280
cagagttccc atgttttccc ttccagtgaa tctccatccc ccattagaac agacaataac 104340
tgtcctaatt actgtcactg tagcttactt ttgtctgctc tagaatttct tatgaatgga 104400
atcttatgta cttgtactgc atgaagactc tttagattca tccatgttat tgcattgatt 104460
tatagtgcct tttaaaaaat tatagagtag tgttgcatta tatgaatacg caaagtgttt 104520
ttttttacc tgttggtgga cagttggatt gtttccagtt tgggactatt gtgaataaag 104580
ctgtgtagtc ttattgtgga aatgttttat ttctcctggg caaacatgta ggagtggagt 104640
ttccaaagca tatagcaggt gcatatttaa ctaaaagtgt cttttcctca tttttaatat 104700
tggatttttg tatttctatt gactatagat attttcttaa aatatagcag tatgtcttat 104760
ccttagtttt gcttttttt ggtttcagtt atctttggtc agcagtggtc caaaaatatt 104820
tattaagtag aaaattccat gaataattca gggtttttga tgtatgtgtg tgttggcggg 104880
tgcagggcag ggagagttgg ttggttggtt cgttggtttt ttttttttta aagagacaaa 104940
gtctctgtca tccaggctgg agtgcagtag catgactaca gattgttata aactgaaact 105000
cctgggctca tgcaatcttc ttacctcagt cctctgagta tctgggctca tgcaatcttc 105060
ttacgtcagc cctctgagta gctggtacta caggtgtgca gctaattttt agttggttat 105120
ttttttgtag aaacagggtc tcactatgtt gcccaggctg gtttcaaacc cctggactct 105180
agcaattctt ccacttcagc cttccaaagt gctgggatta caggcgtgag ccactgcacc 105240
cagccaacaa ctcttaagtt ttaaattaca tgctattctg agtaacatgg tgaaatctcc 105300
cacctttcca cccagggcat gaattatccc tttttccagt atatcgttgt tgtctagact 105360
acccaccact tttagtctac tggttatcag atcgactgtt gcagtatcac atgcttgtgt 105420
```

tcaagtaacc cttattttac ttaataatgg ccctaaagca caagagcagt gatgttggaa 105480
attcgaatat atatgccaaa gagaagctgg aaagtgcttc ctttaaggaa agaatttaaa 105540
aatcatatgt tgaggttgct aaaatctatg gtaaaaatga gtattgtatc tatgaaattg 105600
tgaagaagga aaaataaatc atgcatagta tatacagggt tcagtactat ttgcaatttc 105660
agacatcact ggaggtcttg gaacgtattc cccatgggta agtggggaat actgtatatt 105720
ctatataaaa ggcccatttc tgataagtag tttatgatta ttttctccaa gttttcattt 105780
tcttaagtgt cttctggtga gcagaaatta ttcatttttt gaggtctaat ttattttttc 105840
ttttatggtt ttttatgtcc ttttatatct ttgcctagcc caaagccaca aatatcttat 105900
gttttcttct aattgtgtaa tataggttta acttttatgt gtaaatctgt gatccaccac 105960
caataaaatt ttgtgatgct gttagacagt ggatgtcatt cattttctaa atagttttat 106020
ttatttgttc cagtaccatt tgttaaagag acttttcttt ccccattgaa ttgcctttgc 106080
acctttgttg aaaatcaatc tgtgtgtgag ccgtgtttct ggattctcca ttctgttcta 106140
ttaatttgtt ttgtcctttt gccaaaatga cactgttatg gttactgcag cttcaaatca 106200
gatgctgtga gtcccacaac tttttcatta ggttgctttg acttttattt gcatataaat 106260
attagaatca gttaattttt acaaacaaaa gggcaaagcc tgcagagatt ttgatttggg 106320
ttgccttgac tggggcaggt caatttggag agaattcaca ttttaacaat atattcttcc 106380
aatccttgaa caccgtacgt ctctccattt atttagatgt ttgttagttt atctcagcac 106440
tgttttatag tttttaatgt tgaaatcatg tactctttgg ttaggaataa acttaaaata 106500
tgtttctaat gctattagtg gtattttttta aatactgctt ttcacttgtt tattactatc 106560
ttgaaataaa atcgattttt atatattgat cttatatcct ataacctttc taaattgact 106620
tattctagta gttatttagt agatttcata gggttttcta gtaaacagct atgtcatcta 106680
caaatcaaga caggtttctt tctttccaat gtttatgtta tttattactg ttcctctatt 106740
gcactggcta gaacctttgg tagaaggtat tcttacttta ttcctcattt tattgagaga 106800
gactataata tttaccatta actgtgatgt tacttgtaaa caaaaagttt gtatttctct 106860
gggattaaaa accaagagtc catttggttt tttactgttg agttttaagg gttccttatg 106920
tattttctag gtatgttctt ccttcattga attgtttttt tcacatacgt taaaaatcac 106980
ttgagaatat ttatataggt ctgcttctga gatttatctg tttatcaggt tttgtttcat 107040
ttattttgag gctctatcat ttggttcata cccatttaga attactatgt cttggtgatt 107100
ggtcctttat cattatataa gttttttctg ttttgcgatt ttctttgctc tgaatctgat 107160
atgagtgtaa ccatttgttt ttttttaaat taatgtttgc atgatctgtc ttttactatc 107220
attttacttt catcctgtgt tgctgaattt gaaacgaatc tcttgtaaac agcatatagt 107280
tgtcatttta ataaaaactg ttagtctctg ccttttaatt tttttattta gaccatttat 107340
atttaaggta attattgata tgttagggag aggtctgcca ttttattatt tgttttctgt 107400
ttctgtcttc tgtttatggt tatttattta ttgccttcca tgattacttg aacatttttt 107460
aagattttta agacccttga tttatttagt gtttgggttt tgttttgttt gtttgtttgt 107520
ttttgtttcg agacacagtc tcgctctgtt gcccaggctg gagtgcagtg gcacaatctc 107580
agctcactgc aacatcggct tcccaggttc aagcaatcct cccgcctcag cctcctgggt 107640
agctgggact acaggcacat gccaccacac ctggctaatt tttgtatttt tattagagat 107700
gaggtttcac catattggcc aggctggtct cgaactcttg accttgtgat ctgtccacct 107760
cagcctccca aagtgctgga attacaggca tgagccacca tgcctggcct tctatgtgtt 107820
ttttatagtt gttttcacgg tcattgtggg tatcacatta tagataatgt gacttaccac 107880
cattcactgc catcaatacc attacatgga atgagatatg gaaaccttaa tttcagttgg 107940
gtctctttcc ccacttttaa atagtattgt tttgaggatt aatgctatta cagtttttgt 108000
atcagttatc caatatgact tatagaactt atcaagggag tgatgctctg ttgtatgtac 108060
ccatgtttct gctatttcca ttattttttc caagattcca tcttttatta cttccattag 108120
ccagtcttca aaggcagttc tgctagtgag aaattctttt tgtttttctc tttctgaaga 108180
tgactttatt ttccctttat tcccaaagaa tagttttatt tgtgctattt ggggttcgct 108240
cagcttcttg aagctgtaag tttgtgtctt ttgccaaaca tggaaaattt tcaaccatta 108300
tttcttcagg tgttctttca gcgtcactct tttctccatt ctaggcctct aatgatacaa 108360
atgttgagtc atttgttact gttccacatg gacctgaggc atggttcatt tttcagtcta 108420
ttttctctct tttgttcaga tttctctcct ttgtcatctt cactctactg ttgagcccat 108480
ctaatgatta tttttctcct attgtatttt ttaggtctat aatttccatt tgcttttttt 108540
tccttgtatc ttgtttcctt gctgagattt tctattgttt cgtttttgaa acagtagaac 108600
ttgtaattgc ttgtcaaatc atttctctga tggcagcatt aagatccttg ccagataatt 108660
tcagcatctt actcatccca gtgttggcgt tttctttcct tcatgtaatt ttcctggttc 108720
ttggtatgac agataatttt tggattgtgt ctcggacatt ttagttatta tatcaggaga 108780
ctctgtactt tttaaaaatt ttaacttcag tagtaacctg ttaaggtata gcatgtaggt 108840
actagcatat atttgtgagc tgtggttcca gtgaccattt ttcagaggct ttatggtgct 108900
gttttggttt gttgctttta tctcagtcca ctggggctcg cactggttcc tagtagtgct 108960
gcttgagggg ccttctccag gctgagctgc gcagagtgtg tttgggtgag ggaagaggac 109020
ccccactaga ttttcgtggg ctggagagtg cttcctgagc cttgtgcctg ttgtggcagg 109080 ctccccccttg ctggtgttcc tggcagtgct cctgaccaca ttgtgtccct gggctgtgga 109140
acacttgcag gaaaggtgaa cactgccagg accaattata gcagaattcc tcctgccagt 109200
acacagcagc actgtggctc tggaccagca aggagagtct caagcatggg tttgtttctt 109260
tttgatttta agatttttct tctgccttca ggttctggta ttattgttct gttttattca 109320
cctttatgtt tcttctagtt tagttttagt ttctttgtat ttgatgggat ttttttcctt 109380
gcatttctaa ttactcctta gttgtgtcat gtcttccttt ttttcagtta ccctcattca 109440
gaaatttccc atttctaatg atttgttatt ttttaaattc tttttagctc agtttgaaat 109500
ttgtttacag ttttcatgtt ttatttgcat attgtttcat gtactttgat tttctgtagg 109560
gacaccattc tcatgtatat gcacatactt tttctctaat aattacactg tttcactctg 109620
ttctgttatt tatttatttg tgtgtgtgtg tgtgtgtgtg tgagtgaaat gagtttctca 109680
tacttggacg agggagagat gggccaggat aactttttttc gctttttagg gacgaggaga 109740
agtctgtgtt tttgtaaaat ggtcaaaaat atgcccttgt gctttctgaa actgccttct 109800
ttactcctct atcccacaca tatatttgaa cttttttttg gtttttatta ctgacctggt 109860
ccattcggaa gttattccca gaagtttttc ctcggtacaa ggtttgtttc tggtgggggt 109920
ttggtattcg ggtgttttaa gggcccagag cttactacat catgatccct ttgtaatcat 109980
ctgcaaatta gatcctgtag aactttttaa aactttaagc cctgttttca gattggcctg 110040
tgctttccag tgggttggca gtgttctcag ggctgtcaga aacccagtca gttaccttgc 110100
atctgcttcc ttactaacca gtcttgtagt tgtcagagct ttgtttctgt ccaattatat 110160
gcaatggttc atggttttgt tgtagataat gtctctgggt ctttggtttt ctcattcagt 110220
ttgctgtttt tgtaggggag gttgggaggg aataaaacaa aaaataataa taataataac 110280
tatgtcgttg ccatcatcat ctttccagaa cctgctacct gcccttcacc tgattttcgt 110340
atttatcagt atcattacct taatctgtta tctcattggg gattgcaaaa tggctgtttg 110400
gggaaaaaaa atttccatct gcttgtccta catatatacc tggcattctt ttttctcatc 110460
attgggtgcc atttgattac cttgaaaaac agttctacag aaaaggcatg ataaaataga 110520
tttaaggttt ttagagtaag gagttaatgt aataatttta atagtgacaa tttaattttg 110580
ttttttggtt ggtttttgct gccttttttga atattacgaa ctaatgaatg tttttgtatt 110640
taatacgttt cacagtcatt actctaaatg atattcaaat tgcttagcta tcgtgtgctt 110700
ttaaaatgac cctattagat tttgagattt ctaactaatc tcgaacattc attctcaggc 110760
ctggaataag ttatttttcc aataaattgt tggagaatgg catttagaag tcagatttta 110820
gatgcaaagt atggcctttg cttttgaacg ttactgcttg taggccttat cagaggacag 110880
aactaggaaa ataatcttcc tagtgtatcc tgagaatcat cccacattat tgcagaggtg 110940
ttttccattt tgttttgtat gactgaatac tgctcctttg tgtggatgca gcatagctta 111000
tcaatattta tgggcatcga ggttattttt aacctttttgc tgttagtact aatgtcacag 111060
tgaatcctct taatgttcat gcattattcc gtacatatgt aaagtatcat taagataaat 111120
tgttagaagt gggattgttg catcaaatgg tagatgcatg tgtaattttg ctagatactg 111180
ccaaatcctc cttcacagaa aaataacatt ttgcattccc accagcagtt tacaacagta 111240
tctcttttct taaaactttc caaacagaat gtgttgttaa atgtggatgt ttacttattt 111300
gccaattgag aaatggtatt ttactatagt tacaattttt gagcttacct caattatgaa 111360
tgataatgga catttttttct tgtagagctg tttatagttt tatatagtct tttgctcatt 111420
ttgctgctca gctggtcgtt ttcttcactt ttagaaactt tatatgttaa ggagattagt 111480
cctttaacgc tggtaaattc gcaaatattt tttcccagtt tgtcatttgt cttttaacct 111540
tgcttatagg atttttttgc caaatgaaag gttttatgtt tatgtagtta gctattaatc 111600
tttttcgtta ttatgctttg atatgcattt ctttagttat gtttatttta ttcattttct 111660
ttgtttttta attttctaga gtctgtcctc agtagaaatt ttagtcatac tgcttcttct 111720
ttggtcacct tataataaaa ttagccttta tttccaaagt taccttgcat atttcttcag 111780
tattttttag tattcttatt tttatttaag atgtgctcat ttctttctga atttgtattt 111840
ctcatcactg gtggtctgtc ttgtctgctg ctgcattctc cttttgtgtt ggaatgtggt 111900
gttactagtt tcccattgtt tatgactgaa tttttctggt ctacttttgt ctaccggaaa 111960
gttttgcttc tcattcgcca gactcttccc ataataactt tatttagact tccgaattct 112020
gtttttcttg tttatgtttc tataacagat gttacttttt tctggacctg ttattactag 112080
acctcatggt ggagcaggga ggaattgtgt ggctttaggg gtcttggttg aagggatccc 112140
tcttctgttg ctttagtaag ggcagaatca ccactttctg atttttcagc tccatgtagc 112200
ttaatgaaga ctctttttca ttagctgctt ccaccccttt acagccgctt aagggacact 112260
tctgcttttg aaggtacccc ccttcctttc atgcatggtg ccttcctgag cctgccattg 112320
ctggacccaa gtacttttct gtagtccttc ctttaaccac cctgttgcca gtgctctaac 112380
ctacactcag tagtgctctg ttgaggggca ggtggtggag ggggtggggt ctggccttgg 112440
gtgatcccta atcagtatga ttccgcacaa gccactcttc gatgtagctc ctgctggacc 112500

```
ctgctcattt ccccacttct ttggtatttg gagtttattg ttctgtctcc tagttttact 112560
ctagacctaa gtcataggtt ttttttttat tttcccccttt ttgatccggg tagattttta 112620
gagatgtgag taggatgtga tcgatacagc caccactttt atgtggaaac ctggaagctt 112680
cttcgtgttt tcttcagctt tctaaatata tgcattcttg tttaattcaa aatgttaatg 112740
taacacacat aacacttata ggaatagaga tgcattttgt tccctgtttt cattgtataa 112800
aatttttaaa ggtttcgttt aaaagtccaa agaaacagct ccgtaataat atagccagac 112860
tggtcattgt gaccactgct gatctgccac ttcctgcagg gtctgtctct gttcttcggt 112920
ggtgctcttt ggtctacctc cttaggtgta gctggttcag ttaagcttca gagccctcct 112980
gcagtgtgag gaggctttat taccacccac tgcagggcag cttttctgct atgttggagg 113040
gttctgtgct acagcagact tgttttctct tgtcagcctc cccaaaagga gtatcatgaa 113100
ctggggtccg attcctctcc tccttacctg agagatgctc ctgcaagttt catgtccagt 113160
tttctgttgt tgtgtgtttc ttttttgttt tctcttgctg actggtggat ttgtaaaggg 113220
gcagggaagg gaagtggcaa gagattggag aaagccaaga attctaataa aacttttaag 113280
ttatttcaga taaatggtgt tgcagcacca aaaatgccag cattttggta ataaaaatag 113340
tatgttggga tattagaata tcaaaaggta gaaaattgta attactggtt tgggatgtgt 113400
gatgttctct gctaacattc tggaattttt tttttttttt tttttgagat gaaatttttt 113460
ttttttttg agatggctca aaatgtttcc caggctagag tgcaatggtg tgatctcagc 113520
tcattgcagc ctccgcctcc catgttcaag caattcttct gccttggcct cccaagtagc 113580
tgagattaca ggcatctgcc accacgcccg gctaattttt gtattttagt agagacaggg 113640
tttcaccacg ttggtcaggc tgatcttgaa cccctgacct caggtgatcc actggcctca 113700
gcctcccaaa gtgctgggat tacaggcatg agccaccaca cctggctctg gaaagaactt 113760
tctaaataac tattaaaatg cattttatat tatataagca actaaaaata cttttaattt 113820
ttttttaat tttttaatct taacattatt tagctatagg ccaggcgcgg tggctcatgc 113880
ctgcaatccc agcactttgg gaggccaagg tgggcggatc acgaggtcag gagatcgaga 113940
cccatcctgg ctaacatggt gaaatcctgc ctctacttaa acgtacagaa aattagccag 114000
gcgtggtggc aggcacctat agtcccagcc acttgggagg ctgaggcagg acaatggcgc 114060
gaacccagga ggcggagctt gcaatgagcc gagatcgcgc cactgcactc cagcctgagc 114120
gacagagcaa gactctgtct caaaaaaaaa aaaatttatt tagctatgaa ctagtgtata 114180
tatgttttat agatgcctga ttattcaaat aaacttcaag attgcacttt atgagcttgt 114240
atttcgtttt ttagaactca aactaacata agtgtcatta aaacatagct tttattacat 114300
agattttagg aatgccacag gataaatcat tctcttaaaa taactgcagg tggcagaaat 114360
gtcagaataa ttctcctcct ccatacacag cacatattac ttgtttaaag tattctagtt 114420
catataaaaa ttgaactttt gtattactgc tattaggtat gtagttgttt gcatttgggg 114480
ccagttggtt ggggcagggg gtcttttttt cttttgtcct taatctgtat cactttttcc 114540
tcccaaagtt gagttaaagg atgagtagac caggagaata aaggagaaag gataaataaa 114600
atatataccc aaaggcacct ggagttaatt tttccaaata ttcatttcag tctttttcaa 114660
ttcataggat tttgtctttt gctcattact gactgcataa tgtgattata ccatagttta 114720
aatagtcact tcctgttact acacacttgg gttttctcaa ttttttacta ttgtagtact 114780
aatattttac tatattgtaa tctaatctaa atttttacgt attcagagct gttcaggata 114840
aatttgcttg gaaattttta aatcaccaga agtgatacta tcctgataat taacttccaa 114900
```

gttgtctctt aatatagttt taatgcaaat cataagctta tgttagtacc agtcataatg 114960
aatgccaaac tgaaaccagt attgtatttt ttctcattag ggagttctgg gaaatcgttc 115020
attcatttac agatgaacag aaaagactct tcttgcagtt tacaacgggc acagacagag 115080
cacctgtggg aggactagga aaattaaaga tgattatagc caaaaatggc ccagacacag 115140
aaaggtaggt aattattaac ttgtgactgt atacctaccg aaaaccttgc attcctcgtc 115200
acatacatat gaactgtctt tatagtttct gagcacattc gtgattttat atacaaatcc 115260
ccaaatcata ttagacaatt gagaaaatac tttgctgtca ttgtgtgagg aaacttttaa 115320
gaaattgccc tagttaaaaa ttattatggg gctcacattg gtttggaatc aaattagtgt 115380
gattcattta ctttttgat tcccagcttg ttaattgaaa gccatataac atgatcatct 115440
atttagaatg gttacattga ggctcggaag attatcattt gattgtgcta gaatcctgtt 115500
atcaaatcat tttcttagtc atattgccag cagtgtttct aataagcatt taagagcaca 115560
cactttgcag tcttgtaaaa caggtttgag tattttctcc accttagagg aagttacttg 115620
acttctcagt gacctaacct ctaaagtgca tttactgatg tcctctctgt ggttttgttg 115680
tggaaagatt tagttaaatg aactgtaaga attcagtacc taaaatggta tctgttatgt 115740
agtaaaaact caatggatac agtatcttat catcgtcact agctttgagt aatttatagg 115800
ataaaggcaa cttggtagtt acacaacaaa aagtttatga tttgcattaa tgtatagttt 115860
gcattgcaga ccgtctcaac tatatacaat ctaaaaatag gagcatttaa ttctaagtgt 115920
atttcccatg acttacagtt ttcctgtttt tttcccctt tctctattta ggttacctac 115980
atctcatact tgctttaatg tgcttttact tccggaatac tcaagcaaag aaaaacttaa 116040
agagagattg ttgaaggcca tcacgtatgc caaaggattt ggcatgctgt aaaacaaaac 116100
aaaacaaaat aaaacaaaaa aaaggaagga aaaaaaaaga aaaaatttaa aaaattttaa 116160
aaatataacg agggataaat ttttggtggt gatagtgtcc cagtacaaaa aggctgtaag 116220
atagtcaacc acagtagtca cctatgtctg tgcctccctt ctttattggg gacatgtggg 116280
ctggaacagc agatttcagc tacatatatg aacaaatcct ttattattat tataattatt 116340
tttttgcgtg aaagtgttac atattctttc acttgtatgt acagagaggt ttttctgaat 116400
atttatttta agggttaaat cacttttgct tgtgtttatt actgcttgag gttgagcctt 116460
ttgagtattt aaaaaatata taccaacaga actactctcc caaggaaaat attgccacca 116520
tttgtagacc acgtaacctt caagtatgtg ctactttttt gtccctgtat ctaactcaaa 116580
tcaggaactg tatttttttt aatgatttgc ttttgaaact tgaagtcttg aaaacagtgt 116640
gatgcaatta ctgctgttct agccccccaaa gagttttctg tgcaaaatct tgagaatcaa 116700
tcaataaaga aagatggaag gaagggagaa attggaatgt tttaactgca gccctcagaa 116760
ctttagtaac agcacaacaa attaaaaaca aaaacaactc atgccacagt atgtcgtctt 116820
catgtgtctt gcaatgaact gtttcagtag ccaatcctct ttcttagtat atgaaaggac 116880
agggattttt gttcttgttg ttctcgttgt tgttttaagt ttactgggga aagtgcattt 116940
ggccaaatga aatggtagtc aagcctattg caacaaagtt aggaagtttg ttgtttgttt 117000
attataaaca aaaagcatgt gaaagtgcac ttaagataga gtttttatta attacttact 117060
tattacctag attttaaata gacaatccaa agtctcccct tcgtgttgcc atcatcttgt 117120
tgaatcagcc attttatcga ggcacgtgat cagtgttgca acataatgaa aaagatggct 117180
actgtgcctt gtgttactta atcatacagt aagctgacct ggaaatgaat gaaactatta 117240
ctcctaagaa ttacattgta tagccccaca gattaaattt aattaattaa ttcaaaacat 117300
gttaaacgtt actttcatgt actatggaaa agtacaagta ggtttacatt actgatttcc 117360
agaagtaagt agtttcccct ttcctagtct tctgtgtatg tgatgttgtt aatttctttt 117420
attgcattat aaaataaaag gattatgtat ttttaactaa ggtgagacat tgatatatcc 117480
ttttgctaca agctatagct aatgtgctga gcttgtgcct tggtgattga ttgattgatt 117540
gactgattgt tttaactgat tactgtagat caacctgatg atttgtttgt ttgaaattgg 117600
caggaaaaat gcagctttca aatcattggg gggagaaaaa ggatgtcttt caggattatt 117660
ttaattaatt tttttcataa ttgagacaga actgtttgtt atgtaccata atgctaaata 117720
aaactgtggc acttttcacc ataatttaat ttagtggaaa aagaagacaa tgctttccat 117780
attgtgataa ggtaacatgg ggtttttctg ggccagcctt tagaacactg ttagggtaca 117840
tacgctacct tgatgaaagg gaccttcgtg caactgtagt catcttaaag gcttctcatc 117900
cactgtgctt cttaatgtgt aattaaagtg aggagaaatt aaatactctg agggcgtttt 117960
atataataaa ttcgtgaaga aatgtgtgct cttcagttct caagttttat tattatggta 118020
tttattaaag ttctacaatt gtaataacgt atccatatga caagttttaa agtggtaatt 118080
gaaataggtt atcagatata gagttgttca catcaagtag acttttaaca gagtcagaat 118140
gaacctaccc ttaaaatttt agagaaaaaa aatcgtcggt tgcacagaat agctgctcta 118200
gcttgcttaa ttatgccggg catgttgtca ctcctcttac ttttgctgcc ttttcattac 118260
tatttaatgg aatgtccctg aacaataagg aagagcaaaa catagacatt ttgactacag 118320
tggatacttc ctctacccca aatgttatgt tataaaagta ctttttttgc ccaggtactc 118380
tattatatat tttggttttc tttgaattag acctcaatct ccaggaagct ctggagggaa 118440
aaaaaggaac cataaactaa agtaactggt tttccaaata aatgtaaact tttttaacct 118500
tttattatta tagaacattt caaacataca taaaacatga aaacagcctg cagccaaact 118560
tttctggacc ttggcagctc cagcaaatga gctggtcatc ctaaccctgg tttcctgaga 118620
caactacttt tggggatgct tgcttgtata gggagatgat agatagatag atacatatca 118680
aaaagaaact tgaaaaaggc ttcgaacaga acttgccgat gttactcatc cctcctcggt 118740
acagacattc tgttagaaca gatggttgta atggggcagc atcactccct attcccatta 118800
aaaacatgac cattctgaga tttcaggccc cttcgaggaa tttttctcaa gaattccata 118860
caaactgtca gaggaagaaa tgtcgtccca agactagtcc ctgtgtagtc ttgatccctt 118920
tacctgctta ctgtaatttt ttttctctga ctttccgcca gtgtctaagg gccatctgta 118980
cccctcccac ccttccatga gccactgtat aatccaaaaa cacaccttcc atttgctccc 119040
tcacttgtct ccttttacct caacagtgtt agtgtgtaaa gaattgcctg gggagggtag 119100
agggttttac aagtacagag tcccaagtct tttctcccct ccccgttagt gggttggcat 119160
ttattaatag gcactgcaag attttgatgc aggtgtgggg tagatatcac tgtgaaaggc 119220
tactaatgca tggtagtttc accgaaagta cagtcttcaa ggatccttat aatctcctca 119280
ttgccaaaat cagtaacatc tataaccttg acaacaccct agcttgggct gttgcttctc 119340
tggctacttg tttttccatc ccagtttacc cagattttag atggatactc ctccaattct 119400
gcttaaagtc cttacctgtt cttgcccagt tccctctagt caacctcagt cactcccaaa 119460
gattcttccc caatcccata tcttttgctc agacctctgt ctctgggatt tctttgttac 119520
ctcatagtca gtagtcctaa aaacaaaatt cttcatcttg catctctatc gaccgaccat 119580
tctttgtttc tttttaagaa atgtaacctt caccccaatc atcaaaatct ctcattcctc 119640

```
aattgtcaca ggttgtcact tctttccccc taaacctctc ccatcattcc ttccttcttt 119700
atactgccct tacaggtcct gatcctctga ctcacccgga cattcttagc agctgcctaa 119760
tttcactccc tgactctcat ctccctcttc caatcctttt cattgtgcta gaacactatc 119820
ttgctaattt taatatcctc tgcattcagt gcctccacag attgccccct cactgacctt 119880
tccaatttgg ccttgtgtta cacactttcc tcgctgcatt cctacccagc atcttcactt 119940
gtcatatttc tcaaatactc ttcatgacca gatatttaaa gtacctcatc catgaagact 120000
tcatcaaccc ccaaagtgcc tccaatgctt ccgtggtagc acagcataat ggggtacatt 120060
tcttagttga acagtgagga gtcactggga ttcttacaga gtgtcttagg gtctcctctt 120120
gatactcttt ccacatttca gttaaggaat tttcttacat ctttttttct tctaataacc 120180
tttgcctgga gtgtaagtaa attcatgata gagactgtca tttttaaaaa aaaaaacaaa 120240
ccattttgcc tttcacatgt tattacctcc atctttctgt tatcttgtca gtgttgccac 120300
ctaaatgatt gaaaatgacc gagcatgcag tagaatgtag tgaagtttcc tatttcatcc 120360
atttttgca taagtgcatt ggtatctgta tatccatctg cccaagcacc agttgttgaa 120420
aagactatta tttccccatg aatggtcctg gtacccttgt caaagaacag ttgaccataa 120480
atataagact ttctggattc tcagtcttac tccattgccc tatatgtctg tcgttatacc 120540
agcaccgcac tgtcttgatg gctgtagctt ggtagtaagt ttagatttgg gatgtgcaag 120600
tcctccattt tttttttttt tttccccaaa atcattttgt ctgttttggg tcccttgcat 120660
tgcatatgaa tttttatatg atcattgtgt caattcctgc aaaacagctg ggatcttgat 120720
agggatttag ttgaattggt agataaattt gagaaataac tgctatttta atggtgttag 120780
gttttctgtt ccatgactgt gggatgtctt tgcatttgct taggtcttta tttcagtgat 120840
gttttagaga tttcagtgtg caagtcttga cgtctttaat ttttttctaa gtattttact 120900
gatgccactt taattatatg attattttct aatttttatt tttgtattca tcactggtgt 120960
tagaaataaa attaattttt gtatattgat tttgtatatt gtagcttttc taaaattctt 121020
tttttgtcac ttagtatttt ttgcatatga gatcatgcat ctgtgaacag aaatactttt 121080
acttcttcct ttccagtcta gattcctatt atttcatttt cttgccttag tgtgctggct 121140
agcacctcca gtacaatatt ggatagaagt gacaagagca gacatctttt tcttgttcct 121200
gattttaagg ggaaagcatt cagtctttca ccattgagta tgatgttagc tagctgtggg 121260
tttgcttcaa gttgaggaaa ttcttttatt aaacctagtt tactgagtgt tttttaatca 121320
aaaaaaaaaa aaggaggggc tgtgggtttt gttaaatgct tcttctgtat caagattttc 121380
atgttgtttt gtcctttatt aatatgttgt attaatggac ttttgtatat tgaattaact 121440
ttgcattcct gggataatct cagttgtcca tgctacataa accttgttct atgctgctgg 121500
atttggtttg ctagtatttt gtttagaatg tttgcatcta tattcataag gaatattggt 121560
ctgtagtttt catattatat atctgtccag tttggggatg agagtcatac tcctgacaga 121620
atgaattggg agctttccct gttcttaaac ctactgaggt attttttaag tgaactactt 121680
ggagaccttc acctgtgatc ttcagatgct gggggacaca gggatggtac ctgactctga 121740
aaaggctctc agggtaagac gtgtctgaac tggcctgtgg cagttaacta aagagtactc 121800
ctaccaataa tggagtcaag atgtatgttt cccataggcc acgctggtca ctgaaagaga 121860
tgggctatga gccatcttga aaactaccct gcacaaatgg actgccggcc tggagccagg 121920
caccctgcag ctgagtgcca tataatgttg aagctgttga gggaggagag gttggaagct 121980
```

gccagcttag agaatctcag ctgtggtttc cagcagggtg tattccagga aagaaagtca 122040
ttccccaccc tggctcaaag taataattaa cagtgactgg gtaaggcagg atcttttttt 122100
ctaattccct cccctccaga aagggcagca acagctcttg aatgggaaag aaggtggagg 122160
gaggaaaaga aaaaccaatt gccccaacac tgctgtcttt aagcttccca cccaaagacc 122220
tcagtaagag gcagaattat gttttcaatt aagagagagt ttggcctctt ggtgtttcaa 122280
aagtgtaggc tttttaatac ctagagaaac tgatgatttg ttgattacca aaaagggacc 122340
agaaaagcta catagcctga gatttcatcc ccagaaaaac gaatccagag agcagacttg 122400
caaaaaaaaa aaaaaaccgt tctgtctctg cctctcccac tacacataca cagtgagaaa 122460
gagagtcttc atgatttggt aaattagacc catggaaaga ctcgggacat ttaggatgat 122520
gatatttacg atgaggaaga tttctatggg aaactttttt ttaacttgtc tctaatccta 122580
ttccaactga agtttgaatt tttttccttt cattaacatt tactgggcaa atacctattg 122640
aatgtttgcc attttgcagt gtgccatagg tttcaggctg attcagagct gctttgttga 122700
atcaagaagt ctgttacagg gagacaatct agttagacca ggcataagta caaaccacta 122760
agggtaaaag aagtatgtga aagtacaatg tgggcagaga attcagatcc aaaaatactg 122820
cagataggta ggtgatgaag gtcaagccga atcttgacat acaggatagg tgtatgtgag 122880
tgagttaggt ggaaagtcta gtatgtctga gtgtcaggct gtaagggatt aagatgagat 122940
tgggaaggca ggcaggtcag ataatgaggg ccttatagac cataccaagg actttggact 123000
tttattttgc agacgttaag caaagacata atcacttttc attttatatt tattacaaac 123060
tgaaagagca caagtgcaca tgtggtcttt gcagttaagt tattgccata attctaaaaa 123120
ggcagataat ctgaagatag aagggaggcc acagtccaag acatgctagg gactctgatt 123180
gattcagtgc tcatgcatgg gaaagataag agtcaaagac aactcccaca tttcaggttt 123240
tgagagctgg acggacagtg ttgctgttag gtctatagag aagaggagtg gattttgaag 123300
ggaaaattat taatagtaca attgaatgat gttttagttg tgtctgaggg atatccaggg 123360
agagctgtcc taaggcaatt aaaaatatgg gtctagagaa aaacgtacac agaagataaa 123420
aatgtatgac tccagcacat agaccatagc tgaacctgtg gctaggaaaa ttctcctgga 123480
aaaggcagag aggagagaag gacaaggatg gaatgcatgg aaatgctagc atttgagagt 123540
tatacacgga acccacagta gaggcaaatg agaaaaagca ggtttgtttt tgtctgctcc 123600
agtagacaga caccaagctc catgagggca gagactttgt cttattcgtg gctgtacctg 123660
cagtgcatag agcagactgt acatgtgctt tgtggaccca tgcagttact ggggtgtctc 123720
agaaacttcc catcctcctc cctactgtgt ctttgcataa ccctggctgg gcctcccttt 123780
tctcaatgtc aactctcact gtaacttttt tttttttttt tttttttttt ttgagacgga 123840
gtctcgctca ttgccctggc tggagtgcag tggcggaatc tcagctcact gcaagctccg 123900
cctcccgggt tcacgccatt ctcctgcctc agcttcctga gtagctggga ctacaggcgc 123960
ccgccaccac gcccggctaa ttttttgta tttttagtag agacggagtt tcaccgtgtt 124020
agccagaatg gtctcaatct cctgacctca tgatctgccc acctcggcct tccaaagtgc 124080
tgggattata ggcgtgagcc accgctccca gcctcttact gtaactttta agaagggcat 124140
atatctacgt agtgtcatca ccataaagat aaatcaacca agtgaaaata ttttgaaact 124200
ttggaaatgt ataaactcca aaatcatcat cagttacatc atcaattatg tccctaaaga 124260
tcccatcact ctgcctcaca ctggggtctt gcctacttct ctgttccaaa agggcacagt 124320
agtggtatca aatctgtttc ttgaggcaaa tgaagtacct tgctccaaaa taatcaccca 124380

```
cagcaggcag ataacctcca agtgcttcaa gctgagattg agcaggagga tcccagctca 124440
tcacaactgg gtggtaaata tacacttggg cccaaatgga aggaaatgca ttaccctaca 124500
atgcataccc aacatgcttg catccaggcc ccaaatccag caaaacaatg ctattcccct 124560
tcaacatgtg ttaacggaac tgagatattt ttccaattta aattgtgttc cccaaagtct 124620
tcattattct ctagtgccta ttacaatctg tgtttttatg tttacttcat gactgcctag 124680
ttccctcctg aaattttaag cctcgtgaga gtaagaacta tctgttttct ttactccact 124740
gtcctgtaca tacatacttg ttgaatgaat gtatgaatgc caccgtgatt gcaaagtcca 124800
agggaaatga tgttgattca ctgcacactg tacaggaggg tgtcaaccag acttccagat 124860
ttctacagaa attaccagta aagggtagta taagaatggt tcctgcatgt gaaaaatgat 124920
cttggatgga gctgttgtgg cattcacctg ctcctcatac tctcctgcca ctgtgcaggg 124980
acagcacaac ccccgtgctg ctttcttgag tgtagctcat ttcagaaaag cagtaaaagg 125040
aaaacccact tgtttgcttt atgttcctaa gaaggtggtg agtaaatcaa tcacgttatc 125100
ctaagaagtg acttgaattt tatgaaggct cctttgtttc cattgcactc ctttctaccc 125160
atctctactc ccacctccac ccccaccctc aaatcatgct tataatttcc attattcaat 125220
taagggtggc tttttctca tcacaaacat ctgtgtgctt taaatagctt ctacataacc 125280
gaagtggaag tagtcatgta gaacagcaca tggccactcc aggggacatg agaagcctct 125340
gcctaaaggt agttctccct tctgtcatct gatctcacac atggcactgc aaacctgcag 125400
ttatttagcc atgtgctttg tgacattgat ttcacttcct tgggttattc ttaccgtctt 125460
taggaactta aatatttaag aaataaacaa atactattca aagagagctg taccattatt 125520
atatgcattt aagtgaaaaa ctaccacttc ccatatatat ttatctcatg accacctaat 125580
tgataaaaac atgttaactg ttatcttata ttgcctcagg gaaaaagtct gaatgttgat 125640
tggaggcact gcaggatagc cattcgatac ctgcttttgt gacaataaac taaagcattg 125700
gattttggtg gattagggat aaaaatggct tgacagatca tcttgtccag ccctcagtat 125760
atagatgaga agacttaggt ctcaagctct gaagcgcttt gctcaggatc gctggccatt 125820
tcatatatgt aacaagctcc cacttcatgc tcatttcaca gtagcgtgtc actttcaggt 125880
cagcttcctt cagtgggcgt tgtctttgct taattaaatg tcaggaggtc cccccagaag 125940
gcttgactca gggaaggagg gcagaccctc ccagttctct cactgactag ctttcgtttg 126000
ttggattgtt tttactgata aaaaagttca gaaattagag ccaggttcct gttcacgttc 126060
cctacccaag cccctgaaga agcaaattgg tgaatgttcc ccaaattctt ttactctcta 126120
gtatacagta agcagtactg ccaaaaagtt tcccaaagtc atgttcctct tagatatttt 126180
tccttgaaaa ctgttgtctg gcatggagat ccaacctgtg tggaaagttc cagatgccct 126240
ggtcctagct tcacctgccc tgcttttgct tcctgttctc actgcttgtc tccaggtttc 126300
catttgaagg cttgcagtgc tactgtgccc ttactgttaa atcctgcctt gcttgccatg 126360
ttttatagac aaggaaagca ttttctacca gagctcagga gcagccttga ggtcaggggt 126420
aacgtttttc attggtaagt attcagtagt tgctgaatga caattgggtg gaaaggggag 126480
gggtgcctta gaaaaaatgt ctgttctttg tggtaatgaa attgcttcca atttattttc 126540
tgatctcttt gagaactatt tcctgtcgtc ttcccgcacc atgcattctg atttctgggg 126600
cattcagtgc tccctccctt cctttattca aggggctctt ggaaaagaaa tctctgaaga 126660
aaaaatgtgt gggcagtggg agacttctca ttctctccac caaatactta gccctttcat 126720
```

-continued

```
tcatgagaaa cccctgcttt aggatggtgt ggatctgagt cagcagggct gggttcattt 126780
gtatatactc caggttgtgg aggttgttcc tgggtcttgg cctttcattt tgggagtgct 126840
ccacacttct gtctccatat actatgtatt taagaagctt gcctttcgat ttcctgccag 126900
tggctggatc ttggggatca ctgcacaatg cttgtatgcc ccactggaga agtctctcat 126960
ggcacctttc ccctcccatg gtggtggaat gctgtccaca gaaagcttct cttcactgtt 127020
cagagactct aaaaataaga cctgaactga cttgctctgc ctactgaaag gggacctcct 127080
tatattcacc attgccctca caccctttc cttggagtct gtctttaggg tcaccctggg 127140
agctgcctgg gcctccacct tcttaaggag gcaactcctg agagctgggt agggactgtc 127200
tttgtccaga ctgtctgaag agcatcttgt tctttacctc cctctcctgt tcttgactat 127260
tgccttcact gctgcctcgc tctcgtctac cagggtggta ttataaagta tgtccttgga 127320
ggtgagctgt ttgaccagct ccttgttgcc tagaaaccta agaaattgtc agaacaatcc 127380
ggcatgcatc agctctgacc tttggagctt tgactggcat tatttataaa aggctttctg 127440
ctctgttagc cgagcattgg cttcatattt ctccatggac tccagaaaac tgggtttctt 127500
ttttgcaagt tctcttgttt tcagttgaga acggtattga gtaggacttc tctgtttcct 127560
tgagttttat gttctctcca aatatggaat agcacttgct tccctgggtg ccaacgctgg 127620
ccgaccagct ctgaaagttg ctctgcttgt ggttcttccc tgagatgcta gttgggcctg 127680
ggaatcttcc atttctctgc ccaccaggtg acctggcagt cagtgttctg tcaaagacct 127740
gtgagggtgc ttagtgaact gtgggcacta tgaccacagg gtactattct gggtcccagt 127800
gtttgttttt aagaactctg taggttgaca ggacatgctg tctggtggcc aagtgcttct 127860
gccaagagta tggggcctgg gagacatgtt tcctggcctg cttattgcag gcctagcttc 127920
cacctaagag ctatccgctt cccaagggga catccaccat gtctctgtga taggagctga 127980
atagtagggg caggactgaa aggtctgtat gtttgctttt cagtcaggta caggtgttgg 128040
aggtttctta aatttggttt cttttgatct ccctggcagg cagtgatggg gaagttttta 128100
gtaaggttat taacagagat agaggattta gagttaaaat ttaataggga aatttttcta 128160
taggatggtt gaaaatgatg ctttgtatag ttttattgta tgaacttttc agggatagaa 128220
ttagtcaatt tgtagaaatt gggccgcctc tgttattgtg atatattaga actgtattga 128280
atgatgagac ttcccaaaag tttaaaacaa aaaaaggagg cagaagagaa cgaggatata 128340
aatgaggaca ctctcgctga ggacacatca gctgttagca gtctgtctct gtgtaccgag 128400
ctcaagaact gtgactttgg ttggaagtta gaccttttct atccagcttc agacatggta 128460
accttcacat aagctgctgg atttgttcta ccagaaattt agtctgttgt gtgactccag 128520
ccactttgca actcaagatt attacttgtt caggtttctt tcattaaata gctaaccatt 128580
taacaactat tatcttctta gggtcgactg atggttaccc atacagtata tacatcatcc 128640
atatcctttc ctctcctact atatctcact cctattttcc agtccatcct catctctcct 128700
caagatcaac agaccccaac ctcttttact taaacgttgt attcctgaag tagtcctgcc 128760
ctttccttca gcctgcgaag ccttctcaaa gacttctttt ccatgcatct agactctgcc 128820
tggttattct ccttccttca gagttatttc tttgtcaaat gctgctaatg tataaaaaca 128880
caaagctttg atagttcctt ctgtcccaac ggagccttac gcttggctga catttagggt 128940
aaaggtggta tttttattag taaaattaaa tgatacagaa gtgaattcta aaaatagtta 129000
cataaatcta agagagtttt catgaattca ggttgcccca aagatttagg ccatacctct 129060
tccatggaat ggctgtcatg cagtttggat ggttgacctc aaaattattc ccagccccag 129120
```

aagtggagta ggtatattag tctaaggcag tcagggtaat gctatcttcc atgccacaga 129180
ttggcttgga atggggataa ccaaaagcac tttgggcctg tgagatttga cagagtgttt 129240
actgtgagcc tagggaaaga acatgcctgc tctcatgtga gagtatgaag aaacactgcc 129300
taagcaagga atcatgtggc tccagttttt actgtcagcc tttctaccac cagggagacc 129360
agccttgaga tgatgcaggt gcatggacag ctgtgtggag ggatagaaga atccagtttt 129420
taaaccagat ggctgagcta tttcattaag tcaccccaga agtcttcaac taacagtatc 129480
ttaactggtg aactcctgtg actgatacag gaaaatttta cttcgtaaca aagtatgata 129540
attcctttgt gcaggaagga ggttttgtgg aaatgatgtt gattcactgc acactgtaca 129600
ggagggtgtc tctttgacac caccaacctt aaatagtagg aaagccatca cagtgggttg 129660
ggtggttgga ttgctttatt gcaactaata aagggtcagt tgtgcagttg ttaactatct 129720
ttcacttccc tcagaactgt atctcctagc ccagtgccct ataggtcaaa aatgccagtt 129780
tgttgtacag tcagcagagc ccagtactat gctttaaaac attcggggat aatcatcaaa 129840
tatttaatca gaacagatgc tgcctgtaaa caaccactgc agccaagaac agtctgcatc 129900
tgaaacactg cctgcaacta taaatatgcc catatgcttg aacaatttta gtgttgtaaa 129960
aatcttgttt ttataagcaa ttagtttcat ctcctattat atgaggatta actttgcagt 130020
gatgtactga tgttaaaaga gaaaagaatc aaaaaagcct tggttgtggt gaaacccagc 130080
aaaatgtggg tctgcaccaa gttccagatg aatatcaaac agcactgtcc cagttggatt 130140
aaggtgatga cacccctacc atggctacag taccaggtca tttgattttc cccagggtca 130200
taggagtgtt agcccaggtg atcagctcaa cacccccctga gatccatgag gtatatactt 130260
tgaaatttca attccattac tactgactgc atctcaatcc tatgttaata ctttcttgag 130320
taatattctg ttgacctagt tatccacgtt ggaaacttca aaggcatcat cttcagctct 130380
ttgtttctga ctccctatcc agttctccag ttctgtatac accatcccag aaatggtcct 130440
cgcatccagt taatctctga catggactaa taggcctttc tacagcttca gtgtattctc 130500
ttctctgctt ctggaaccca ggatttaggt gctacagtca tactatcttt gacattccat 130560
ctccctggag aatttggaaa tggggaaata acattactct taacaaagca agattaacag 130620
tcctgtaacc agacccaagg cactgaccct tctgtgaaag cctatatcca accagctaca 130680
ggaacctcta cagagagact aaaaaaggcc agccctggag gagccagtgg tcaggagaac 130740
ataggcataa agcctcctaa ggatgtagcc catcaaccct gggagtgggt tcctataagg 130800
aataggcact tcgggcaaat atggcccgat gacaccagcc actgggatct tctgactctc 130860
tcctgtataa tgtgagttca tttgtttatt gtgtttaaag tgaattctgc ctccctaaag 130920
gctgagaact tcctttggct cagtgttcac ttcgtttggc ctctgacttc caactgatgc 130980
atcaagccaa tgcgcaagaa aagttaataa ataaaaataa gatttattac agagccagct 131040
gggcactcat acatacatgg aggagtccct gtgtcattgg aacactgtag cttttctcta 131100
caacagtccc aggctaggca gctctttgta ggcccaaggg aattgatgca taagtaaggc 131160
atggtcttcc ttgactacac atcttgtata caaggtatta aggcccttgg ccacctgact 131220
tcggcccatt ttttcaatct caactctacc ctaaattccc cacacaggtc attcattctc 131280
caatgaggtt attctcctga tctctgtgtg ggttcttata cataatggaa ttgtgtgttt 131340
ttctcctgtt taaagtttgg aacatcatgt tagccatcat tttattctct ttgctttcac 131400
tgtattgcac tcacatactg tatgtggaat cagtgctacc cattagaccc atggctcatc 131460

-continued

```
agtgggaaat ggtgtcagat ctcacagagg gcagcttcat ggggctctag gttcttcagg 131520
cttccttcac agcctaagct ccatatttaa atccagcatt caaccctaat cactgctgtt 131580
cactagcatc tgctacatat tcttgctgac agacactgtg tttgctcttg aaagataaca 131640
aaatgcttga agcttccctc caacgagtga taattcactg aagctcagag gcagcaggag 131700
ctccagtctg ctctgctgct ctgaaattgt ggaaagtagg aaaggtgtcc agaggtcata 131760
tggcccaagt gatgacatat ctgaagcaca gagaggggat gggctaagag tcacctgtat 131820
ccaaaattca agttaacacc tatcaagttg tgaaaagtta ctttgggaca tcccaaagtt 131880
acacagagag ctagagctag gactcagacc tggaacacca gacttcagtc tctctgaact 131940
gcactgggtt gtctctgctc aagccttatt ggagagagaa ctgacaaaag gcaaggctaa 132000
ggagtgctct ttgtggatgc agcaggagaa gaaacaccct tccaatgagg ggtccacaca 132060
gagttcaaat gtcccctttg ttcatactga acgtgggtat ggttttcctc ttttgctgtc 132120
tgcacaggtg gcatagaagg cagcacctga tccttcaggt ctgggggagg agtccccaga 132180
taatgcatag atcttttaaa ctcttcacgt caaactgaca tctgcttatg tagctcagct 132240
caatgtgtta gtcattttgt ttcgtttatt atcaaacaca tcttctgaaa aatgagaaga 132300
ggaagggaaa aaggagtctg ggaaaggacc acactttcta ccacccctgt aaacagtgag 132360
ctttactctg caatacacca agtggaagga gacaggctat gagatgggca cagtaaagag 132420
ccacctaagg gaagtgggca gaactccaga agacttcctg aggaggcatt tattctttat 132480
gaatctttga aatgtttttt taaatcatct ttgatttgac ttttgctcta aaagtatcac 132540
aaggtaagac tcagctgtga aactaagcac atccgatagt caaactatga aaacttttac 132600
acgctagtgg ggcactgtga caccactgat ttccttaaac tgagctcctt tcaaggtgtt 132660
ttgacctaac tggcctttgg gtcggatata gcttttacat acttttggta ggtaactacg 132720
ggttcctatt tgtcagggaa agtgggtaag agttagctat tccccacaac cttgatagca 132780
gcttataaag agagccagtg tcaaatcaat ttgtgccaca ggcattattt taaaagcatt 132840
tcttagaaag cacacacagg agtgttcagg caagaggtac tgtaagccct ttgctttttc 132900
ggggcttaca acctctcaat ttaaatgaaa ggtttattac acaaggtatt ggtaacagtg 132960
accagcaata ggctctgctg tgttactact ggcatcagtc aaaacatgtt ctgacctcgt 133020
ttctgtatat gtttatatgt ttagaggtca agccctgtgt gtcctttctg agggccatgt 133080
taaaggcctc ctcagattcc tatactctat tcttgcaaag ctggagaggt tctttagaag 133140
tattttagcc gggatacgta tatcgaatac cctcaacttc accaatgcaa gccagcttct 133200
aacatactaa ttagcaagcc actgatttta tcaataaaaa cccatttcta acatttactg 133260
tggaattagc aaagtttctg gtgtacattg gatatgaaag ctccagtaac agactcagaa 133320
gaaatggaga cctgtgaaat gacaaataat ttagactaat cctcttaagt tcaacaaagt 133380
acaagaaaat atggatagaa aaatgaaatt tggaaaacaa catctgaaca gaatgagaag 133440
tttaacaaat ataaacaaaa acaatagaaa ttctaaagat aaagaataca gtaactgaac 133500
tgaaaatcta agtagaacgc ttcaacagca gacttgatca agcagaagaa tcaatgagct 133560
caaaggtaag acatttgaaa ttatccaatg agaaacaaaa acaaaaaaga atgcctataa 133620
gaattacagg acacatcaag ctagctaact tttgcataat aggaggtcct taaggagaaa 133680
agaaagaaaa aggcctagaa agcatattta aggaagtaat agctgaaaaa ttcccaaatc 133740
tgagaaaaga tgacaaaatt caggaacagg aagctgaggt caccgatcag attcaaccta 133800
aagagttcac caagacacat cacaaccaag ttatcaaaaa tcaaagacaa agaatactga 133860
```

aagcagcaaa gataagaaac atcacattca aggtagcccc aatacagatt cagtggcttt 133920
atcagcaaaa gccttacagg ccagtagaga gtgggatggt atattcaaag tgctgaagga 133980
aacaaagctg ttaattaaga atactttact tggcaaaggg agaaataaac acttttccag 134040
ataaacaatg cctaagggag tttgtcacta ctaggcctgc tctactggaa ttactaaaag 134100
ggagttcttt aggcttaaat aaaagactgc tagttaatga gaaacataaa agtaaaaaac 134160
taaatggtat aagtaattca tagtcagaat tctctagtat tgtaaaggtg gcaggtaaag 134220
caatgttatt cctattagga ggtttaaaag atgaaactat taaaaacaac tgtagctaca 134280
ataagttgta gctacaagaa gtaattgtaa ctgtagctac aataagagat acaaatttaa 134340
aaaagtgtaa actttgacat caaaatcacg aaaggcgggg gggttgtgaa agcgtagagt 134400
ttttgtatgc aactaaaggc aagtttttat cgcttaaagt agcctaagga taaaatgttt 134460
taagttagcc ttacagcaaa tacaatggta atcgcatata ctataaaaga aaggattcaa 134520
agcacaccac cacagaaaac caccaaacca caaaggaagg tagcaatagg gaaaaaagaa 134580
acaagggacc tacaaaacaa tcagaaaaca aattacaaaa tgacactagc agtttcttac 134640
caatagttac cttgaatgta aacggattag attctccaac aaaaagacat agaatgacag 134700
aatggatttt tttttttttt taagtcacaa ccacatactg cctataagag actcactttt 134760
ttttcttttt ctttttcttt ttttgagacg gagttttgct attgtcaagg ctggagtgca 134820
atggcatgat ctcagctcac cgcaacctcc acctcccggg tttaagcaat tctcctgcct 134880
cagcctctcg agtagctggg attacaaggg cccacaacca cgcctggcta attttgtatt 134940
tttaatagag acaggttttc tccatgttgg tcaggctggt ctctaactcc caacctctgg 135000
tgatcccgcc gccttggcct cccaaagtgc tgggattaca ggagtgagcc actgcgcccg 135060
gcaagagatt cacttttcta ctaaacatac acatagactg aaagtgaagg gatggaaaaa 135120
gatattctat ataaatggaa attgagagca ggggtagcta tacttctatc agacaaaata 135180
gactttaagt caatactata aaaagaaaga agtttgttat ataatgataa agggattaat 135240
tcaccaagaa gacataacaa ttgtaaaagt atatgcaccc aacattgacc cacctaaata 135300
cataaagcaa tttttaaatg atgtgaagag ggagataggc tgcaatacta taatacggga 135360
cctcaatact ctacttttca ccatgggcag attgatcacc tagacagaaa atcaataaag 135420
aaacaatgga tttcaattac actttagacc aaacggactt aacaggcata tatgaaacat 135480
tccatccaga agcagcaaaa tacattttgt tctcaaatgc ccatggaaca ttctccagga 135540
tatatgttag tccacaaaac taatcttaag tttaagtgga cagaaatcat atcaaatccc 135600
ttttctgatt acaatggcgt gaaactagaa atcaagaaca agaatcaatt ctggtggaaa 135660
atacagcaat atgtggaaat taaacaatat gctcccaaac aactaatagt tcacagaaga 135720
agtcaaaaag taaataaaaa attaccttga gacaaatgaa aatggaaaca aaacttatgt 135780
gatgcagcaa aatcagtcct aatggaaatt tatagcgata caaacctacg ccaataaaga 135840
agaaggatca caatctcact tttcacctaa aggaactagg aaaagaacag actaagcccg 135900
aaagttagca taaagaagta agtaacaaag atcacagttg aaataaagac tggaaaaaaa 135960
tgaacaaaac taagagttgc taagagttgg tttttttttt ttttgaaaga taaaatcaac 136020
aaattcttac ctagactagg agaaaaaaag agtactcaaa taagatcaga aatgaaagag 136080
gagacattta ctactgatat caccaaaata caaaggatta taagaaacta ctatgaagtt 136140
atgcaccatc aaattggatg acctaaagaa atgaataaat tcctagacat atacaaccta 136200

-continued

```
caaagagtga atcatgaaga aacaaatctg aataagccaa taacaagaaa agagattgag 136260

ccagtaataa aaagtatccc accaaaggaa agcccaggat taggcagctt cactactgaa 136320

ttttaccaga catttaaaga actaataaaa attctcaaac ttttccaaaa caatgaagca 136380

gagggaatac ttctaaattc attttacaag ggtagtgtta cactgttatt aaagccagag 136440

aaagacactt taaggacaga aacttacaaa gtaatatccc tgatgaacat ggatgcaaaa 136500

atcctcaaca atatattagc aaactggatt cacgaataca aagaatgatt caccatgatg 136560

aagtgggatt tatccttagg atgcaagggt ggttcaacat atgcacatca aaaagtgtga 136620

tataccacat aacaaaatgg agggtgtaaa tcaaatcata tgatcatctc aatggatgca 136680

gaaaaagcat ttgacaaaat tcaacctggt ttcatggtaa aaactctcaa cagattaggt 136740

atggaggcca tgtacgaccc tcatcacttt ttgacatagt actagaagtc ctaaccagag 136800

cagttggaca agagaaagaa aaaaaaggca tcctaatagg aaaggaatag gttaaatcat 136860

ctgtaattac tgatgacata accatataca aaaaactgta atgtctccac cagaacaaaa 136920

ctaaaacctg gtagaactga tacacaaact cagtaaagtt ccgtaataca aaatcatctt 136980

acagaaatca gtagtgtttc catctactat taatgagcta tctgaaaagg aaattatgaa 137040

aatctcataa tagcaacaaa tattaaatac tgaggtgtaa atttaaggag gtaaaagatc 137100

tgcatactga aaagtataaa aggacagggt cttcaataaa tggtgttggg aaaactggat 137160

atccacatgc aaaagaatta aattagaccc ttatttacac catataaaaa aatagattta 137220

aaacttaaca tataagacct aaaactgtac acctactgaa gaaaacatag ggggaaatct 137280

ccacagcatt ggtcttggga atgatttttt tggatatgac tgcaaaagca tggcaaaaat 137340

agacaaatgg                                                        137350
```